US012636009B2

(12) United States Patent
Shelton, IV et al.

(10) Patent No.: US 12,636,009 B2
(45) Date of Patent: May 26, 2026

(54) METHOD FOR CONTROLLING SURGICAL SYSTEM DURING TISSUE TREATMENT MOTION

(71) Applicant: Cilag GmbH International, Zug (CH)

(72) Inventors: Frederick E. Shelton, IV, Hillsboro, OH (US); Taylor W. Aronhalt, Loveland, OH (US); Michael J. Vendely, Lebanon, OH (US); Shane R. Adams, Lebanon, OH (US); Nicholas J. Ross, Franklin, OH (US); Matthew D. Cowperthwait, Cincinnati, OH (US); Jason L. Harris, Lebanon, OH (US); Kevin M. Fiebig, Cincinnati, OH (US); Eric B. LaFay, Madeira, OH (US); Jose Luis De Cordoba Matilla, Malaga (ES); Raymond E. Parfett, Loveland, OH (US); Curtis A. Maples, Cincinnati, OH (US); Sarah A. Worthington, Cincinnati, OH (US); Jacqueline C. Aronhalt, Loveland, OH (US)

(73) Assignee: CILAG CMBH INTERNATIONAL, Zug (CH)

( * ) Notice: Subject to any disclaimer, the term of this patent is extended or adjusted under 35 U.S.C. 154(b) by 882 days.

(21) Appl. No.: 17/957,917

(22) Filed: Sep. 30, 2022

(65) Prior Publication Data

US 2024/0108334 A1     Apr. 4, 2024

Related U.S. Application Data

(60) Provisional application No. 63/411,445, filed on Sep. 29, 2022.

(51) Int. Cl.
A61B 17/072     (2006.01)
A61B 17/068     (2006.01)
(Continued)

(52) U.S. Cl.
CPC ...... *A61B 17/07207* (2013.01); *A61B 17/068* (2013.01); *A61B 17/0684* (2013.01); *A61B 17/072* (2013.01); *A61B 17/320092* (2013.01); *A61B 18/1445* (2013.01); *A61B 34/30* (2016.02); *G16H 40/63* (2018.01);
(Continued)

(58) Field of Classification Search
CPC ........... A61B 2017/00075; A61B 2017/00132; A61B 17/07207; A61B 17/072; A61B 2090/065; A61B 2090/066
See application file for complete search history.

(56) References Cited

U.S. PATENT DOCUMENTS 5,403,312  A     4/1995   Yates et al.
5,817,084  A    10/1998   Jensen
(Continued)

OTHER PUBLICATIONS

IEEE Std 802.3-2012 (Revision of IEEE Std 802.3-2008, published Dec. 28, 2012.
(Continued)

*Primary Examiner* — Himchan Song
(74) *Attorney, Agent, or Firm* — Troutman Pepper Locke LLP

(57) ABSTRACT

Methods, devices, and systems for controlling a tissue-treatment motion by a surgical instrument are disclosed.

12 Claims, 141 Drawing Sheets

(51) Int. Cl.

| | |
|---|---|
| *A61B 17/32* | (2006.01) |
| *A61B 18/14* | (2006.01) |
| *A61B 34/30* | (2016.01) |
| *G16H 40/63* | (2018.01) |
| *H02K 7/116* | (2006.01) |
| *H02K 7/14* | (2006.01) |
| *A61B 17/00* | (2006.01) |
| *A61B 17/29* | (2006.01) |
| *A61B 18/00* | (2006.01) |
| *A61B 34/20* | (2016.01) |
| *A61B 90/00* | (2016.01) |

(52) U.S. Cl.

CPC ............. *H02K 7/116* (2013.01); *H02K 7/145* (2013.01); *A61B 2017/00017* (2013.01); *A61B 2017/00022* (2013.01); *A61B 2017/00039* (2013.01); *A61B 2017/00075* (2013.01); *A61B 2017/00132* (2013.01); *A61B 2017/00185* (2013.01); *A61B 2017/0019* (2013.01); *A61B 2017/00221* (2013.01); *A61B 2017/00398* (2013.01); *A61B 2017/07257* (2013.01); *A61B 2017/07271* (2013.01); *A61B 2017/07278* (2013.01); *A61B 2017/07285* (2013.01); *A61B 2017/2932* (2013.01); *A61B 2017/320074* (2017.08); *A61B 2018/00642* (2013.01); *A61B 2018/0072* (2013.01); *A61B 2034/2059* (2016.02); *A61B 2090/064* (2016.02)

(56) References Cited

U.S. PATENT DOCUMENTS

| | | | |
|---|---|---|---|
| 5,878,193 | A | 3/1999 | Wang et al. |
| 6,132,368 | A | 10/2000 | Cooper |
| 7,000,818 | B2 | 2/2006 | Shelton, IV et al. |
| 7,422,139 | B2 | 9/2008 | Shelton, IV et al. |
| 7,464,849 | B2 | 12/2008 | Shelton, IV et al. |
| 7,524,320 | B2 | 4/2009 | Tierney et al. |
| 7,670,334 | B2 | 3/2010 | Hueil et al. |
| 7,753,245 | B2 | 7/2010 | Boudreaux et al. |
| 7,845,537 | B2 | 12/2010 | Shelton, IV et al. |
| 7,980,443 | B2 | 7/2011 | Scheib et al. |
| 8,210,411 | B2 * | 7/2012 | Yates ................. A61B 17/3205 227/19 |
| 8,220,688 | B2 * | 7/2012 | Laurent ................ A61B 17/068 227/181.1 |
| 8,308,040 | B2 | 11/2012 | Huang et al. |
| 8,393,514 | B2 | 3/2013 | Shelton, IV et al. |
| 8,505,802 | B2 | 8/2013 | Viola et al. |
| 8,561,870 | B2 | 10/2013 | Baxter, III et al. |
| 8,608,045 | B2 | 12/2013 | Smith et al. |
| 8,685,004 | B2 * | 4/2014 | Zemlock .............. A61B 17/068 606/1 |
| 8,733,613 | B2 | 5/2014 | Huitema et al. |
| 9,016,540 | B2 * | 4/2015 | Whitman ............. A61B 17/072 227/176.1 |
| 9,050,083 | B2 * | 6/2015 | Yates ............... A61B 17/07207 |
| 9,072,535 | B2 * | 7/2015 | Shelton, IV ........... A61B 34/35 |
| 9,101,358 | B2 * | 8/2015 | Kerr ..................... A61B 17/068 |
| 9,345,481 | B2 | 5/2016 | Hall et al. |

| | | | |
|---|---|---|---|
| 9,804,618 | B2 * | 10/2017 | Leimbach ................. B25F 3/00 |
| 9,808,246 | B2 * | 11/2017 | Shelton, IV ......... A61B 17/068 |
| 9,913,642 | B2 * | 3/2018 | Leimbach ........... A61B 17/072 |
| 9,987,095 | B2 | 6/2018 | Chowaniec et al. |
| 9,999,472 | B2 | 6/2018 | Weir et al. |
| 10,159,483 | B2 | 12/2018 | Beckman et al. |
| 10,368,865 | B2 | 8/2019 | Harris et al. |
| 10,448,948 | B2 | 10/2019 | Shelton, IV et al. |
| 10,639,037 | B2 | 5/2020 | Shelton, IV et al. |
| 10,646,220 | B2 | 5/2020 | Shelton, IV et al. |
| 10,695,057 | B2 | 6/2020 | Shelton, IV et al. |
| 10,716,565 | B2 | 7/2020 | Shelton, IV et al. |
| 10,758,226 | B2 | 9/2020 | Weir et al. |
| 10,828,028 | B2 | 11/2020 | Harris et al. |
| 10,835,245 | B2 | 11/2020 | Swayze et al. |
| 10,842,523 | B2 | 11/2020 | Shelton, IV et al. |
| 10,881,399 | B2 | 1/2021 | Shelton, IV et al. |
| 10,888,321 | B2 | 1/2021 | Shelton, IV et al. |
| 10,973,519 | B2 | 4/2021 | Weir et al. |
| 11,324,501 | B2 | 5/2022 | Shelton, IV et al. |
| 11,369,366 | B2 | 6/2022 | Scheib et al. |
| 11,382,704 | B2 | 7/2022 | Overmyer et al. |
| 11,419,630 | B2 | 8/2022 | Yates et al. |
| 11,628,006 | B2 | 4/2023 | Henderson et al. |
| 2007/0175955 | A1 | 8/2007 | Shelton et al. |
| 2009/0289096 | A1 * | 11/2009 | Shelton, IV ..... A61B 17/07207 227/180.1 |
| 2011/0017801 | A1 * | 1/2011 | Zemlok ........... A61B 17/07207 227/175.1 |
| 2011/0022032 | A1 * | 1/2011 | Zemlok ........... A61B 17/07207 606/1 |
| 2012/0209314 | A1 * | 8/2012 | Weir ...................... A61B 90/08 606/205 |
| 2014/0263541 | A1 | 9/2014 | Leimbach et al. |
| 2014/0263552 | A1 * | 9/2014 | Hall ................... A61B 17/0686 227/176.1 |
| 2015/0209035 | A1 * | 7/2015 | Zemlok ........... A61B 17/07207 73/1.01 |
| 2015/0297225 | A1 * | 10/2015 | Huitema .............. A61B 17/105 227/176.1 |
| 2016/0256071 | A1 * | 9/2016 | Shelton, IV ......... A61B 17/068 |
| 2017/0079642 | A1 * | 3/2017 | Overmyer ................. H02P 6/14 |
| 2017/0296180 | A1 | 10/2017 | Harris et al. |
| 2018/0360471 | A1 | 12/2018 | Parfett et al. |
| 2019/0000447 | A1 * | 1/2019 | Shelton, IV ..... A61B 17/07292 |
| 2019/0183591 | A1 * | 6/2019 | Johnson ............... B25J 9/1666 |
| 2019/0200981 | A1 | 7/2019 | Harris et al. |
| 2019/0200986 | A1 * | 7/2019 | Shelton, IV ... A61B 17/320092 |
| 2019/0201027 | A1 | 7/2019 | Shelton, IV et al. |
| 2019/0201146 | A1 * | 7/2019 | Shelton, IV ..... A61B 17/07207 |
| 2019/0314015 | A1 * | 10/2019 | Shelton, IV ........... A61B 90/03 |
| 2020/0281592 | A1 * | 9/2020 | Adams ................ A61B 17/1114 |
| 2020/0345356 | A1 | 11/2020 | Leimbach et al. |
| 2020/0405311 | A1 * | 12/2020 | Shelton, IV ..... G06K 19/07758 |
| 2020/0405313 | A1 * | 12/2020 | Shelton, IV ......... A61B 17/072 |
| 2021/0059773 | A1 * | 3/2021 | Overmyer ............. A61B 17/29 |
| 2021/0244407 | A1 | 8/2021 | Shelton, IV et al. |

OTHER PUBLICATIONS

"ATM-MPLS Network Interworking Version 2.0, af-aic-0178.001" ATM Standard, The ATM Forum Technical Committee, published Aug. 2003.

* cited by examiner

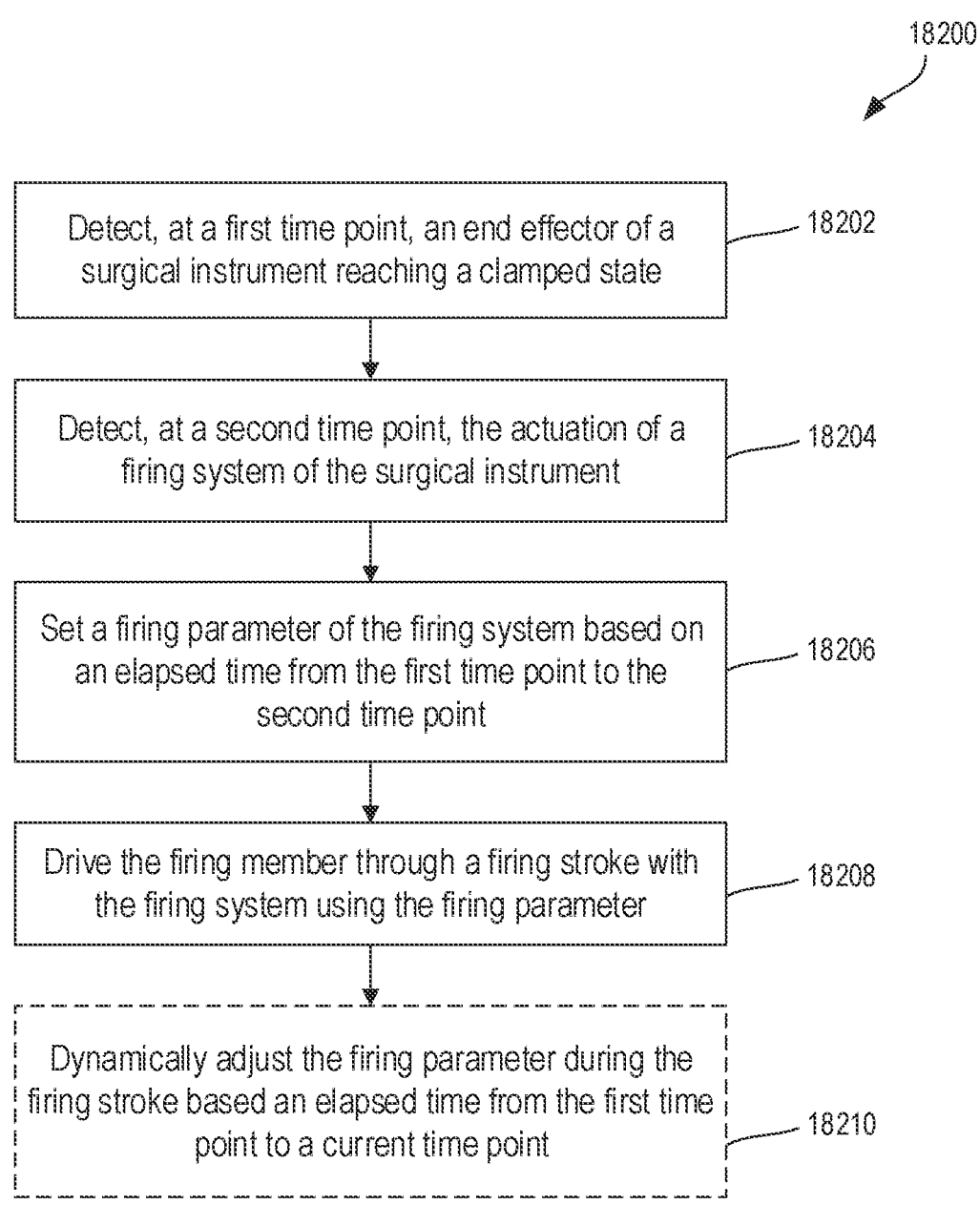

18200

Detect, at a first time point, an end effector of a
surgical instrument reaching a clamped state — 18202

Detect, at a second time point, the actuation of a
firing system of the surgical instrument — 18204

Set a firing parameter of the firing system based on
an elapsed time from the first time point to the
second time point — 18206

Drive the firing member through a firing stroke with
the firing system using the firing parameter — 18208

Dynamically adjust the firing parameter during the
firing stroke based an elapsed time from the first time
point to a current time point — 18210

FIG. 17

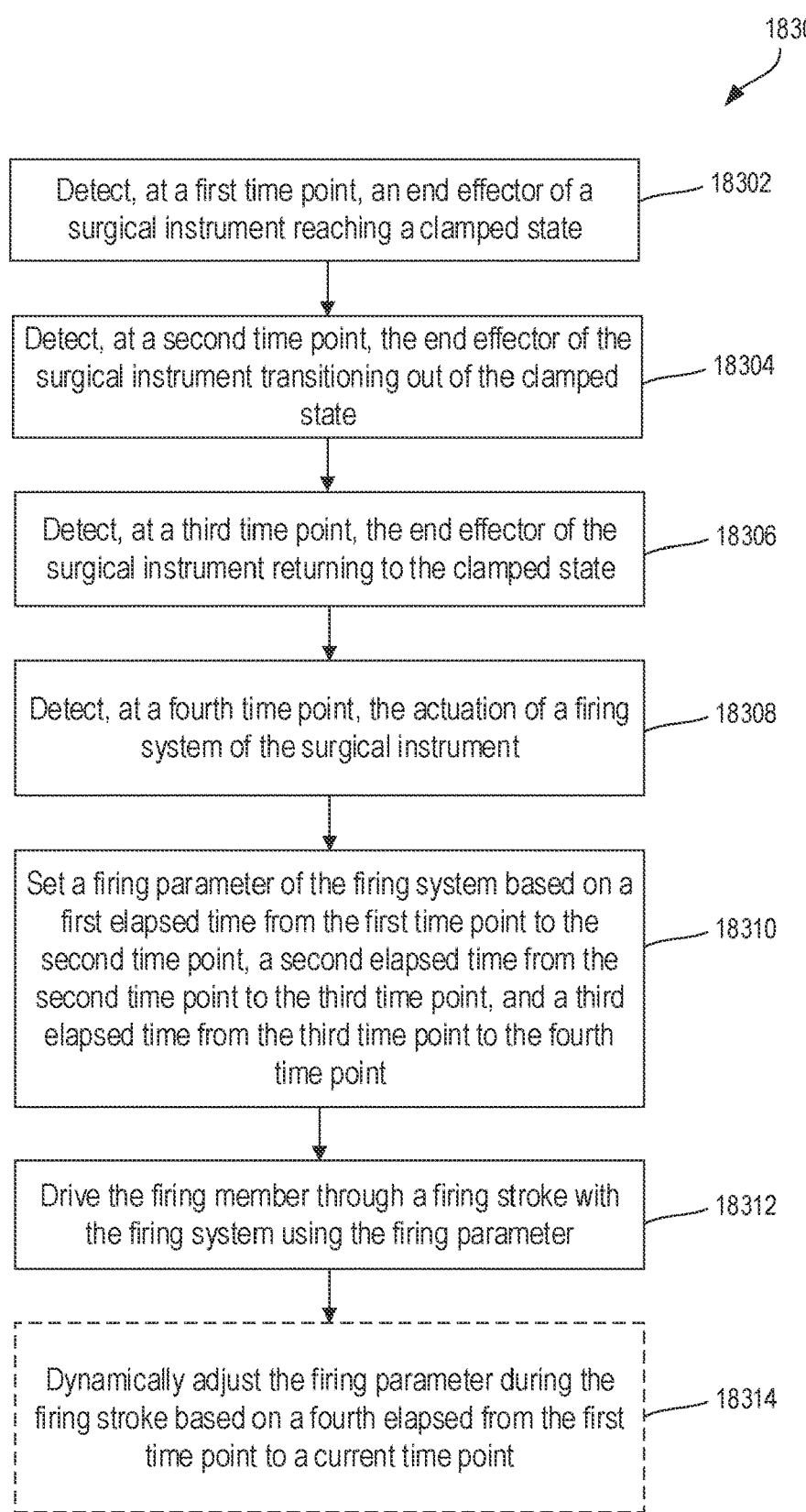

18300

Detect, at a first time point, an end effector of a surgical instrument reaching a clamped state — 18302

Detect, at a second time point, the end effector of the surgical instrument transitioning out of the clamped state — 18304

Detect, at a third time point, the end effector of the surgical instrument returning to the clamped state — 18306

Detect, at a fourth time point, the actuation of a firing system of the surgical instrument — 18308

Set a firing parameter of the firing system based on a first elapsed time from the first time point to the second time point, a second elapsed time from the second time point to the third time point, and a third elapsed time from the third time point to the fourth time point — 18310

Drive the firing member through a firing stroke with the firing system using the firing parameter — 18312

Dynamically adjust the firing parameter during the firing stroke based on a fourth elapsed from the first time point to a current time point — 18314

FIG. 19

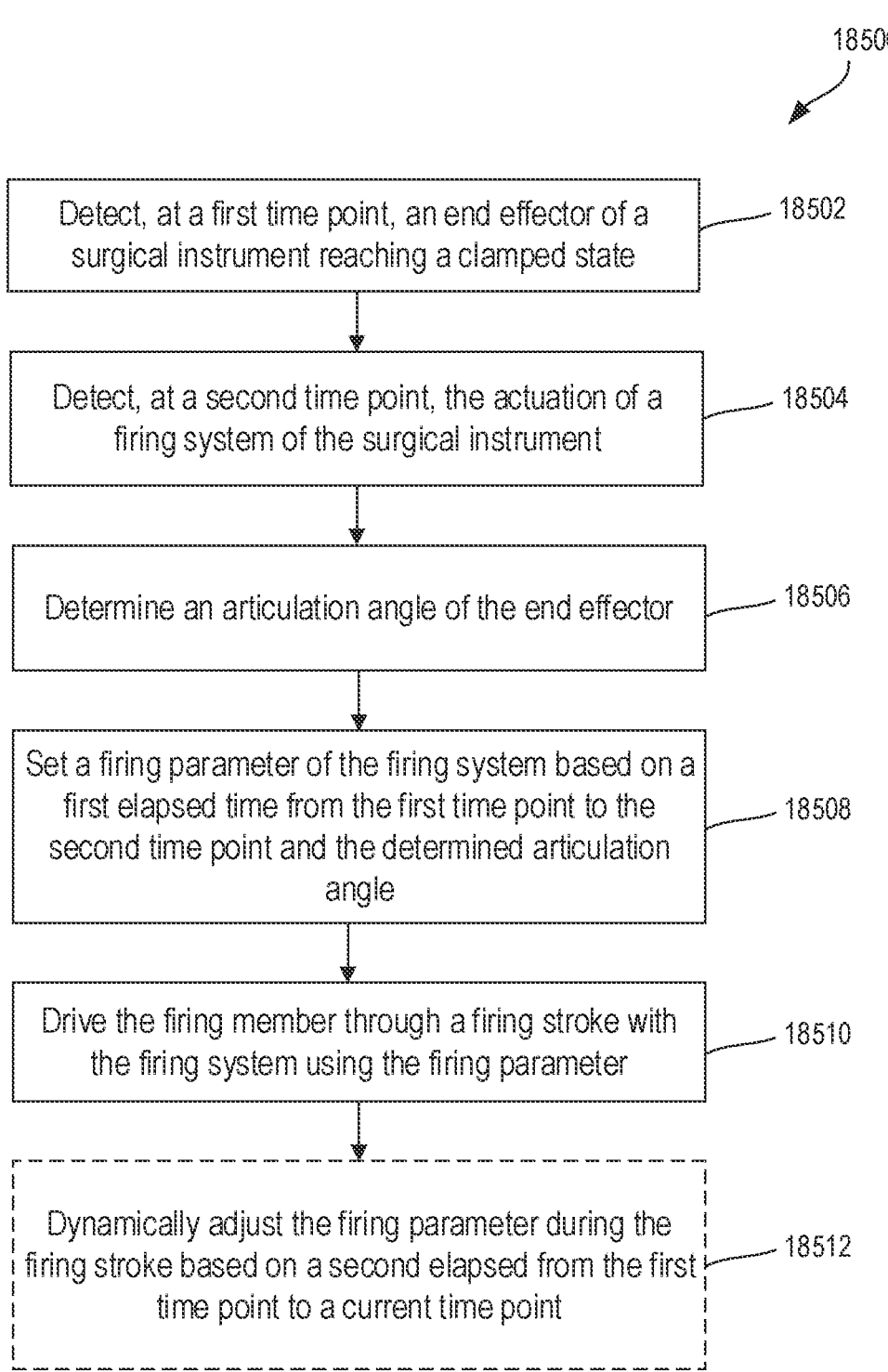

18500

Detect, at a first time point, an end effector of a surgical instrument reaching a clamped state — 18502

Detect, at a second time point, the actuation of a firing system of the surgical instrument — 18504

Determine an articulation angle of the end effector — 18506

Set a firing parameter of the firing system based on a first elapsed time from the first time point to the second time point and the determined articulation angle — 18508

Drive the firing member through a firing stroke with the firing system using the firing parameter — 18510

Dynamically adjust the firing parameter during the firing stroke based on a second elapsed from the first time point to a current time point — 18512

FIG. 23

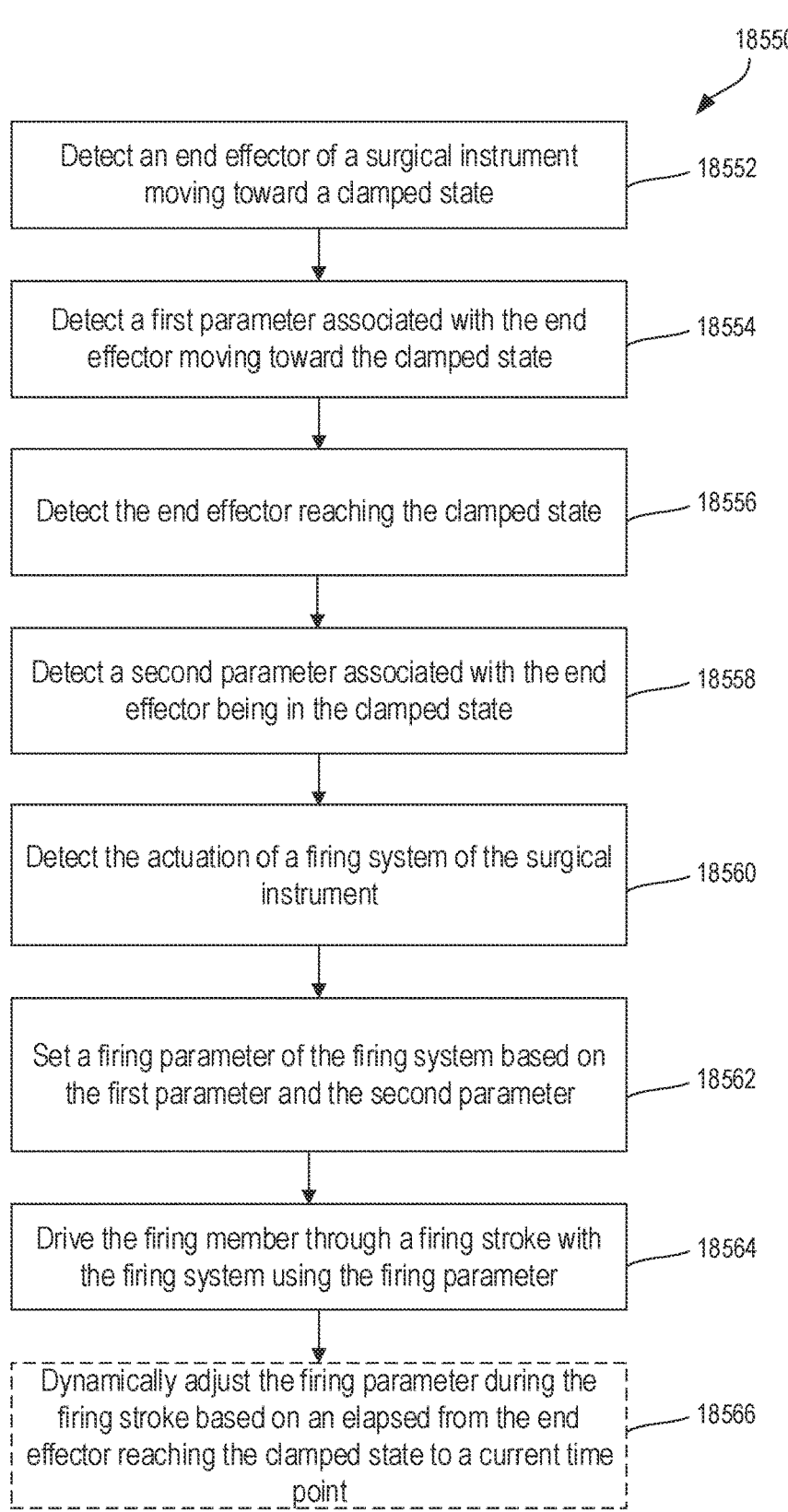

18550

Detect an end effector of a surgical instrument moving toward a clamped state — 18552

Detect a first parameter associated with the end effector moving toward the clamped state — 18554

Detect the end effector reaching the clamped state — 18556

Detect a second parameter associated with the end effector being in the clamped state — 18558

Detect the actuation of a firing system of the surgical instrument — 18560

Set a firing parameter of the firing system based on the first parameter and the second parameter — 18562

Drive the firing member through a firing stroke with the firing system using the firing parameter — 18564

Dynamically adjust the firing parameter during the firing stroke based on an elapsed from the end effector reaching the clamped state to a current time point — 18566

FIG. 24

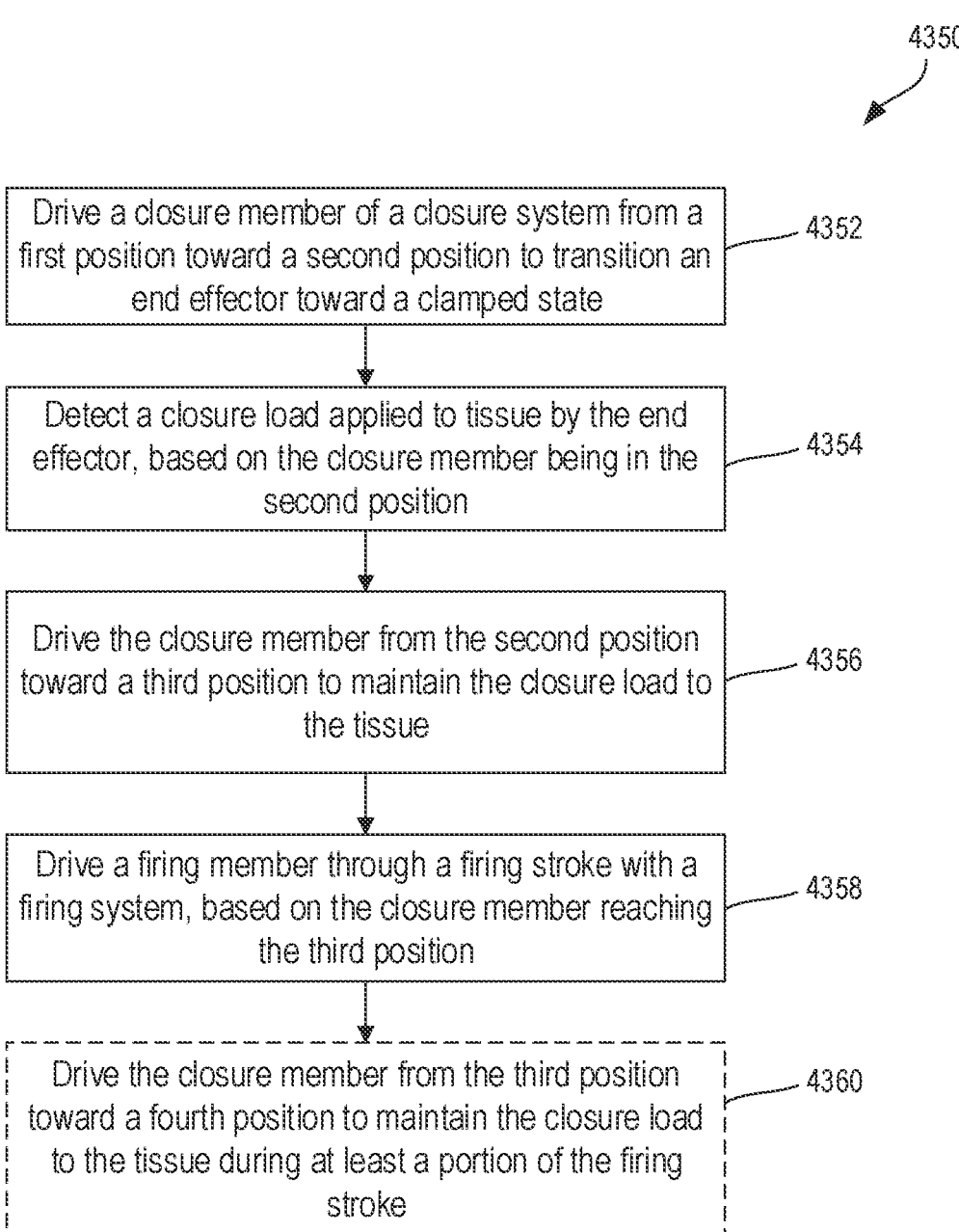

4350

Drive a closure member of a closure system from a first position toward a second position to transition an end effector toward a clamped state — 4352

Detect a closure load applied to tissue by the end effector, based on the closure member being in the second position — 4354

Drive the closure member from the second position toward a third position to maintain the closure load to the tissue — 4356

Drive a firing member through a firing stroke with a firing system, based on the closure member reaching the third position — 4358

Drive the closure member from the third position toward a fourth position to maintain the closure load to the tissue during at least a portion of the firing stroke — 4360

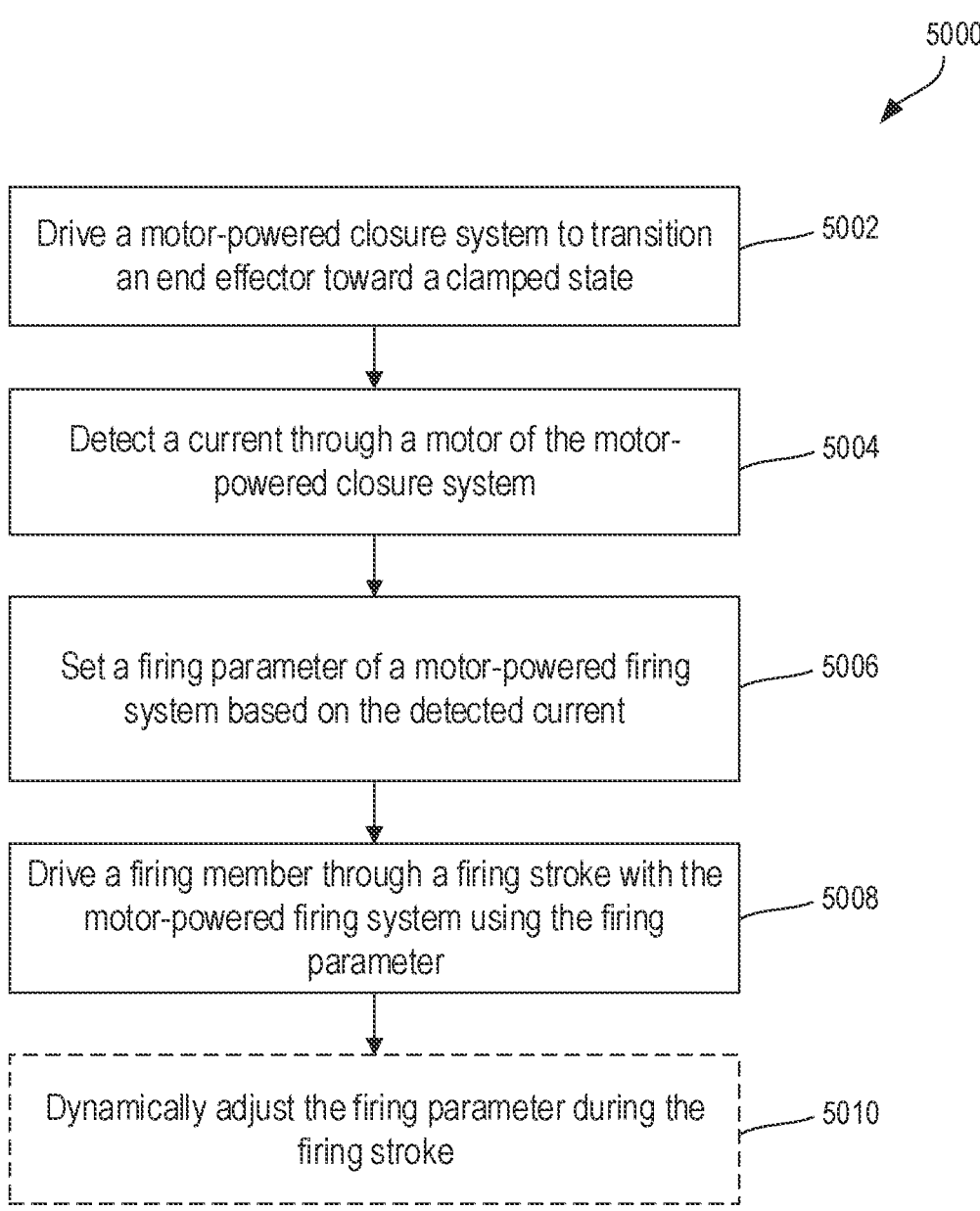

5000

Drive a motor-powered closure system to transition an end effector toward a clamped state — 5002

Detect a current through a motor of the motor-powered closure system — 5004

Set a firing parameter of a motor-powered firing system based on the detected current — 5006

Drive a firing member through a firing stroke with the motor-powered firing system using the firing parameter — 5008

Dynamically adjust the firing parameter during the firing stroke — 5010

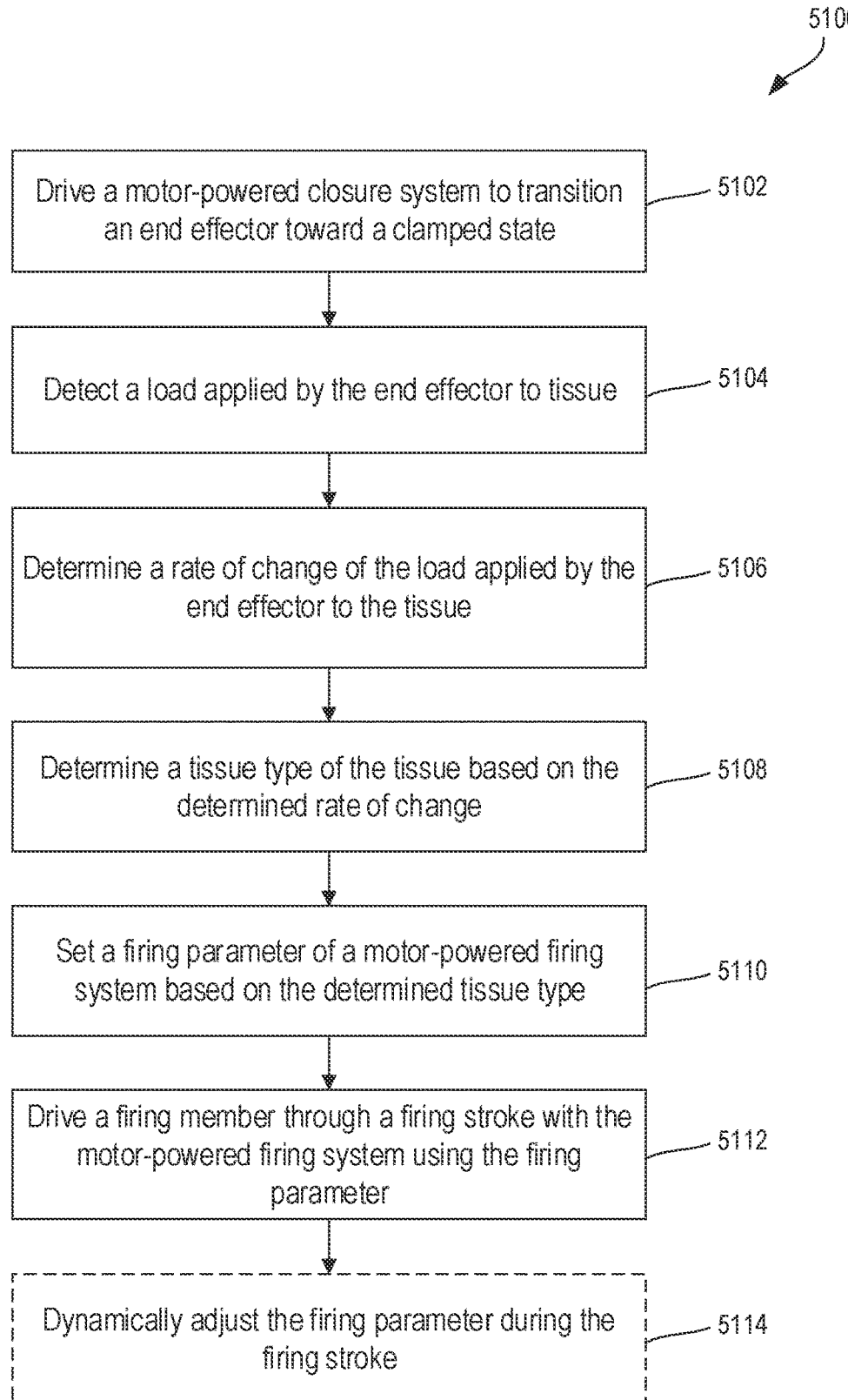

Drive a motor-powered closure system to transition an end effector toward a clamped state — 5102

Detect a load applied by the end effector to tissue — 5104

Determine a rate of change of the load applied by the end effector to the tissue — 5106

Determine a tissue type of the tissue based on the determined rate of change — 5108

Set a firing parameter of a motor-powered firing system based on the determined tissue type — 5110

Drive a firing member through a firing stroke with the motor-powered firing system using the firing parameter — 5112

Dynamically adjust the firing parameter during the firing stroke — 5114

FIG. 46

| Cartridge Color | Tissue Category | Tissue Type | Tissue Thickness |
|---|---|---|---|
| Color A | Minimum / Indicated | Type A | $t_1$ |
| Color A | Maximum / Design | Type B | $t_2$ |
| Color A | Overstress | Type B | $t_3$ |
| Color B | Minimum / Indicated | Type C | $t_4$ |
| Color B | Maximum / Design | Type C | $t_5$ |
| Color B | Overstress | Type C | $t_6$ |
| Color C | Minimum / Indicated | Type C | $t_7$ |
| Color C | Maximum / Design | Type C | $t_8$ |
| Color C | Overstress | Type C | $t_9$ |
| Color D | Minimum / Indicated | Type C | $t_{10}$ |
| Color D | Maximum / Design | Type C | $t_{11}$ |
| Color D | Overstress | Type C | $t_{12}$ |
| Color E | Minimum / Indicated | Type C | $t_{13}$ |
| Color E | Maximum / Design | Type C | $t_{14}$ |
| Color E | Overstress | Type C | $t_{15}$ |

Drive a firing member from an unfired position toward a fired position with a firing system — 6302

Detect a force to fire the firing member toward the fired position — 6304

Predict a future force to fire the firing member, based on the detected force to fire — 6306

Adjust a firing algorithm of the firing system, based on the prediction — 6308

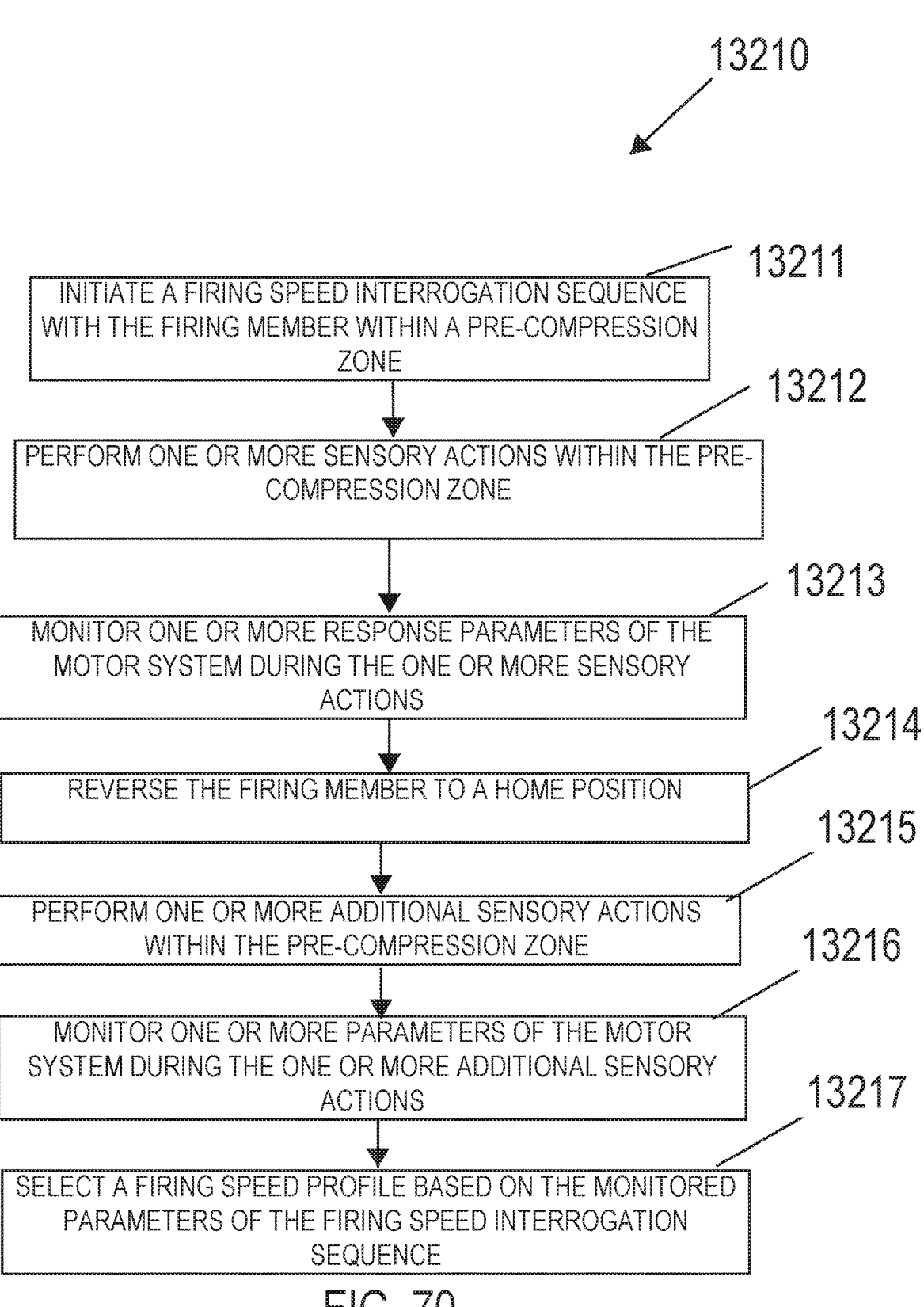

13210

13211

INITIATE A FIRING SPEED INTERROGATION SEQUENCE WITH THE FIRING MEMBER WITHIN A PRE-COMPRESSION ZONE

13212

PERFORM ONE OR MORE SENSORY ACTIONS WITHIN THE PRE-COMPRESSION ZONE

13213

MONITOR ONE OR MORE RESPONSE PARAMETERS OF THE MOTOR SYSTEM DURING THE ONE OR MORE SENSORY ACTIONS

13214

REVERSE THE FIRING MEMBER TO A HOME POSITION

13215

PERFORM ONE OR MORE ADDITIONAL SENSORY ACTIONS WITHIN THE PRE-COMPRESSION ZONE

13216

MONITOR ONE OR MORE PARAMETERS OF THE MOTOR SYSTEM DURING THE ONE OR MORE ADDITIONAL SENSORY ACTIONS

13217

SELECT A FIRING SPEED PROFILE BASED ON THE MONITORED PARAMETERS OF THE FIRING SPEED INTERROGATION SEQUENCE

Sensory Actions for Increasing Firing Speed, PWM steps that are not audible to the user ---------- Target
————— Achieved

| Clamp | Pre-Fire (Pause) | Fire |

Closure Load (lb)

$T_{fc}$ $T_{pc}$ $T_{cp}$

Closure Stroke (in)

Force To Fire (lbf)

13093  13091

Velocity I-beam (mm/s)

$V_2$  13096

$V_0$  $t_1$  $t_2$  $t_3$  13092

$t_0$  13095

PWM (%)

$PWM_0$  $t_3$ $t_1$  $t_2$  13097  13094

$t_0$  $t_4$

Time

16010

16011
PERFORM A FIRST SENSORY ACTION

16012
MONITOR A RESULT OF THE FIRST SENSORY ACTION

16013
ADJUST A PARAMETER OF A SUBSEQUENT SENSORY ACTION
BASED ON THE MONITORED RESULT OF THE FIRST SENSORY
ACTION

16014
PERFORM THE SUBSEQUENT SENSORY ACTION WITH
THE ADJUSTED PARAMETER

Figure 83:
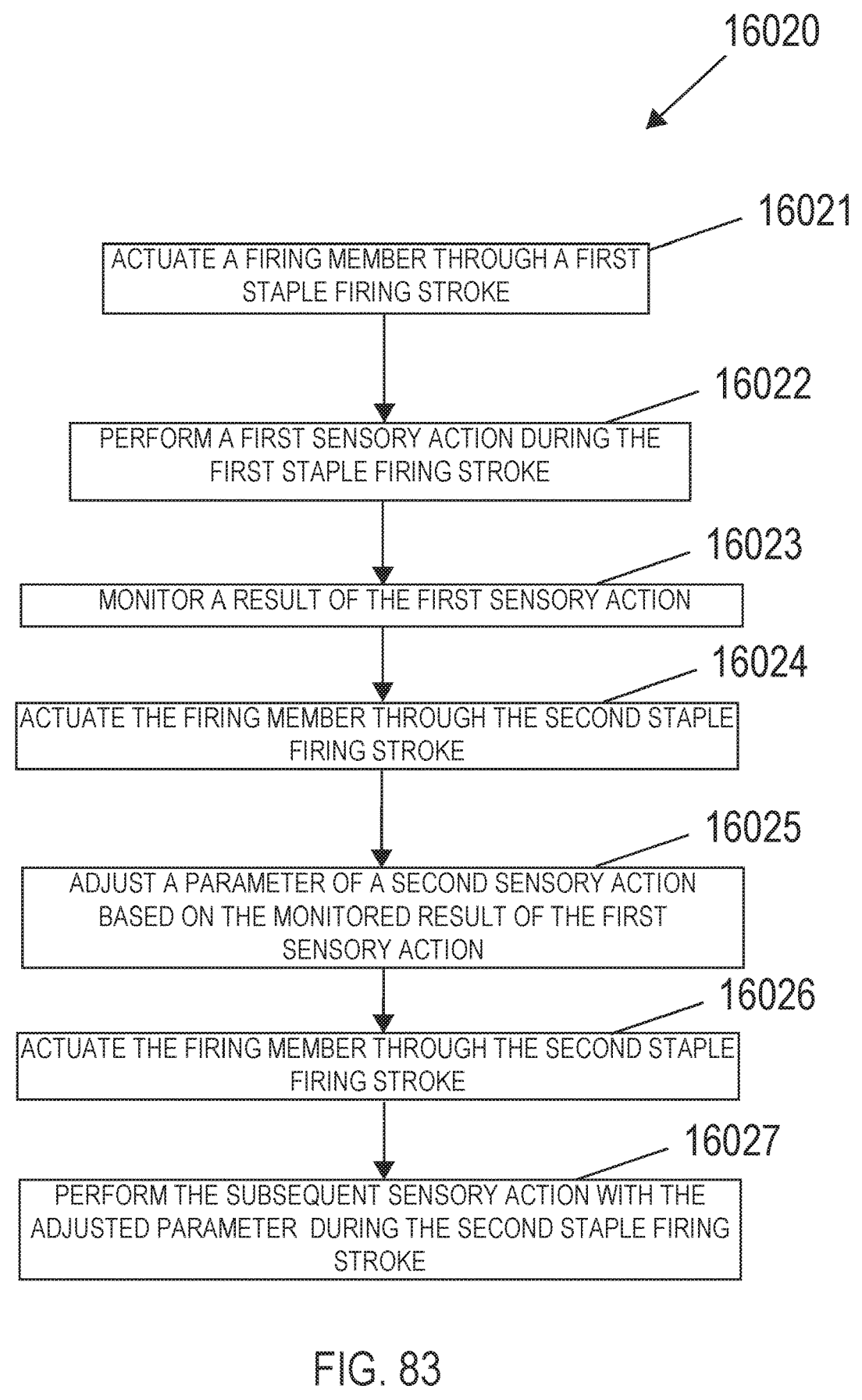

16020

16021

ACTUATE A FIRING MEMBER THROUGH A FIRST STAPLE FIRING STROKE

16022

PERFORM A FIRST SENSORY ACTION DURING THE FIRST STAPLE FIRING STROKE

16023

MONITOR A RESULT OF THE FIRST SENSORY ACTION

16024

ACTUATE THE FIRING MEMBER THROUGH THE SECOND STAPLE FIRING STROKE

16025

ADJUST A PARAMETER OF A SECOND SENSORY ACTION BASED ON THE MONITORED RESULT OF THE FIRST SENSORY ACTION

16026

ACTUATE THE FIRING MEMBER THROUGH THE SECOND STAPLE FIRING STROKE

16027

PERFORM THE SUBSEQUENT SENSORY ACTION WITH THE ADJUSTED PARAMETER DURING THE SECOND STAPLE FIRING STROKE

Figure 101:
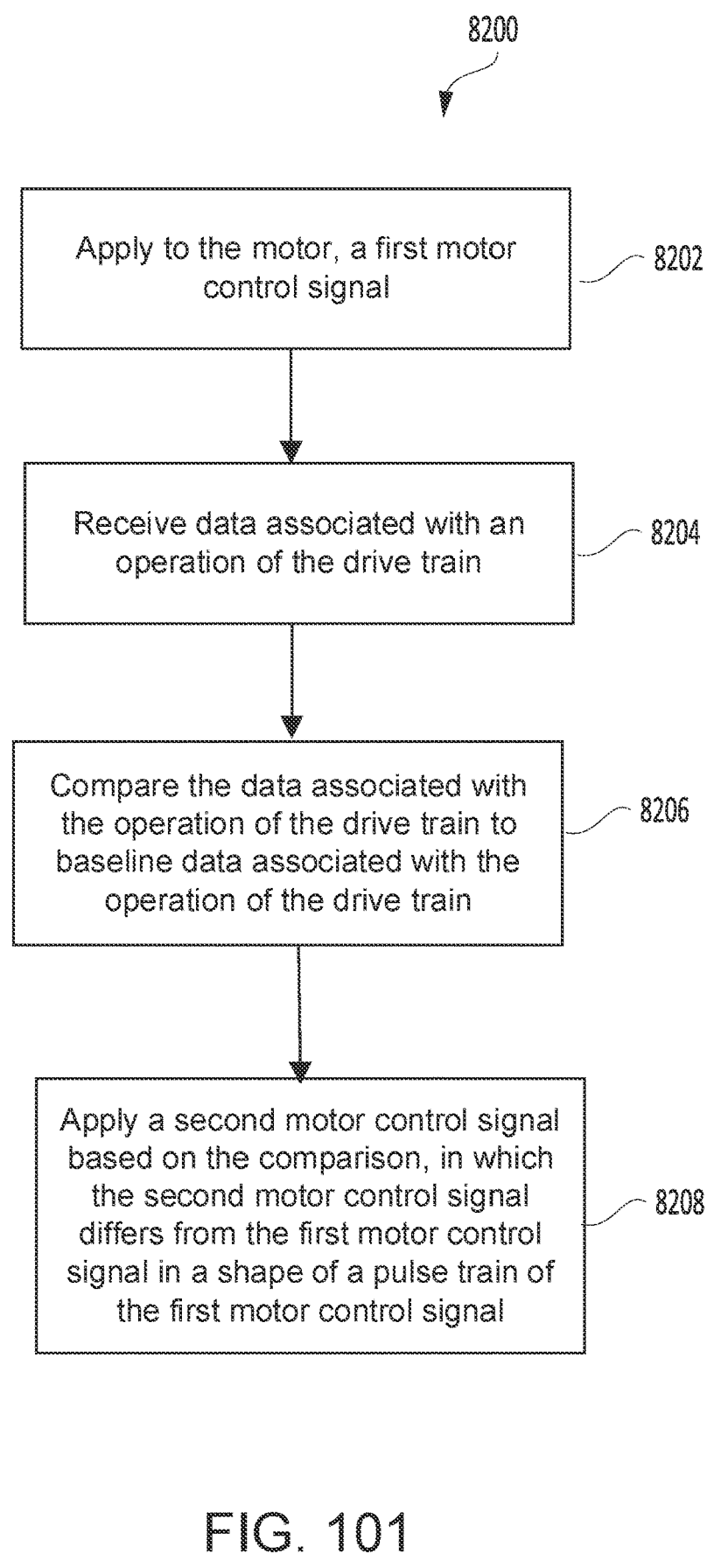

Apply to the motor, a first motor control signal    8202

Receive data associated with an operation of the drive train    8204

Compare the data associated with the operation of the drive train to baseline data associated with the operation of the drive train    8206

Apply a second motor control signal based on the comparison, in which the second motor control signal differs from the first motor control signal in a shape of a pulse train of the first motor control signal    8208

Transmit a motor perturbation signal to the motor — 8502

Receive one or more motor function parameters — 8504

Determine one or more automated surgical stapler system characteristics based on the one or more motor function parameters — 8506

Adjust one or more functions of the motor controller — 8508

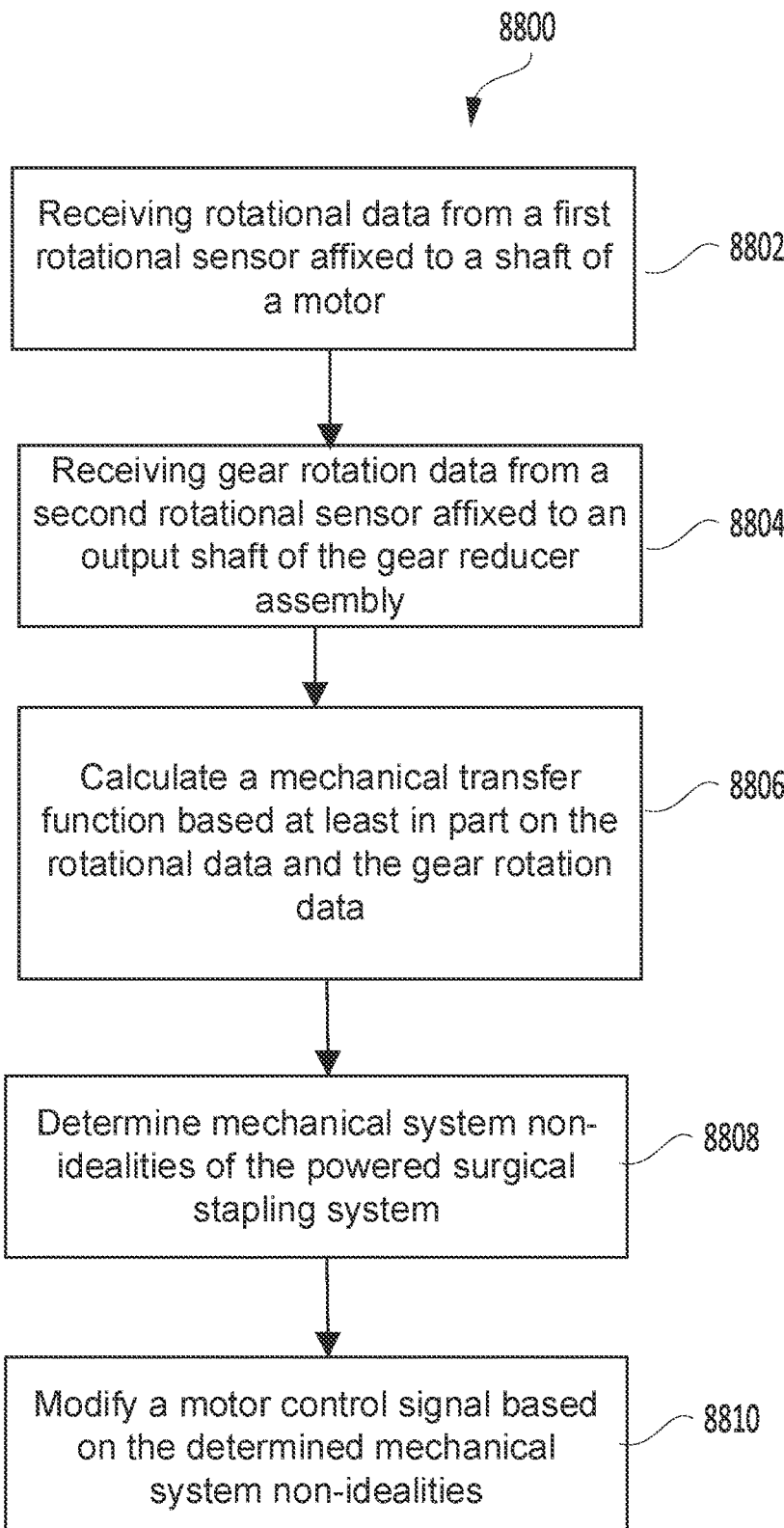

8800

Receiving rotational data from a first rotational sensor affixed to a shaft of a motor — 8802

Receiving gear rotation data from a second rotational sensor affixed to an output shaft of the gear reducer assembly — 8804

Calculate a mechanical transfer function based at least in part on the rotational data and the gear rotation data — 8806

Determine mechanical system non-idealities of the powered surgical stapling system — 8808

Modify a motor control signal based on the determined mechanical system non-idealities — 8810

Control a pulse-width modulated motor control signal to the motor — 10022

Receive data related to an interaction between the tissue cutting blade and a tissue clamped by the anvil — 10024

Adjust a frequency of the pulse-width modulated motor control signal based on the interaction between the tissue cutting blade and the tissue clamped by the anvil — 10026

11010

11012

17000

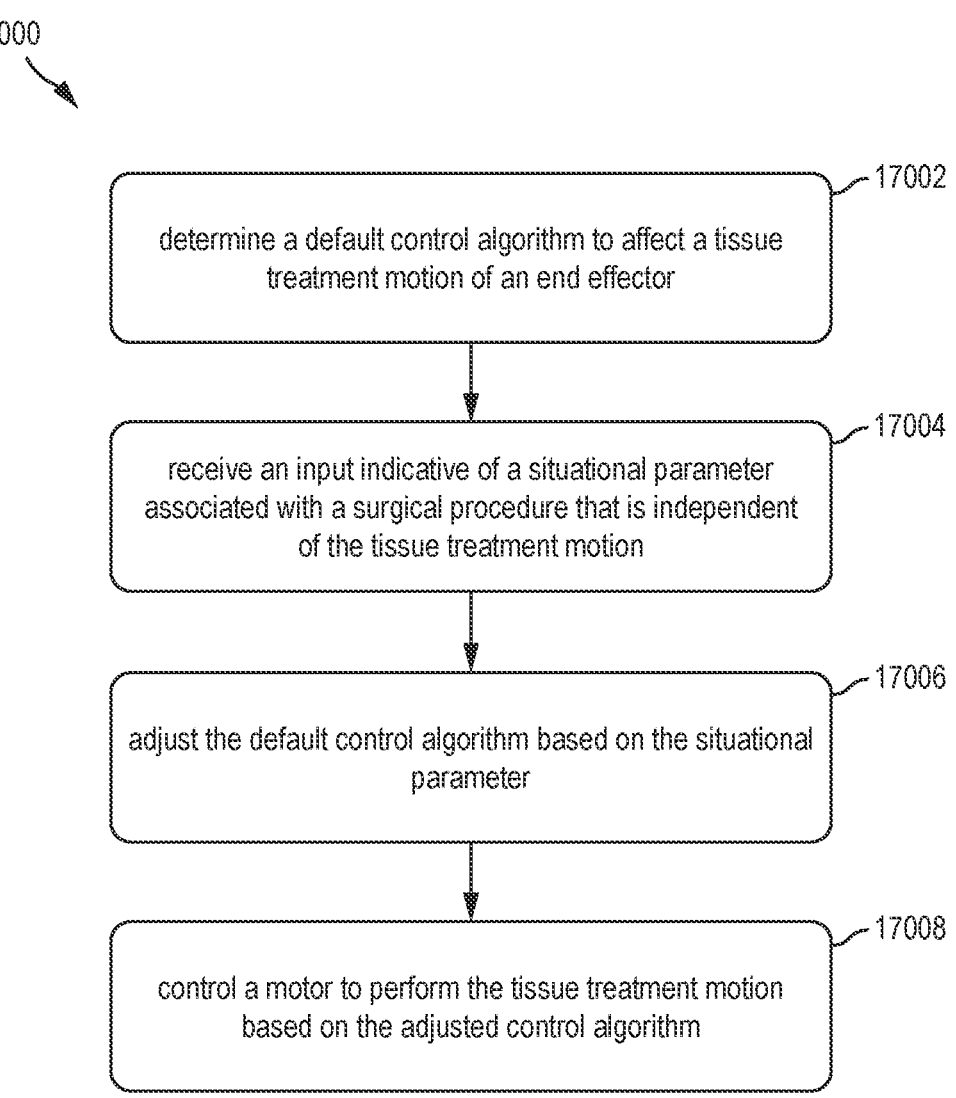

17002 determine a default control algorithm to affect a tissue treatment motion of an end effector

17004 receive an input indicative of a situational parameter associated with a surgical procedure that is independent of the tissue treatment motion

17006 adjust the default control algorithm based on the situational parameter

17008 control a motor to perform the tissue treatment motion based on the adjusted control algorithm

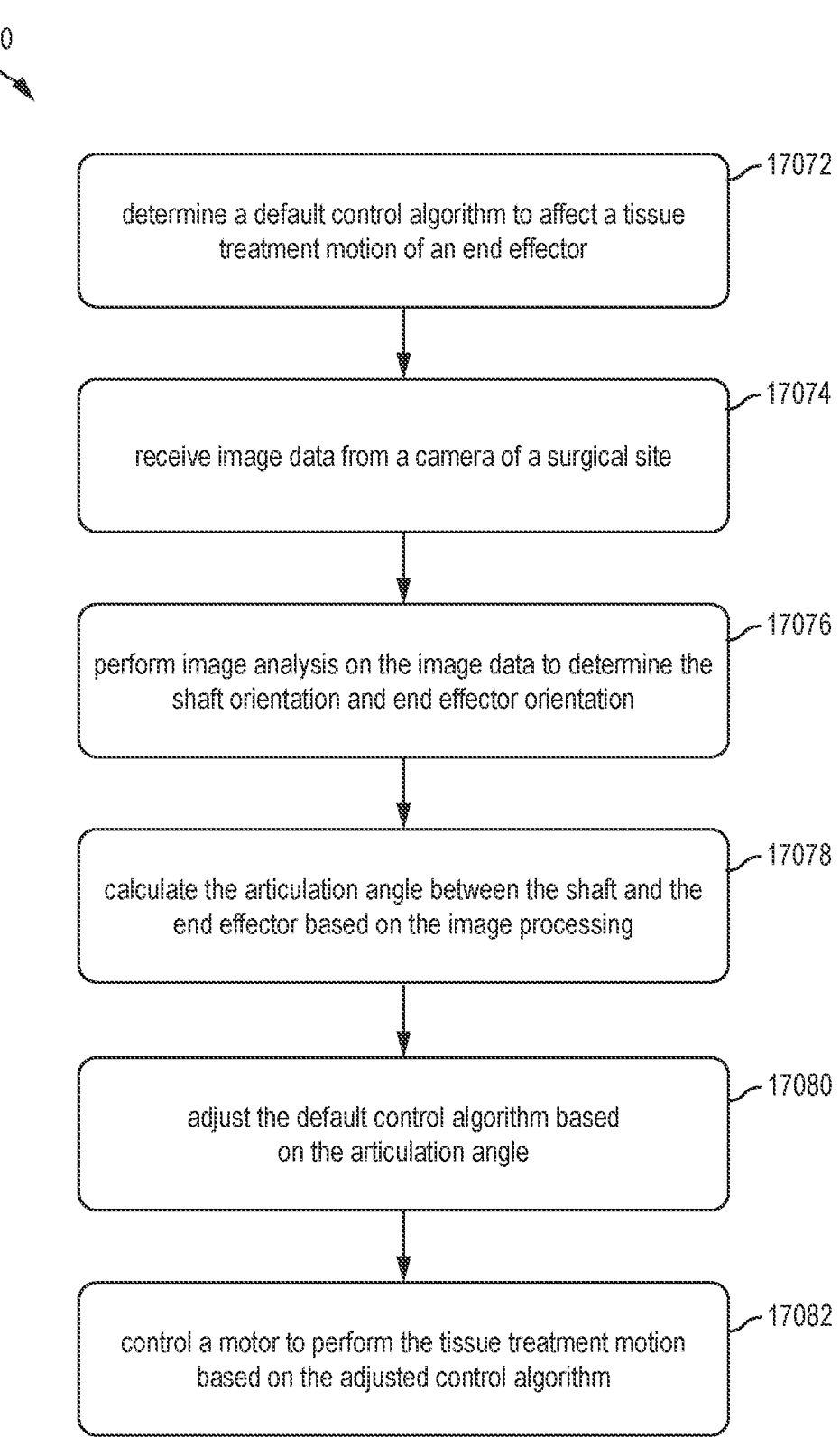

17072 determine a default control algorithm to affect a tissue
treatment motion of an end effector

17074 receive image data from a camera of a surgical site

17076 perform image analysis on the image data to determine the
shaft orientation and end effector orientation

17078 calculate the articulation angle between the shaft and the
end effector based on the image processing

17080 adjust the default control algorithm based
on the articulation angle

17082 control a motor to perform the tissue treatment motion
based on the adjusted control algorithm

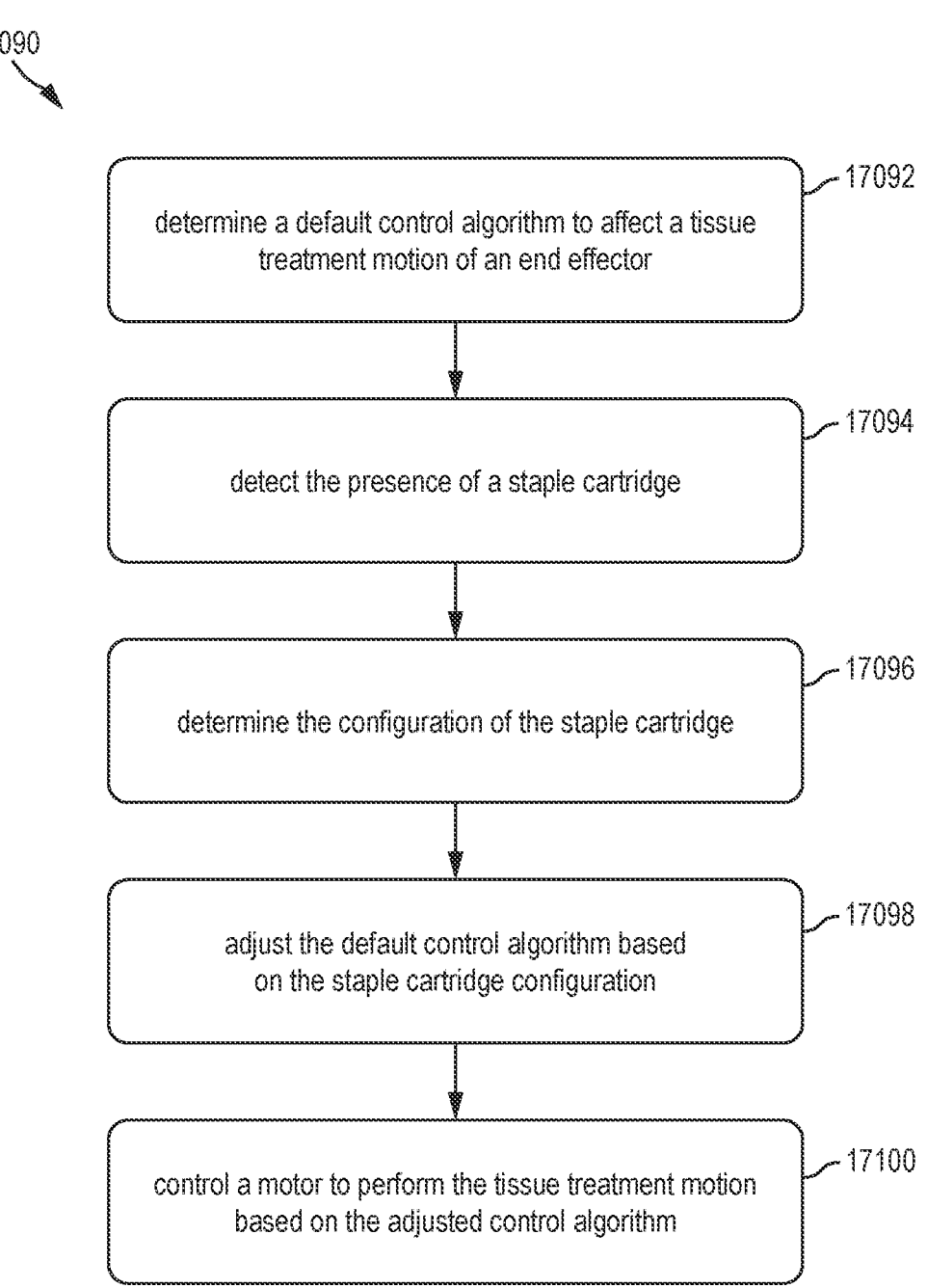

17090

17092 determine a default control algorithm to affect a tissue
treatment motion of an end effector

17094 detect the presence of a staple cartridge

17096 determine the configuration of the staple cartridge

17098 adjust the default control algorithm based
on the staple cartridge configuration

17100 control a motor to perform the tissue treatment motion
based on the adjusted control algorithm

17112 determine a default control algorithm to affect a tissue treatment motion of an end effector

17114 detect the presence of a buttress

17116 determine the configuration of the buttress

17118 adjust the default control algorithm based on the buttress configuration

17120 control a motor to perform the tissue treatment motion based on the adjusted control algorithm

17130

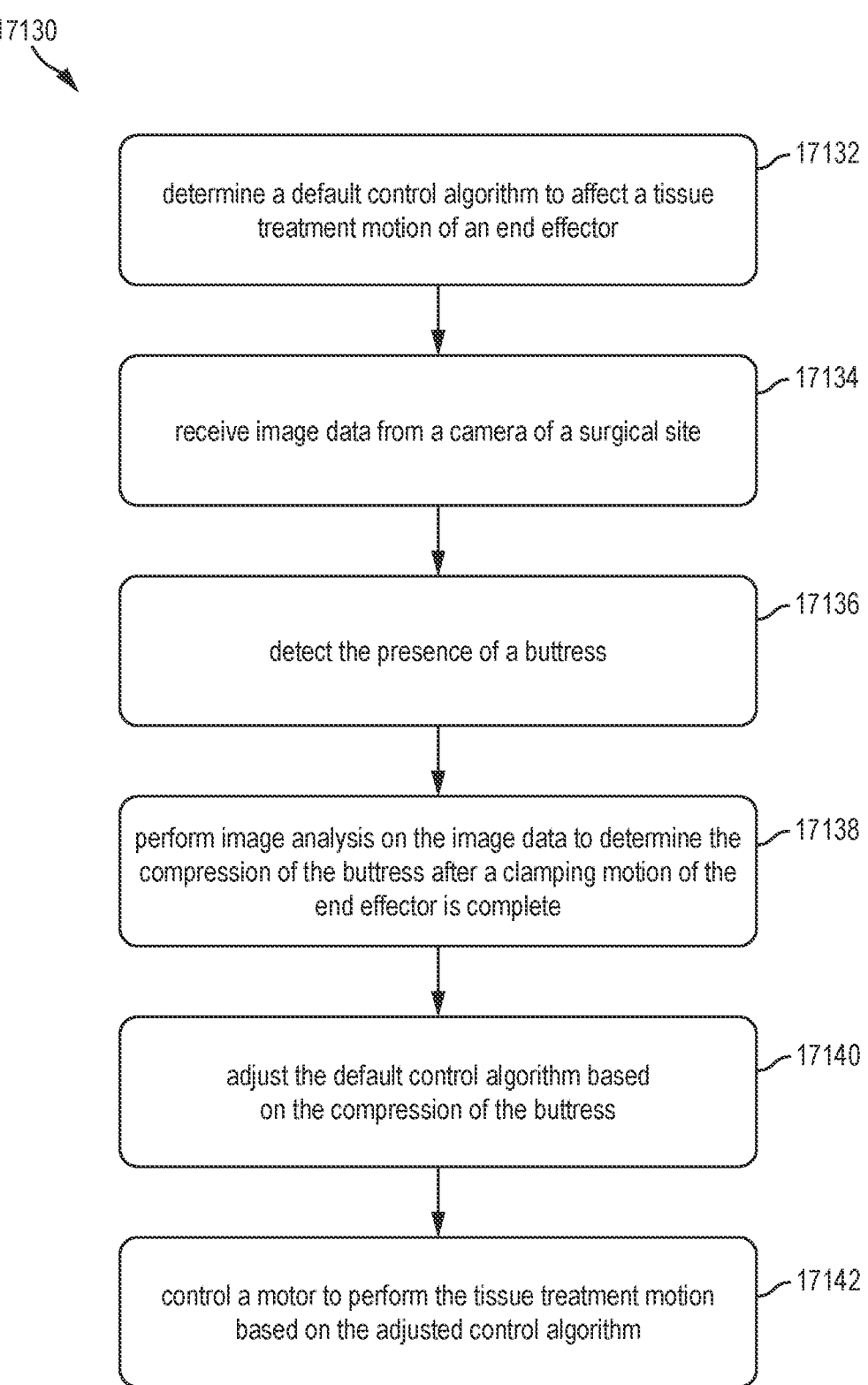

determine a default control algorithm to affect a tissue treatment motion of an end effector ⎯ 17132 receive image data from a camera of a surgical site ⎯ 17134 detect the presence of a buttress ⎯ 17136 perform image analysis on the image data to determine the compression of the buttress after a clamping motion of the end effector is complete ⎯ 17138 adjust the default control algorithm based on the compression of the buttress ⎯ 17140 control a motor to perform the tissue treatment motion based on the adjusted control algorithm ⎯ 17142

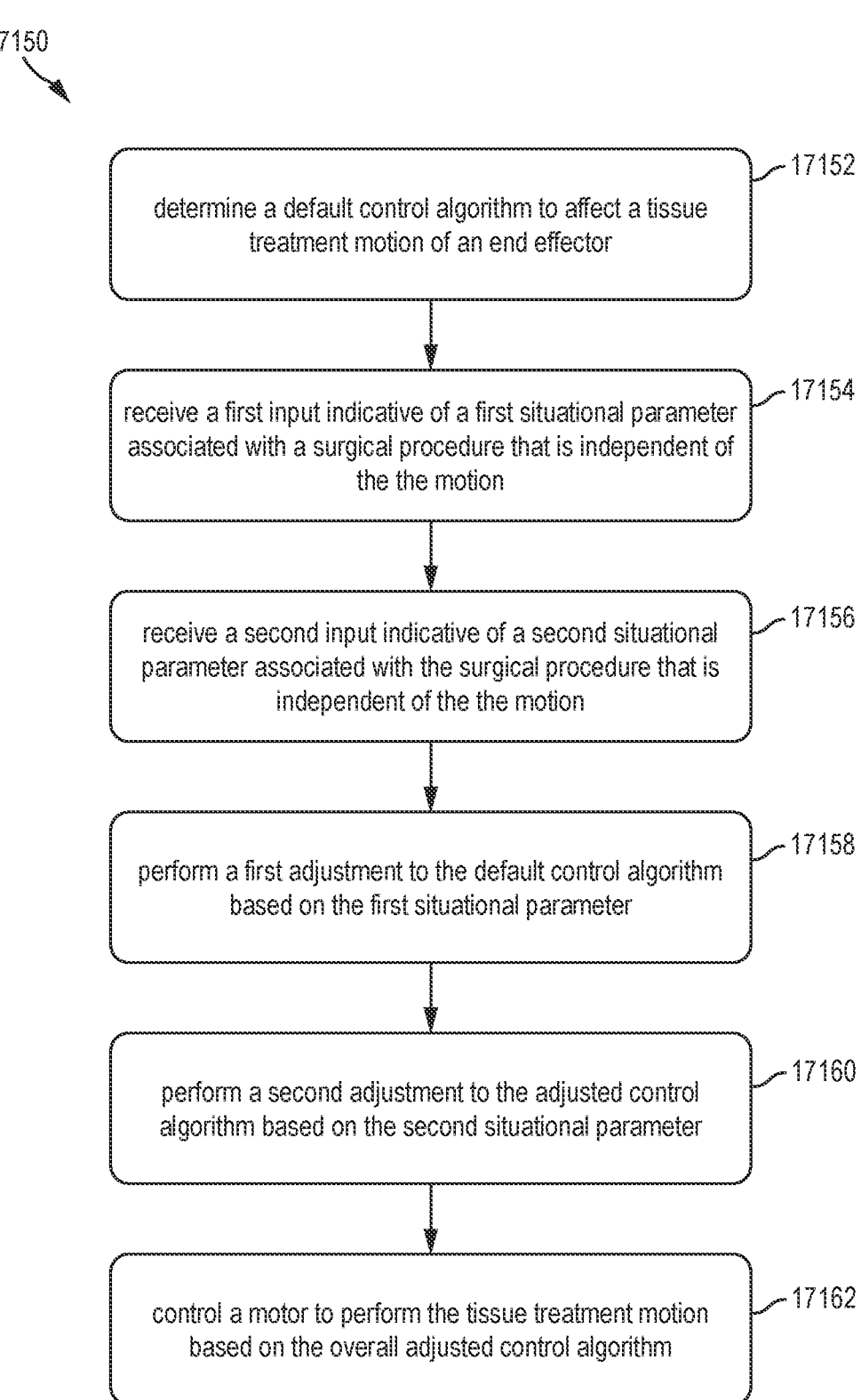

determine a default control algorithm to affect a tissue
treatment motion of an end effector — 17152 receive a first input indicative of a first situational parameter
associated with a surgical procedure that is independent of
the the motion — 17154 receive a second input indicative of a second situational
parameter associated with the surgical procedure that is
independent of the the motion — 17156 perform a first adjustment to the default control algorithm
based on the first situational parameter — 17158 perform a second adjustment to the adjusted control
algorithm based on the second situational parameter — 17160 control a motor to perform the tissue treatment motion
based on the overall adjusted control algorithm — 17162

FIG. 128

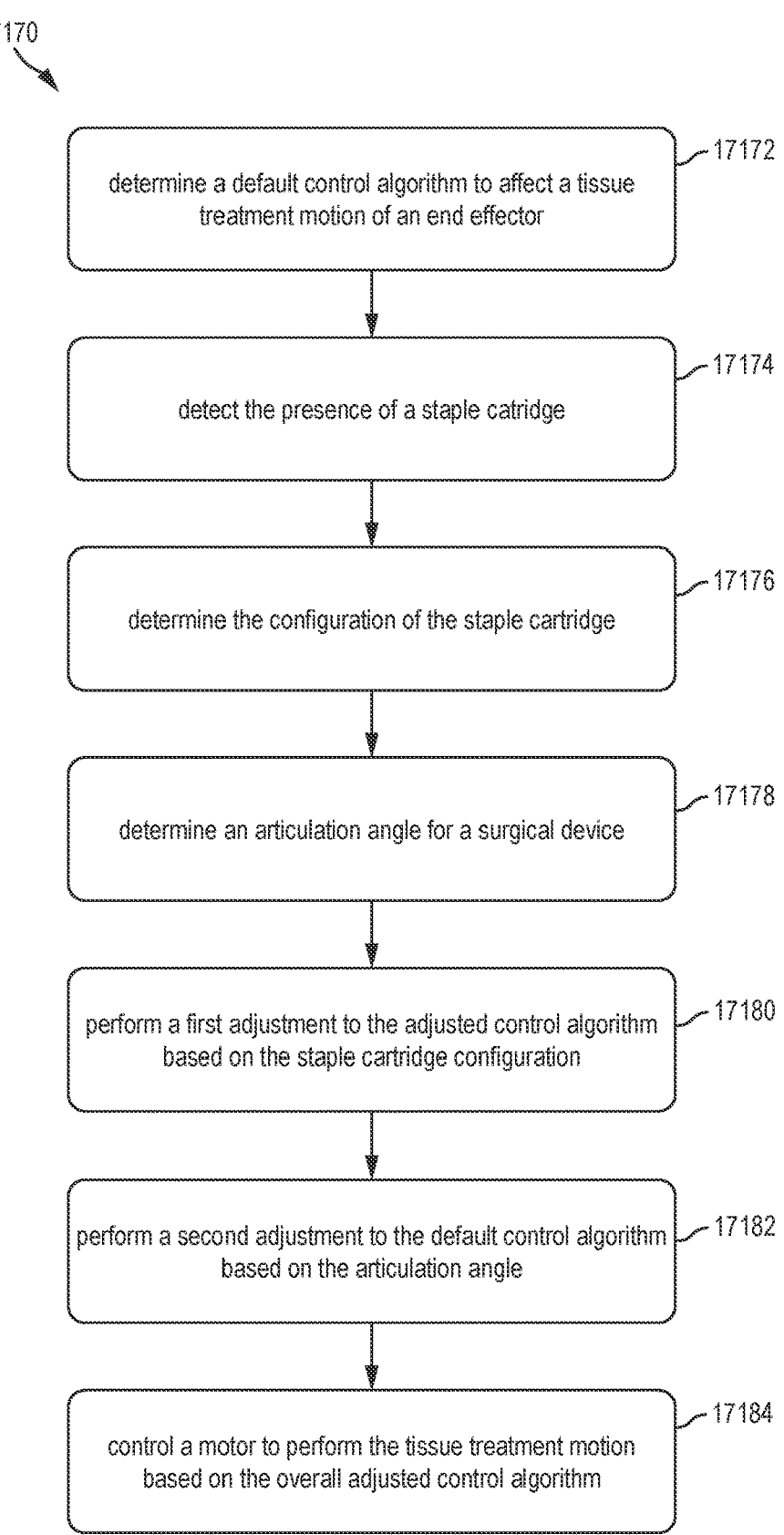

17170 determine a default control algorithm to affect a tissue treatment motion of an end effector — 17172 detect the presence of a staple catridge — 17174 determine the configuration of the staple cartridge — 17176 determine an articulation angle for a surgical device — 17178 perform a first adjustment to the adjusted control algorithm based on the staple cartridge configuration — 17180 perform a second adjustment to the default control algorithm based on the articulation angle — 17182 control a motor to perform the tissue treatment motion based on the overall adjusted control algorithm — 17184

FIG. 129

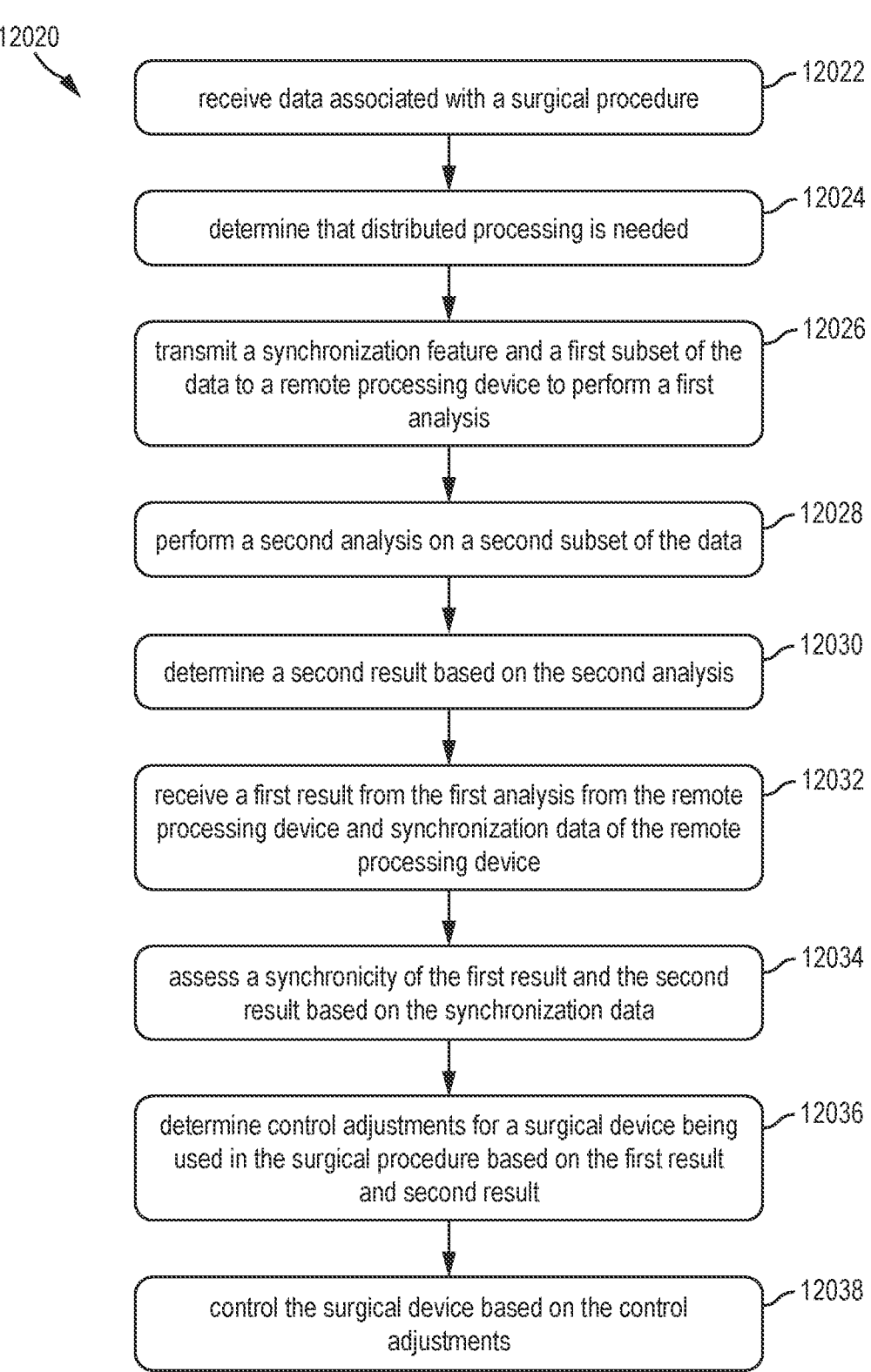

12020

12022 — receive data associated with a surgical procedure

12024 — determine that distributed processing is needed

12026 — transmit a synchronization feature and a first subset of the data to a remote processing device to perform a first analysis 12028 — perform a second analysis on a second subset of the data 12030 — determine a second result based on the second analysis 12032 — receive a first result from the first analysis from the remote processing device and synchronization data of the remote processing device 12034 — assess a synchronicity of the first result and the second result based on the synchronization data 12036 — determine control adjustments for a surgical device being used in the surgical procedure based on the first result and second result 12038 — control the surgical device based on the control adjustments

FIG. 134

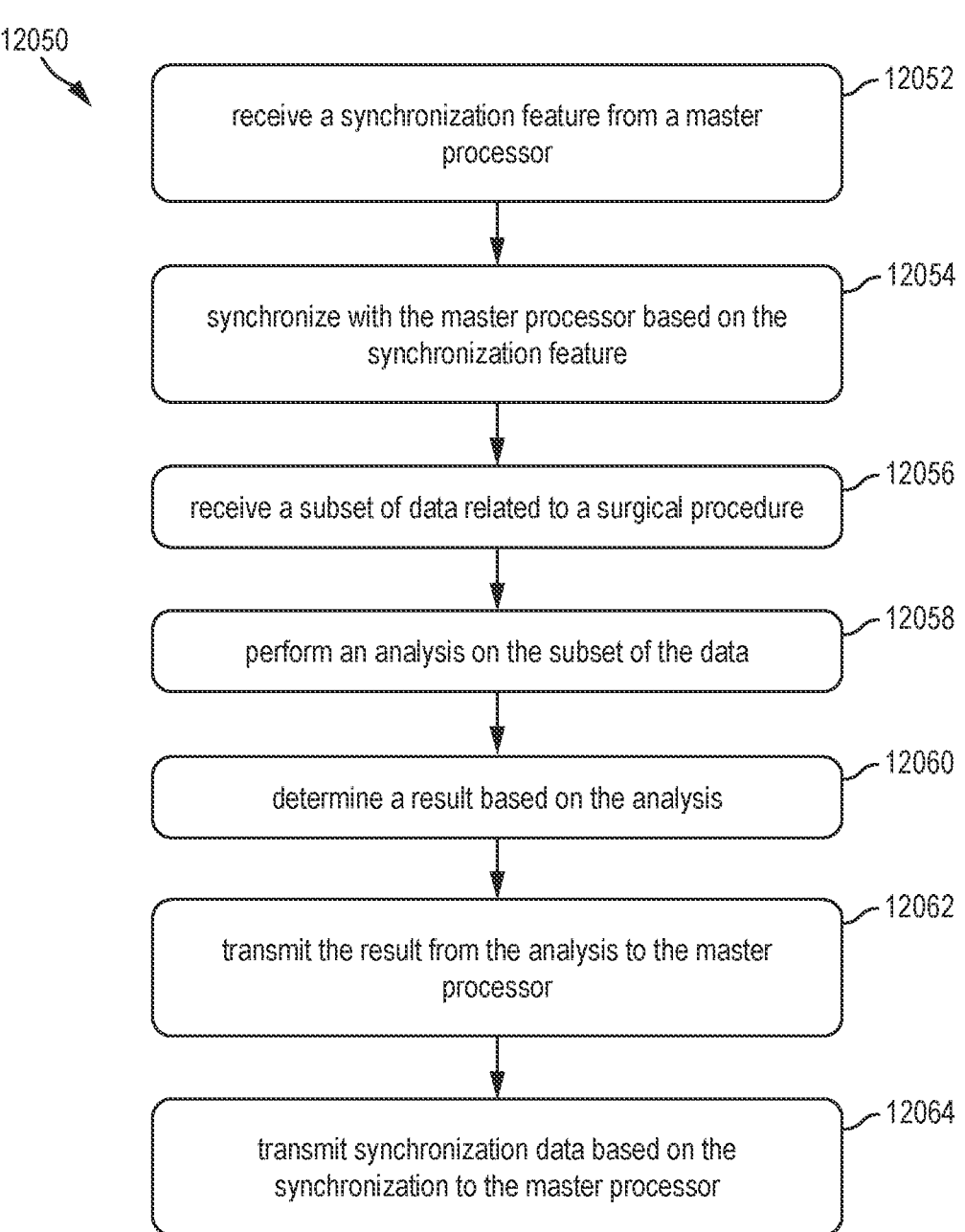

12050 receive a synchronization feature from a master processor — 12052 synchronize with the master processor based on the synchronization feature — 12054 receive a subset of data related to a surgical procedure — 12056 perform an analysis on the subset of the data — 12058 determine a result based on the analysis — 12060 transmit the result from the analysis to the master processor — 12062 transmit synchronization data based on the synchronization to the master processor — 12064

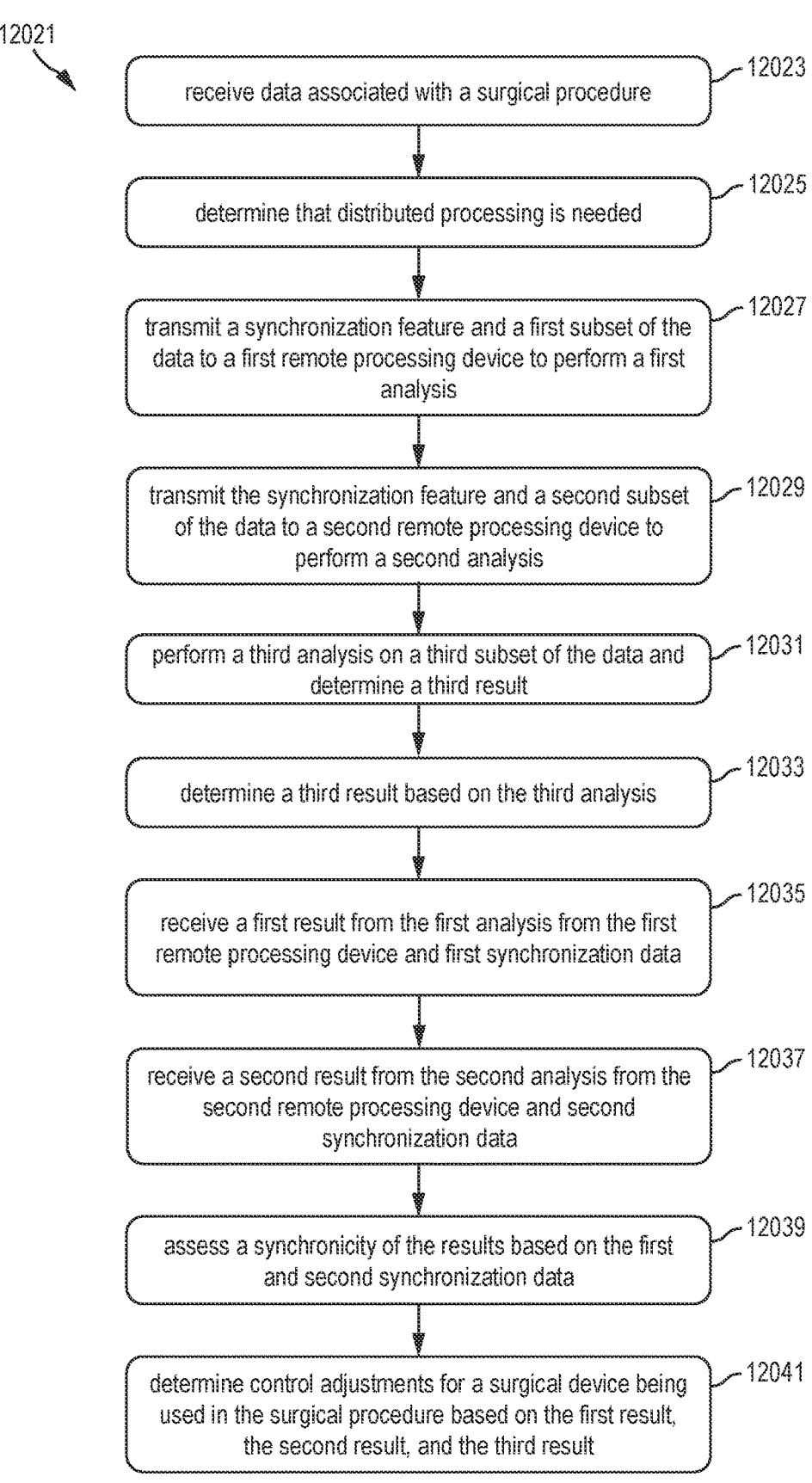

12023 — receive data associated with a surgical procedure

12025 — determine that distributed processing is needed

12027 — transmit a synchronization feature and a first subset of the data to a first remote processing device to perform a first analysis 12029 — transmit the synchronization feature and a second subset of the data to a second remote processing device to perform a second analysis 12031 — perform a third analysis on a third subset of the data and determine a third result 12033 — determine a third result based on the third analysis 12035 — receive a first result from the first analysis from the first remote processing device and first synchronization data 12037 — receive a second result from the second analysis from the second remote processing device and second synchronization data 12039 — assess a synchronicity of the results based on the first and second synchronization data 12041 — determine control adjustments for a surgical device being used in the surgical procedure based on the first result, the second result, and the third result

FIG. 136

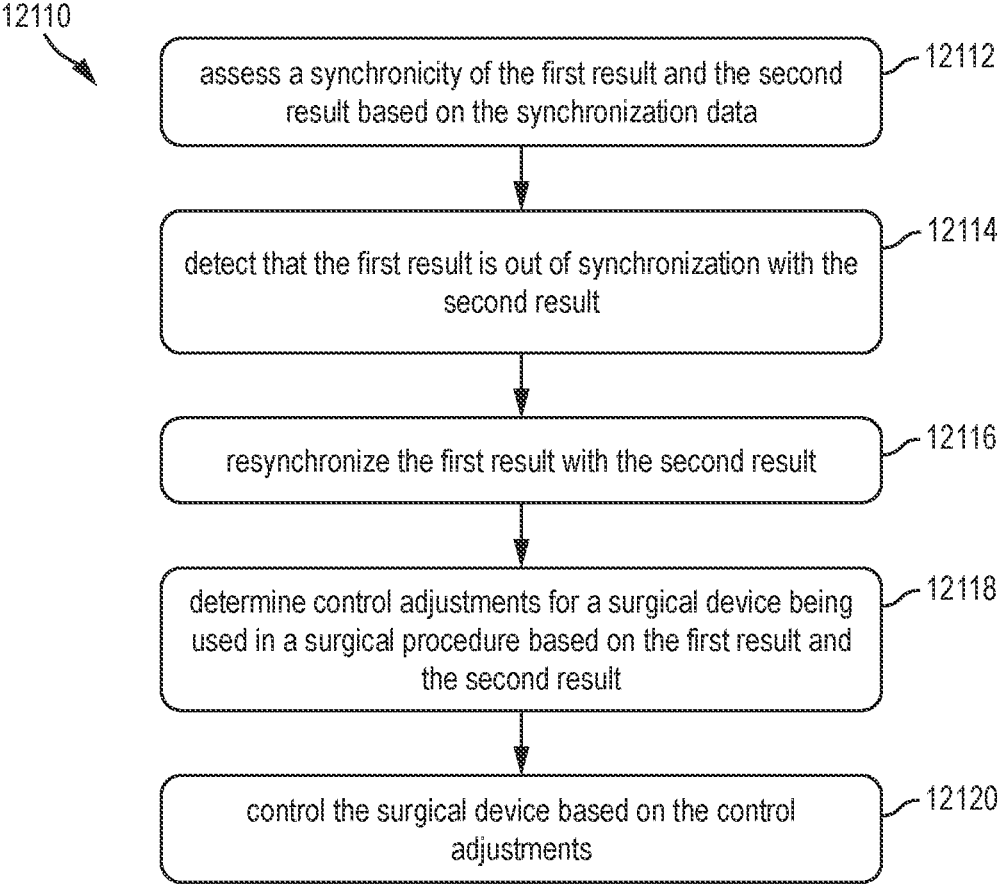

12110 assess a synchronicity of the first result and the second result based on the synchronization data — 12112 detect that the first result is out of synchronization with the second result — 12114 resynchronize the first result with the second result — 12116 determine control adjustments for a surgical device being used in a surgical procedure based on the first result and the second result — 12118 control the surgical device based on the control adjustments — 12120

FIG. 139

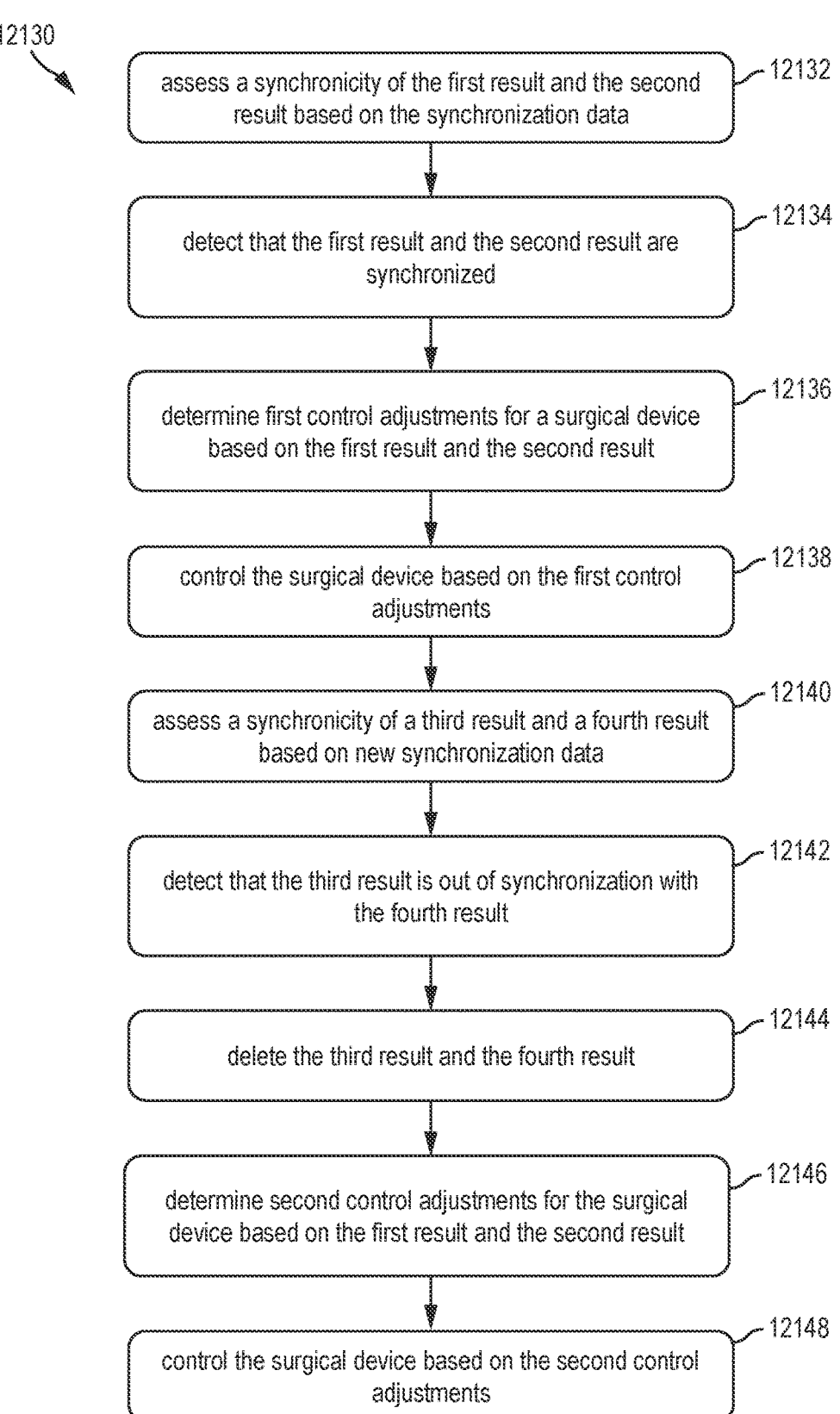

12130 assess a synchronicity of the first result and the second result based on the synchronization data — 12132 detect that the first result and the second result are synchronized — 12134 determine first control adjustments for a surgical device based on the first result and the second result — 12136 control the surgical device based on the first control adjustments — 12138 assess a synchronicity of a third result and a fourth result based on new synchronization data — 12140 detect that the third result is out of synchronization with the fourth result — 12142 delete the third result and the fourth result — 12144 determine second control adjustments for the surgical device based on the first result and the second result — 12146 control the surgical device based on the second control adjustments — 12148

FIG. 140

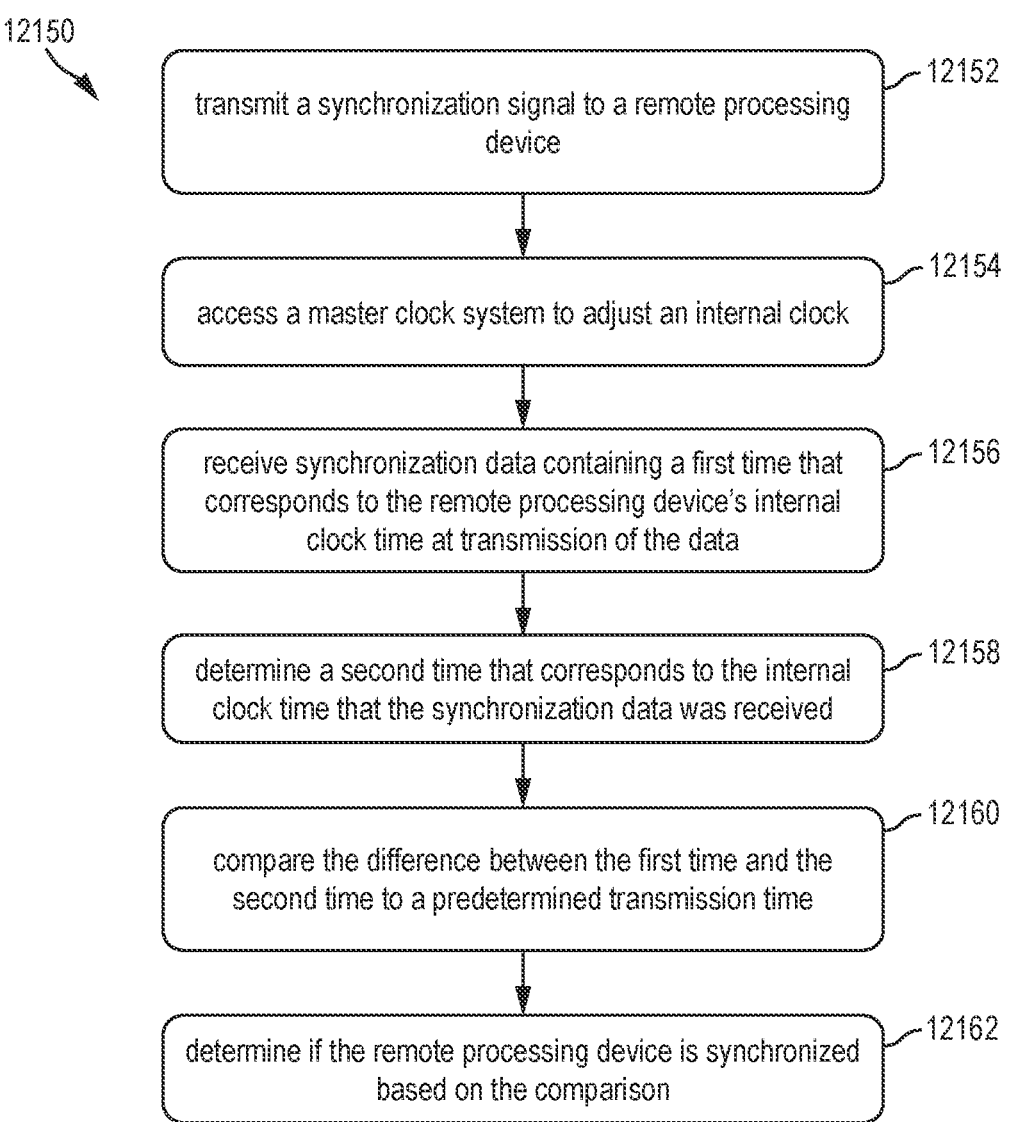

12150 transmit a synchronization signal to a remote processing device   12152 access a master clock system to adjust an internal clock   12154 receive synchronization data containing a first time that corresponds to the remote processing device's internal clock time at transmission of the data   12156 determine a second time that corresponds to the internal clock time that the synchronization data was received   12158 compare the difference between the first time and the second time to a predetermined transmission time   12160 determine if the remote processing device is synchronized based on the comparison   12162

FIG. 141

12170 receive a message containing a fixed frequency for a sync pulse    12172 receive a sync pulse from a control circuit    12174 calculate the actual frequency of the sync pulse    12176 compare the fixed frequency to the actual frequency    12178 adjust an internal clock based on the comparison    12180

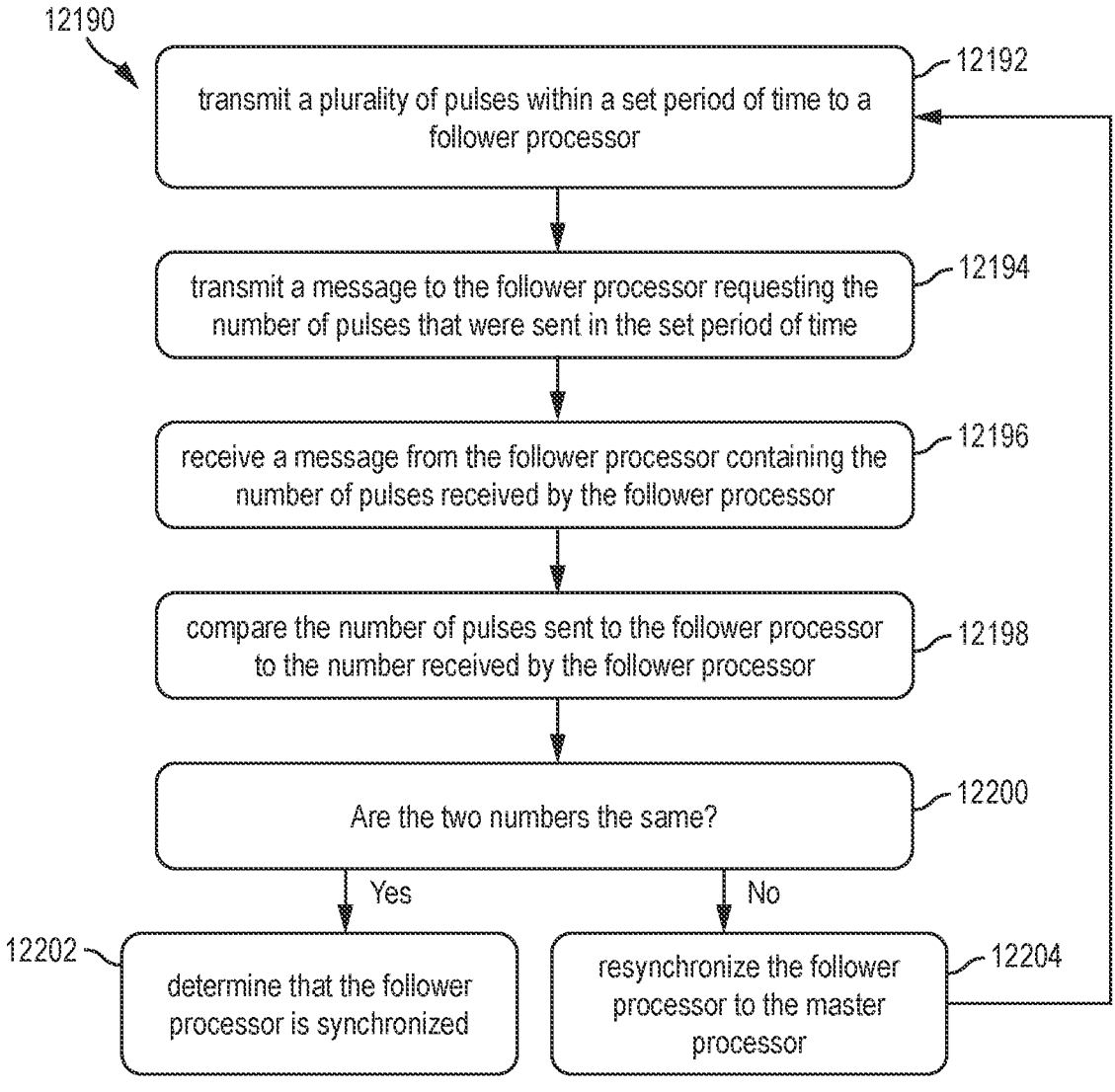

12190

12192　transmit a plurality of pulses within a set period of time to a follower processor 12194　transmit a message to the follower processor requesting the number of pulses that were sent in the set period of time 12196　receive a message from the follower processor containing the number of pulses received by the follower processor 12198　compare the number of pulses sent to the follower processor to the number received by the follower processor 12200　Are the two numbers the same?

Yes

No 12202　determine that the follower processor is synchronized 12204　resynchronize the follower processor to the master processor

FIG. 143

METHOD FOR CONTROLLING SURGICAL SYSTEM DURING TISSUE TREATMENT MOTION

CROSS-REFERENCE TO RELATED APPLICATIONS

This application claims the benefit under 35 U.S.C. § 119(e) to U.S. Provisional Patent Application Ser. No. 63/411,445, titled METHOD FOR CONTROLLING SURGICAL SYSTEM DURING TISSUE TREATMENT MOTION, filed Sep. 29, 2022, the disclosure of which is herein incorporated by reference in its entirety.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 17 illustrates a method for controlling a surgical instrument, according to at least one aspect of the present disclosure;

FIG. 19 illustrates a method for controlling a surgical instrument, according to at least one aspect of the present disclosure;

FIG. 23 illustrates a method for controlling a surgical instrument, according to at least one aspect of the present disclosure;

FIG. 24 illustrates a method for controlling a surgical instrument, according to at least one aspect of the present disclosure;

FIG. 37 illustrates a method for controlling a surgical instrument, according to at least one aspect of the present disclosure;

FIG. 45 illustrates a method for controlling a surgical instrument, according to at least one aspect of the present disclosure;

FIG. 46 illustrates a method for controlling a surgical instrument, according to at least one aspect of the present disclosure;

FIG. 49 is a table illustrating the transection performance of various staple cartridges, according to at least one aspect of the present disclosure;

FIG. 70 is a logic flow chart depicting a process executable by a control circuit, wherein the process includes actions for controlling the motor of a surgical instrument system, wherein the control circuit is configured to perform a plurality of sensory action sequences during a pre-compression stage to determine a firing speed of the motor for a staple firing stroke;

FIG. 83 is a logic flow chart depicting a process executable by control circuit for use in a surgical instrument system, wherein the control circuit is configured to adjust a parameter of one or more sensory actions performed during a second staple firing stroke, and wherein the adjustment is based on a monitored result of a first sensory action performed during a first staple firing stroke;

FIG. 101 is a flow chart of a method of controlling a motor in a powered surgical stapling system based on changing a shape of a motor control signal according to one aspect of this disclosure;

FIG. 108 is a flow chart of a method of controlling a motor in a powered surgical stapling system based on data received from multiple sensors of the operation of sub-system components, according to one aspect of this disclosure;

FIG. 119 is a flow diagram depicting a process for controlling a tissue treatment motion, according to at least one aspect of the present disclosure;

FIG. 120 illustrates articulation angles of an end effector of a surgical instrument, according to at least one aspect of the present disclosure;

FIG. 121 is a flow diagram depicting a process for controlling a tissue treatment motion, according to at least one aspect of the present disclosure;

FIG. 122 is a diagram depicting a method to determine an articulation angle of an end effector of a surgical instrument, according to at least one aspect of the present disclosure;

FIG. 123 is a flow diagram depicting a process for controlling a tissue treatment motion, according to at least one aspect of the present disclosure;

FIG. 124 illustrates an RFID scanner and an end effector wirelessly connected to the RFID scanner, according to at least one aspect of the present disclosure;

FIG. 125 is a flow diagram depicting a process for controlling a tissue treatment motion, according to at least one aspect of the present disclosure;

FIG. 126 is a flow diagram depicting a process for controlling a tissue treatment motion, according to at least one aspect of the present disclosure;

FIG. 127 is a flow diagram depicting a process for controlling a tissue treatment motion, according to at least one aspect of the present disclosure;

FIG. 128 is a flow diagram depicting a process for controlling a tissue treatment motion, according to at least one aspect of the present disclosure;

FIG. 129 is a flow diagram depicting a process for controlling a tissue treatment motion, according to at least one aspect of the present disclosure;

FIG. 130 is a diagram depicting a distributed processing system, according to at least one aspect of the present disclosure;

Figures 130, 131:
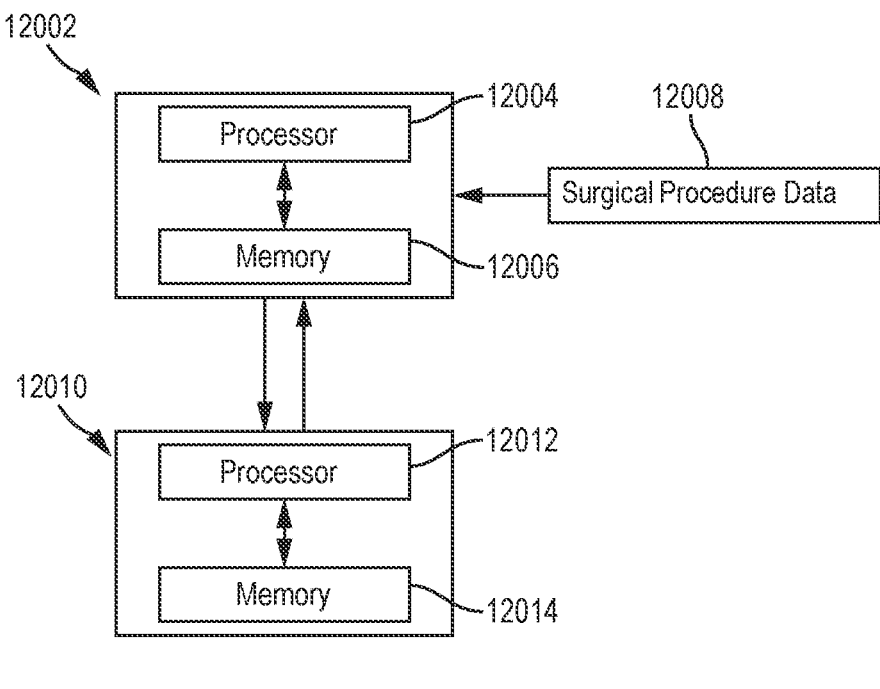
Figure 132:
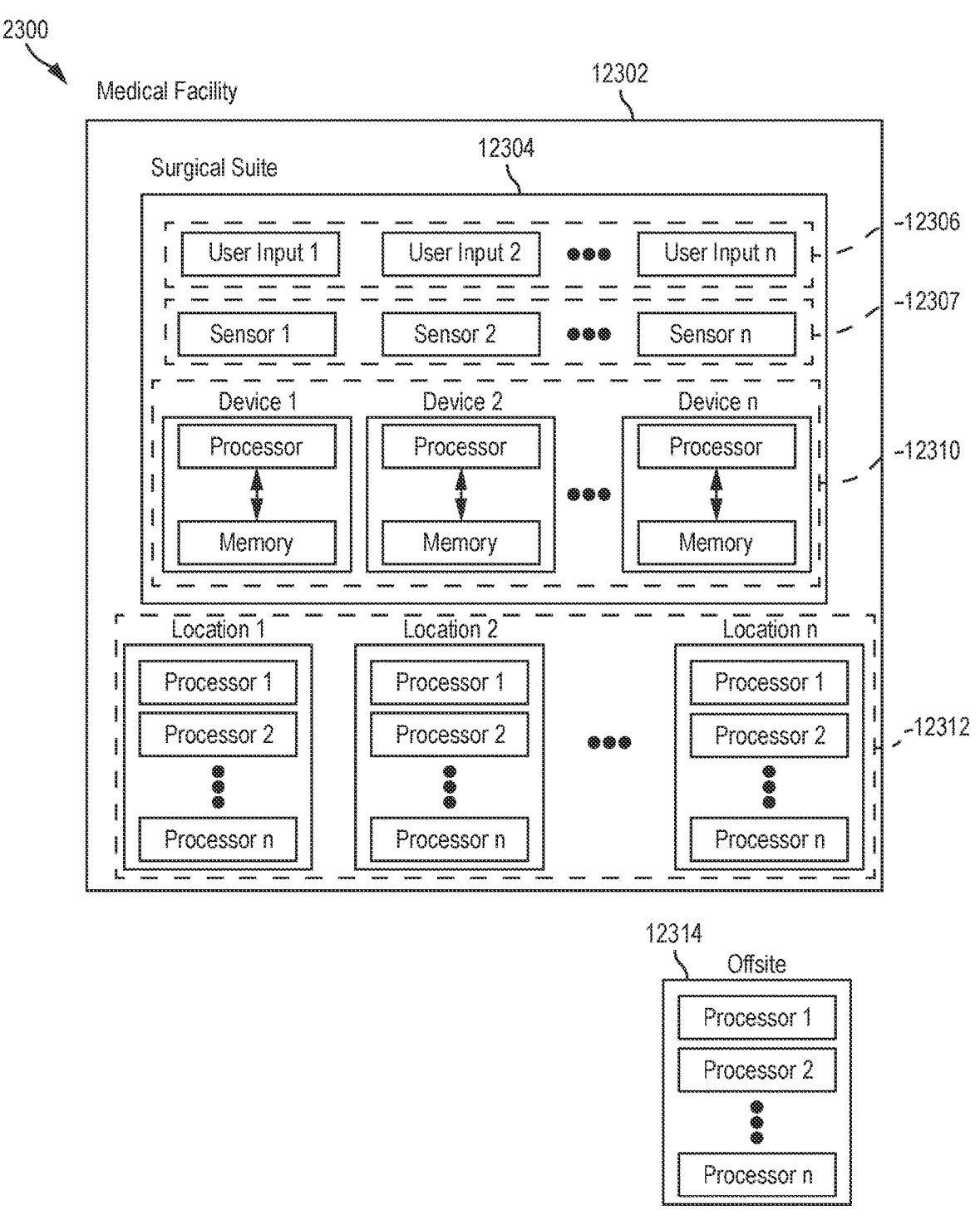
Figure 133:
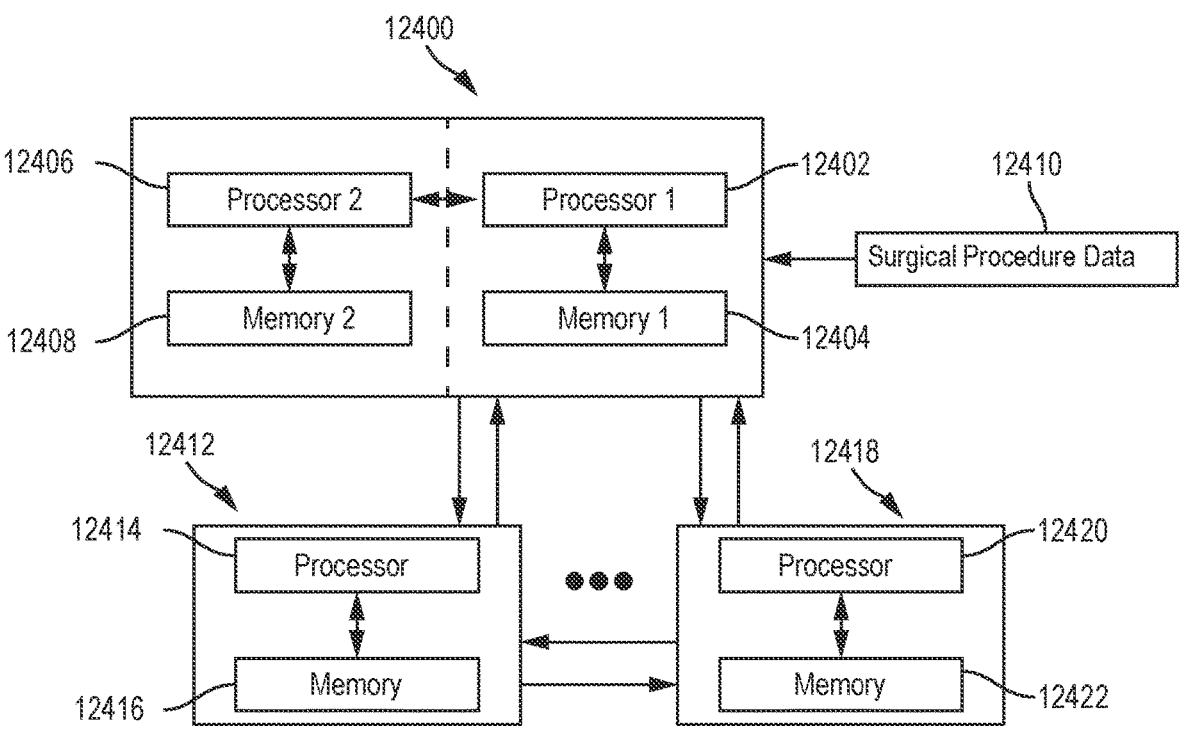
Figure 137:
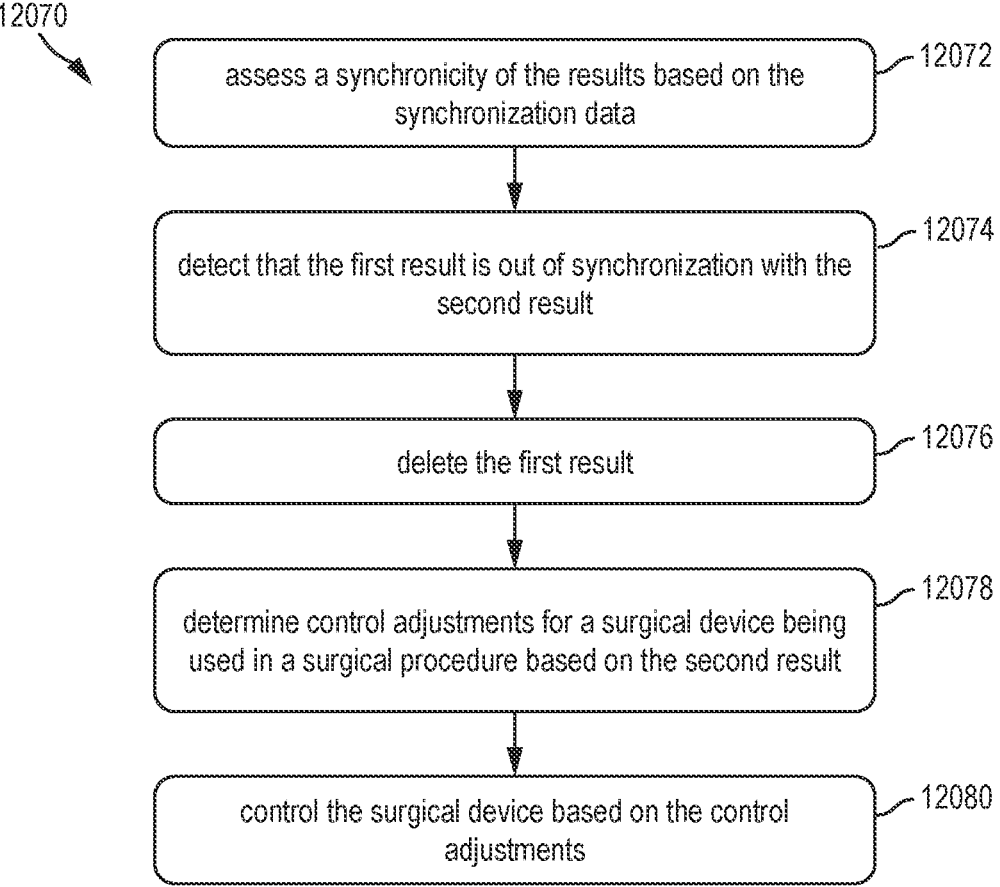
Figure 138:
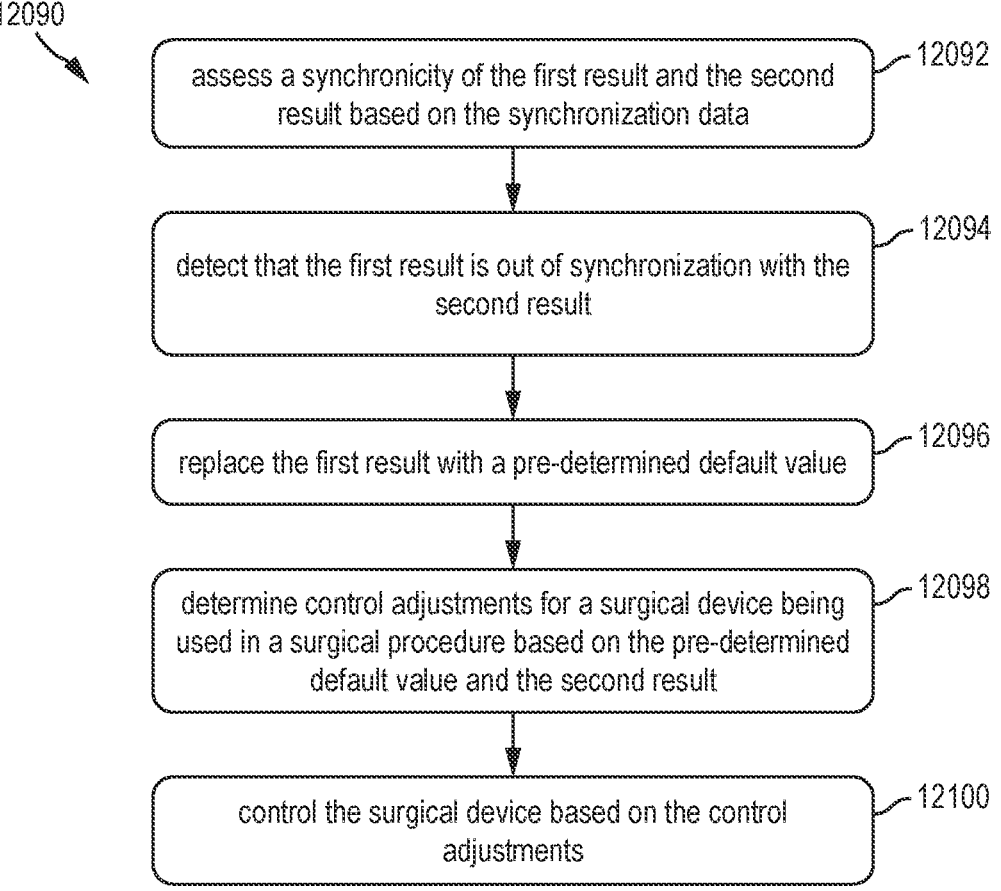
Figure 142:
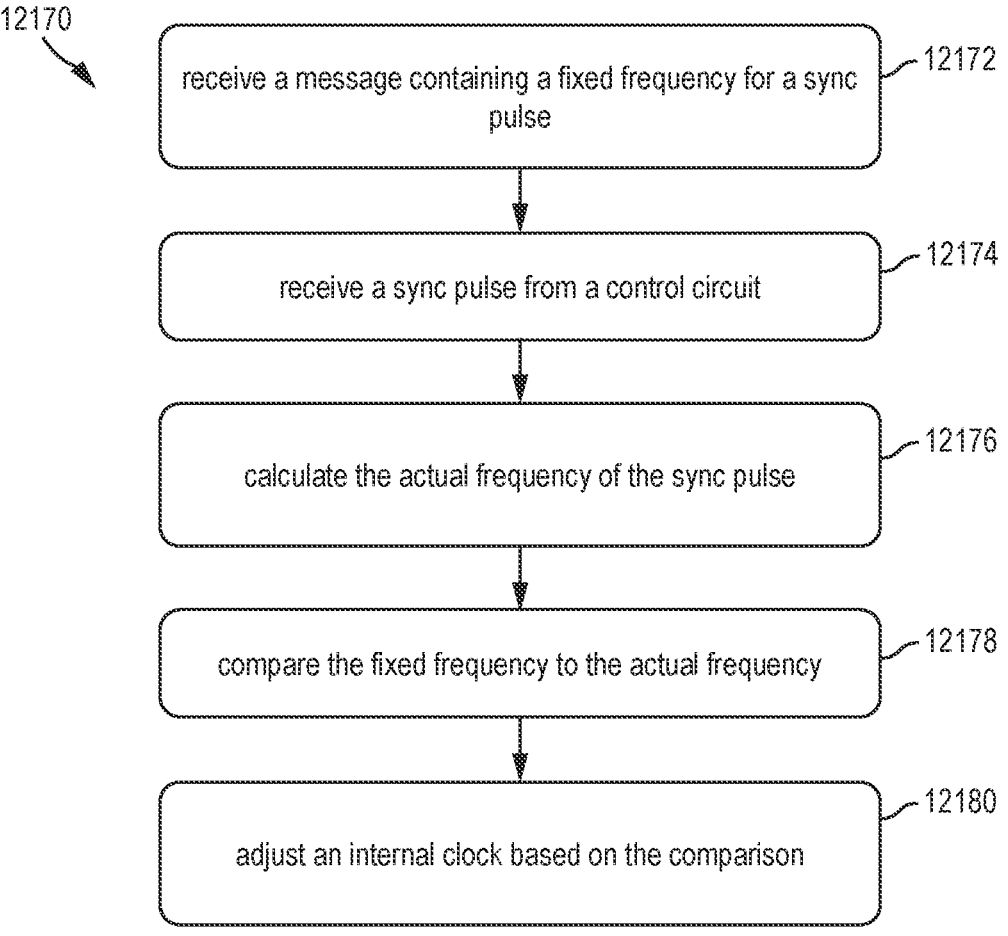
Figure 144:
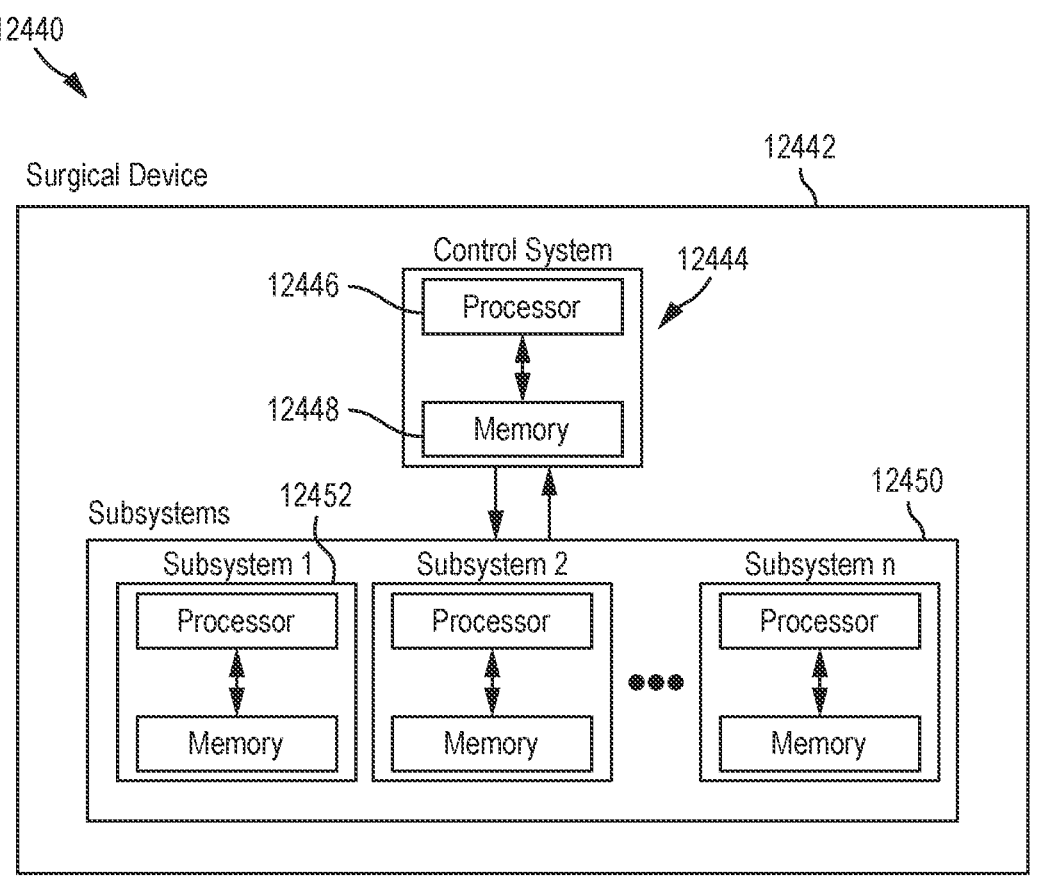
Figure 145:
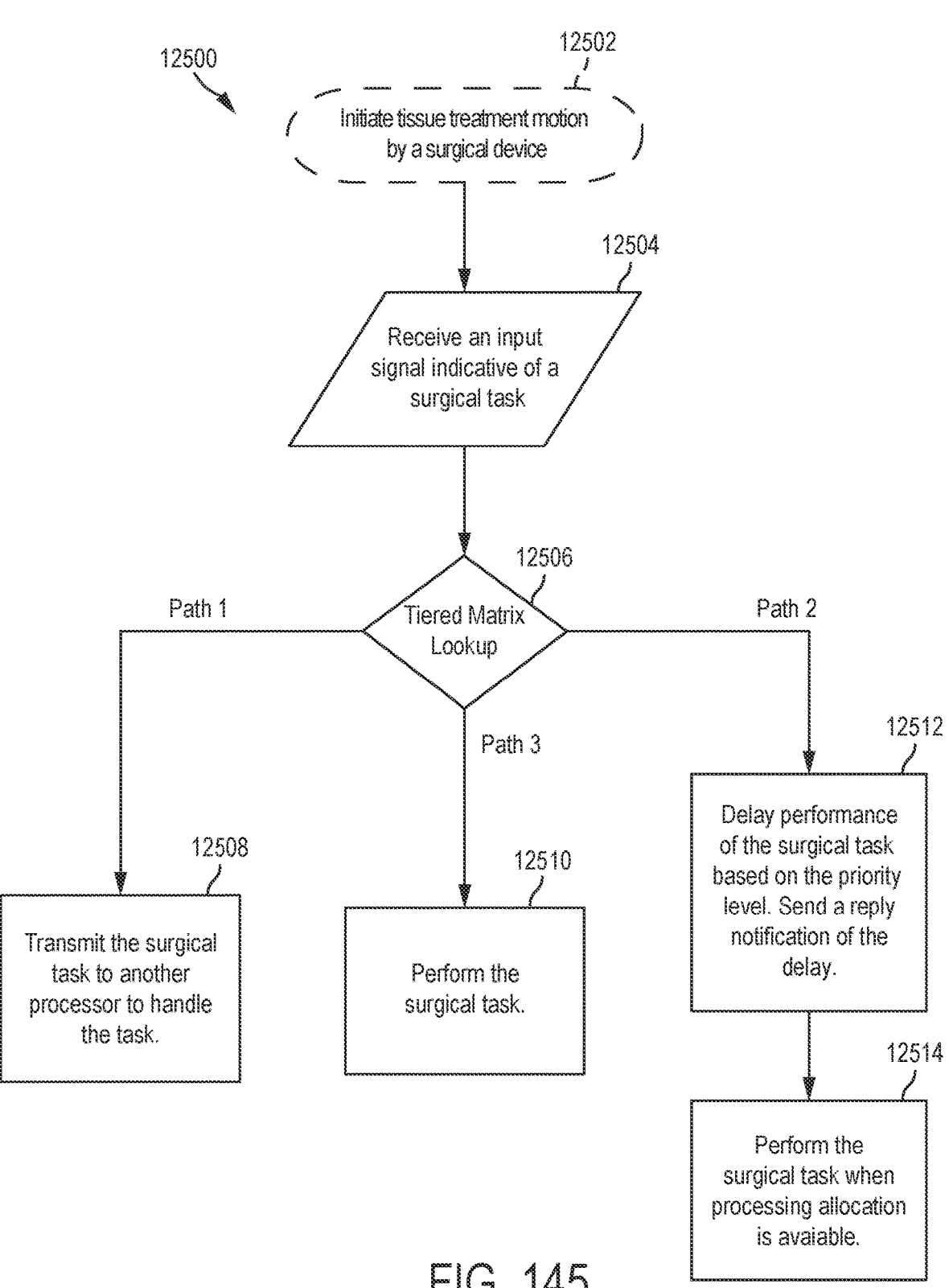

FIG. 131 is a diagram depicting a distributed processing system, according to at least one aspect of the present disclosure;

FIG. 132 is a diagram depicting different devices and inputs accessible by a control circuit in a surgical suite, according to at least one aspect of the present disclosure;

FIG. 133 is a diagram depicting a distributed processing system, according to at least one aspect of the present disclosure;

FIG. 134 is a flow diagram depicting a distributed processing method that can be executed by a control circuit, according to at least one aspect of the present disclosure;

FIG. 135 is a flow diagram depicting a distributed processing method that can be executed by a control circuit, according to at least one aspect of the present disclosure;

FIG. 136 is a flow diagram depicting a distributed processing method that can be executed by a control circuit, according to at least one aspect of the present disclosure;

FIG. 137 is a flow diagram depicting a method for a control circuit to execute when results of a distributed processing method are out of synchronization, according to at least one aspect of the present disclosure;

FIG. 138 is a flow diagram depicting a method for a control circuit to execute when results of a distributed processing method are out of synchronization, according to at least one aspect of the present disclosure;

FIG. 139 is a flow diagram depicting a method for a control circuit to execute when results of a distributed processing method are out of synchronization, according to at least one aspect of the present disclosure;

FIG. 140 is a flow diagram depicting a method for a control circuit to execute when results of a distributed processing method are out of synchronization, according to at least one aspect of the present disclosure;

FIG. 141 is a flow diagram depicting a method for a control circuit to execute to synchronize with another control circuit, according to at least one aspect of the present disclosure;

FIG. 142 is a flow diagram depicting a method that can be executed by a control circuit to characterize the latency of another synchronized control circuit, according to at least one aspect of the present disclosure;

FIG. 143 is a flow diagram depicting a method 12190 that can be executed by a control circuit to characterize the latency of another synchronized control circuit, according to at least one aspect of the present disclosure;

FIG. 144 is a diagram depicting a surgical device with multiple subsystems, according to at least one aspect of the present disclosure; and FIG. 145 is a flow diagram depicting a prioritization method that can be executed by a control circuit for processor tasks based on a tiered matrix, according to at least one aspect of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. Patent Applications that were filed on Sep. 30, 2022 and which are each herein incorporated by reference in their respective entireties:

U.S. patent application Ser. No. 17/957,923, titled ADAPTING TISSUE TREATMENT MOTION PARAMETERS BASED ON SITUATIONAL PARAMETERS, published as U.S. Patent Application Publication No. 2024/0108331;

U.S. patent application Ser. No. 17/957,933, titled ADAPTIVE FIRING CONTROL ALGORITHM BASED ON MECHANICAL ACTUATION OF USER CONTROLS, issued as U.S. Patent No. 12,310,585;

U.S. patent application Ser. No. 17/957,946, titled ADAPTATION OF INDEPENDENT FIRING AND CLOSURE POWERED STAPLING SYSTEMS, issued as U.S. Pat. No. 12,396,727;

U.S. patent application Ser. No. 17/957,954, titled MONITORING ONE DRIVE SYSTEM TO ADAPT THE MOTOR DRIVEN ASPECT OF A SECOND DRIVE SYSTEM, published as U.S. Patent Application Publication No. 2024/0108337;

U.S. patent application Ser. No. 17/957,975, titled ADJUSTMENT OF THE MOTOR CONTROL PROGRAM BASED ON DETECTION OF INDIVIDUAL DEVICE DRIVE TRAIN PROPERTIES, issued as U.S. Pat. No. 12,262,890;

U.S. patent application Ser. No. 17/957,984, titled ADJUSTMENT OF A MOTOR CONTROL COMMAND SIGNAL TO ADAPT TO SYSTEM CHANGES, issued as U.S. Pat. No. 12,239,319;

U.S. patent application Ser. No. 17/957,990, titled MOTOR ADJUSTMENTS IN ABSENCE OF MOTOR DRIVE SIGNAL, issued as U.S. Pat. No. 11,974,825;

U.S. patent application Ser. No. 17/957,995, titled SURGICAL SYSTEMS WITH SYNCHRONIZED DISTRIBUTED PROCESSING CAPABILITIES, published as U.S. Patent Application Publication No. 2024/0112798;

U.S. patent application Ser. No. 17/958,001, titled SURGICAL SYSTEM WITH MOTOR RELATIVE CAPACITY INTERROGATIONS, issued as U.S. Patent No. 12,414,767;

U.S. patent application Ser. No. 17/958,008, titled MOTOR CONTROL OF SURGICAL INSTRUMENT SYSTEMS, issued as U.S. Pat. No. 12,527,572;

U.S. patent application Ser. No. 17/958,013, titled SURGICAL SYSTEM WITH AMPLITUDE AND PULSE WIDTH MODULATION ADJUSTMENTS, issued as U.S. Pat. No. 12,383,266;

U.S. patent application Ser. No. 17/958,024, titled SURGICAL ALGORITHMS WITH INCREMENTAL SENSORY ACTIONS, issued as U.S. Pat. No. 12,295,575;

U.S. patent application Ser. No. 17/958,028, titled UTILIZING LOCAL FIRING PARAMETERS TO INITIATE MOTOR CONTROL ADJUSTMENTS IN SURGICAL SYSTEMS, issued as U.S. Pat. No. 12,453,554; and U.S. patent application Ser. No. 17/958,037, titled SURGICAL SYSTEMS WITH DYNAMIC FORCE TO FIRE ADJUSTMENTS, issued as U.S. Pat. No. 11,931,037.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 1:
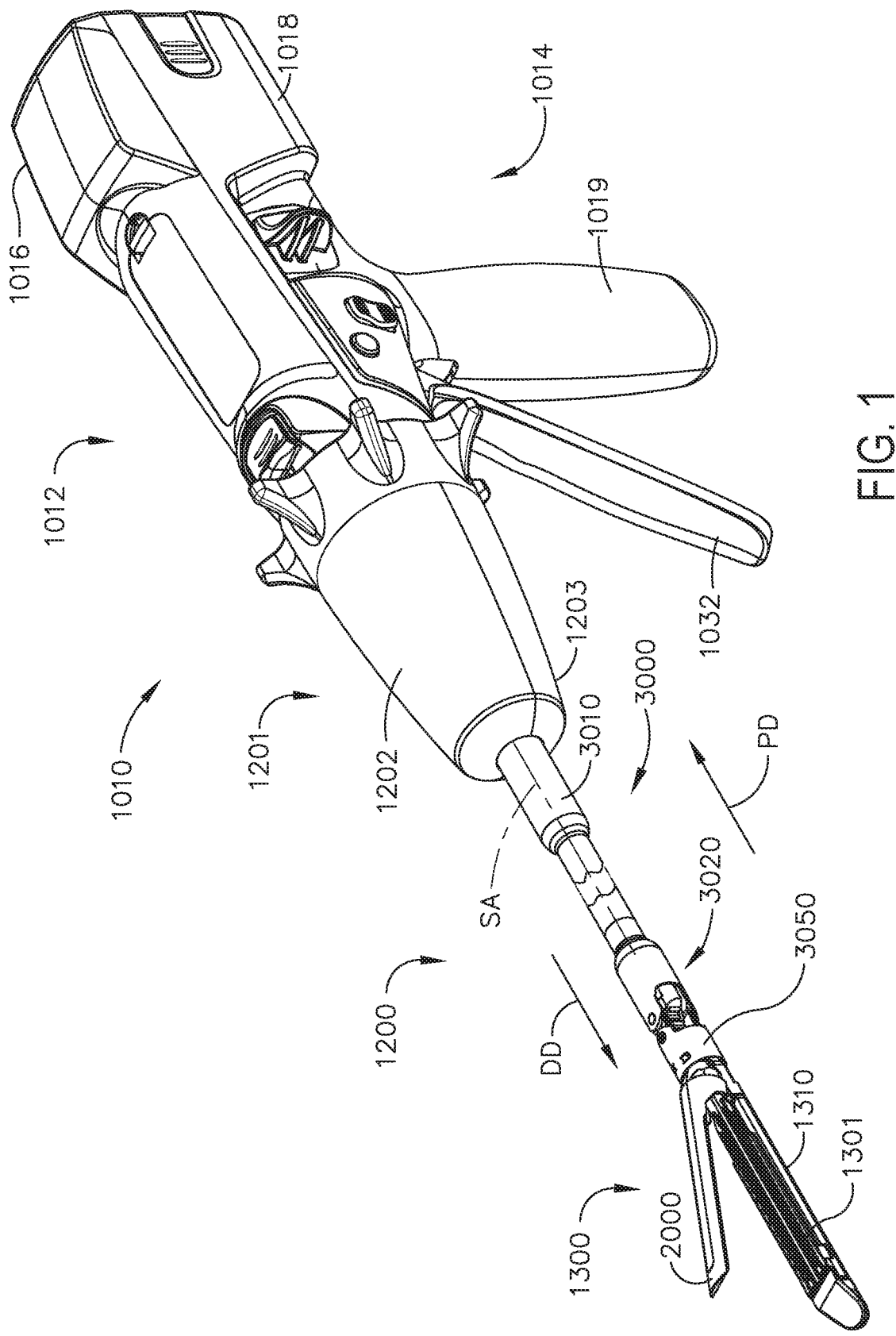
FIG. 1 is a perspective view of a powered surgical stapling system.
Figure 2:
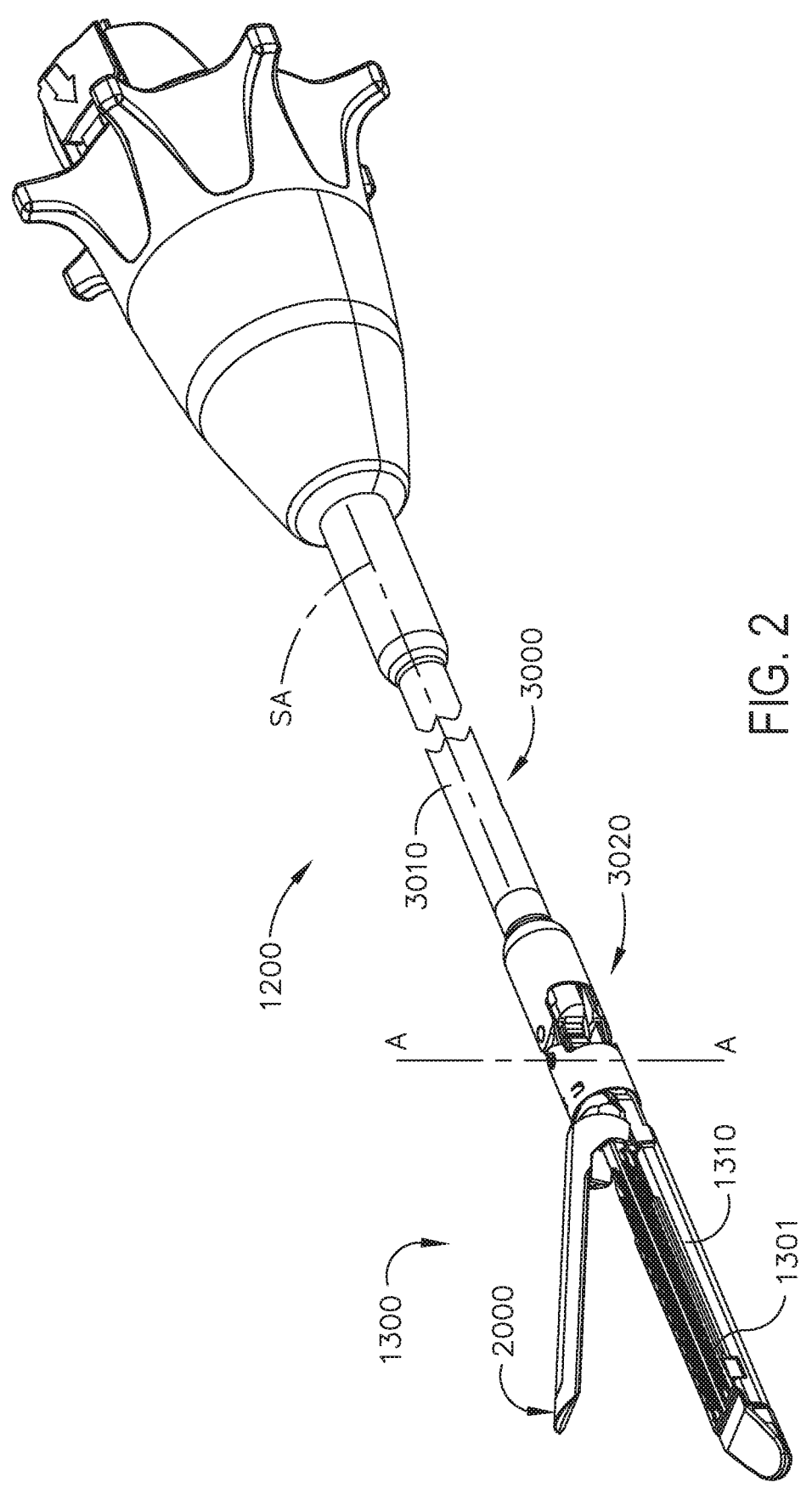
FIG. 2 is a perspective view of an interchangeable surgical shaft assembly of the powered surgical stapling system of FIG. 1.
Figure 3:
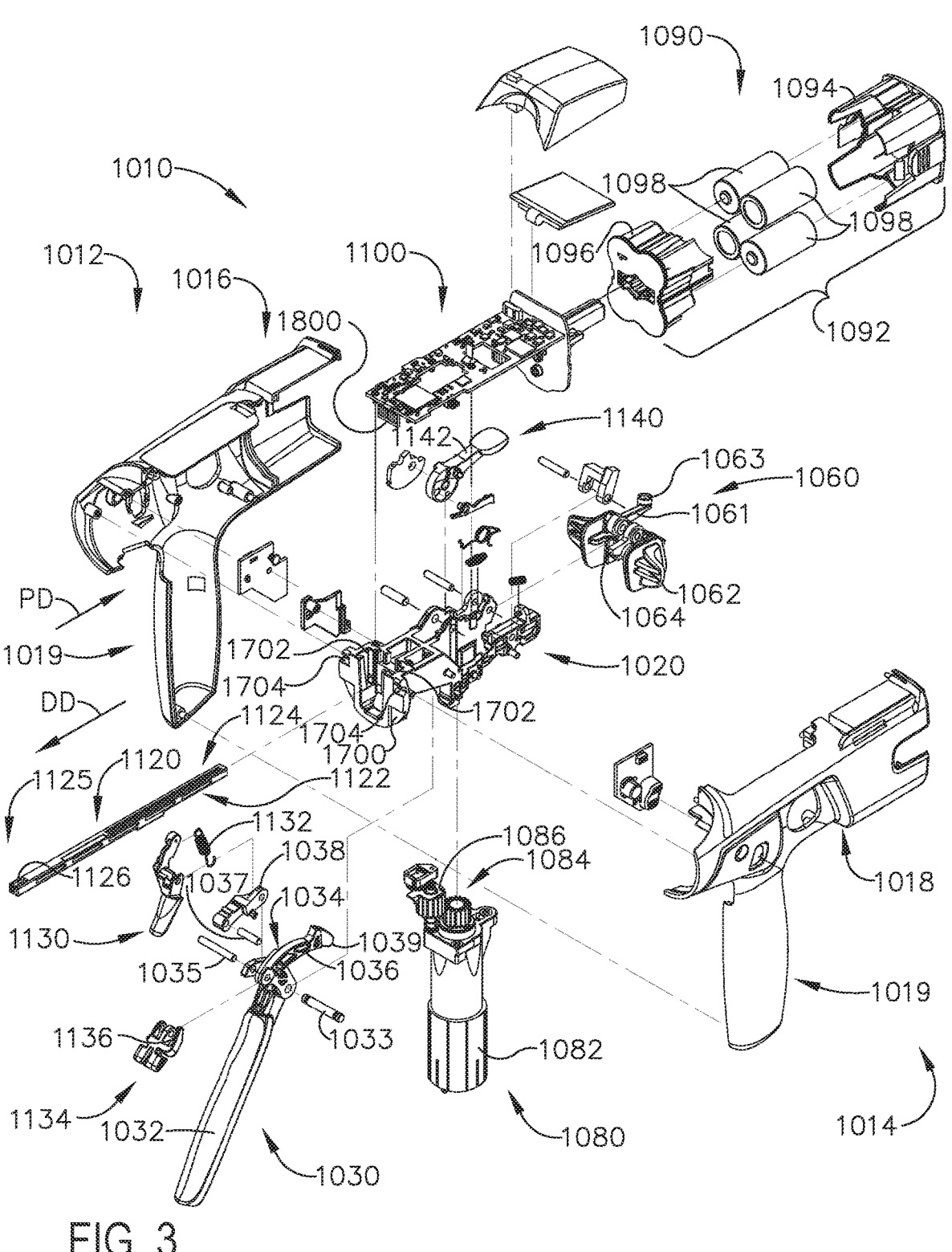
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a proximal housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The proximal housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 1301 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button assembly 1062. A magnetic element 1063, such as a permanent magnet, for example, may be mounted to the arm 1061. When the closure release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a set, or rack, of drive teeth 1122 on a longitudinally movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 1082 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014.

The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
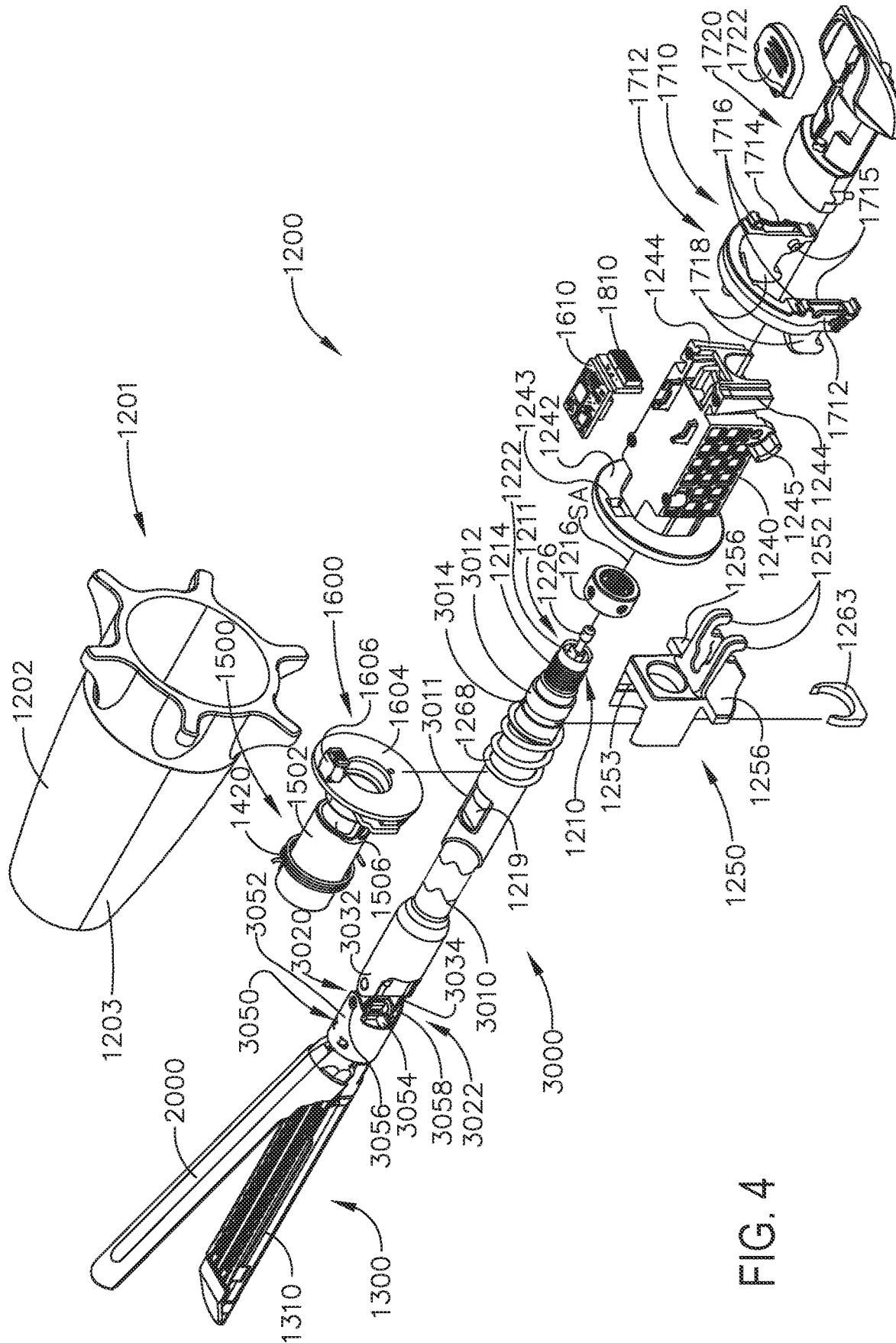
FIG. 4 is an exploded assembly view of the interchangeable surgical shaft assembly of FIG. 2.
Figure 5:
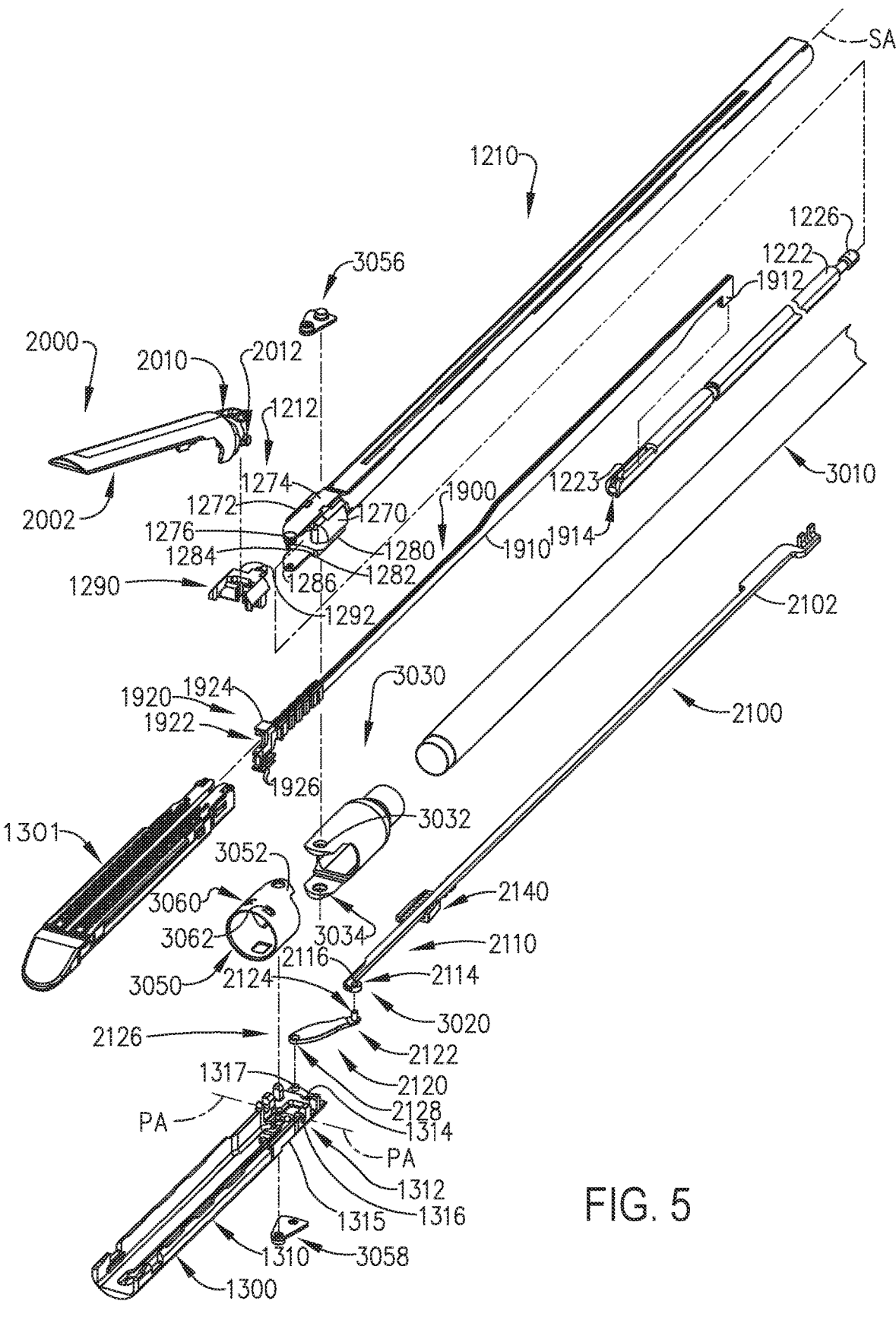
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 1301 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 1301 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

Embodiments are also envisioned where, in lieu of a slip joint 1914, a shifter assembly can be used. Details of such a shifter assembly and corresponding components, assemblies, and systems can be found in U.S. patent application Ser. No. 15/635,521, entitled SURGICAL INSTRUMENT LOCKOUT ARRANGEMENT, which is incorporated by reference herein in its entirety.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receiving an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled SURGICAL INSTRUMENT COMPRISING A SENSOR SYSTEM, the entire disclosures of each being hereby incorporated by reference herein. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to the distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame 1020 or spine 1210 of the shaft assembly 1200 with the frame 1020 of the handle 1014. Another system can comprise a closure drive system 1030 which can operably connect the closure trigger 1032 of the handle 1014 and a closure tube of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the circuit board 1100. Further details regaining the circuitry and control systems may be found in U.S. patent application Ser. No. 13/803,086, now U.S. Patent Application Publication No. 2014/0263541 entitled ARTICULATABLE SURGICAL INSTRUMENT COMPRISING AN ARTICULATION LOCK, and U.S. patent application Ser. No. 14/226,142, now U.S. Pat. No. 9,913,642 entitled SURGICAL INSTRUMENT COMPRISING A SENSOR SYSTEM, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
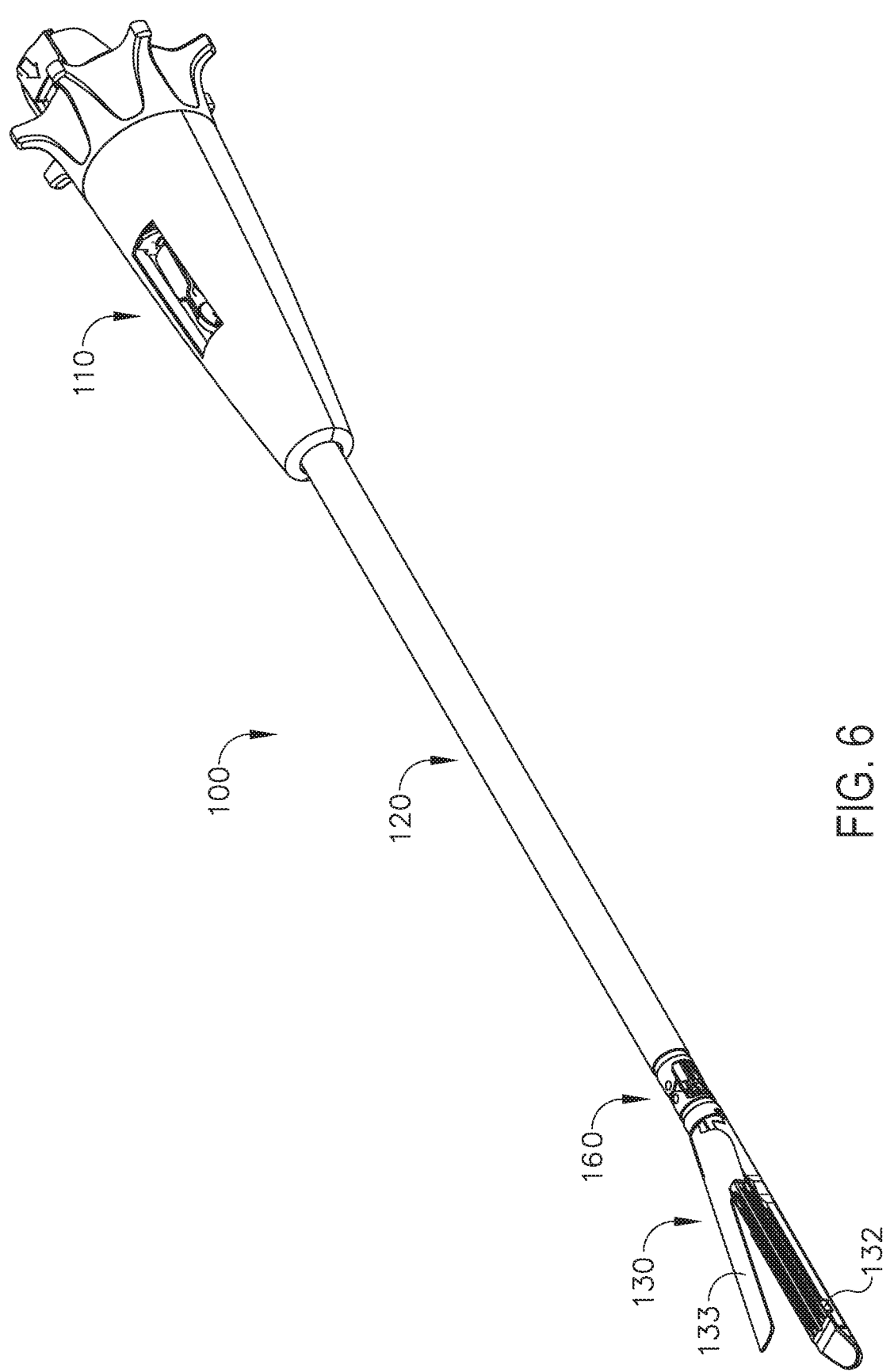
FIG. 6 is a perspective view of a shaft assembly in accordance with at least one embodiment.
Figure 7:
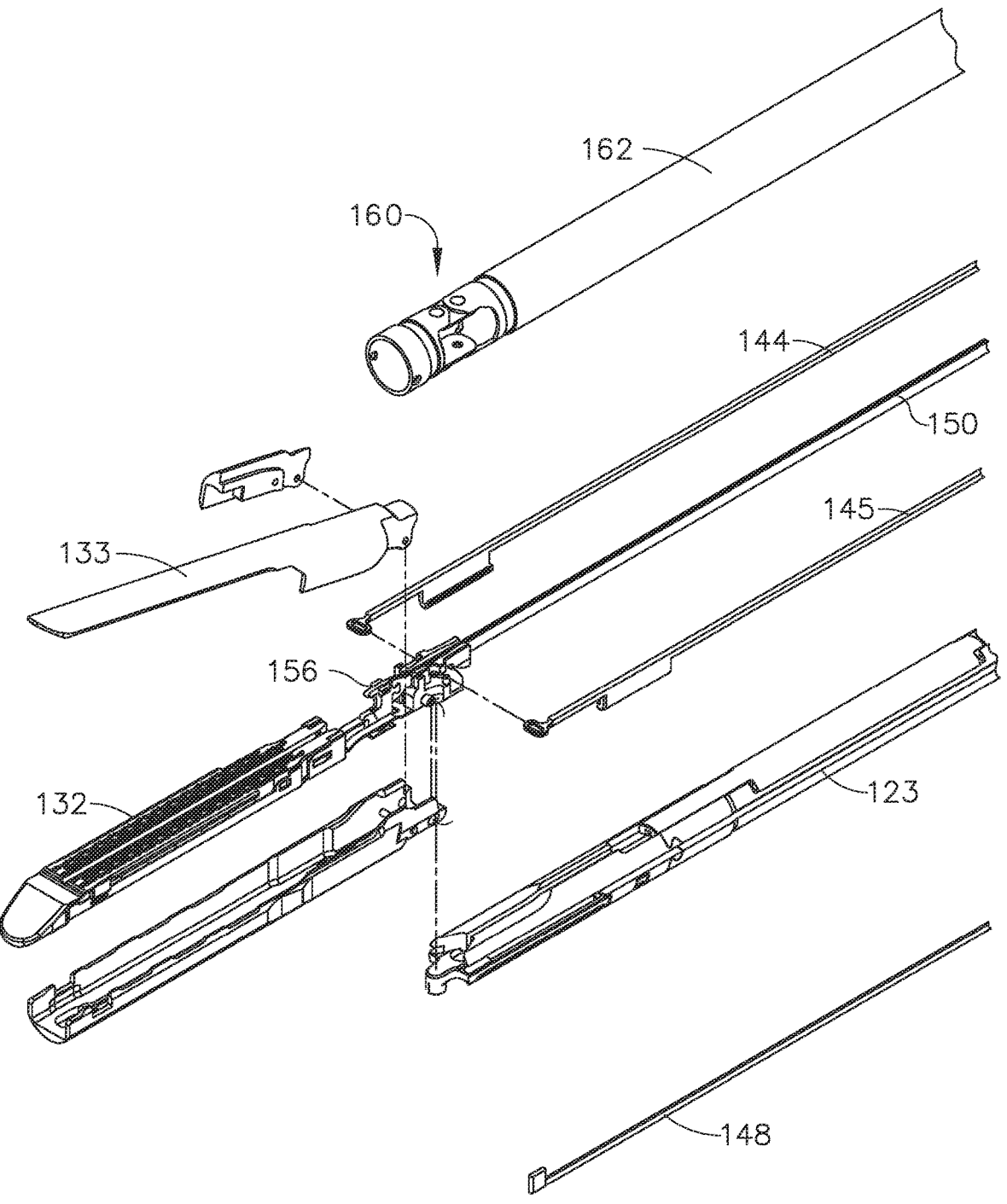
FIG. 7 is an exploded view of a distal end of the shaft assembly of FIG. 6.

A shaft assembly 100 is illustrated in FIGS. 6 and 7. The shaft assembly 100 comprises an attachment portion 110, a shaft 120 extending distally from the attachment portion 110, and an end effector 130 attached to the shaft 120. The shaft assembly 100 is configured to clamp, staple, and cut tissue. The attachment portion 110 is configured to be attached to a handle of a surgical instrument and/or the arm of a surgical robot, for example.

Referring to FIG. 7, the shaft assembly 100 comprises cooperating articulation rods 144, 145 configured to articulate the end effector 130 relative to the shaft 120 about an articulation joint 160. The shaft assembly 100 further comprises an articulation lock bar 148, an outer shaft tube 162, and a spine portion 123.

Referring to FIG. 7, the shaft assembly 100 comprises a firing shaft 150 including a firing member 156 attached to a distal end of the firing shaft 150. The firing member 156 comprises upper camming flanges configured to engage an anvil jaw 133 and lower camming members configured to engage a cartridge jaw 132. The firing shaft 150 is configured to be advanced distally through a closure stroke to clamp the anvil jaw 133 relative to the cartridge jaw 132 with the camming members. Further advancement of the firing shaft 150 through a firing stroke is configured to advance the firing member 156 through the cartridge jaw 132 to deploy staples from the cartridge jaw 132 and cut tissue during the firing stroke. More details of the shaft assembly 100 can be found in U.S. patent application Ser. No. 15/385,887 entitled METHOD FOR ATTACHING A SHAFT ASSEMBLY TO A SURGICAL INSTRUMENT AND, ALTERNATIVELY, TO A SURGICAL ROBOT, which is incorporated by reference in its entirety.

Figure 8:
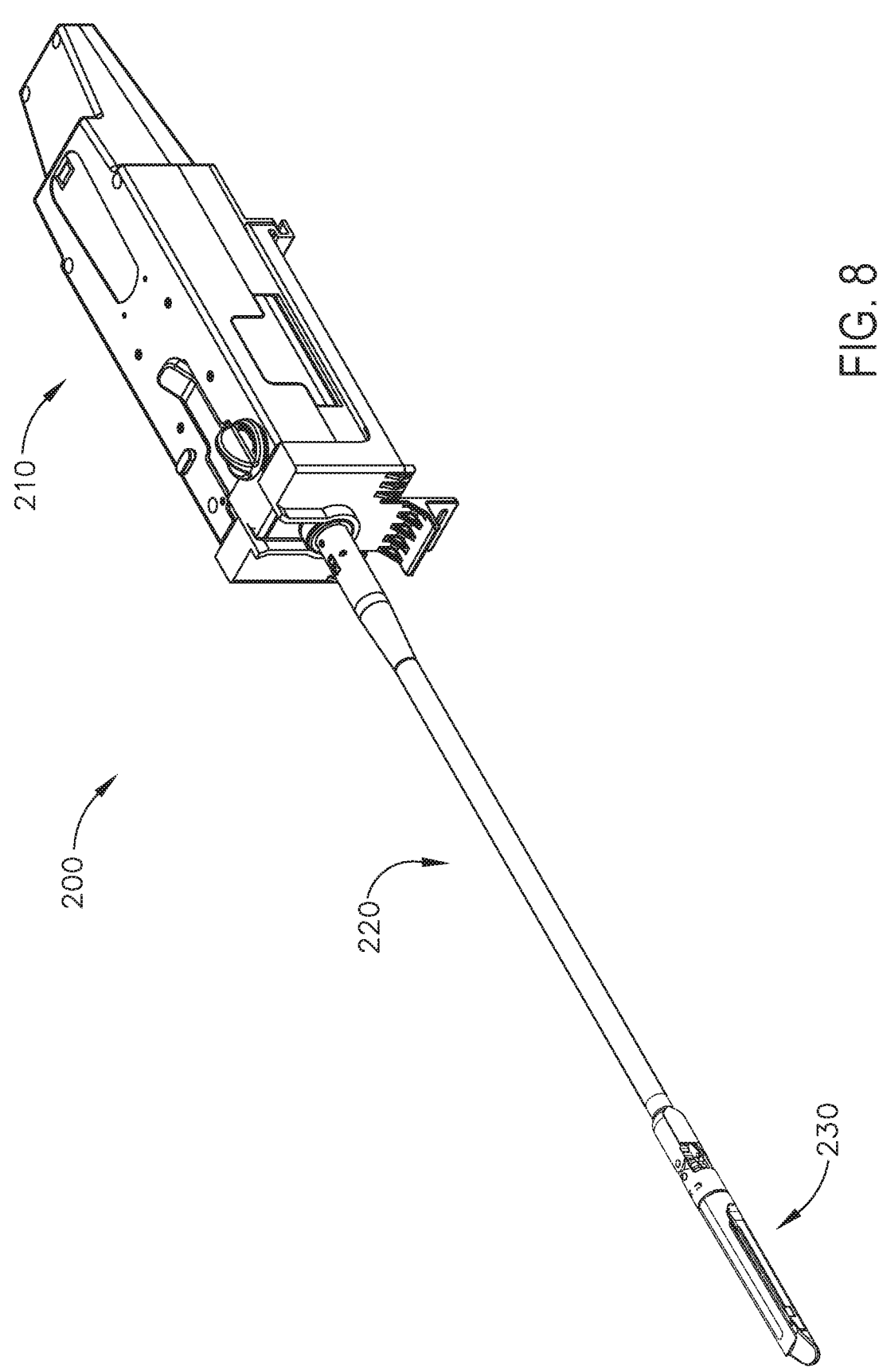
FIG. 8 is a perspective view of a surgical instrument assembly comprising a proximal control interface, a shaft assembly, and an end effector assembly.
Figure 9:
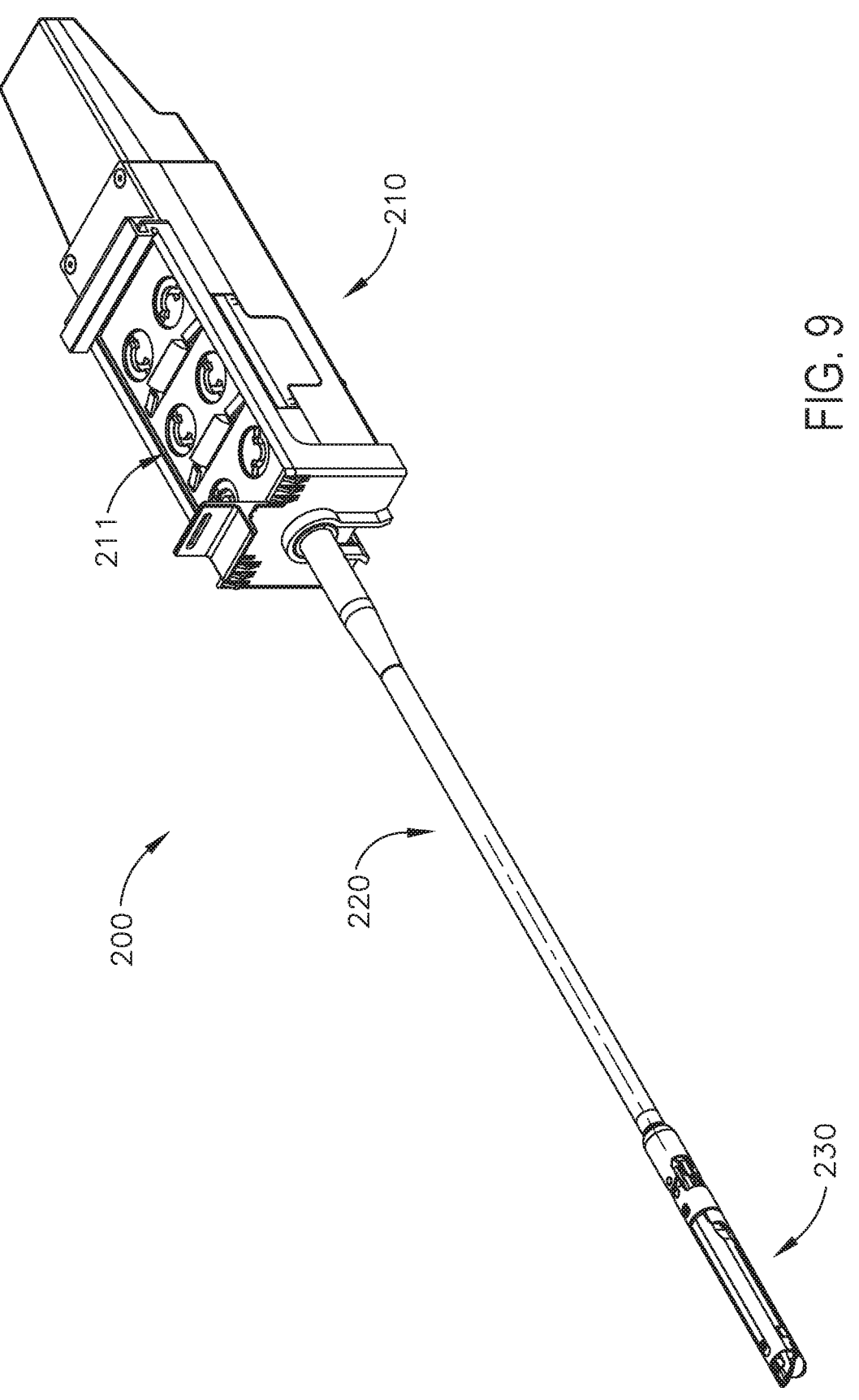
FIG. 9 is a bottom perspective view of the surgical instrument assembly of FIG. 8.

FIGS. 8 and 9 depict a surgical instrument assembly 200 configured to be used with a surgical robot. The surgical instrument assembly 200 is configured to staple and cut tissue, although the surgical instrument assembly 200 could be adapted to treat tissue in any suitable way, such as by applying heat energy, electrical energy, and/or vibrations to the tissue, for example. The surgical instrument assembly 200 comprises a proximal control interface 210 configured to be coupled to a robotic arm of a surgical robot and a shaft assembly 220 configured to be attached to the proximal control interface 210. The shaft assembly 220 comprises an end effector 230 configured to clamp, cut, and staple tissue. The proximal control interface 210 comprises a plurality of drive discs 211, each for actuating one or more functions of the surgical instrument assembly 200. Each drive disc 211 can be independently driven and/or cooperatively driven with one or more other drive discs 211 by one or more motors of the surgical robot and/or robotic arm of the surgical robot. More details about the surgical instrument assembly 200 can be found in U.S. patent application Ser. No. 15/847,297, entitled SURGICAL INSTRUMENTS WITH DUAL ARTICULATION DRIVERS, which is incorporated by reference in its entirety.

Figure 10:
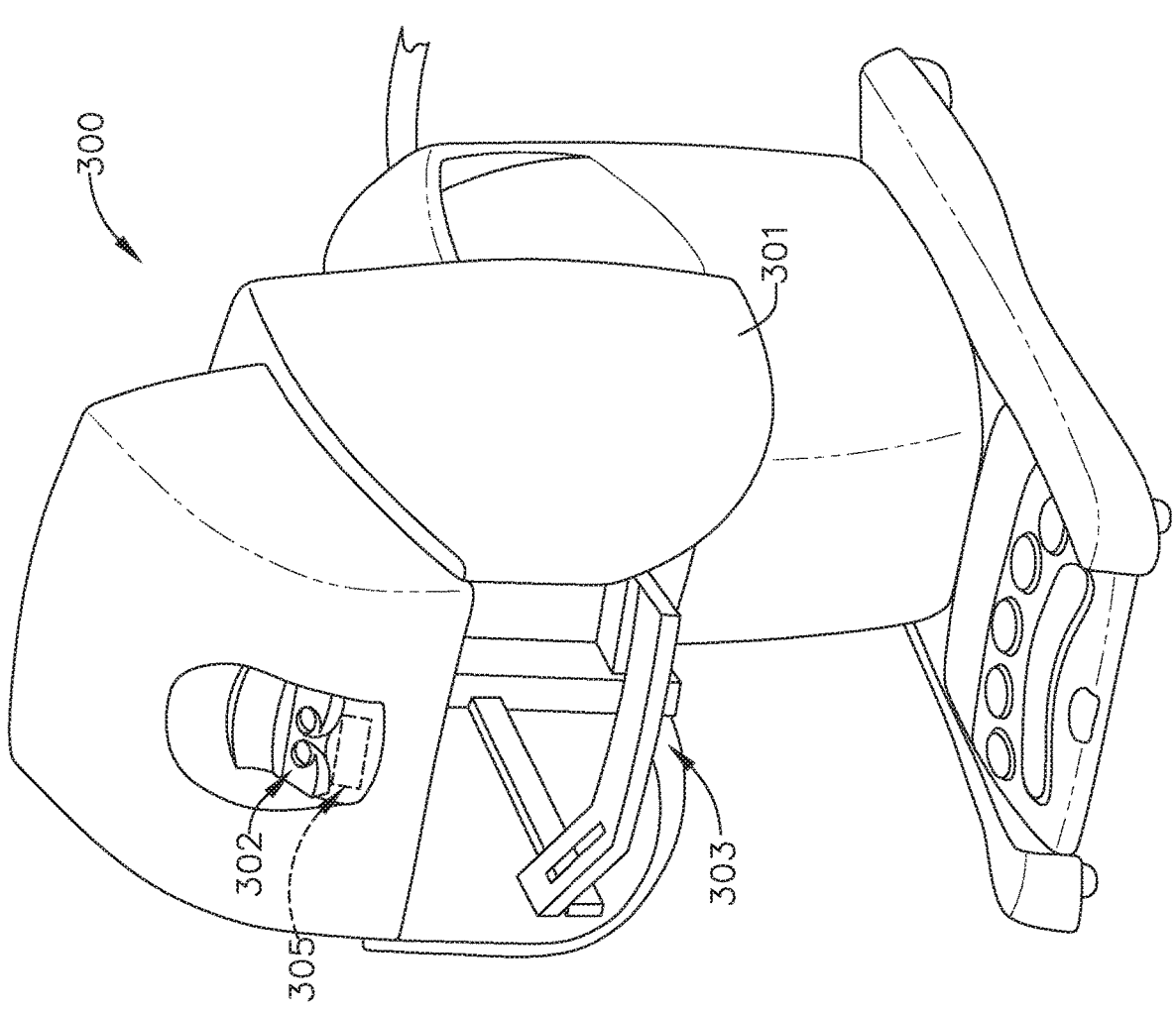
FIG. 10 is a perspective view of an example of one form of robotic controller according to one aspect of this disclosure.
Figure 11:
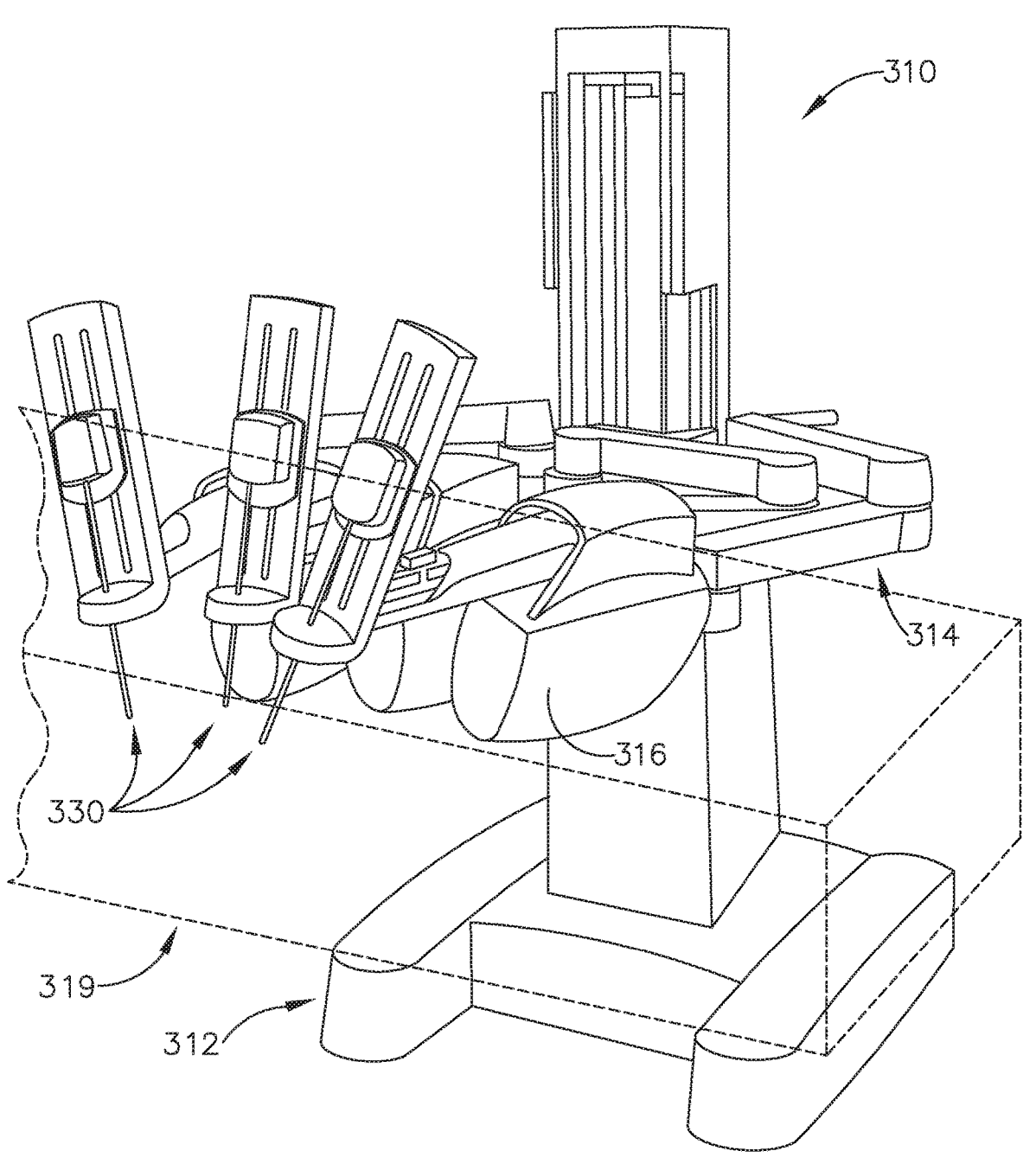
FIG. 11 is a perspective view of an example of one form of robotic surgical arm cart/manipulator of a robotic surgical system operably supporting a plurality of surgical tools according to one aspect of this disclosure.
Figure 12:
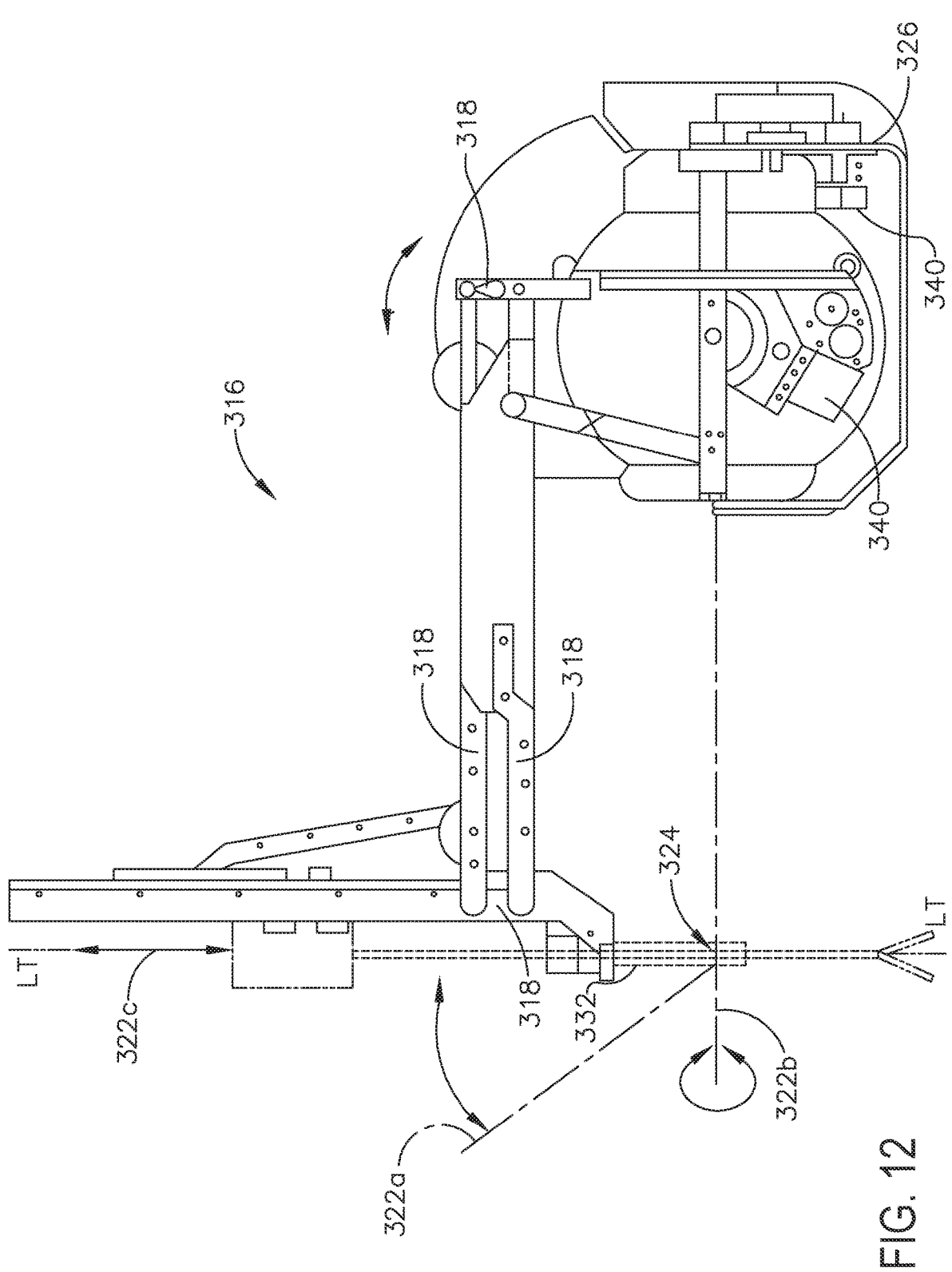
FIG. 12 is a side view of the robotic surgical arm cart/manipulator depicted in FIG. 11 according to one aspect of this disclosure.

Various embodiments disclosed herein may be employed in connection with a robotic system 300 of the type depicted in FIGS. 10-12, for example. FIG. 10 depicts one version of a master controller 301 that may be used in connection with a robotic arm slave cart 310 of the type depicted in FIG. 11. Master controller 301 and robotic arm slave cart 310, as well as their respective components and control systems are collectively referred to herein as a robotic system 300. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. Thus, various details of such devices will not be described in detail herein beyond that which may be necessary to understand various embodiments and forms of the present disclosure. As is known, the master controller 301 generally includes master controllers (generally represented as 303 in FIG. 10) which are grasped by the surgeon and manipulated in space while the surgeon views the procedure via a stereo display 302. The master controllers 301 generally comprise manual input devices which preferably move with multiple degrees of freedom, and which often further have an actuatable handle for actuating tools (for example, for closing grasping jaws, applying an electrical potential to an electrode, or the like).

As can be seen in FIG. 11, in one form, the robotic arm cart 310 may be configured to actuate one or more surgical tools, generally designated as 330. Various robotic surgery systems and methods employing master controller and robotic arm cart arrangements are disclosed in U.S. Pat. No. 6,132,368, entitled MULTI-COMPONENT TELEPRESENCE SYSTEM AND METHOD the entire disclosure of which is hereby incorporated by reference herein. In various forms, the robotic arm cart 310 includes a base 312 from which, in the illustrated embodiment, surgical tools may be supported. In various forms, the surgical tool(s) may be supported by a series of manually articulatable linkages, generally referred to as set-up joints 314, and a robotic manipulator 316. In various embodiments, the linkage and joint arrangement may facilitate rotation of a surgical tool around a point in space, as more fully described in issued U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 322a, sometimes called the pitch axis. The links supporting the parallelogram linkage are pivotally mounted to set-up joints 314 (FIG. 11) so that the surgical tool further rotates about an axis 322b, sometimes called the yaw axis. The pitch and yaw axes 322a, 322b intersect at the remote center 324, which is aligned along an elongate shaft of a surgical tool. The surgical tool may have further degrees of driven freedom as supported by manipulator 316, including sliding motion of the surgical tool along the longitudinal axis "LT-LT". As the surgical tool slides along the tool axis LT-LT relative to manipulator 316 (arrow 322c), remote center 324 remains fixed relative to base 326 of manipulator 316. Hence, the entire manipulator is generally moved to reposition remote center 324. Linkage 318 of manipulator 316 may be driven by a series of motors 340. These motors actively move linkage 318 in response to commands from a processor of a control system. The motors 340 may also be employed to manipulate the surgical tool. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein. Additionally, while the data communication between a robotic component and the processor of the robotic surgical system is primarily described herein with reference to communication between the surgical tool and the master controller 301, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 10-12 and described in the aforementioned references.

Figure 13:
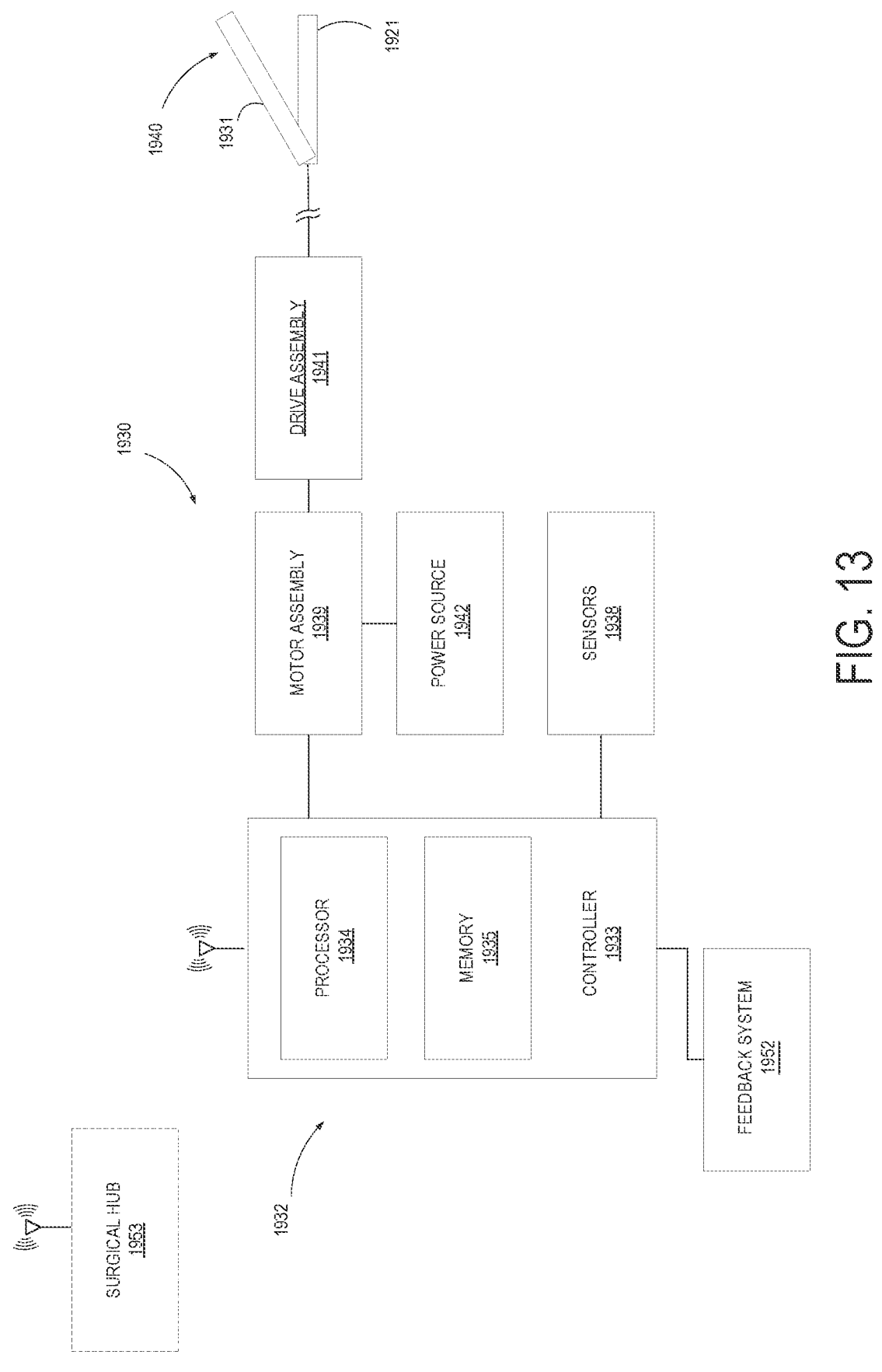
FIG. 13 illustrates a block diagram of a surgical system for use with one or more surgical instruments, tools, and/or robotic systems in accordance with one or more aspects of the present disclosure.

FIG. 13 illustrates a block diagram of a surgical system 1930 for use with one or more surgical instruments, tools, and/or robotic systems in accordance with one or more aspects of the present disclosure. The system 1930 includes a control circuit 1932. The control circuit 1932 includes a microcontroller 1933 comprising a processor 1934 and a storage medium such as, for example, a memory 1935.

A motor assembly 1939 includes one or more motors, driven by motor drivers. The motor assembly 1939 operably couples to a drive assembly 1941 to drive, or effect, one or more motions at an end effector 1940. The drive assembly 1941 may include any number of components suitable for transmitting motion to the end effector 1940 such as, for example, one or more linkages, bars, tubes, and/or cables, for example.

One or more of sensors 1938, for example, provide real-time feedback to the processor 1934 about one or more operational parameters monitored during a surgical procedure being performed by the surgical system 1930. The operational parameters can be associated with a user performing the surgical procedure, a tissue being treated, and/or one or more components of the surgical system 1930, for example. The sensor 1938 may comprise any suitable sensor, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

Further to the above, in various arrangements, the sensors 1938 may comprise any suitable sensor for detecting one or more conditions at the end effector 1940 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 1938 may include one or more sensors located at, or about, an articulation joint extending proximally from the end effector 1940. Such sensors may include, for example, a potentiometer, a capacitive sensor (slide potentiometer), piezo-resistive film sensor, a pressure sensor, a pressure sensor, or any other suitable sensor type. In some arrangements, the sensor 1938 may comprise a plurality of sensors located in multiple locations in the end effector 1940.

In certain aspects, the system 1930 includes a feedback system 1952 which includes one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The microcontroller 1933 may be programmed to perform various functions such as precise control over the speed and position of the drive assembly 1941. In one aspect, the microcontroller 1933 may be any single-core or multicore processor such as those known under the trade name ARM Cortex by Texas Instruments. In one aspect, the main microcontroller 1933 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 1933 may be configured to compute a response in the software of the microcontroller 1933. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 1939 includes one or more electric motors and one or more motor drivers. The electric motors can be in the form of a brushed direct current (DC) motor with a gearbox and mechanical links to the drive assembly 1941. In one aspect, a motor driver may be an A3941 available from Allegro Microsystems, Inc.

In various forms, the motor assembly 1939 includes a brushed DC driving motor having a maximum rotational speed of approximately 25,000 RPM. In other arrangements, the motor assembly 1939 may include a brushless motor, a cordless motor, a synchronous motor, a stepper motor, or any other suitable electric motor. The motor driver may comprise an H-bridge driver comprising field-effect transistors (FETs), for example.

The motor assembly 1939 can be powered by a power source 1942. In certain aspects, the power source 1942 includes one or more batteries which may include a number of battery cells connected in series that can be used as the power source to power the motor assembly 1939. In certain circumstances, the battery cells of the power assembly may be replaceable and/or rechargeable. In at least one example, the battery cells can be lithium-ion batteries which can be couplable to and separable from the power assembly.

Further to the above, the end effector 1940 includes a first jaw 1921 and a second jaw 1931. At least one of the first jaw 1921 and the second jaw 1931 is rotatable relative to the other during a closure motion that transitions the end effector 1940 from an open configuration toward a closed configuration. The closure motion may cause the jaws 1921, 1931 to grasp tissue therebetween. In certain arrangements, sensors, such as, for example, a strain gauge or a micro-strain gauge, are configured to measure one or more parameters of the end effector 1940, such as, for example, the amplitude of the strain exerted on the one or both of the jaws 1921, 1931 during a closure motion, which can be indicative of the closure forces applied to the jaws 1921, 1931. The measured strain is converted to a digital signal and provided to the processor 1934, for example. Alternatively, additionally, sensors such as, for example, a load sensor, can measure a closure force and/or a firing force applied to the jaws 1921, 1931.

In various arrangements, a current sensor can be employed to measure the current drawn by a motor of the motor assembly 1939. The force required to advance the drive assembly 1941 can correspond to the current drawn by the motor, for example. The measured force is converted to a digital signal and provided to the processor 1934.

In one form, strain gauge sensors can be used to measure the force applied to the tissue by the end effector 1940, for example. A strain gauge can be coupled to the end effector 1940 to measure the force on the tissue being treated by the end effector 1940. In one aspect, the strain gauge sensors can measure the amplitude or magnitude of the strain exerted on a jaw of an end effector 1940 during a closure motion which can be indicative of the tissue compression. The measured strain is converted to a digital signal and provided to a processor 1934.

The measurements of the tissue compression, the tissue thickness, and/or the force required to close the end effector on the tissue, as respectively measured by the sensors 1938 can be used by the microcontroller 1933 to characterize the selected position of one or more components of the drive assembly 1941 and/or the corresponding value of the speed of one or more components of the drive assembly 1941. In one instance, a memory (e.g. memory 1935) may store a technique, an equation, and/or a look-up table which can be employed by the microcontroller 1933 in the assessment.

The system 1930 may comprise wired or wireless communication circuits to communicate with surgical hubs (e.g. surgical hub 1953), communication hubs, and/or robotic surgical hubs, for example. Additional details about suitable interactions between a system 1930 and the surgical hub 1953 are disclosed in U.S. patent application Ser. No. 16/209,423 entitled METHOD OF COMPRESSING TIS-SUE WITHIN A STAPLING DEVICE AND SIMULTANE-OUSLY DISPLAYING THE LOCATION OF THE TISSUE WITHIN THE JAWS, now U.S. Patent Application Publication No. 2019/0200981, the entire disclosure of which is incorporated by reference in its entirety herein.

In various aspects, the control circuit 1932 can be configured to implement various processes described herein. In certain aspects, the control circuit 1932 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, in certain instances, the control circuit 1932 can be in the form of a combinational logic circuit configured to implement various processes described herein. The combinational logic circuit may comprise a finite state machine comprising a combinational logic configured to receive data, process the data by the combinational logic, and provide an output.

Alternatively, in certain instances, the control circuit 1932 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. In certain instances, the sequential logic circuit may be synchronous or asynchronous. In other instances, the control circuit 1932 may comprise a combination of a processor (e.g., processor 1934) and a finite state machine to implement various processes herein. In other aspects, the finite state machine may comprise a combination of a combinational logic circuit (and the sequential logic circuit, for example.

Figure 14:
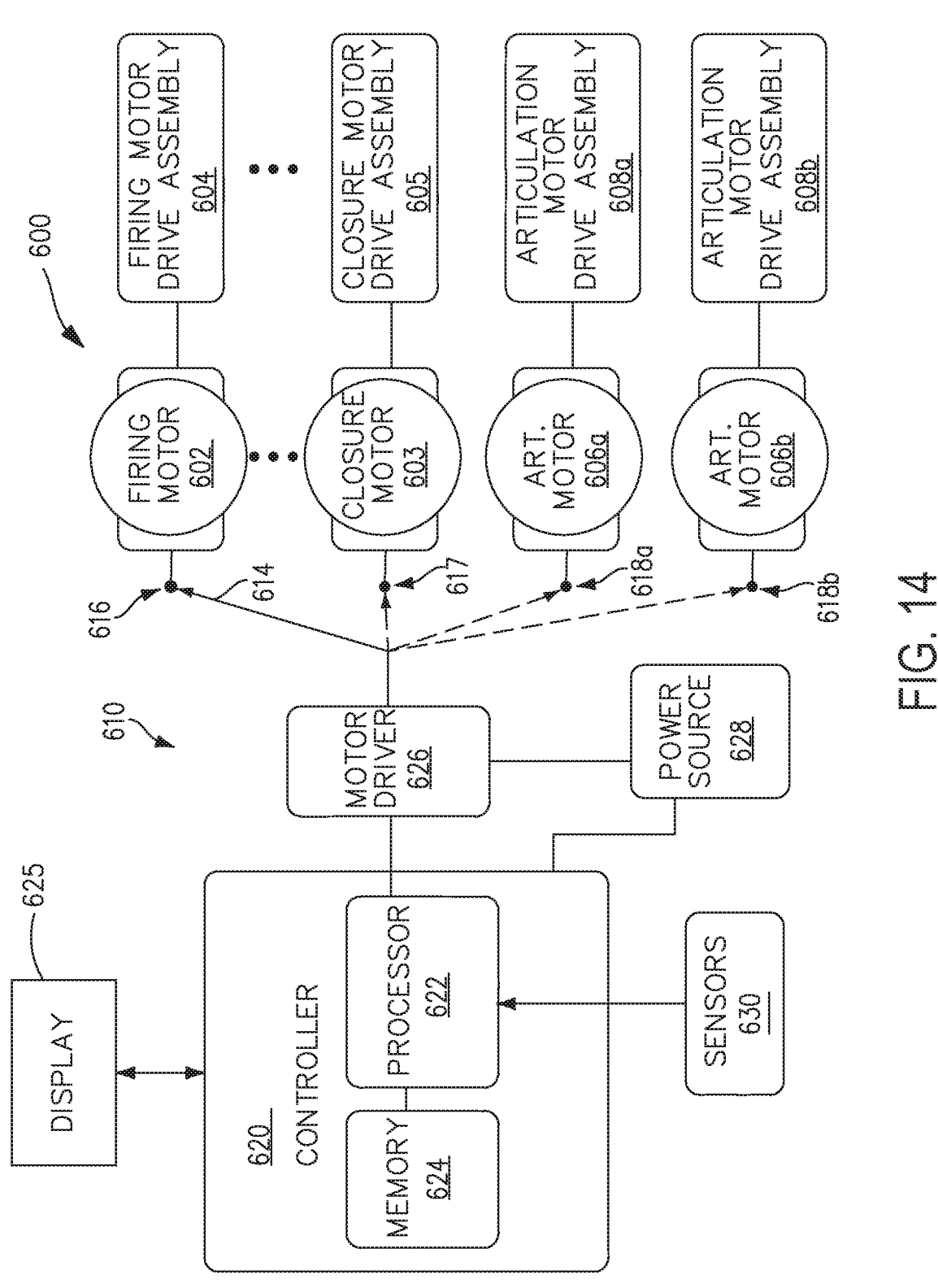
FIG. 14 illustrates a block diagram of a surgical system for use with one or more surgical instruments, tools, and/or robotic systems in accordance with one or more aspects of the present disclosure.

FIG. 14 illustrates a block diagram of a surgical system 600 for use with one or more surgical instruments, tools, and/or robotic systems in accordance with one or more aspects of the present disclosure. The surgical system 600 is similar in many respects to the surgical system 1930, which are not repeated herein at the same of detail for brevity. For example, like the surgical system 1930, the surgical system 600 includes a control circuit comprising a microcontroller 620 comprising a processor 622 and a memory 624, sensors 630, and a power source 628, which are similar, respectively, to the microcontroller 1933, the processor 1934, the memory 1935, and the power source 1942. Additionally, the surgical system 600 includes a plurality of motors and corresponding driving assemblies that can be activated to perform various functions.

In certain instances, a first motor can be activated to perform a first function, a second motor can be activated to perform a second function, a third motor can be activated to perform a third function, a fourth motor can be activated to perform a fourth function, and so on. In certain instances, the plurality of motors can be individually activated to cause firing, closure, and/or articulation motions in an end effector 1940, for example. The firing, closure, and/or articulation motions can be transmitted to the end effector 1940 through a shaft assembly, for example.

In certain instances, the system 600 may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from a staple cartridge into tissue captured by the end effector 1940 and/or the cutting edge of the I-beam element to be advanced to cut the captured tissue, for example. The I-beam element may be retracted by reversing the direction of the motor 602.

In certain instances, the system 600 may include a closure motor 603. The closure motor 603 may be operably coupled to a closure motor drive assembly 605 which can be configured to transmit closure motions, generated by the motor 603 to the end effector 1940, in particular to displace a closure tube to close an anvil and compress tissue between the anvil and the staple cartridge. The closure motions may cause the end effector 1940 to transition from an open configuration to an approximated configuration to grasp tissue, for example. The end effector 1940 may be transitioned to an open position by reversing the direction of the motor 603.

In certain instances, the system 600 may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to a shaft, for example.

As described above, the system 600 may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the system 600 may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 14, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

In one aspect, the amount of compression applied to tissue may impact the desired firing speed of the firing member, such as firing member 1900, during a firing stroke. The amount of time a surgeon chooses to pre-compress tissue prior to firing is a valuable input to a successful firing. Accordingly, it would be beneficial to establish a modifier for the firing speed, or various other firing motion parameters, based on parameters associated with applying compression to the tissue.

In some embodiments, a parameter associated with applying compression can be an elapsed amount of time that an end effector, such as end effector 1300, has been in a clamped state. In some embodiments, the clamped state is defined as a state where the end effector 1300 is in the closed configuration and the closure trigger 1032 is in the actuated position. In other embodiments, the clamped state is defined as a state where the elongate channel 1310 and the anvil 2000 of the end effector 1300 are within a threshold distance of one another. In other embodiments, the clamped state is defined as a state where the closure trigger 1032 has pivoted a threshold distance away from the unactuated position.

In various embodiments, a timer, as an example, is utilized to measure the elapsed amount of time between when the end effector has entered the clamped state and when a user actuates a firing system, such as the firing drive system 1080, of the surgical instrument. In some embodiments, actuation of the firing drive system 1080 is detected when the firing trigger 1130 is pivoted to the actuated position, such as with a position sensor or a Hall-Effect sensor, as examples. In some embodiments, actuation of the firing system is detected when the power source 1090 supplies an electric current or voltage to the motor 1082, as detected by a current sensor or voltage sensor, respectively.

According to the elapsed amount of time measured by the timer, a control system, such as handle circuit board 1100, can set a firing motion parameter of the firing system. In various embodiments, setting a firing motion parameter includes selecting a value for the firing motion parameter from a look-up table, or based on an equation stored in a memory, for example. It should be understood that other embodiments are envisioned where the control system is similar to controller 1933, and includes a processor, such as processor 1934, and a memory, such as memory 1935. Other embodiments are envisioned where the control system is similar to the controller 620, or any other suitable control system described elsewhere herein.

In some embodiments, the firing motion parameter comprises a duty cycle of a motor, such as motor 1082, that drives the firing member. In some embodiments, the firing motion parameter comprises a velocity of the motor. In some embodiments, the firing motion parameter comprises a current supplied to the motor from a power source, such as power source 1090, power source 1942, or power source 628, as examples. In some embodiments, the firing motion parameter comprises a voltage supplied to the motor. In some embodiments, the firing motion parameter comprises a velocity of the firing member. In some embodiments, the firing motion comprises an acceleration of the firing member. In some embodiments, the firing motion parameter comprises a firing force to the firing member. In some embodiments, the firing motion parameter comprises any suitable parameter associated with the firing system described elsewhere herein.

In various embodiments, setting the firing motion parameter of the firing system comprises adjusting a default firing motion parameter according to the elapsed amount of time measured by the timer. In various embodiments, the default firing motion parameter is stored in a memory and retrieved by the control system. In various other embodiments, the default firing motion parameter comprises a user defined default firing motion parameter.

Figure 15:
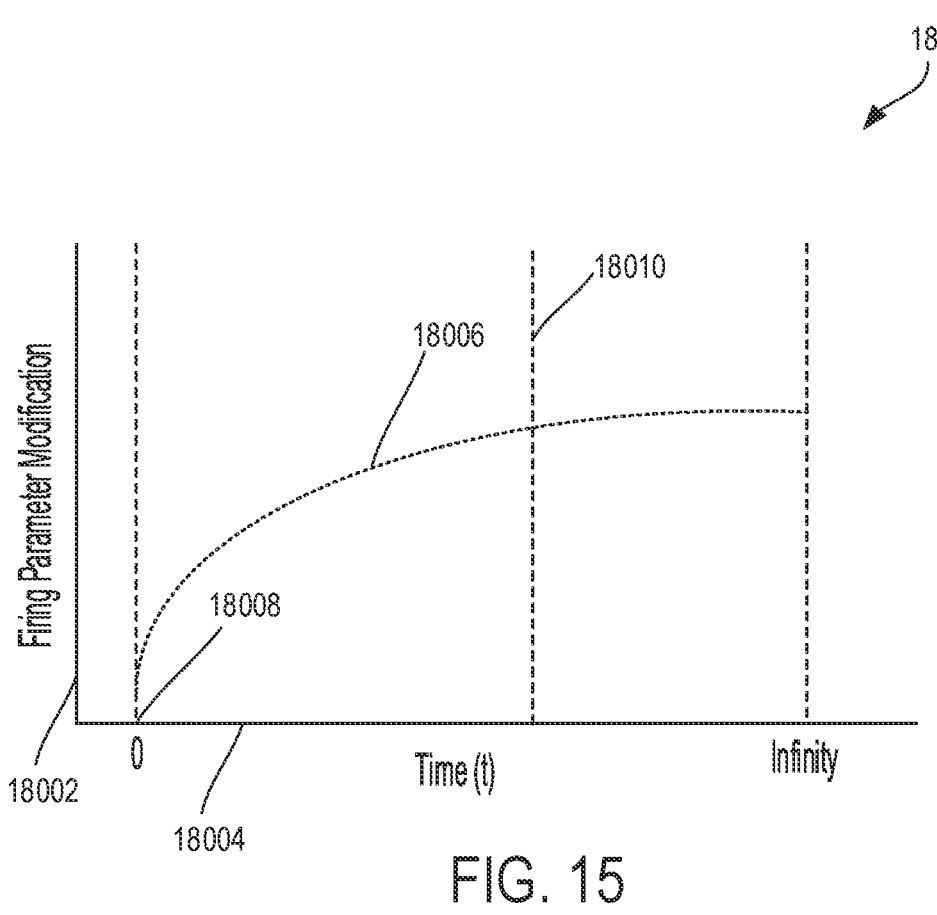
FIG. 15 is a graph that illustrates a firing motion parameter modification of a default firing motion parameter over time, according to at least one aspect of the present disclosure.

Referring now to FIG. 15, a graph 18000 is provided according to at least one aspect of the present disclosure. In various embodiments, aspects of the graph 18000 are stored in a memory, such as memory 1935, and can be retrieved by the control system. For example, one or more portions of the graph 18000 can be stored in the form of one or more equations, look-up tables, and/or any other form suitable for representing the relationship depicted by the graph 18000. As seen in FIG. 15, the graph 18000 illustrates a relationship between a firing motion parameter modification 18002 of the default firing motion parameter and an elapsed time 18004 from which an end effector of a surgical instrument has entered the clamped state. Various techniques can be implemented to measure time lapsed from entry of the clamped state. In one example, once the end effector reaches the clamped state, a timer is initiated. In various instances, as described in greater detail elsewhere in the present disclosure, an end effector of a surgical instrument is operable to grasp tissue between jaws of the end effector. At least one of the jaws can be moved relative to the other jaw toward the clamped state. After attaining the clamped state, a clinician activates a firing system that is responsible for deploying staples into the clamped tissue and, in some instances, advancing a cutting member through the tissue.

Once the control system detects that the firing system has been actuated, the control system identifies a point along a modification curve 18006 of the graph 18000 and adjusts the default firing motion parameter according to the corresponding value from the modification curve 18006. The actuation can, for example, be detected based on one or more sensor readings. For example, the actuation detection can be based on detecting motion a trigger or depression of an actuation button. Additionally, or alternatively, the actuation detection can be based on detecting an initial motion of one or more components of the firing system such as, for example, a firing member, such as firing member 1900.

In some embodiments, the default firing motion parameter can comprise a default duty cycle of a motor, such as motor 1082, as an example. In some embodiments, the default firing motion parameter can comprise a default current supplied to the motor. In some embodiments, the default firing motion parameter can comprise a default voltage applied to the motor. In some embodiments, the default firing motion parameter can comprise a default velocity at which to the motor drives the firing member. Other firing motion parameters are described elsewhere herein. Based on the elapsed length of time measured between the end effector reaching the clamped state and the firing system being actuated, the control system can modify the default firing motion parameter to an adjusted firing motion parameter. In one embodiment, a user can actuate the firing system immediately upon the end effector reaching the clamped state, i.e., at point 18008 on the modification curve 18006. Accordingly, the control system can modify the default firing motion parameter according to the identified value at point 18008 along the modification curve 18006.

In some embodiments, point 18008 corresponds to a value that is less than 1. Utilizing a modifier less than 1 prevents the firing system from driving the firing member at the default parameter, given that the tissue has not been given a sufficient amount of time to relax upon the end effector entering the clamped state. In one embodiment, with a default velocity of $V_1$ and point 18008 corresponding to a value less than 1, the control system causes the motor to drive the firing member at an adjusted velocity of $V_2$ which is less than $V_1$. Accordingly, utilizing the graph 18000 can encourage clinicians to give tissue a sufficient amount of time to relax such that the firing member is not driven using a firing motion parameter that is less than the default firing motion parameter value. Other embodiments are envisioned wherein point 18008 corresponds to a value of 1 or greater than 1.

As can be seen on graph 18000, a threshold 18010 corresponding to a point along modification curve 18006 is provided at which the firing system can be driven using the default firing motion parameter. In some embodiments, the control system can provide feedback to the clinician, such as audible, haptic, visual, or the like, when the threshold 18010 amount of time has been reached or exceed, informing the clinician that a sufficient amount of time has elapsed to allow the default firing motion parameter to be utilized.

In various embodiments, the modification curve 18006 can be represented by an equation defined by:

$$Y=C(A^*\log(t+1)+B)$$

wherein A and B are constants, C is the default firing motion parameter, t is time, and Y is the adjusted firing motion parameter. In various embodiments, constants A and B are stored in a memory and retrievable by the control system. In various embodiments, constants A and B are provided by a user at an input interface. In one aspect, constant B corresponds to the modification value at point 18008. In one embodiment, where constant A is 1, constant B is 0.25, and the default firing motion parameter C is a firing speed of $V_1$, the following look-up table can be stored in the memory:

| Time "t" | Adjusted Firing Speed "Y" |
|----------|---------------------------|
| 0 | $0.25 \, V_1$ |
| 1 | $0.55 \, V_1$ |
| 2 | $0.73 \, V_1$ |
| 3 | $0.85 \, V_1$ |
| 4 | $0.95 \, V_1$ |
| 4.62 (threshold 18010) | $V_1$ |
| 5 | $1.03 \, V_1$ |
| 6 | $1.09 \, V_1$ |

Accordingly, in certain instances, where the firing motion parameter is a firing speed (e.g. speed of a firing member effecting a firing stroke of the firing system), the graph 18000 provides an algorithm that modifies the speed of the firing member according to an elapsed amount of time after the end effector has reached the clamped state. It should be noted that the foregoing equation, values, and table are merely examples representing a manner for performing a dynamic modification of the default parameter. Other equations and/or other suitable forms of representing the dynamic modification over time can be implemented.

In various embodiments, the control system can dynamically adjust the firing motion parameter after the firing system has been actuated. In some embodiments, the control system can continuously adjust the firing motion parameter. In some embodiments, the control system can discretely adjust the firing motion parameter, such as adjusting the firing motion parameter every second or every few seconds. In some embodiments, the firing motion parameter can continue to be adjusted according to the modification curve 18006. In one embodiment utilizing the foregoing table, the firing system is actuated after 4 seconds, which causes the firing system to drive the firing member at an adjusted velocity of $0.95 \, V_1$. One second into the firing stroke, the control system can adjust the adjusted firing speed to $1.03 \, V_1$ (the 5 second point on the foregoing table). Two seconds into the firing stroke, the control system can adjust the firing speed to $1.09 \, V_1$ (the 6 second point on the table). Accordingly, the control system can dynamically adjust the firing motion parameter utilized by the firing system based on an elapsed amount of time that the end effector has been in the clamped state, taking into account the time prior to the firing system being actuated and the time after the firing system has been actuated.

Figure 16:
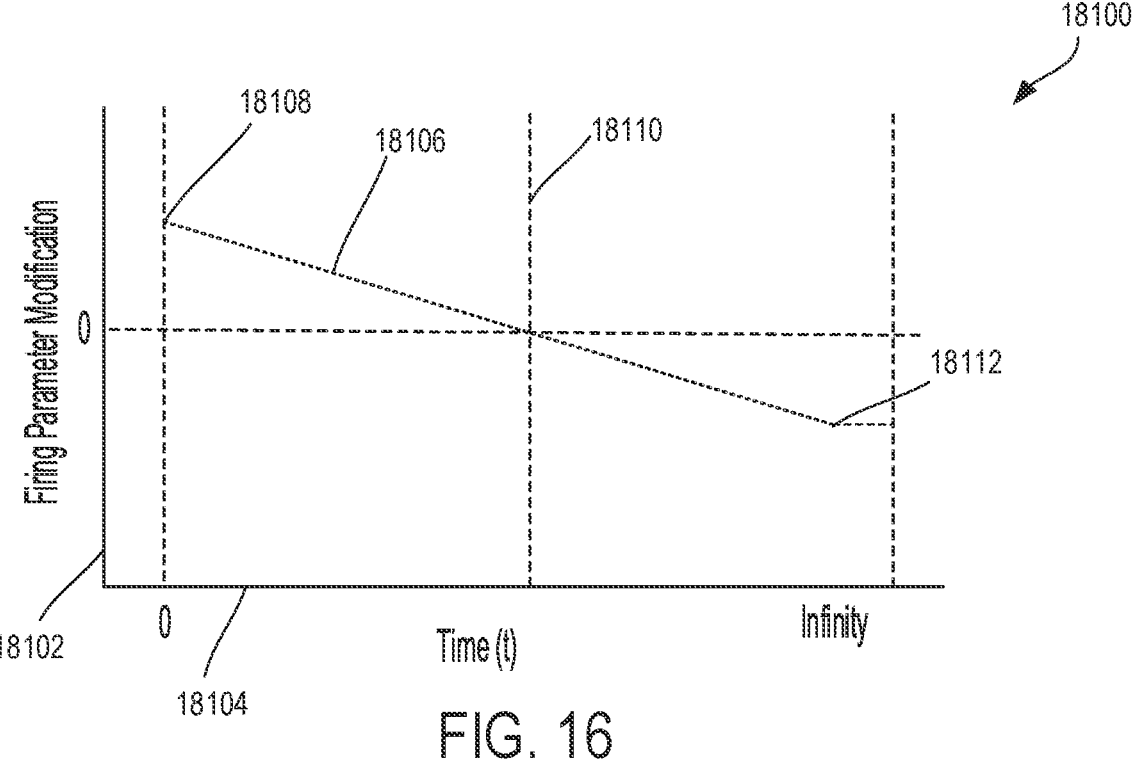
FIG. 16 is a graph that illustrates a firing motion parameter modification of a default firing motion parameter over time, according to at least one aspect of the present disclosure.

Referring now to FIG. 16, a graph 18100 is provided according to at least one aspect of the present disclosure. In various instances, aspects of the graph 18100 can be stored in a memory, such as memory 1935, and can be retrievable by the control system. In various other embodiments, one or more portions of the graph 18100 can be stored in the memory in the form of one or more equations, look-up tables, or any other form suitable for representing the relationship depicted by the graph 18100. As seen in FIG. 16, the graph 18100 illustrates a relationship between a firing motion parameter modification 18102 of the default firing motion parameter and an elapsed time 18104 from which the end effector has entered the clamped state. Various techniques can be implemented to measure time lapsed from entry of the clamped state. In one example, once the end effector reaches the clamped state, a timer is initiated. In various instances, as described in greater detail elsewhere in the present disclosure, an end effector of a surgical instrument is operable to grasp tissue between jaws of the end effector. At least one of the jaws can be moved relative to the other jaw toward the clamped state. After attaining the clamped state, a clinician activates a firing system that is responsible for deploying staples into the clamped tissue and, in some instances, advancing a cutting member through the tissue.

Once the control system detects that the firing system has been actuated, the control system identifies a point along a modification curve 18106 of the graph 18100 and adjusts the default firing motion parameter according to the corresponding value from the modification curve 18006. The actuation can, for example, be detected based on one or more sensor readings. For example, the actuation detection can be based on detecting motion a trigger or depression of an actuation button. Additionally, or alternatively, the actuation detection can be based on detecting an initial motion of one or more components of the firing system such as, for example, a firing member, such as firing member 1900.

In various embodiments, point 18108 corresponds to a value that is greater than 1. In various other embodiments, the point 18108 corresponds to a value of 1. In one embodiment, with a default velocity of $V_1$ and point 18108 corresponding to a 1.5 modification, the control system can cause the motor to drive the firing member at an adjusted velocity of $1.5 \, V_1$. In another embodiment, with a default velocity of $V_1$ and point 18108 corresponding to a 1 modification, the control system can cause the motor to drive the firing member at the default velocity of $V_1$.

As can be seen on graph 18100, the modification curve 18106 has a negative slope, resulting in a diminishing adjusted firing motion parameter over time. In various embodiments where the value at point 18108 is greater than 1, a threshold 18110 is provided along curve where the firing system is be driven using the default firing motion parameter. In some embodiments, the control system can provide feedback to the clinician, such as audible, haptic, visual, or the like, when the threshold 18110 amount of time has been reached or exceed, informing the clinician that a sufficient amount of time has elapsed that will result in the default firing motion parameter to be utilized. In various embodiments, the graph 18100 can include a threshold 18112 where the firing parameter no longer diminishes.

In various embodiments, the modification curve 18106 can be represented by an equation defined by:

$$Y = -A * t + (B + C)$$

wherein A and B are constants, C is the default firing motion parameter, t is time, and Y is the adjusted firing motion parameter. In various embodiments, constants A and B are stored in a memory and retrievable by the control system. In various embodiments, constants A and B are provided by a user at an input interface. In one embodiment where point 18108 is desired to be the default firing motion parameter, C is equal to 0. In one embodiment where constant A is 2, constant B is 6, and the default firing motion parameter C is a firing speed of $V_1$, the following look-up table can be stored in the memory:

| Time "t" | Adjusted Firing Speed "Y" |
|----------|---------------------------|
| 0 | $V_1 + 6$ |
| 1 | $V_1 + 4$ |
| 2 | $V_1 + 2$ |
| 3 (threshold 18110) | $V_1$ |
| 4 | $V_1 - 2$ |
| 5 | $V_1 - 4$ |
| 6 | $V_1 - 6$ |
| 7 | $V_1 - 8$ |

Accordingly, the foregoing graph 18100 provides an algorithm that decreases the speed of the firing member according to an elapsed amount of time after the end effector has reached the clamped state. It should be noted that the foregoing equation, values, and table are merely examples representing a manner for performing a dynamic modification of the default parameter. Other equations and/or other suitable forms of representing the dynamic modification over time can be implemented.

In various embodiments, the control system can dynamically adjust the firing motion parameter after the firing system has been actuated. In some embodiments, the control system can continuously adjust the firing motion parameter. In some embodiments, the control system can discretely adjust the firing motion parameter, such as adjusting the firing motion parameter every second or every few seconds. In some embodiments, the firing motion parameter can continue to be adjusted according to the modification curve 18106 on graph. In one embodiment utilizing the foregoing table, the firing system is actuated after 4 seconds, which causes the firing system to drive the firing member at an adjusted velocity of $V_1-2$. One second into the firing stroke, the control system can adjust the adjusted firing speed to $V_1-4$ (the 5 second point on the table). Two seconds into the firing stroke, the control system can adjust the firing speed to $V_1-6$ (the 6 second point on the table). Accordingly, the control system can dynamically adjust the firing motion parameter utilized by the firing system based on an elapsed amount of time that the end effector has been in the clamped state, taking into account the time prior to the firing system being actuated and the time after the firing system has been actuated.

In various embodiments, the control system can utilize a different graph/look-up table after the firing system has been actuated. In one embodiment utilizing the foregoing table, the firing system is actuated after 4 seconds, which causes the firing system to drive the firing member at an adjusted velocity of $V_1-2$. Once the firing system has been actuated, the control system can utilize a different graph/look-up table, such as graph 18000. Utilizing the example graph from above, one second into the firing stroke, the control system can adjust the adjusted firing speed to $1.03\ V_1$ (the 5 second point on the example table in connection with graph 18000). Accordingly, the control system can switch between a diminishing and increasing firing motion parameter adjustment.

In various other embodiments, a graph and/or look-up take is provided according to a modification curve that is parabolic. In various other embodiments, a graph and/or look-up take is provided according to a modification curve that is exponential. In various other embodiments, a graph and/or look-up take is provided that is represented by $Y=A*\sqrt{t}+B$ where A and B are constants, t is time, and Y is the adjusted firing motion parameter. Various other equations and/or other suitable forms of representing the dynamic modification over time can be implemented.

Referring now to FIG. 17, a method 18200 for controlling a surgical instrument is provided, according to at least one aspect of the present disclosure. The method 18200 comprises detecting 18202, at a first time point, an end effector of a surgical instrument reaching a clamped state. In one embodiment, the circuit board 1100 detects when the end effector 1300 reaches the clamped state using a position sensor that can sense when the closure trigger 1032 has reached the actuated position. In one embodiment, the circuit board 1100 detects when the end effector 1300 reaches the clamped state using a Hall-Effect sensor that can sense when the anvil 2000 is within a threshold distance from the elongate channel 1310. In various embodiments, the circuit board 1100 detects when the end effector 1300 reaches the clamped state using any number of sensors that detect the position of components associated with the closure system 3000, such as a position of the closure shuttle 1250, a position of the closure link 1038, or a position of the distal closure tube segment 3030, as examples.

The method 18200 further comprises detecting 18204, at a second time point, the actuation of a firing system of the surgical instrument. In one example embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18200 further comprises setting 18206 a firing motion parameter of the firing system based on an elapsed time from the first time point to the second time point. In various embodiments, the circuit board 1100 can measure, using a timer, an elapsed length of time that has transpired between the end effector 1300 reaching the clamped state and the actuation of the firing drive system 1080. In some embodiments, the circuit board 1100 can retrieve the firing motion parameter from a look-up table stored in a memory, such as memory 1935, according to the elapsed length of time. In some embodiments, the circuit board 1100 can retrieve a modification value from a graph or look-up table, such as graphs 18000, 18100, stored in a memory according to the elapsed length of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18200 further comprises driving 18208 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18200 provides the clinician with the freedom to choose how long they wish to maintain the end effector in the clamped state prior to actuating the firing system. Based on an elapsed amount of time in the clamped state, the control system will automatically select an appropriate firing motion parameter for the firing system. In one aspect, "automatically" refers to the control system's ability to select a firing motion parameter without a user input.

In various embodiments, the method 18200 optionally further comprises dynamically adjusting 18210 the firing motion parameter during the firing stroke based an elapsed time from the first time point to a current time point. In some embodiments, the circuit board 1100 can measure, using a timer, an elapsed amount of time, from the end effector reaching the clamped state to a current time point during the firing stroke and dynamically adjust the firing motion parameter. In one embodiment, a user can maintain the end effector in the clamped state for 5 seconds before actuating the firing system and the circuit board 1100 can set the firing motion parameter according to a value corresponding to being in the clamped state at 5 seconds found in a look-up table. During the firing stroke, such as 3 seconds into the firing stroke, as an example, the control system can look to the same look-up table, or a different look-up table, and the corresponding value to being in the clamped state for 8 seconds (5 seconds prior to actuation of the firing system plus 3 seconds into the firing stroke). Accordingly, the control system can dynamically adjust the firing motion parameter according to an elapsed length of time that the tissue has been clamped by the end effector.

In another embodiment, a user can maintain the end effector in the clamped state for 5 seconds before actuating the firing system and the circuit board 1100 can set the firing motion parameter according to a modification value corresponding to being in the clamped state at 5 seconds, such as a modification value determined from FIG. 15 or 16. During the firing stroke, such as 3 seconds into the firing stroke, the control system can look to the same graphs (FIG. 15 or FIG. 16) and the corresponding modification value to being in the clamped state for 8 seconds (5 seconds prior to actuation of the firing system plus 3 seconds into the firing stroke). Accordingly, the control system can continuously adjust the firing motion parameter according to an elapsed length of time that the tissue has been clamped by the end effector utilizing the modification curves.

In some scenarios, a clinician may transition the end effector to the clamped state to clamp onto tissue. After a period of time, the clinician may decide that they wish to reposition the end effector at a different location on the tissue, or the clinician unintentionally, or intentionally, eases their grip on a closure actuator. Therefore, the clinician transitions the end effector from the clamped state toward an unclamped state and reclamps the tissue at the new location. As the tissue had already been clamped prior to the clinician repositioning the tissue, less clamping time may be required to allow the tissue to sufficiently relax before performing a firing stroke. Accordingly, an algorithm is desired that accounts for a clinician unclamping and reclamping onto tissue, such as unclamping and reclamping onto the same tissue that had already been given the opportunity to relax.

Figure 18:
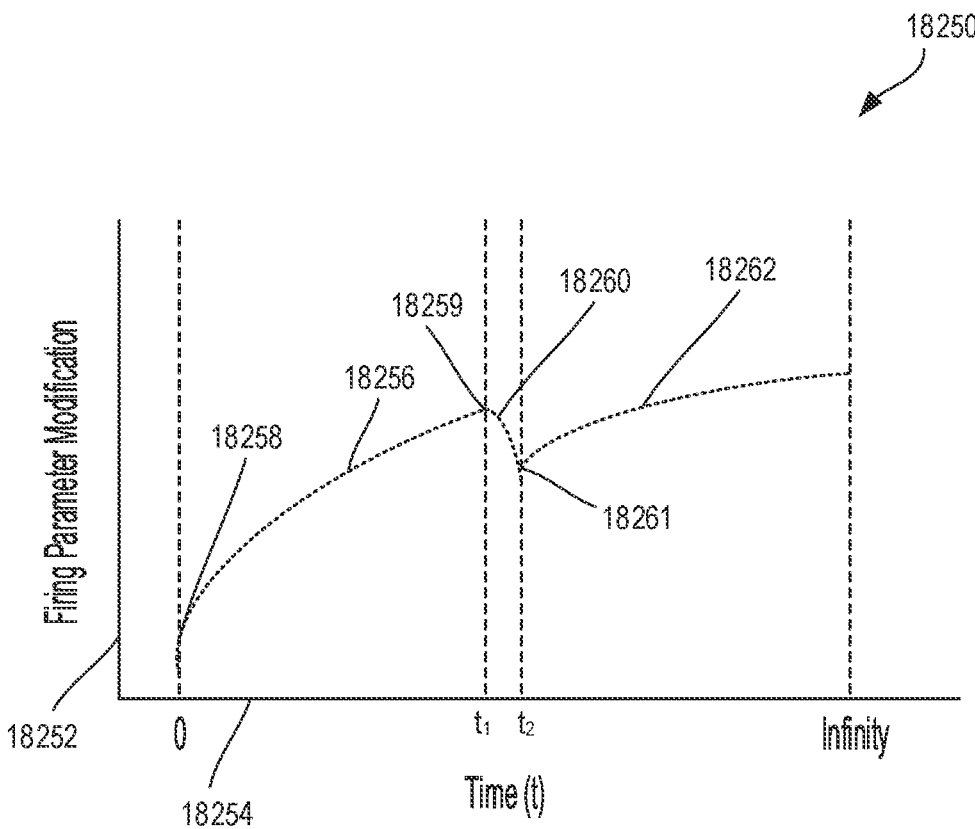
FIG. 18 is a graph that illustrates a firing motion parameter modification of a default firing motion parameter over time, according to at least one aspect of the present disclosure.

Referring now to FIG. 18, a graph 18250 generated by an algorithm is provided according to at least one aspect of the present disclosure. In various instances, the algorithm can be stored in a memory, such as memory 1935, and can be executed by a processor, such as processor 1934. As seen in FIG. 18, the graph 18250 illustrates a relationship between a firing motion parameter modification 18252 of the default firing motion parameter and an elapsed time 18254 from which the end effector has entered the clamped state, taking into account elapsed time that the end effector transitions out of and returns to the clamped state, as will be described in more detail below.

In operation, when a user transitions the end effector to the clamped state, a timer is initiated. In addition, the algorithm implements a first modification curve to track a firing motion parameter modification that will be implemented to a default firing motion parameter to produce an adjusted firing motion parameter. In various embodiments, the first modification curve is represented by an equation, such as a linear equation, a logarithmic equation, a parabolic equation, a $\sqrt{t}$ equal, or any other suitable equation. Referring to FIG. 18, when the control system detects the end effector reaching the clamped state, i.e., point 18258, the control system initiates a timer and a first modification curve 18256 to track a firing motion parameter modification to the default firing motion parameter. In one embodiment, if a user actuates the firing system, the control system will identify a corresponding point along modification curve

18256 according to the determined elapsed time that will be used to modify the default firing motion parameter.

At a point in time after the end effector reaches the clamped state, but before the firing system is actuated, a user may choose to temporarily transition the end effector out of the clamped state to reposition the end effector. Accordingly, the control system detects the end effector transitioning out of the clamped state and implements a second modification curve different from the first modification curve. In various embodiments, the second modification curve is represented by an equation, such as a linear equation, a logarithmic equation, a parabolic equation, a $\sqrt{t}$ equal, or any other suitable equation.

In some embodiments, the control system detects the end effector 1300 transitioning out of the clamped state using a position sensor that can sense when the closure trigger 1032 has moved away from the actuated position. In one embodiment, the control system detects the end effector 1300 transitioning out of the clamped state using a Hall-Effect sensor that can sense when the anvil 2000 has moved a threshold distance from the elongate channel 1310. In various embodiments, the control system detects the end effector 1300 transitioning out of the clamped state using any number of sensors that detect the position of components associated with the closure system 3000, such as a position of the closure shuttle 1250, a position of the closure link 1038, or a position of the distal closure tube segment 3030, as examples.

In one embodiment, referring to FIG. 18, at time $t_1$, the control system detects the end effector transitioning out of the clamped state at point 18259 on the first modification curve 18256. Based on the detection, the control system can initiate a second timer to measure how long the end effector is out of the clamped state, as well as implement a second modification curve 18260. As seen in FIG. 18, the second modification curve 18260 adjusts the value associated with the modification point 18259 from the point along the first modification curve 18256 at the time of the end effector transitioning out of the clamped state. In some embodiments, the second modification curve 18260 can be a negative modification curve, thereby lowering the adjustment to the default firing motion parameter that was provided by the first modification curve 18256. In various other embodiments, the second modification curve 18260 can be a positive modification curve, thereby increasing the adjustment to the default firing motion parameter when the first modification curve was a diminishing modification curve, similar to modification curve 18106. It should be understood that the firing system cannot be actuated while the second modification curve 18260 is being implemented, as the end effector is not within the clamped state.

At a point in time after the end effector transitions out of the clamped state, the end effector can be returned to the clamped state. Accordingly, the control system detects the end effector returning to the clamped state and implements a third modification curve different from the second modification curve. In various embodiments, the third modification curve can be the same as the first modification curve. In various embodiments, the third modification curve can be different from the first modification curve. In various embodiments, the third modification curve is represented by an equation, such as a linear equation, a logarithmic equation, a parabolic equation, a $\sqrt{t}$ equal, or any other suitable equation.

In one embodiment, referring to FIG. 18, at time $t_2$, the control system detects the end effector returning to the clamped state at point 18261 on the second modification curve 18260. Based on the detection, the control system can initiate a third timer to measure how long the end effector is in the clamped state, as well as implement a third modification curve 18262. As seen in FIG. 18, the third modification curve 18262 adjusts the value associated with the modification point 18261 from the point along the second modification curve 18260 at the time of the end effector returning to the clamped state. In one embodiment, if a user actuates the firing system, the control system will identify a point along the third modification curve 18262 according to the determined elapsed time that will be used to modify the default firing motion parameter.

Accordingly, the foregoing algorithm allows a clinician to transition the end effector into and out of the clamped state without entirely resetting the amount of time required to clamp tissue and receive the benefits of the firing motion parameter modification. The algorithm accounts for the time that the end effector is out of the clamped state, while also accounting for the time that the end effector has already clamped onto the tissue. It should be understood that the graph 18250 provided is merely exemplary and can be different depending on the number of times a user transitions the end effector into and out of the clamped state, the amount of time that the end effector is out of the clamped state, and if the end effector is transitioned to the unclamped state at all. In a scenario where the end effector is not transitioned to the unclamped state after point 18258, the algorithm will merely implement the first modification curve, such as first modification curve 18256, when determining the firing motion parameter modification to use when the firing system is actuated.

Referring now to FIG. 19, a method 18300 for controlling a surgical instrument is provided, according to at least one aspect of the present disclosure. The method 18300 comprises detecting 18302, at a first time point, an end effector of a surgical instrument reaching a clamped state. In one embodiment, the circuit board 1100 detects when the end effector 1300 reaches the clamped state using a position sensor that can sense when the closure trigger 1032 has reached the actuated position. In one embodiment, the circuit board 1100 detects when the end effector 1300 reaches the clamped state using a Hall-Effect sensor that can sense when the anvil 2000 is within a threshold distance from the elongate channel 1310. In various embodiments, the circuit board 1100 detects when the end effector 1300 reaches the clamped state using any number of sensors that detect the position of components associated with the closure system 3000, such as a position of the closure shuttle 1250, a position of the closure link 1038, or a position of the distal closure tube segment 3030, as examples.

The method 18300 further comprises detecting 18304, at a second time point, the end effector of the surgical instrument transitioning out of the clamped state. In one embodiment, the control system detects the end effector 1300 transitioning out of the clamped state using a Hall-Effect sensor that can sense when the anvil 2000 has moved a threshold distance from the elongate channel 1310. In various embodiments, the control system detects the end effector 1300 transitioning out of the clamped state using any number of sensors that detect the position of components associated with the closure system 3000, such as a position of the closure shuttle 1250, a position of the closure link 1038, or a position of the distal closure tube segment 3030, as examples.

The method 18300 further comprises detecting 18306, at a third time point, the end effector returning to the clamped state. In various embodiments, the control system can detect the end effector returning to the clamped state using the various sensors described above with respect to block 18302.

The method 18300 further comprises detecting 18308, at a fourth time point, the actuation of a firing system of the surgical instrument. In one example embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current being supplied to the motor 1082 from the power source 1090 via a current sensor.

The method 18300 further comprises setting 18310 a firing motion parameter of the firing system based on a first elapsed time from the first time point to the second time point, a second elapsed time from the second time point to the third time point, and a third elapsed time from the third time point to the fourth time point. In various embodiments, the circuit board 1100 can measure, using a timer, an elapsed length of time that has transpired from the first time point to the second time point, the second time point to the third time point, and the third time point to the fourth time point. In some embodiments, the circuit board 1100 can retrieve the firing motion parameter from a look-up table stored in a memory, such as memory 1935, according to the elapsed lengths of time. In some embodiments, the circuit board 1100 can implement an algorithm, such as the algorithm discussed above with respect to graph 18250, to determine a modification value that can be used to adjust a default firing motion parameter.

In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18300 further comprises driving 18312 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18300 provides the clinician with the freedom to choose how long they wish to maintain the end effector in the clamped state prior to actuating the firing system, while also enabling the clinician to unclamp and reclamp the tissue without a modification accumulated from a first modification curve being completely ignored. Based on the elapsed amounts of time, the control system will automatically select an appropriate firing motion parameter for the firing system. In one aspect, "automatically" refers to the control system's ability to select a firing motion parameter without a user input.

In various embodiments, the method 18300 optionally further comprises dynamically adjusting 18314 the firing motion parameter during the firing stroke based an elapsed time from the first time point to a current time point. In some embodiments, the circuit board 1100 can measure, using a timer, an elapsed amount of time, from the end effector reaching the clamped state to a current time point during the firing stroke and dynamically adjust the firing motion parameter. In one embodiment, referring to FIG. 18, in a scenario where a clinician actuates the firing system after time $t_2$, the control system can continue to modify the firing motion parameter during the firing stroke according to the third modification curve 18262. Accordingly, the control system can dynamically adjust the firing motion parameter according to an elapsed length of time that the tissue has been clamped by the end effector utilizing the modification curve.

As referenced above, the amount of compression applied to tissue may impact the desired firing speed of the firing member, such as firing member 1900, during a firing stroke. As an end effector, such as end effector 1300, is transitioned from an open state toward a clamped state, the end effector can reach a partially clamped state. In one aspect, a partially clamped state is defined as a state between the open state and the clamped state where the end effector makes initial contact with the tissue positioned therein. In one aspect, a partially clamped state is defined as a state where the anvil of the end effector is within a threshold distance of the elongate channel of the end effector. In one aspect, a partially clamped state is defined as a state wherein the closure trigger has moved a threshold amount toward the actuated state from the unactuated state. In one aspect, a partially clamped state is defined as a state wherein a firing member responsible for the closure of the end effector has moved a threshold linear distance.

In the partially clamped state, the end effector can begin to apply pressure to the tissue positioned therein, which can cause fluid within the tissue to begin to egress, before the end effector has reached the clamped state. Once the end effector has reached the clamped state, the fluid within the tissue can continue to egress from the tissue positioned between the anvil and the elongate channel of the end effector, further stabilizing the tissue in preparation for stapling and, optionally, cutting. Accordingly, a desired firing speed of the firing member can be dependent upon, among other things, factors that influence tissue stabilization.

Figure 20:
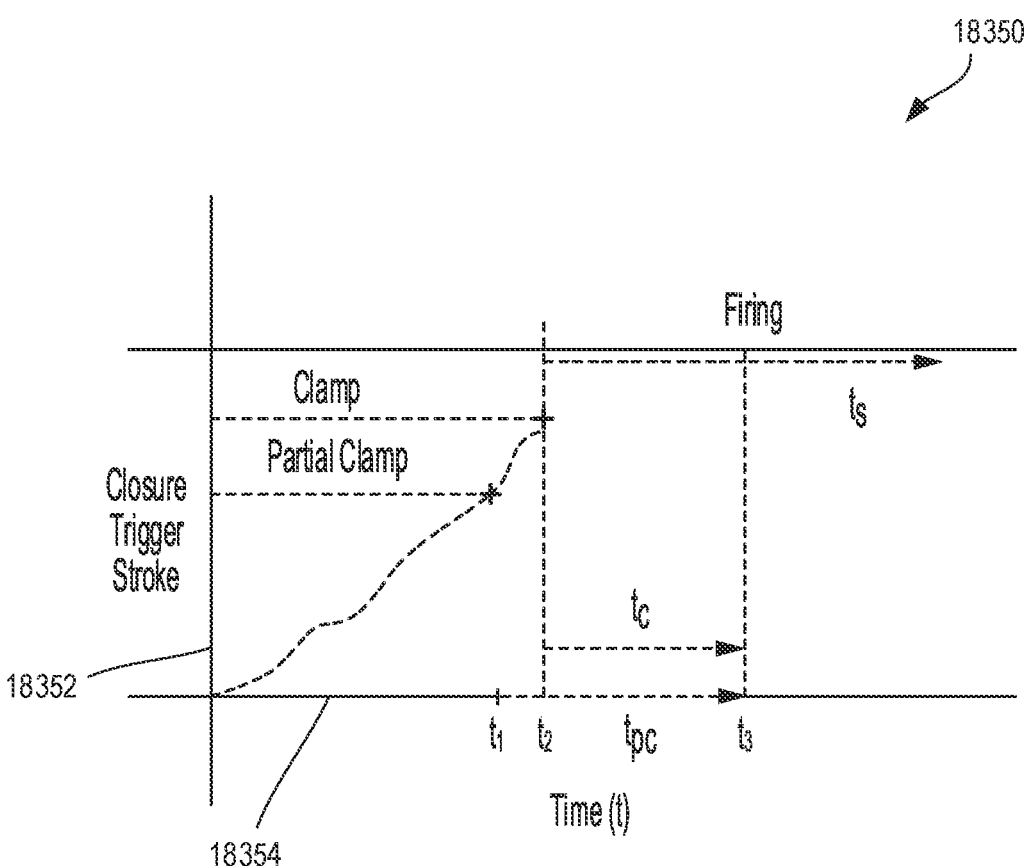
FIG. 20 is a graph that illustrates a closure trigger stroke over time, according to at least one aspect of the present disclosure.

Referring now to FIG. 20, a graph 18350 is provided according to at least one aspect of the present disclosure that illustrates a closure trigger stroke 18352 against time 18354. As shown at to, the closure trigger, such as closure trigger 1032, is in an unactuated position. In one aspect, the unactuated position of the closure trigger can correspond to the open state of the end effector, such as end effector 1300. In some embodiments, the position of the closure trigger can be monitored by a control system, such as by circuit board 1100, using any number of sensors described elsewhere herein.

From $t_0$ to $t_1$, the closure trigger is pivoted from the unactuated position toward the actuated position, which causes the end effector to transition from the open state toward the clamped state. At $t_1$, the end effector reaches a partially clamped state, which, as described above, can be a state where the end effector makes initial contact with the tissue within the end effector. In some embodiments, the end effector can include a pressure sensor that can detect the initial contact with the tissue as the end effector transitions toward the clamped state. In various embodiments, the inflection point of the load curve is used as a tissue contact or tissue compression initiation point. Upon detection of the end effector reaching the partially clamped state, the control system can initiate a timer to measure an amount of time that the end effector is within the partially clamped state $t_{pc}$ prior to a firing system, such as firing drive system 1080, being actuated. In one aspect, determining the inflection of tissue load versus. a time curve (tissue creep stabilization) could be used to determine the time of tissue stability or completed tissue compression.

In various other embodiments, the closure system can comprise a motor-driven closure system, such as closure motor drive assembly 605, with a closure motor, such as closure motor 603. With the motor driven closure system, the control system can determine the initial tissue contact by monitoring the current provided to the closure motor as a way of determining the magnitude of the clamping load on the jaw of the end effector. In one aspect, a spike in current provided to the closure motor indicates initial tissue contact, which can be indicative of the end effector reaching the partially clamped state.

From $t_1$ to $t_2$, the closure trigger can continue to pivot toward the actuated state, which continues to drive the end effector toward the clamped state. As the end effector transitions toward the clamped state, the anvil of the end effector can apply pressure to the tissue captured within the end effector, forcing fluid within the tissue to egress away and prepare the tissue for being cut and stapled.

At $t_2$, the closure trigger reaches the actuated state, which corresponds to the end effector reaching the clamped stated. In various embodiments, the control system can detect the closure trigger reaching the actuated position and/or the end effector reaching the clamped state utilizing various sensors as described elsewhere herein. Once the end effector reaches the clamped state, the control system can initiate a second timer to measure an amount of time that the end effector is within the clamped state $t_c$ prior to the firing system being actuated.

From $t_2$ to $t_3$, the end effector is maintained in the clamped state to allow for fluid within the tissue to egress away, further stabilizing the tissue prior to cutting and stapling the tissue. In one aspect, the control system can monitor this tissue creep by monitoring the amount of pressure applied by the end effector to the tissue over time. In one aspect, after the end effector reaches the clamped state, pressure detected by the pressure sensor can continuously diminish owing to the fluid moving away from the tissue clamped within the end effector. The control system can determine when the tissue within the end effector has stabilized by monitoring this change in pressure over time. In some embodiments, the tissue can be stabilized when the pressure change over time detected by the pressure sensor is substantially zero. In some embodiments, the tissue can be stabilized when the pressure change over time is less than a threshold rate of change over time. In some embodiments, the control system can determine that the tissue has stabilized after a threshold amount of time has passed after the end effector has reached the clamped state. In some embodiments, the control system can determine that the tissue has stabilized after a threshold amount of time has passed after the end effector has reached the partially clamped state.

At $t_3$, the control system can detect the actuation of the firing system. In some embodiments, the control system detects actuation of the firing system by detecting the firing trigger 1130 being pivoted to the actuated position. In some embodiments, the control system detects actuation of the firing system by detecting the power source 1090 providing a current or voltage to the motor 1082. Other embodiments of how the control system can detect actuation of the firing system are described elsewhere herein. Upon detecting actuation of the firing system, the control system can set a firing motion parameter of the firing system based upon a variety of factors measured by the control system from $t_0$ to $t_3$. In various embodiments, the firing motion parameter can be based on an elapsed time between $t_1$ and $t_2$, an elapsed time from $t_2$ to $t_3$, or combinations thereof.

In various embodiments, after setting the firing motion parameter of the firing system, the control system can drive the firing member through a firing stroke with the firing system using the firing motion parameter. In some embodiments, the firing system can control the motor to drive the firing member through the firing stroke using the firing motion parameter. In one embodiment, the firing motion parameter comprises a current supplied to the motor. In one embodiment, the firing motion parameter comprises a voltage supplied to the motor. In one embodiment, the firing motion parameter comprises a duty cycle of the motor. In one embodiment, the firing motion parameter comprises a velocity of the motor. In one embodiment, the firing motion parameter comprises a velocity of the firing member. Other exemplary firing motion parameters are described elsewhere herein.

In various embodiments, during the firing stroke, the control system can dynamically adjust the firing motion parameter. In one aspect, the control system can continue to monitor stabilization of the tissue and adjust the firing motion parameter as the tissue becomes more stable. In some embodiments, the control system dynamically adjusts the firing motion parameter based on an elapsed time from $t_1$ to a current time point of the firing stroke. In some embodiments, the control system dynamically adjusts the firing motion parameter based on an elapsed time from $t_2$ to a current time point of the firing stroke, i.e., the tissue stabilization time $t_s$. In some embodiments, the control system dynamically adjusts the firing motion parameter based on an elapsed time from $t_3$ to a current time point of the firing stroke. In some embodiments, the control system dynamically adjusts the firing motion parameter based on elapsed times from $t_1$, $t_2$, and $t_3$ to a current time point of the firing stroke. Accordingly, the firing motion parameter is dynamically adjusted during the firing stroke as the tissue becomes more stable.

Figure 21:
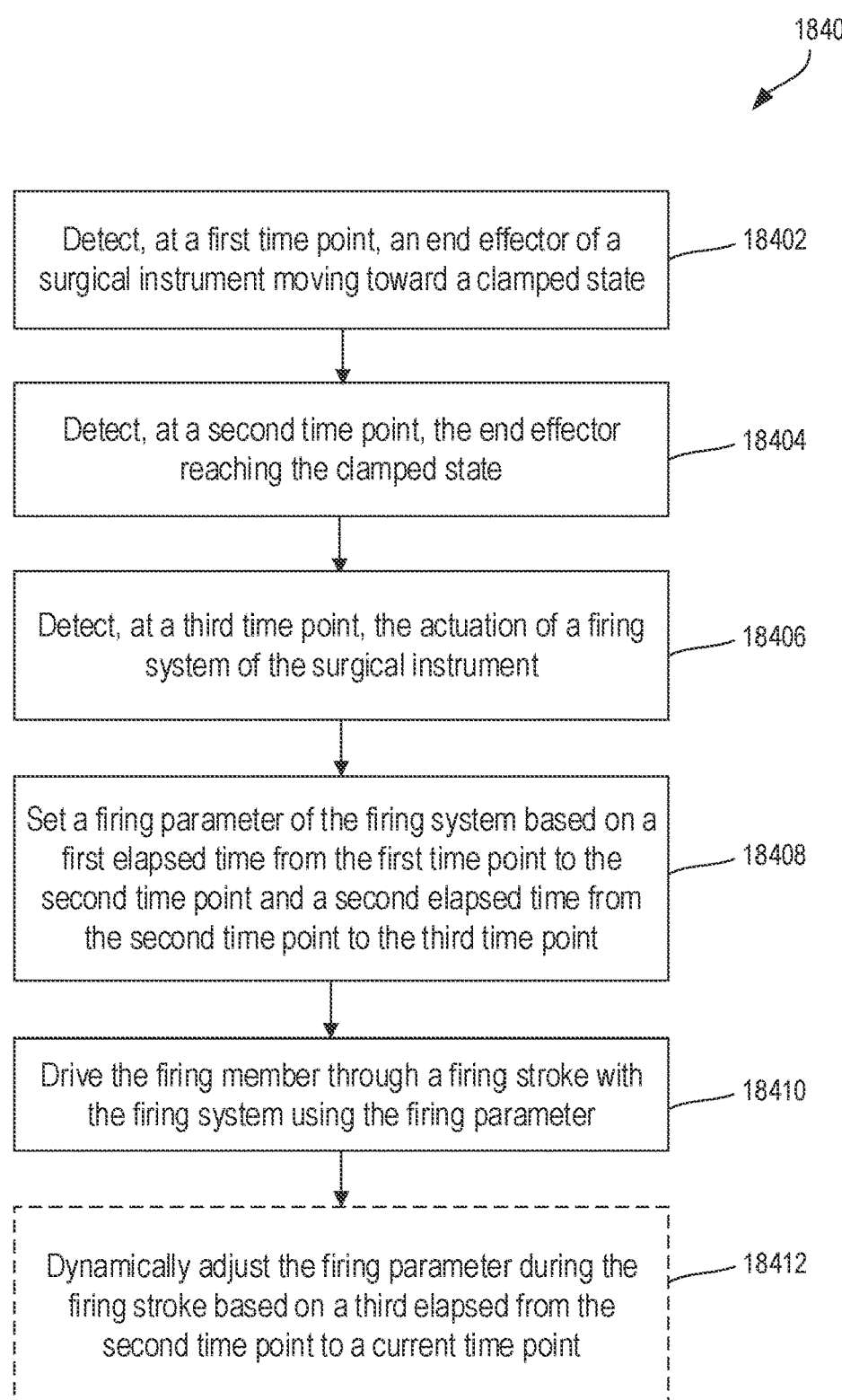
FIG. 21 illustrates a method for controlling a surgical instrument, according to at least one aspect of the present disclosure.

Referring now to FIG. 21, a method 18400 for controlling a surgical instrument is provided, according to at least one aspect of the present disclosure. The method 18400 comprises detecting 18402, at a first time point, an end effector of a surgical instrument moving toward a clamped state. In one embodiment, the circuit board 1100 detects the end effector 1300 moving toward the clamped state using a position sensor that can sense when the closure trigger 1032 is moving toward the actuated position. In one embodiment, the circuit board 1100 detects when the end effector 1300 moves toward the clamped state using a Hall-Effect sensor that can sense the anvil 2000 moving relative to the elongate channel 1310. In various embodiments, the circuit board 1100 detects when the end effector moves toward the clamped state using any number of sensors that detect the position of components associated with the closure system 3000, such as a position of the closure shuttle 1250, a position of the closure link 1038, or a position of the distal closure tube segment 3030, as examples.

The method 18400 further comprises detecting 18404, at a second time point, the end effector reaching the clamped state. In various embodiments, the control system can detect the end effector reaching the clamped state using various sensors described elsewhere herein.

The method 18400 further comprises detecting 18406, at a third time point, the actuation of a firing system of the surgical instrument. In one example embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18400 further comprises setting 18408 a firing motion parameter of the firing system based on a first elapsed time from the first time point to the second time point and a second elapsed time from the second time point to the third time point. In various embodiments, the circuit board 1100 can measure, using a timer, the elapsed lengths of time that has transpired from when the end effector began to move toward the clamped state, reached the clamped state, and when the firing system was actuated. In some embodiments, the circuit board 1100 can retrieve the firing motion parameter from a look-up table stored in a memory, such as memory 1935, according to the elapsed lengths of time. In some embodiments, the circuit board 1100 can retrieve a modification value from a graph or look-up table according to the elapsed lengths of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18400 further comprises driving 18410 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18400 provides the clinician with the freedom to choose how fast or slow they wish to transition the end effector to the clamped state and how long to maintain the end effector in the clamped state prior to actuating the firing system. In one aspect, closure speed acts as both effectively a portion of the clamped timing and since tissue is viscoelastic, also the tissue compression magnitude magnifier. Based on the elapsed amounts of time, the control system will automatically select an appropriate firing motion parameter for the firing system. In one aspect, "automatically" refers to the control system's ability to select a firing motion parameter without a user input.

In various embodiments, the method 18400 optionally further comprises dynamically adjusting 18412 the firing motion parameter during the firing stroke based an elapsed time from the second time point to a current time point. In some embodiments, the circuit board 1100 can measure, using a timer, an elapsed amount of time, from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

Figure 22:
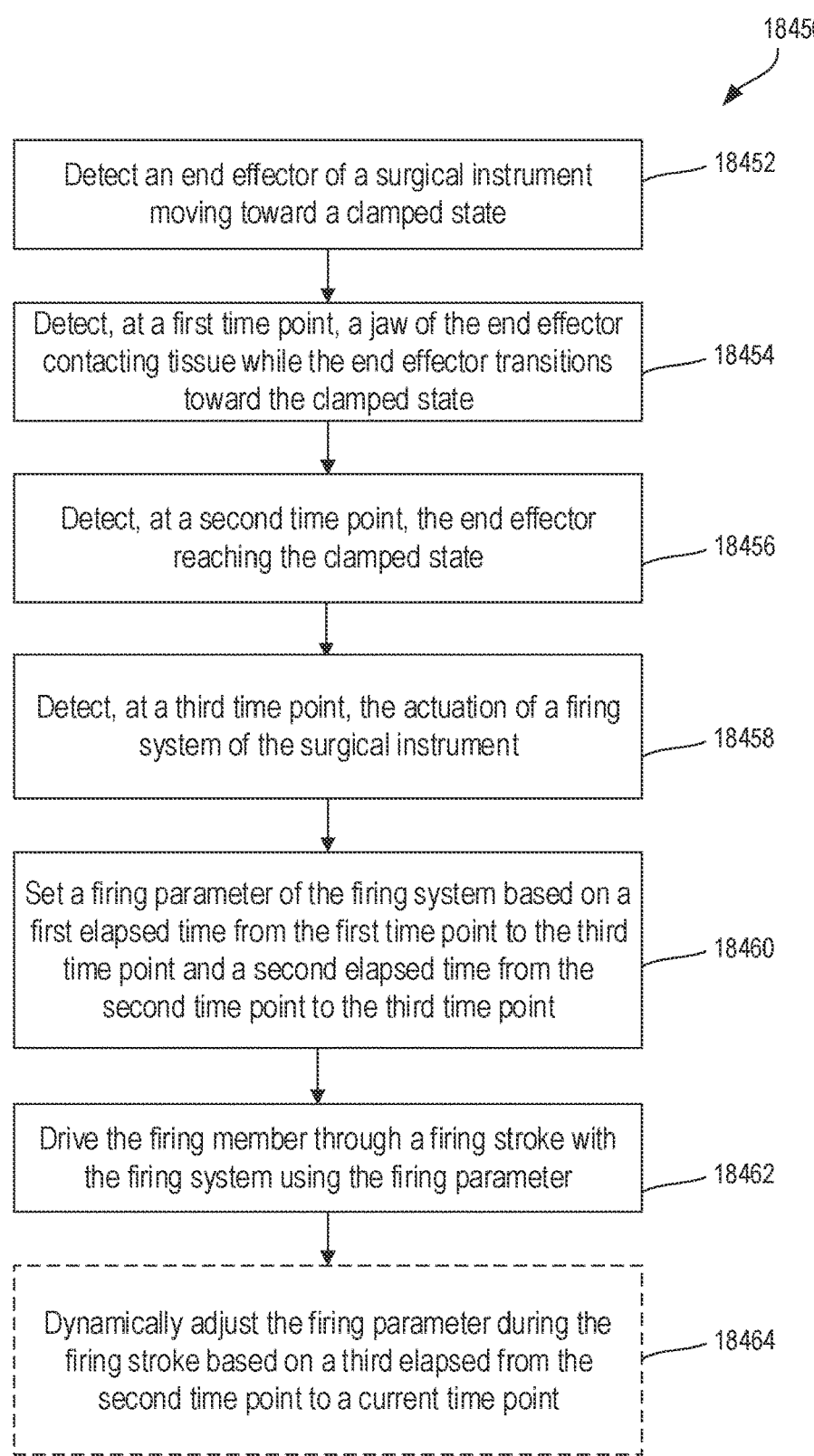
FIG. 22 illustrates a method for controlling a surgical instrument, according to at least one aspect of the present disclosure.

Referring now to FIG. 22, a method 18450 for controlling a surgical instrument is provided, according to at least one aspect of the present disclosure. The method 18450 comprises detecting 18452 an end effector of a surgical instrument moving toward a clamped state. In one embodiment, the circuit board 1100 detects the end effector 1300 moving toward the clamped state using a position sensor that can sense when the closure trigger 1032 is moving toward the actuated position. In one embodiment, the circuit board 1100 detects when the end effector 1300 moves toward the clamped state using a Hall-Effect sensor that can sense the anvil 2000 moving relative to the elongate channel 1310. In various embodiments, the circuit board 1100 detects when the end effector moves toward the clamped state using any number of sensors that detect the position of components associated with the closure system 3000, such as a position of the closure shuttle 1250, a position of the closure link 1038, a position of the distal closure tube segment 3030, as examples.

The method 18450 further comprises detecting 18454, at a first time point, a jaw of the end effector contacting tissue while the end effector transitions toward the clamped state. In various embodiments, the control system can detect initial contact of the anvil 2000 of the end-effector 1300 with the tissue utilizing a pressure sensor. In some embodiments, the control system is able to detect initial contact of the anvil 2000 with the tissue using various other sensors described elsewhere herein.

The method 18450 further comprises detecting 18456, at a second time point, the end effector reaching the clamped state. In various embodiments, the control system can detect the end effector reaching the clamped state using various sensors described elsewhere herein.

The method 18450 further comprises detecting 18458, at a third time point, the actuation of a firing system of the surgical instrument. In one embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18450 further comprises setting 18460 a firing motion parameter of the firing system based on a first elapsed time from the first time point to the second time point and the second time point to the third time point. In various embodiments, the circuit board 1100 can measure, using a timer, the elapsed lengths of time that has transpired from when the end effector makes initial contact with the tissue, reaches the clamped state, and when the firing system is actuated. In some embodiments, the circuit board 1100 can retrieve the firing motion parameter from a look-up table stored in a memory, such as memory 1935, according to the elapsed lengths of time. In some embodiments, the circuit board 1100 can retrieve a modification value from a graph or look-up table according to the elapsed lengths of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18450 further comprises driving 18462 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18450 provides the clinician with the freedom to choose how long they wish to apply pressure to the tissue, both between when the end effector first applies pressure in the partially clamped state and when the end effector reaches the clamped state, prior to actuating the firing system. Based on the elapsed amounts of time, the control system will automatically select an appropriate firing motion parameter for the firing system. In one aspect, "automatically" refers to the control system's ability to select a firing motion parameter without a user input.

In one aspect, part of the total clamping time includes portions of the closure stroke where the closure system is actuated enough, such as beyond the partially clamped state, or clamped slow enough and adequately enough to induce creep effects. This would enable the surgeon to utilize known techniques of slow clamping or repetitive clamping (more pressure followed by less pressure repeatedly as they urge the end effector to the clamped state). In this manner, the user is encouraged to use what has worked for them in the past, and the algorithms counts or further improves from that technique. In various embodiments, feedback on the rate or magnitude of this slow or repeated clamp is provided to the user on a display to allow the user to produce a more repeatable effect from patient to patient.

In various embodiments, the method 18450 optionally further comprises dynamically adjusting 18464 the firing motion parameter during the firing stroke based an elapsed time from the second time point to a current time point. In some embodiments, the circuit board 1100 can measure, using a timer, an elapsed amount of time, from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

In one aspect, a firing motion parameter of the firing system can be set according to the amount of compression applied to the tissue prior to the actuation of the firing system. In one embodiment, with a precompression time of $t_1$ (a lower precompression threshold), the initial firing speed of the firing member can be a constant value, such as $V_1$. In one embodiment, $t_1$ comprises 5 seconds and $V_1$ comprises 6 mm/sec. With a precompression time between $t_1$ and $t_2$ (an intermediate precompression threshold range), the initial firing speed can be a function represented as:

$$Y = (A + B(t - C))$$

where Y is the initial firing speed, t is precompression time, and A, B, and C are constants. In some embodiments, $t_2$ comprises 15 seconds, A is 6, B is 1.6, and C is 5, such that, at 10 seconds of precompression, as an example, the initial firing speed is 14 mm/sec. With a precompression time greater than of $t_2$ (an upper precompression threshold), the initial firing speed can be a constant value, such as $V_2$. In some embodiments, $V_2$ comprises 22 mm/sec. Accordingly, the firing motion parameter can vary according to the amount of precompression applied to the tissue before actuation of the firing system.

In various embodiments, the articulation angle of the end effector is utilized, along with the other parameters described herein above, such as clamping time, clamping speed, tissue pressure level, etc., to determine an appropriate firing motion parameter for the firing system. Referring to FIG. 1, the interchangeable shaft assembly 1200 can define a shaft axis extending from a proximal end thereof to a distal end thereof. Furthermore, the end effector 1300 can define an end effector axis extending from a proximal end thereof to a distal end thereof. In one aspect, the end effector is considered to be in a "home position" when the end effector axis is aligned with the shaft axis, as can be seen in FIG. 1. In some embodiments, the control system, such as circuit board 1100, can detect the angle of the end effector away from the home position when selecting a firing motion parameter for the firing system. In various embodiments, the control system can detect the angle of articulation using various sensors, encoders, or the like described elsewhere herein. When the end effector is articulated, slowing down the speed and reducing firing loads may help to minimize tip movement of the end effector, as well as reduce stalling.

In various embodiments, the firing motion parameter can be adjusted a certain percentage for every degree of articulation that the end effector is away from the home position. In one embodiment, the firing motion parameter can be decreased 1% for each angle of articulation. In one embodiment, the firing motion parameter can be decreased more than 1% for each angle of articulation. In some embodiments, the firing motion parameter can be adjusted the more the end effector is articulated away from the home position, i.e., a non-linear change.

In one aspect, rather than adjusting the firing motion parameter, the control system can require additional clamping time to the tissue prior to allowing actuation of the firing system. In some embodiments, the surgical instrument can include a lockout that prevents actuation of the firing system prior to a required amount of clamping time elapsing, as determined by the control system from the articulation angle. In one embodiment, when the end effector is in the home position, the control system can require a first amount of clamping time $t_1$ prior to enabling the firing system. In some embodiments, the first amount of clamping time $t_1$ comprises 15 seconds of clamping time. When the end effector is articulated a first angle $\theta_1°$ from the home position, the control system can require an additional amount of clamping time $t_2$ in addition to the first amount of clamping time $t_1$ prior to enabling the firing system. In some embodiments, the first angle $\theta_1$ comprises 45° and the additional clamping time comprises 5 seconds of clamping time.

Referring now to FIG. 23, a method 18500 for controlling a surgical instrument is provided, according to at least one aspect of the present disclosure. The method 18500 comprises detecting 18502, at a first time point, an end effector of a surgical instrument reaching a clamped state. In one embodiment, the circuit board 1100 detects the end effector 1300 reaching the clamped state using a position sensor that can sense when the closure trigger 1032 has reached the actuated position. In one embodiment, the circuit board 1100 detects when the end effector 1300 has reached the clamped state using a Hall-Effect sensor that can sense the anvil 2000 is within a threshold distance from the elongate channel 1310. In various embodiments, the circuit board 1100 detects when the end effector has reached the clamped state using any number of sensors that detect the position of components associated with the closure system 3000, such as a position of the closure shuttle 1250, a position of the closure link 1038, or a position of the distal closure tube segment 3030, as examples.

The method 18500 further comprises detecting 18504, at a second time point, the actuation of a firing system of the surgical instrument. In one embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18500 further comprises detecting 18506 the actuation angle of the end effector. In one embodiment, the circuit board 1100 can detect the articulation angle of the end effector by detecting an angle of the end effector relative to the elongate shaft using any number of sensors or encoders described elsewhere herein.

The method 18500 further comprises setting 18508 a firing motion parameter of the firing system based on a first elapsed time from the first time point to the second time point and the articulation. In various embodiments, the circuit board 1100 can measure, using a timer, the elapsed length of time that has transpired from when the end effector reaches the clamped state and when the firing system is actuated. In some embodiments, the circuit board 1100 can retrieve the firing motion parameter from a look-up table stored in a memory, such as memory 1935, according to the elapsed length of time and the articulation angle. In some embodiments, the circuit board 1100 can retrieve a modification value from a graph or look-up table according to the elapsed length of time and the articulation angle that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18500 further comprises driving 18510 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18500 provides the clinician with the freedom to choose how long they wish to apply pressure to the tissue in the clamped state and what angle they wish the end effector to be at prior to actuating the firing system. Based on the elapsed amount of time and the articulation angle, the control system will automatically select an appropriate firing motion parameter for the firing system. In one aspect, "automatically" refers to the control system's ability to select a firing motion parameter without a user input.

In various embodiments, the method 18500 optionally further comprises dynamically adjusting 18512 the firing motion parameter during the firing stroke based an elapsed time from the first time point to a current time point. In some embodiments, the circuit board 1100 can measure, using a timer, an elapsed amount of time, from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

Referring now to FIG. 24, a method 18550 for controlling a surgical instrument is provided, according to at least one aspect of the present disclosure. The method 18550 comprises detecting 18502, at a first time point, an end effector of a surgical instrument moving toward a clamped state. In one embodiment, the circuit board 1100 detects the end effector 1300 moving toward the clamped state using a position sensor that can sense when the closure trigger 1032 is moving toward the actuated position. In one embodiment, the circuit board 1100 detects when the end effector 1300 moves toward the clamped state using a Hall-Effect sensor that can sense the anvil 2000 moving relative to the elongate channel 1310. In various embodiments, the circuit board

1100 detects when the end effector 1300 moves toward the clamped state using any number of sensors that detect the position of components associated with the closure system 3000, such as a position of the closure shuttle 1250, a position of the closure link 1038, or a position of the distal closure tube segment 3030, as examples.

The method 18550 further comprises detecting 18554 a first parameter associated with the end effector moving toward the clamped state. In one embodiment, the first parameter comprises a time taken to reach the clamped state. In one embodiment, the first parameter comprises a time taken to reach the partially clamped state. In one embodiment, the first parameter comprises a time taken to reach the clamped state from the partially clamped state. In one embodiment, the first parameter comprises a rate at which the end effector transitions to the clamped state. In one embodiment, the first parameter comprises a speed at which the end effector transitions to the clamped state. In one embodiment, the first parameter comprises an amount of pressure applied to tissue within the end effector as the end effector transitions to the clamped state. In one embodiment, the first parameter comprises an elapsed time from when the end effector first applies pressure to tissue to when the end effector reaches the clamped state. In various embodiments, the first parameter comprises any combination of the foregoing parameters or other parameters associated with the end effector transitioning to the clamped state, as described elsewhere herein.

The method 18550 further comprises detecting 18556 the end effector reaching the clamped state. In various embodiments, the control system detects the end effector reaching the clamped state using any number of sensors or encoders described elsewhere herein.

The method 18550 further comprises detecting 18558 a second parameter associated with the end effector being in the clamped state. In one embodiment, the second parameter comprises an elapsed time the end effector is in the clamped state until the actuation of the firing system of the surgical instrument. In one embodiment, the second parameter comprises an articulation angle of the end effector. In one embodiment, the second parameter comprises a rate of change of pressure applied to the tissue within the end effector. In various embodiments, the second parameter comprises any combination of the foregoing parameters or other parameters associated with the end effector being in the clamped state, as described elsewhere herein.

The method 18550 further comprises detecting 18560 the actuation of a firing system of the surgical instrument. In one embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18550 further comprises setting 18552 a firing motion parameter of the firing system based on the first parameter and the second parameter. In some embodiments, the circuit board 1100 can retrieve the firing motion parameter from a look-up table stored in a memory, such as memory 1935, according to the first parameter and the second parameter. In some embodiments, the circuit board 1100 can retrieve a modification value from a graph or look-up table according to the first parameter and the second parameter that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18550 further comprises driving 18564 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18550 provides the clinician with the freedom to manipulate the end effector in numerous ways of their choosing prior to actuating the firing system. Based on the detected parameters, the control system will automatically select an appropriate firing motion parameter for the firing system. In one aspect, "automatically" refers to the control system's ability to select a firing motion parameter without a user input.

In various embodiments, the method 18550 optionally further comprises dynamically adjusting 18566 the firing motion parameter during the firing stroke based an elapsed time from the end effector reaching the clamped state to a current time point. In some embodiments, the circuit board 1100 can measure, using a timer, an elapsed amount of time from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

During a surgical procedure, a clinician may transition the end effector to the clamped state to capture tissue within the end effector. While clamped, fluid may egress away from the clamped tissue, therefore stabilizing the tissue in preparation for cutting and stapling. Furthermore, a timer can be initiated such that an appropriate firing motion parameter can be utilized when the firing system is actuated, as described elsewhere herein. However, prior to actuating the firing system, the clinician may decide that they wish to reposition the end effector to a new location on the tissue that is more suitable for cutting and stapling. To accomplish this, the clinician may transition the end effector out of the clamped state and reclamp the tissue at the new location on the tissue.

In some instances, when the end effector is transitioned away from the clamped state, the timer can be reset such that, when the end effector is returned to the clamped state, the timer can be reinitiated as if it were the first time the tissue had been clamped. However, in some instances, when the end effector is transitioned less than a threshold amount away from the clamped state, the timer may resume as if the end effector were still in the clamped state. Accordingly, the firing motion parameter can be selected based on not only an elapsed time that the tissue is held in the clamped state but also the time that the end effector is transitioned away from the clamped state less than a threshold amount. Accordingly, the control system can allow a clinician to modify a position of the end effector without losing the clamping time that was accumulated prior to repositioning the tissue.

Figure 25:
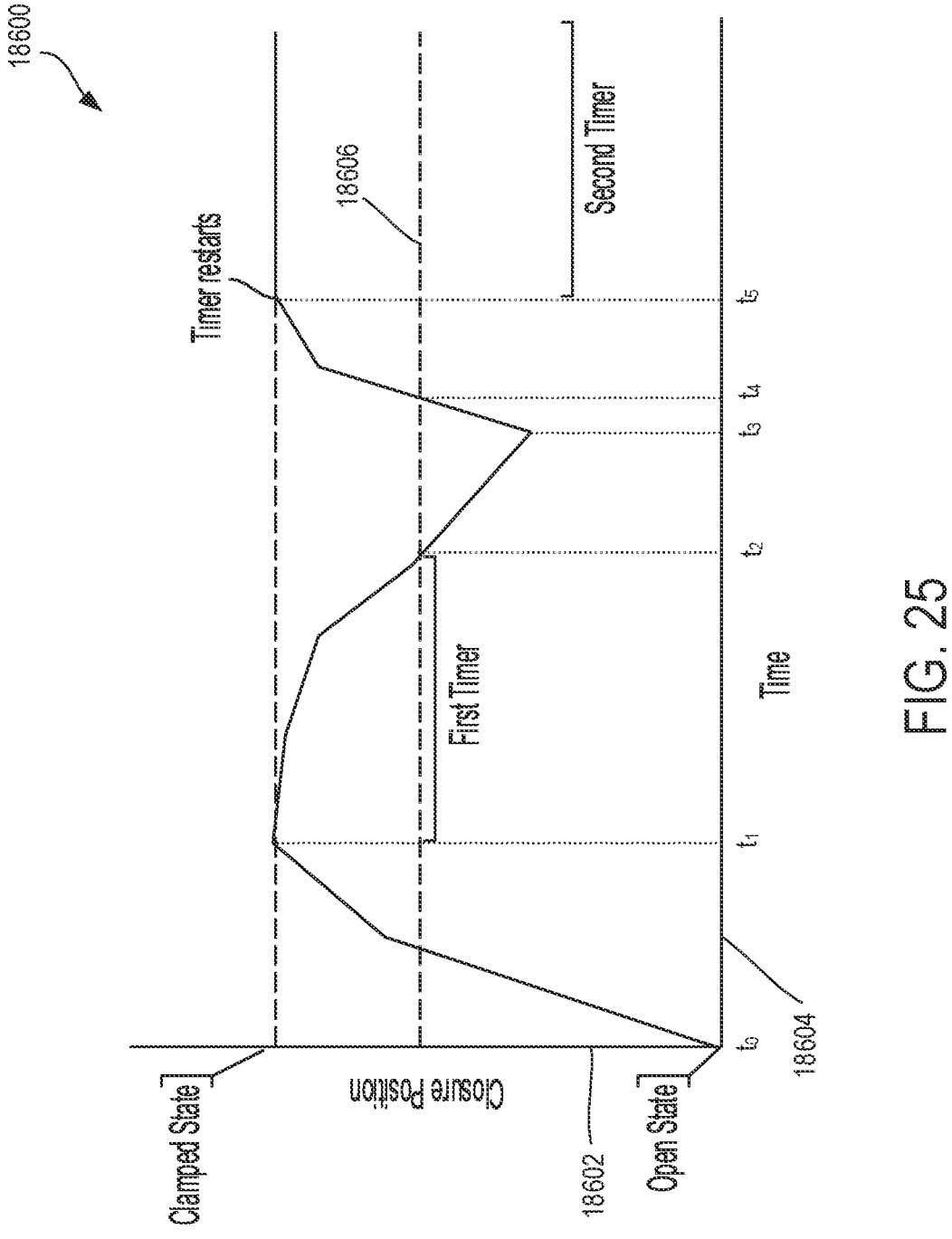
FIG. 25 is a graph that illustrates a closure state of an end effector over time, according to at least one aspect of the present disclosure.

Referring now to FIG. 25, a graph 18600 is provided according to at least one aspect of the present disclosure. The graph illustrates closure position of the end effector 18602 over time 18604. In some embodiments, the closure position can be the position of the closure trigger 1032 between the unactuated position and the actuated position.

At to, the anvil 2000 is in an open state, which can correspond to the closure trigger being in the unactuated position. From $t_0$ to $t_1$, the anvil 2000 is moved toward the clamped state using the closure trigger 1032. At $t_1$, the control system detects the end effector reaching the clamped state, as described elsewhere herein, and initiates a timer.

At $t_1$, a clinician decides that they wish to reposition the end effector to a new location more appropriate for cutting and stapling. Accordingly, as seen after $t_1$, the anvil 2000 is moved out of the clamped state toward the unclamped state. As the anvil 2000 moves from the unclamped state, the control system can maintain the timer running until the control system detects that the anvil 2000 has moved a threshold amount 18606 away from the elongate channel 1310. In various embodiments, the threshold amount can be stored in a memory and retrieved by the control system. In various embodiments, the threshold amount can be user defined and input at an input interface. In various embodiments, the control system can detect the position of the anvil 2000 relative to the elongate channel 1310 using any number of sensors or the like described elsewhere herein. In various embodiments, the threshold amount 18606 can be a distance that the anvil 2000 travels from the elongate channel 1310 while still maintaining contact with the tissue positioned within the end effector. Accordingly, despite being out of the clamped state, within a partially clamped state, the anvil 2000 is still applying pressure to the tissue, causing fluid to egress away.

At $t_2$, the control system detects that the anvil 2000 has transitioned the threshold amount away from the elongate channel 1310 and, therefore, resets the timer. From $t_2$ to $t_3$, the clinician continues to move the anvil 2000 away from the elongate channel 1310. During the time from $t_2$ to $t_3$, the timer is not running. At $t_3$, the clinician starts to move the anvil 2000 back towards the clamped state. At $t_4$, the anvil 2000 reaches the threshold amount from the elongate channel 1310, but the timer does not restart. However, various embodiments are envisioned where the timer reinitiates when the anvil 2000 is within the threshold amount from the elongate channel 1310. Various other embodiments are envisioned where the timer reinitiates when the anvil 2000 makes contact with the tissue prior to reaching the clamped state.

At $t_5$, the anvil 2000 is returned to the clamped state and the timer is reinitiated. At this time, the clinician can maintain the end effector in the clamped state until they wish to actuate the firing system. When the firing system is actuated, the firing system only takes into account the second elapsed time, not the first elapsed time, as the end effector was transitioned a threshold amount away from the clamped state.

Figure 26:
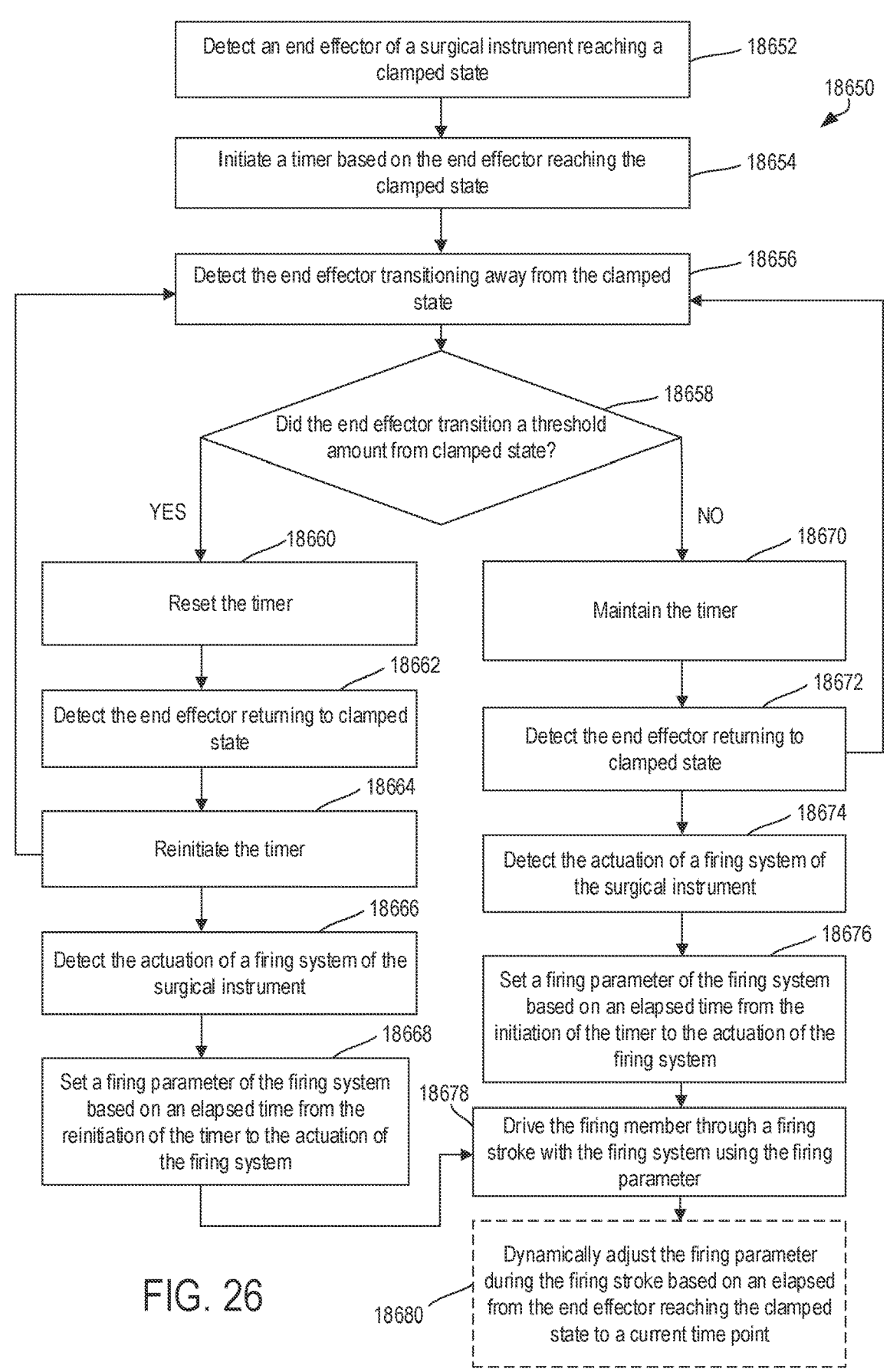
FIG. 26 illustrates a method for controlling a surgical instrument, according to at least one aspect of the present disclosure.

Referring now to FIG. 26, a method 18650 for controlling a surgical instrument is provided, according to at least one aspect of the present disclosure. The method 18650 comprises detecting 18652 an end effector of a surgical instrument reaching a clamped state. In one embodiment, the circuit board 1100 detects the end effector 1300 reaching the clamped state using a position sensor that can sense when the closure trigger 1032 has reached the actuated position. In one embodiment, the circuit board 1100 detects when the end effector 1300 has reached the clamped state using a Hall-Effect sensor that can sense the anvil 2000 is within a threshold distance from the elongate channel 1310. In various embodiments, the circuit board 1100 detects when the end effector 1300 has reached the clamped state using any number of sensors that detect the position of components associated with the closure system 3000, such as a position of the closure shuttle 1250, a position of the closure link 1038, or a position of the distal closure tube segment 3030, as examples.

The method 18650 further comprises initiating 18654 a timer based on the end effector reaching the clamped state. In some embodiments, the circuit board 1100 can measure an elapsed time that the end effector is in the clamped state until the control system detects actuation of the firing system. In one embodiment, after initiation of the timer at 18654, the control system detects actuation of the firing system. Accordingly, the method 18650 can set a firing motion parameter of the firing system based on the elapsed times, similar to what is described for method 18200.

The method 18650 further comprises detecting 18656 the end effector transitioning away from the clamped state. In some embodiments, the control system can detect the end effector transitioning away from the clamped state using any suitable sensors described elsewhere herein.

The method 18650 further comprises determining 18658 if the end effector transitioned a threshold amount from the clamped state. In some embodiments, the control system determines if the end effector transitioned the threshold amount by comparing a distance between the anvil 2000 and the elongate channel 1310 to the threshold value. In some embodiments, the control system determines if the end effector transitioned the threshold amount by comparing a distance that the closure trigger traveled from the actuated position.

Based on the control system determining that the end effector transitioned the threshold amount from the clamped state, the method 18650 proceeds with resetting 18660 the timer. In some embodiments, resetting the timer comprises resetting the timer back to zero. In some embodiments, resetting the timer can comprise setting the timer to a value other than zero.

The method 18650 further comprises detecting 18662 that the end effector returned to the clamped state. In some embodiments, the control system can detect the end effector returning to the clamped state using any number of sensors described elsewhere herein.

The method 18650 further comprises reinitiating 18664 the timer, based on the end effector returning to the clamped state. In some embodiments, the control system can reinitiate the reset timer based on the detection of the end effector retuning to the clamped state, similar to what is seen at is of FIG. 25.

After reinitiation 18664 of the timer, the user can choose to again transition the end effector away from the clamped state to reposition the end effector. Accordingly, the method can proceed again to detecting 18656 the end effector transitioning away from the clamped state, as described above. Furthermore, after reinitiation of the timer, the method 18650 further comprises detecting 18666 the actuation of a firing system of the surgical instrument. In some embodiments, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18650 further comprises setting 18668 a firing motion parameter of the firing system based on an elapsed time from the reinitiation of the timer to the actuation of the firing system. In various embodiments, the circuit board 1100 can interrogate the timer to determine an elapsed length of time that has transpired from reinitiation of the timer and when the firing system was actuated. In some embodiments, the circuit board 1100 can retrieve the firing motion parameter from a look-up table stored in a memory, such as memory 1935, according to the elapsed length of time. In some embodiments, the circuit board 1100 can retrieve a modification value from a graph or look-up table according to the elapsed length of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18650 further comprises driving 18678 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

In various embodiments, the method 18650 optionally further comprises dynamically adjusting 18680 the firing motion parameter during the firing stroke based an elapsed time from the end effector reaching the clamped state to a current time point. In some embodiments, the circuit board 1100 can measure, using a timer, an elapsed amount of time, from the end effector reaching the clamped state to a current time point during the firing stroke and dynamically adjust the firing motion parameter. In some embodiments, the elapsed time is measured only after the end effector returned to the clamped state. In some embodiments, the elapsed time is measured from the end effector initially reaching the clamped state. Accordingly, the control system can dynamically adjust the firing motion parameter according to an elapsed length of time that the tissue has been clamped by the end effector and been allowed to stabilize.

Based on the control system determining that the end effector did not transition the threshold amount from the clamped state, the method 18650 proceeds with maintaining 18670 the timer. In some embodiments, maintaining the timer comprises allowing the timer to continue to run and measure the elapsed time from the end effector reaching the clamped state.

The method 18650 further comprises detecting 18672 that the end effector returned to the clamped state. In some embodiments, the control system can detect the end effector returning to the clamped state using any number of sensors described elsewhere herein.

After detecting 18672 the end effector returning to the clamped state, the user can choose to again transition the end effector away from the clamped state to reposition the end effector. Accordingly, the method can proceed again to detecting 18656 the end effector transitioning away from the clamped state, as described above. Furthermore, after detecting 18672 the end effector returning to the clamped state, the method 18650 further comprises detecting 18674 the actuation of a firing system of the surgical instrument. In some embodiments, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18650 further comprises setting 18676 a firing motion parameter of the firing system based on an elapsed time from the initiation of the timer to the actuation of the firing system. In various embodiments, the circuit board 1100 can interrogate the timer to determine an elapsed length of time that has transpired from the initiation of the timer and when the firing system was actuated. In some embodiments, the circuit board 1100 can retrieve the firing motion parameter from a look-up table stored in a memory, such as memory 1935, according to the elapsed length of time. In some embodiments, the circuit board 1100 can retrieve a modification value from a graph or look-up table according to the elapsed length of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters. In various embodiments, setting the firing motion parameter can be based on a variety of other parameters described elsewhere herein, such as the articulation angle, the time since initiation tissue contact, the speed of moving toward the clamped state, or combinations thereof, as examples.

Similar to above, the method 18650 comprises driving 18678 the firing member through a firing stroke with the firing system using the firing motion parameter and dynamically adjusting 18680 the firing motion parameter during the firing stroke based an elapsed time from the end effector reaching the clamped state to a current time point. In some embodiments, the elapsed time is measured only after the end effector returned to the clamped state. In some embodiments, the elapsed time is measured from the end effector initially reaching the clamped state.

Accordingly, the foregoing method 18650 provides the clinician with the freedom to manipulate the end effector in numerous ways of their choosing prior to actuating the firing system, while also allowing the end effector to transition away from the clamped state without potentially losing the benefit of accumulated clamping time already incurred. Based on the detected parameters, the control system will automatically select an appropriate firing motion parameter for the firing system. In one aspect, "automatically" refers to the control system's ability to select a firing motion parameter without a user input.

Clamping systems that utilize position control closure are plagued by operating in a manner where a closure stoke produces a specific force to tissue captured within the end effector after the end effector has been placed into a clamped state. As the tissue thins due to tissue creep, this specific force applied to the tissue diminishes over time. For example, referring to FIGS. 27 and 28, a response profile 4000 from a clamping system utilizing position control closure is provided, according to at least one aspect of the present disclosure. At $t_0$, the end effector begins in an open state, during which time the closure force 4002 applied by the end effector to the tissue is zero. From $t_0$ to $t_1$, the end effector is transitioned toward a clamped state by a closure member, which causes a gradual increase in the closure force 4002 applied to the tissue. At $t_1$, the closure member reaches the end of its closure stroke, corresponding to the end effector reaching the clamped state. In the clamped state, the closure force 4002 reaches a maximum closure force $FTC_{maxPC}$.

Figure 27:
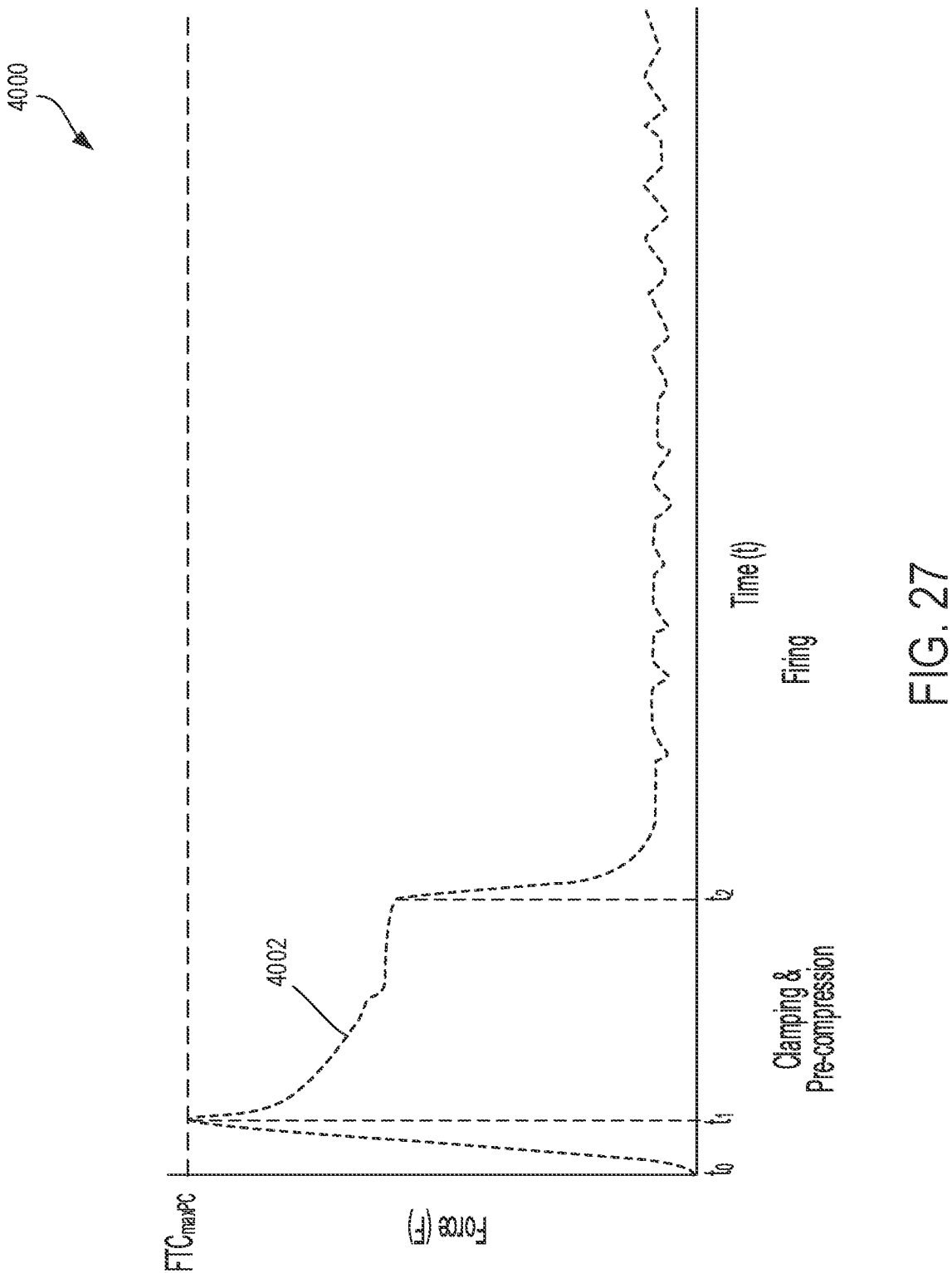
FIG. 27 illustrates a response profile from a clamping system utilizing a position control closure system, according to at least one aspect of the present disclosure.
Figure 28:
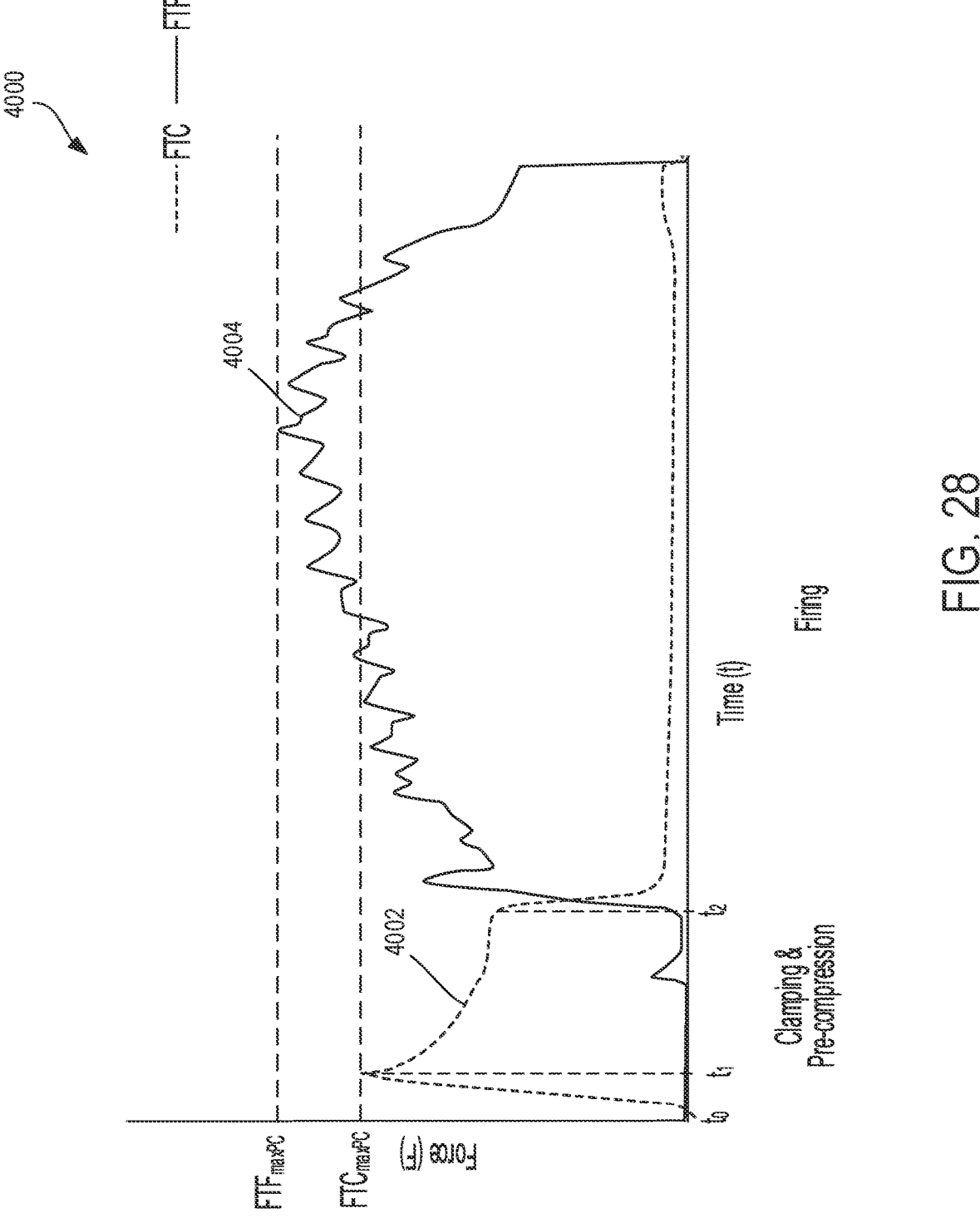
FIG. 28 illustrates a response profile from a clamping system utilizing a position control closure system, according to at least one aspect of the present disclosure.

A problem with these clamping systems is that they do not have the ability to continue to advance their closure members once they have completed their closure stroke, and thus, the force applied to the tissue drops over time, as fluid egresses from the clamped tissue. For example, as seen in FIGS. 27 and 28, once the maximum closure force $FTC_{maxPC}$ is applied to the tissue at $t_1$, the closure force 4002 gradually diminishes over time because of tissue creep/tissue thinning. At $t_2$, the firing system of the surgical instrument is actuated, causing the closure force 4002 to sharply drop.

Referring to FIG. 27, as a result of the diminishing closure force 4002 after reaching $FTC_{maxPC}$, the force to fire 4004 the firing drive, such as firing motor drive assembly 604, of the surgical instrument reaches a force $FTF_{maxPC}$ that is greater than $FTC_{maxPC}$. This large force to fire places a lot of stress on the firing motor, such as firing motor 602, of the firing drive.

Some attempts have been made to store energy in a spring or other mechanical storing means, and then allow the clamping system to continue to advance, but these means also lower force as the tissue thins, just not as abruptly. A preferred manner would be to hold the load constant or even "overload" the tissue slightly with each adjustment to creep and bring the tissue to its thinnest, stable state as quickly, uniformly, and repeatably as possible. This preferred manner can result in better surgical outcomes and lower stresses on the firing system.

In one aspect, load control of the closure system enables the closure load, and therefore, the clamping force, to stay at an elevated level, improving the pre-firing compression of the tissue, and ultimately, resulting in lower forces to fire. Viscoelastic creep of tissue is maximized by the magnitude of the force, the duration of the force and the rate that the force was applied.

Figure 29:
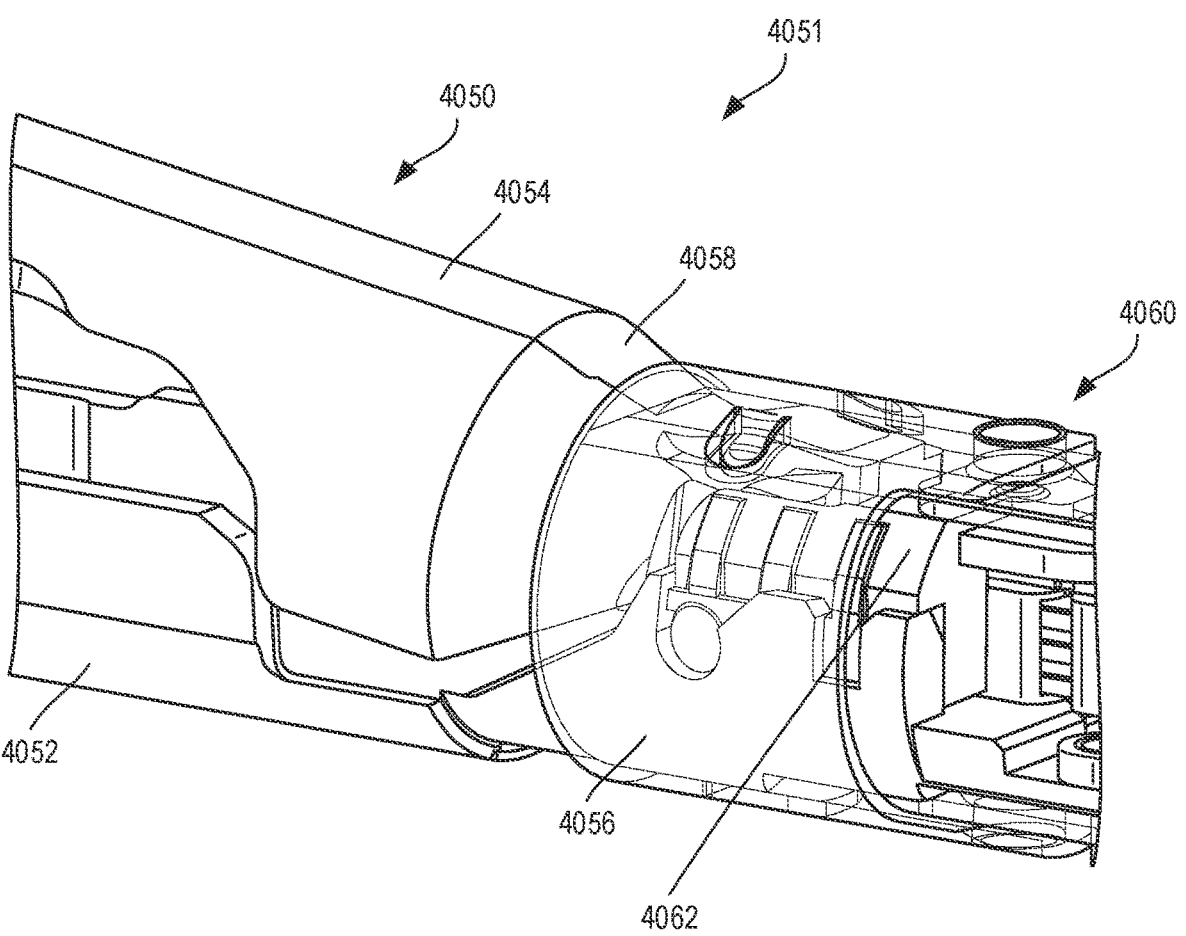
FIG. 29 illustrates an end effector of a surgical instrument in an open state, according to at least one aspect of the present disclosure.
Figure 30:
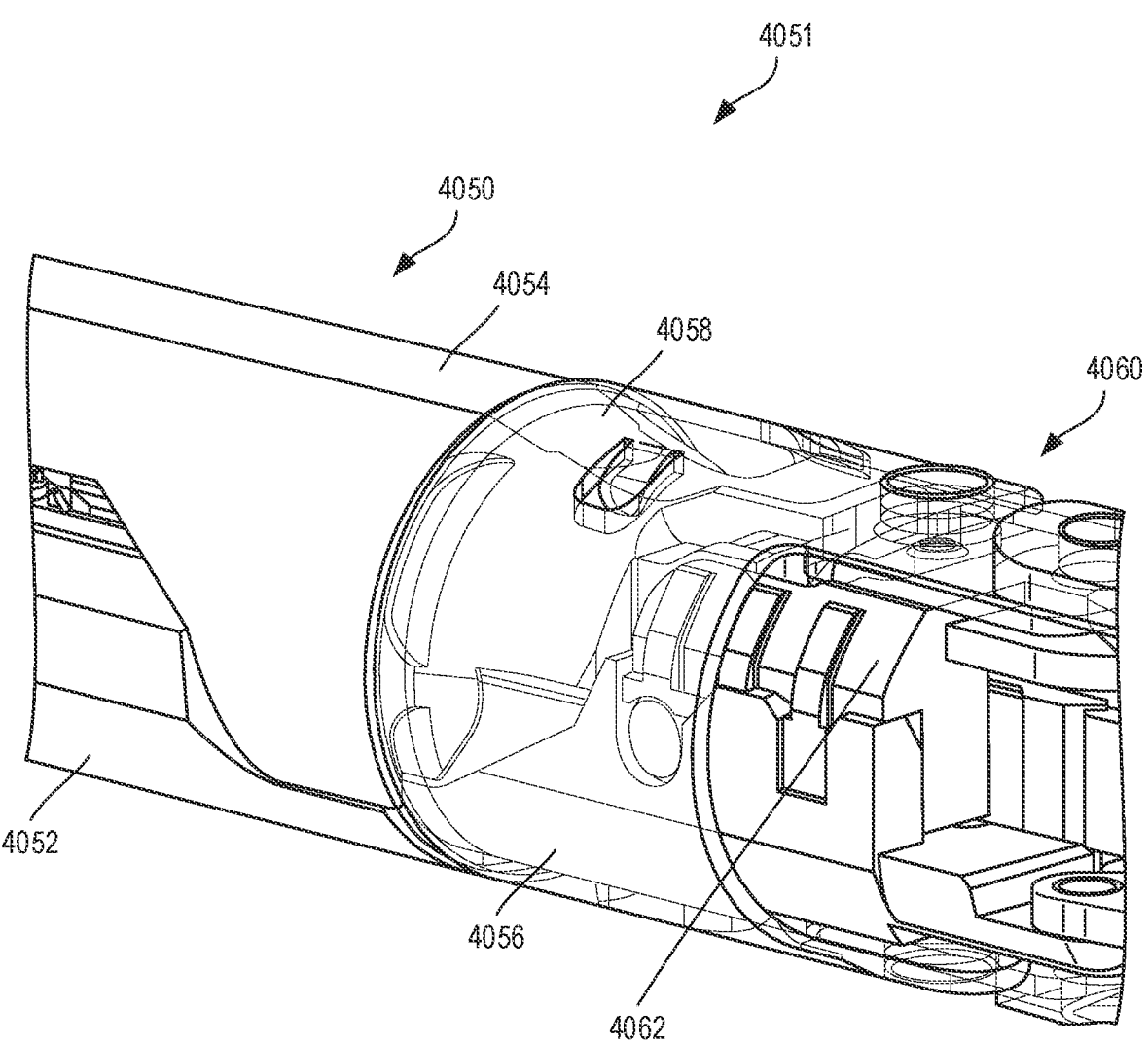
FIG. 30 illustrates the end effector of FIG. 29 in a clamped state, according to at least one aspect of the present disclosure.
Figure 31:
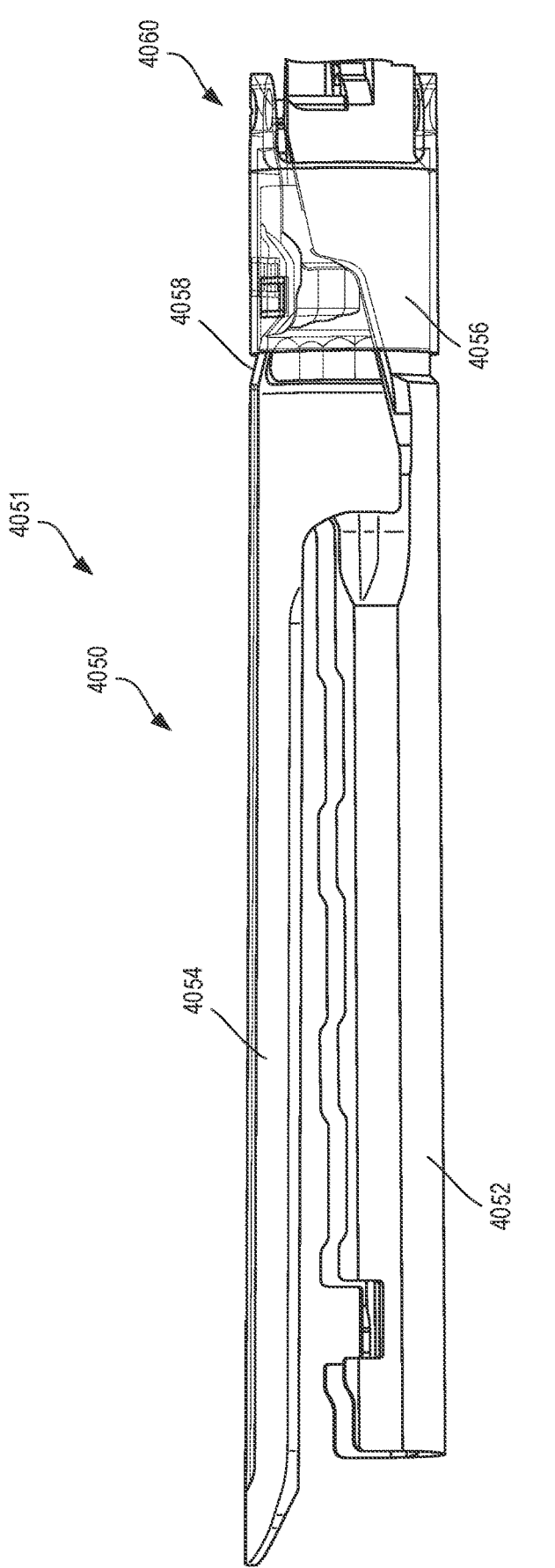
FIG. 31 illustrates a side view of the end effector of FIG. 30, according to at least one aspect of the present disclosure.

Referring now to FIGS. 29-31, an end effector 4050 of a surgical instrument 4051 is provided, according to at least one aspect of the present disclosure. The end effector 4050 includes an elongate channel 4052, which is similar in many respects to elongate channel 1310, and an anvil 4054, which is similar in many respects to anvil 2000, pivotally supported relative to the elongate channel 4052. The surgical instrument 4051 includes a closure ring 4056 that is axially movable relative to the end effector 4050 between a proximal position, illustrated in FIG. 29, and a distal position, illustrated in FIG. 30. In various embodiments, the closure ring 4056 is part of a motor-driven closure system, such as closure motor drive assembly 605, and is drivable between the proximal position and distal position by a motor, such as closure motor 603. In various embodiments, the closure ring 4056 is part of a manually driven closure system, such as closure system 3000, and is drivable between the proximal position and distal position in response to a manual input, such as rotation of a closure trigger 1032 by a clinician.

The surgical instrument 4051 further includes an articulation joint 4060 that rotatably connects the end effector 4050 to an elongate shaft of the surgical instrument, allowing the end effector 4050 to rotate relative to the elongate shaft into a plurality of articulation positions away from a central axis extending centrally through the elongate shaft. The surgical instrument 4051 further includes a spine 4062 configured to provide structural support to the surgical instrument 4051 and to protect various internal components of the surgical instrument 4051.

In operation, the closure ring 4056 is driven from the proximal position toward the distal position by the closure system, such as the motor-driven closure system or manually driven closure system. As the closure ring 4056 is driven toward the distal position, the closure ring 4056 cammingly engages a ramp 4058 formed at a proximal end of the anvil 4054, thereby camming the anvil 4054 toward a clamped state, as shown in FIG. 30, to grasp tissue by the end effector. In some embodiments, the closure ring 4056 is similar in manner to the distal closure tube segment described in U.S.

Pat. No. 11,324,501, which is hereby incorporated reference in its entirety herein. In various embodiments, the end effector 4050 includes a spring that biases the anvil 4054 toward the open position when the closure ring 4056 is moved toward the proximal position.

In some embodiments, the clamped state is defined as a state where the end effector 1300 is in the closed configuration and the closure trigger 1032 is in the actuated position. In other embodiments, the clamped state is defined as a state where the elongate channel 1310 and the anvil 2000 of the end effector 1300 are within a threshold distance of one another. In other embodiments, the clamped state is defined as a state where the closure trigger 1032 has pivoted a threshold distance away from the unactuated position.

In other embodiments, the closure system causes the elongate channel to move toward the anvil to achieve a closed position. In yet other embodiments, the closure system causes the anvil and the elongate channel to move toward each other to achieve the closed position. A number of embodiments described by the present disclosure include a closure system comprising a movable anvil and a fixed elongate channel. Nonetheless, it is readily understood that such embodiments can be equally implemented using a movable elongate channel and a fixed anvil or a movable elongate channel and a movable anvil.

Figure 32:
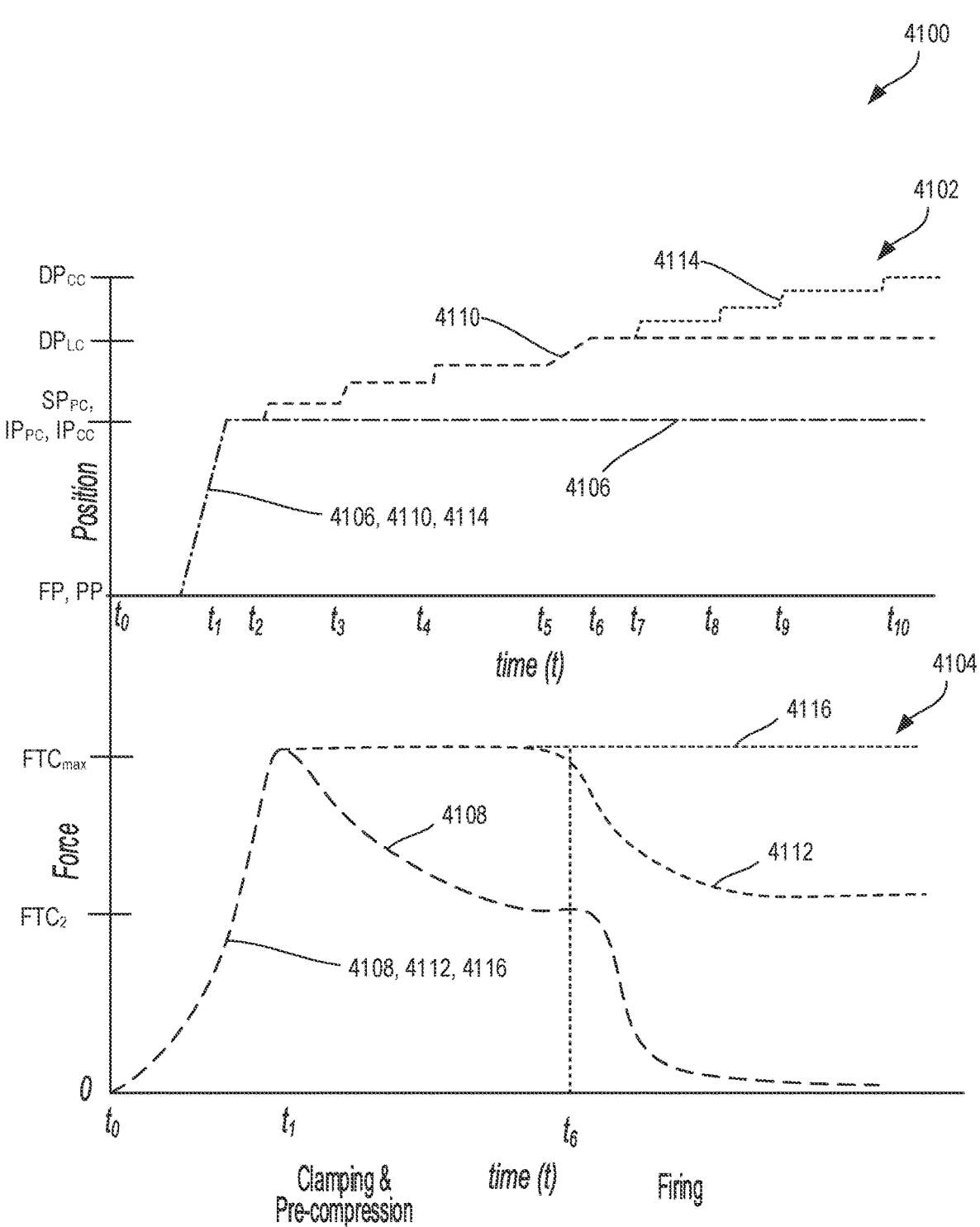
FIG. 32 illustrates graphs illustrating the differences between a position control closure system and load control closure systems, according to at least one aspect of the present disclosure.

Referring now to FIG. 32, graphs 4100 illustrating the differences between a position control closure system and load control closure systems are provided, according to at least one aspect of the present disclosure. The upper graph 4102 illustrates the position of the respective closure members of each system, as will be discussed in more detail below, over time. The lower graph 4104 illustrates the relationship between the closure loads applied by the respective end effectors over time.

With a position control closure system, a closure member moves between a first position, corresponding to an end effector being in the open state, and a second position, corresponding to the end effector being in the clamped state. Referring to the upper graph 4102, at to, the closure member begins in the first position FP, corresponding to the end effector being in the open state. When the end effector is in the open state, no force is applied to the tissue captured within the end effector, as seen in the lower graph 4104.

As the closure member moves toward the second position $SP_{PC}$, represented by line 4106, the end effector transitions toward the clamped state, causing the closure force applied by the end effector, represented by line 4108, to increase. At $t_1$, the closure member reaches the second position $SP_{pc}$, which corresponds to the end effector being in the clamped state. As seen in lower graph 4104, in the clamped state, the end effector applies a maximum closure force $FTC_{max}$ to the tissue.

As the closure member is no longer able to advance beyond the second position $SP_{PC}$, the force applied to the tissue begins to diminish as a result of tissue thinning and tissue creep. From $t_2$ to $t_3$, the tissue force 4108 drops below $FTC_{max}$. At $t_3$, the firing system is actuated, causing the applied force to further sharply drop.

As referenced above, utilizing a load control closure system would enable the closure load, and therefore, the clamping force, to stay at an elevated level, improving pre-firing compression of the tissue. In various embodiments, the surgical instrument 4051 is utilized to provide such load control. In some embodiments, a control system, such as controller 620, can control the closure of the end effector 4050 with the closure ring 4056 according to forces sensed with sensors, such as any suitable sensor described elsewhere herein, such as a force sensor or a current sensor, as explained in more detail below. It should be understood that the control system can be any suitable control system described elsewhere herein, such as circuit board 1100 or controller 1933, as examples.

Referring to the upper graph 4102, at t0, the closure ring 4056 begins in the proximal positon PP, corresponding to the end effector 4050 being in the open state, i.e., the anvil 4054 being spaced apart from the elongate channel 4052, as seen in FIG. 29. When the end effector 4050 is in the open state, no force is applied to the tissue captured within the end effector 4050, as seen in the lower graph 4104.

As the closure ring 4056 moves toward the distal position $DP_{LC}$, represented by line 4110, the end effector transitions toward the clamped state, causing the closure force applied by the end effector, represented by line 4112, to increase. It should be understood, as seen in the graphs 4100, that line 4106 and line 4110 overlap and line 4108 and line 4112 overlap, and are, therefore, represented as single lines for the sake of simplicity. At $t_1$, the closure ring 4056 reaches an intermediate position $IP_{LC}$ that is intermediate the proximal position PP and the distal position $DP_{LC}$, which corresponds to the end effector 4050 being in a partially clamped state. As seen in the lower graph 4104, in the partially clamped state, the end effector 4050 applies a maximum closure force $FTC_{max}$ to the tissue. It should be understood that further advancement of the closure ring 4056 would result in an $FTC_{max}$ greater than what is represented in lower graph 4104.

In one aspect, a partially clamped state is defined as a state between the open state and the clamped state where the end effector makes initial contact with the tissue positioned therein. In one aspect, a partially clamped state is defined as a state where the anvil of the end effector is within a threshold distance of the elongate channel of the end effector. In one aspect, a partially clamped state is defined as a state wherein the closure trigger has moved a threshold amount toward the actuated state from the unactuated state. In one aspect, a partially clamped state is defined as a state wherein a firing member responsible for the closure of the end effector has moved a threshold linear distance.

In the intermediate position $IP_{LC}$, the control system halts advancement of the closure ring 4056. In various embodiments, the intermediate position $IP_{LC}$ corresponds to a position that is a threshold distance away from the proximal position PP. In various embodiments, the intermediate position $IP_{LC}$ corresponds to a positon where a threshold amount of force is applied to the tissue. In some embodiments, the threshold amount of force is stored in a memory, such as memory 1935, and is retrievable by the control system. In some embodiments, the threshold amount of force is user-provided at an input interface. In some embodiments, the intermediate position $IP_{LC}$ corresponds to a predefined distance up the ramp 4058 of the anvil 4054.

In the partially clamped state, the control system monitors the force applied by the anvil 4054 by interrogating, or receiving signals from, the sensors. In various embodiments, the sensors comprise force sensors positioned at the end effector to directly measure the force applied to the tissue. In various embodiments, the sensors comprise current sensors that measure an amount of current supplied to the closure motor to determine the closure force.

After the occurrence of an event, the control system controls the closure system to resume advancement of the closure ring 4056 toward the distal position $DP_{LC}$. In various embodiments, the event comprises a threshold amount of time elapsing from when the closure ring 4056 was halted.

In various embodiments, the event comprises the control system detecting a decrease in the force applied by the anvil 4054. In various embodiments, the event comprises the control system detecting the force applied by the anvil 4054 dropping a threshold amount from the maximum closure force $FTC_{max}$.

As seen in the upper graph 4102 and the lower graph 4104, the control system continuously monitors the force applied by the end effector 4050 and discretely advances 4110 the closure ring 4056. Specifically, as seen at times $t_2$, $t_3$, $t_4$, and $t_5$ of the upper graph 4102, the control system discretely advances the closure ring such that the closure force 4112 applied by the end effector remains constant, or at least substantially constant. In one embodiment, the control system causes the closure system to drive 4110 the closure ring 4056 at $t_2$ such that the force 4112 remains at the $FTC_{max}$. Once the $FTC_{max}$ is achieved, the control system causes the closure ring 4056 to again halt advancement and the control system again monitors for an event, as described above, to continue advancement of the closure ring 4056, such as again at $t_3$ upon occurrence of an event. In various other embodiments, rather than discretely advancing the closure ring, the control system continuously moves the closure ring 4056 at a rate that results in the force 4112 applied by the end effector remaining constant, or at least substantially constant.

The control system continues the above-described halting and advancement of the closure ring 4056 until the closure ring 4056 reaches the distal position $DP_{LC}$, shown on the upper graph 4102 at $t_6$. Once in the distal position $DP_{LC}$ at $t_6$, the user can actuate the firing system, such as firing motor drive assembly 604, to drive a firing member, such as firing member 1900, with a motor, such as firing motor 602, to cut and deploy staples from a staple cartridge, such as staple cartridge 1301, positioned in the end effector 4050. In various embodiments, the control system can provide haptic, visual, audible, or any other suitable feedback, informing the clinician that the closure ring 4056 has reached the distal position $DP_{LC}$. In various embodiments, once the closure ring 4056 reaches the distal position $DP_{LC}$, the user can wait an amount of time prior to actuating the firing system, giving the end effector 4050 the opportunity to apply additional force to the tissue. In various other embodiments, the control system can require a threshold amount of time to transpire prior to enabling the firing system. In some embodiments, the control system can provide haptic, audible, or visual feedback once the threshold amount of time has transpired, informing the clinician that the firing system can be actuated.

Figure 33:
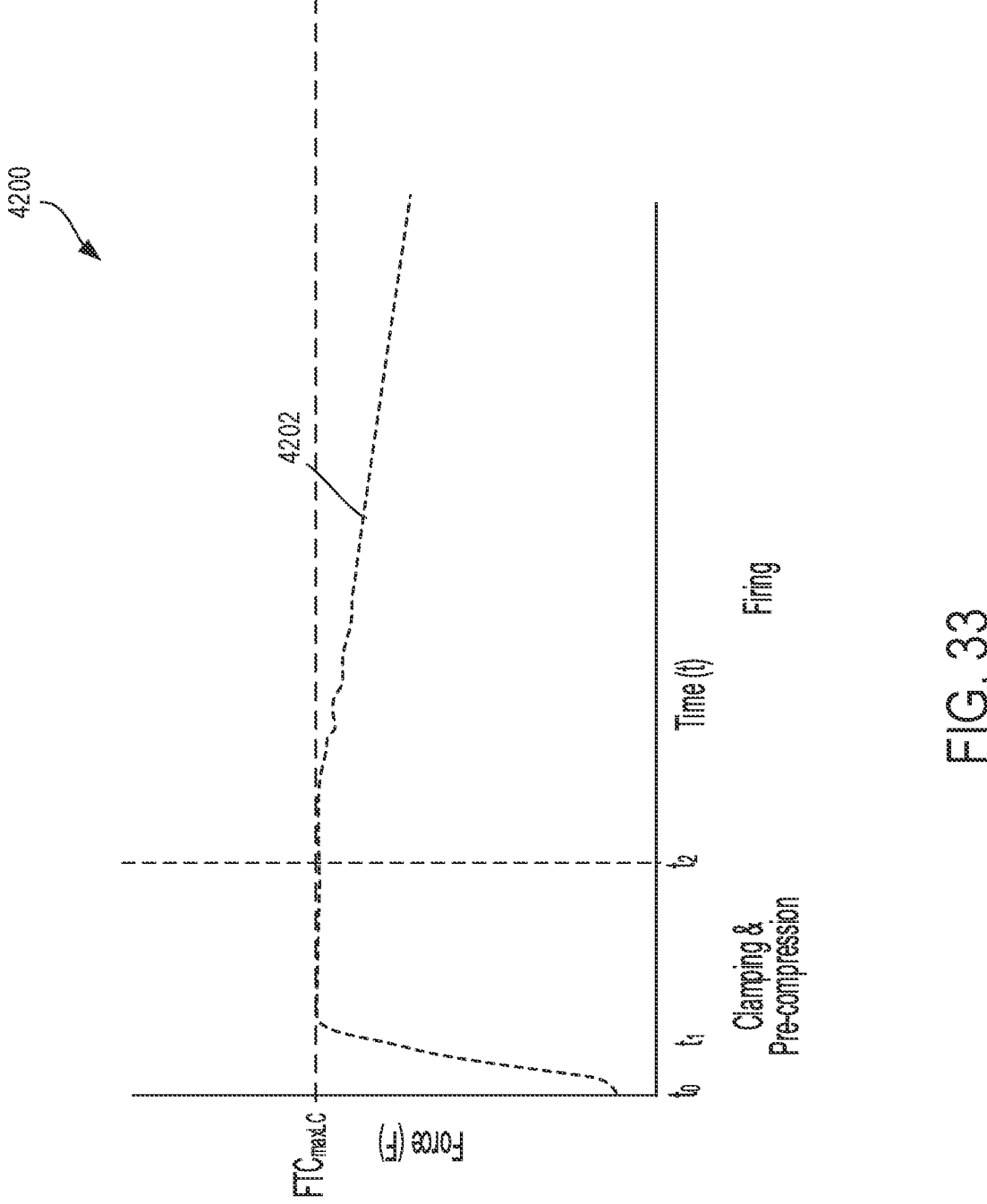
FIG. 33 illustrates a response profile from a clamping system utilizing a load control closure system, according to at least one aspect of the present disclosure.
Figure 34:
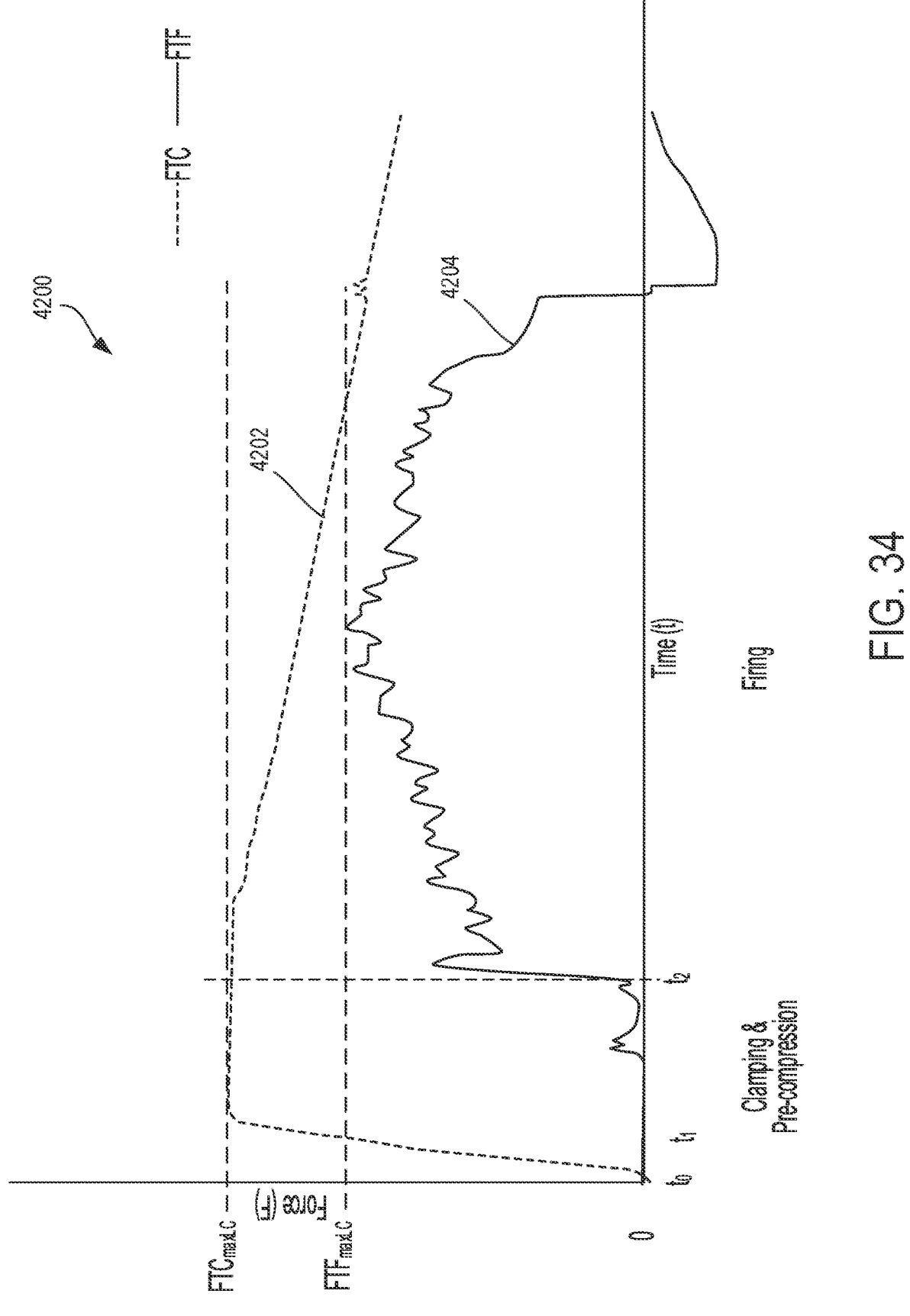
FIG. 34 illustrates a response profile from a clamping system utilizing a load control closure system, according to at least one aspect of the present disclosure.

Referring now to FIGS. 33 and 34, a response profile 4200 from a clamping system, such clamping system utilizing closure ring 4056, utilizing load control closure is provided. At t0, the end effector, such as end effector 4050, begins in an open state, during which time the closure force 4202 applied by the end effector to the tissue is zero. From $t_0$ to $t_1$, the end effector is transitioned toward the clamped state by a closure member, such as closure ring 4056, which causes a gradual increase in the closure force 4202. At $t_1$, the closure member reaches an intermediate closure stroke position, such as intermediate position $IP_{LC}$, corresponding to the end effector reaching a partially clamped state. In the partially clamped state, the closure force 4202 reaches a maximum closure force $FTC_{max}$.

As seen in FIGS. 33 and 34 and as described above, once the maximum amount of force $FTC_{maxLC}$ is applied to the tissue at $t_1$, the closure member can be discretely, or continuously, advanced such that the maximum amount of force $FTC_{maxLC}$ is maintained, or at least substantially maintained. At $t_2$, the closure member reaches its distal position, such as distal position $DP_{LC}$, and the firing system is actuated. As seen in FIG. 34, the force to fire 4204 the firing drive of the surgical instrument reaches a force $FTF_{maxLC}$ that is less than that of the $FTC_{max}$, as well as being less than the force to fire $FTF_{maxPC}$ for a position control closure system, as described above and shown in FIG. 27. Accordingly, the load control closure system reduces the force to fire necessary by the firing system, which can prolong the life of the firing system. The load control closure system brings the tissue to its thinnest, stable state as quickly, uniformly, and repeatably as possible and results in better surgical outcomes.

As described above, the load control closure system utilizing end effector 4050 utilizes a closure ring 4056 that is discretely, or continuously, advanced such that the load provided by the end effector can be maintain at a maximum value for a longer period of time prior to the actuation of the firing system. In various other embodiments, the present disclosure provides a load control closure system that discretely, or continuously, advances a closure member during at least a portion of the firing stroke to maintain a constant, or at least substantially constant, closure load during at least a portion of the firing stroke.

Referring again to the upper graph 4102 of FIG. 32, at to, the closure ring 4056 begins in the proximal positon PP, corresponding to the end effector 4050 being in the open state, i.e., the anvil 4054 being spaced apart from the elongate channel 4052, as seen in FIG. 29. When the end effector 4050 is in the open state, no force is applied to the tissue captured within the end effector 4050, as seen in the lower graph 4104.

As the closure ring 4056 moves toward the distal position $DP_{CC}$, represented by line 4114, the end effector transitions toward the clamped state, causing the closure force applied by the end effector, represented by line 4116, to increase. It should understood, as seen in the graphs 4100, that line 4114 overlaps lines 4110, 4106 and line 4116 overlaps lines 4112, 4108, and are, therefore, represented as a single line for the sake of simplicity. At $t_1$, the closure ring 4056 reaches an intermediate position $IP_{CC}$ that is intermediate the proximal position PP and the distal position $DP_{CC}$, which corresponds to the end effector 4050 being in a partially clamped state. As seen in the lower graph 4104, in the partially clamped state, the end effector 4050 applies a maximum closure force $FTC_{max}$ to the tissue. It should be understood that further advancement of the closure ring 4056 would result in an $FTC_{max}$ greater than what is represented in lower graph 4104.

In the intermediate position $IP_{CC}$, the control system halts advancement of the closure ring 4056. In various embodiments, the intermediate position $IP_{CC}$ corresponds to a position that is a threshold distance away from the proximal position PP. In various embodiments, the intermediate position $IP_{CC}$ corresponds to a positon where a threshold amount of force is applied to the tissue. In some embodiments, the threshold amount of force is stored in a memory, such as memory 1935, and is retrievable by the control system. In some embodiments, the threshold amount of force is stored in a look-up table in the memory or is a retrievable value from the memory. In some embodiments, the threshold amount of force is user-provided at an input interface. In some embodiments, the intermediate position $IP_{CC}$ corresponds to a predefined distance up the ramp 4058 of the anvil 4054.

In the partially clamped state, the control system monitors the force applied by the anvil 4054 by interrogating, or receiving signals from, the sensors. In various embodiments, the sensors comprise force sensors positioned at one or more portions of the closure system and/or the end effector to measure the force applied by the end effector to the tissue. In various embodiments, the sensors comprise current sensors that measure an amount of current supplied to the closure motor to determine the closure force.

After the occurrence of an event or a condition, as referenced above, the control system controls the closure system to resume advancement of the closure ring 4056 toward the distal position $DP_{CC}$. In various embodiments, the event comprises a threshold amount of time elapsing from when the closure ring 4056 was halted. In various embodiments, the event comprises the control system detecting a decrease in the force applied by the anvil 4054. In various embodiments, the event comprises the control system detecting the force applied by the anvil 4054 dropping a threshold amount from the maximum closure force $FTC_{max}$.

As seen in the upper graph 4102 and the lower graph 4104, the control system continuously monitors the force applied by the end effector 4050 and discretely advances 4114 the closure ring 4056. Specifically, as seen at times $t_2$ through $t_{10}$ of the upper graph 4102, the control system discretely advances the closure ring such that the closure force 4116 applied by the end effector remains constant, or at least substantially constant. It should be understood that line 4114 and line 4110 overlap and line 4116 and line 4112 overlap between $t_2$ and $t_7$ and are, therefore, represented as single lines for simplicity.

In one embodiment, the control system causes the closure system to drive 4114 the closure ring 4056 at $t_2$ such that the force 4116 remains at the $FTC_{max}$. Once the $FTC_{max}$ is achieved, the control system causes the closure ring 4056 to again halt advancement and the control system again monitors for an event, as described above, to continue advancement of the closure ring 4056, such as again at $t_3$ upon occurrence of an event. In various other embodiments, rather than discretely advancing the closure ring, the control system continuously moves the closure ring at a rate that results in the force 4112 applied by the end effector tp remain constant, or at least substantially constant.

The control system continues the above-described halting and advancement of the closure ring 4056 until the firing system is actuated at $t_6$, which is a time prior to the closure ring reaching its distal position $DP_{CC}$. Once the firing system has been actuated, the control system continues to advance the closure ring 4056 toward the distal position $DP_{CC}$, as described above, such that the closure system and the firing member of the firing system are operating simultaneously. The continued advancement of the closure ring maintains the force 4116 applied by the end effector at the $FTC_{max}$ during at least a portion of the firing stroke.

Figure 35:
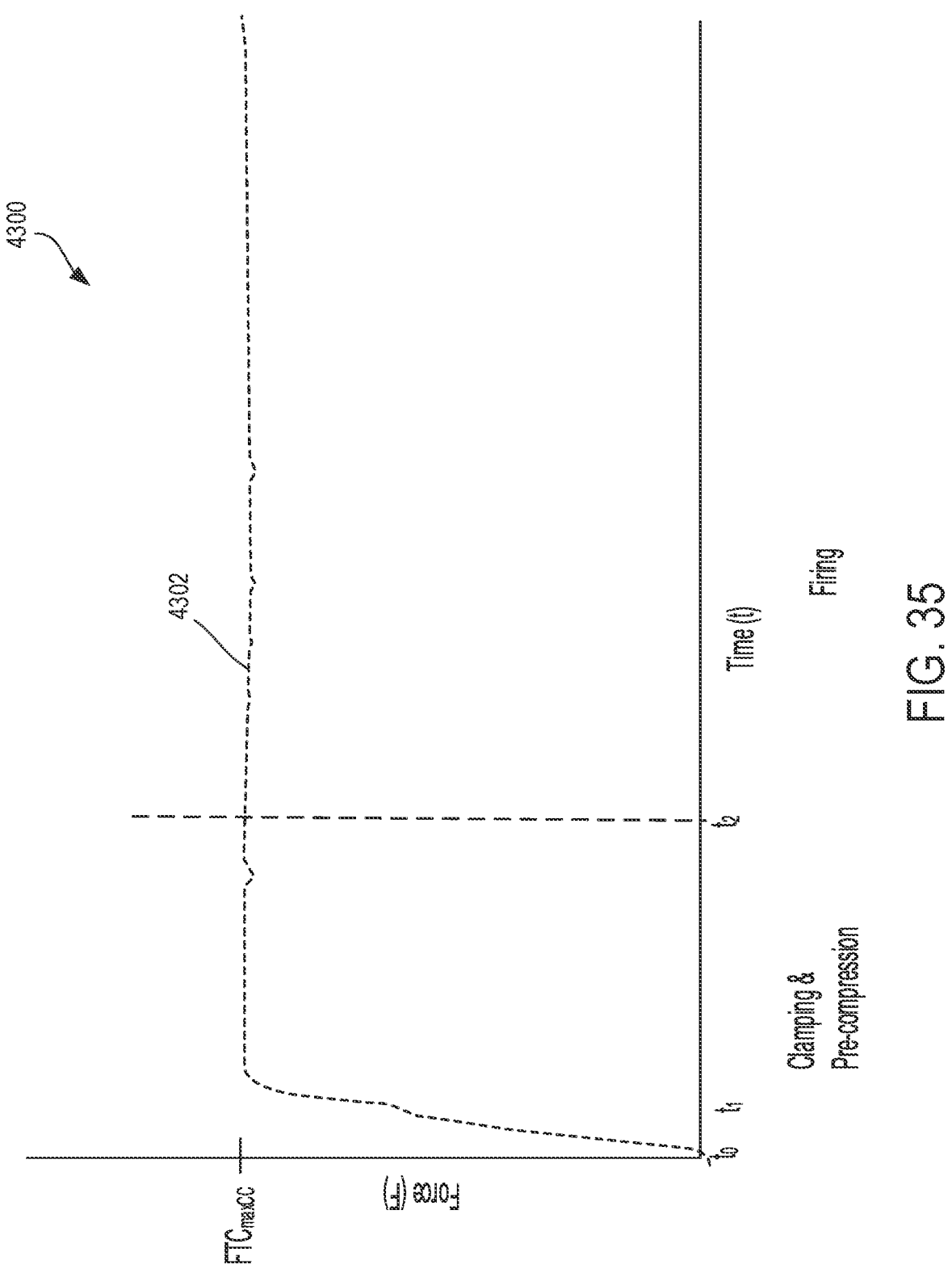
FIG. 35 illustrates a response profile from a clamping system utilizing a load control closure system, according to at least one aspect of the present disclosure.
Figure 36:
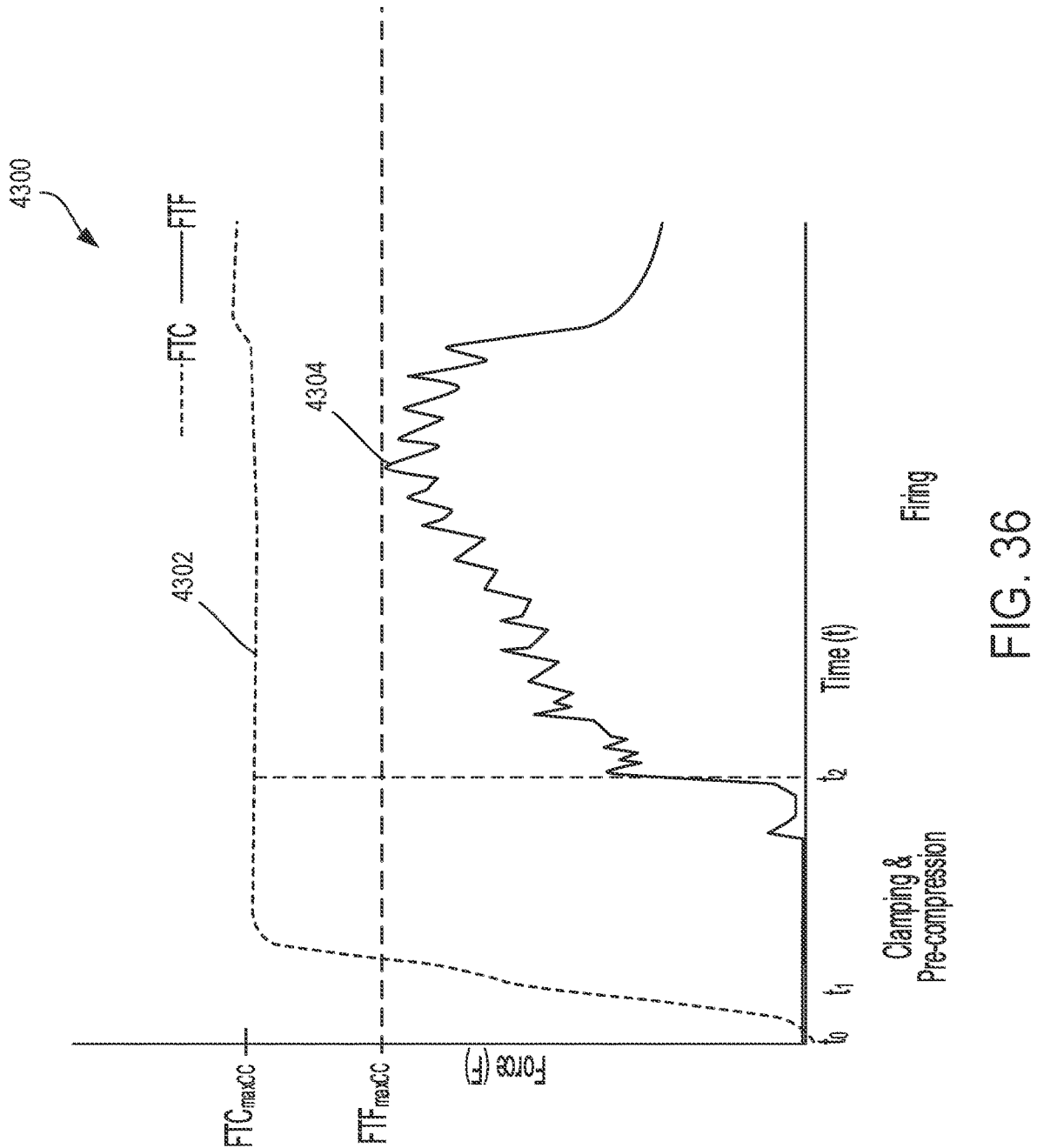
FIG. 36 illustrates a response profile from a clamping system utilizing a load control closure system, according to at least one aspect of the present disclosure.

Referring now to FIGS. 35 and 36, a response profile 4300 from a clamping system, such clamping system utilizing closure ring 4056, utilizing load control closure during a portion of the firing stroke is provided, according to at least one aspect of the present disclosure. At to, the end effector, such as end effector 4050, begins in an open state, during which time the closure force 4302 applied by the end effector to the tissue is zero. From $t_0$ to $t_1$, the end effector is transitioned toward the clamped state by a closure member, such as closure ring 4056, which causes a gradual increase in the closure force 4302. At $t_1$, the closure member reaches an intermediate closure stroke position, such as intermediate position $IP_{CC}$, corresponding to the end effector reaching a partially clamped state. In the partially clamped state, the closure force 4302 reaches a maximum closure force $FTC_{max}$.

As seen in FIGS. 35 and 36 and as described above, once the maximum amount of force $FTC_{maxCC}$ is applied to the tissue at $t_1$, the closure member can be discretely, or continuously, advanced such that the maximum amount of force $FTC_{maxCC}$ is maintained. At $t_2$, the firing system is actuated. As shown in FIGS. 35 and 36, the closure member continues to advance towards its distal position, such as $DP_{CC}$, to maintain the maximum closure force $FTC_{maxCC}$ to the tissue during at least a portion of the firing stroke. As seen in FIG. 36, the force to fire 4304 the firing drive of the surgical instrument reaches a force $FTF_{maxCC}$ that is less than that of the $FTC_{max}cc$, as well as is less than the force to fire $FTF_{maxPC}$ for a position control closure system, as described above and shown in FIG. 27. In various embodiments, the continued advancement of the closure member during at least a portion of the firing stroke can also result in a force to fire profile that is different than the force to file profile for load control closure systems where the closure member reaches its distal position prior to the actuation of the firing system. Accordingly, the load control closure system reduces the force to fire necessary by the firing system, which can prolong the life of the firing system. The load control closure system brings the tissue to its thinnest, stable state as quickly, uniformly, and repeatably as possible, and results in better surgical outcomes.

Referring now to FIG. 37, a method 4350 for controlling a surgical instrument is provided, according to at least one aspect of the present disclosure. The method 4350 comprises driving 4352 a closure member of a closure system from a first position toward a second position to transition an end effector toward a clamped state. In some embodiments, a control system, such as controller 620, can control a motor, such as closure motor 603, of a motor-powered closure system, such as closure motor drive assembly 605, to drive a closure member, such as closure ring 4056, from a first position, such as the proximal position PP, toward a second position, such as intermediate position $IP_LC$ or intermediate position $IP_{CC}$. Driving the closure member can cause an end effector, such as end effector 4050, to transition toward a clamped state to capture and apply force to tissue within the end effector.

The method 4350 further comprises detecting 4354 a closure load applied to tissue by the end effector, based on the closure member being in the second position. In various embodiments, the control system detects a force applied by the end effector utilizing force sensors or current sensors with the closure member in the second position. In some embodiments, the closure force can be a maximum closure force to be applied to the tissue, as described elsewhere herein.

The method 4350 further comprises driving 4356 the closure member from the second position toward a third position to maintain the closure load to the tissue. In various embodiments, as described elsewhere herein, the control system can control the closure system to discretely, or continuously, move the closure member, such as closure ring 4056, so as to maintain a constant, or least substantially constant, closure load to the tissue.

The method 4350 further comprises driving 4358 a firing member through a firing stroke with a firing system, based on the closure member reaching the third position. In various embodiments, as described elsewhere herein, the control system can control a motor, such as firing motor 602, of a firing system, such as firing motor drive assembly 604, to drive a firing member, such as firing member 1900, through a firing stroke. In some embodiments, driving the firing member causes staples to be deployed from a staple cartridge, such as staple cartridge 1301. In various embodiments, the third position of the closure member comprises a distal position of the closure member, such as $DP_LC$. In various embodiments, the third position of the closure member comprises a position that is proximal to its distal position, such as distal position $DP_{CC}$.

The method 4350 optionally further comprises driving 4360 the closure member from the third position toward a fourth position to maintain the closure load to the tissue during at least a portion of the firing stroke. In various embodiments, as described above, when the firing system is actuated, the closure member can be in a position that is proximal to its distal position, such as distal position $DP_{CC}$. Accordingly, the control system can continue to control the closure system to discretely, or continuously, advance the closure member during at least a portion of the firing stroke to maintain the closure load constant, or at least substantially constant. In various embodiments, the fourth position corresponds to the distal position $DP_{CC}$. In various embodiments, the fourth position corresponds to a position that is proximal to the distal position $DP_{CC}$. In various embodiments, the closure member is moving during the entirety of the firing stroke. In some embodiments, the closure member and the firing member complete their respective strokes at the same, or at least substantially the same, time. In various embodiments, the closure member finishes its closure stroke prior to the firing member completing its firing stroke. In various embodiments, the firing member finishes its firing stroke prior to the closure member completing its closure stroke.

During a closure stroke of a surgical instrument, it is desirable for all tissue layers to be captured within the jaws of the end effector such that all of the tissue layers are captured within the staple line for any given transection. During the closure of the end effector, excessive clamping speed can cause the tissue layers to be pushed out of the end effector, ultimately resulting in a non-optimal staple line seal. This tissue flow during clamping can also cause the desired transection location on the tissue to shift within the end effector, such as pushing tissue out of the distal tip of the end effector, ultimately resulting in additional firings of the surgical instrument being required. Managing this clamping speed can help maintain the desired transection location of the tissue within the end effector.

In various embodiments, a surgical instrument including an end effector and a clamping system, such as closure motor drive assembly 605, can be utilized to clamp tissue during a clamping stroke. Sensors, such as any suitable sensors described elsewhere herein, can be utilized to monitor the amount of clamping force applied by the end effector during the clamping stroke. During the clamping process, a control system, such as controller 620, coupled to the sensors can monitor the load curve, predict an expected tissue load, and compare the predicted tissue load to a closure load threshold.

In some embodiments, if the predicted load is expected to reach or exceed the closure load threshold, the control system causes the closure system to slow the closure speed, allowing for relaxation of the tissue during clamping and maintaining the desirable tissue in the jaws of the end effector. In various embodiments, the closure load threshold is stored in a memory, such as memory 624, and is retrievable by the control system. In various embodiments, the closure load threshold is user defined by a user at an input interface.

In some embodiments, if the predicted load is expected to reach or exceed the closure load threshold, the control system causes the closure system to intermittently pause the clamping stroke, allowing for relaxation of the tissue during clamping and maintaining the desirable tissue in the jaws of the end effector. In various embodiments, if the predicted load is expected to reach or exceed the closure load threshold, the control system causes the closure system to intermittently pause and slow the clamping stroke, allowing for relaxation of the tissue during clamping and maintaining the desirable tissue in the jaws of the end effector.

In some embodiments, when the control system causes the end effector to pause its clamping stroke, the control system causes the jaws to maintain the clamp force for a period of time. In various embodiments, the period of time is a predefined period of time. In various embodiments, the period of time is a variable period of time. In some embodiments, the variable period of time is based on a rate of change of the clamping load. In some embodiments, the variable period of time is based on a predicted amount that the closure load was expected to exceed the closure load threshold, such as at the time of the closure stroke completing. In various embodiments, the variable period of time is based on a gap between the anvil and the elongate channel of the end effector. In various embodiments, the variable period of time is based on a type of staple cartridge removably positioned in the end effector. In various embodiments, the variable period of time is based on a magnitude of the closure load. In various embodiments, the variable period of time is based on an amount of time that has elapsed since the end effector first made contact with the tissue during the clamping stroke. In various embodiments, the variable period of time is based on an elapsed time since the user actuated a secondary closure system of the surgical instrument.

In various embodiments, the period of time is an adaptive period of time. In various embodiments, the adaptive period of time is based on a location of the anvil relative to the elongate channel. In various embodiments, the adaptive period of time is based on the success and failures of previous clamping strokes. In some embodiments, the success and failures of previous clamping strokes is stored in a memory, such as memory 624, and is retrievable by the control system in order to set the variable period of time. In various embodiments, the adaptive period of time is based on techniques used by the clinician for the manual operation or positioning of the end effector. In various embodiments, the adaptive period of time is based on outputs from a surgical hub, such as the surgical hub described in U.S. Patent Application Publication No. 2020/0078070, which is hereby incorporated by reference in its entirety herein. In various embodiments, the adaptive period of time is based on outputs from a multispectral imaging system, such as the imaging system described in U.S. Pat. No. 11,369,366, which is hereby incorporated by reference in its entirety herein.

Once the predefined period of time has elapsed, the control system can cause the end effector to reattempt its clamping stroke at a speed to manage the tissue flow. In various other embodiments, the speed is a set speed. In various embodiments, the speed is a stepped speed. In various embodiments, the speed is a reduced speed compared to the speed prior to the end effector pausing its clamping stroke. In various embodiments, the speed is the same speed compared to the speed prior to the end effector pausing its clamping stroke.

Figure 38:
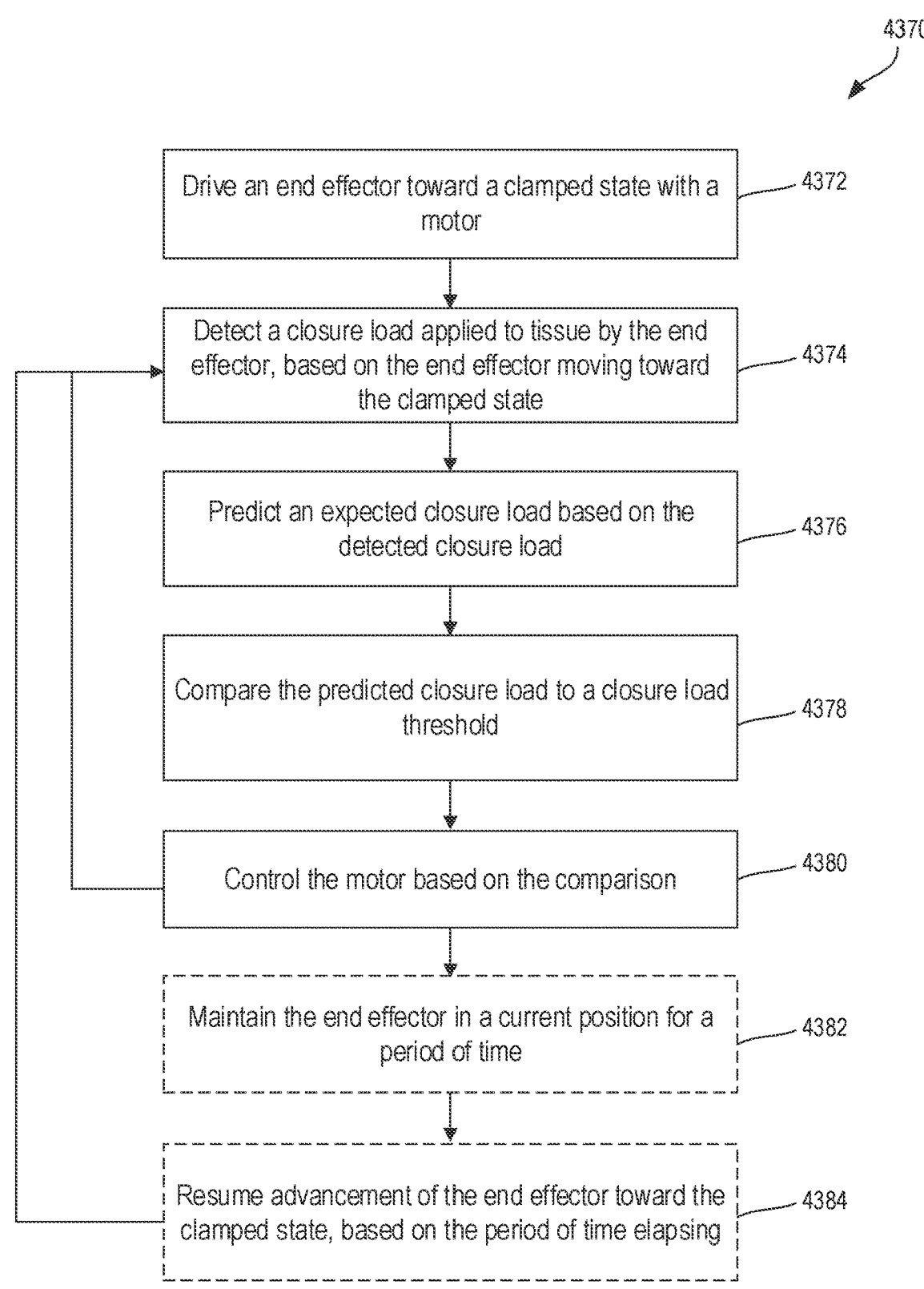
FIG. 38 illustrates a method for controlling a surgical instrument, according to at least one aspect of the present disclosure.

Referring now to FIG. 38, a method 4370 for controlling a surgical instrument is provided, according to at least one aspect of the present disclosure. The method 4370 comprises driving 4372 an end effector toward a clamped state with a motor. In various embodiments, a control system, such as controller 620, transmits a control signal to a motor, such as closure motor 603, to cause a closure system, such as closure motor drive assembly 605, to drive an end effector, such as end effector 1300, toward a clamped state.

The method 4370 further comprises detecting 4374 a closure load applied to tissue by the end effector, based on the end effector moving toward the clamped state. In various embodiments, the control system detects the closure load the end effector applies to tissue using sensors, such as any suitable sensors described elsewhere herein. In some embodiments, the sensors comprise force sensors that detect an amount of force the end effector applies to the tissue. In some embodiments, the sensors comprise current sensors that sense an amount of current applied to the motor.

The method 4370 further comprises predicting 4376 an expected closure load based on the detected closure load. In various embodiments, the control system can predict an expected closure load based on a rate of change of the closure load. In various embodiments, the control system can predict an expected closure load based on a trajectory of the closure load. In various embodiments, the control system can predict an expected closure load based on various sensor readings obtained from the sensors.

The method 4370 further comprises comparing 4378 the predicted closure load to a closure load threshold. In some embodiments, the control system can compare the predicted closure load to the closure load threshold to determine if the predicted closure load will reach or exceed the closure load threshold. In various embodiments, the control system can determine if the predicted closure load will reach or exceed the closure load threshold prior to the end effector reaching the clamped state. In various embodiments, the closure load threshold is stored in a memory, such as memory 624, and is retrievable by the control system. In various embodiments, the closure load threshold is user defined by a user at an input interface.

The method 4370 further comprises controlling 4380 the motor based on the comparison. In various embodiments, based on the results of the comparison, the control system can transmit a control signal to the motor. In some embodiments, if the predicted closure load is expected to reach or exceed the closure load threshold prior to completion of the closure stroke, the control system transmits a control signal to the motor. In some embodiments, if the predicted closure load is expected to reach or exceed the closure load threshold prior to the anvil reaching a threshold distance from the elongate channel, the control system transmits a control signal to the motor. In some embodiments, the control signal decreases the speed of the motor, thereby slowing the rate at which the end effector transitions to the clamped state. In some embodiments, the control signal pauses the motor, thereby halting the end effector from transitioning to the clamped state. In various embodiments, if the predicted closure load is expected to reach or exceed the closure load threshold, the control system can allow the end effector to continue applying a load to the tissue. In such embodiments, the control system can predict a time in which the closure load threshold will be exceeded and, accordingly, control the motor at the predicted time. Accordingly, the control system predicts and plans for when a closure load threshold will be reached or exceeded, rather than being reactive when the control system detects the closure load threshold being exceeded. Such planning and predicting allows the control system to devise a suitable response before the closure load threshold is reached or exceeded.

In various embodiments, based on the control system decreasing the speed of the motor, the control system continues to predict an expected closure load and compare the predicted closure load to the closure load threshold as the end effector transitions to the clamped state. If the control system again detects that the predicted closure load is expected to reach or exceed the closure load threshold prior to the end effector reaching the clamped state, the control system further decreases the speed of the motor such that the predicted closure load stays below the closure load threshold. In various other embodiments, the control system pauses the motor and resumes movement of the end effector toward the clamped state after a period of time. Accordingly, the method 4370 is an iterative method to maintain the tissue within the end effector.

The method 4370 further comprises maintaining 4382 the end effector in a current position for a period of time. In various embodiments, when the control system transmits a control signal to the motor to halt the end effector from transitioning toward the clamped state, the control system maintains the jaws of the end effector in its current position for a period of time. In various embodiments, the period of time comprises a predefined period of time. In various embodiments, the period of time comprises a variable period of time, as described elsewhere herein. In various embodiments, the period of time comprises an adaptive period of time, as described elsewhere herein.

The method 4370 further comprises resuming 4384 advancement of the end effector toward the clamped state, based on the period of time elapsing. In various embodiments, after the period of time has elapsed, the control system causes the motor to resume advancement of the end effector toward the clamped state utilizing the closure drive system.

In various embodiments, similar to above, after the control system resumes advancement of the end effector toward the clamped state, the control system continues to predict an expected closure load and compare the predicted closure load to the closure load threshold as the end effector transitions to the clamped state. If the control system again detects that the predicted closure load is expected to reach or exceed the closure load threshold prior to the end effector reaching the clamped state, the control system again halts the end effector from transitioning toward the clamped state and waits a period of time. In various other embodiments, the control system slows the motor if the control system has already paused and resumes movement of the end effector toward the clamped state. Accordingly, the method 4370 is an iterative method to maintain the tissue within the end effector.

Figure 39:
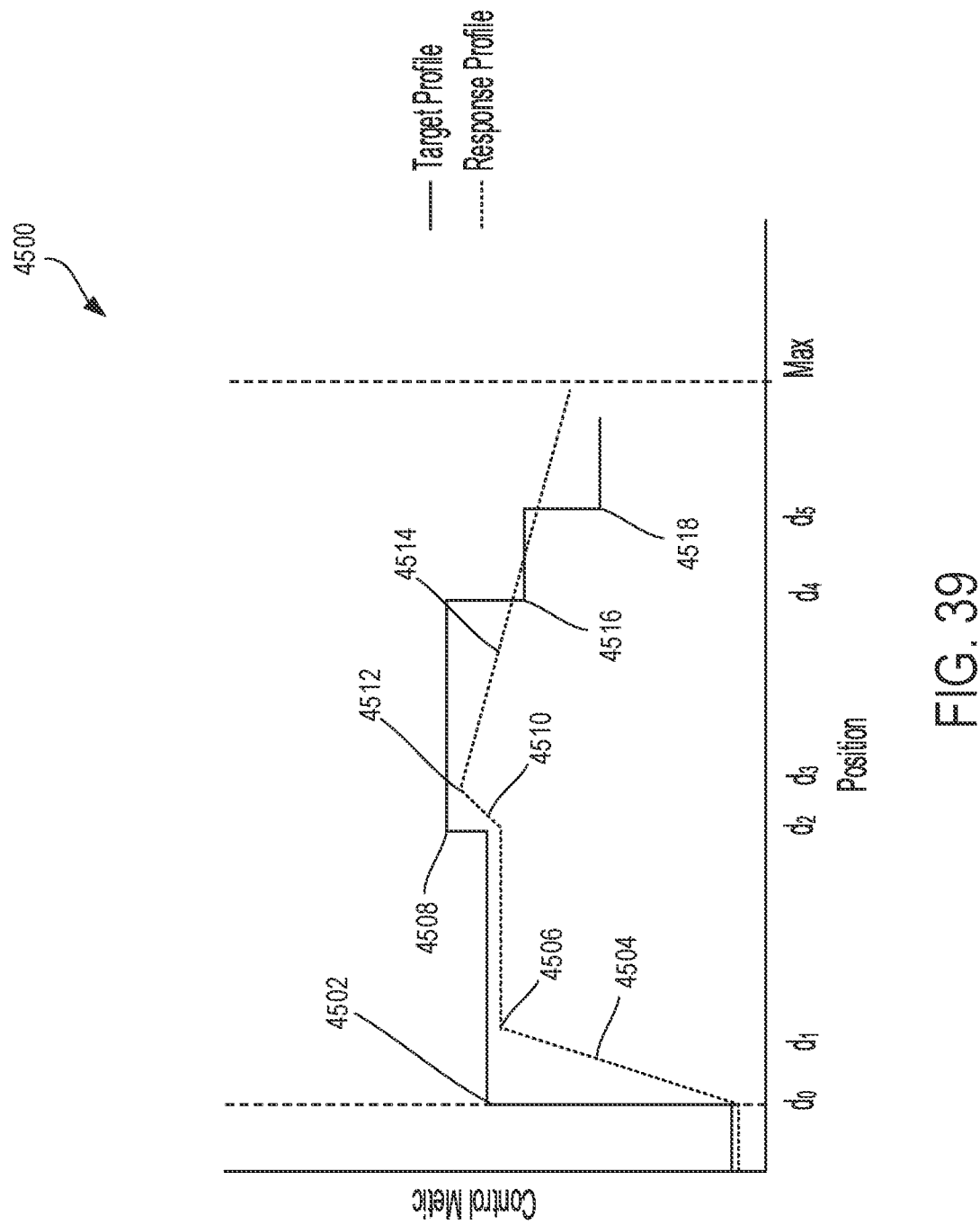
FIG. 39 illustrates a target and response signal profiles of a motor, according to at least one aspect of the present disclosure.

Referring now to FIG. 39, a graph 4500 illustrating a target and response profile for a motor is provided, according to at least one aspect of the present disclosure. The graph 4500 illustrates a control metric against a position of a closure member, as will be described in more detail below. In some embodiments, the control metric comprises a speed of the motor. In some embodiments, the control metric comprises a PWM of the motor.

In operation, a control system, such as controller 620, sets a target control metric for a motor, such as any number of motors described elsewhere herein, to drive a function of the surgical instrument. In various embodiments, the motor comprises a firing motor, such as firing motor 602, that drives a firing member, such as firing member 1900, through a firing stroke. In various embodiments, the motor comprises a closure motor, such as closure motor 603, that drives a closure member, such as closure ring 4056, through a closure stroke.

As shown in FIG. 39, at position do of a firing member, such as an unfired position thereof, the control system sets a first target control metric 4502 of the motor. In response to the first target control metric 4502, the motor ramps up 4504 toward the first target control metric 4502, ultimately reaching a first response control metric 4506, less than the first target control metric 4502, at position $d_1$ of the firing stroke of the firing member. The control system maintains the first target control metric 4502 of the motor until the firing member reaches $d_2$ of the firing stroke, at which point the control system sets a second target control metric 4508 of the motor. In response to the second target control metric 4508, the motor ramps up 4510 toward the second target control metric 4508, ultimately reaching a second response control metric 4512 less that the second target control metric 4508, at position $d_3$ of the firing stroke of the firing member.

Owing to various external factors, such as frictional losses of the system and/or thick tissue positioned within the end effector of the surgical instrument, the response control metric of the firing member ramps down 4514 despite the control system maintaining the second target control metric 4508. In response to the downward slopping response profile, in order to optimize the system and not drive the motor at a target control metric that it is unable to achieve, the control system sets diminishing target control metrics 4516, 4518 at positions $d_4$ and $d_5$ of the firing stroke, respectively. The reductions in target control metrics prevent the motor from overworking. Accordingly, the control system dynamically adjusts the target control metrics to more suitable target control metrics, based on the response profile of the motor.

During the foregoing setting of target profiles to drive the motor, any number of sensors can be utilized by the control system in order to determine the actual response profile of the motor. In some embodiments, analog signals indicative of the response profile can be fed back to a processor, such as processor 622, of the control system in order to make the necessary adjustments to the target control metrics. Upon receipt of the analog signal, the processor converts the analog signal to a digital signal using an integral A/D converter such that the processor can process the signal indicative of the response profile. In one aspect, servo motors controlled by the processor must utilize digital signals and will not work with analog signals. These A/D conversions within the processor, however, take computing cycles and resources that the processor could deploy elsewhere, thus limiting a speed at which the processor operates. Accordingly, it is desirable to feed a digital signal to the processor in order to allow the processor to focus its resources on other tasks.

In various embodiments, an A/D converter is placed upstream of the processor, such as prior to the input of the processor. The upstream A/D converter receives any number of analog signals from sensors through the surgical instrument and converts these signals to digital signals. These digital signals are fed into the processor, allowing the processor to make necessary adjustments without needing to allocate bandwidth to perform the A/D conversion itself.

Figure 40:
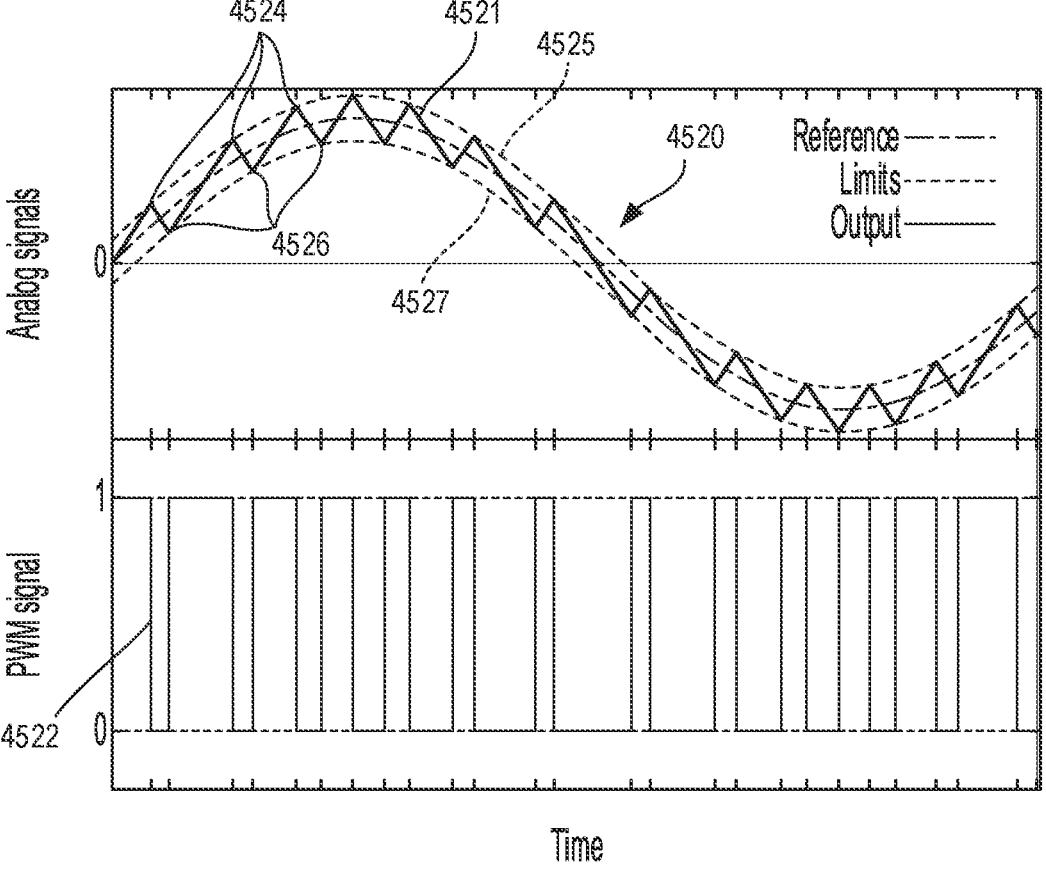
FIG. 40 illustrates the conversion of an analog signal to a PWM digital signal, according to at least one aspect of the present disclosure.

In some embodiments, the input signal to the A/D converter comprises a ramped analog signal 4520, such as is shown in FIG. 40. In various embodiments, the A/D converter converts the analog signal 4520 to a PWM digital signal 4522 according to the peaks 4524 and valleys 4526 of the output signal 4521 of the analog signal 4520 reaching limits 4525, 4527 that bind the output signal 4521. As shown in FIG. 40, the input signal to the A/D converter transitions low when a peak 4524 reaches the upper limit 4525 and transitions high when a valley 4526 reaches the lower limit 4527. Furthermore, the length of the PWM signal is controlled according to the elapsed time between peaks 4524 and valleys 4526.

In various embodiments, the analog signal fed to the A/D converter comprises an analog speed signal. In some embodiments, the analog speed signal is indicative of the speed of the motor. The A/D converter converts this signal to a digital signal and feeds the converted signal to the processor. In various embodiments, the analog speed signal can be generated using 1-wire tach speed sensing. In some embodiments, the 1-wire tach speed sensing measures the speed of the shaft of the motor. In various embodiments, the analog speed signal is generated by using a varistor that can monitor the voltage spikes applied to the motor. In various embodiments, the analog speed signal is generated using PWM angle-based sensors that determine the rate of change of the speed of the motor. In various embodiments, the analog speed signal is generated using a raw signal from a sensor with a comparator circuit that can be used to determine the speed of the motor.

In various embodiments, a resistive slide sensor is placed in one or both of the anvil, such as anvil 2000, and the elongate channel, such as elongate channel 1310, or an end effector, such as end effector 1300, to determine the relative and/or absolute position of a firing member, such as firing member 1900, during a firing stroke. Based on the sensed position and a timer, an analog signal indicative of the speed of the firing member can be generated and fed to the A/D converter. In various embodiments, the resistive slide sensor(s) determine a rate of change in the resistance to generate a signal indicative of the speed of the firing member. In some embodiments, a slope detector is utilized to determine the rate of change. In some embodiments, a differentiator amplifier is utilized to determine the rate of change.

In various embodiments, an analog signal indicative of the speed of the motor is generated based on variations in sound that emit from the motor. In some embodiments, the sound variations are detected by a microphone. In some embodiments, the sound variations are detected by a sound card. In some embodiments, the sound variations are generated and/or amplified by placing a component, such as a card, in the motor assembly. In various embodiments, the analog signal indicative of the speed of the motor is generated using strobing speed sensors.

As described elsewhere herein, a closure system can utilize a motor to drive an end effector of a surgical instrument to a clamped state to capture tissue within the end effector. As the effector transitions to the clamped state, the anvil of the end effector makes contact with the tissue. The resulting impact can slow the motor output and, in some cases, can even cause the motor to stall. In another aspect, a firing system can utilize a motor to drive a firing member of a surgical instrument through a firing stroke to cut tissue captured within the end effector and deploy staples from a staple cartridge positioned in the end effector. Similarly, the impact of the firing member on the tissue and the staple drives can result in the motor output being slowed and potentially stalling. In such scenarios, higher torques from the motor are required that would cause a standard motor to stall. Accordingly, it would be desirable to add inertia to the motor(s) in order to compensate for losses associated with high torque requirements. Furthermore, it would be desirable to add inertia to the motor(s) to compensate for losses associated with 25% motor speed losses.

Figure 41:
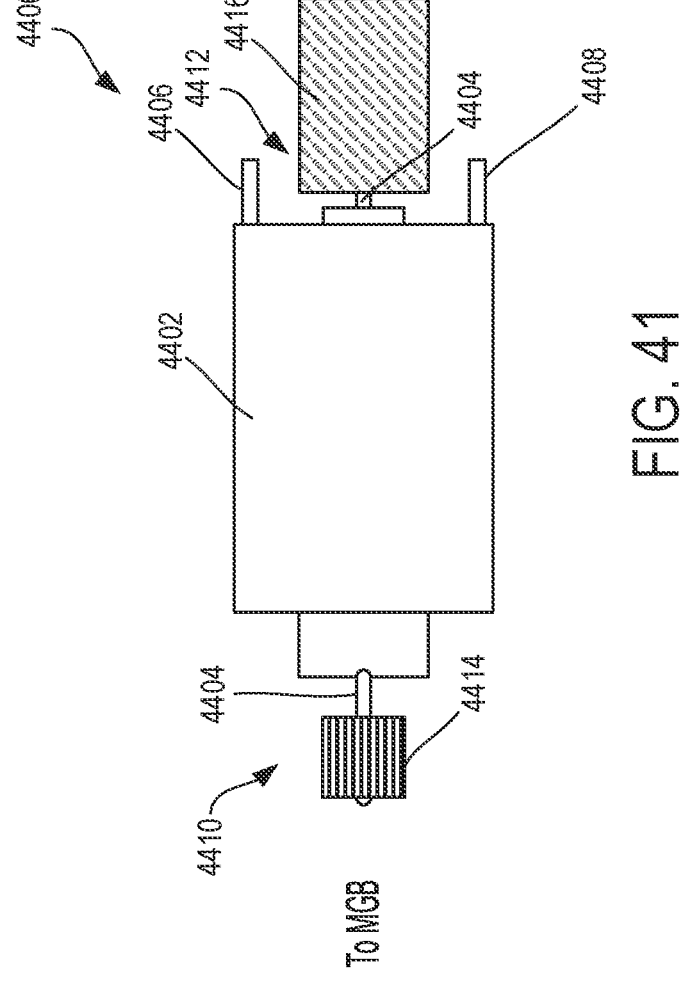
FIG. 41 illustrates a motor with improved inertia, according to at least one aspect of the present disclosure.

Referring now to FIG. 41, a motor 4400 is provided, according to at least one aspect of the present disclosure. The motor 4400 includes a housing 4402, an output shaft 4404, a first contact 4406, and a second contact 4408. In various embodiments, a first wire from a power source couples to the first contact 4406 and a second wire from the power source couples to the second contact 4408. In one aspect, to rotate the output shaft 4404 in a first, clockwise direction, a positive polarity is provided to the first contact 4406 and a negative polarity is provided to the second contact 4408 from the power source. To rotate the output shaft 4404 in a second, counterclockwise direction, a negative polarity is provided to the first contact 4406 and a positive polarity is provided to the second contact 4408, from the power source.

As seen in FIG. 41, the output shaft 4404 includes a first end 4410 that extends from a first side of the housing 4402 and a second end 4412 that extends from a second side of the housing 4402. In various embodiments, a gear 4414 is coupled to the first end 4410 of the output shaft 4404. In some embodiments, the gear 4414 is in mechanical communication with a motor gear box ("MGB") downstream of the motor 4400 such that the motor 4400 can drive a function of the surgical instrument. In some embodiments, the function is transitioning an end effector between an open and clamped state. In some embodiments, the function is driving a firing member through a firing stroke. In various embodiments, the gear 4414 is comprised of a metal, such as tungsten, platinum, hafnium, tantalum, rhenium, osmium, iridium, gold, mercury, thallium, lead, or any other suitable transition or post-transition metal, to add inertia to the motor 4400 in order to make up for inertial losses when operating the motor 4400. In various embodiments, a ring or flywheel 4416 is coupled to the second end 4412 of the output shaft 4404 to further add inertia to the motor 4400 in order to make up for inertial losses when operating the motor 4400. In various embodiments, the ring 4416 is comprised of a metal, such as tungsten, platinum, hafnium, tantalum, rhenium, osmium, iridium, gold, mercury, thallium, lead, or any other suitable transition or post-transition metal.

Figure 42:
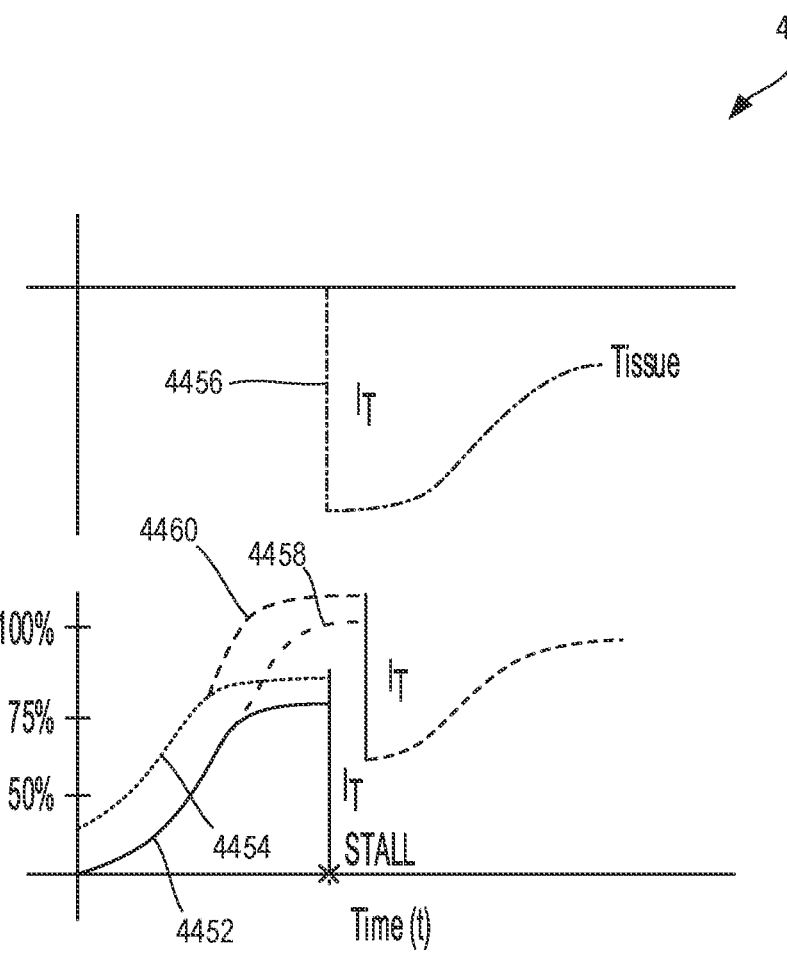
FIG. 42 illustrates a graph that illustrates current motors against the motor of FIG. 41, according to at least one aspect of the present disclosure.

Referring now to FIG. 42, a graph 4450 is provided that illustrates current motors against the improved motor 4400, according to at least one aspect of the present disclosure. In operation, current motors operate with a motor speed 4452 of 75% and an inertial speed 4454 of 75%. When current motors encounter thick tissue, inertial resistance $I_T$ 4456 from the thick tissue causes the motor speed 4452 and inertial speed 4454 of the current motors to stall. With the improved motor 4400, the motor 4400 is able to operate with a greater speed 4458 (100%) and greater inertial speed 4460 (100%) such that the inertial resistance from the tissue $I_T$ 4456 does not result in the motor stalling.

Figure 43:
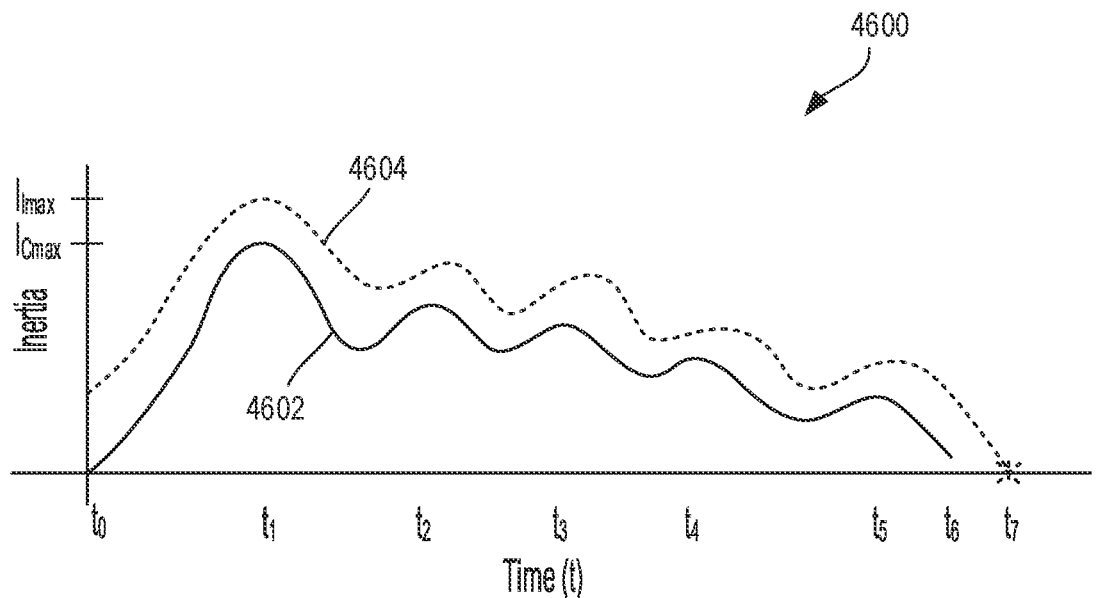
FIG. 43 illustrates a graph that illustrates current motors against the motor of FIG. 41, according to at least one aspect of the present disclosure.

Referring now to FIG. 43, a graph 4600 is provided that illustrates current motors against the improved motor 4400, according to at least one aspect of the present disclosure. In operation, current motors operate to perform a function of the end effector, such as driving a firing member through a firing stroke to cut tissue and deploy staples. As shown in the graph 4600, the inertia 4602 of the current motor ramps up to $I_{Cmax}$ from $t_0$ to $t_1$. At $t_1$, the firing member encounters resistance, such as thick tissue, that causes the current motor to lose inertia. The current motor attempts to ramp up to $I_{Cmax}$ after $t_1$, but again encounters resistance at $t_2$ prior to reaching $I_{Cmax}$. This attempted ramp up and resistance continues as the motor drives the firing member through the firing stroke from $t_2$, such as at $t_3$, $t_4$, and $t_5$. As the motor is unable to sufficiently recover inertia during the firing stroke prior to experiencing the additional resistance at $t_3$, $t_4$, and $t_5$, the motor ultimately stalls at $t_6$.

With the improved motor 4400, the motor 4400 is able to encounter additional resistance prior to stalling. As shown in the graph 4600, the inertia 4604 of the motor 4400 ramps up to $I_{Imax}$, which is greater than $I_{Cmax}$, from $t_0$ to $t_1$. Similar to the current motors, the firing member encounters resistance as the motor 4400 drives the firing member through its firing stroke, such as at $t_1$-$t_5$. However, owing to the additional inertia added to the system, the motor 4400 does not stall until $t_7$, which is a time later than $t_6$. Accordingly, the improved motor 4400 is able to withstand greater resistance than current motors.

In various embodiments, a control system, such as controller 620, can control the motor 4400 such that vibrations are induced within the closure system and/or firing system, such that fluid within the tissue is driven away from the tissue. A method of such vibration control is described in U.S. Patent Application Publication No. 2021/0059773, which is hereby incorporated by reference in its entirety herein. In various embodiments, the control system can oscillate or pulse the closure and/or firing system in order to induce fluid movement from the tissue and, thus, provide relief to the motor during operation thereof.

In some instances, it would be beneficial to control a firing system, such as firing motor drive assembly 604, based on various types of feedback received by sensors, such as any suitable sensors described elsewhere herein. In some embodiments, the feedback includes a selected staple cartridge reload, an articulation angle of the end effector, the amount of precompression applied to the tissue prior to firing the firing system, or various combinations thereof. In one aspect, clamping and precompression feedback, along with reload selection and articulation angle, are predictive of firing loads. Accordingly, the control system can compensate for predictive firing loads based on these parameters.

In various embodiments, a control system, such as controller 620, can predict a firing load based on one or multiple of the foregoing parameters. Before enabling the firing system, the control system can predict if the firing loads are outside an expected range. In various embodiments, the expected range is stored in a memory, such as memory 624, and retrievable by the control system. In various embodiments, the expected range is user defined. In one aspect, if the predicted firing load is outside of the expected range, the control system can cause the closure system, such as closure motor drive assembly 605, to continue to advance a closure member, such as closure ring 4056, to increase the closure force, which will decrease the predicted firing load. The closure force can be increased until the predicted firing load is within range.

In various embodiments, the control system provides feedback to the clinician, such as feedback on a display, informing the clinician if the predicted firing load cannot be brought within range. In such embodiments, the control system can suggest a corrective action, such as suggesting a more appropriate staple cartridge reload, a different articulation angle, or any other suitable corrective action that will lower the predicted firing load.

In some aspects, the predicted firing load is used to assign the initial firing speed of a firing member, such as firing member 1900. During the firing stroke of the firing member, the control system causes the closure member, such as closure ring 4056, to discretely, or continuously, advance, as discussed elsewhere herein, in order to lower the firing loads experienced by the firing system.

In many instances, it would be desirable to adapt both the closure system and the firing system during a surgical cutting and stapling procedure. In one aspect, adapting both systems based on inputs obtained before and/or during the surgical stapling and cutting procedure optimizes the systems and ensures that proper parameters are utilized, resulting in better surgical outcomes. In addition, it would be desirable to adapt the firing system based on monitored inputs received while the closure system transitions an end effector of a surgical instrument to the clamped state, both before and/or during actuation of the firing system.

Figure 44:
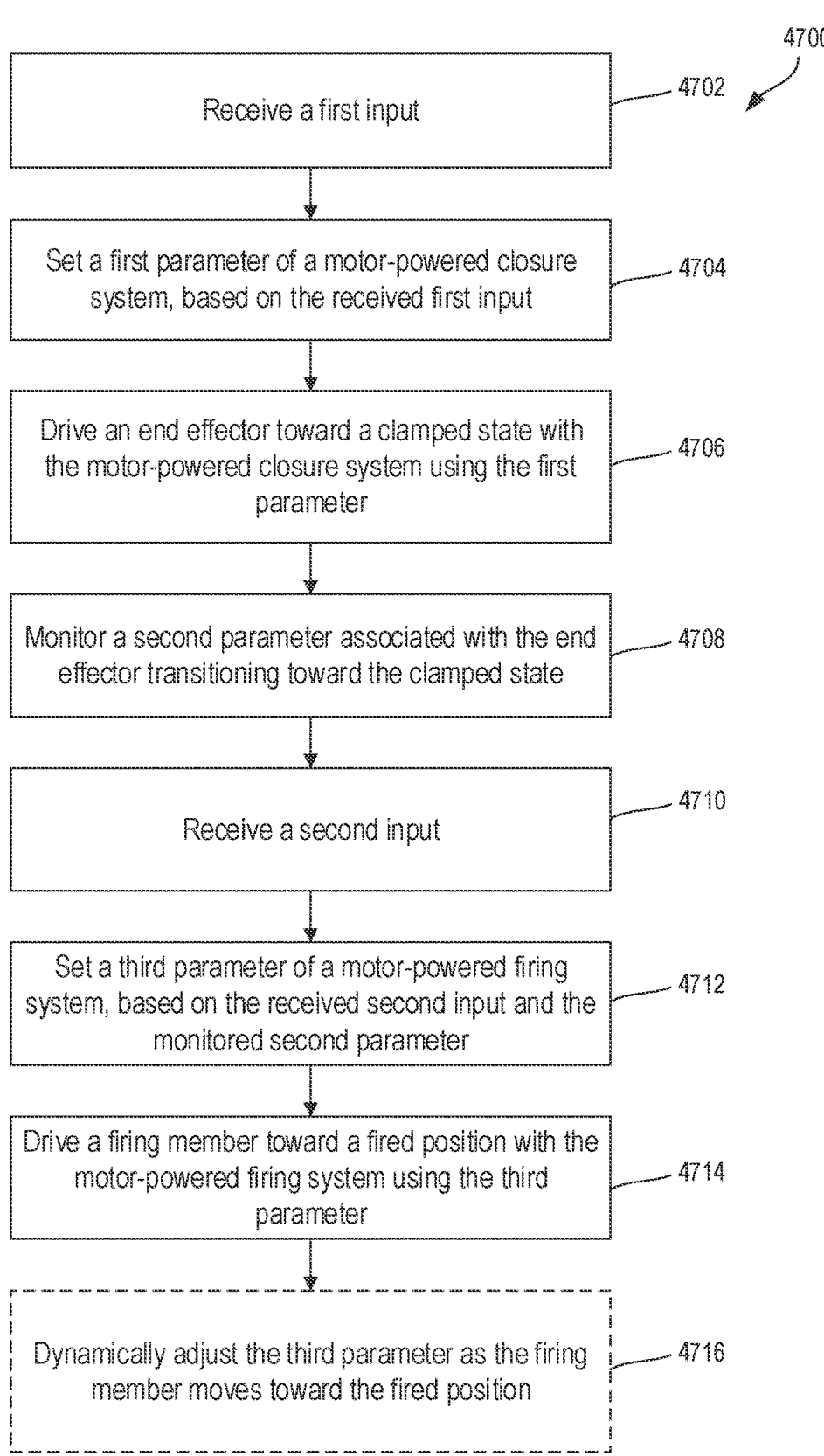
FIG. 44 illustrates a method for controlling a surgical instrument, according to at least one aspect of the present disclosure.

Referring now to FIG. 44, a method 4700 for controlling a surgical instrument is provided, according to at least one aspect of the present disclosure. The method 4700 comprises receiving 4702 a first input. In various embodiments, the first input comprises a user-provided input at an input interface. In various embodiments, the first input comprises an input received from a sensor within the surgical instrument, such as any suitable sensor described elsewhere herein. In some embodiments, the received input comprises a type of staple cartridge positioned within the end effector. In various embodiments, the surgical instrument includes a radio-frequency identified ("RFID") scanner in operable communication with a control system, such as controller 620, of the surgical instrument and the staple cartridge comprises an RFID tag. The RFID scanner can interrogate the RFID tag such that the control system can determine the type of staple cartridge positioned in the end effector.

In various embodiments, the receive input comprises a parameter associated with an end effector, such as end effector 1300, transitioning to a clamped state. In some embodiments, the parameter comprises an amount of time taken for a closure system, such as closure motor drive assembly 605, to transition the end effector to the clamped state. In some embodiments, the parameter comprises an amount of time taken for a closure system to transition the end effector to a partially clamped state. In some embodiments, the parameter comprises a load that the end effector is applying to tissue within the jaws of the end effector. In some embodiments, the received input comprises a parameter associated with the tissue captured within the end effector. In some embodiments, the parameter comprises an impedance of the tissue. In some embodiments, the parameter comprises a rate of change of force applied to the tissue. In some embodiments, the parameter comprises a type of tissue captured by the end effector.

The method 4700 further comprises setting 4704 a first parameter of a motor-powered closure system, based on the received first input. In various embodiments, the control system can utilize the received input(s) to set a parameter for a motor-powered closure system, such as closure motor drive assembly 605. In some embodiments, the control system compares the received input(s) to predefined values stored in a memory, such as memory 624, in order to determine the first parameter. In some embodiments, the first parameter comprises a speed of a closure motor, such as closure motor 603. In some embodiments, the first parameter comprises a duty cycle to the closure motor. In some embodiments, the first parameter comprises an amount of current or voltage supplied to the closure motor from a power source, such as power source 628. Other parameters for a motor-powered closure system are described elsewhere herein. Accordingly, the control system is able to adapt the closure system according to received inputs.

The method 4700 further comprises driving 4706 an end effector toward a clamped state with the motor-powered closure system using the first parameter. In various embodiments, the control system can transmit a control signal to the closure motor, causing the motor-powered closure system, such as closure-motor drive assembly 605, to drive the end effector toward the clamped state using the first parameter.

The method 4700 further comprises monitoring 4708 a second parameter associated with the end effector transitioning toward the clamped state. In various embodiments, the control system can interrogate any number of sensors within the surgical instrument, such as force sensors or pressure sensors, as examples, to monitor parameters associated with the end effector transitioning toward the clamped state. In various embodiments, the second parameter comprises an amount of time taken to transition the end effector to the clamped state. In various embodiments, the second parameter comprises a rate at which the end effector transitions toward the clamped state. In various embodiments, the second parameter comprises an amount of force applied to the tissue captured within the end effector. In various embodiments, the second parameter comprises an amount of time taken to transition the end effector to the partially clamped state. Other parameters associated with transitioning an end effector toward a clamped state are described elsewhere herein. In various embodiments, the method 4700 further comprises dynamically adjusting the first parameter, based on the monitored second parameter. Accordingly, the control system is capable of adapting the closure system based on monitored inputs as the end effector transitions to the clamped state.

The method 4700 further comprises receiving 4710 a second input. In various embodiments, the second input comprises a user-provided input at an input interface. In various embodiments, the second input comprises an input received from a sensor within the surgical instrument, such as any suitable sensor described elsewhere herein. In some embodiments, the received input comprises a type of staple cartridge positioned within the end effector. In various embodiments, the surgical instrument includes an RFID scanner in operable communication with a control system, such as controller 620, of the surgical instrument, and the staple cartridge comprises an RFID tag. The RFID scanner can interrogate the RFID tag such that the control system can determine the type of staple cartridge positioned in the end effector.

The method 4700 further comprises setting 4712 a third parameter of a motor-powered firing system, based on the received second input and the monitored second parameter. In various embodiments, the control system can utilize the received input(s), as well as the monitored parameter of the end effector moving to the clamped state, to set a parameter for a motor-powered firing system, such as firing motor drive assembly 604. In some embodiments, the control system compares the received input(s) and monitored parameter to predefined values stored in a memory, such as memory 624, in order to determine the third parameter. In some embodiments, the third parameter comprises a speed of a firing motor, such as firing motor 602. In some embodiments, the third parameter comprises a duty cycle to the firing motor. In some embodiments, the third parameter comprises an amount of current or voltage supplied to the firing motor from a power source, such as power source 628. Other parameters for a motor-powered firing system are described elsewhere herein. Accordingly, the control system is able to adapt the firing system according to received inputs and inputs obtained while the end effector is transitioned to the clamped state.

The method 4700 further comprises driving 4714 a firing member toward a fired position with the motor-powered firing system using the third parameter. In various embodiments, the control system can transmit a control signal to the firing motor, causing the motor-powered firing system, such as firing motor drive assembly 604, to drive a firing member, such as firing member 1900, toward a fired position, which causes staples removably stored in a staple cartridge, such as staple cartridge 1301, to be deployed therefrom.

In some embodiments, the control system is configured to drive the firing member toward the fired position at a time after the motor-powered closure system has placed the end effector into the clamped state. In various other embodiments, the control system is configured to drive the firing member toward the fired position as the control system drives the end effector toward the clamped state. In such embodiments, the firing system and the closure system are simultaneously operated, or operated in an overlapping fashion, by the control system. Such simultaneous operation allows the control system to monitor parameters associated with the closure of the end effector and adapt the firing system based on these monitored parameters. In various embodiments, the control system can monitor parameters associated with driving the firing member, such as a force to fire, and adapt the closure system based on these monitored parameters. Accordingly, the control system can dynamically adapt one system according to inputs received from the other system while both systems are being operated.

The method 4700 optionally further comprises dynamically adjusting 4716 the third parameter as the firing member moves toward the fired position. In various embodiments, the control system monitors parameters associated with the clamping system or the firing system and dynamically adjusts, or adapts, the third parameter accordingly. In some embodiments, the control system adapts the third parameter based on how long the end effector has been in a clamped state. In some embodiments, the control system adapts the third parameter based on how long the end effector has been in a partially clamped state. In some embodiments, the control system adapts the third parameter based on a rate of change in force applied to the tissue within the jaws of the end effector. In some embodiments, the control system adapts the third parameter based on a force to fire the firing member. In some embodiments, the control system adapts the third parameter based on parameters associated with the end effector transitioning toward the clamped state, as described above. Accordingly, the control system can dynamically adjust the firing system during the firing stroke of the firing member.

In some instances, when a closure system is driven in a position control manner, as discussed elsewhere herein, the load applied by the end effector to the tissue drops based on both tissue creep and other shaft actuation systems operated in a similar direction to the closure system. This relationship could be used to not only affect the load control of the closure system to balance loading, but also as a measure of the firing system load state. Accordingly, this relationship could be used to determine an optimal firing parameter, such as an optimal advancement speed, of a firing member, such as firing member 1900. Furthermore, this relationship can be used to determine the timing and length of pauses of wait cycles for the firing member during the firing stroke, such as firing member 1900.

In addition, the type of tissue and/or disease state thereof can be detected during closure of the end effector based on tissue creep and clamp pressures. The detected type of tissue and/or disease state thereof can further be used to control the advancement speed of the firing member to minimize tearing and load on to the tissue. Accordingly, the present disclosure provides, among other things, a means of controlling the advancement speed of a firing system based on closure loads of a control system and types of tissue, as described in more detail below.

In various embodiments, a surgical instrument including an end effector and a clamping system, such as closure motor drive assembly 605, is utilized to clamp tissue during a clamping stroke. Sensors, such as any number of sensors described elsewhere herein, can be utilized to monitor the load applied by the end effector during the clamping stroke. In various embodiments, the sensors measure the load applied by the end effector by measuring a current through a closure motor, such as closure motor 603, of the clamping system. In various other embodiments, the sensors measure the load applied by the end effector utilizing force sensors positioned on at least one of the jaws of the end effector. During the clamping process, a control system, such as controller 620, interrogates the sensors to determine the clamping load and uses the determined load to set a firing parameter of a firing system, such as firing motor drive assembly 604.

In some embodiments, the control system sets the firing parameter based on an amount of current delivered to the closure motor during the clamping stroke. In some embodiments, the control system sets the firing parameter based on a rate at which current is delivered to the closure motor during the clamped stroke. In some embodiments, the control system sets the firing parameter based on a comparison of a maximum current supplied to the motor against a current threshold or a plurality of current thresholds. In some embodiments, the current threshold(s) are stored in a memory, such as memory 624, and are retrievable by the control system. In some embodiments, the current threshold(s) are user-defined at an input interface. In various embodiments, the control system sets the firing parameter based on the amount of time the current has been delivered to the closure motor.

In various embodiments, the control system also determines a tissue type or a disease state of the tissue captured within the end effector. In some embodiments, once the end effector reaches a clamped state, the control system utilizes sensors, such as force sensors or current sensors, to determine a rate of change of force applied by the end effector to the tissue. In some embodiments, the clamped state is defined as a state where the end effector 1300 is in the closed configuration and the closure trigger 1032 is in the actuated position. In other embodiments, the clamped state is defined as a state where the elongate channel 1310 and the anvil 2000 of the end effector 1300 are within a threshold distance of one another. In other embodiments, the clamped state is defined as a state where the closure trigger 1032 has pivoted a threshold distance away from the unactuated position.

In some embodiments, as the end effector transitions to the clamped state, the control system utilizes sensors, such as force sensors or current sensors, to determine a rate of change of force applied by the end effector to the tissue. The control system compares the determined rate of change to rates of change associated with types/disease states of tissue stored in a memory, such as memory 624. In one embodiment, the control system detects that the rate of change of force captured in the end effector is a first rate of change. The control system compares the first rate of change to rates of change stored in the memory, where each stored rate of change corresponds to a tissue type and/or disease state of various types of tissue. Based on the comparison, the control system can identify the type and/or disease state of the tissue captured within the end effector.

Based on at least one of the determined clamping load applied to the tissue and the determined tissue type/disease state thereof, the control system sets a firing parameter of the firing system. In various embodiments, setting a firing parameter of a firing system comprises setting a duty cycle of the motor of the firing system. In various embodiments, setting a firing parameter of a firing system comprises setting a speed of the motor of the firing system. In various embodiments, setting a firing parameter of a firing system comprises controlling an amount of current to deliver to the motor of the firing system.

In one aspect, after the control system sets the firing parameter of the firing system, the control system can cause the firing system to drive a firing member, such as firing member 1900, through a firing stroke using a firing motor, such as firing motor 602. In some embodiments, the control system continues to monitor the current through the closure motor during the firing stroke and dynamically adjusts the firing parameter based on the monitored current. In various other embodiments, the control system monitors an elapsed time that the end effector has been in the clamped state and dynamically adjusts the firing parameter based on the elapsed time. In various other embodiments, the control system monitors an elapsed time since the end effector first made contact with tissue as the end effector transitioned to the clamped state and dynamically adjusts the firing parameter based on the elapsed time. In some embodiments, the control system can pause the advancement of the firing member based on a comparison of the current through the closure motor to a closure load threshold.

Referring now to FIG. 45, a method 5000 for controlling a surgical instrument is provided, according to at least one aspect of the present disclosure. The method 5000 comprises driving 5002 a motor-powered closure system to transition an end effector toward a clamped state. In various embodiments, a control system, such as controller 620, can transmit a control signal to a closure motor, such as closure motor 603, of a motor-powered closure system, such as closure motor drive assembly 605, to cause the motor-powered closure system to transition an end effector, such as end effector 1300, toward a clamped state.

The method 5000 further comprises detecting 5004 a current through a motor of the motor-powered closure system. In various embodiments, sensors, such as any number of sensors described elsewhere herein, can monitor a current provided to the closure motor 603 from a power source, such as power source 628.

The method 5000 further comprises setting 5006 a firing parameter of a motor-powered firing system based on the detected current. In various embodiments, the control system can utilize the detected current through the motor, as described elsewhere herein, in order to set a firing parameter of the a motor-powered firing system, such as firing motor drive assembly 604. In some embodiments, the firing parameter comprises a duty cycle of a firing motor, such as firing motor 602. In various embodiments, the firing parameter comprises a speed of the firing motor.

The method 5000 further comprises driving 5008 a firing member through a firing stroke with the motor-powered firing system using the firing parameter. In various embodiments, the control system can cause the motor-powered firing system to drive a firing member, such as firing member 1900, through a firing stroke using the firing motor 602 and the firing parameter. In some embodiments, the firing stroke of the firing member causes staples removably stored in a staple cartridge, such as staple cartridge 1301 removably positioned in the end effector, to be deployed into the tissue captured by the end effector.

The method 5000 optionally further comprises dynamically 5010 adjusting the firing parameter during the firing stroke. In various embodiments, the control system continues to monitor the current through the closure motor during the firing stroke and dynamically adjust the firing parameter based on the monitored current. In various embodiments, the control system measures an elapsed time from when the end effector first made contact with the tissue while transitioning to the clamped state and adjusts the firing parameter based on the elapsed time. In various embodiments, the control system measures an elapsed time from when the end effector reached the clamped state and adjusts the firing parameter based on the elapsed time.

Referring now to FIG. 46, a method 5100 for controlling a surgical instrument is provided, according to at least one aspect of the present disclosure. The method 5100 comprises driving 5102 a motor-powered closure system to transition an end effector toward a clamped state. In various embodiments, a control system, such as controller 620, can transmit a control signal to a closure motor, such as closure motor 603, of a motor-powered closure system, such as closure motor drive assembly 605, to cause the motor-powered closure system to transition an end effector, such as end effector 1300, toward a clamped state.

The method 5100 further comprises detecting 5104 a load applied by the end effector to tissue. In various embodiments, sensors, such as any number of sensors described elsewhere herein, monitor a current provided to the closure motor 603 from a power source, such as power source 628, to measure the load applied by the end effector to the tissue. In various embodiments, force sensors positioned on the end effector measure the load applied by the end effector. In various embodiments, the control system interrogates, or receives signals from, the sensors to determine the load applied by the end effector to the tissue.

The method 5100 further comprises determining 5106 a rate of change of the load applied by the end effector to the tissue. In various embodiments, the control system monitors the readings from the sensors over time to determine a rate of change of the load over time. In various embodiments, the control system determines the rate of change as the end effector transitions toward the clamped state. In various embodiments, the control system determines the rate of change after the end effector has reached the clamped state. In various embodiments, the control system determines the rate of change as the end effector is transitioning to the clamped state and after the end effector has reached the clamped state.

The method 5100 further comprises determining 5108 a tissue type of the tissue based on the determined rate of change. In various embodiments, the control system, as described in more detail elsewhere herein, can determine the tissue type, and/or the disease state, of the tissue by comparing the determined rate of change to rates of change stored in a memory, where the stored rates of change correspond to different types of tissue and/or disease states of tissue.

The method 5100 further comprises setting 5110 a firing parameter of a motor-powered firing system based on the determined tissue type. In various embodiments, the control system can utilize the determined tissue type in order to set a firing parameter of a motor-powered firing system, such as firing motor drive assembly 604. In some embodiments, the firing parameter comprises a duty cycle of a firing motor, such as firing motor 602. In various embodiments, the firing parameter comprises a speed of the firing motor. In various embodiments, the firing parameter comprises a parameter suitable for cutting and stapling the determine type of tissue.

The method 5100 further comprises driving 5112 a firing member through a firing stroke with the motor-powered firing system using the firing parameter. In various embodiments, the control system can cause the motor-powered firing system to drive a firing member, such as firing member 1900, through a firing stroke using the firing motor 602 and the firing parameter. In some embodiments, the firing stroke of the firing member causes staples removably stored in a staple cartridge, such as staple cartridge 1301, removably positioned in the end effector to be deployed into the tissue captured by the end effector.

The method 5100 optionally further comprises dynamically 5114 adjusting the firing parameter during the firing stroke. In various embodiments, the control system monitors the current through a closure motor of the closure system during the firing stroke and adjusts the firing parameter based on the monitored current. In various embodiments, the control system measures an elapsed time from when the end effector first made contact with the tissue while transitioning to the clamped state and adjusts the firing parameter based on the elapsed time. In various embodiments, the control system measures an elapsed time from when the end effector reached the clamped state and adjusts the firing parameter based on the elapsed time.

Several surgical instruments have a portion of a stroke that requires a first compression level and would benefit from a second portion that has a different tissue compression level. In some embodiments, the force of a motorized clamp arm of an ultrasonic surgical instrument, similar to the ultrasonic instruments described in U.S. Pat. No. 10,842, 523, which is hereby incorporated by reference in its entirety herein, would benefit from an increase in compression when the system is ready to cut, but a lower level when the system is tissue welding. In some other embodiments, RF energy activation of an electrosurgical instrument, similar to the electrosurgical instruments described in U.S. Pat. No. 10,842,523, which is hereby incorporated by reference in its entirety herein, benefits from a first compression at the beginning of welding, but a lower compression at the termination of welding to balance tissue heating and tissue sticking. In some other embodiments, a stapler, such as any of the surgical stapling instruments described elsewhere herein, would benefit from better tissue stability of higher compression at the start of the firing member staple deployment, but that same compression in combination with the anvil pressure could translate to higher frictions and force to fire (FTF) in the later portions of the stroke.

A surgical stapler utilizes different types of staple cartridges depending on the tissue thickness to be cut and staple. As one example, during a gastric surgery, the tissue thickness increases as portions of the stomach are resected. Accordingly, clinicians will use sequential cartridges for the increasing tissue thickness. In one aspect, the clamping system adapts as it is fired to account for the increased thickness and/or reduce the motor speed to prevent tissue flow and/or stall as it goes into the thicker tissue. In various embodiments, a control system, such as controller 620, determines the tissue thickness based on a tissue gap between the anvil and the elongate channel of the end effector once the end effector has reached the clamped state. In various embodiments, the control system includes a radio-frequency identification (RFID) scanner than scans an RFID tag on the inserted staple cartridge to determine the intended tissue thickness to be cut. Based on the determined tissue thickness, the control system sets a firing speed of the firing system.

In various embodiments, the control system dynamically adjusts the firing system of the surgical instrument based on, among other things, a stroke location of the firing member, a time since the activation of the firing system, a time since the activation of the electrosurgical system, such as a generator, a time since the activation of an ultrasonic system, such as an ultrasonic generator, loading measured on the firing activation system, or combinations thereof. Based on the foregoing parameters, the control system can dynamically adjust the surgical instrument as the tissue is cut and/or sealed to provide an appropriate tissue force.

In various embodiments, the control system causes a closure motor, such as closure motor 603, to apply a first force to tissue captured within the end effector. In some embodiments, in the context of an ultrasonic surgical instrument, the control system causes the closure motor to apply a first force prior to the ultrasonic blade beginning to cut and weld tissue. In some embodiments, in the context of an electrosurgical instrument, the control system causes the closure motor to apply a first force as the electrosurgical instrument begins to apply energy to the tissue. In some embodiments, in the context of a surgical stapling instrument, the control system causes the closure motor to apply a first force as a firing member, such as firing member 1900, begins to move through a staple firing stroke.

While applying the first force, the control system monitors for the occurrence of a predefined event. Based on detecting the predefined event, the control systems causes the closure motor to apply a second force different from the first force. In various embodiments, the control system utilizes sensors, such as any number of the sensors described elsewhere herein, to monitor for the predefined event. In various embodiments, in the context of an ultrasonic surgical instrument, the predefined event comprises the ultrasonic blade of the ultrasonic surgical instrument beginning to weld tissue. In some embodiments, the control system detects the ultrasonic blade beginning to weld tissue by detecting the actuation of a trigger on the ultrasonic instrument. In some embodiments, the control system detects the ultrasonic blade beginning to weld tissue by detecting an electric current being provided to the ultrasonic transducer. In some embodiments, the control system detects the ultrasonic blade beginning to weld tissue by detecting a change in the impedance of the tissue utilizing a sensor.

In various embodiments, in the context of an electrosurgical surgical instrument, the predefined event comprises the electrosurgical instrument ceasing to apply energy to the tissue. In some embodiments, the control system detects the cease in energy utilizing a sensor to detect the current flow to the electrodes in the end effector of the electrosurgical instrument. In some embodiments, the control system detects the cease in energy utilizing a sensor to detect energy being provided by an electrosurgical generator to the electrosurgical instrument. In one aspect, lowering the force at the termination of the welding process balances tissue heating and tissue sticking, resulting in a better surgical outcome.

In various embodiments, in the context of a surgical stapling instrument, the predefined event comprises the firing member reaching a predefined point along the firing stroke. In some embodiments, the control system detects the firing member reaching the predefined point using a position sensor, such as any number of position sensor described elsewhere herein. In some embodiments, the predefined position comprises a predefined position away from the starting position of the firing member. In some embodiments, the predefined position comprises a predefined position away from the ending position of the firing member. In one aspect, lowering the force at the end of the firing stroke results in lower frictions and lower forces to fire, resulting in a better surgical outcome.

In some embodiments, the second force is greater than the first force. In some embodiments, the second force is less than the first force. In some embodiments, the control system causes the end effector to gradually transition from the first force to the second force. In some embodiments, the control system causes the end effector to quickly transition from the first force to the second force.

Figure 47:
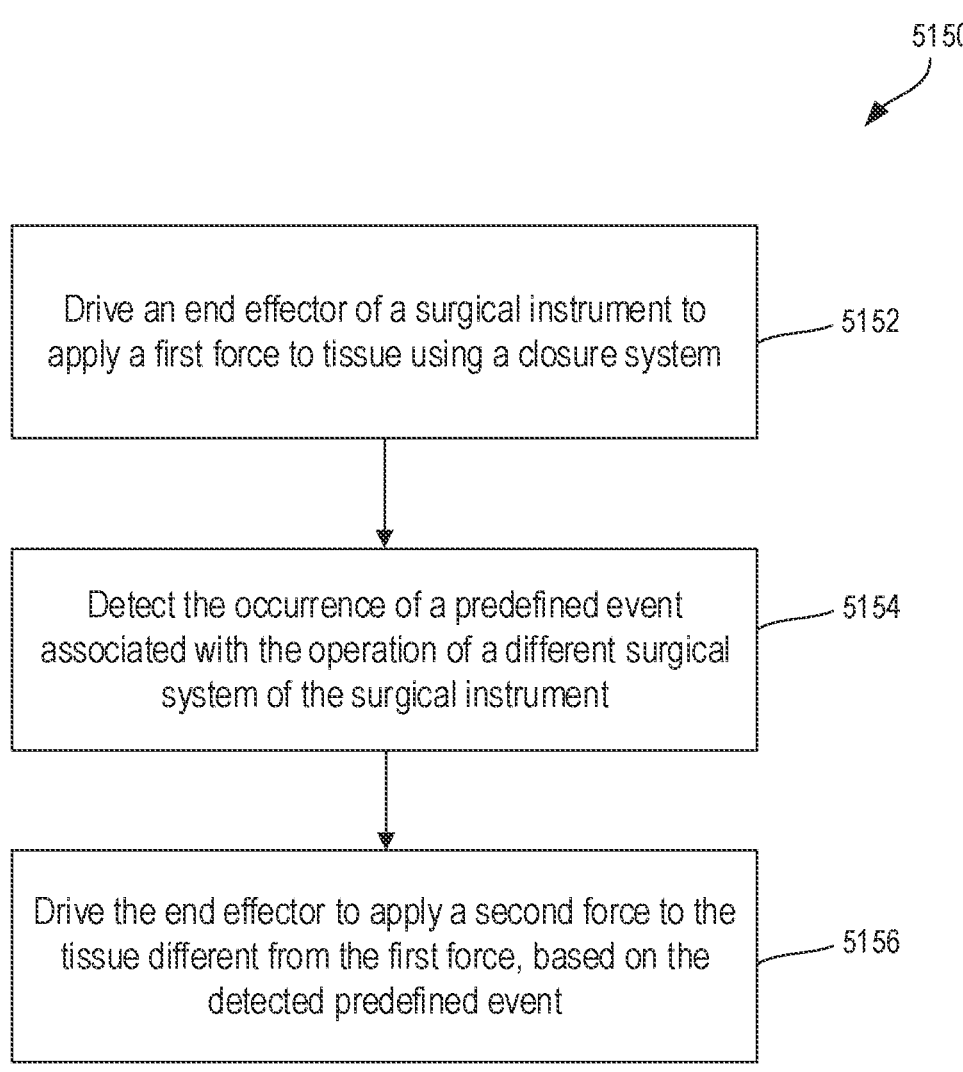
FIG. 47 illustrates a method for controlling a surgical instrument, according to at least one aspect of the present disclosure.

Referring now to FIG. 47, a method 5150 for controlling a surgical instrument is provided, according to at least one aspect of the present disclosure. In various embodiments, the method 5150 comprises driving 5152 an end effector of a surgical instrument to apply a first force to tissue using a closure system. In some embodiments, a control system, such as controller 620, drives a closure motor, such as closure motor 603, of a closure system, such as closure motor drive assembly 605, to cause an end effector, such as end effector 1300, to apply a first force to tissue.

The method 5150 further comprises detecting 5154 the occurrence of a predefined event associated with the operation of a different surgical system of the surgical instrument. In some embodiments, in the context an ultrasonic instrument, the different surgical system comprises an ultrasonic drive system that includes an ultrasonic blade and the predefined event comprises the ultrasonic blade beginning to cut and weld tissue. In some embodiments, in the context of an electrosurgical instrument, the different surgical system comprises an electrosurgical system that includes electrodes that apply energy to the tissue, and the predefined event comprises the electrodes ceasing to apply energy to the tissue. In some embodiments, in the context of a surgical stapling instrument, the different surgical system comprises a firing system, such as the firing motor drive assembly 604, and the predefined event comprises the firing member reaching a predefined location along the firing stroke. In various embodiments, the control system detects the predefined events described above using any number of sensors described elsewhere herein.

The method 5150 further comprises driving 5156 the end effector to apply a second force to the tissue different from the first force. In various embodiments, based on detecting the predefined event, the control system can control the closure system to adjust the closure force applied by the end effector. In various embodiments, the second force is less than the first force. In various embodiments, the second force is greater than the first force. In some embodiments, the control system causes the end effector to gradually transition from the first force to the second force. In some embodiments, the control system causes the end effector to quickly transition from the first force to the second force. In one aspect, changing the force applied by the end effector results in better surgical outcomes.

In one aspect, as a firing member, such as firing member 1900, is driven through the firing stroke, an upper flange, such as anvil engagement tab 1924, and a lower flange, such as lower channel engagement tabs 1926, thereof engage the jaws of the end effector. The engagement between the upper/lower flanges and the end effector causes the load applied by the end effector to the tissue to be distributed to both the upper/lower flanges and the closure system, such as closure motor drive assembly 605. Stated another way, prior to advancing the firing member through the firing stroke, the closure system is responsible for the closure load applied to the tissue. As the firing member traverses through the firing stroke, the firing member "lightens the load" on the closure system, causing the load to be distributed between the two systems of the surgical instrument. In various embodiments, the control system can detect how much load is being applied to the tissue by the closure system during the firing stroke. In some embodiments, the control system detects how much load is applied by the closure system using a current sensor that detects the current flow through the closure motor, such as closure motor 603, of the closure system. Based on the detected current flow, the control system can adjust the current supplied to the closure motor in order to maintain or adjust the closure load collectively applied by the closure system and firing member during the firing stroke. In one aspect, as described elsewhere herein, the control system can adjust the closure load applied by the closure system by controlling a position of a closure ring 4056 during the firing stroke.

During operation of a surgical instrument, a user can transition an end effector, such as end effector 1300, from an open state toward a clamped state using a clamping system, such as closure system 3000 or closure motor drive assembly 605, as examples. As the end effector transitions toward the clamped state, the end effector can reach a partially clamped state intermediate the open state and the clamped state. In some embodiments, the partially clamped state is defined as a state where the end effector first makes contact with and begins to apply force to the tissue. In some embodiments, the partially clamped state is defined as a state where the anvil of the end effector is within a threshold distance from the elongate channel of the end effector. After reaching the partially clamped state, the end effector can continue to transition toward the clamped state. In some instances, it would be desirable to provide a clinician with non-visual feedback indicative of how long the end effector has been in the partially clamped state and/or the clamped state. Providing non-visual feedback helps the clinician maintain their focus on the task at hand without needing to look to a visual indicator, such as an external display, to determine how long the end effector has been in the partially clamped or clamped states.

In various embodiments, the surgical instrument includes a control system, such as a circuit board 1100 or controller 620, as examples, that creates a haptic tactile response repeatably at a predetermined cadence cycle to provide the clinician with feedback regarding the time since the end effector reached the partially clamped state and/or the clamped state. In some embodiments, the magnitude of the vibration could be minimized every cycle or every several cycles to provide the user with "visibility" regarding the number of cycles that have passed and, thus, ascertain how long the end effector has been in the partially clamped state and/or the clamped state.

In some embodiments, the clinician transitions an end effector toward a clamped state using a motor drive closure system, such as closure motor drive assembly 605. The control system can detect the end effector reaching the clamped state using any number of sensors described elsewhere herein, such as with a Hall-Effect sensor, as an example. Based on the detection, the control system can cause a haptic device to operate at a predefined frequency, such as every other second, with each vibration decreasing in magnitude by a predefined amount, such as 50% per pulse. Accordingly, the clinician can ascertain how long the end effector has been in the clamped state based on the noticeable and decreasing feedback from the haptic device until the firing system is actuated.

In various embodiments, the control system can provide haptic feedback using motors of the surgical instrument. In some embodiments, after detecting the end effector has reached the clamped state and/or the partially clamped state, the control system, such as controller 620, can cause a 200 ms forward and 200 ms backward inrush current through the closure motor, such as closure motor 603, to induce slight movement in the motor pinion gear. This inward and outward rush of current causes noticeable handle movement that is detectable by the clinician but does not substantially move the closure drive train. In various other embodiments where the surgical instrument does not include a closure motor, the control system causes an inrush and backward rush of current through the firing motor to generate the haptic feedback. In various embodiments, the control system adjusts the inrush/backrush of current into the motor in order to provide decreasing feedback to the clinician, informing the clinician of the passing time since the end effector has been in the partially clamped or clamped state. In some embodiments, as time elapses, the control circuit decreases the amount of time in the forward and backward inrush current through the motor. In some embodiments, as time elapses, the control circuit decreases the intensity of the forward and backward inrush current through the motor.

In many instances, it would be desirable to adapt one drive system of a surgical instrument in accordance with measurements obtained while monitoring a second drive system of the surgical instrument. For instance, a control system of the surgical instrument can monitor a parameter, or parameters, associated with operating a first drive system of the surgical instrument. Such monitoring allows the control system to determine information about the type of tissue that is being worked on by the surgical instrument. Based on the monitored parameter(s), the surgical instrument can adjust, or adapt, a parameter, or parameters, of a second, different drive system of the surgical instrument. Such adaptation allows the control system to ensure that proper, optimal parameters of the second drive system are utilized according to information obtained when operating the first drive system.

In some instances, a surgical stapling instrument can be utilized by a clinician to cut and staple tissue captured within the jaws of an end effector. In some embodiments, the surgical stapling instrument can be similar to surgical instrument 1010 or any other suitable surgical instrument described elsewhere herein. In operation, the clinician can actuate the closure system, such as closure system 3000 or closure motor drive assembly 605, as examples, to cause an end effector, such as end effector 1300, to move toward a clamped state. A control system, such as circuit board 1100 or controller 620, as examples, can be in operable communication with sensors of the surgical instrument in order to monitor a parameter associated with the end effector moving toward the clamped state. In some embodiments, the parameter comprises a clamp load applied by the end effector to the tissue. In various other embodiments, the parameter comprises an amount of time taken to reach the clamped state. In various other embodiments, the parameter comprises an amount of time taken to reach a partially clamped state. In various other embodiments, the parameter comprises an amount of time that the end effector is in the clamped state prior to actuation of a second drive system. In various other embodiments, the parameter comprises a speed at which the end effector moves toward the clamped state. In various other embodiments, the parameter comprises a rate of change of force applied by the end effector to the tissue.

Based on the parameter monitored by the control system, via the sensors, the control system sets a parameter of a second drive system, such as a firing system, of the surgical instrument. In some embodiments, setting a parameter of a second drive system comprises setting a firing parameter of a firing system, such as firing drive system 1080 or firing motor drive assembly 604, as examples. In some embodiments, setting a parameter of the second drive system comprises setting a parameter for a motor, such as motor 1082 or firing motor 602, as examples, that drives a firing member, such as firing member 1900, through a firing stroke. In some embodiments, the parameter for the motor comprises a duty cycle of the motor. In some embodiments, the firing parameter comprises a speed of the motor. In some embodiments, the firing parameter comprises an amount of current or voltage supplied to the motor from a power source. In some embodiments, setting a firing parameter of the second drive system comprises setting multiple parameters of the second drive system.

In various other embodiments, the control system monitors a parameter associated with the second drive system, such as the firing system, in order to set a parameter for the first drive system, such as the closure system. In some embodiments, the control system monitors a parameter associated with driving the firing member through the firing stroke, such as the firing load on the firing member, an amount of current applied to the motor, or the speed of the motor, as examples. Based on the monitored parameter, the control system sets a parameter of the first drive system. In some embodiments, setting a parameter of the first drive system comprises setting a clamp load of the end effector. Accordingly, based on parameter(s) monitored during the firing of the surgical instrument, the control system can effect a change in the clamping system of the surgical instrument. In some embodiments, the change can comprise varying the clamping load applied to the tissue by the end effector during and/or after the firing stroke of the firing system.

In some instances, an electrosurgical instrument, similar to the electrosurgical instruments described in U.S. Pat. No. 10,842,523, which is hereby incorporated by reference in its entirety herein, can be utilized by a clinician to weld and cut tissue captured within the jaws of an end effector. In operation, the clinician can actuate a closure system of the electrosurgical instrument to move a clamp arm toward a clamped state. A control system, such as circuit board 1100 or controller 620, as examples, can be in operable communication with sensors of the electrosurgical instrument in order to monitor a parameter associated with the end effector moving toward the clamped state, similar to those described herein above concerning the surgical stapling instrument. In various embodiments, the control system can monitor a parameter associated with the end effector applying energy to the tissue. In some embodiments, the parameter associated with the end effector applying energy to the tissue comprises a magnitude of the energy applied to the tissue via an electrode. In some embodiments, the parameter associated with the end effector applying energy to the tissue comprises an amount of time that the end effector has been applying energy to the tissue via an electrode. In some embodiments, the parameter associated with the end effector applying energy to the tissue comprises an impedance of the tissue. In some embodiments, the parameter associated with the end effector applying energy to the tissue comprises a rate of change of the impedance of the tissue.

Based on the parameter monitored by the control system, via the sensors, the control system can set a parameter of a second drive system, such as a cutting system or a clamping system of the electrosurgical instrument. In some embodiments, setting a parameter of a second drive system comprises setting a firing parameter of the cutting system. In some embodiments, setting a firing parameter of the cutting system comprises setting a parameter for a motor that the drives a cutting member through a cutting stroke. In some embodiments, the parameter for the motor comprises a duty cycle of the motor. In some embodiments, the firing parameter comprises a speed of the motor. In some embodiments, the firing parameter comprises an amount of current or voltage supplied to the motor from a power source. In some embodiments, setting a firing parameter of the second drive system comprises setting multiple parameters of the second drive system.

In various embodiments, setting a parameter of the second drive system comprises setting a parameter of the closure system. In some embodiments, setting a parameter of the closure system comprises an amount of force applied to the tissue. In some embodiments, setting a parameter of the closure system comprises a rate of change of force applied to the tissue. In some embodiments, setting a parameter of the closure system comprises a speed at which the end effector moves toward the clamped state. Various other parameters associated with clamping systems are described elsewhere herein.

In some instances, an ultrasonic instrument, similar to the ultrasonic instruments described in U.S. Pat. No. 10,842,523, which is hereby incorporated by reference in its entirety herein, can be utilized by a clinician to cut tissue captured within the jaws of an end effector. In operation, the clinician can actuate a closure system of the ultrasonic instrument to move a clamp arm toward a clamped state. A control system, such as circuit board 1100 or controller 620, as examples, can be in operable communication with sensors of the ultrasonic instrument in order to monitor a parameter associated with the end effector moving toward the clamped state, similar to those described herein above concerning the surgical stapling instrument and the electrosurgical instrument.

In various embodiments, the control system can monitor a parameter associated with the end effector applying energy to the tissue. In some embodiments, the parameter associated with the end effector applying energy to the tissue comprises a magnitude of the energy applied to the tissue via an ultrasonic blade. In some embodiments, the parameter associated with the end effector applying energy to the tissue comprises an amount of time that the end effector has been applying energy to the tissue via an ultrasonic blade. In some embodiments, the parameter associated with the end effector applying energy to the tissue comprises an impedance of the tissue. In some embodiments, the parameter associated with the end effector applying energy to the tissue comprises a rate of change of the impedance of the tissue. In various embodiments, the parameter associated with the end effector applying energy to the tissue comprises a frequency of the ultrasonic blade.

Based on the parameter monitored by the control system, via the sensors, the control system can set a parameter of a second drive system, such as an ultrasonic drive system or a clamping system of the ultrasonic instrument. In some embodiments, setting a parameter of a second drive system comprises setting a parameter of the ultrasonic drive system. In some embodiments, setting a firing parameter of the ultrasonic drive system comprises setting a parameter for an ultrasonic transducer that oscillates an ultrasonic blade to cut tissue. In some embodiments, the parameter for the motor comprises a duty cycle of the motor. In some embodiments, the parameter comprises a frequency of the ultrasonic blade. In some embodiments, the parameter comprises an amount of current or voltage supplied to the transducer from a power source. In some embodiments, setting a parameter of the second drive system comprises setting multiple parameters of the second drive system.

In various embodiments, setting a parameter of the second drive system comprises setting a parameter of the closure system. In some embodiments, setting a parameter of the closure system comprises an amount of force applied to the tissue. In some embodiments, setting a parameter of the closure system comprises a rate of change of force applied to the tissue. In some embodiments, setting a parameter of the closure system comprises a speed at which the end effector moves toward the clamped state. Various other parameters associated with clamping systems are described elsewhere herein.

Figure 48:
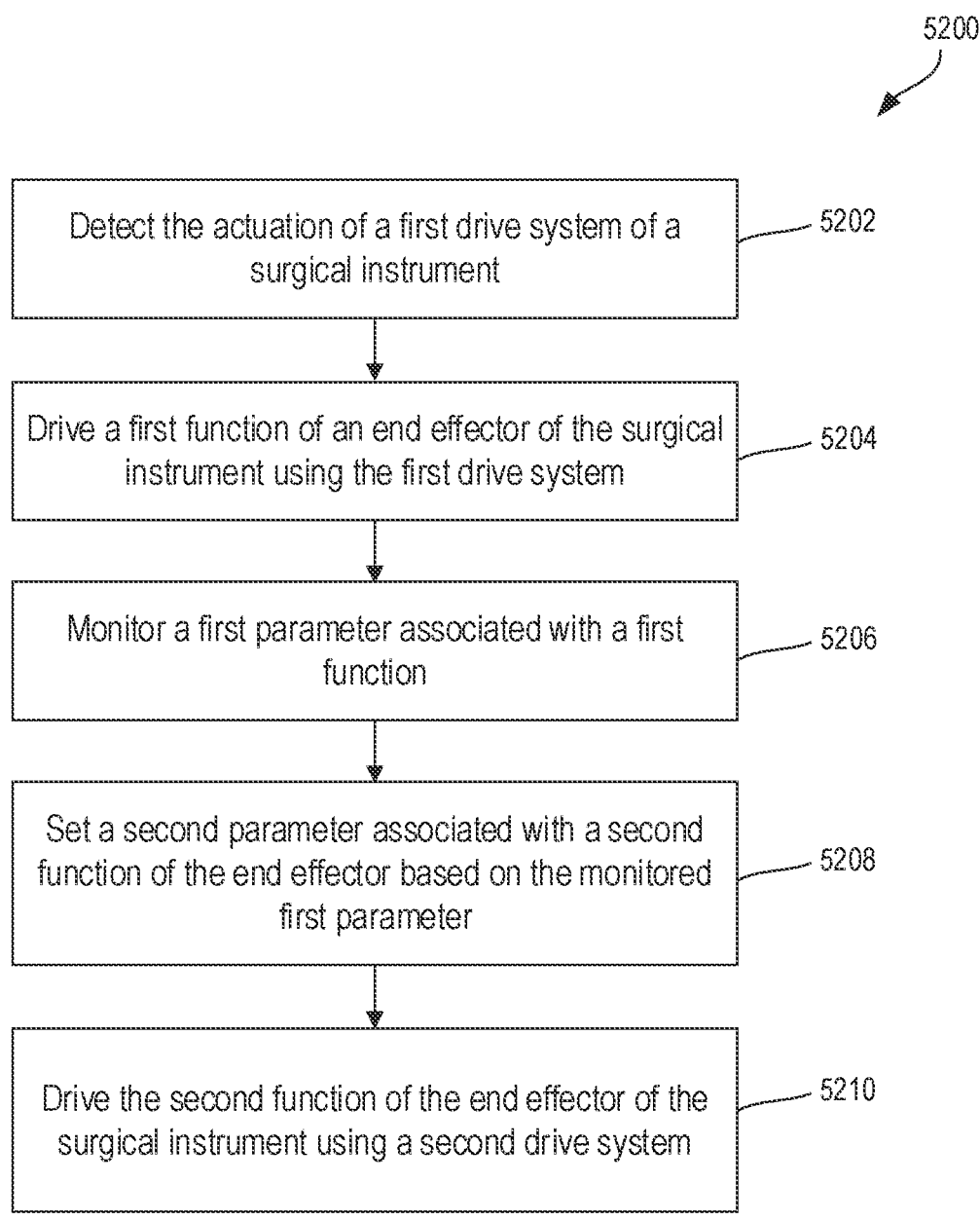
FIG. 48 illustrates a method for controlling a surgical instrument, according to at least one aspect of the present disclosure.

Referring now to FIG. 48, a method 5200 for controlling a surgical instrument is provided, according to at least one aspect of the present disclosure. The method 5200 comprises detecting 5202 the actuation of a first drive system of a surgical instrument. In various embodiments, a control system, such as controller 620, can detect the actuation of the first drive system utilizing any number of sensors described elsewhere, such as current sensors or position sensors, as examples. In some embodiments, the control system detects the actuation of the first drive system by monitoring a position of an actuator, such as the closure trigger 1032 or a firing trigger 1130, as examples. In various embodiments, the surgical instrument comprises a surgical stapling instrument, such as surgical instrument 1010. In various embodiments, the surgical instrument comprises an electrosurgical instrument. In various embodiments, the surgical instrument comprises an ultrasonic instrument.

The method 5200 further comprises driving 5204 a first function of an end effector of the surgical instrument using the first drive system. In various embodiments, the first function comprises transitioning a jaw of the end effector toward the clamped position. In various embodiments, the first function comprises applying energy to tissue positioned within the end effector with an energy delivery component. In various embodiments, the energy delivery component comprises an ultrasonic blade. In various embodiments, the energy delivery component comprises an electrode. In various embodiments, the first function comprises driving a firing member to deploy staples removably stored in a staple cartridge positioned within the end effector.

The method 5200 further comprises monitoring 5206 a first parameter associated with the first function. In various embodiments, the first parameter can be monitored by the control system using any number of sensors described elsewhere herein. In various embodiments, the first parameter comprises a load applied by the jaw to tissue positioned within the end effector. In various embodiments, the first parameter comprises an amount of time that energy has been applied to the tissue with the energy delivery component. In various embodiments, the first parameter comprises a rate of change in impedance of tissue. In various embodiments, the first parameter comprises a speed of a firing member or a cutting member through the end effector. In various embodiments, the first parameter comprises a current or voltage supplied to a motor or an ultrasonic transducer of the surgical instrument.

The method 5200 further comprises setting 5208 a second parameter associated with a second function of the end effector based on the monitored first parameter. In various embodiments, the control system utilizes the monitored first parameter to set a second parameter associated with a second function of the end effector. In various embodiments, the control system compares the monitored parameter to data stored in a memory, such as memory 624, in order to set the second parameter. In various embodiments, the second function comprises driving a firing member toward a fired position to deploy staples removably stored in a staple cartridge. In various embodiments, the second function comprises transitioning a jaw toward the clamped position. In various embodiments, the second function comprises applying energy to tissue positioned within the end effector with an energy delivery component. In various embodiments, the energy delivery component comprises an ultrasonic blade. In various embodiments, the energy delivery component comprises an electrode.

The method 5200 further comprises driving 5210 the second function of the end effector of the surgical instrument using a second drive system. In various embodiments, the control system transmits a control signal to a second drive system to cause the second drive system to drive the second function utilizing the second parameter. Accordingly, the foregoing method 5200 adapts one drive system in accordance with monitored parameters from a second, separate and distinct drive system of the surgical instrument. Such adaptation results in better surgical outcomes, such as cleaner cuts, as the control system utilizes dynamically obtained information to alter parameters associated with different drive systems of the same surgical instrument.

Referring now to FIG. 49, a table illustrating the transection performance of various staple cartridges is provided, according to at least one aspect of the present disclosure. As seen in FIG. 49, parameters associated with different staple cartridges of different colors are provided. The staple cartridges include a staple cartridge with a first color (Color A), a staple cartridge with a second color (Color B), a staple cartridge with a third color (Color C), a staple cartridge with a fourth color (Color D), a staple cartridge with a fifth color (Color E). Each of the staple cartridges can include at least one parameter different from the other staple cartridges. As one example, the Color A cartridge includes staples with a first unformed staple height and the Color B cartridge includes staples with a second unformed staple height greater than the first unformed staple height. As another example, the Color A cartridge includes staples comprised of a first material and the Color B cartridge includes staples comprised of a second material different than the first material. As another example, the Color A cartridge includes staples with a first wire diameter and the Color B cartridge includes staples with a second wire diameter. Various other parameters associated with staple cartridges are discussed elsewhere herein. It is understood that the different colors are merely visual representations of staple cartridges with different configurations. In certain aspects, instead of colors, the different staple cartridges can be equally represented with any suitable identifying, or distinguishing, characteristics.

Each of the staple cartridges is designed for a minimum (indicated) use, a maximum (design) use, and an overstress use. Each use corresponds to a recommended type of tissue and a recommended tissue thickness. As one example, the minimum (indicated) application for a Color A staple cartridge is for a Type A tissue and a corresponding tissue thickness of $t_1$.

As shown in FIG. 49, the Color A staple cartridge is designed to be used with a first tissue type (Type A) and a second tissue type (Type B) and with tissue in a tissue thickness range of $t_1$ to $t_3$. The Color B staple cartridge is designed to be used with a third tissue type (Type C) and with tissue in a tissue thickness range of $t_4$ to $t_6$. The Color C staple cartridge is designed to be used with the third tissue type (Type C) and with tissue in a tissue thickness range of $t_7$ to $t_9$. The Color D staple cartridge is designed to be used with the third tissue type (Type C) and with tissue in a tissue thickness range of $t_{10}$ to $t_{12}$. The Color E staple cartridge is designed to be used with the third tissue type (Type C) and with tissue in a tissue thickness range of $t_{13}$ to $t_{15}$.

In various embodiments, the tissue thickness values (minimum/maximum/overstressed) for the Color B staple cartridge are greater than the respectively tissue thickness values for the Color A staple cartridge. Similarly, the tissue thickness values for the Color C staple cartridge are greater than the respectively tissue thickness values for the Color B staple cartridge. Similarly, the tissue thickness values for the Color D staple cartridge are greater than the respectively tissue thickness values for the Color C staple cartridge. Similarly, the tissue thickness values for the Color E staple cartridge are greater than the respectively tissue thickness values for the Color D staple cartridge.

In various embodiments, the first tissue type (Type A) comprises jejunum tissue, the second tissue type (Type B) comprises colon tissue, and the third tissue type (Type C) comprises stomach tissue. In various embodiments, the tissue thickness for minimum design use ($t_4$, $t_7$, $t_{10}$, and $t_{13}$) and maximum design use ($t_5$, $t_8$, $t_{11}$, and $t_{14}$) can be less than the overstress design use for a lower cartridge ($t_3$, $t_6$, $t_9$, and $t_{12}$, respectively). In operation, a clinician can select an appropriate staple cartridge to use according to the data provided in the table of FIG. 49.

Figure 50:
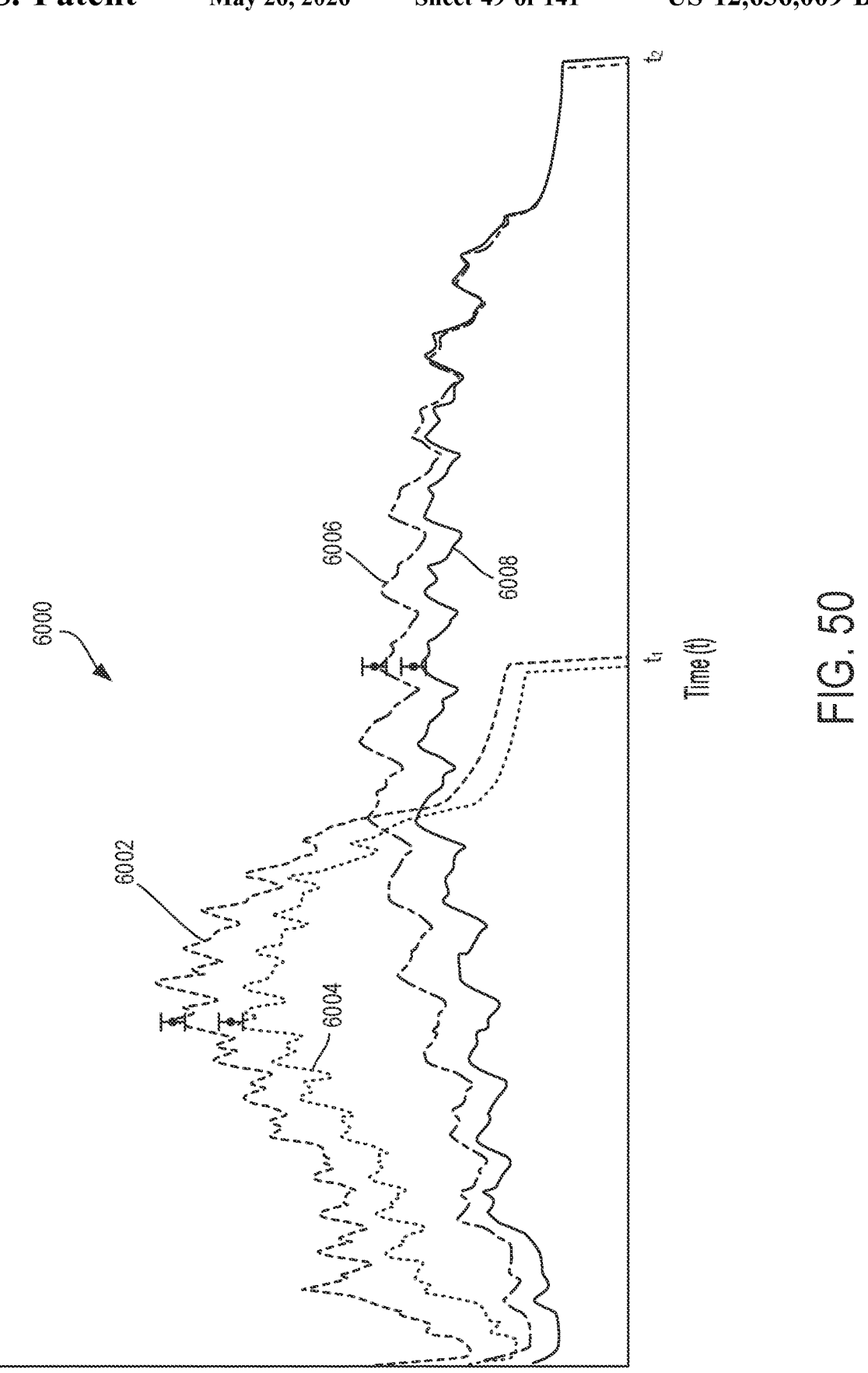
FIG. 50 is a graph illustrating the force to fire ("FTF") for a firing member at varying speeds, according to at least one aspect of the present disclosure.

Referring now to FIG. 50, a graph 6000 illustrates the force to fire ("FTF") for a firing member at varying speeds, according to at least one aspect of the present disclosure. The graph 6000 illustrates four instances of a motor, such as motor 1082 or motor 602, as examples, driving a firing member, such as firing member 1900, through similar types of tissue.

In two instances 6002, 6004, the motor drove the firing member at a first speed $V_1$ through a firing stroke. In two other instances 6006, 6008, the motor drove the firing member at a second speed $V_2$ less than the first firing speed $V_1$ through a firing stroke. As shown in FIG. 50, for instances 6002, 6004, driving the firing member at the first speed $V_1$ resulted in the firing stroke completing in approximately a first amount of time $t_1$ with a first general firing force profile. On the other hand, for instances 6006, 6008, driving the firing member at the second speed $V_2$ resulted in the firing stroke completing in approximately a second amount of time $t_2$ greater than the first amount of time $t_1$, owing to the slower speed, and a second general firing force profile. As seen in graph 600, owing to the slower speed, the maximum force to fire for the instances 6006, 6008 was less than the maximum force to fire for the instances 6002, 6004. Accordingly, firing speed plays a factor in force to fire through a firing stroke.

Force to fire is a significant issue causing limitations in articulation, shaft size, and even resultant formed staple height. With higher force to fire causing the need for more metal and support, the result is poor control in formed staple heights. It would be beneficial to leverage tissue creep and pausing of the firing stroke to drive down the FTF during the firing stroke.

Figure 51:
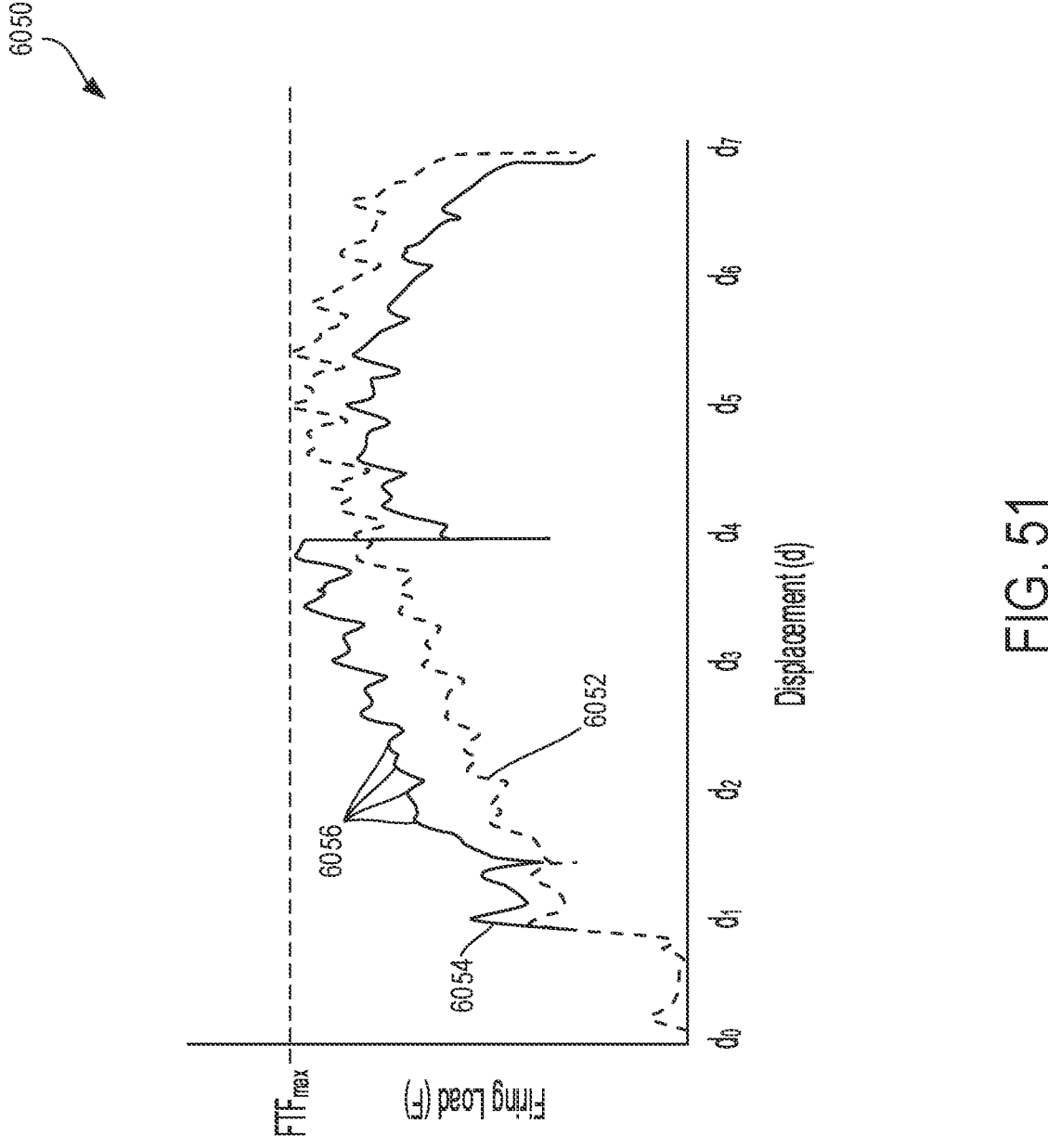
FIG. 51 is a graph illustrating the effects of pausing on FTF, according to at least one aspect of the present disclosure.

Referring now to FIG. 51, a graph 6050 illustrating the effects of pausing on FTF is provided, according to at least one aspect of the present disclosure. Graph 6050 illustrates firing loads on a firing member, such as firing member 1900, against the displacement of the firing member through firing strokes, as explained in more detail below.

In various instances, a firing system drives a firing member through a firing stroke to cut tissue captured between the jaws of an end effector, as well as to deploy staples removably stored in a staple cartridge. Referring to FIG. 51, the firing member begins at an unfired position, do, prior to initiation of the firing stroke. Based on the initiation of the firing stroke, such as actuation of a firing trigger, a firing system drives the firing member from the unfired position toward a fired position, $d_7$, to deploy staples from a staple cartridge and, optionally, to cut tissue captured within the end effector.

In certain instances, at $d_1$, the FTF 6052 the firing member ramps up based on the firing member encountering the tissue captured within the end effector and beginning to deploy staples from the staple cartridge. From $d_1$ to $d_5$, the FTF 6052 gradually increases during the firing stroke, ultimately reaching a $FTF_{max}$ around $d_5$. From $d_5$ to the fired position, $d_7$, the FTF gradually decreases.

The present disclosure provides a way of controlling the FTF during a firing stroke of the firing member. In some embodiments, a control system, such as controller 620, can predict higher, upcoming forces to fire based on the size of the FTF peaks early in the firing stroke. Based on the prediction, the control system can trigger changes to a firing algorithm, an algorithm defining parameters of a firing stroke, to control the force to fire during the firing stroke.

In some embodiments, the change to the firing algorithm includes pausing the firing stroke. In some embodiments, the change to the firing algorithm includes adjusting the length of the pause of the firing stroke. In some embodiments, the change to the firing algorithm includes changing the speed of the firing member. In some embodiments, the change to the firing algorithm includes later trigger adjustments heights. In some embodiments, the change to the firing algorithm includes controlling a voltage or current applied to the motor of the firing system that drives the firing member. In some embodiments, the change to the firing algorithm includes changing a duty cycle of the motor that drives the firing member.

In some embodiments, the control system predicts, at a first time in the firing stroke, that the force to fire will exceed a force to fire threshold at a second time subsequent to the first time. Based on the prediction, the control system allows the firing member to continue through the firing stroke for a period of time before reaching or exceeding the force to fire threshold. In some embodiments, the control system predicts a time in which the force to fire will exceed the force to fire threshold. Based on the prediction, the control system allows the firing member to continue through the firing stroke for the predicted amount of time. In some embodiments, the control system can take other proactive actions, such as slowing the firing speed of the firing member or making adjustments to the motor, as examples. In some embodiments, the control system proactively determines how long the firing stroke will need to be paused, based on the prediction. In some embodiments, the control system proactively determines how long the firing stroke will need to be paused, based on a rate of change of the force to fire prior to the starting of the pause. In some embodiments, the control system proactively determines how long the firing stroke will need to be paused based on the number and/or magnitude of the force to fire peaks and valleys detected by the control system prior to the starting of the pause. In some embodiments, the control system proactively determines how many times the firing stroke will need to be paused in order to maintain the force to fire below a force to fire maximum threshold.

Accordingly, the control system proactively determines if a force to fire threshold will be reached or exceeded and takes proactive measures prior to reaching the force to fire threshold. This proactive action is an improvement over systems that take no action until the force to fire reaches or exceeds a force to fire threshold. By waiting until a force to fire threshold is reached or exceeded, the force to fire may inadvertently exceed the force to fire threshold and reach unacceptable levels while the control system is reacting exceeded threshold, which would result in the firing motor stalling. By taking proactive measures, the control system recognizes, ahead of time that, a force to fire threshold may, or will, be reached or exceeded, and plans accordingly.

Referring again to FIG. 51, a firing member, such as firing member 1900, begins at an unfired position, do, prior to initiation of the firing stroke. Based on the initiation of the firing stroke, such as actuation of a firing trigger, a firing system, such as firing motor drive assembly 604, drives the firing member from the unfired position toward a fired position, $d_7$, to cut tissue captured within the end effector, such as end effector 1300, and to deploy staples from a staple cartridge, such as staple cartridge 1301.

At $d_1$, the FTF 6054 the firing member ramps up based on the firing member encountering the tissue captured within the end effector and beginning to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine FTF. In some embodiments, the control system is in operably communication with a force sensor in order to determine FTF.

Based on the detected FTF, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the magnitude of the force to fire peaks, such as peaks 6056, as the firing member traverses through the firing stroke. In some embodiments, the control system predicts the force to fire based on a change in magnitude of the force to fire peaks, such as peaks 6056, as the firing member traverses through the firing stroke. In some embodiments, the control system predicts the force to fire based on the shape of the force to fire peaks. In some embodiments, the control system predicts the force to fire based on the number of occurrences of force to fire peaks, such as peaks 6056, as the firing member traverses through the firing stroke. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future forces to fire based on data discretely, or continuously, received from the sensors.

Based on the predicted force to the fire, the control system can trigger changes to the firing algorithm to control the force to fire during the firing stroke, as described herein above. Referring to graph 6050, based on the prediction, the control system triggers the firing algorithm to pause displacement of the firing member at $d_4$. As seen on graph 6050, pausing the displacement causes the force to fire to drop. At a later time, such as a predefined or variable amount of time from the occurrence of the pause, as determined by the control system, the control system triggers the algorithm to resume advancement of the firing member toward the fired position $d_7$. In some embodiments, the length of the pause is based on the force to fire profile prior to the pause. In some embodiments, the length of the pause is based on the force to fire dropping below a force to file minimum threshold. In some embodiments, the control system further causes the firing member to resume advancement with a decreased speed. As seen on graph 6050, as the firing member resumes advancement, the force to fire has now dropped below the $FTF_{max}$ and gradually increases again toward $FTF_{max}$. However, owing to the triggered changes to the firing algorithm by the control system, the force to fire for the remainder of the firing stroke stays below $FTF_{max}$.

While the foregoing example illustrated on graph 6050 shows a single pause, it should be understood that the control system can continuously predict future force to fire loads during the firing stroke and trigger additional changes to the firing algorithm based on the predictions. For instance, referring now to FIG. 52, a graph 6070 illustrating the effects of multiple pauses on FTF is provided, according to at least one aspect of the present disclosure. Graph 6070 illustrates a firing load of a firing member, such as firing member 1900, against the displacement of the firing member through a firing stroke.

Similar to the above, graph 6070 illustrates a system in which, from do to $d_5$, the FTF 6072 the firing member ramps up as the firing member encounters the tissue captured within the end effector and begins to deploy the staples, ultimately reaching a $FTF_{max}$ around $d_5$. From $d_5$ to the fired position, $d_7$, the FTF gradually decreases.

The present disclosure provides a way of controlling the FTF during a firing stroke of the firing member using multiple pauses and other changes to the firing algorithm, such as changing the speed of the firing member. In some embodiments, a control system, such as controller 620, predicts higher, upcoming forces to fire based on the FTF peaks early in the firing stroke. Based on the prediction, the control system can trigger changes to the firing algorithm to control the force to fire during the firing stroke.

In some embodiments, the change to the firing algorithm includes pausing the firing stroke multiple times. The control system can make predictions, early on in the firing stroke, in order to control the force to fire during the firing stroke. In some other embodiment, the control system can continuously make predictions during the firing stroke in order to control the force to fire. In some embodiments, a first control action taken in response to a first prediction is used to influence a subsequent prediction and a second control action taken to control the force to fire. In one embodiment, in response to a first prediction, the control system adjusts the firing algorithm to pause the firing stroke for a first amount of time. In response to a second prediction subsequent to the first prediction, the control system adjusts the firing algorithm to pause the firing stroke for a second amount of time different from the first amount of time, as well as slowing the speed of the firing member. In one aspect, the second prediction is made based on the FTFs response to the first pause.

Referring again to FIG. 52, a firing member, such as firing member 1900, begins at an unfired position, do, prior to initiation of the firing stroke. Based on the initiation of the firing stroke, such as actuation of a firing trigger, a firing system, such as firing motor drive assembly 604, drives the firing member from the unfired position toward a fired position, $d_7$, to cut tissue captured within the end effector, such as end effector 1300, and to deploy staples from a staple cartridge, such as staple cartridge 1301.

From do, the FTF 6074 the firing member ramps up as the firing member begins to encounter the tissue captured within the end effector and begins to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor positioned on the firing member in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the rate of change of the force to fire. In some embodiments, the control system predicts the force to fire based on the magnitude of the force to fire peaks, such as peaks 6076, as the firing member traverses through the firing stroke. In some embodiments, the control system predicts the force to fire based on a change in magnitude of the force to fire peaks, such as peaks 6076, as the firing member traverses through the firing stroke. In some embodiments, the control system predicts the force to fire based on the number of occurrences of force to fire peaks, such as peaks 6076, as the firing member traverses through the firing stroke. In some embodiments, the control system predicts the force to fire based on both peaks and valleys in the force to fire profile. In some embodiments, the control system predicts the force to fire based on the shape of the force to fire peaks. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future force to fire based on data discretely, or continuously, received from the sensors.

Further to the above, in some instances, the control system implements a first adjustment to one or more parameters influencing FTF such as, for example, a first pause, then monitors the effect, or result, of the first pause on the FTF profile. Additional adjustments can be implemented based on the effect, or result, of the first adjustment. For example, a second pause can be implemented at a set time period after the first pause, wherein the set time period is determined based on the effect, or result, of the first pause. In some instances, additional pauses can be implemented based on the effect, or result, of the second pause, or a combined effect, or result, of the first and second pauses. In such instances, the adjustments are dynamic adjustments that are influenced by the effects, or results, of one or more previous adjustments.

Based on the predicted force to fire, the control system can trigger changes to the firing algorithm to control the force to fire during the firing stroke, as described herein above. Referring to graph 6070, based on the prediction, the control system triggers the firing algorithm to pause displacement of the firing member at $d_1$. As seen on graph 6070, pausing the displacement causes the force to fire to drop. At a later time, such as a predefined or variable amount of time from the occurrence of the pause, as determined by the control system, the control system triggers the algorithm to resume advancement of the firing member toward the fired position $d_7$. In some embodiments, the length of the pause is based on the FTF profile prior to the pause. In some embodiments, the length of the pause is based on the force to fire dropping below a force to fire minimum threshold. In some embodiments, the length of the pause is based on the length of time from a previous pause. In some embodiments, the length of the pause is based on the number of occurrences of pauses during the firing stroke. For instance, the first pause is a first amount of time and the second pause subsequent to the first pause is a different amount of time, such as a greater or less amount of time. As seen on graph 6070, as the firing member resumes advancement, the force to fire has dropped below the force to fire value at the time of pausing. In some embodiments, when the firing member resumes advancement, the firing algorithm can be adjusted by the control system to change the speed of the firing member to further control the force to fire profile.

As the control system continues to drive the firing member toward the fired position, the control system continues to monitor the force to fire profile and continues to make predictions about future force to fire values. In some instances, the control system can monitor force to fire profile, such as peaks and valleys thereof, as the firing member is driven toward the fired position. Based on the prediction, referring again to graph 6070, the control system pauses displacement of the firing member again at $d_2$. At a later time, such as a predefined or variable amount of time from the occurrence of the pause, as determined by the control system, the control system triggers the algorithm to resume advancement of the firing member toward the fired position $d_7$. In some embodiments, the length and time of the second pause at $t_2$ can be based on the length and time of the first pause at $t_1$. In some instances, the length of the second and time of the second pause at $t_2$ is based on the FTF response of the first pause at $t_1$.

In some embodiments, the control system can proactively decide the time for a subsequent pause based on data receive prior to a previous pause. For instance, prior to the pause at $d_1$, the control system can determine that a pause will be necessary at $d_1$, and also at $d_2$. Accordingly, the control system can manage the force to fire profile for the entire, or at least a substantial amount, of the firing stroke based on data determined in an early portion of the firing stroke. In some embodiments, the control system can adaptively manage pauses and resumptions of the firing stroke to maintain the force to fire between a force to fire maximum value and a force to fire minimum value that can be retrieved from a memory, for example. In some embodiments, the control system can make other dynamic adjustments, such as changing the speed of the firing member or changing a current/voltage applied to the firing motor to control the force to fire during the firing stroke based on the FTF response to previous adjustments. In some embodiments, after each pause, the control system can change the speed of the firing member to change the rate at which the FTF the firing member rises based on the FTF response to previous adjustments.

Figure 52:
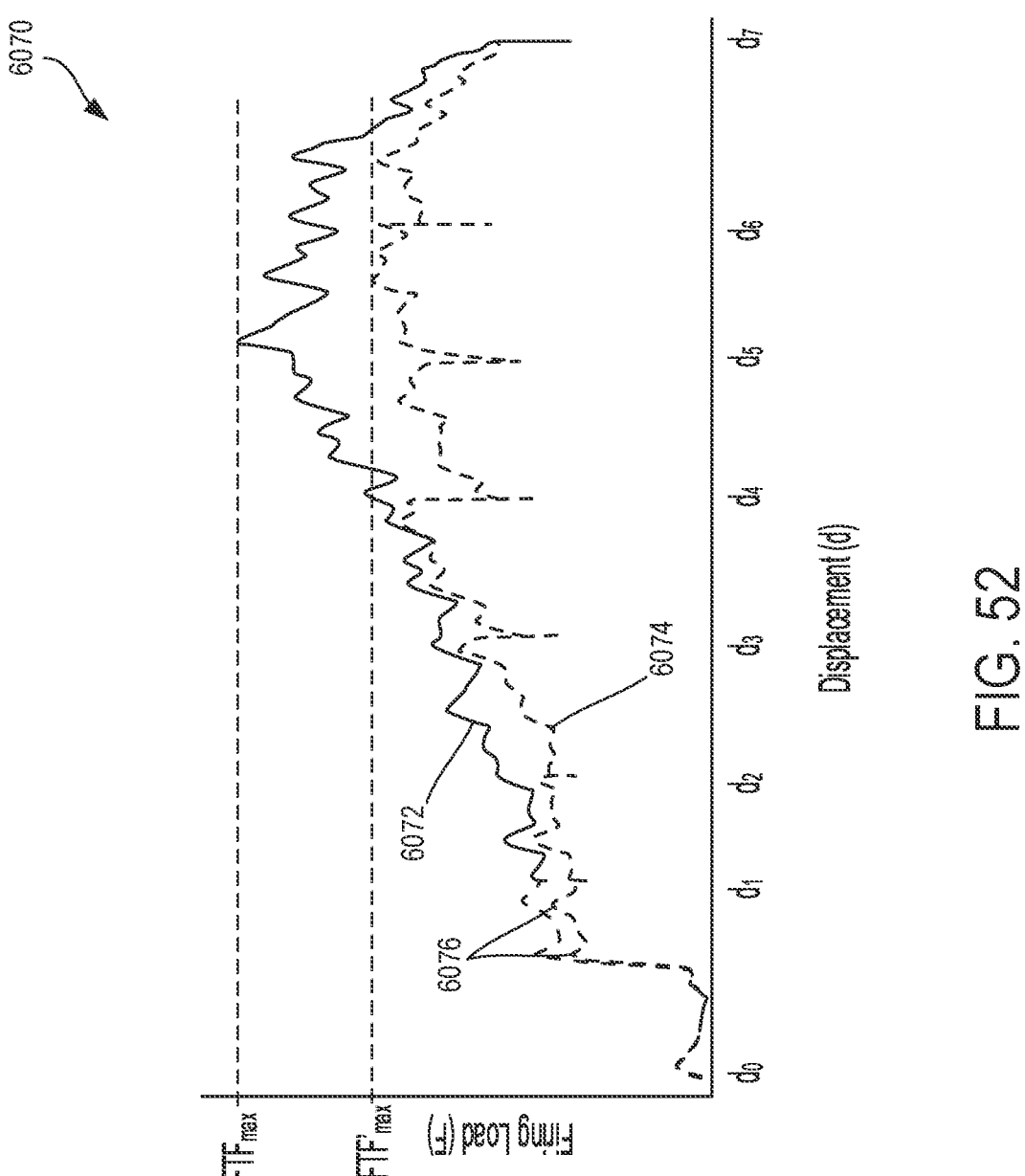
FIG. 52 is a graph illustrating the effects of pausing on FTF, according to at least one aspect of the present disclosure.

The control system can continue monitoring the firing force profile, dynamically making predictions, and taking corrective actions until the firing member reaches the fired position at $d_7$. As shown in FIG. 52, owing to the predictions and corrective actions taken by the control system, the force to fire reaches a $FTF'_{max}$ during the firing stroke, which is less than the $FTF_{max}$ for current systems. Accordingly, the predictive and corrective actions taken by the control circuit lowers the force to fire during a firing stroke.

In various embodiments, during a firing stroke and based on a first prediction, the control system can cause a default firing algorithm to be changed in a first way, such as pausing advancement of the firing member for a first amount of time. By analyzing the FTF response to the first pause, a second prediction can be made by the control system. Based on the second prediction, the control system can cause the default firing algorithm to be changed in a second way that can be different than the first way, such as pausing advancement for a second amount of time, different than the first amount of time, as well as decreasing a speed of the firing member. Accordingly, the control system dynamically adjusts the firing algorithm during the firing stroke based on an observed response of the FTF to one or more previous adjustment in order to maintain the force to firing the firing member within a predetermined threshold range that lowers the strain on the firing system.

Figure 53:
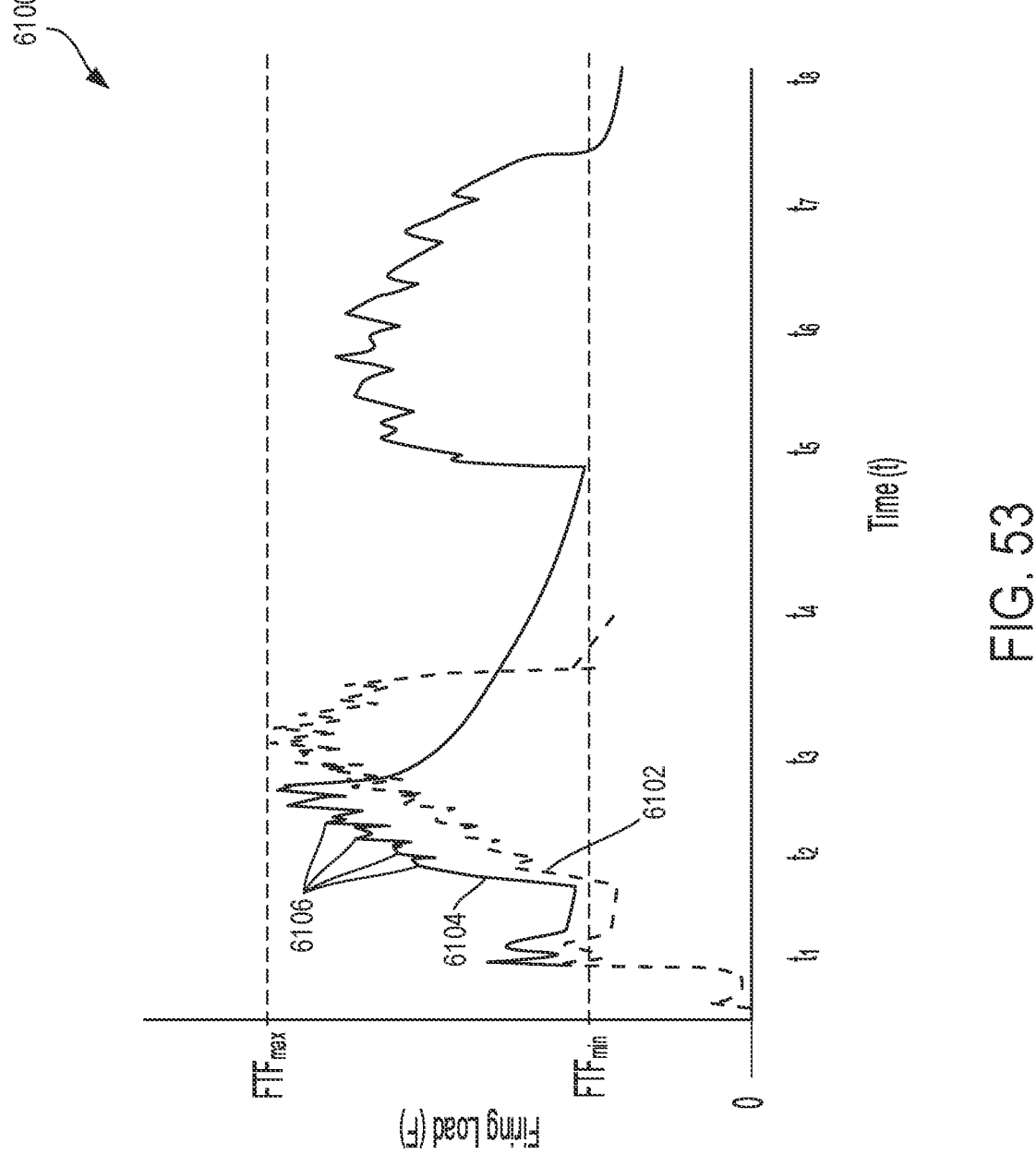
FIG. 53 is a graph illustrating the effects of pausing on FTF, according to at least one aspect of the present disclosure.

Referring now to FIG. 53, a graph 6100 illustrating the effects of pausing on FTF is provided, according to at least one aspect of the present disclosure. Graph 6100 illustrates firing loads of a firing member, such as firing member 1900, against time, as explained in more detail below.

In current systems, a firing system drives a firing member through a firing stroke to cut tissue captured between the jaws of an end effector, as well as to deploy staples removably stored in a staple cartridge. Referring to FIG. 53, at to, the firing member begins at an unfired position, prior to initiation of the firing stroke. At the initiation of the firing stroke, such as actuation of a firing trigger, a firing system drives the firing member from the unfired position toward a fired position to cut tissue captured within the end effector and to deploy staples from a staple cartridge.

For current systems, at $t_1$, the FTF 6102 peaks owing to the initial resistance of moving the firing member from the unfired position. At around $t_2$, the FTF 6102 begins to climb as the firing member encounters the tissue captured within the end effector and begins to deploy the staples. The FTF 6102 gradually increases over the firing stroke, ultimately reaching an $FTF_{max}$ around $t_3$. From $t_3$ to the fired position of the firing member, around $t_4$, the FTF sharply decreases.

As discussed above, the present disclosure provides a way of dynamically controlling the FTF during a firing stroke. Referring again to FIG. 53, a firing member, such as firing member 1900, at to, begins at an unfired position, prior to initiation of the firing stroke. At the initiation of the firing stroke, such as actuation of a firing trigger, a firing system, such as firing motor drive assembly 604, drives the firing member from the unfired position toward a fired position to cut tissue captured within the end effector, such as end effector 1300, and to deploy staples from a staple cartridge, such as staple cartridge 1301.

At $t_1$, the FTF 6104 the firing member peaks owing to the initial resistance of moving the firing member from the unfired position. At around $t_2$, the FTF 6104 begins to climb as the firing member encounters the tissue captured within the end effector and begins to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the magnitude of the force to fire peaks, such as peaks 6106, as the firing member traverses through the firing stroke. In some embodiments, the control system predicts the force to fire based on a change in magnitude of the force to fire peaks, such as peaks 6106, as the firing member traverses through the firing stroke. In some embodiments, the control system predicts the force to fire based on the number of occurrences of force to fire peaks, such as peaks 6106, as the firing member traverses through the firing stroke. In some embodiments, the control system predicts the force to fire based on the shape of the force to fire peaks. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future forces to fire based on data discretely, or continuously, received from the sensors.

Based on the predicted force to the fire, the control system triggers changes to the firing algorithm to control the force to fire during the firing stroke, as described herein above. Referring to graph 6100, based on the prediction, the control system triggers the firing algorithm to pause advancement of the firing member at $t_3$ until $t_5$. In various embodiments, the control system pauses the force to fire 6104 until the force to fire reaches a force to fire threshold $FTF_{min}$. In various embodiments, the control system pauses the force to fire 6104 for a predetermined, or variable, amount of time. In some embodiments, the variable amount of time is determined based on the forces sensed as the control system was predicting the future force to fire. In some embodiments, the length of the pause is based on the force to fire profile prior to the pause. As seen on graph 6100, pausing the advancement between $t_3$ and $t_5$ causes the force to fire to gradually drop to a $FTF_{min}$. At $t_5$, the control system triggers the algorithm to resume advancement of the firing member toward the fired position. As seen on graph 6100, as the firing member resumes advancement, the force to fire gradually increases again to $FTF_{max}$. However, owing to the adjustments to the default firing algorithm by the control system, the force to fire for the remainder of the firing stroke stays well below $FTF_{max}$. In some embodiments, the control system can adjust the firing algorithm such that the firing member resumes advancement at a slower speed than prior to the pause of the firing stroke.

While the foregoing example illustrated on graph 6100 shows a single pause, it should be understood that the control system can continuously predict future force to fire loads during the firing stroke and trigger additional changes to the firing algorithm based on the predictions. For instance, referring now to FIG. 54, a graph 6120 illustrating the effects of multiple pauses on FTF is provided, according to at least one aspect of the present disclosure. Graph 6120 illustrates firing loads on a firing member, such as firing member 1900, against time, as explained in more detail below.

Similar to the above, graph 6120 illustrates a current system in which, from $t_0$ to $t_3$, the FTF 6122 the firing member ramps up as the firing member encounters the tissue captured within the end effector and begins to deploy the staples, ultimately reaching a $FTF_{max}$ around $t_3$. From $t_3$ to the end of the stroke, $t_4$, the FTF decreases.

The present disclosure provides a way of dynamically controlling the FTF during a firing stroke of the firing member. In some embodiments, a control system, such as controller 620, can predict higher, upcoming forces to fire based on the FTF peaks early in the firing stroke. Based on the prediction, the control system can trigger changes to the firing algorithm to control the force to fire during the firing stroke.

In some embodiments, the change to the firing algorithm includes pausing the firing stroke multiple times. The control system can make predictions, early on in the firing stroke, in order to control the force to fire during the firing stroke. In some other embodiment, the control system can continuously make predictions during the firing stroke in order to control the force to fire. In some embodiments, a first control action taken in response to a first prediction is used to influence a subsequent prediction and a second control action to take to control the force to fire. In one embodiment, in response to a first prediction, the control system adjusts the firing algorithm to pause the firing stroke for a first amount of time. In response to a second prediction subsequent to the first prediction, the control system adjusts the firing algorithm to pause the firing stroke for a second amount of time different from the first amount of time, as well as slowing the speed of the firing member.

Further to the above, in some instances, the control system implements a first adjustment to one or more parameters influencing FTF such as, for example, a first pause, then monitors the effect, or result, of the first pause on the FTF profile. Additional adjustments can be implemented based on the effect, or result, of the first adjustment. For example, a second pause can be implemented at a set time period after the first pause, wherein the set time period is determined based on the effect, or result, of the first pause. In some instances, additional pauses can be implemented based on the effect, or result, of the second pause, or a combined effect, or result, of the first and second pauses. In such instances, the adjustments are dynamic adjustments that are influenced by the effects, or results, of one or more previous adjustments.

Referring again to FIG. 54, a firing member, such as firing member 1900, begins at an unfired position, at to, prior to initiation of the firing stroke. Based on the initiation of the firing stroke, such as actuation of a firing trigger, a firing system, such as firing motor drive assembly 604, drives the firing member from the unfired position toward a fired position to cut tissue captured within the end effector, such as end effector 1300, and to deploy staples from a staple cartridge, such as staple cartridge 1301.

From $t_0$, the FTF 6124 the force to fire ramps up as the firing member encounters the tissue captured within the end effector and begins to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the rate of change of the force to fire. In some embodiments, the control system predicts the force to fire based on the magnitude of the force to fire peaks, such as peaks 6076, as the firing member traverses through the firing stroke. In some embodiments, the control system predicts the force to fire based on a change in magnitude of the force to fire peaks, such as peaks 6076, as the firing member traverses through the firing stroke. In some embodiments, the control system predicts the force to fire based on the number of occurrences of force to fire peaks, such as peaks 6076, as the firing member traverses through the firing stroke. In some embodiments, the control system predicts the force to fire based on the shape of the force to fire peaks and valleys as the firing member traverses through the firing stroke. In some embodiments, the control system predicts the force to fire based on both peaks and valleys in the force to fire profile. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future force to fire based on data discretely, or continuously, received from the sensors.

Based on the predicted force to fire, the control system triggers changes to the firing algorithm to control the force to fire during the firing stroke, as described herein above. Referring to graph 6120, based on the prediction, the control system triggers the firing algorithm to pause displacement of the firing member at $t_1$. As seen on graph 6120, pausing the displacement causes the force to fire to drop. At a later time, such as a predefined or variable amount of time from the occurrence of the pause, as determined by the control system, the control system triggers the algorithm to resume advancement of the firing member toward the fired position. In some embodiments, the length of the pause is based on the force to fire profile prior to the pause. In some embodiments, the length of the pause is based on the force to fire dropping below a force to file minimum threshold. In some embodiments, the length of the pause is based on the number of occurrences of pauses during the firing stroke. For instance, the first pause can be a first amount of time and the second pause subsequent to the first pause can be a different amount of time from the first pause. As seen on graph 6120, as the firing member resumes advancement, the force to fire has dropped below the force to fire value at the time of pausing.

In some embodiments, the control system can monitor the effect, or result, of the first pause. For instance, the control system can detect the rate at which the force to fire dropped as a result of the pause. In other instances, the control system can detect a magnitude at which the force to fire dropped as a result of the pause. Based on the effect, or result, of the first pause, the control system can determine a second time period after the first pause to re-pause the firing stroke. Furthermore, in some instances, based on the effect, or result, of the first pause, the control system can determine a length of the pause at the second time period after the first pause. Accordingly, the control system dynamically adjusts the firing algorithm during the firing stroke.

As the control system continues to drive the firing member toward the fired position, the control system continues to monitor the force to fire profile and continues to make predictions about future force to fire values. In some instances, the control system can monitor force to fire peaks, such as peaks and valleys, as the firing member is driven toward the fired position. Based on the prediction, referring again to graph 6120, the control system can pause displacement of the firing member again at $t_2$. In other instances, the control system can pause advancement of the firing stroke at $t_2$ based on the prediction and an adjustment made to the firing algorithm during a previous pause, as discussed above.

At a later time, such as a predefined or variable amount of time from the occurrence of the pause, as determined by the control system, the control system triggers the algorithm to resume advancement of the firing member toward the fired position. In some embodiments, the length and time of the second pause at $t_2$ can be based on the length and time of the pause at $t_1$. In some embodiments, the length and time of the second pause at $t_2$ can be based on the effect, or result, of the first pause. In some embodiments, the control system can proactively decide the time for a subsequent pause based on data receive prior to a previous pause. For instance, prior to the pause at $t_1$, the control system can determine that a pause will be necessary at $t_1$, but also at $t_2$. Accordingly, the control system can manage the force to fire profile for the entire, or at least a substantial amount, of the firing stroke based on data determined in an early portion of the firing stroke. In some embodiments, the control system can manage pauses and resumptions of the firing stroke to maintain the force to fire between a force to fire maximum value and a force to fire minimum value. In some embodiments, the control system can make other adjustments, such as changing the speed of the firing member or changing a current/voltage applied to the firing motor to control the force to fire during the firing stroke. In some embodiments, after each pause, the control system can decrease the speed of the firing member to decrease the rate at which the FTF the firing member rises.

Figure 54:
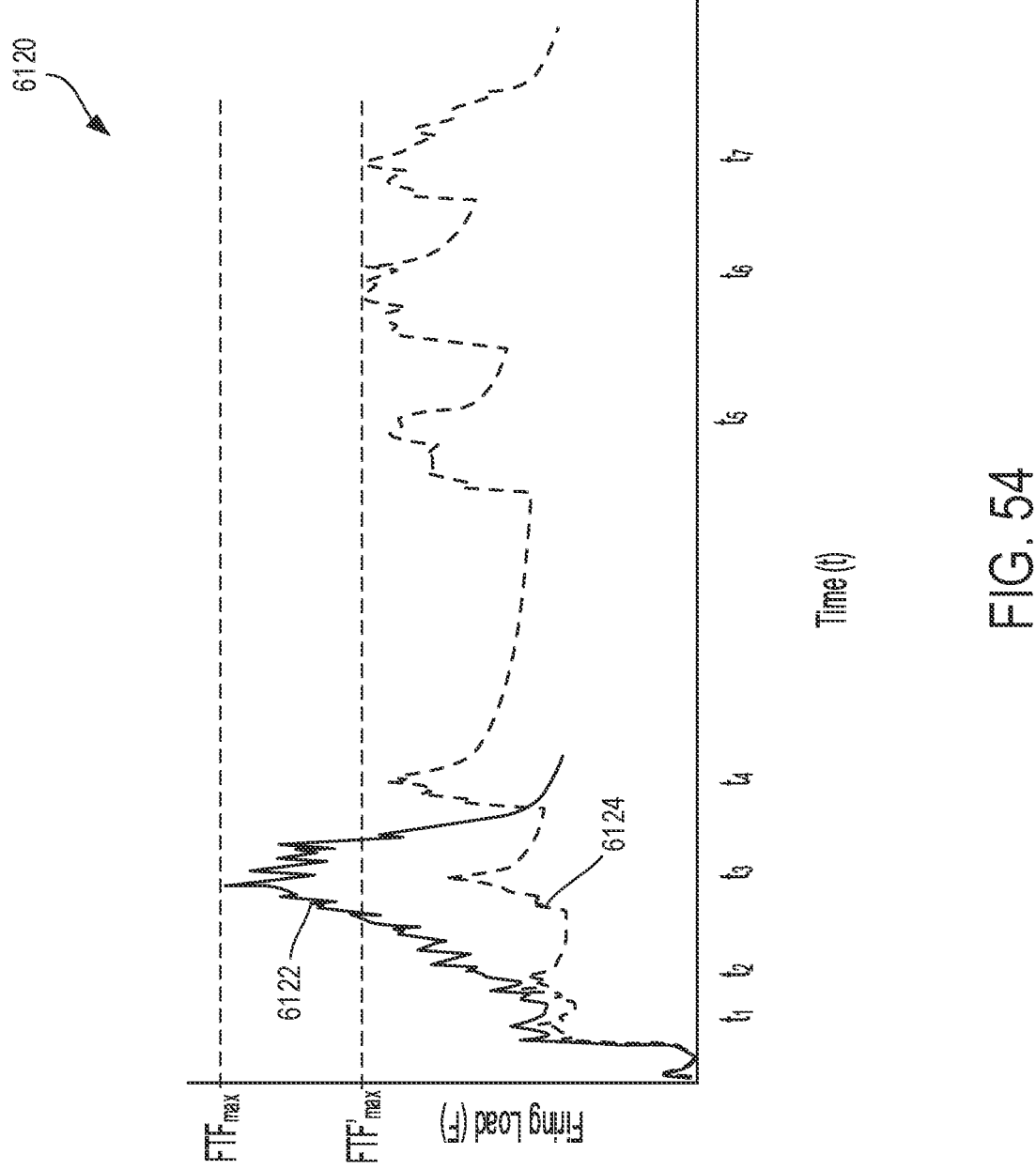
FIG. 54 is a graph illustrating the effects of pausing on FTF, according to at least one aspect of the present disclosure.

The control system can continue monitoring the firing force profile, making predictions, and taking corrective actions until the firing member reaches the fired position, such as at $t_3$, $t_4$, $t_5$, $t_6$, and $t_7$. As shown in FIG. 54, owing to the predictions and corrective actions taken by the control system, the force to fire reaches a $FTF'_{max}$ during the firing stroke, which is less than the $FTF_{max}$ for current systems. Accordingly, the predictive and corrective actions taken by the control circuit lower the force to fire during a firing stroke.

In various embodiments, during a firing stroke and based on a first prediction, the control system can cause the firing algorithm to be changed in a first way, such as pausing advancement for a first amount of time. Based on a second prediction during the firing stroke subsequent to the fire prediction, the control system can cause the firing algorithm to be changed in a second way different than the first way, such as pausing advancement for a second amount of time, different than the first amount of time, as well as decreasing a speed of the firing member. Accordingly, the control system dynamically adjusts the firing algorithm during the firing stroke in order to control the force to firing the firing member. Controlling the force to fire to remain low can lower the strain on the firing system and ultimately result in cleaner staple cuts on patient tissue.

Figure 55:
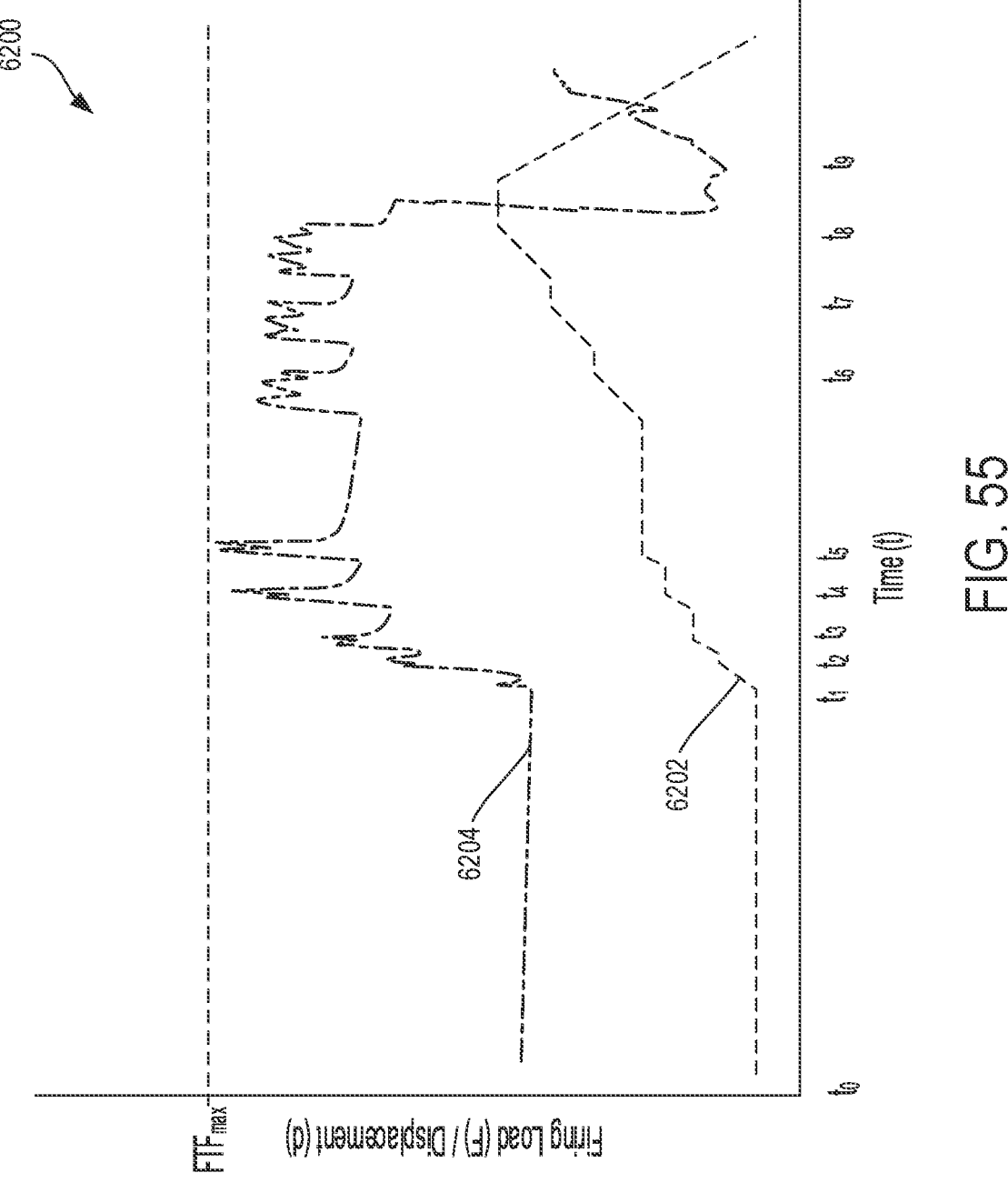
FIG. 55 is a graph illustrating the effects of pausing on FTF, according to at least one aspect of the present disclosure.

Referring now to FIG. 55, another graph 6200 illustrating the effects of pausing on FTF is provided, according to at least one aspect of the present disclosure. Graph 6200 illustrates both a firing load of a firing member, such as firing member 1900, against time (dash/dot line) and position of the firing member against time (dashed line).

As shown in graph 6200, the firing member begins in an unfired position at to. At $t_1$, a clinician initiates the firing stroke, such as by actuating a firing trigger, such as firing trigger 1130, causing forward displacement 6202 of the firing member toward a fired position. As the firing member traverses through the firing stroke, the force to fire 6204 the firing member increases.

During the firing stroke, as discussed above, a control system, such as controller 620, predicts future forces to fire and proactively adjusts the firing algorithm, as described elsewhere herein. For instance, at $t_2$, based on the predictions, the control system pauses displacement 6202 of the firing member for a period of time, resulting in the force to fire 6204 diminishing.

The above-described predicting and corrective actions by the control system continues for the remainder of the firing stroke. Specifically, as shown in FIG. 55, the control system causes displacement 6202 of the firing member to be paused at $t_2$, $t_3$, $t_4$, $t_5$, $t_6$, and $t_7$, controlling the force to fire 6204 to remain below a force to fire maximum threshold $FTF_{max}$. As shown in FIG. 55, the control system controls the force to fire using multiple pauses with varying lengths. In some embodiments, the lengths of the pauses are based on the force to fire detected by the control system early in the firing stroke, such as between $t_1$ and $t_2$. In some embodiments, the lengths of the pauses are based on the force to fire detected by the control system after the firing member resumes advancement from a pause. In some embodiments, the control system can pause the firing stroke until the force to fire has dropped a predefined amount. In some embodiments, the control system pauses the firing stroke for a predefined, or variable, amount of time, as described elsewhere herein. In some embodiments, the length of the pause is based on the rate of change of the firing stroke prior to the pause. In some embodiments, the length of the pause is based on the length of a previous pause.

As shown in FIG. 55, at $t_8$, the firing member reaches the fired position, resulting in the force to fire sharply dropping. At $t_9$, the firing system retracts the firing member toward starting position of the firing member.

In many instances, a first pause within the firing stroke is used to influence a second, subsequent pause in the firing stroke. In some embodiments, the control system pauses the firing stroke at a first time for a first amount of time. In one aspect, the first amount of time is selected by the control system to allow the force to fire to drop a predefined amount. In one aspect, the first amount of time is selected by the control system to allow the force to fire to drop to a force to fire minimum threshold. Various other ways that the control system selects an appropriate pause length are described elsewhere herein.

After the first amount of time, the control system can resume advancement of the firing member through the firing stroke. At a second time subsequent to the first time, the control system pauses the firing stroke again. In some embodiments, the second pause is influenced by the first pause. In one aspect, the length of the second pause is the same as the length of the first pause. In one aspect, the length of the second pause is less than the length of the first pause. In one aspect, the length of the second pause is greater than the length of the first pause. In one aspect, the time at which the second pause occurs is the same amount of time as before the first pause occurred. Stated another way, at a first time point, the clinician actuates the firing system and at a second time, the control system pauses the firing stroke. After the first pause, at a third time point, the control system resumes advancement of the firing stroke and at a fourth time, the control system pauses the firing stroke again. In many instances, the elapsed time between the first and second time points is the same, or at least substantially the same, as the elapsed time between the third and fourth time points.

In various embodiments, a first pause in the firing stroke is used to influences multiple pauses later in the firing stroke. In one instance, during the firing stroke, the control system detects a rapid increase in the force to fire and predicts that a force to fire threshold will be reached. Based on the detection and prediction, the control system pauses the firing stroke at a first time for a first amount of time. Based on the detected increase in the firing stroke, the control system can determine that multiple pauses will be required to complete the firing stroke so as to stay below the force to fire threshold. Accordingly, the control system sets times and lengths of pauses based on the detected force to fire early in the firing stroke. In many instances, the length of the first pause is used to influence the length and time for subsequent pauses in the firing stroke. In one aspect, the control system pauses the firing stroke for a first amount of time to lower the force to fire the firing member. The control system then resumes advancement of the firing member and pauses the firing stroke at later times to maintain the force to fire below the force to fire threshold. In some embodiments, a first pause in the firing stroke causes a cascade of pauses later in the firing stroke to maintain the force to fire below the force to fire threshold.

Figure 56:
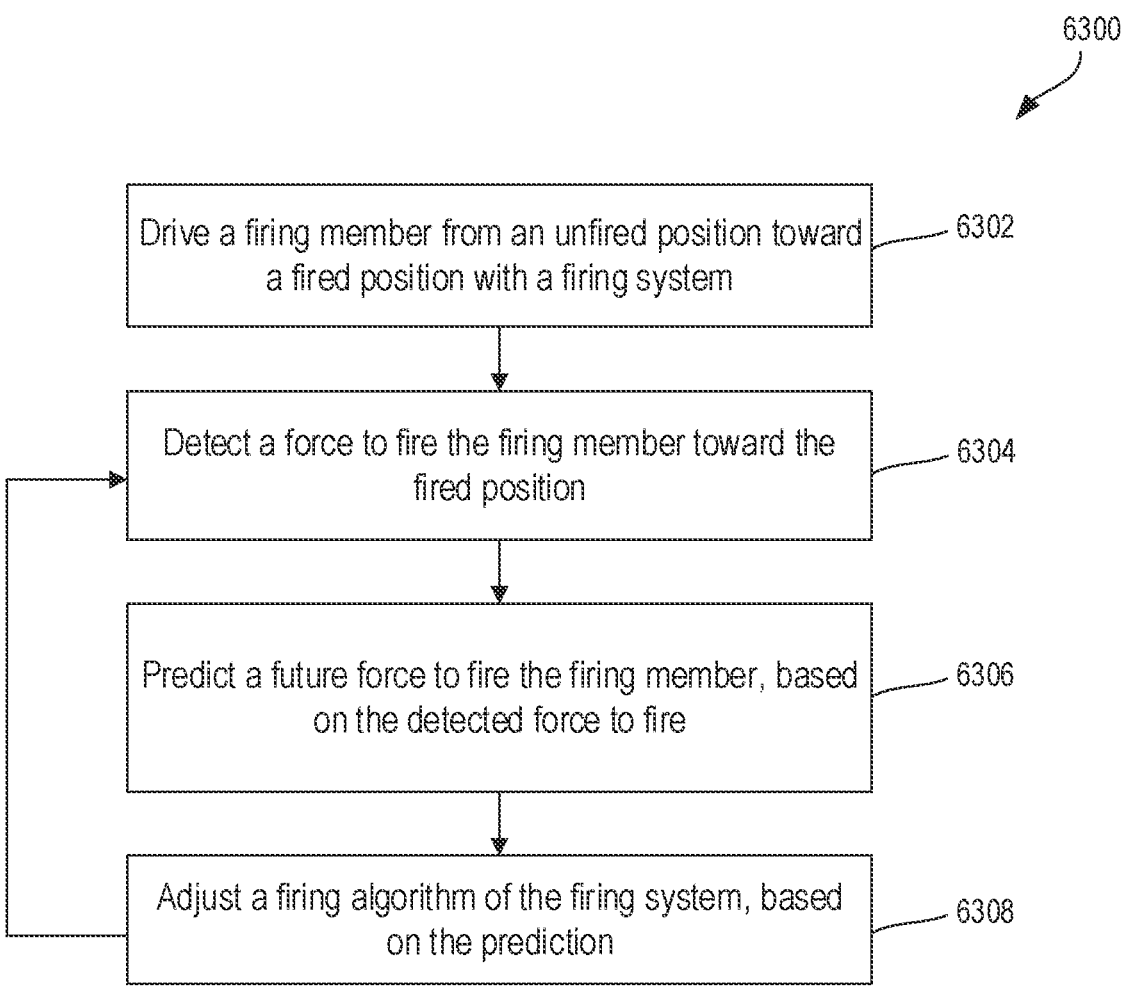
FIG. 56 illustrates a method of controlling a surgical instrument, according to at least one aspect of the present disclosure.

Referring now to FIG. 56, a method 6300 for controlling a surgical instrument is provided, according to at least one aspect of the present disclosure. The method 6300 comprises driving 6302 a firing member from an unfired position toward a fired position with a firing system. In various embodiments, a control system, such as controller 620, drives a firing member, such as firing member 1900, in response to the actuation of a firing system, such as firing motor drive assembly 604. In one aspect, driving the firing member toward a fired position causes the firing member to deploy staples removably stored in a staple cartridge, such as staple cartridge 1301, into tissue captured between an end effector, such as end effector 1300.

The method 6300 further includes detecting 6304 a force to fire the firing member toward the fired position. In various embodiments, the control system monitors the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

The method 6300 further includes predicting 6306 a future force to fire the firing member, based on the detected force to fire. In various embodiments, the algorithm is stored in a memory, such as memory 624, and is executable by a processor, such as processor 622. In some embodiments, the control system predicts the force to fire based on the rate of change of the force to fire. In some embodiments, the control system predicts the force to fire based on the magnitude of the force to fire peaks as the firing member traverses through the firing stroke. In some embodiments, the control system predicts the force to fire based on a change in magnitude of the force to fire peaks as the firing member traverses through the firing stroke. In some embodiments, the control system predicts the force to fire based on the number of occurrences of force to fire peaks as the firing member traverses through the firing stroke. In some embodiments, the control system predicts the force to fire based on both peaks and valleys in the force to fire profile. In some embodiments, the control system predicts the force to fire based on the shape of the peaks and valleys of the firing force profile. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future force to fire based on data discretely, or continuously, received from the sensors.

The method 6300 further includes adjusting 6308 a firing algorithm of the firing system, based on the prediction. In various embodiments, the control system dynamically adjusts the algorithm that is currently being used to drive the firing member toward the fired position, based on the prediction. In some embodiments, the dynamic adjustment to the firing algorithm includes pausing the firing stroke. In some embodiments, the dynamic adjustment to the firing algorithm includes adjusting the length of the pause of the firing stroke. In some embodiments, the dynamic change to the firing algorithm includes changing the speed of the firing member. In some embodiments, the adjustment to the firing algorithm includes late trigger adjustments heights. In some embodiments, the dynamic adjustment to the firing algorithm includes controlling a voltage or current applied to the motor of the firing system that drives the firing member. In some embodiments, the dynamic adjustment to the firing algorithm includes changing a duty cycle of the motor that drives the firing member. In some embodiments, the dynamic adjustment comprises planning multiple pauses of the firing stroke in order to maintain the force to fire within a force to fire range, such as between an upper and lower threshold. In some embodiments, the dynamic adjustment is based on a previous adjustment made to the algorithm.

In various embodiments, the dynamic adjustment to the firing algorithm occurs at a time after the control system makes the prediction. For instance, at a first time, the control system makes a prediction that the force to fire will exceed a force to fire threshold. Based on the prediction, the control system causes the firing algorithm to be changed at a second time subsequent to the first time. In some embodiments, the control system allows the firing algorithm to resume for a predefined, or variable, amount of time from the prediction. In some embodiments, the amount of time is based on a prediction of how long it will take until the force to fire will reach the force to fire threshold.

In various embodiments, the method 6300 can further include monitoring the effect, or result, of the adjustment to the firing algorithm. In some embodiments, monitoring the effect, or result, of the adjustment to the firing algorithm comprises monitoring a rate of change of the force to fire profile as a result the adjustment. In some embodiments, monitoring the effect, or result, of the adjustment to the firing algorithm comprises monitoring a magnitude of change in the force to fire profile as a result of the adjustment. Based on the monitored effect, or result, of the adjustment, the method 6300 can further include implementing a second adjustment to the firing system, based on the effect, or result, of the first adjustment. For instance, where the first adjustment is a first pause in the firing stroke, the control system can implement a second pause at a subsequent time based on the effect, or result, of the first pause. In some instances, the subsequent time can be determined based on the effect, or result, of the first pause. In some instances, the length of the second pause can be based on the effect, or result, of the first pause. In some instances, additional adjustments can be implemented based on the effect, or result, of the first adjustment. In such instances, the adjustments are dynamic adjustments that are influenced by the effects, or results, of one or more previous adjustments. In some other embodiments, the first adjustment is a change in the speed of the firing member and a subsequent adjustment to the firing algorithm is based on the response to the force to fire profile in changing the speed of the firing member. Accordingly, the method 6300 adapts the firing algorithm in order to control the force to fire profile associated with driving the firing member through the firing stroke.

As described herein above, the control system can dynamically adjust the firing algorithm during the firing stroke to control the force to fire. In various embodiments, as seen in FIG. 56, after the firing algorithm is adjusted 6308, the method 6300 can again detect 6304 a force to fire the firing member toward the fired position and predict 6306 a future force to fire the firing member, based on the detected force to fire such that subsequent adjusts to the firing algorithm can be made. In some instances, the subsequent adjustments to the firing algorithm are based on both predictions, as well as adjustments to the firing algorithm made at a previous pause, as explained above.

Figure 57:
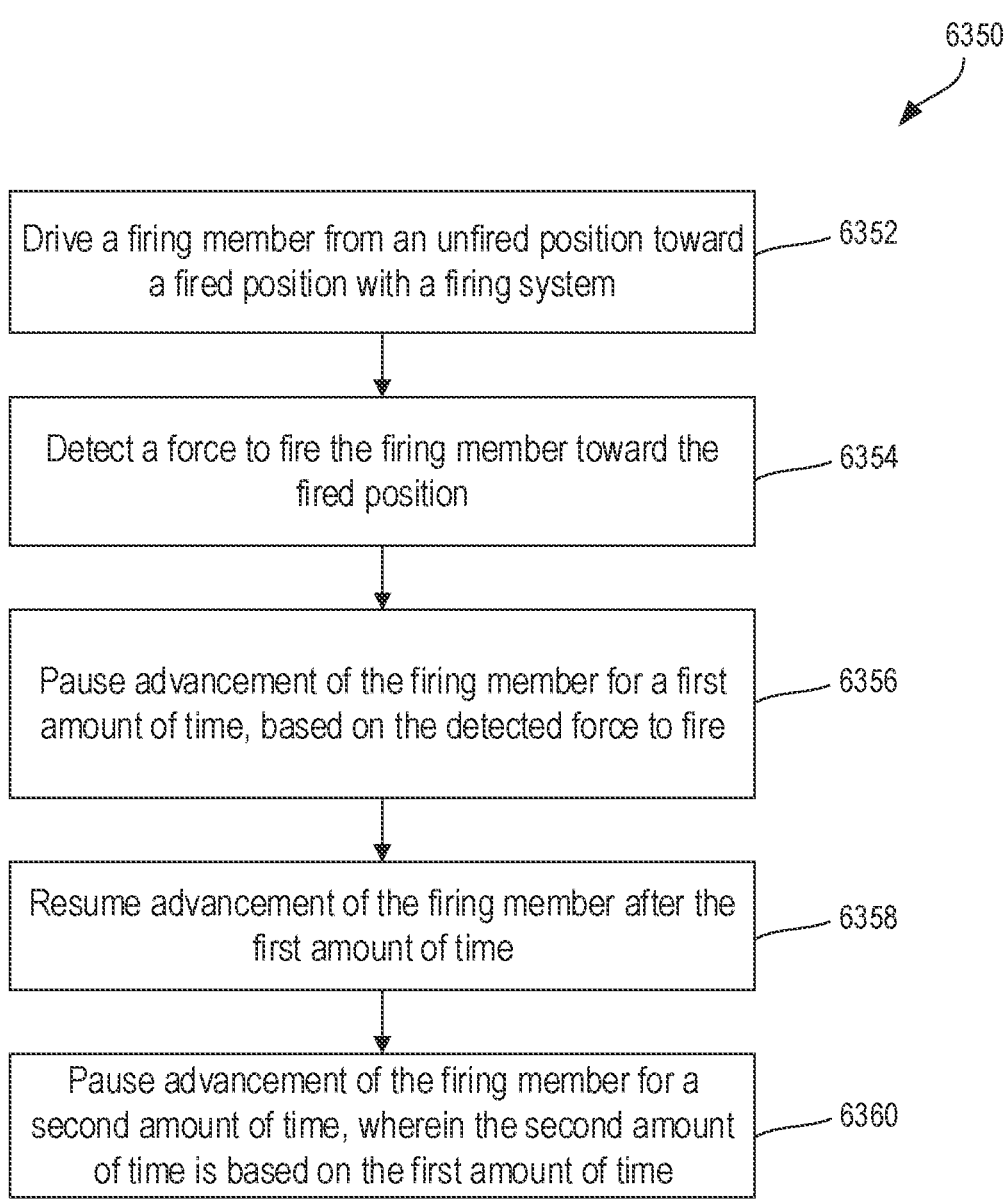
FIG. 57 illustrates a method of controlling a surgical instrument, according to at least one aspect of the present disclosure.

Referring now to FIG. 57, a method 6350 for controlling a surgical instrument is provided, according to at least one aspect of the present disclosure. The method 6350 comprises driving 6352 a firing member from an unfired position toward a fired position with a firing system. In various embodiments, a control system, such as controller 620, drives a firing member, such as firing member 1900, in response to the actuation of a firing system, such as firing motor drive assembly 604. In one aspect, driving the firing member toward a fired position causes the firing member to deploy staples removably stored in a staple cartridge, such as staple cartridge 1301, into tissue captured between an end effector, such as end effector 1300.

The method 6350 further includes detecting 6354 a force to fire the firing member toward the fired position. In various embodiments, the control system monitors the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

The method 6350 further includes pausing 6356 advancement of the firing member for a first amount of time, based on the detected force to fire. In various embodiments, the control system pauses the firing stroke of the firing member based on the detected force to fire. In some embodiments, the pause is based on a prediction made by the control system that the force to fire will reach or exceed a force to fire threshold. In some embodiments, the first amount of time is based on the rate of change of the force to fire prior to the pause. In some embodiments, the first amount of time is a time required to lower the force to fire a predefined amount. In some embodiments, the first amount of time is a time required to lower the force to fire to a force to fire minimum threshold. In some embodiments, the first amount of time is predefined. In some embodiments, the first amount of time is selected based on the shape of the force to fire profile, such as the shape of the peaks and valleys in the force to fire profile. In some embodiments, the first amount of time is selected based on the magnitude of the force to fire peaks and valleys in the force to file profile.

In various embodiments, after pausing 6356 advancement of the firing member, the method 6300 includes monitoring the effect, or result, of the pause. In some embodiments, monitoring the effect, or result, of the pause comprises monitoring a rate of change of the force to fire as a result the pause. In some embodiments, monitoring the effect, or result, of the pause comprises monitoring a magnitude of change in the force to fire as a result of the pause. Based on the monitored effect, or result, of the pause, the method 6300 can further include implementing an adjustment to firing algorithm, based on the effect, or result, of the pause. For instance, the control system can implement a second pause at a subsequent time based on the effect, or result, of the first pause. In some instances, the subsequent time can be determined based on the effect, or result, of the first pause. In some instances, the length of the second pause can be based on the effect, or result, of the first pause. In some instances, additional adjustments can be implemented based on the effect, or result, of the first pause. In such instances, the adjustments are dynamic adjustments that are influenced by the effects, or results, of one or more previous adjustments.

The method 6350 further includes resuming 6358 advancement of the firing member after the first amount of time. In various embodiments, the control system can control the firing system to resume advancement of the firing member, based on the first amount of time elapsing.

The method 6350 further includes pausing 6360 advancement of the firing member for a second amount of time, wherein the second amount of time is based on the first amount of time. In various embodiments, after the control system resumes advancement of the firing member, the control system again pauses the firing stroke. In various embodiments, the control system pauses the firing stroke of the firing member based on the detected force to fire. In some embodiments, the pause is based on a prediction made by the control system that the force to fire will reach or exceed a force to fire threshold. In various embodiments, the control system pauses the firing stroke of the firing member based on an amount of time elapsing from when the control system paused the firing stroke the first time. For instance, the control system pauses the firing stroke for a first time in response to a detected force to firing early in the firing stroke.

In one aspect, the control system can adapt the firing algorithm such that multiple pauses will be performed in order to maintain the force to fire below a force to fire threshold. For instance, at the first pause, the control system can detect the effect, or result, of the first pause by detecting a change in the force to fire profile and dynamically plan when and how long future pauses in the firing stroke should be. In some embodiments, the control system determines that a pause should occur after a predefined amount of time after resuming advancement of the firing stroke. Accordingly, after resuming advancement of the firing stroke, the firing stroke is paused again according to the plan created by the control system. In various other embodiments, the control system dynamically adjusts the pausing plan at each pause to determine if the current pausing plan is still suitable for use. For instance, if the rate of change in the force to fire profile after a pause is less than the rate of change prior to a pause, the control system determines that thinner tissue is being encountered and, thus, dynamically adjusts the firing algorithm such that less pauses are performed for the remainder of the firing stroke. In some instances, additional pauses can be implemented based on the effect, or result, of the second pause, or a combined effect, or result, of the first and second pauses. In such instances, the adjustments are dynamic adjustments that are influenced by the effects, or results, of one or more previous adjustments.

In various embodiments, the second amount of time that the firing stroke is paused is based on the first amount of time that the firing stroke is paused. In some embodiments, the second amount of time is the same as the first amount of time. In some embodiments, the second amount of time is greater than the first amount of time. In some embodiments, the second amount of time is less than the first amount of time. In various embodiments, the second amount of time is based on the plan created by the control system at the first pause.

Figure 58:
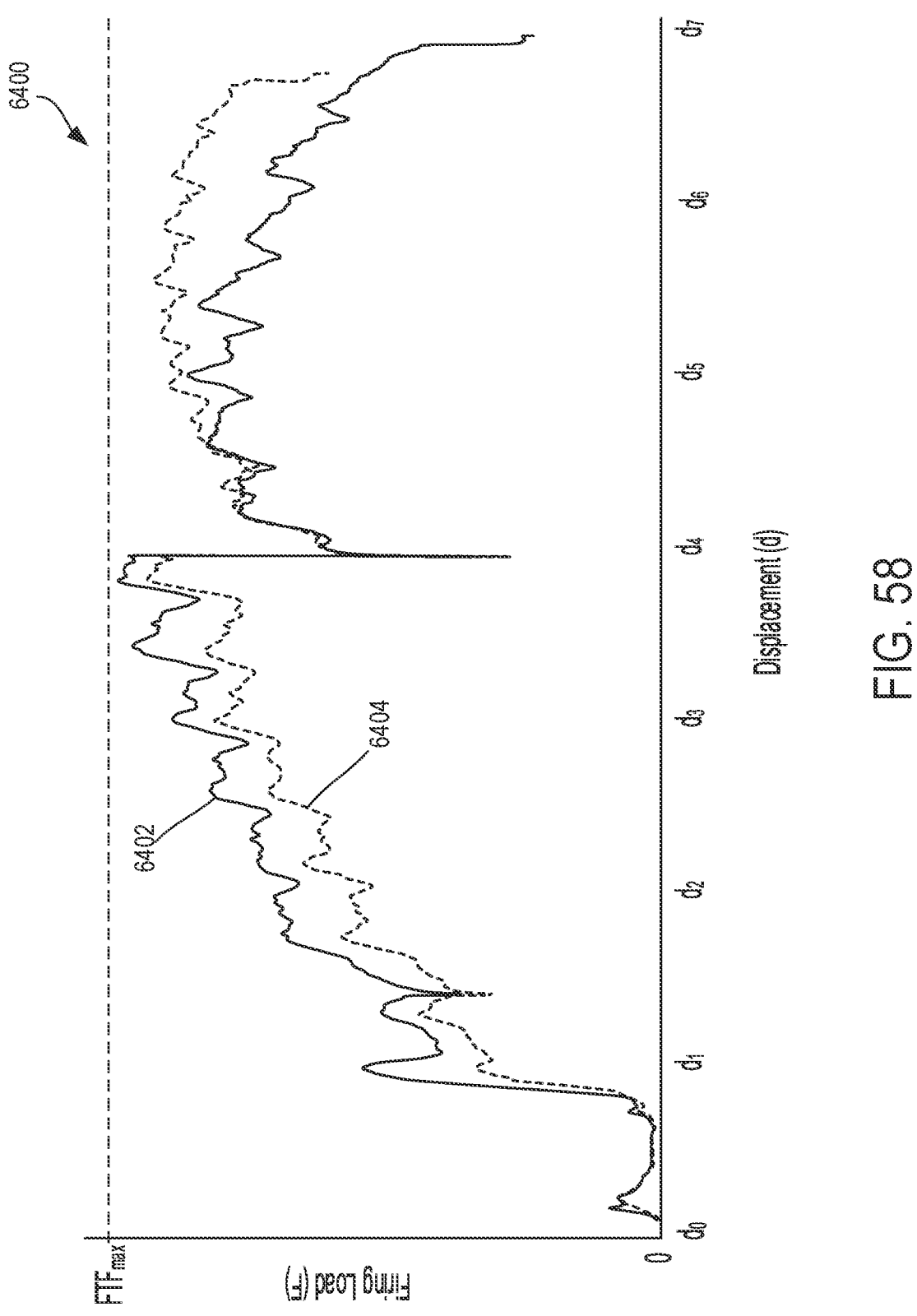
FIG. 58 is a graph illustrating the effects of pausing on FTF with varying closure loads, according to at least one aspect of the present disclosure.

Referring now to FIG. 58, a graph 6400 illustrating the impact of a closure system for separate and distinct firing and closing systems is provided, according to at least one aspect of the present disclosure. Graph 6400 illustrates the firing loads on a firing member, such as firing member 1900, against time. Graph 6400 illustrates two firing load profiles—a first firing load profile 6402 of a first surgical instrument that applies a first closure load and a second firing load profile 6404 of a second surgical instrument that applied a second closure load that is 1.75 times greater than the fire closure load.

As shown in graph 6400, the firing stroke for both systems initiates at do, resulting in a slight uptick in the firing load as the firing member overcomes the initial static resistance. At $d_1$, the firing members of the respective surgical instruments encounter tissue and begin to deploy staples from a staple cartridge. As seen in graph 6400, from $d_1$ to around $d_4$, the firing load of the second surgical instrument (which applies a closure load greater than the first surgical instrument) is less than that of the firing load of the first surgical instrument.

During the firing strokes of the two surgical instruments, a control system, such as controller 620, for each respective surgical instrument predicts future firing loads and adjusts the respective firing algorithms to control the force to fire. As shown in graph 6400, each control system causes the firing strokes to pause around $d_4$, resulting in a drop of the firing load in each instrument.

After a predefined, or variable, amount of time from the pauses, as determined by the control system (described elsewhere herein), the control systems reinitiate the firing strokes of the surgical instruments. As shown in graph 6400, after the respective pauses, the firing load 6404 on the surgical instrument with the increased closure load saw a larger firing load than the surgical instrument without the increased closure load until the end of the firing strokes at $d_7$. In some embodiments, the second surgical instrument is paused for a shorter time than the first surgical instrument, resulting in the increased firing load relative to the first surgical instrument. In some embodiments, the firing member of the second surgical instrument is maintained at the same speed as prior to the pause, resulting in the increased firing load relative to the first surgical instrument which had its firing member speed reduced. In various embodiments, the increased closure load prior to the pause allows the control system to make fewer changes to the firing algorithm, yet still remain below a force to fire threshold $FTF_{max}$. As one example, with an increased closure load, the control system only needs to pause the firing stroke for a first amount of time and make no adjustments to the speed of the firing member. With a "regular" closure load, the control system needs to adjust the firing algorithm to pause the firing stroke for a second amount of time greater than the first amount of time, as well as change the speed of the firing member, in order to maintain the force to fire below the force to fire threshold $FTF_{max}$. Accordingly, an increase in the closure load can result in fewer changes being needed to the firing control algorithm.

Figure 59:
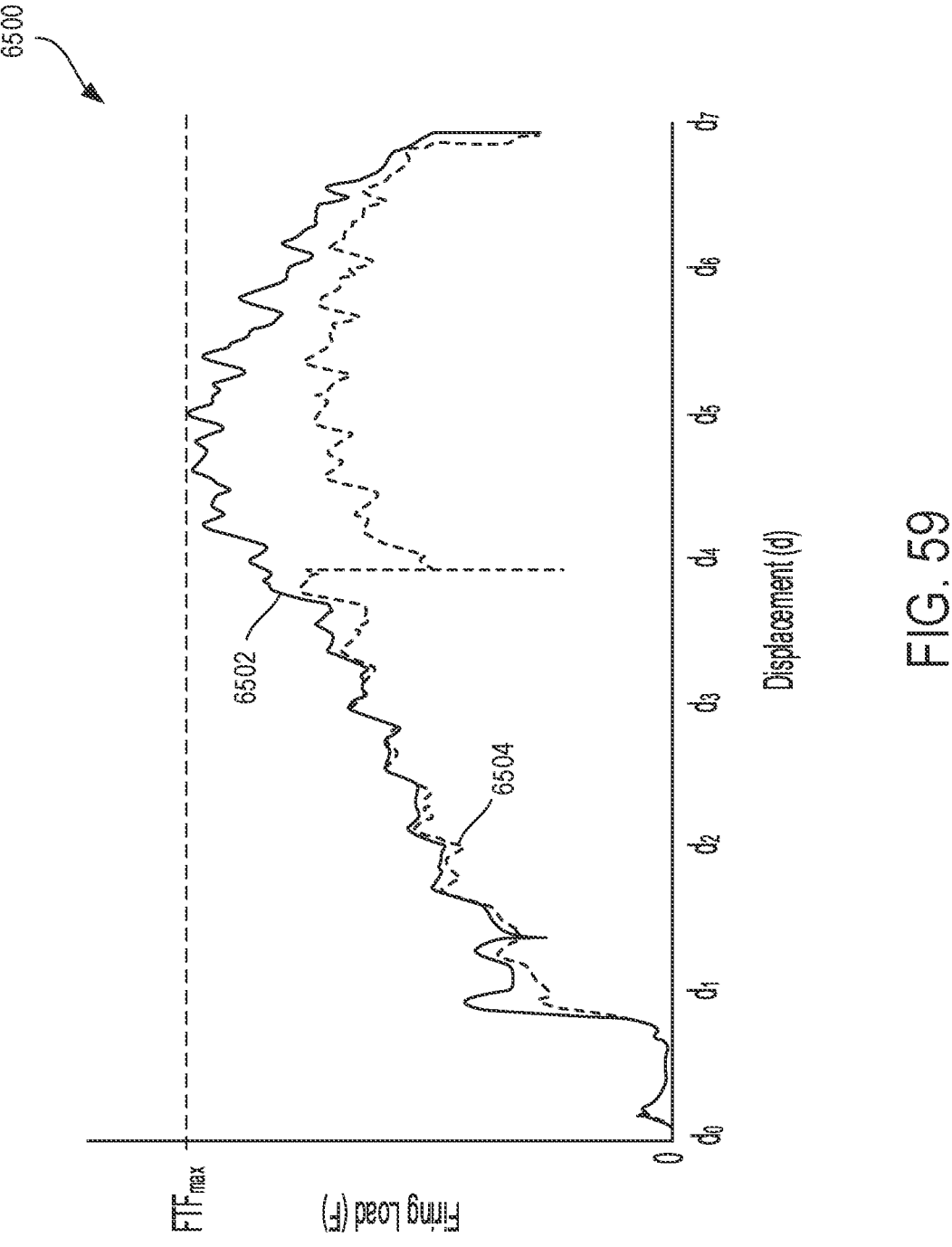
FIG. 59 is a graph illustrating the effects of pausing on FTF with varying tissue thicknesses during a firing stroke, according to at least one aspect of the present disclosure.

Referring now to FIG. 59, a graph 6500 illustrating firing force profiles is provided, according to at least one aspect of the present disclosure. The graph 6500 illustrates firing loads on a firing member, such as firing member 1900, over time. As seen in FIG. 59, the graph 6500 illustrates two firing force profiles—a first firing force profile 6502 during a first firing stroke and a second firing force profile 6504 during a second firing stroke. For both firing strokes, the thickness of the tissue encountered by the firing member doubled at $d_3$.

For the first firing force profile 6502, a firing member is driven through the firing stroke from do to $d_7$. As seen in graph 6500, the firing load steadily increases at a first rate from $d_1$ to $d_3$ and then increases at a second rate (owing to the thicker tissue) from $d_3$ until ultimately reaching a maximum force to fire $FTF_{max}$ at around $d_5$. From $d_5$, the firing load drops below until the firing member completes its firing stroke.

For the second firing force profile 6504, the firing member is driven through its firing stroke from do. As the firing member is driven through its firing stroke, a control system, such as controller 620, predicts future force to fire loads and adjusts the firing algorithm based on the predictions. For instance, as described above, the control system detects an increase in the force to firing when the thickness doubles in size at $d_3$. In some embodiments, the control system detects the increase in thickness based on a change in the peaks and valleys of the firing load profile. In some embodiments, the change comprises a change in magnitude of the peaks and valleys. In some embodiments, the change comprises a change in shape of the peaks and valleys. In some embodiments, the change comprises a change in the number of occurrences of the peaks and valleys. In some embodiments, the control system detects the increase in thickness based on the change the magnitude of the peaks and/or valleys of the firing load profile. In some embodiments, the control system detect the increase in thickness based on the rate of change of the firing load. Based on the detected increase in thickness, the control system predicts a future force to fire that will exceed a force to fire threshold, and thus, adjusts the firing control algorithm, causing the firing stroke to be paused at around $d_4$.

In some embodiments, based on the detection and prediction from the control system, the control system determines that resuming the firing stroke at the same speed as prior to the pause would result in an increase in the firing load and quickly lead to another pause being required. Accordingly, after the pause, the control system can decrease the speed of the firing member to maintain the firing load within an acceptable range, such as below the maximum force to fire threshold $FTF_{max}$. For instance, as shown in graph 6500, after the firing stroke of the firing member is paused and the speed of the firing member is decreased, the second firing force profile 6504 does not reach or exceed the firing load that was experienced prior to the firing stroke being paused. Accordingly, the control system is able to take multiple control actions, such as pausing the firing stroke and changing the firing speed of the firing member, in response to predictions from the control system in order to control the force to fire. Furthermore, the control system is able to adapt its predictions based on changing characteristics of the tissue, such as an increase in the tissue thickness. In some embodiments, the control system determines other parameters associated with the tissue, such as a type of tissue or a disease state of the tissue, and adapt the predictions accordingly.

Figure 60:
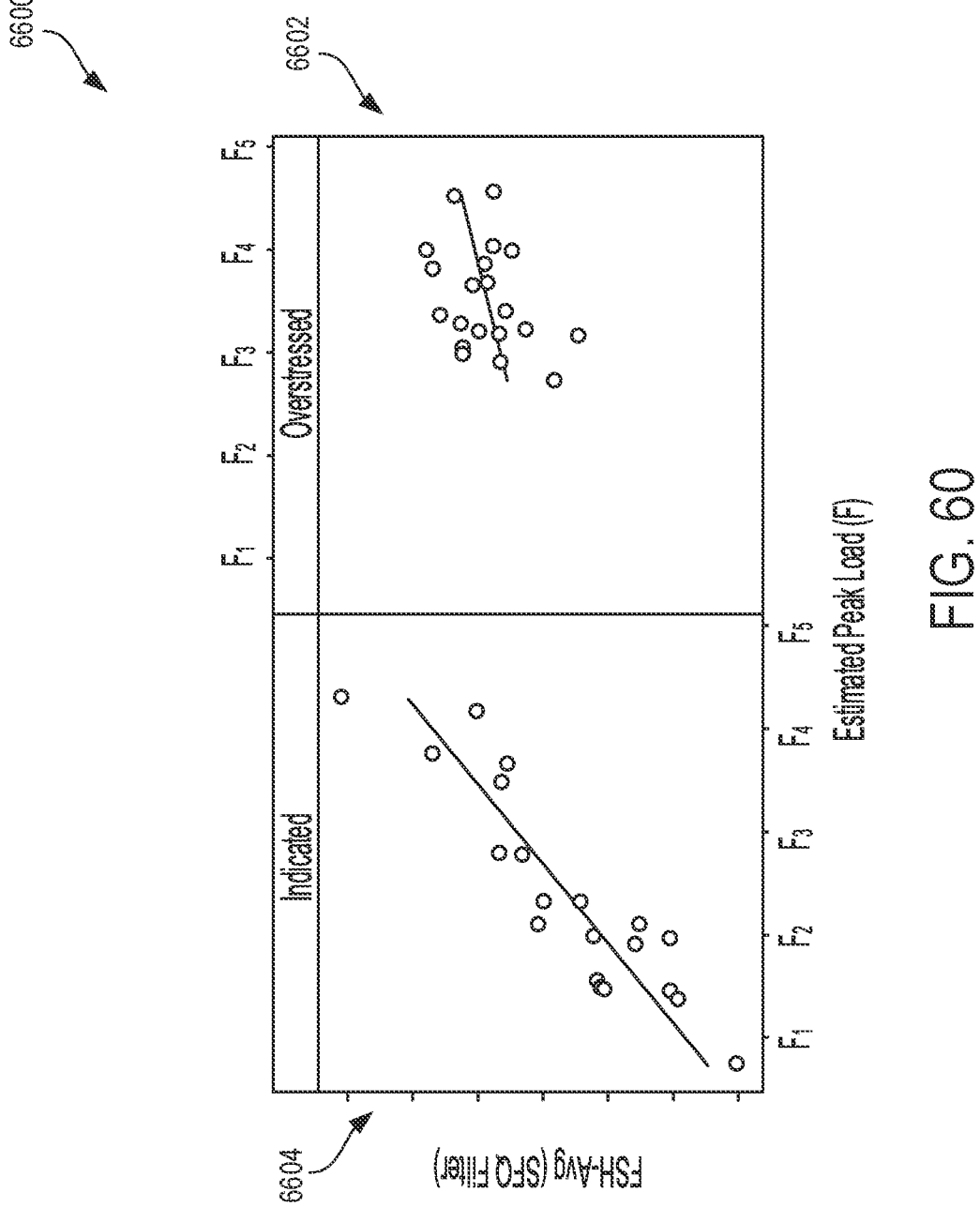
FIG. 60 is a scatterplot showing the effects of force to fire on staple heights, according to at least one aspect of the present disclosure.

Referring now to FIG. 60, a scatterplot 6600 showing the effects of force to fire on staple height for the Color D cartridge from FIG. 49 is provided, according to at least one aspect of the present disclosure. The scatterplot 6600 illustrates a correlation between the FSH average (SGQ filter) against estimated peak loads. The left hand portion 6602 of the scatterplot illustrates the minimum (indicated) use of the Color D cartridge and the right hand portion 6604 of the scatterplot 6600 illustrates the overstress use of the Color D cartridge at various estimated peak loads ($F_1$-$F_5$). As seen in scatterplot 6600, the $R^2$ value of the trendline for the minimum (indicated) use is greater than the $R^2$ value of the trendline for the overstressed use.

Figure 61:
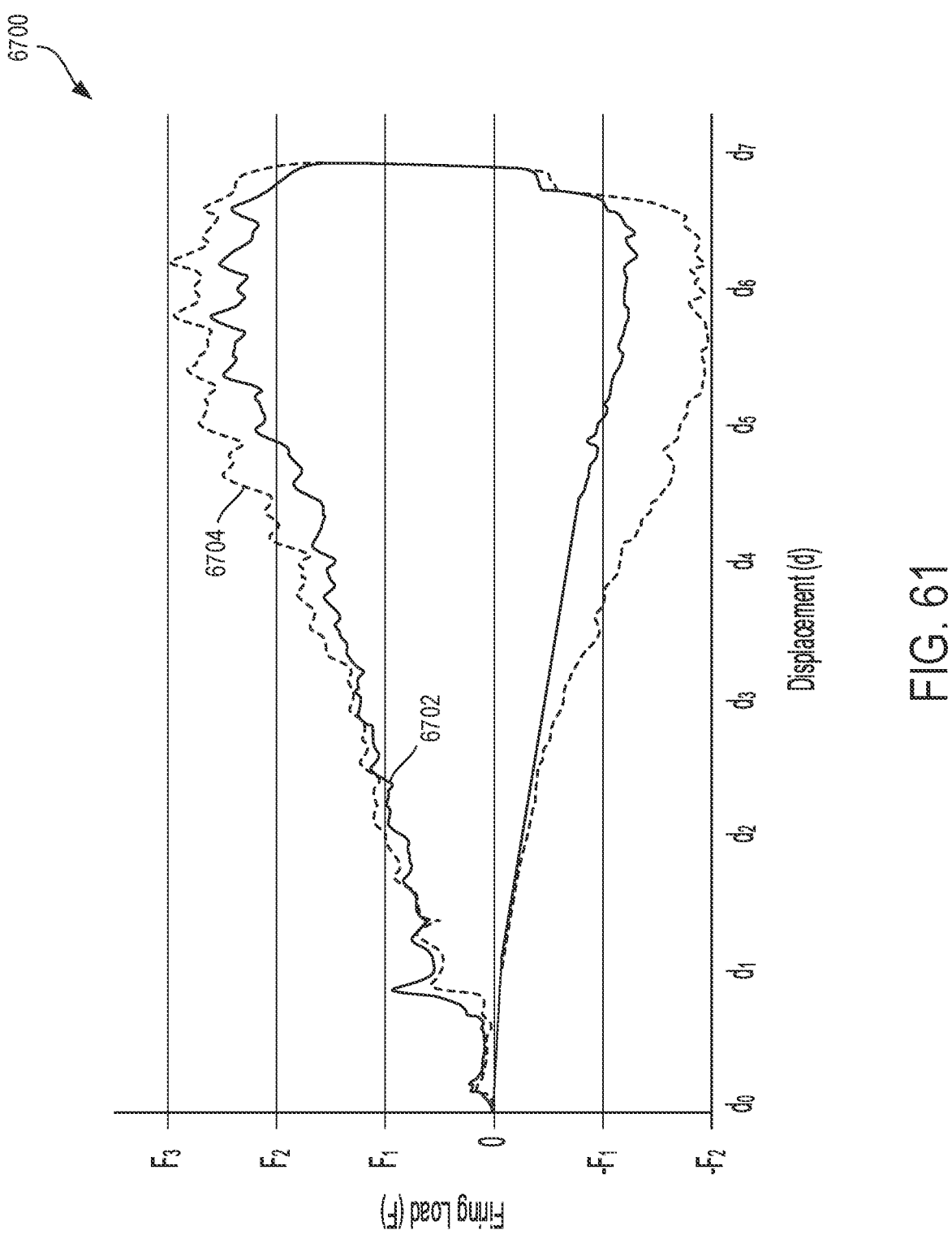
FIG. 61 is a graph showing firing force profiles for firing member that encounter a changing tissue thickness during a firing stroke, according to at least one aspect of the present disclosure.

Referring now to FIG. 61, a graph 6700 illustrating firing force profiles is provided, according to at least one aspect of the present disclosure. The graph 6700 illustrates the firing load on a firing member, such as firing member 1900, over time. As seen in FIG. 61, the graph 6700 illustrates two firing force profiles—a first firing force profile 6702 during a first firing stroke and a second firing force profile 6704 during a second firing stroke. For both firing strokes, the thickness of the tissue encountered by the firing member doubled at $d_3$.

As described above, the present disclosure provides a way of controlling the FTF during a firing stroke of the firing member. In some embodiments, a control system, such as controller 620, can predict higher, upcoming forces to fire based on the size of the FTF peaks early in the firing stroke. Based on the prediction, the control system can trigger changes to the firing algorithm to control the force to fire during the firing stroke.

As seen in FIG. 61, for both firing force profiles 6702, 6704, a firing member, such as firing member 1900, begins at an unfired position, do, prior to initiation of the firing stroke. Based on the initiation of the firing stroke, such as actuation of a firing trigger, a firing system, such as firing motor drive assembly 604, drives the firing member from the unfired position toward a fired position, $d_7$, to cut tissue captured within the end effector, such as end effector 1300, and to deploy staples from a staple cartridge, such as staple cartridge 1301.

At $d_1$, the FTF 6054 the firing member ramps up based on the firing member encountering the tissue captured within the end effector and beginning to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the magnitude of the force to fire peaks as the firing member traverses through the firing stroke. In some embodiments, the control system predicts the force to fire based on a change in magnitude of the force to fire peaks as the firing member traverses through the firing stroke. In some embodiments, the control system predicts the force to fire based on the shape of the force to fire peaks. In some embodiments, the control system predicts the force to fire based on the number of occurrences of force to fire peaks as the firing member traverses through the firing stroke. For instance, as referenced above, at around $d_3$, the thickness of the tissue doubles. Accordingly, the control system can detect the changes in the peaks/valleys of the firing force profiles 6702, 6704 in order to make predictions about the future forces to fire and trigger changes to the firing algorithms.

Furthermore, in various embodiments, the control system can determine the thickness of the tissue based on the detected properties of the force to fire peaks and valleys. In some embodiments, the control system can compare the firing force profile (and peaks and/or valleys thereof) to firing force profiles stored in a memory, such as memory 624, in order to determine the type of tissue and/or the thickness of the tissue that is currently being encountered. Based on the determined tissue type and/or thickness, the control algorithm can trigger adjustments to the firing algorithm that are appropriate for the determined type and/or thickness of tissue.

Based on the predicted forces to the fire, the control system can trigger changes to the firing algorithms to control the force to fire profiles 6702, 6704, as described elsewhere herein. In some embodiments, based on the predictions, the control system triggers the firing algorithms to slow the speed of the firing member rather than pausing the displacement of the firing member. Based on the slower speed, the force to fire profiles 6702, 6704 are controlled and maintained below a force to fire maximum threshold ($F_3$).

As seen in FIG. 61, the firing members reach the fired position at $d_7$. In various embodiments, the control system determines the thickness of the tissue based on the peaks and valleys of the firing force profile at the fired position $d_7$. In some embodiments, the control system determines the thickness of the tissue based on a final portion of the firing stroke, such as the peaks and valleys detected from $d_6$ to $d_7$. Based on the determined thickness at the fired position, the control system can communicate the determined thickness to the clinician, such as via a display. Based on the determined thickness, the control system can also recommend an appropriate staple cartridge to use for a subsequent stapling operation. For example, a first cutting and stapling operation is performed using a Color A staple cartridge, seen in FIG. 49. At the end of the cutting and stapling operation, the control system can determine that the tissue has a tissue thickness of $t_6$, based on the peaks and valleys of the force to fire profile. Based on the determined tissue thickness $t_6$, the control system can recommend that a user utilize either a Color B staple cartridge (which would be utilized in an overstressed application) or a Color C staple cartridge (which would utilize in a minimum/maximum application). Accordingly, the peaks and valleys from a first cutting and stapling operation can be utilized to determine a tissue thickness and influence a staple cartridge that will be utilize for subsequent cutting and stapling operation.

Figure 62:
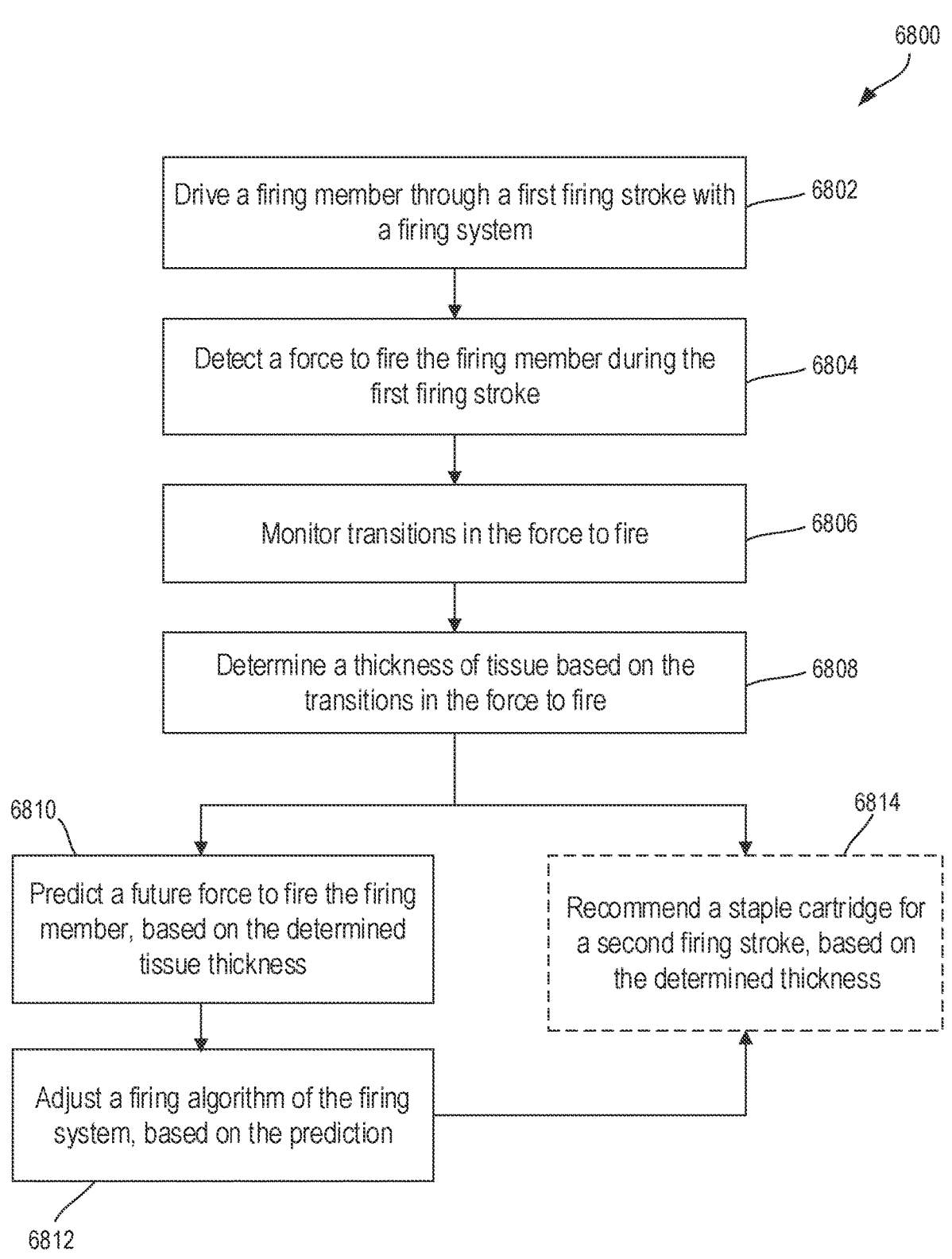
FIG. 62 illustrates a method of controlling a surgical instrument, according to at least one aspect of the present disclosure.

Referring now to FIG. 62, a method 6800 of controlling a surgical instrument is provided, according to at least one aspect of the present disclosure. The method 6800 comprises driving 6802 a firing member through a first firing stroke with a firing system. In various embodiments, a control system, such as controller 620, drives a firing member, such as firing member 1900, in response to the actuation of a firing system, such as firing motor drive assembly 604. In one aspect, driving the firing member through a firing stroke causes the firing member to deploy staples removably stored in a staple cartridge, such as staple cartridge 1301, into tissue captured between an end effector, such as end effector 1300.

The method 6800 further includes detecting 6804 a force to fire the firing member. In various embodiments, the control system monitors the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

The method 6800 further includes monitoring 6806 transitions in the force to fire. In some embodiments, the transitions comprise peaks in the firing force profile. In some embodiments, the transitions comprise valleys in the firing force profile. In some embodiments, the transitions comprise peaks and valleys in the firing force profile. In some embodiments, monitoring the transitions in the force to fire comprises monitoring the magnitude or the peaks and/or valleys during the firing stroke. In some embodiments, monitoring the transitions in the force to fire comprises the shapes of the peaks and/or valleys. In some embodiments, monitoring the transitions in the force to fire comprises monitoring the number of occurrences of peaks and/or valleys. In some embodiments, monitoring the number of occurrences of peaks and/or valleys comprises monitoring the number of occurrences of peaks and/or valleys over a predefined amount of time. In some embodiments, monitoring the number of occurrences of peaks and/or valleys comprises monitoring the number of occurrences of the peaks and/or valleys over a portion of the firing stroke.

The method 6800 further comprises determining 6808 a thickness of the tissue based on the transitions in the force to fire. In various embodiments, the control system can compare parameters associated with the peaks and valleys to values stored in a memory, such as memory 624. In some embodiments, the memory includes a look-up table that can be utilized to determine a corresponding tissue thickness based on parameters associated with the peaks and valleys. In some embodiments, the parameters of the peaks and valleys comprise a number of occurrences in peaks and/or valleys, a magnitude of the peaks and/or valleys, or a shape of the peaks and/or valleys, as examples.

The method 6800 further comprises predicting 6810 a future force to fire the firing member, based on the determined tissue thickness. In various embodiments, the control system can predict a future force to fire the firing member, as described elsewhere herein. The method 6800 further comprises adjusting a firing algorithm of the firing system, based on the prediction. In various embodiments, the control system can adjust the firing algorithm based on the predictions, such as pausing the firing stroke and/or slowing the speed of the firing member, as examples, as described elsewhere herein.

The method 6800 optionally further includes recommending 6814 a staple cartridge for a second firing stroke, based on the determined thickness. In various embodiments, as described elsewhere herein, based on the determined thickness, the control system can recommend to a clinician, via a display, as an example, a staple cartridge to use for a subsequent staple firing stroke. In various embodiments, the recommendation can occur at the conclusion of the staple firing stroke. In various embodiments where the firing algorithm isn't adjusted based on predictions from the control system, the control system can still recommend a staple cartridge for a subsequent staple firing stroke.

In various instances, one or more mechanical outputs of a motor system including a motor and a drive train connected to the motor can be used as an input to a motor control circuit which controls the motor to increase the efficiency of the motor system. In at least one instance, the drive train includes a closure member coupled to a motor configured to clamp tissue with an end effector. In at least one instance, the drive train includes a firing member coupled to a motor configured to move a firing member through a firing stroke. In at least one instance, the firing stroke includes a staple firing stroke. In at least one instance, the firing stroke includes a portion of which where the firing member clamps tissue with jaws of the end effector and another portion of which where the firing member deploys staples from the end effector to staple and cut the tissue clamped with the end effector.

Mechanical outputs of the motor can include any suitable mechanical output. For example, mechanical outputs may include the actual speed of the motor, the actual displacement of the motor (measured with an encoder, for example), and/or the amount of elapsed time the motor runs. Further to the above, mechanical outputs may include heat generated by the motor and/or forces generated with the drive train, for example. Such outputs can be measured in any suitable fashion directly and/or indirectly.

In various instances, a motor system including a motor and a drive train connected to the motor may be underutilized (the motor speed can be increased without fear of overstraining the motor system, for example), over utilized (the motor is running at a speed which may be close to, or is already, overstraining the motor system, for example), and/or adequately utilized (the motor is running at a speed where the motor system is not overstrained nor is there room for a speed increase of the motor, for example). In other words, the motor system is operating below maximum, or optimal, capacity, motor system is operating at maximum capacity, and/or the motor system is operating beyond its maximum capacity.

Depending on the degree of utilization of the motor system, adjustments can be made by a motor control circuit so as to increase the efficiency of the motor system, for example. Such adjustments can include dynamic adjustments of the motor. In at least one instance, the adjustments include dynamic control of the speed of the motor. Overstraining the motor system may include running a motor at a duty cycle outside of a threshold duty cycle range which may cause a motor to fail sooner than expected, for example. In various instances, the capacity of the motor system can be measured to determine the degree of utilization of the motor system. Duty cycles of pulse width modulation (PWM) motor control can differ in width percentage and magnitude, for example.

In at least one instance, a motor control circuit is configured to interrogate and/or determine the relative capacity of a motor system. In at least one instance, interrogation of the relative capacity of the motor system includes monitoring a parameter of one or more components of the drive train and/or the motor. The relative capacity of the motor system may be monitored at any suitable time, for example. In at least one instance, the relative capacity of the motor system is automatically monitored prior to a clamping stroke, during the clamping stroke, after the clamping stroke but before a staple firing stroke, during the staple firing stroke, near an end of the staple firing stroke, and/or after the end of the staple firing stroke. In at least one instance, interrogation of the relative capacity of the motor system is manually initiated by a user of the instrument. Relative capacity of the motor system can be also be referred to as the unused, or available, capacity of the motor and/or motor system relative to a maximum capacity, for example.

Adjustments of the motor system can be made by a motor control circuit at any suitable time. For example, adjustments of the motor system can be made simultaneously, and/or at least substantially simultaneously, when the motor system is interrogated and the relative capacity of the motor system is determined. Interrogation of the motor system may be referred to as the interrogation action, a sensory action, and/or a micro-step. These actions can also be referred to as steps such as, for example, interrogation steps and/or sensory steps. In at least one instance, adjustments of the motor system can be made after a predetermined set time interval measured from the time of the interrogation action and/or after the completion of the interrogation action, for example.

In at least one instance, the relative capacity of a motor system is repeatedly monitored, and/or measured, over a period of time at a desired frequency. Further to the above, adjustments can be made to the motor system based on the measured relative capacity. Such adjustments can be made with the same and/or different frequency as the frequency at which the relative capacity of the motor system is measured. Each frequency can be adjusted automatically and/or manually to better suit different scenarios, for example. For example, the frequency at which the relative capacity of a motor system which clamps a jaw of an end effector is measured may be higher than the frequency at which a motor system which deploys a firing member or vice versa. In at least one instance, the frequency at which the relative capacity of a motor system which deploys a firing member is monitored is higher than the corresponding frequency at which adjustments are made to the same motor system. Such an arrangement can increase the stability of the motor system during the staple firing stroke, for example.

Various types of adjustments can be made upon determining the relative capacity of the motor system. For example, the motor system can be paused, a lockout can be activated, the motor can be slowed down, the motor can be sped up, the speed of the motor can be kept the same, and/or another interrogation action can be performed to verify the previously determined relative capacity.

In at least one instance, the speed of the motor is increased incrementally at a frequency in an effort to maximize the operational efficiency of the motor system, for example. With each incremental speed increase, the relative capacity of the motor system is determined by measuring an actual mechanical output of the motor system such as, for example, the actual speed of the motor. The actual speed of the motor can be used to determine if the motor system is operating at a predicted, or anticipated, state in response to each incremental increase in motor speed. For example, if the actual speed of the motor is as anticipated after an incremental speed increase is made to the motor, it may be determined that the motor system is operating at or below its maximum, or optimal, capacity. In such an instance, the speed of the motor is, again, increased incrementally and the relative capacity of the motor system is, again, determined. After one or more incremental speed increases, the actual speed of the motor may be not as anticipated and it may be determined that the motor system is operating beyond its maximum capacity. In such an instance, a variety of things can happen, discussed in greater detail below.

If the motor system is determined to be operating at or beyond maximum, or optimal, capacity after an incremental speed increase, a user may be alerted, the motor system can be adjusted in any suitable manner, and/or no adjustments are made to the motor system. In at least one instance, the speed of the motor is reduced back to its previous speed. For example, if the motor undergoes five incremental speed increases from a starting speed and at the fifth incremental speed increase it is determined that the motor system is operating beyond its maximum capacity, the speed of the motor can be reverted back to the speed set for the fourth incremental speed increase. In at least one instance, the reversion speed is equal to the speed set for the fourth incremental speed increase. In at least one instance, the reversion speed is a percentage of the speed set for the fourth incremental speed increase so as to not operate the motor system near its maximum capacity, but, operate the motor system a percentage below maximum capacity. Such an arrangement may increase the longevity of the motor system, for example, by rarely operating the motor system at its maximum capacity. In at least one instance, the maximum capacity is predefined below an actual maximum capacity, such as absolute mechanical capacity, for example, of the motor system. The actual maximum capacity of the motor system may be manufacturer-suggested, for instance.

In various instances, the incremental speed increases are not noticeable, or imperceptible, to a user. Such imperceptibility can be measured by vibration yield of the surgical instrument system, for example, being below a predefined perceptible threshold, for example. In at least one instance, a time period with which a speed increase is executed is below a perceptible time threshold so as to reduce the likelihood of a user noticing the speed increase. In at least one instance, the frequency at which the speed is increased is high but the magnitude of each incremental speed increase is low compared to the actual speed of the motor. Thus, the motor system is capable of constantly adjusting the speed of the motor to improve efficiency and/or maintain maximum efficiency, for example, while not effecting the user's experience. Such an arrangement may prevent jerkiness of a system which increases the speed of a motor substantially during a staple firing stroke, for example.

In at least one instance, after it is determined that the motor system is operating at maximum, or optimal, capacity, a delay is employed so as to not immediately reinitiate the interrogation of the motor system. In at least one instance, a delay is not employed and the motor system is constantly interrogated regardless of the adjustments made to the motor.

Interrogating the relative capacity of the motor system may also be referred to as sensing the relative capacity of the motor system. One or more sensory actions can be performed to determine when the speed of the motor can be increased, for example.

Figure 63:
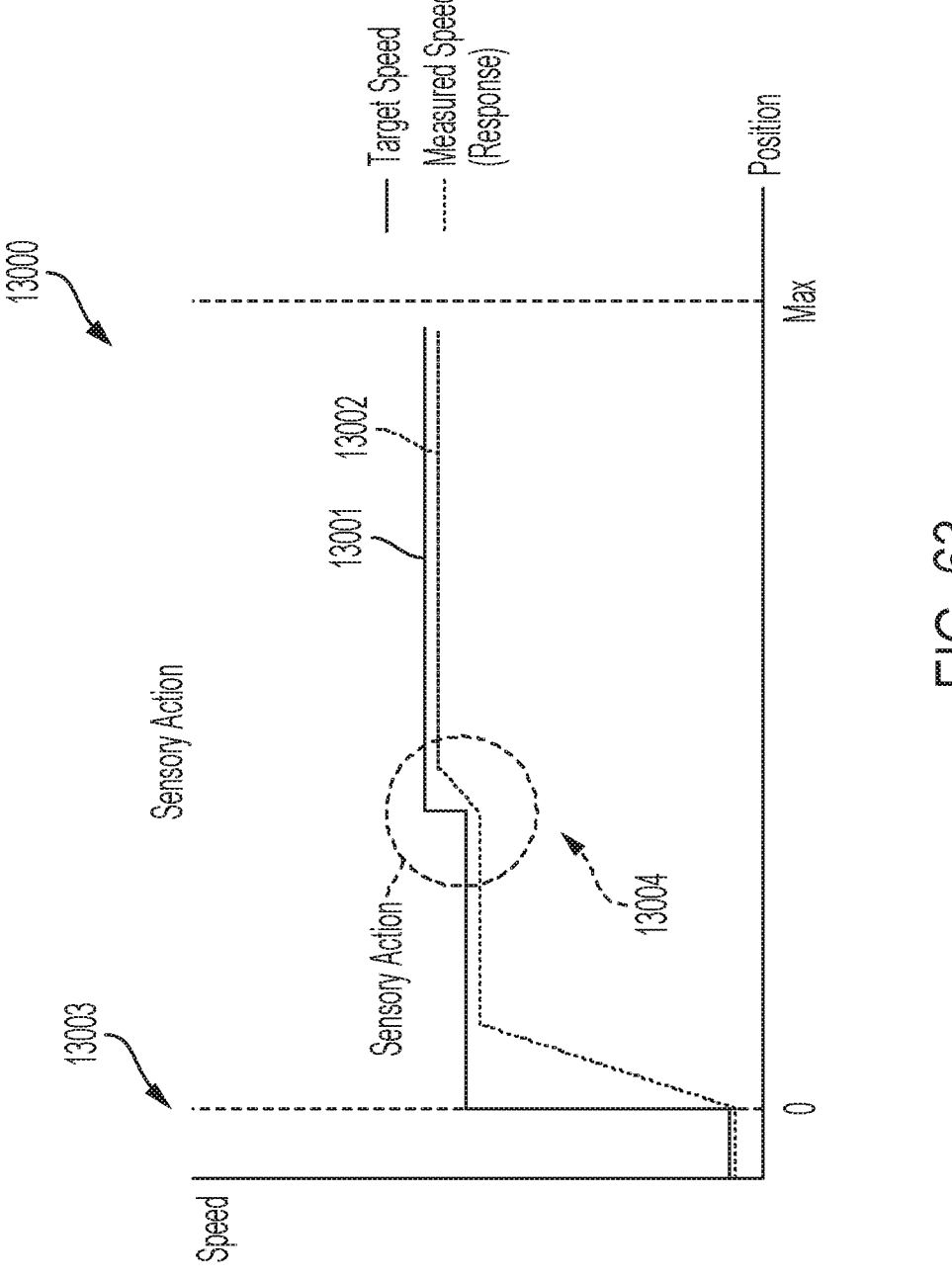
FIG. 63 is a graph depicting a firing stroke performed by a motor system that includes a motor, a drive train, and a motor control circuit, wherein the motor control circuit performs a sensory, or interrogation, action during a firing stroke in order to determine if the speed of the motor is capable of being increased to a target speed.

FIG. 63 is a graph 13000 depicting an example of a sensory action 13004 performed in order to determine if the speed of the motor is capable of being increased. As can be seen in the graph 13000, the target speed 13001 is increased at the beginning of the stroke 13003 (position 0) to a first target, or set, speed. In response, the measured speed 13002 increases until the motor reaches a first measured speed. In at least one instance, the first measured speed is as anticipated and thus a sensory action can be performed. The first target speed and the first measured speed may or may not be identical. At the sensory action 13004, the speed of the motor is increased a predetermined amount to a second target speed. In response, the measured speed 13002 gradually increases to a second measured speed. The measured, or actual, speed 13002 may vary due to a variety of factors such as, for example, motor performance, type of tissue encountered, and/or drive train backlash. At such point, based on the system response (actual measured speed of the motor relative to the second target speed, for example) to the sensory action 13004, the second target speed is maintained to run the motor at the second target speed. It may be determined that additional, or excess, capacity was, in fact, present based on the difference, or magnitude of deviation, between the actual measured speed of the motor relative to the second target speed. In at least one instance, the target speed may be reverted back to the first target speed if excess capacity is not available.

In various instances, a sensory action leads into a permanent action where a final, or optimal, speed is set by a control circuit. In other words, the increase in speed of the motor performed during the interrogation action of the motor system is maintained for the rest of a stroke or, in the case where a target speed, or predetermined percentage of the target speed, is not attained upon the performance of the sensory action, it is determined that additional capacity is not available and the speed of the motor is reverted back to the speed at which the motor was operating prior to the speed increase.

Figure 64:
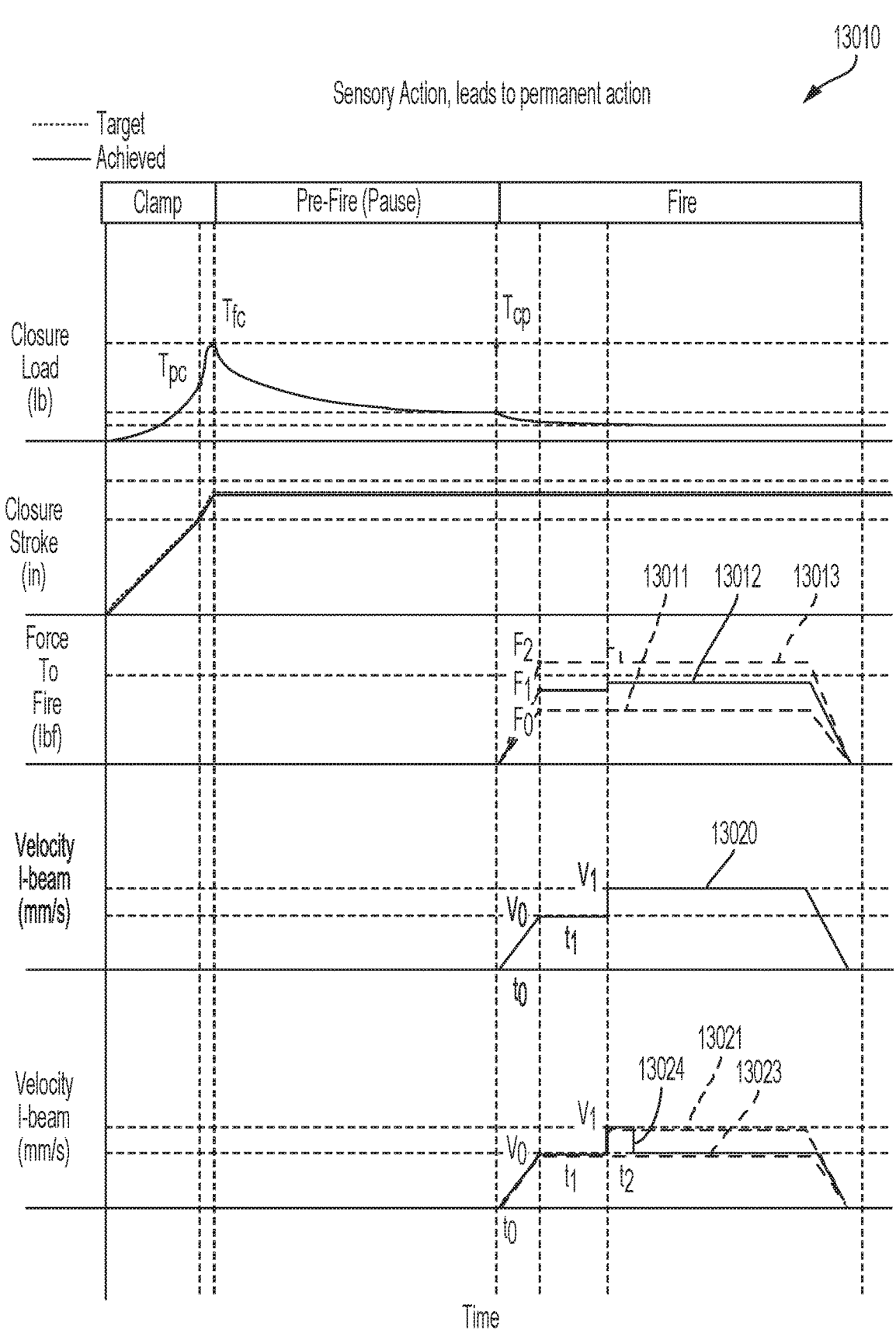
FIG. 64 is a graph depicting several firing strokes performed by a motor system that includes a motor, a drive train, and a motor control circuit, wherein different sensory actions are performed with different outcomes.

FIG. 64 is a graph 13010 depicting different staple firing strokes 13011, 13012, and 13013 and the results of interrogating a motor system performing the different staple firing strokes 13011, 13012, and 13013 in an effort to determine the relative capacity of the motor system. Closure load (the load experienced by clamping the jaws) and stroke position (the position of the firing member throughout the closure stroke and firing stroke) are also depicted. The force required to fire a firing member, for example, is also depicted for each staple firing stroke 13011, 13012, and 13013. The initial force to fire for stroke 13011 is F0, the initial force to fire for stroke 13012 is F1, and the initial force to fire for stroke 13013 is F2. As can also be seen in FIG. 64, various events corresponding to a surgical stapling instrument, for example, are also illustrated on the graph 13010: the clamping time period (with a partial clamp indicator Tpc and a fully clamp indicator Tfc), the pre-fire, or pause, time period, and the fire time period.

In addition to the above, the actual speed, or velocity, of the I-beam, or firing member, for example is depicted for each staple firing stroke 13011, 13012, and 13013 as well as the target speed 13020 utilized in the sensory action for each firing stroke. As can be seen in the graph 13010, the target speed 13020 increases from zero to V0 in the beginning of the firing stroke by a motor control circuit, for example. Speed V0 can be used to apply full clamping pressure to the jaws of an end effector with an i-beam, for example. After time t1, a sensory action is performed by the motor control circuit and an attempt is made to increase the speed of the motor to V1 for each staple firing stroke 13011, 13012, and 13013.

In response to the speed increase of the motor during staple firing stroke 13011, the force to fire is relatively low and, thus, the actual speed 13021 of the motor remains at or within an acceptable percentage of the target speed of V1. The actual speed 13021 is measured and, once it is determined that the actual speed 13021 of the motor is at or within the acceptable percentage of the target speed of V1, a motor control circuit maintains the target speed of V1 through the rest of the staple firing stroke 13011. In response to the speed increase of the motor during staple firing stroke 13012 where an increased force to fire is experienced in addition to a mid-stroke increase of the force to fire, the actual speed of the motor remains within an acceptable level relative to the target speed V1. For clarity, the actual speed of the staple firing stroke 13012 is represented as being identical to the actual speed 13021. In such an instance, the motor control circuit maintains the target speed of V1 through the rest of the staple firing stroke 13012. In response to the speed increase of the motor during staple firing stroke 13013 where the force to fire is relatively high to begin with and a larger mid-stroke increase of the force to fire is experienced, the actual speed 13023 of the motor is not able to achieve the target speed of V1 nor is the actual speed 13023 of the motor able to achieve a speed within the acceptable percentage of the target speed of V1. In such an instance, the motor control circuit reverts the target speed of the motor back to target speed V0 after a time period t2. In at least one instance, the motor control circuit reverts the target speed of the motor back to a predetermined percentage of target speed V0 and/or a predetermined magnitude of speed above and/or below the target speed V0. In at least one instance, the magnitude of the adjustment is based on the magnitude of the deviation between the actual measured speed and the target speed.

The sensory action performed during the staple firing strokes 13011, 13012, and 13013 includes a time period of t2. In other words, target speed V1 may be held at V1 for the time period t2. The time period t2 may be any suitable time period.

In various instances, the sensory action occurs before, or prior to, a reaction, or permanent action, for example. In other words, the speed of the motor is increased, the relative capacity of the motor system is determined, the speed of the motor is reverted back to its original speed and, later during the staple firing stroke, the speed of the motor is increased in response to the determined relative capacity of the motor system attained during the sensory action. In at least one instance, a plurality of sensory actions are performed prior to a reaction.

Figure 65:
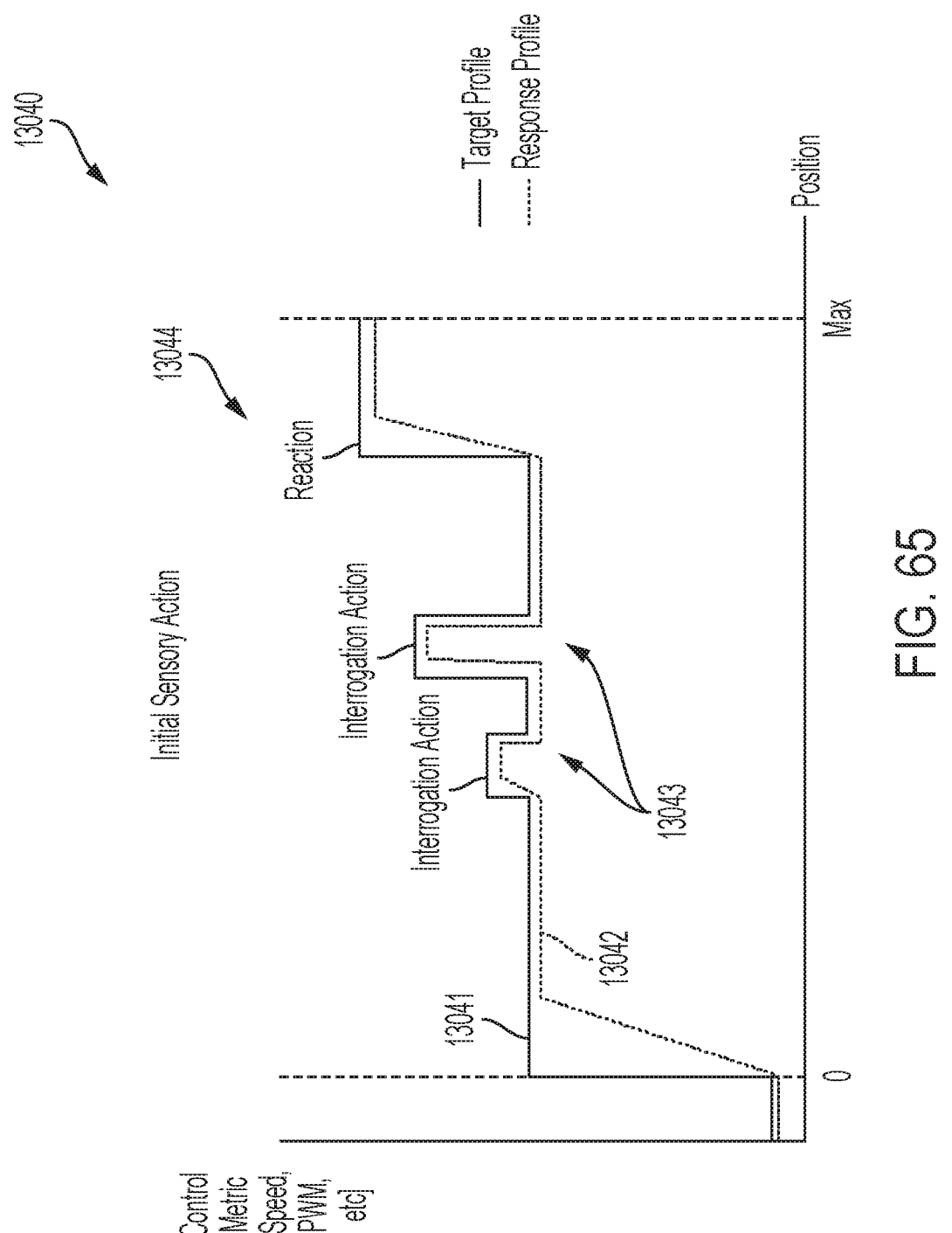
FIG. 65 is a graph depicting a firing stroke performed by a motor system that includes a motor, a drive train, and a motor control circuit, wherein the motor control circuit performs multiple discrete sensory actions and, in response to the sensory actions, performs a reaction a period of time after the completion of the sensory actions.

FIG. 65 is a graph 13040 depicts actual speed 13042 of a staple firing stroke relative to a target speed 13041 of the staple firing stroke. The relative capacity of the motor system is interrogated during interrogation actions 13043. The interrogation actions 13043 occur prior to a reaction, or optimized action, 13044. The interrogation actions 13043 each include an increase in motor speed. In at least one instance, the interrogation actions 13043 include different target speeds. In at least one instance, the target speed of subsequent interrogation actions 13043 is set based on the response, or determined relative capacity, of the motor system during previous interrogation actions 13043. During the staple firing stroke, the target speed is increased after the completion of one or more interrogation actions during the reaction, or optimized action, 13044. In at least one instance, a period of time elapses after the last interrogation action 13043 before the target speed of the motor is increased during the reaction action 13044.

In at least one instance, a user is alerted prior to a reaction, or optimized action, being performed. For example, a user may be notified through a user interface that the motor system is operating below maximum capacity after a motor control circuit performs one or more unnoticeable interrogation actions. A user may then be able to select whether or not to perform a recommended reaction and/or modify the recommended reaction, for example.

Figure 66:
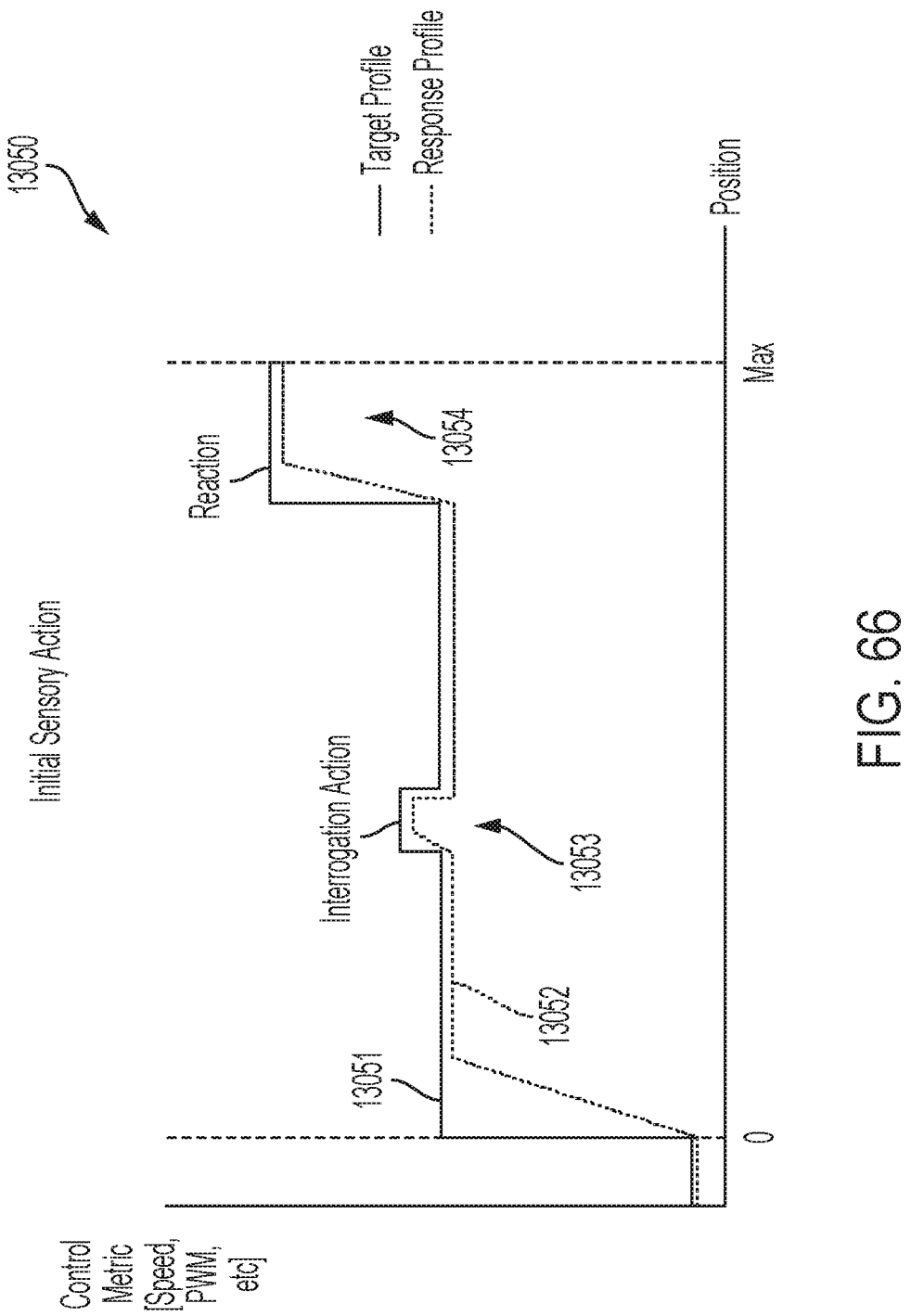
FIG. 66 is a graph depicting a firing stroke performed by a motor system including a motor, a drive train, and a motor control circuit, wherein the motor control circuit performs a sensory action and, in response to the sensory action, performs a reaction a period of time after the completion of the sensory action.

In various instances, the magnitude of the speed increase of the motor during a plurality of sensory, or interrogation, actions gradually increases in magnitude for each subsequent interrogation action. FIG. 66 is a graph 13050 depicting a target speed 13051 and an actual speed 13052 of a staple firing stroke including an interrogation action 13053 and a reaction 13054. During the staple firing stroke, the speed of the motor is increased to a first target speed from a first current speed during the interrogation action 13053. Subsequent to the completion of the interrogation action 13043, a reaction 13054 takes place where, upon determining that the relative capacity of the motor system is not near, at, or above maximum capacity during the interrogation action 13053, the speed of the motor is increased to a second target speed which is greater than the first target speed. In at least one instance, the ratio of the first target speed and second target speed is predefined. For example, the target speed of the interrogation action may include between about 10% and 90% of the target speed of the reaction, for example. In at least one instance, the target speed of the interrogation action may include half of, a quarter of, and/or a third of the target speed of the reaction, for example. Any suitable ratio can be utilized. In at least one instance, the target speed of the interrogation action is greater than the target speed of the reaction.

Figure 67:
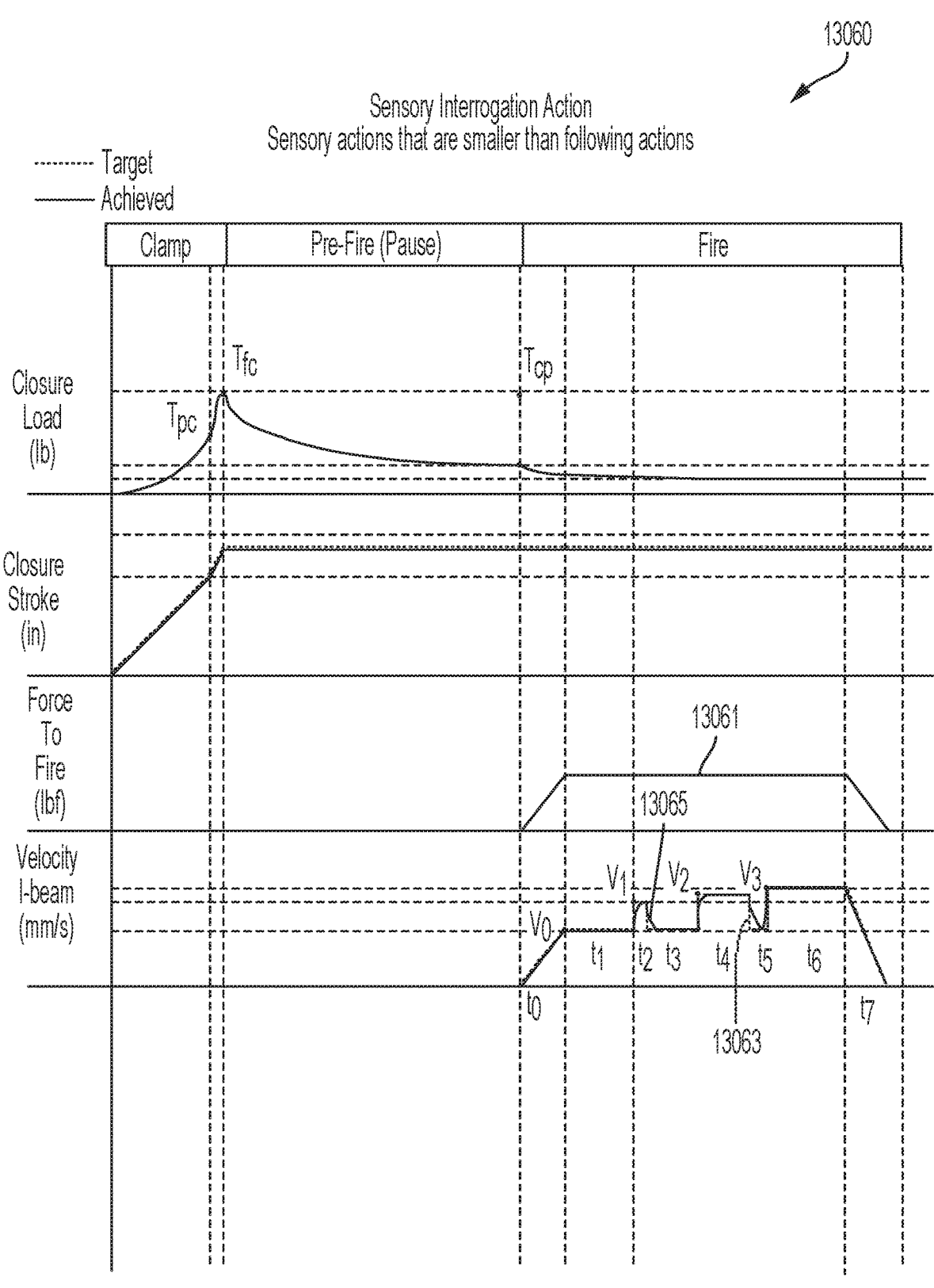
FIG. 67 is a graph depicting a firing stroke performed by a motor system including a motor, a drive train, and a motor control circuit, wherein multiple sensory actions are performed, each including a different target speed magnitude and different time periods.

FIG. 67 is a graph 13060 depicting a staple firing stroke 13061 of a motor system undergoing a plurality of interrogation actions. Closure load (the load experienced by clamping the jaws) and stroke position (the position of the firing member throughout the closure stroke and firing stroke) are also depicted. The force required to fire a firing member, for example, is also depicted for the staple firing stroke 13061. In addition to the above, the actual, or response, speed, or velocity 13065, of the i-beam, or firing member, for example is depicted for the staple firing stroke 13061 as well as the target speed 13063. As can be seen in graph 13060, a plurality of sensory actions are performed targeting speed V1, V2, and V3. Target speed V1 is interrogated for time t2, target speed V2 is interrogated for time t4, and target speed V3 is interrogated for time t6. The time periods t2, t4, and t6 are different. In at least one instance, the time periods of each sensory action are identical. As can be seen in graph 13060, the times t2, t4, and t6 get gradually longer for each subsequent sensory action. As can be also be seen in graph 13060, the magnitude of each target speed increase gradually increases for each subsequent sensory action. During the staple firing stroke 13061, the actual speed 13065 of the motor is within an acceptable level relative to the target speed 13063 for each sensory action. As can be seen in FIG. 67, the load experienced by the firing member does not cause the target speeds V1, V2, and V3 to be missed. In other words, the control circuit determines that the motor system can be run at the target speeds V1, V2, and V3 with the load. In at least one instance, however, the actual speed may vary if the load increases and, as a result, the motor system may not achieve the target speeds V1, V2, and/or V3. In at least one instance, the target speed V3 is a final, optimal, speed set by the control circuit as a result of achieving target speeds V1 and V2.

In at least one instance, the time period at which a target speed is maintained for each sensory action doubles for each subsequent sensory action. In at least one instance, the magnitude of the target speed for each sensory action is identical until the target speed can be achieved. In such an instance, the speed of the motor is permanently set at the target speed and a new target speed is set for subsequent sensory actions until the new target speed can be achieved.

In at least one instance, the collection of target speeds selected for sensory actions during a staple firing stroke can be referred to as a target speed profile. In at least one instance, the target speed profile can be preselected for different types of instruments and/or predefined by a user. For example, a surgical stapling instrument with a 60 mm cartridge may include a first target speed profile while a surgical stapling instrument with a 45 mm cartridge may include a second target speed profile which is different than the first target speed profile. In at least one instance, one surgical stapling instrument may require sensory actions which include target speeds having a greater magnitude than another surgical stapling instrument to increase operating efficiency of each corresponding motor. In other words, a motor of one system designed to operate at a higher speed as compared to a motor of a second system designed to operate at a lower speed may require sensory actions with target speeds having greater magnitude than the second system to have more effective reactions during a staple firing stroke, for example. In at least one instance, the time period of each sensory action includes a length which is imperceptible to a user during use of a surgical stapling instrument, for example. In at least one instance, the magnitude of the target speed of each sensory action includes a magnitude which is imperceptible to a user during use of a surgical stapling instrument, for example.

Figure 68:
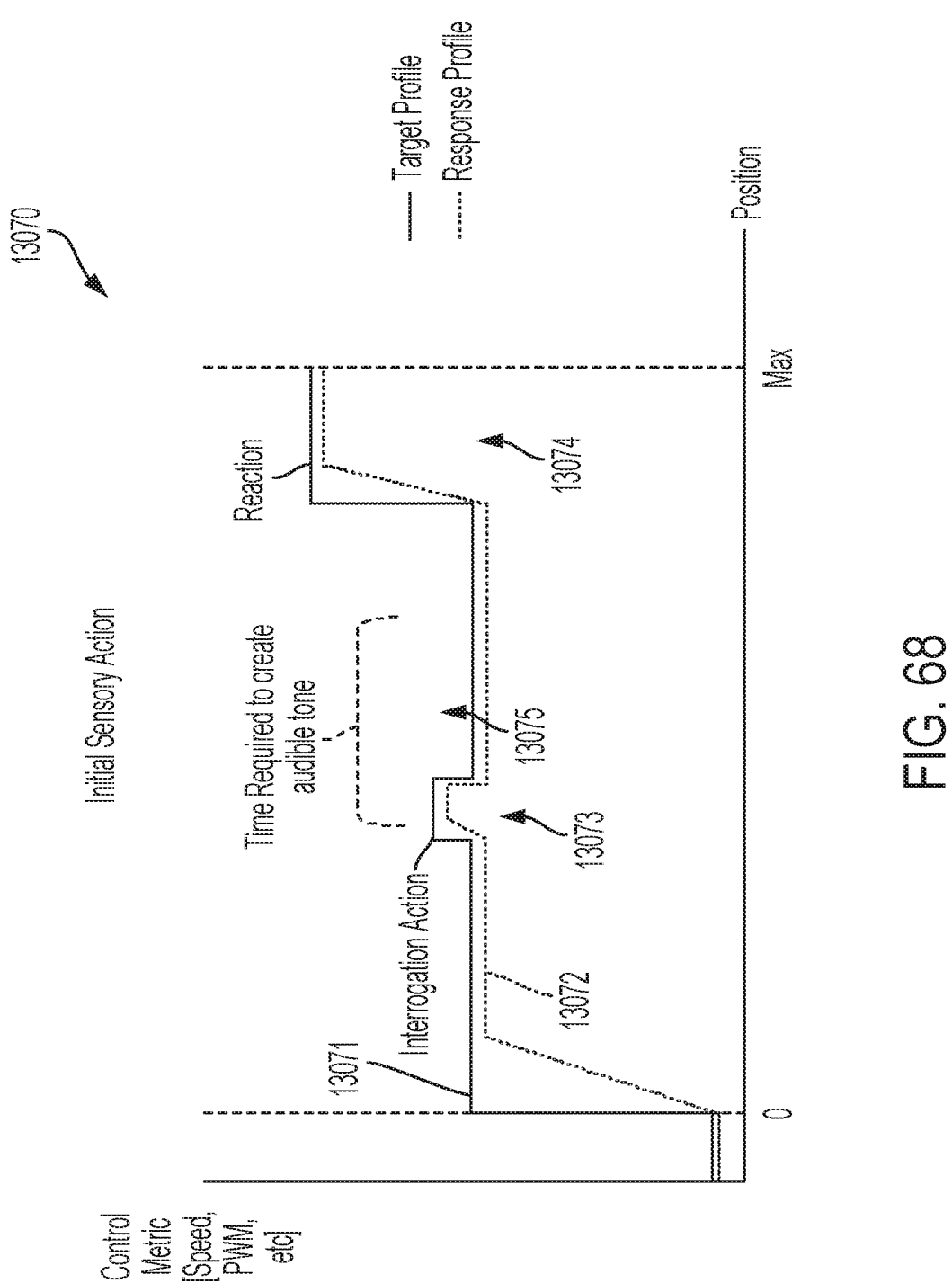
FIG. 68 is a graph depicting a firing stroke performed by a motor system including a motor, a drive train, and a motor control circuit, wherein the motor control circuit performs a sensory action and, in response to the sensory action, after a predefined time period, performs a reaction.

FIG. 68 is a graph 13070 depicting a target speed 13071 and an actual speed 13072 of a staple firing stroke including an interrogation action 13073 and a reaction 13074. During the staple firing stroke, the speed of the motor is increased to a first interrogation target speed during the interrogation action 13073. Subsequent to the completion of the interrogation action 13073, a reaction 13074 takes place where, upon determining that the relative capacity of the motor system is not near, at, or above maximum capacity during the interrogation action by comparing an interrogation response speed to the first interrogation target speed, the speed of the motor is increased to a second reaction target speed which is greater than the first interrogation target speed. In at least one instance, a time period 13075 is set to alert a user, for example, that a reaction is about to take place. Because the first interrogation target speed was achieved, or at least an acceptable percentage of the first interrogation target speed was achieved, during the interrogation action 13073, the motor control circuit alerts a user that a condition has been met to set a reaction, or permanent action, within the time period 13075. In at least one instance, the time period 13075 includes audibly alerting a user at the beginning of the time period 13075 and, at the end of the time period 13075, the reaction 13074 is initiated (the motor is set to the second reaction target speed).

In various instances, a sensory action involves a motor control circuit setting a sensory, or interrogation, target speed for a motor to achieve. However, any suitable variable of the motor system can be set. For example, in at least one instance, displacement of a firing member is set and measured. For instance, a target displacement may be set and actual displacement measured and compared to the target displacement to determine if the motor system is below, near, at, and/or above maximum capacity. In at least one instance, motor current, motor voltage, motor duty cycle, and/or motor displacement are used to set a target variable and compare a measured, or response, variable against the target variable.

Figure 69:
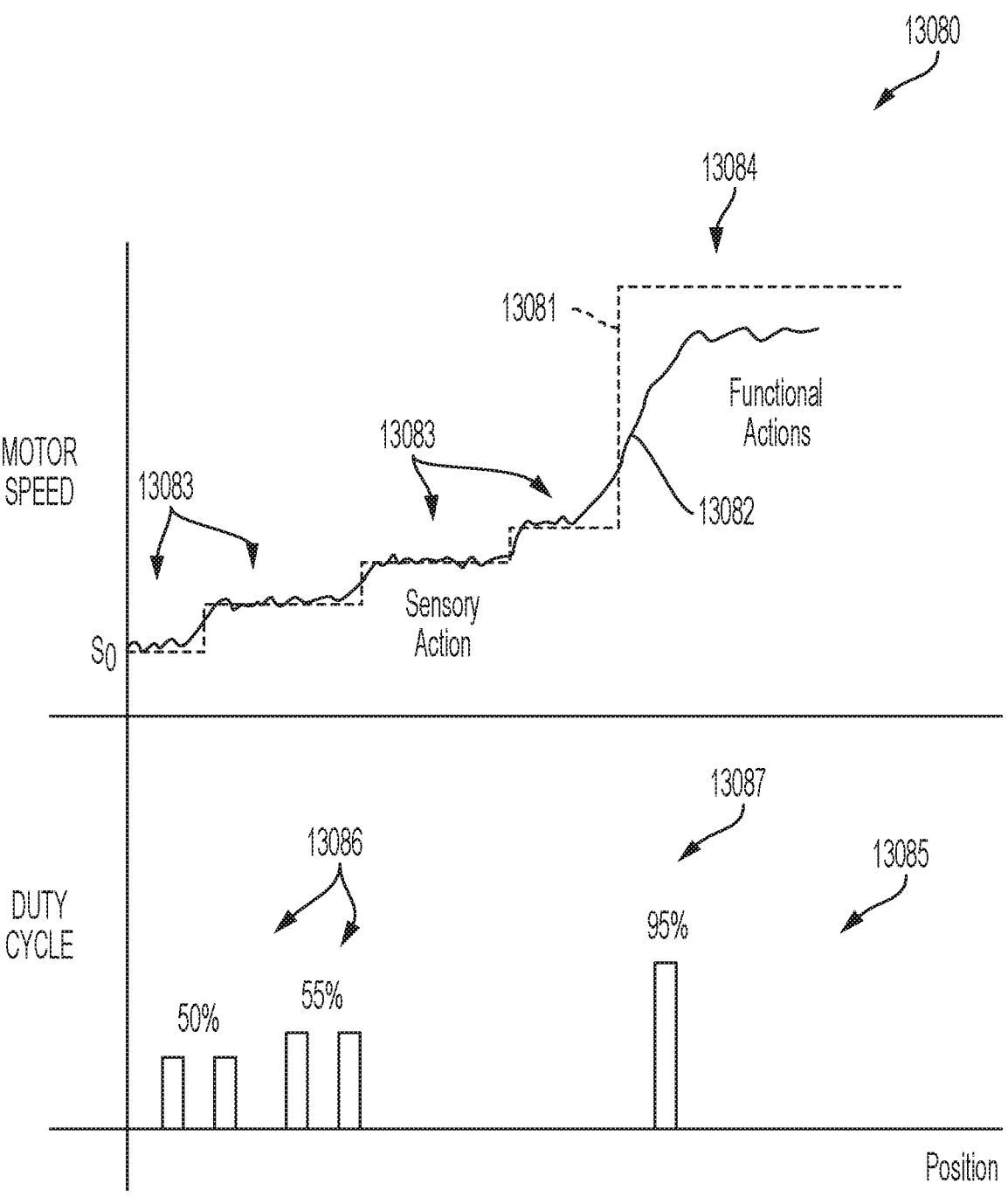
FIG. 69 is a graph depicting a firing stroke performed by a motor system including a motor, a drive train, and a motor control circuit, wherein the motor control circuit performs multiple sensory actions by increasing a target motor duty cycle and, after the completion of the sensory actions, performs a functional action or reaction.

FIG. 69 is a graph 13080 depicting a target speed 13081 and an actual speed 13082 of a staple firing stroke including a plurality of incremental interrogation actions 13083 and a reaction, or functional action, 13084. The graph 13080 also illustrates the set duty cycle 13085 of a pulse width modulation circuit of the motor during the staple firing stroke. As can be seen in the graph 13080, the set duty cycle incrementally increases 13086 during the sensory, or interrogation, actions 13083 and the set duty cycle is increased substantially 13087 during the reaction 13084. The duty cycle may be incrementally increased at any suitable rate at any suitable magnitude. In at least one instance, the rate of change of the duty cycle and/or the magnitude of the duty cycle changes is based on the length of the interrogation actions, the length of the staple firing stroke, and/or the desired speed of the staple firing stroke. In at least one instance, the delta between each set duty cycle is small enough to be imperceptible to a user during a staple firing stroke. As can be seen in FIG. 69, an incremental increase of 5% is made to the duty cycle during each interrogation action and an increase to 95% is made during the reaction. In at least one instance, the incremental increase includes increasing the duty cycle between about 1% and about 10%, for example. In at least one instance, the increase made to the duty cycle during the reaction includes increasing the duty cycle a predefined percentage (between about 25% and about 50%, for example). In at least one instance, the increase made to the duty cycle during the reaction includes increasing the duty cycle to a maximum percentage such as, for example, about 85%, about 90%, about 95%, and/or about 99%.

In at least one instance, type, thickness, and/or toughness of tissue, force to fire a firing member during a staple firing stroke, and/or system losses (backlash, for example) can be the deciding factor for determining whether or not the motor system can handle a substantive speed increase during either a subsequent interrogation action and/or a reaction. For example, thicker tissue may cause higher forces to fire which may place the motor system at, near, and/or above its maximum capacity. Thinner tissue may cause lower forces to fire which may place the motor system well below its maximum capacity. In such an instance, the magnitude of the set variable of the reaction can be substantially increased to reflect the increased relative capacity of the motor system.

As discussed herein, the relative capacity of the motor system can be determined in any suitable manner. In at least one instance, the relative capacity of the motor system can be determined by monitoring a relationship between a set target variable and the corresponding actual measured variable during either an interrogation action and/or a reaction.

In the instance of motor speed, for example, a first target speed is set and the corresponding actual speed is measured. This speed can be measured at the motor output (the speed of the output shaft) and/or within the end effector (the speed of the firing member, knife and/or sled, for example). In at least one instance, the actual speed of the motor output shaft as well as the actual speed of the firing member within the end effector are compared and averaged. At any rate, the actual speed of the motor output shaft, for example, is compared to the set first target speed. In at least one instance, the difference in target speed and actual measured speed can reflect relative capacity of the motor system. For example, it may be determined that a 10% difference in speed indicates that the motor system is not at full capacity (and/or anywhere between about 5% and about 95%, for example). The 10% difference may be a result of system losses such as heat and/or backlash, for example. If the difference in target speed and actual measured speed is 15% (greater difference than at 10%), this may indicate less relative capacity of the motor system is available. If the difference in target speed and actual measured speed is near or at about 100%, this may indicate that the motor system is near, at, or beyond maximum capacity.

In at least one instance, a threshold magnitude is set by a user, automatically set by a control circuit, or predetermined for one or more sensory actions and/or one or more reactions. In various instances, the threshold magnitudes for the sensory actions and/or the reactions are tuned based on the type of instrument, a length of the staple cartridge, the size of the staples in the staple cartridge, the type of tissue being incised and stapled, and/or the articulated position of the end effector. For example, in some instances, firing shafts are flexible and traverse an articulation joint into the end effector. In such an instance, the firing shaft may experience increased load when the end effector is in an articulated position such as, for example, a fully articulated position. As a result, the threshold magnitude of a target variable for the sensory actions and/or the reactions can be reduced so as to prevent overstraining the motor system more quickly.

In at least one instance, a control circuit monitors the articulation position based on inputs from one or more sensors. The control circuit may select the threshold magnitude of a target variable for the sensory actions and/or the reactions based on the inputs from the one or more sensor that are indicative of the articulation position.

It may be desirable to reduce the threshold magnitude of the target parameter (such as target speed, for example) for one or more sensory actions when the end effector is in an articulated position so as to reach optimal efficiency at a similar rate at which optimal efficiency is attained while the end effector is in its straight configuration. In other words, more torque may be required to drive a flexible firing member, for example, through an articulation joint when the end effector is articulated and, thus, through a staple firing stroke. In such an instance, a control circuit can determine that, notwithstanding any other variable, more motor capacity is going to be used to deploy the firing member through a staple firing stroke when the end effector is in an articulated position. In such an instance, the control circuit can automatically reduce the target speed, for example, when the end effector is articulated relative to a target speed at which the control circuit would set for an end effector in a straight configuration in an effort to reduce one or more failed sensory actions.

In at least one instance, the duration of the sensory actions may be tuned based on the type of instrument, a length of the staple cartridge, the size of the staples in the staple cartridge, the type of tissue being incised and stapled, and/or the articulated position of the end effector, for example. In at least one instance, a maximum time threshold is set for the duration of the sensory actions. In at least one instance, a minimum time threshold is set for the initiation of a reaction, or functional action. For example, a request for an increase in speed of the motor, by a user or automatically by a motor control circuit, can be made at which point a timer is set so as to prevent a reaction from occurring until the timer has concluded. In at least one instance, a reaction including a further increase of speed is delayed until the timer has concluded. In at least one instance, a reaction including a decrease in speed is delayed until the timer has concluded.

In at least one instance, a sensory action is performed on a motor system by a motor control circuit during pre-compression. In at least one instance, pre-compression is referred to as the time after the tissue is initially clamped but before the beginning of the staple firing stroke where additional clamping load may be applied to the tissue. In at least one instance, the I-beam within an end effector is configured to travel a predefined amount of distance prior to the beginning of the firing stroke (such as, for example, prior to contacting an unfired sled and/or a lockout) and after the tissue is initially clamped. As discussed herein, the firing and clamping functions may be actuated independently with separate and distinct drive systems. As also discussed herein, the firing and clamping functions may be actuated with a single firing drive member. Pre-compression may be present in each of these arrangements. In at least one instance, pre-compression is defined as the time, or distance, between partially clamping tissue and fully clamping tissue.

Within the predefined amount of distance, one or more sensory actions may be performed to determine a speed at which to deploy the firing member through the staple firing stroke. In at least one instance, the firing member is driven forward, reversed, and forward again one or more times within the predefined amount of distance so as to continuously monitor the relative capacity of the motor system prior to beginning the staple firing stroke, for example. In at least one instance, the number of times the firing member is driven forward and reversed to perform the one or more sensory actions is dependent on the tissue clamped within the end effector. The tissue clamped within the end effector can require time to settle and/or stabilize, for example. In at least one instance, the firing member is repeatedly cycled through a forward and reverse cycle until the tissue is stabilized. This initial movement of the firing member prior to contacting the sled may provide an arrangement which is capable of assessing initial firing loads to be expected during the staple firing stroke. As discussed herein, the length, time, and/or speed of this initial movement in addition to the sensory actions and/or reactions occurring within the initial movement of the firing member may be selected, set, and/or defined so as to be imperceptible to a user.

FIG. 70 is a logic flow chart depicting a process 13210 executable by a control circuit, such as the control circuit 1932 illustrated in FIG. 13 and/or the control circuit illustrated in FIG. 14, for example, for controlling the motor of a motor system of a surgical instrument system such as those disclosed herein. The control circuit is configured to initiate 13211 a firing speed interrogation sequence of a firing member within a pre-compression zone. The control circuit is configured to perform 13212 one or more sensory actions within the pre-compression zone. During the one or more sensory actions, the control circuit is configured to monitor 13213 one or more response parameters of the motor system. The control circuit is configured to reverse 13214 the firing member to a home position. The control circuit is configured to perform 13215 one or more additional sensory actions within the pre-compression zone. During the one or more additional sensory actions, the control circuit is configured to monitor 13216 one or more response parameters of the motor system. In at least one instance, the firing speed interrogation sequence occurs one or more times such as, for example, 3, 5, and/or about 10 times, for example. In at least one instance, the firing speed interrogation sequence occurs a predetermined number of times before a firing speed is selected for a subsequent staple firing stroke. Nonetheless, the control circuit is configured to select 13217 a firing speed profile based on the monitored parameters of the cyclical sensory actions performed within the pre-compression zone. In at least one instance, the firing speed interrogation sequence occurs within a clamping zone of the firing member and/or after clamping but before firing any staples, for example.

In at least one instance, cycling the firing member in the manner discussed above during the pre-compression stage can also help identify and understand the process of the tissue stabilization. For example, if relatively thick tissue is clamped, a firing member cycled during the pre-compression stage in the manner discussed herein may reveal that the motor system is near, at, and/or above maximum, or optimal, capacity prior to firing, for example, indicating that relatively thick tissue has been clamped and/or indicating that the relatively thick tissue clamped within the end effector is taking longer than expected to stabilize. Adjustments can be made to various parameters of the motor system based on information gleaned from the initial movement of the firing member during the pre-compression stage. For example, if thick tissue is clamped within the end effector and determined during the pre-compression stage, the parameters and variables of the sensory actions and/or the reactions can be tuned based on the detection of the thick tissue during the pre-compression stage, for example. The information gleaned from the initial movement of the firing member during the pre-compression stage can also be used to decide how long to allow the tissue to stabilize. Referring to FIG. 70, the information is gleaned from monitoring 13213 and monitoring 13216 one or more parameters of the motor system during the sensory actions and the additional sensory actions, for example.

In various instances, an imperceptible sensory, or interrogation, action is skipped and reactions, or functional actions, are performed to determine if there exists excess capacity within the motor system. For example, the speed of the motor can be increased a perceptible amount. Similar to the sensory actions discussed above, a motor control circuit can determine if the perceptible increased speed is achieved or not achieved by measuring the actual speed attained in response to the perceptible speed increase. In at least one instance, a functional action configured to increase the speed of the motor until it is determined that the target speed cannot be realized is terminated once it is determined that the target speed cannot be realized. For example, the functional action may gradually increase the speed of the motor in a stepped and/or continuous fashion until the actual speed of the motor deviates from the target speed below a differential threshold.

In at least one instance, sensory actions and/or functional actions are performed throughout an entire staple firing stroke in an effort to maintain optimal operational efficiency of the motor system. For example, the speed of a firing motor may be slowed down and sped up constantly while the relative capacity of the motor system is constantly monitored and evaluated. In at least one instance, a limited number of sensory actions and/or functional actions are performed. In at least one instance, the limited number is set by a user and/or a motor control program, for example. The limited number may be based on the age of the instrument and/or the motor system, the type of the instrument, the function of which the motor system actuates, or any suitable parameter, for example.

Figure 71:
FIG. 71 is a graph depicting a firing stroke performed by a motor system including a motor, a drive train, and a motor control circuit, wherein multiple sensory actions are performed by incrementally increasing the target motor duty cycle and, after the sensory actions are complete, performs a reaction.

FIG. 71 is a graph 13090 illustrating a clamping stroke and a firing stroke of a surgical instrument system. In at least one instance, the clamping and firing strokes are performed by separate drive members. In at least one instance, the clamping and firing stroke are performed by a single drive member. A force-to-fire 13091 is depicted for the staple firing stroke. The target speed 13093 and actual speed 13092 of the firing member during the staple firing stroke are also depicted. In addition to the above, the PWM signal, 13094 of the motor is also illustrated. As can be seen in the graph 13090, the PWM signal 13094 is incrementally increased 13095, by increasing the duty cycle, for example. In at least one instance, it is determined that there exists excess capacity within the motor system to reach a speed V2 at which point a function action 13096 is taken to increase the speed of the motor to speed V2. This is achieved by increasing 13097 the PWM signal. In at least one instance, the PWM signal is increased to a duty cycle 13097.

In at least one instance, sensory actions are also performed during retraction of a firing member through an end effector. Such an arrangement can provide a quicker retraction stroke without increasing the speed of the motor to, or beyond, its maximum, or optimal, capabilities, which could cause instability in a motor system.

Figure 72:
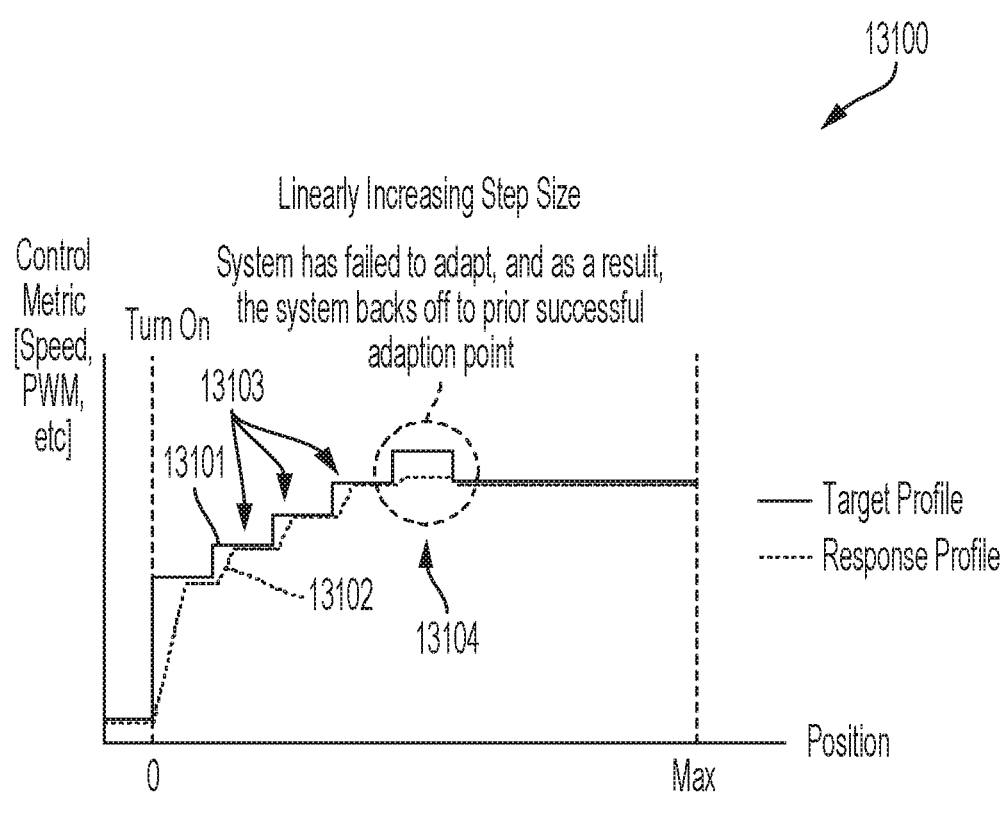
FIG. 72 is a graph depicting a firing stroke performed by a motor system including a motor, a drive train, and a motor control circuit, wherein the motor control circuit performs multiple sensory actions by linearly increasing a target speed magnitude for each subsequent sensory action, wherein the motor control circuit is configured to revert the target speed of the motor back to a target speed achieved during a prior successful sensory action.

FIG. 72 is a graph 13100 depicting a target speed 13101 and an actual speed 13102 of a staple firing stroke of a motor system including a plurality of discrete interrogation actions 13103. In at least one instance, each interrogation action 13103 includes an identical magnitude of change such as, for example, an identical increase in speed. In certain instances, the step size can increase linearly among the discrete interrogations. In other instances, the step size can vary among the discrete interrogations.

In the illustrated example, the plurality of discrete interrogations 13103 includes a final interrogation action 13104. During the staple firing stroke, the speed of the motor is increased incrementally during each interrogation action 13103. At the final interrogation 13104, an anticipated response of the actual speed 13102 is not realized and, thus, a motor control circuit reverts the speed of the motor back to the target speed of the previous interrogation action 13103. In at least one example, the motor control circuit determines that a response is not realized where the difference between the actual speed 13102 and the set target speed is beyond a predetermined threshold.

Figure 73:
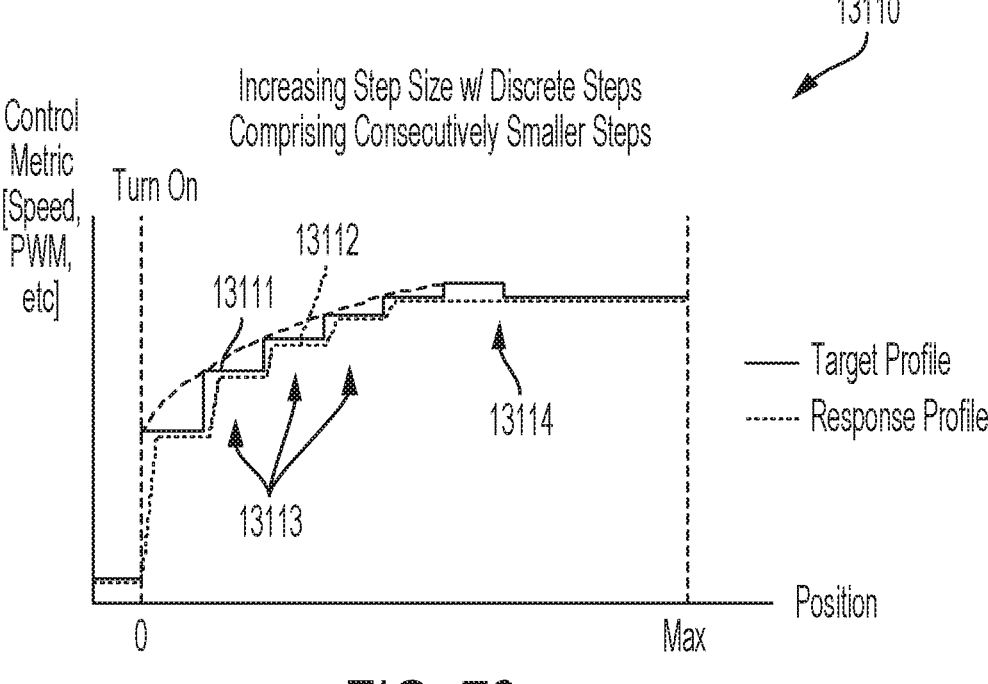
FIG. 73 is a graph depicting a firing stroke performed by a motor system including a motor, a drive train, and a motor control circuit, wherein the motor control circuit performs multiple sensory actions by increasing a target speed magnitude for each subsequent sensory action with consecutively smaller target speed magnitudes, wherein the motor control circuit is configured to revert the target speed of the motor back to a target speed achieved during a prior successful sensory action.

FIG. 73 is a graph 13110 depicting a target speed 13111 and an actual speed 13112 of a staple firing stroke of a motor system including a plurality of discrete interrogation actions 13113. In at least one instance, the magnitude of each interrogation action 13113 decreases with each subsequent action. For example, the increase in speed of the motor for each subsequent interrogation action 13113 decreases. In at least one instance, the decrease in magnitude of each interrogation action 13113 corresponds to the determination of the relative capacity of the motor system through the actual speed, or response profile, 13112 relative to the target speed, or target profile, 13111. For example, if the actual speed 13112, at some point, starts to gradually deviate further away from the anticipated speed with each interrogation action 13113, employing consecutively smaller interrogation actions can help achieve maximum efficiency by reducing overshoot. In at least one instance, the rate at which the magnitude of each interrogation action 13113 decreases is selected by a motor control circuit based on the rate of deviation of the actual speed 13112 relative to the target speed 13111. The plurality of discrete interrogation actions 13113 includes a final action 13114. At the final action 13114, the target speed 13111 is not realized and, thus, the motor control circuit reverts the speed of the motor back to the target speed of the previous interrogation action 13113.

Figure 74:
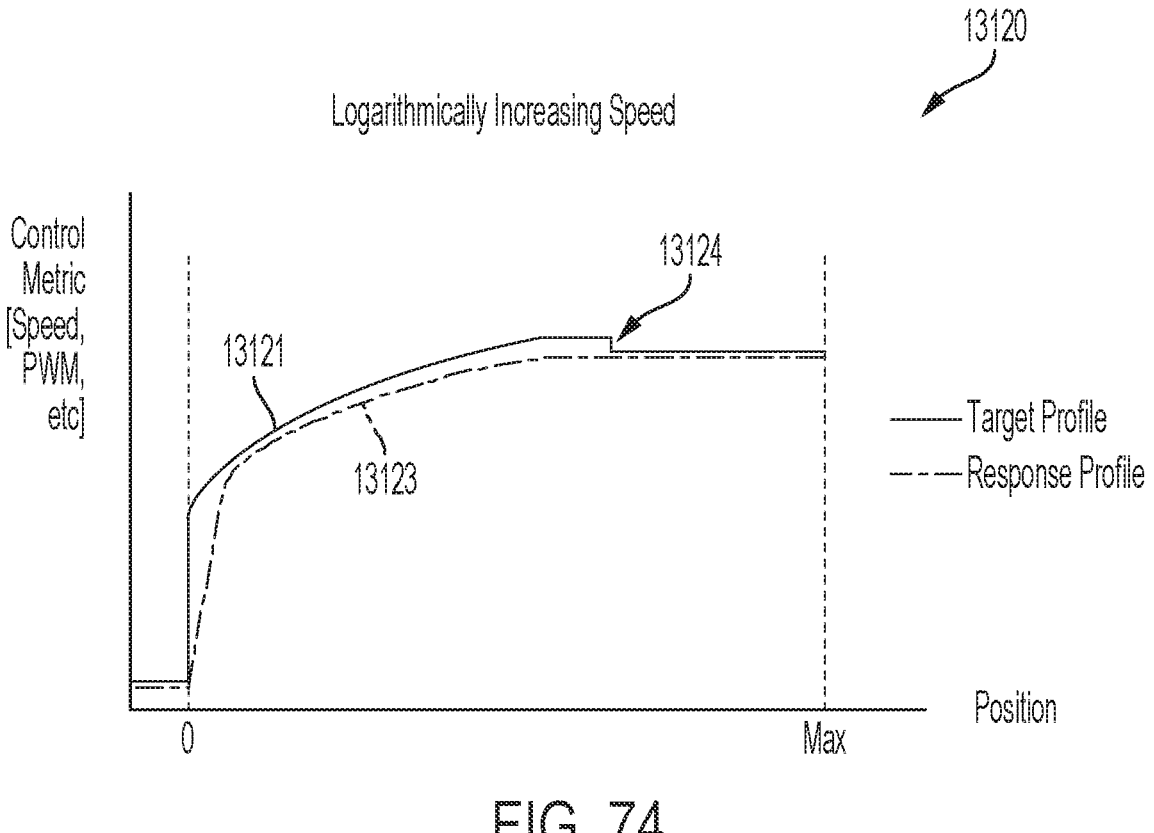
FIG. 74 is a graph depicting a firing stroke performed by a motor system including a motor, a drive train, and a motor control circuit, wherein the motor control circuit performs multiple sensory actions by logarithmically increasing a target speed magnitude for each subsequent sensory action, wherein the motor control circuit is configured to revert the target speed of the motor back to a target speed achieved during a prior successful sensory action.

FIG. 74 is a graph 13120 depicting a target speed 13121 and an actual speed 13123 of a staple firing stroke of a motor system including a target profile including a logarithmic increase in a control metric of the firing stroke such as, for example, a speed or PWM, and a response action 13124. Logarithmically increasing the control metric, e.g. PWM or speed, of the motor may reduce overshoot, for example. As can be seen in the graph 13120, the target speed 13121 is held constant for a period of time following the logarithmic interrogation. In at least one instance, a motor control circuit can hold the target speed 13121 constant upon determining a threshold deviation between the target speed 13121 and the actual speed 13123 has been reached. The period of time may provide the motor system time to settle or overcome an unexpected section of tissue, for example, thus giving the actual speed 13123 time to settle. In at least one instance, the actual speed 13123 never recovers and the response action 13124 is initiated. In at least one instance, the actual speed 13123 recovers to at least a certain degree and the motor system reinitiates interrogation of the motor system and continues to increase the speed of the motor. During the response action 13124, the target speed 13121 is reduced a predefined amount and/or reverted back to a previous target speed threshold. In at least one instance, the magnitude of the reduction of speed at the response action 13124 is based on the magnitude of deviation between the target speed 13121 and the actual speed 13123. In at least one instance, logarithmically increasing the speed of the motor to interrogate the relative capacity of the motor system can increase efficiency and reduce the amount of deviation between actual speed and target speed.

Figure 75:
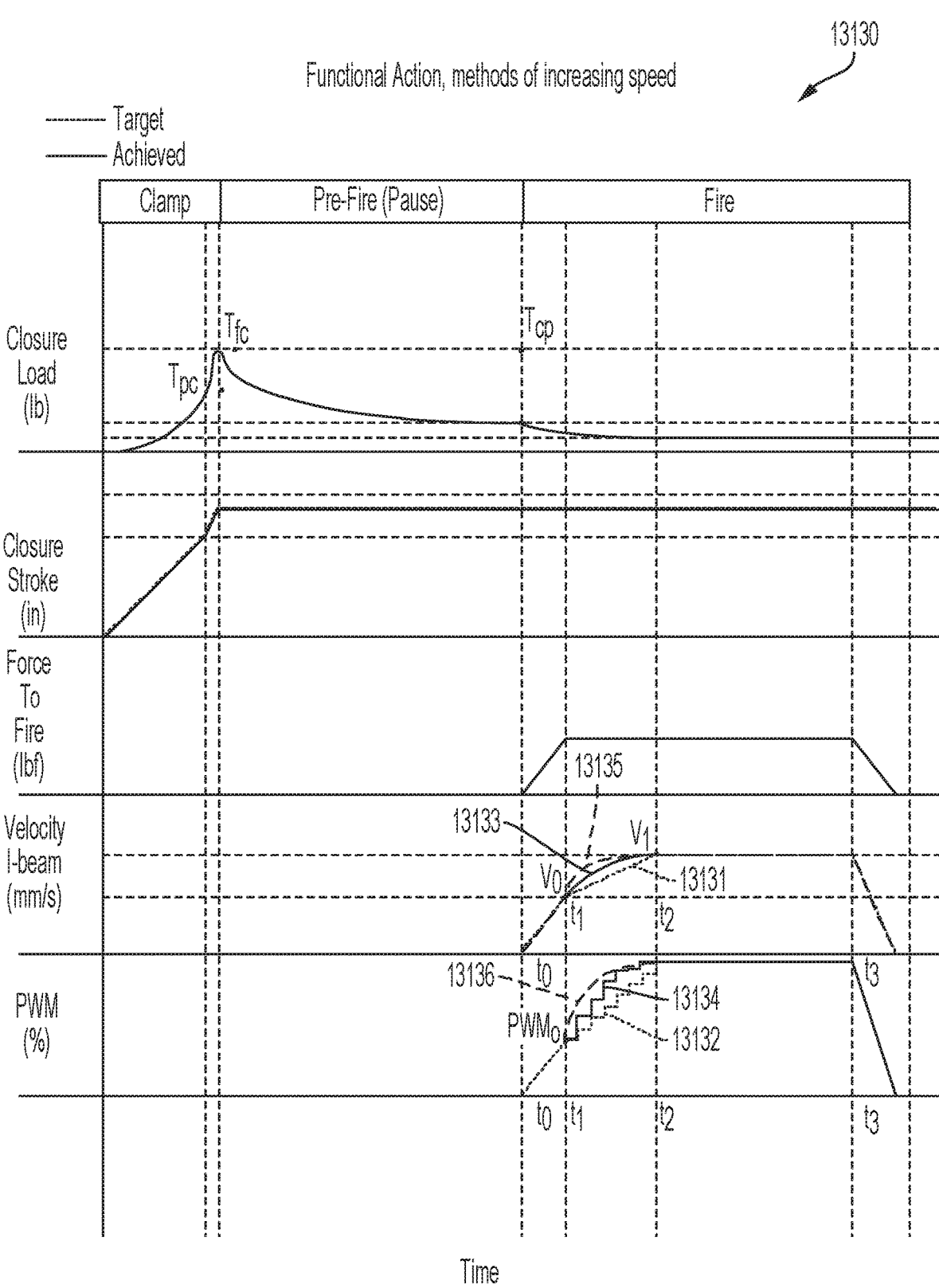
FIG. 75 is a graph depicting several firing strokes performed by a motor system including a motor, a drive train, and a motor control circuit, wherein different sensory action sequences are performed by modulating a motor duty cycle of the motor.

FIG. 75 is a graph 13130 illustrating a clamping stroke and a firing stroke of a surgical instrument system. In at least one instance, the clamping and firing strokes are performed by separate drive members. In at least one instance, the clamping and firing stroke are performed by a single drive member. A force-to-fire is depicted for the staple firing stroke, as well as the closure stroke and the closure load. Three different scenarios are illustrated for interrogating the motor system which drives the firing member. In scenario one, a percentage PWM signal of the motor is increased in discrete linear steps 13132 including an identical magnitude speed increase for each step resulting in a linearly increasing firing member velocity 13131. In scenario two, the percentage PWM signal of the motor is increased in discrete steps 13134; however, the magnitude of each speed increase decreases with each subsequent step resulting in a logarithmically increasing firing member velocity 13133. In scenario three, the percentage PWM signal of the motor is increased logarithmically 13136 resulting in a logarithmically increasing firing member velocity 13135.

Figure 76:
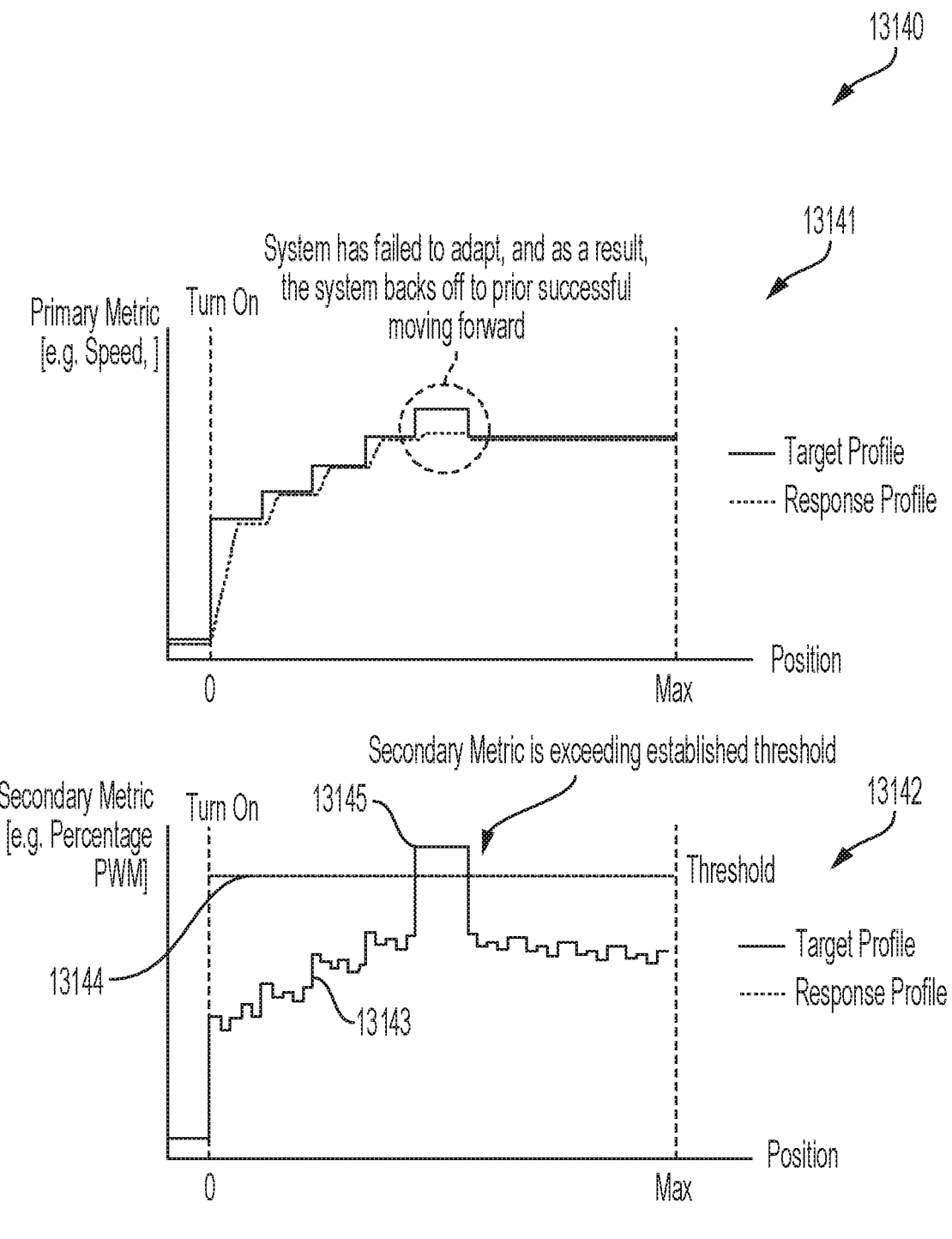
FIG. 76 is a graph depicting a primary sensory metric and a second sensory metric of a motor control circuit configured to control the speed of a motor.

FIG. 76 is a graph 13140 depicting a primary sensory metric 13141 and a secondary sensory metric 13142. In at least one instance, the primary sensory metric 13141 is similar to that of others disclosed herein. For example, the primary sensory metric 13141 involves incrementally increasing the target speed of the motor, monitoring the actual speed of the motor and, upon detecting that the actual speed of the motor deviates from the target speed beyond a predetermined threshold percentage, for example, the motor control circuit reverts the speed of the motor back to a target speed of a prior successful sensory action. In at least one instance, the motor control circuit selects a new target speed based on the failed sensory action which is different than the target speed of the prior successful sensory action and, rather, based on the rate at which the motor deviated from the target speed over time, for example. The secondary sensory metric 13142 is used by the motor control circuit as a redundancy, for example, to reinforce the detected output of the primary sensory metric 13141. For example, a PWM percentage signal 13143 of the motor can be monitored and, upon determining that the PWM percentage signal 13143 exceeds 13145 a predetermined threshold 13144, the motor control circuit determines that the motor system is at or above capacity. In such an instance, this determination coincides with the determination made within the primary sensory metric 13141. Further adjustments to the speed of the motor can be made based on both the primary sensory metric 13141 and the secondary sensory metric 13142. In least one instance, the PWM percentage signal 13143 is attained by converting one or more analog output parameters such as motor speed, for example, to a digital PWM signal.

Figure 77:
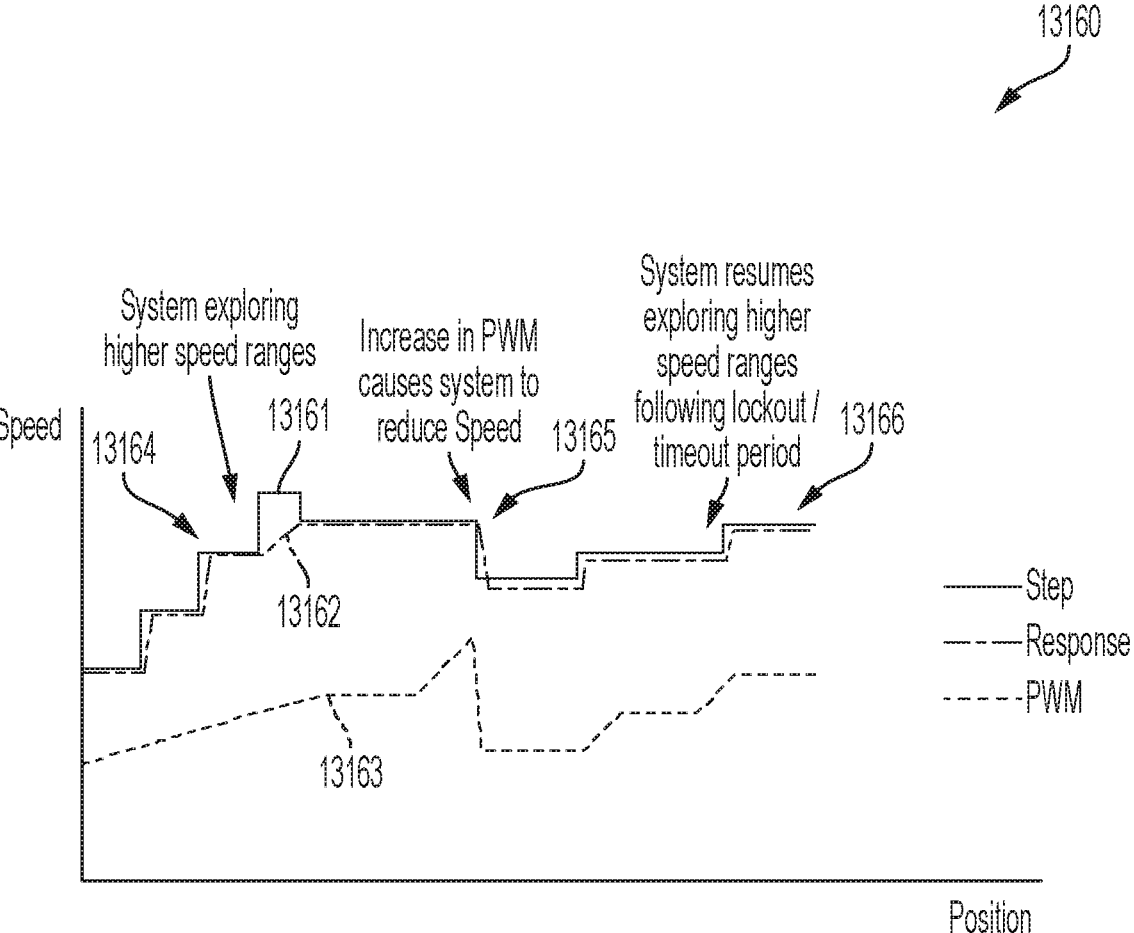
FIG. 77 is a graph depicting a firing stroke performed by a motor system including a motor, a drive train, and a motor control circuit, wherein the motor control circuit employs a speed control algorithm during the firing stroke, and wherein the speed control algorithm utilizes a lockout period upon satisfying a lockout condition.

FIG. 77 is a graph 13160 of an example staple firing stroke performed by a motor system illustrating target speed 13161, actual speed 13162, and pulse width modulation signal 13163 of a motor of the motor system. As can be seen in the graph 13160, the motor system performs sensory actions, or interrogation actions, 13164 in an attempt to increase the speed of the motor within a capacity limit of the motor system. The sensory actions 13164 end when the actual speed 13162 deviates from the target speed 1361 beyond a predetermined threshold, for example.

In at least one instance, the pulse width modulation signal 13163 is increased in an attempt to maintain motor speed through a thick section of tissue, for example. After traversing the thick section of tissue, the PWM signal 13163 is reduced causing a reduction 13165 in speed 13162. At such point, a time delay and/or a lockout period may be instituted by the motor system to prevent the motor system from initiating additional sensory actions, for example. After the time delay and/or the lockout period, the motor system may resume interrogating the relative capacity of the motor system in an effort to achieve an optimal efficiency speed. Such an arrangement may allow for locally optimal speed throughout the length of a staple firing stroke, for example. A cutting member, for example, may encounter a thicker section of tissue but only for a certain length of the staple firing stroke. The tissue may be thinner after the thicker section and, thus, capacity for increasing the speed of the firing stroke may increase after the cutting member passes the thicker section of tissue. At this point, the motor system can reinitiate an interrogation sequence in an effort to maximize the speed of the motor along the entire length of the staple firing stroke. In at least one instance, interrogation sequences initiated after a lockout or time delay is employed may vary in length of time and magnitude as compared to interrogation sequences which occurred prior to the lockout or time delay.

Figure 78:
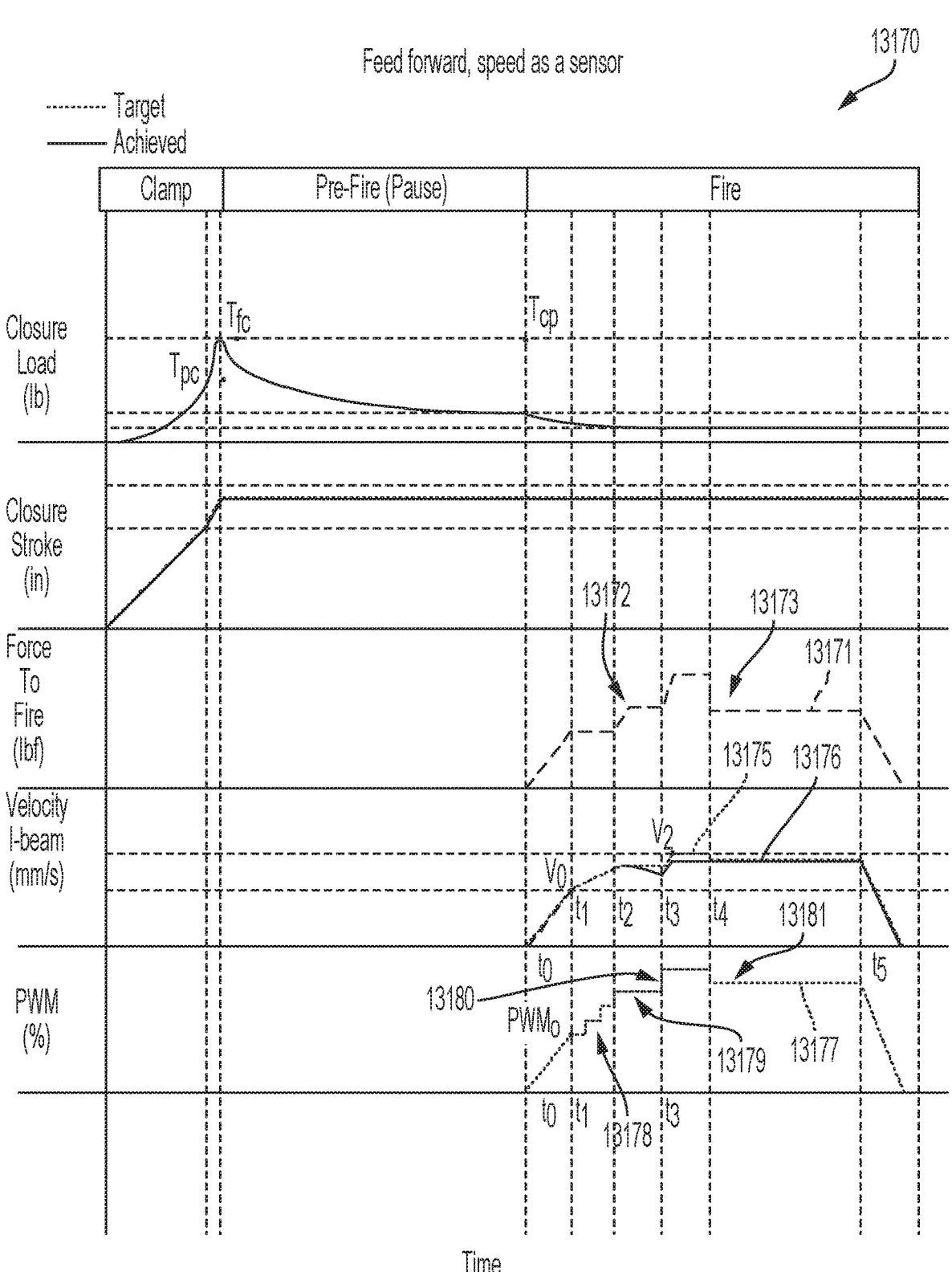
FIG. 78 is a graph depicting a firing stroke performed by a motor system including a motor, a drive train, and a motor control circuit, wherein the motor control circuit performs sensory actions and functional actions.

FIG. 78 is a graph 13170 of a staple firing stroke performed by a motor system including a motor and a firing member configured to be actuated by the motor. The closure load and closure stroke are illustrated. The force to fire 13171 the firing member is also illustrated. As can be seen by the force to fire 13171 plot, the force to fire the firing member increases 13172 between t1, t2, t3, and t4 and decreases 13173 at t4. The actual speed 13176 of the firing member as well as the target speed 13175 of the firing member are also depicted. In at least one instance, the actual speed includes the actual speed of the motor. Further to the above, the PWM percentage 13177 is also depicted. Between t1 and t2, the relative capacity of the motor system is interrogated by increasing the PWM percentage 13177 in discrete steps 13178 in an effort to achieve a set speed. The set speed is achieved at t2. During the time between t1 and t2, the actual speed 13176 of the firing member does not deviate from the target speed 13175.

At t2, the PWM percentage 13177 remains unchanged and the actual speed 13176 begins to deviate from the target speed 13175. At this point, the motor system tries to compensate to re-attain the set speed by sharply increasing the PWM percentage 13177. In at least one instance, the PWM percentage 13177 is unchanged 13179 between t2 and t3 because the actual speed 13176 started to deviate from the target speed 13175. As can also be seen in the graph 13170, the force to fire 13171 the firing member increases between t2 and t3 which may cause the deviation between the actual speed 13176 and the target speed 13175. In at least one instance, the increase in the force to fire can be due to a change in tissue thickness. At time t3, a functional action 13180 is taken by the motor control circuit where the PWM percentage 13177 is sharply increased in an effort to increase the speed 13176 of the motor and/or firing member, for example, back to the previously attained set target speed. Between time t3 and time t4, the speed 13176 of the firing member increases and, while the speed 13176 has not attained the new target speed 13175 of V2, the firing member has re-attained and surpassed the previously attained set speed. In at least one instance, not being able to attain the new speed of V2 is a result of yet another increase in firing force 13171 experienced by the firing member between t3 and t4. Because the target speed V2 is not attained but the previously attained set speed has been re-attained, the PWM percentage 13177 is slightly reduced 13181 (not reverted back to the PWM percentage 13177 utilized between t2 and t3) to achieve optimal efficiency and maintain the optimal speed. At time t4, the PWM percentage is reduced and can be triggered by the reduction in force to fire at t4. At time t4 to time t5, the actual speed 13176 and the target speed 13175 are equal or at least do not deviate beyond a threshold deviation, for example. At such point, the PWM percentage 13177 is held constant until the end of the staple firing stroke. In at least one instance, the set speed is modified during the staple firing stroke based on the response of the motor system to the sharp increase in duty cycle. In at least one instance, the set speed is decreased after the sharp increase in duty cycle. In at least on instance, the set speed is increased after the sharp increase in duty cycle.

In at least one instance, one or more predetermined shifting thresholds are utilized during a sensory action. For example, as the speed of a motor is increased in an effort to determine if there is available capacity to increase the speed of the motor, a relative capacity of the motor system can be defined as a quantifiable amount. For example, it may be determined that the motor system is operating at 50% capacity and has 50% available capacity. A first predetermined shifting threshold can be set at a first percentage of available capacity, for example, to set a threshold for determining that a target speed which is greater than an current speed can be set. Thus, as the speed of the motor is increased and the relative capacity of the motor system is determined, once it is determined that there is the first percentage of available capacity or more available, the motor control signal can be adjusted to shift the speed of the motor to an increased target speed. In at least one instance, the system performs another sensory action and, if there still exists the first percentage of available capacity or more, the speed of the motor is increased again. In at least one instance, an additional predetermined shifting threshold is set to determine when to shift the speed of the motor to a decreased new speed. For example, 5% available capacity can be set as a second predetermined shifting threshold. Thus, when 5% available capacity or less is detected, the motor control circuit can reduce the speed of the motor to the decreased new speed. As discussed herein, the percent deviation from the threshold values can be utilized to determine the magnitude of the new speeds. For example, if there exists 75% relative capacity in a system with a 25% first predetermined shifting threshold, the relatively large availability in capacity can cause the motor control circuit to increase the magnitude of the motor speed increase accordingly. On the other hand, if 0% capacity exists and/or the motor system is beyond maximum capacity (0%, for example), a large magnitude of speed decrease can be utilized to more appropriately adjust the motor toward an optimum operating speed, for example, in response to being at or beyond maximum motor capacity.

Figure 79:
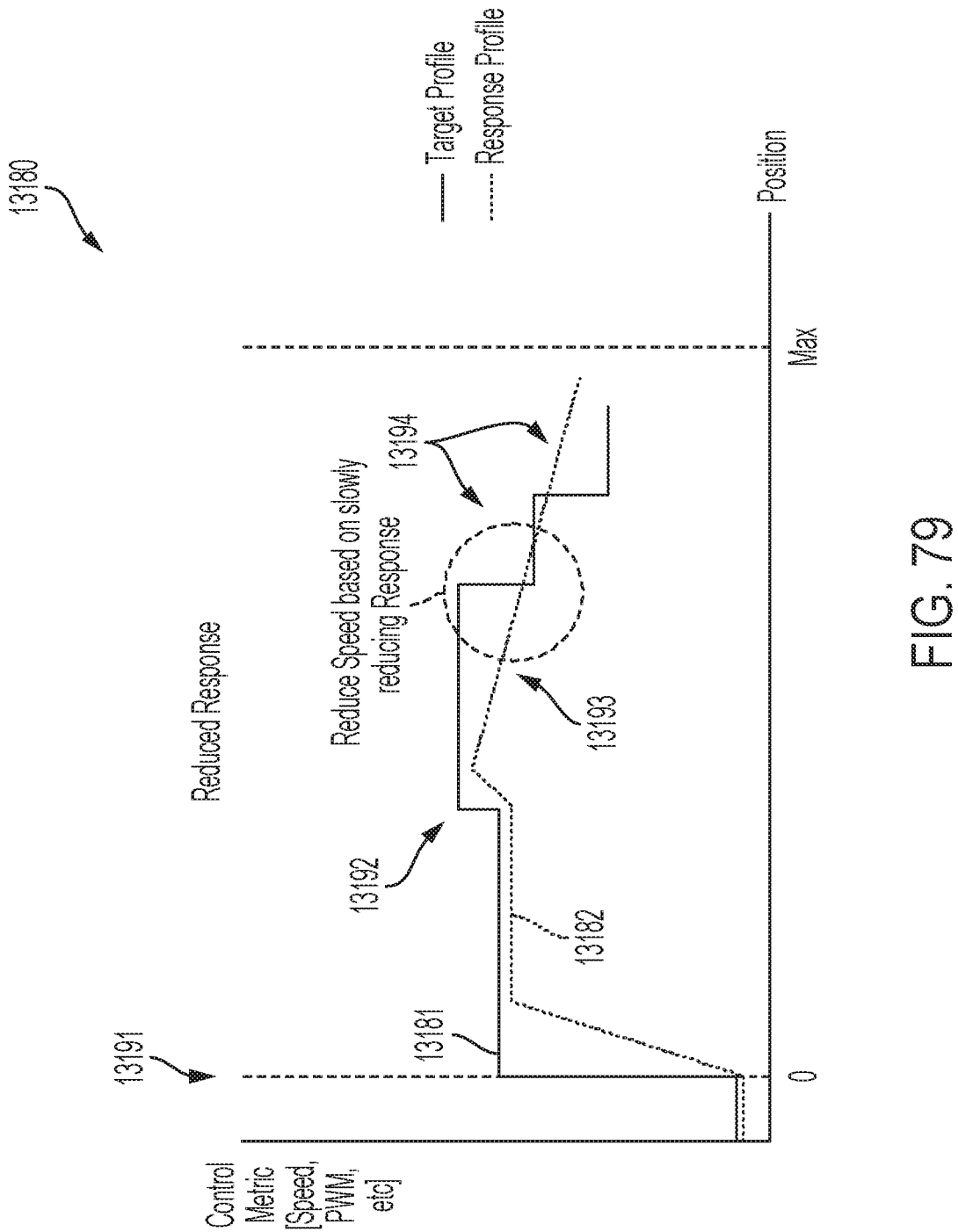
FIG. 79 is a graph depicting a firing stroke performed by a motor system including a motor, a drive train, and a motor control circuit, wherein the motor control circuit performs a sensory action and, in response to the monitored actual speed of the motor during the sensory action gradually declining, performs multiple functional actions to reduce the speed of the motor.

FIG. 79 is a graph 13180 of an example staple firing stroke performed by a motor system illustrating target speed 13181 and actual speed 13182. In at least one instance, the motor control circuit is configured to reduce the speed of the motor upon determining that a threshold deviation between the actual speed 13182 and the target speed 13181 is detected. In at least one instance, the rate at which the deviation between the actual speed 13182 and the target speed 13181 increases and/or decreases is monitored and, upon reaching a rate of change threshold (e.g. the actual speed 13182 is falling too quickly relative to the target speed 13181), speed adjustments are made through one or more reactions. As can be seen in the graph 13180, the motor system initiates 13191 the firing sequence and sets the target speed 13181 to a first target speed. At some point, the motor system then performs a sensory action 13192 by increasing the target speed 13181 of the motor to a second target speed for a specific time period during which the actual speed 13182 and/or percent deviation between the actual speed 13182 and second target speed is monitored. Upon determining that the actual speed 13182 falls below a predetermined threshold and/or upon determining that a threshold deviation between the actual speed 13182 and the target speed 13181 is reached or passed, a reduction reaction 13194 is initiated. As can be seen in the graph 13180 the actual speed 13182 gradually decreases 13193 after the second target speed is attempted. In at least one instance, the rate at which the actual speed 13182 decreases can trigger the reduction reaction. Nonetheless, the motor system reduces the target speed 13181 of the motor to one or more new reduced target speeds relative to the second target speed. In at least one instance, the target speed of the motor is reduced in steps. At such point, additional monitoring of the actual speed relative to the new target speeds can be performed so as to analyze the effect of the reduction reactions on the relative capacity of the motor and determine whether or not further adjustments are necessary.

Figure 80:
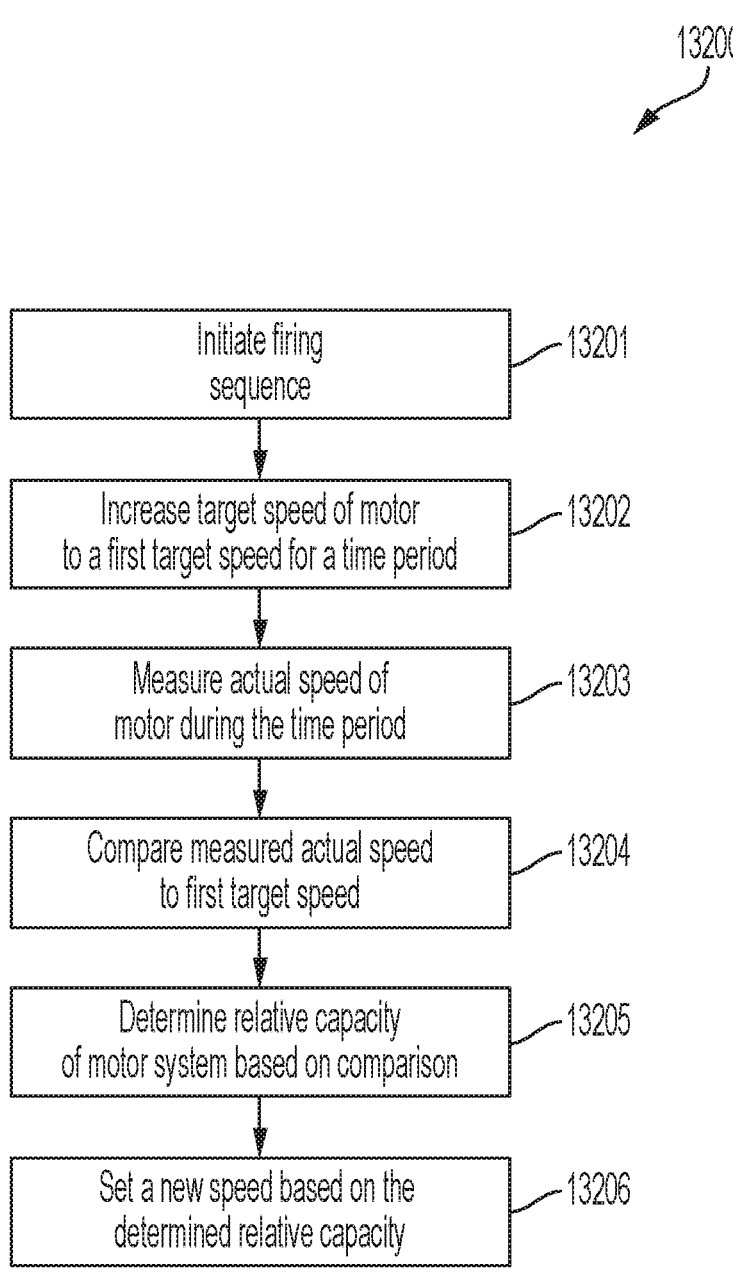
FIG. 80 is a logic flow chart depicting a process executable by a control circuit, wherein the process includes actions which interrogate a motor system to determine whether or not excess capacity exists within the motor system during a drive stroke of a drive train.

FIG. 80 is a logic flow chart depicting a process 13200 executable by a control circuit, such as the control circuit 1932 illustrated in FIG. 13 and/or the control circuit illustrated in FIG. 14, for example, configured to interrogate a motor system to determine whether or not excess capacity exists, for example, within the motor system during a firing sequence of a drive train. In this instance, the control circuit controls a firing sequence. The control circuit initiates 13201 the firing sequence, increases 13202 the target speed of the motor to a first target speed for a time period, measures 13203 the actual speed of the motor during the time period, compares 13204 the measured actual speed to the first target speed, determines 13205 the relative capacity of the motor system based on the comparison 13204, and sets 13206 a new speed based on the determined 13205 relative capacity. In at least one instance, the new speed is equal to the first target speed.

As discussed herein, a motor control circuit can perform the interrogation actions and/or reactions during a closure stroke and/or a firing stroke. The motor control circuit can also measure the speed of the motor in response to the increase in target speed during any suitable time period. The time period of each interrogation, or sensory, action may be predetermined and/or preselected. The time period of each interrogation action may vary from one interrogation action to the next. Comparing the target speed to the actual speed can involve analyzing the percent deviation between the target speed and the actual speed. In at least one instance, a fixed threshold speed is utilized to determine whether or not to perform additional interrogation actions or set a new speed. A pause can be utilized between interrogation actions. In at least one instance, no pause is utilized. In at least one instance, a pause may include a time period during which no interrogation actions are performed. In at least one instance, a pause may include a pause in motion of a firing member, for example, between interrogation actions. In at least one instance, the motor system automatically interrogates the relative capacity of the motor system during an entire stroke of the drive train in an effort to maximum the efficiency of the motor system throughout the entire stroke. In such an instance, a series of speed increases and decreases can occur throughout the stroke.

The control circuits disclosed herein can employ any of the steps and/or actions disclosed herein. The processes can be performed by any suitable components such as those disclosed in FIGS. 13 and 14. The processes disclosed herein can be performed utilizing any suitable drive train such as those disclosed herein in FIGS. 1-12, for example. The processes executable by a control circuit may include any suitable additional steps and/or actions, eliminate one or more steps and/or actions, and/or modify one or more of the steps and/or actions according to any of the scenarios discussed herein.

As discussed herein, a motor control circuit can be configured to perform any combination of and any number of sensory actions, interrogation actions, and/or functional actions, among others in an effort to control the speed, for example, of a motor of a motor system during a drive stroke of a drive train of the motor system. In at least one instance, these actions can be referred to as speed control actions. While speed is one variable capable of being controlled, adjusted, and/or monitored during these actions, any suitable variable can be used such as those disclosed herein, for example. In at least one instance, the outcome of each of these actions can be utilized to modify future actions and/or trigger other events, as discussed in greater detail below. Functional actions may be automatically triggered by one or more events and/or manually triggered by a user. For example, a user may manually trigger a speed increase during a drive stroke at which point a motor control circuit can be configured to increase the target speed of the motor and determine if the target speed can be and/or is achieved. Reactions to the manual increase in speed can include any suitable reactions such as those disclosed herein.

In at least one instance, further speed adaptations and/or speed control actions can be halted if one or more conditions are satisfied as a result of one or more previous actions. The outcomes, or results, of the previous actions can be constantly monitored. In at least one instance, the outcomes, or results, include whether or not the target speed of the previous action was achieved or the target speed was not achieved. Not achieving the target speed can be considered a failed action, for example. In at least one instance, the outcome, or result, includes whether or not the target speed of the previous action was achieved within a predefined deviation percentage, and/or the magnitude of failure and/or success of the previous action. In at least one instance, further actions can be halted temporarily and/or permanently, for example. In at least one instance, further actions to automatically control the speed of a motor can be automatically and/or manually re-activated. In at least one instance, further actions are automatically reactivated when a new firing stroke is initiated, for example.

In various instances, based on previous speed control action outcomes, or results, a motor control circuit can be configured to prevent further speed control actions from occurring whether triggered automatically and/or manually for a predetermined time period. In at least one instance, the motor control circuit is configured to prevent further speed control actions from occurring automatically but not manually or from occurring manually but not automatically.

Figure 81:
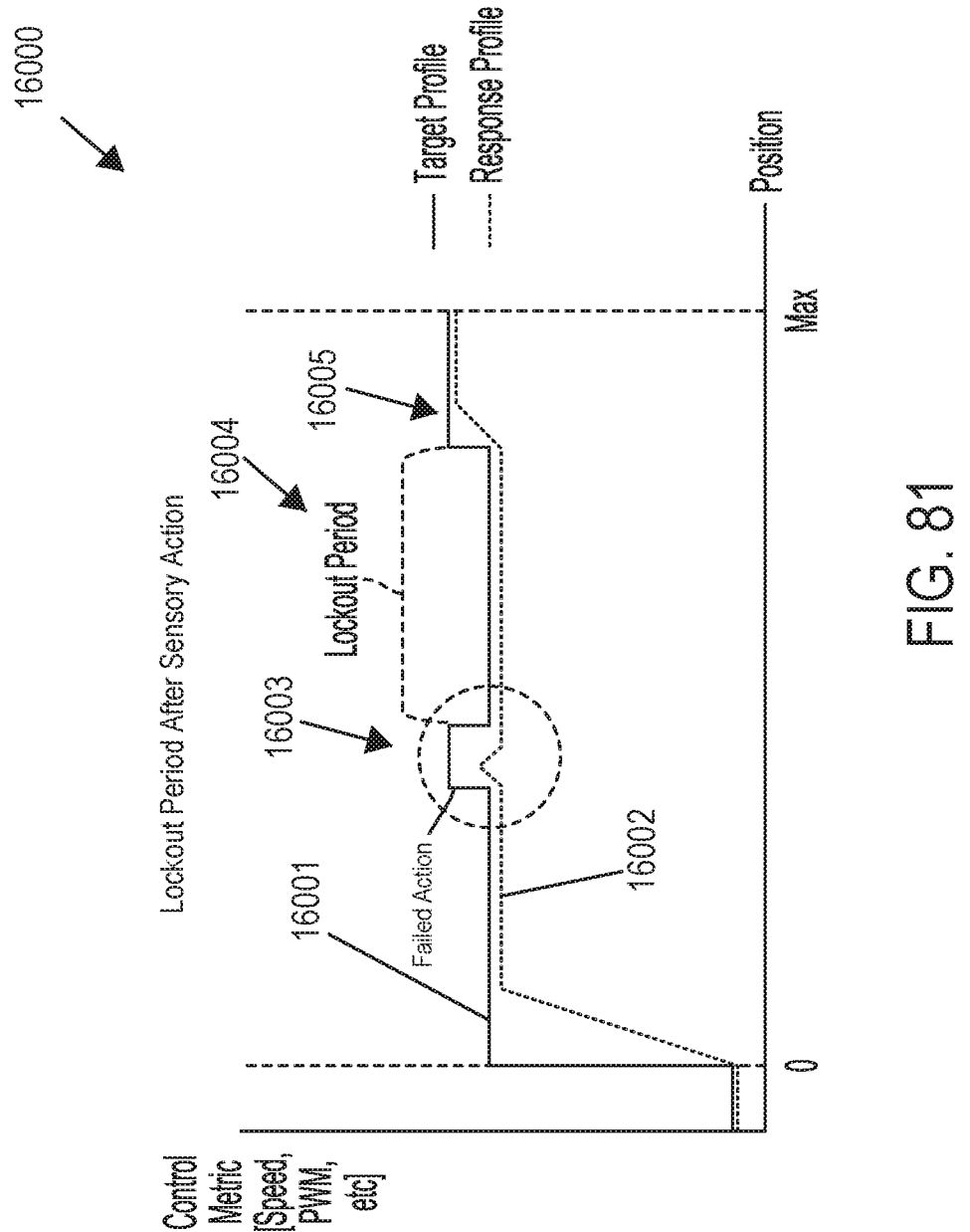
FIG. 81 is a graph depicting a firing stroke performed by a motor control circuit of a motor system, wherein the motor control circuit employs a lockout time period after a failed sensory action to prevent a subsequent action from occurring during the lockout time period.

Prevention of further speed control actions, or motor control adjustment actions, from occurring can protect from oscillation and/or hysteresis, for example, where without a pause, or lockout time period, after a previous action, a motor control circuit can incidentally perform undesirable adjustments based on a default control algorithm, for example. In at least one instance, a motor control circuit is configured to lockout any adjustment action from occurring during a lockout time period after a failed action occurs (a target speed was not achieved, for example). FIG. 81 depicts a graph 16000 depicting an example firing stroke performed by a motor control circuit of a motor system where target speed 16001 and actual monitored speed 16002 are illustrated. As can be seen in the graph 16000, the motor control circuit performs a sensory, or functional, action 16003 attempting to increase the speed of the motor to a new target speed 16001. The actual speed 16002 is monitored and it is determined that there is not capacity to run the motor system at the new target speed. The target speed 16001 is reverted back to the speed prior to the new target speed. As disclosed herein, the success of the sensory action can be referred to the actual speed reaching a desired percentage of the new target speed, for example. A failure of the sensory action can be referred to the actual speed not reaching a desired percentage of the new target speed. In at least one instance, a successful sensory action indicates that there exists excess capacity to permit the motor system to run at the new target speed. In at least one instance, a failed sensory action indicates there does not exist excess capacity to run the motor system at the new target speed.

As can be seen in FIG. 81, the motor control circuit employs a lockout time period 16004 configured to prevent any subsequent actions from occurring during the lockout time period 16004. In at least one instance, the lockout time period 16004 is predefined. In at least one instance, the magnitude of the lockout time period depends on one or more variables of the outcome of the previous failed sensory action. For example, if the magnitude of the previous sensory action fails by a large margin, the lockout time period may be longer as compared to if the sensory action fails by a smaller margin. The magnitude of the failure can be measured in percent deviation as discussed herein. Deviation thresholds can be utilized to determine the length of the lockout time period. After the lockout time period, one or more additional actions 16005 can be performed. In at least one instance, the number of additional actions which can be performed and/or the magnitude of the additional actions which can be performed is limited based on the failed sensory action where, if no failed sensory action occurred, additional actions may not be limited in any way. In at least one instance, additional actions are not limited regardless of the occurrence of a failed sensory action, for example.

In at least one instance, the length of the timeout, or lockout time period, depends on a current speed of the motor. For example, the magnitude of the current speed of the motor can be used to determine the magnitude of the lockout time period. In at least one instance, a faster speed triggers a longer timeout period whereas a slower speed triggers a shorter lockout time period. In at least one instance, a faster speed triggers a shorter timeout period and a slower speed triggers a longer lockout time. In various instances, the success status of one or more previous speed control actions triggers different length timeout periods. For example, a lockout period may be employed during a drive stroke for a successful speed control action and an unsuccessful, or failed, speed control action. In such an instance, the lockout time period may be shorter for the successful speed control action as compared to the lockout time for failed speed control action.

In at least one instance, a prevention, or lockout time period, can prevent inadvertent re-shifting immediately after the motor control circuit intentionally performs a functional action. For example, a user can choose to increase the speed of a motor from a first speed to a second speed. The motor control circuit may determine that the second speed was not achieved. However, instead of reverting back to the first speed, the motor control circuit can employ a lockout time period as result of the manual input change of speed so as not to automatically undo the speed change desired by the user, for example. In at least one instance, the motor control circuit is configured to undo the user desired speed change regardless of the fact that the user manually inputted the speed change. In at least one instance, further intentional manual speed change inputs are prohibited during the lockout time period.

In at least one instance, a motor control circuit is configured to disable automatic speed control after a predetermined number of lockout time periods are triggered during a firing stroke. Such an arrangement can prevent a motor system from continuously being adjusted when a certain adjustment constantly results in a failed action.

In at least one instance, a lockout distance period is employed by a motor control circuit. For example, after a failed action occurs, the motor control circuit is configured to prevent any speed control action from occurring during a predefined distance of a drive stroke. In other words, when the firing member is determined to be within a lockout zone between position A and position B, for example, further adjustment actions are prohibited. For example, the motor control circuit can prevent any speed control actions, or adjustments, from occurring for the following 10 mm after the previous failed action is complete. The magnitude of the lockout distance may vary based on the magnitude of the failed action, for example. For example, if the actual speed of the motor deviates from the target speed above a threshold deviation percentage, the lockout distance can be set at a first distance. If the actual speed of the motor deviates from the target speed below a threshold deviation percentage but still fails, the lockout distance can be set at a second distance which is less than the first distance. In at least one instance, the second distance is half of the first distance.

In at least one instance, speed adjustment actions are prohibited from occurring prior to the staple firing stroke. In at least one instance, speed adjustment actions are prohibited from occurring between an unfired position of a firing member and a defeated lockout position of the firing member. The defeated lockout position may be the position at and/or just after the firing member has passed a lockout of a surgical stapling instrument such as, for example, a no cartridge lockout and/or a spent cartridge lockout. In at least one instance, speed adjustments are prohibited from occurring when the firing member is positioned within a zone immediately preceding an end of the staple firing stroke and/or the end of the staple cartridge.

Firing members discussed herein may refer to any suitable component such as, for example, any combination of an I-beam of a firing shaft and/or any portion thereof, a sled configured to eject staples from a staple cartridge and/or any portion thereof, a firing shaft and/or any portion thereof, a firing rod and/or any portion thereof, and/or any portion of a firing drive train.

In at least one instance, the average actual speed monitored during the time period of the sensory, functional, and/or interrogation action can be utilized to determine if the target speed is achieved or not achieved. In at least one instance, the maximum actual speed monitored during the time period of the sensory, functional, and/or interrogation action can be utilized to determine if the target speed is achieved or not achieved. In at least one instance, the minimum actual speed monitored during the time period of the sensory, functional, and/or interrogation action can be utilized to determine if the target speed is achieved or not achieved. In at least one instance, any combination of the aforementioned metrics can be utilized to determine if the target speed is achieved or not achieved. Predetermined deviation percentages can be stored in a memory and can be accessed when determining if the target speed is achieved or not achieved. Predetermined deviation percentages can change for different types, such as length and/or staple height, for example, of staple cartridges being fired.

In various instances, a motor control circuit is configured to halt, or prohibit, motor control parameter adjustments (such as PID controller parameters, for example) during the lockout time periods and/or lockout distance. In at least one instance, PID controller parameter adjustments could be frozen for a period of time which is the same as or different than the predefined lockout time period. In at least one instance, the thresholds and/or conditions required to be met by the motor control circuit to change one or more of the PID controller parameters during a drive stroke can be widened or softened, for example, to minimize the number of noticeable, or perceptible, re-adjustments of speed after a failed action. For example, a greater error may be required in order to trigger an adjustment of one or more PID controller parameters after a failed action than an error required in order to trigger an adjustment prior to the failed action.

In various instances, the motor control circuit is configured to learn over time and adjust future speed control actions of future drive strokes according to previous drive stroke data. In at least one instance, certain outputs monitored during a drive stroke can be utilized to identify opportunities to update feedforward network weights. The network weights can include thresholds. The thresholds can indicate an out of bounds condition.

In at least one instance, a motor control circuit is configured to revert the motor system back to a last known good state. This can be triggered by a failed action, for example. In at least one instance, the last known good state includes a state where the motor system was running adequately and not near and/or at full capacity.

In at least one instance, a motor control circuit is configured to perform speed control actions during firing member advancement and/or firing member retraction.

In various instances, a motor control circuit is configured to alter a speed control algorithm in response to a cumulative sequence of events and/or triggers, for example. In at least one instance, a predetermined number of failed actions have to occur, failed actions have to occur at a predetermined frequency, and/or a predetermined plurality of failed actions have to fail by a certain percentage before the motor control circuit reacts. Any suitable reaction can occur such as those disclosed herein. For example, parameters of further actions can be adjusted, lockout time periods and/or lockout zones can be employed, PID motor controller parameters can be adjusted etc. In at least one instance, both a sequence of events must occur in addition to a predetermined single event to cause the motor control circuit to react. Such an arrangement can provide greater situation-specific control of a motor system during a firing stroke. For example, during a firing stroke, a predetermined plurality of sensory actions may fail. While this alone will not trigger further action, this in combination with a single event such as, for example, a single sensory action fails below a certain threshold, may trigger a cool down period or a pause. The sequence of failed actions in addition to the larger failed action may indicate that the motor was struggling to perform the firing stroke to begin with and, at the detection of the larger failed action, indicated to the motor control circuit that the motor may have been overheating and/or operating beyond its maximum, or optimal, capacity. The automatic activation of a cool down period can allow tissue to relax as well as the motor to cool down, for example.

In various instances, a motor control circuit is configured to utilize events of previous firings of an instrument to adjust and/or alter speed control algorithms of a subsequent firing. For example, a first cartridge may be used with an instrument and, during the firing of the first cartridge, data collected about the outcomes of various speed control actions, for example, performed during the firing stroke of the first cartridge. The motor control circuit can then be configured to adjust one or more parameters of the firing stroke of a second cartridge to be fired based on the data collected about the outcomes of the various speed control actions performed during firing of the first cartridge. Such an arrangement can allow a motor control circuit of a specific motor system to be more efficiently operated between multiple different staple cartridges by monitoring events of each cartridge firing and optimizing each subsequent firing based on the performance of previous firings.

One example of a motor control circuit utilizing data from multiple different firings as discussed herein is discussed below. A motor system of a surgical instrument fires two different staple cartridges. At the 50 mm position the motor control circuit detects an irregularity in the firing stroke. In at least one instance, there is a speed discrepancy detected at the 50 mm mark. In at least one instance, there is a displacement discrepancy detected between the motor and the firing member at the 50 mm mark. The motor control circuit is configured to adjust any subsequent firing of another staple cartridge to increase the speed of the motor prior to the 50 mm mark such as, for example, at the 45 mm mark. Such an increase in speed can ensure that for any subsequent firing with that instrument that the motor system does not lag and/or compensates for the known, recurring, irregularity at the 50 mm mark of that instrument. In at least one instance, the motor control circuit is configured to perform a speed burst at and/or near the 50 mm mark. In at least one instance, the motor control circuit is configured to pulse an additional burst of power to the motor just before the 50 mm mark and only for a short period of time. In at least one instance, the motor control circuit is configured to adjust a speed control algorithm of subsequent firings in an effort to maintain a constant speed through the 50 mm mark and eliminate the irregular stroke. Such a configuration can overcome recurring stroke irregularities between firings which may distract a user, cause abnormal cutting of tissue, and/or unpredictable staple formation.

In various instances, a predetermined level of repeatability threshold must be met before speed control adjustments are made to subsequent firing strokes. For example, a motor control circuit can determine a stroke irregularity, or anomaly, at a 30 mm mark during both an advancement stroke and a retraction stroke. This may indicate a location where interfacing components (such as I-beam and channel and/or anvil, for example) have a tighter interference. Such a tighter interference can be caused by tissue ingress and/or a manufacturing anomaly, for example, which are increasing forces to fire at this location. Because of this stroke irregularity, staple formation and/or tissue cutting may not be as predictable. In at least one instance, a motor control circuit adjusts parameters for all subsequent strokes at this location to reduce the force to fire at this location in an effort to more predictably form staples and/or cut tissue, for example. In at least one instance, the adjusted parameters could be reverted back to normal after passing this location; either during advancement and/or during retraction, for example. In at least one instance, the motor control circuit is configured to anticipate the previously detected stroke irregularity during subsequent strokes by adjusting parameters of subsequent strokes to specifically look for the stroke irregularity but not taking any action unless the newly monitored irregularity is detected. In at least one instance, spikes in force are monitored and associated with stroke irregularities.

In various instances, a sequence of stroke irregularities are detectable and acted upon to adjust motor control of a drive stroke. For example, a motor control circuit can detect a plurality of force spikes within the motor system each time a staple leg contacts an anvil to be formed. In at least one instance, this initial contact can cause the largest spike in the motor system within the staple formation process which can be detectable and stand out in a plurality of force spikes of a firing stroke. This spike can be detected by the motor control circuit as being the highest peak force during the formation of each staple each of which include a known location relative to the firing stroke. In at least one instance, if the spike detected for a staple, or a plurality of staples (sequence of stroke irregularities), exceeds a predetermined threshold, or predetermined threshold profile, the motor control circuit can perform one or more speed control actions to reduce the spike in force for each leg-anvil contact event. In at least one instance, the spike exceeding a threshold during initial leg-anvil contact could indicate that the leg is not hitting the anvil in an anticipated and/or desired location. Such a spike could indicate that tissue is being bunched up by the knife and pushing the staple legs distally relative to the anvil causing the tips of the staples to miss target pocket locations and, as a result, increasing the force to fire the staples and, also, causing staple malformation, for example. Reducing the speed of the motor to increase the likelihood of the tips of the staples contacting their intended target location can reduce the force to fire and increase the likelihood of proper staple formation.

In at least one instance, a motor control circuit is configured to monitor the number of failed/successful speed control actions and, once a predetermined number of failed/successful speed control actions occur, adjust a magnitude of subsequent speed control actions. For example, a motor control circuit can place a limit on target speeds of subsequent speed control actions when a predetermined number of failed actions occur. In at least one instance, a user can try to increase the speed of the motor by a certain amount; however, the motor control circuit can set a target speed threshold which cannot be surpassed automatically and/or manually, for example. If the user tries to increase the speed of the motor beyond the target speed threshold which is a limit triggered by a sequence of prior failed speed control actions, the motor control circuit can automatically adjust the actual target speed down to the threshold target speed and attempt to increase the speed of the motor to the threshold target speed. In at least one instance, such a configuration can prevent a user and/or a motor control circuit from increasing the speed of an already struggling motor beyond a certain threshold based on a plurality of previously failed speed increase actions, for example. In at least one instance, after a predetermined plurality of successful speed control actions performed with the newly set limit threshold target speed, the limit threshold target speed can be removed, or lifted. In at least one instance, the limit threshold target speed cannot be lifted and/or removed until a new staple cartridge is installed and/or a new firing stroke is performed. In at least one instance, the limit threshold target speed is never lifted for that surgical instrument.

In various instances, a motor control circuit is configured to monitor a pattern of outcomes of speed control actions and based on the pattern, make adjustments to one or more future speed control actions based on the monitored pattern. For example, during a first firing, a plurality of failed actions can occur. If the degree of failure increases for each subsequent failed action to correspond to a predetermined pattern of increased failure, the motor control circuit can detect the predetermined pattern of increased failure and adjust subsequent firings accordingly. In at least one instance, magnitudes and/or frequency of speed control actions of subsequent firings are adjusted. In at least one instance, the motor control circuit is configured to place a limit on the number of subsequent firings permitted of the surgical instrument based on the detected predetermined pattern of increased failure. In at least one instance, a lockout time period is employed and the magnitude, or length, of the lockout time period can be increased based on the detected predetermined pattern of increased failure. Such a configuration can provide an amount of time for the motor system to reduce its power use and/or mechanical energy burden.

In various instances, a motor control circuit is configured to adjust the frequency of subsequent sensory actions based on detecting a predetermined, cumulative, amount of sensory action failures. For example, after detecting the predetermined amount of sensory action failures, the motor control circuit can reduce the frequency at which speed control adjustments are automatically and/or manually made for the rest of the firing and/or subsequent firings. In at least one instance, the motor control circuit is configured to adjust the definition of a failed action for subsequent firings or the rest of a firing based on detecting a predetermined, cumulative, amount of sensory action failures. For example, the motor control circuit can increase the threshold required to be considered a successful sensory action, for example.

Figure 82:
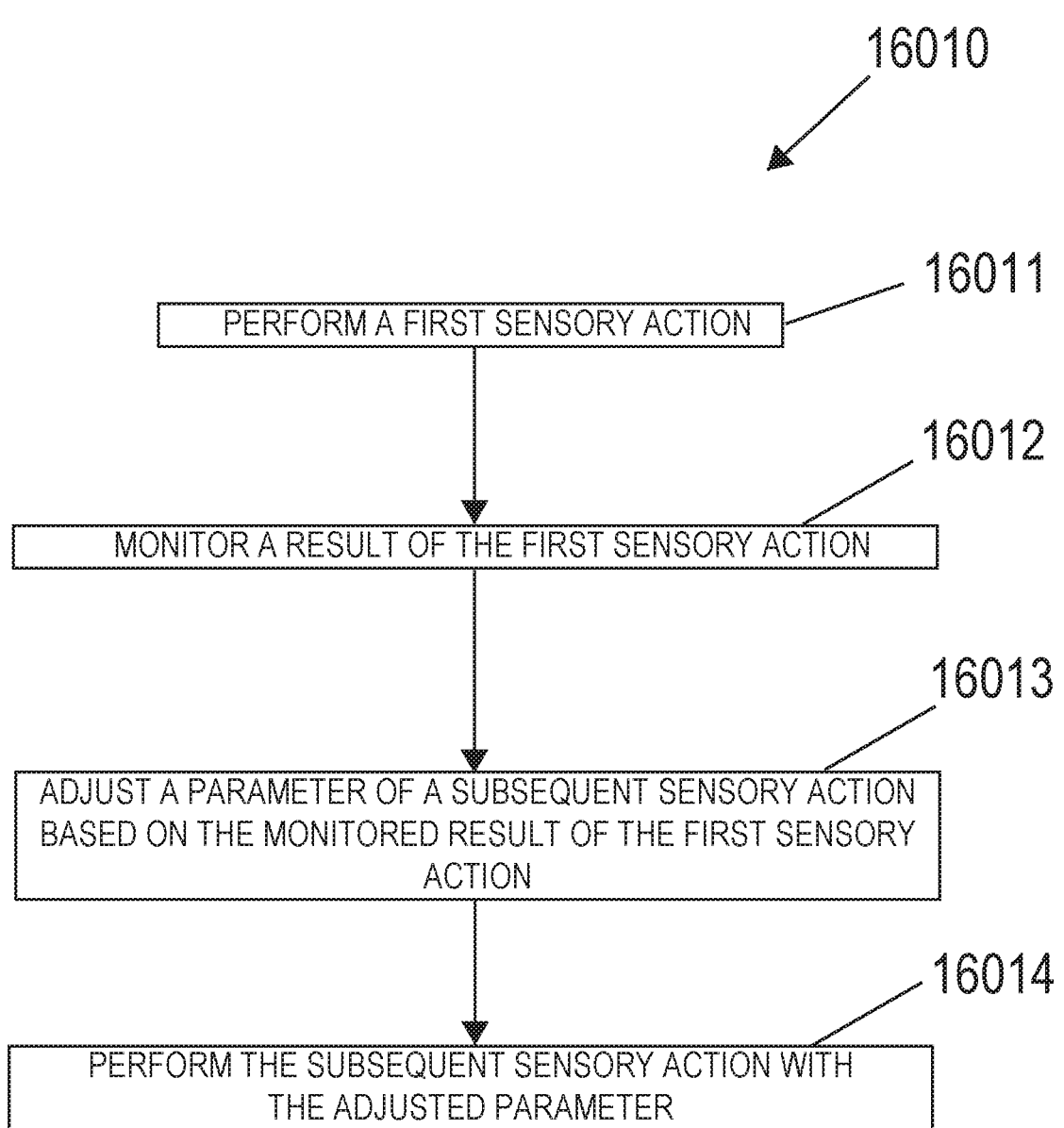
FIG. 82 is a logic flow chart depicting a process executable by a control circuit for use in a surgical instrument system, wherein the control circuit is configured to adjust a parameter of a subsequent sensory action, wherein the adjustment is based on a monitored result of a first sensory action.

FIG. 82 is a logic flow chart depicting a process 16010 executable by a motor control circuit, such as the control circuit 1932 illustrated in FIG. 13 and/or the control circuit illustrated in FIG. 14, for example, for use in a surgical instrument system such as those disclosed herein. The motor control circuit is configured to perform 16011 a first sensory action. In at least one instance, the first sensory action is performed during a staple firing stroke. The sensory action may be manually initiated and/or automatically initiated. In at least one instance, the sensory action is performed in an attempt to increase the speed of the motor. The motor control circuit is configured to monitor 16012 the result of the first sensory action. In at least one instance, the monitored result can include any suitable outcome, or response, of the surgical system as a result of the first sensory action. In at least one instance, the monitored result includes a success status of the first sensory action and/or a percent deviation between a target speed relative to an actual speed of the motor, for example. The motor control circuit is further configured to adjust, or modify, 16013 a parameter of a subsequent sensory action based on the monitored result of the first sensory action. Any suitable parameter can be adjusted such as, for example, the timing of the subsequent sensory action (length of the action, when the action occurs relative to the stroke, etc.), the target of the subsequent sensory action (target speed, target displacement, etc.), and/or the existence of the subsequent sensory action (perform the subsequent sensory action vs. do not perform the subsequent sensory action). The motor control circuit is further configured to perform 16014 the subsequent sensory action with the adjusted parameter. In at least one instance, the subsequent sensory action is performed during the current stroke. In at least one instance, the subsequent sensory action is performed during a subsequent stroke of the surgical instrument system.

FIG. 83 is a logic flow chart depicting a process 16020 executable by a motor control circuit, such as the control circuit 1932 illustrated in FIG. 13 and/or the control circuit illustrated in FIG. 14, for example, for use in a surgical instrument system such as those described herein. The motor control circuit is configured to actuate 16021 a firing member through a first staple firing stroke, perform 16022 a first sensory action during the first staple firing stroke, and monitor 16023 a result of the first sensory action. The motor control circuit is further configured to actuate 16024 the firing member through a second staple firing stroke, adjust 16025 a parameter of a second sensory action based on the monitored result of the first sensory action, and actuate 16026 the firing member through the second staple firing stroke. The motor control circuit is further configured to perform 16027 the subsequent sensory action with the adjusted parameter during the second staple firing stroke.

Figure 84:
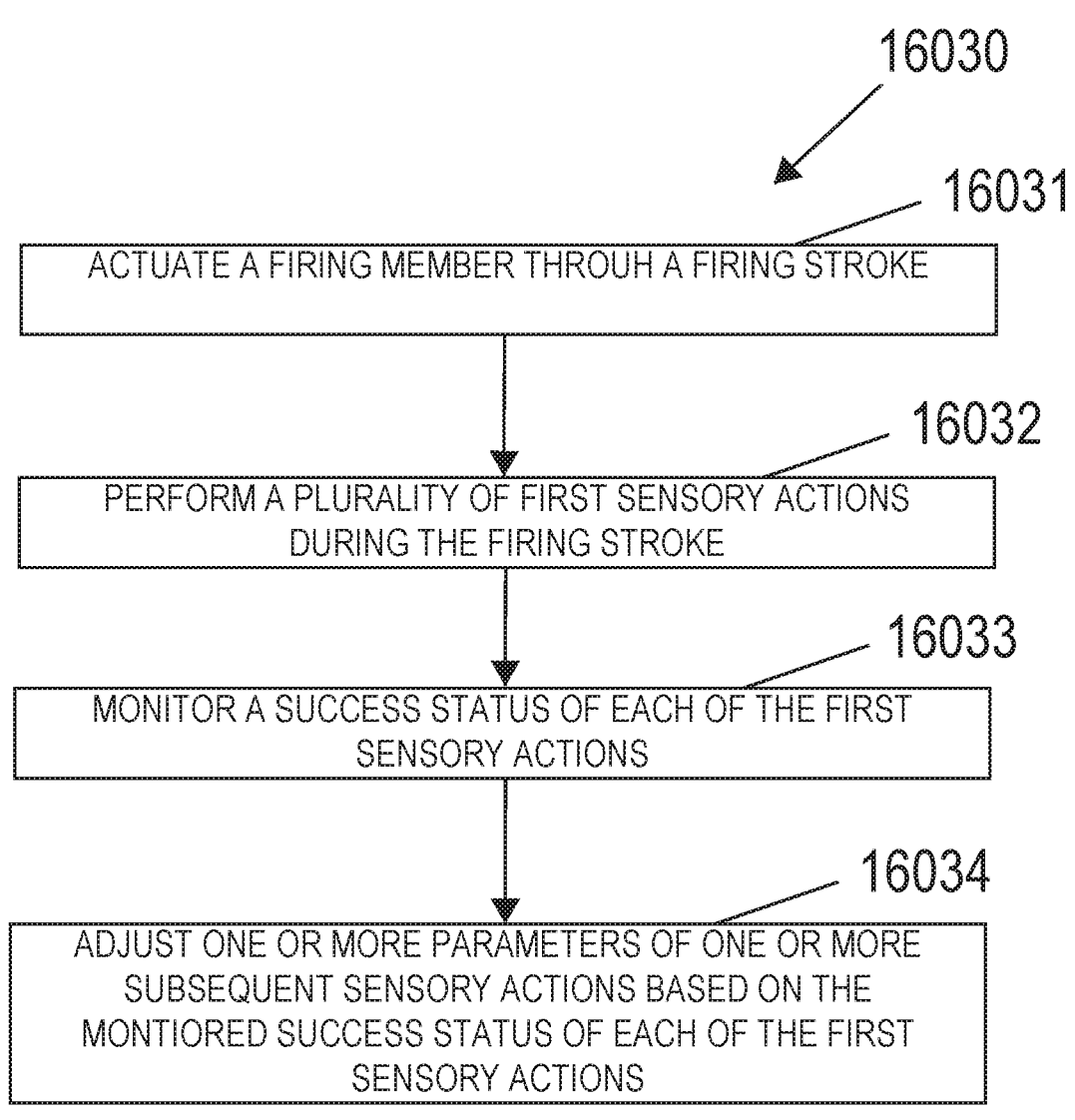
FIG. 84 is a logic flow chart depicting a process executable by control circuit for use in a surgical instrument system, wherein the control circuit is configured to adjust a parameter of one or more subsequent sensory actions, wherein the adjustment is based on a monitored success status of one or more first sensory actions.

FIG. 84 is a logic flow chart depicting a process 16030 executable by a motor control circuit, such as the control circuit 1932 illustrated in FIG. 13 and/or the control circuit illustrated in FIG. 14, for example, for use in a surgical instrument system such as those described herein. The motor control circuit is configured to actuate 16031 a firing member through a firing stroke, perform 16032 a plurality of first sensory actions during the firing stroke, and monitor 16033 a success status of each of the first sensory actions. The motor control circuit is further configured to adjust 16034 one or more parameters of one or more subsequent sensory actions based on the monitored success status of each of the first sensory actions. In at least one instance, adjustments are based on how many previous sensory actions failed as compared to succeeded. In at least one instance, the control circuit is further configured to adjust the parameter according to a first adjustment profile upon monitoring a threshold number of successful first sensory actions. In at least one instance, the threshold number can be automatically determined and/or manually set.

In various instances, a motor control circuit is utilized to control a motor of a motor system including a drive train such as, for example, a firing drive train. In at least one instance, the motor control circuit is operable within a set of adjustable parameters. For example, the motor control circuit may set a minimum speed threshold at a first speed and a maximum speed threshold at a second speed which is greater than the first speed to begin a staple firing stroke. These threshold speeds, for example, can be adjusted and/or fine-tuned during the staple firing stroke of the motor system to optimize operation of the motor system and/or maximize the efficiency of the motor system within a single drive stroke in real-time. Various factors such as, for example, drive train backlash and/or heat loss within the motor can cause the motor system to run less efficiently. However, adjusting the adjustable parameters during the staple firing stroke can account, mitigate, and/or compensate for things like drive train backlash and/or heat loss within the motor, for example. The magnitude of the adjustment made to these threshold speeds can be based on a variety of factors. For instance, any suitable parameter or combination of parameters of the motor system can be monitored. In such an instance, a new threshold speed can be determined based on the magnitude of the monitored parameter and/or the rate at which the monitored parameter changes over a period time, for example. In at least one instance, multiple monitored parameters are compared and analyzed to determine an appropriate adjustment to the adjustable parameters.

In at least one instance, a maximum motor current limit is set by a motor control circuit to limit the amount of current drawn by the motor to a predetermined threshold current. In at least one instance, the predetermined threshold current can be changed in different portions of a drive stroke such as, for example, a staple firing stroke. For example, a first portion of the stroke can include a first threshold current limit and a second portion of the stroke can include a second threshold current limit which is different than the first threshold current limit. In at least one instance, a lower current limit threshold is utilized in the beginning of a drive stroke where a drive member may encounter a lockout condition so as to prevent a relative large amount of current draw during a lockout condition which is detectable based on a small uptick in current and, thus does not need large amounts of current that can unnecessarily overstress the system, for example. Such an arrangement may provide some protection to the drive train through the beginning of a firing stroke. In at least one instance, a threshold current limit for the retraction stroke of a drive member is set relatively high as compared to a threshold current limit set for an advancement part of the stroke so as to ensure the motor can retract the drive member, even if the threshold current limit was met during the advancement part of the stroke. This can be as result of having a threshold current limit for the retraction stroke which is always greater than a maximum threshold current limit for the advancement stroke. In at least one instance, if the drive member cannot retract fully, the jaws of an end effector may be stuck clamped.

Figure 85:
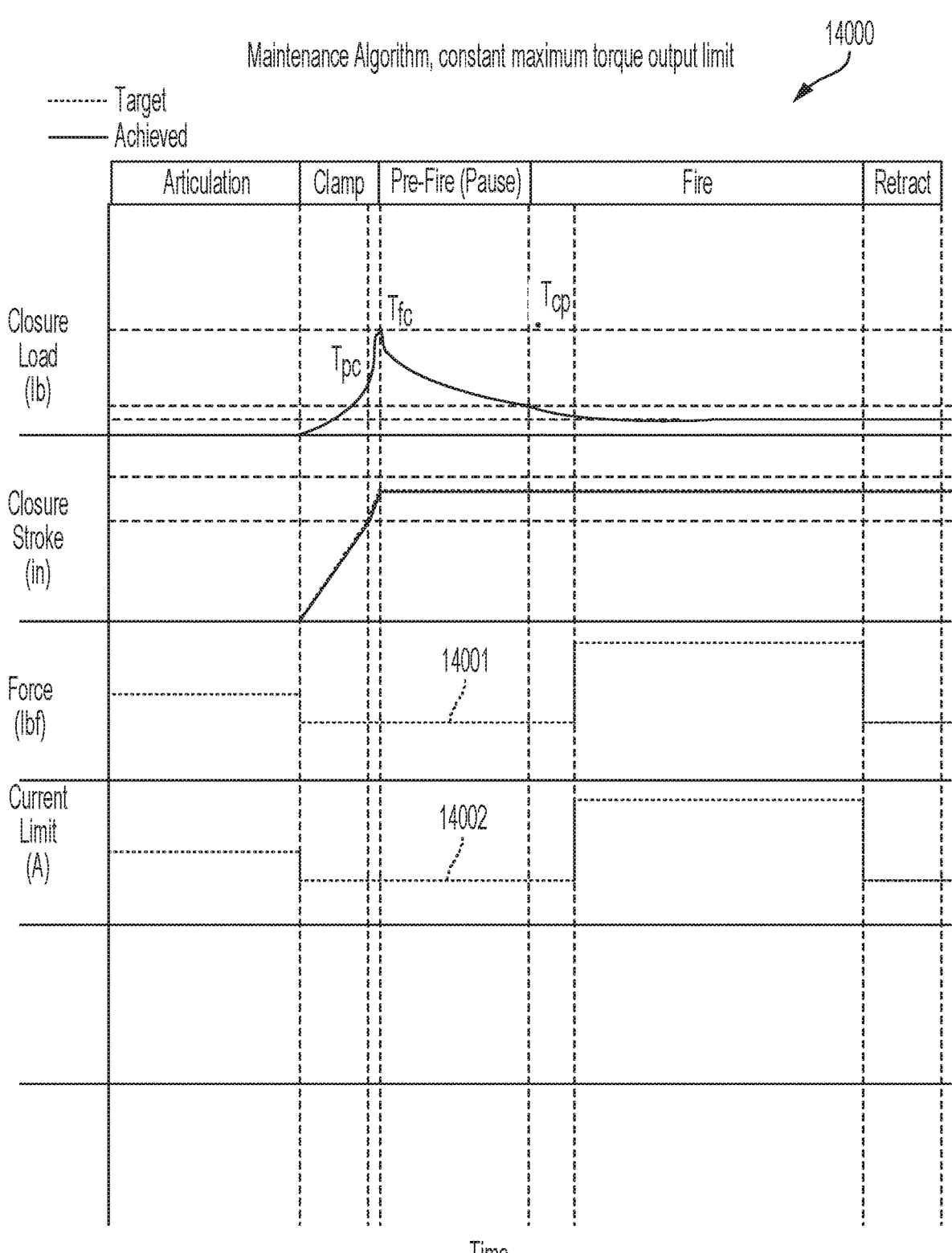
FIG. 85 is a graph depicting a firing stroke performed by a motor system including a motor, a drive train, and a motor control circuit, wherein the motor control circuit is configured to set maximum torque output limits during different periods of the firing stroke.

FIG. 85 is a graph 14000 depicting various parameters of a motor control algorithm executable by a control circuit of a staple firing stroke. The graph 14000 illustrates motor torque limits 14001 and motor current limits 14002 during various stages of use of a surgical instrument system. As can be seen in the graph 14000, the torque limits 14001 and current limits 14002 vary through different portions of the drive stroke. In at least one instance, the torque limit 14001 and the current limit 14002 peak during the staple firing stroke portion of the drive stroke. As discussed herein, the limits 14001, 14002 can be adjusted during the drive stroke based on at least one monitored parameter and at a variety of different times throughout the drive stroke to fine-tune the limits 14001, 14002 in real time during the drive stroke.

Figure 86:
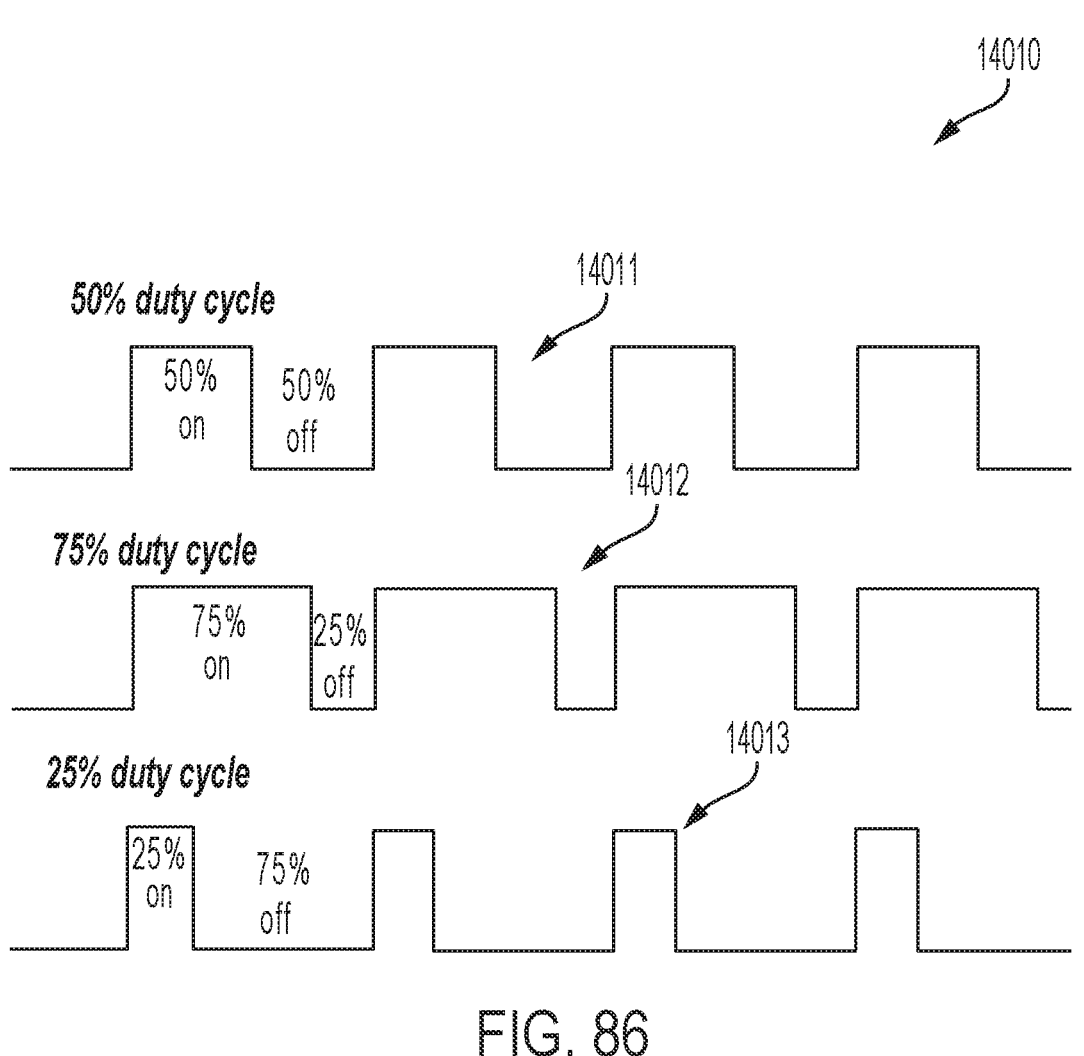
FIG. 86 is a schematic representation of different motor duty cycles for a motor of a surgical instrument.

In various instances, duty cycle ranges of pulse width modulation (PWM) motor control are set by a motor control circuit. In at least one instance, the motor duty cycle ranges are adjusted during a drive stroke based on one or more monitored parameters. FIG. 86 illustrates a plurality of motor duty cycles 14010. In at least one instance, a motor control circuit employs a 25% minimum duty cycle 14013 so that the motor runs with at least a 25% duty cycle and the motor control circuit employs a 75% optimal duty cycle 14012 so that the motor does not run beyond a 75% duty cycle. If the motor control circuit attempts to adjust the speed of the motor, for example, which would cause the motor duty cycle to surpass 75%, the motor control circuit would determine that the 75% duty cycle threshold would be met and/or exceeded and thus the adjustment would not be made and/or a magnitude of the adjustment is altered so that the adjustment would not cause the 75% duty cycle threshold to be met and/or exceeded. An optimal duty cycle 14011 may include 50%, for example. In at least one instance, the motor control circuit is configured to base any speed adjustments based on the optimal duty cycle 14011. Adjustment of PWM duty cycles as disclosed herein can be referred to as PWM speed control.

In various instances, a motor performance curve of the motor is utilized to determine an optimal duty cycle range. In at least one instance, the motor performance curve of the motor is utilized to set a maximum duty cycle threshold and a minimum duty cycle threshold. The motor performance curve can be used to determine the most efficient range of duty cycles. In at least one instance, the minimum duty cycle limit is set based on frictional losses and/or inertial properties of the drive train in an effort to eliminate jerkiness, oscillation, and/or vibration of the motor system. In at least one instance, the maximum duty cycle limit is set based on heat generation of the motor. Further to the above, an older motor may generate more heat over time. In such an instance, the maximum duty cycle limit is adjusted for the increased heat generation owing to the age and/or overall life of the motor, or motor performance degradation over time, for example. Setting the maximum duty cycle limit in such a manner can consistently minimize heat generation in the motor between strokes and/or even during a single stroke, for example. In at least one instance, an ideal range of duty cycle limits includes a maximum duty cycle limit of about 85% and a minimum duty cycle limit of about 25%. In at least one instance, a maximum range of duty limit includes a maximum duty cycle limit of about 90% and a minimum duty cycle limit of about 10%.

In at least one instance, a motor stall condition is set and, once detected, a control circuit can turn off the motor after a predetermined amount of non-moving torque application. For example, if the firing member encounters a piece of tissue which is so thick that the firing member stops moving, the predetermined amount of non-moving torque can be exceeded, which causes the control circuit to cause the motor to shut down reducing inadvertent heat generation upon meeting the motor stall condition.

In at least one instance, motor duty cycle and/or displacement are used to adapt and/or select target motor speeds. For example, a decreased target motor speed may be triggered in an instance where the motor duty cycle is relatively high in percentage and/or magnitude in an attempt to reduce the percentage and/or magnitude of the motor duty cycle. Similarly, an increased target speed may be triggered in an instance where the motor duty cycle is relatively low in percentage and/or magnitude in attempt to increase the utilization of the motor system, for example.

Figure 87:
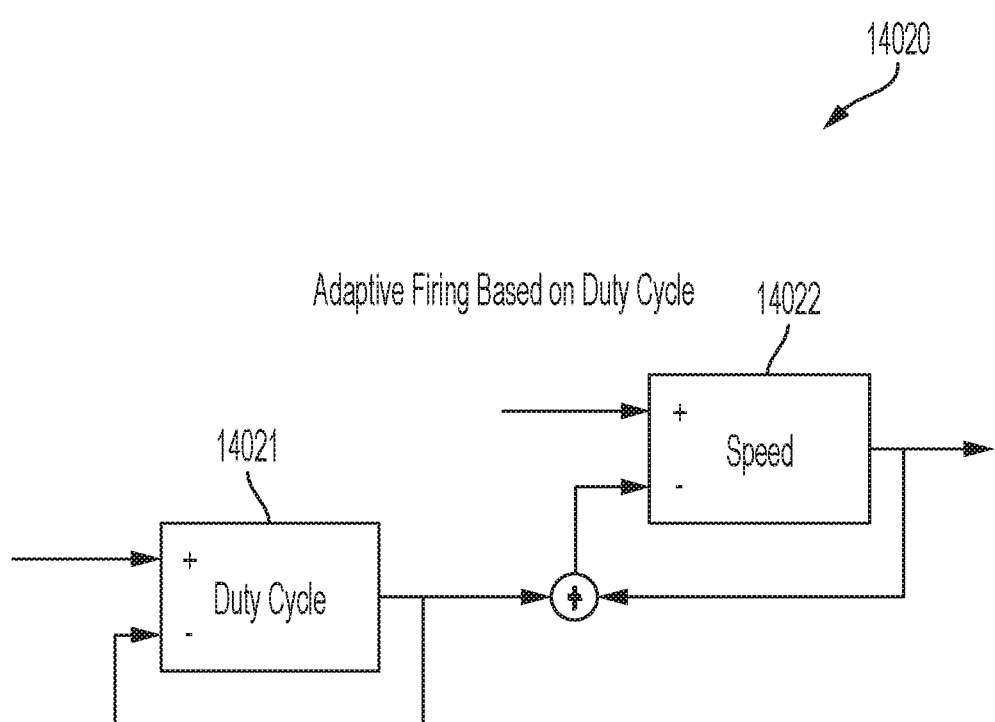
FIG. 87 depicts a control process of a motor control circuit of a surgical instrument configured to utilize both monitored motor duty cycle and monitored motor speed and/or firing member speed as inputs for adjusting the speed of the motor during a drive stroke.

FIG. 87 depicts a control process 14020 configured to utilize both monitored duty cycle 14021 and monitored motor speed and/or firing member speed, for example, 14022 as inputs for adjusting the speed of the motor during a drive stroke, for example. For example, the higher the duty cycle utilization is (for example, close to maximum, or optimal, capacity, for example) when a target velocity and/or target displacement, for example, is not achieved, the higher the magnitude of the speed decrease adjustment will be in an effort to bring the motor system well within its optimal operating range in response to the missed target. Similarly, in at least one instance, if a lower utilization is detected when a target velocity or target displacement is missed, the magnitude of the speed increase adjustment is selected based on the determined level of utilization of the motor system.

One situational non-limiting example will be described. A firing member is moving at 10 mm/sec, for example, in thick tissue and is succeeding in meeting its displacement and/or speed target(s), for example. The firing member then encounters a calcified portion of extra thick tissue and misses one or more displacement targets, for example. At such point, the motor control circuit determines that the motor should be slowed down to allow the tissue to relax, settle, loosen, and/or creep in front of the firing member such as, for example, the cutting knife. In other words, slowing the firing member down relieves some of the load on the firing member applied by a tight, bunched up portion, for example, of extra thick portion of tissue. In at least one instance, it can be determined that the duty cycle is also already at nearly 100% when the displacement target was missed indicating that the motor system may have been already been nearly missing its displacement targets prior to the actual detection of the missed displacement target. The system can then slow the firing member down 150% of its target speed of 10 mm/sec, for example. Where the motor control circuit would have normally slowed the firing member down from 10 mm/sec to 7 mm/sec (a 3 mm/sec anticipated slow down action), the motor control circuit determines to slow down the firing member to 5.5 mm/sec (150% of the original 3 mm/sec anticipated slow down action—4.5%) because the motor system both missed the displacement target and the motor system was nearly at 100% utilization when the displacement target was missed.

In at least one instance, a motor control circuit is config- ured to set target travel lengths, or displacement targets, which the firing member is expected to travel during a predetermined time period. In such an instance, the motor control circuit, utilizing a PID controller, for example, can monitor the error terms (proportional, integral, and deriva- tive terms, for example) and uses these error terms as inputs to the motor control circuit to make adjustments to the motor control. In at least one instance, the error terms include displacement error, velocity error, and overshoot error. Any combination of these errors terms can be utilized as inputs by a motor control circuit.

In at least one instance, one or more parameters are monitored during a firing stroke, for example, and are utilized as inputs into a motor control circuit including a PID controller, for example, for adjusting motor control.

In at least one instance, PID controller parameters, such as proportional, integral, and/or derivative, parameters are adjusted, or fine-tuned, based on one or moor monitored parameters within a motor system. Such monitored param- eters can include motor response, firing member load, speed, displacement, and/or tissue properties, for example.

In at least one instance, a PID feedback control system includes a PID controller comprising a proportional element (P), an integral element (I), and a derivative element (D). The outputs of the P, I, D elements are summed by a summer, which provides the control variable to a process. The output of the process is the process variable. The summer calculates the difference between a desired set point and a measured process variable. The PID controller continuously calculates an error value (e.g., difference between closure force thresh- old and measured closure force) as the difference between a desired set point (e.g., closure force threshold) and a mea- sured process variable (e.g., velocity and direction of closure tube) and applies a correction based on the proportional, integral, and derivative terms calculated by the proportional element (P), integral element (I), and derivative element (D), respectively. The PID controller attempts to minimize the error e(t) over time by adjustment of the control variable (e.g., velocity and direction of the closure tube).

In accordance with a PID algorithm, the "P" element accounts for present values of the error. For example, if the error is large and positive, the control output will also be large and positive. The error term is the difference between a reference, or target, speed, for example and an actual output speed. The "I" element accounts for past values of the error. For example, if the actual speed does not achieve the target speed over a period of time, the integral of the error will accumulate over time, and the controller will respond by applying a stronger action. The "D" element accounts for possible future trends of the error, based on its current rate of change. For example, continuing the P example above, when the large positive control output succeeds in bringing the error closer to zero, it also puts the process on a path to large negative error in the near future. In this case, the derivative turns negative and the D module reduces the strength of the action to prevent this overshoot. More detail of PID control of a surgical instrument system is disclosed in U.S. patent application Ser. No. 15/636,829, now U.S. Patent Application Publication No. 2021/0244407 entitled METHODS FOR CLOSED LOOP VELOCITY CONTROL FOR ROBOTIC SURGICAL INSTRUMENT, which is incorporated by reference herein in its entirety.

Fine tuning the PID controller parameters can provide greater motor control in a variety of scenarios. For example, the PID controller parameters can be adjusted corresponding to the type and/or thickness of tissue that is to be stapled and cut. In at least one instance the PID controller parameters can be adjusted based on the type of cartridge installed within an end effector, size of staples within the installed cartridge, and/or length of the installed cartridge, for example.

In at least one instance, an expected compressive clamp- ing load (pressure owing to clamped tissue within a pre- defined tissue gap between the cartridge and the anvil) can dictate PID tuning, or control, parameters. For example, if the expected compressive clamping load is exceeded during the clamping stage of the end effector, the PID controller parameters can be adjusted accordingly to compensate. Similarly, if the excepted compressive clamping load is not exceeded during the clamping stage of the end effector, the PID controller parameters can be set accordingly or, in at least one instance, not adjusted from a preset parameter profile which was set prior to clamping the tissue.

In at least one instance, outcomes of anticipated stroke events can trigger one or more adjustments to the PID controller parameters. For example, portions of the stroke where anticipated impacts occur (end of stroke where the firing member may ram the end of the staple cartridge, initial contact between the firing member and the sled during the beginning of the stroke, and/or engagement between the jaw camming surfaces which control a tissue gap between the jaws) can all trigger PID control parameter adjustments. For example, a load within the motor system may be detected as the firing member contacts the sled during the beginning of the stroke and, depending on the magnitude of the detected load, the PID controller parameters can be set according to the magnitude of the detected load. In at least one instance, maximum acceptable inertial impacts are set, or predeter- mined, and, if exceeded, PID controller parameters are adjusted and/or safety motor control algorithms are initiated, for example.

In at least one instance, overshoot is monitored through- out a stroke and PID controller parameters are adjusted according to the overshoot during the stroke so as to reduce the possibility of the firing member from traveling too far and/or not far enough. For example, PID controller param- eters are adjusted so the firing member of the motor system does not crash into the end of the staple cartridge and/or end effector. In at least one instance, PID controller parameters are adjusted so the firing member of the motor system does not stop prematurely before achieving its expected full firing stroke distance, for example. Such an arrangement can reduce unnecessary load on the motor system and/or an unfinished staple firing stroke, for example.

In at least one instance, the PID controller parameters are adjusted to place a motor of the motor system into a different efficiency band of the motor curve. Such an arrangement can reduce motor heat generation and performance degradation over time.

In various instances, the PID controller parameters are adjusted, or modified, such as PID controller gain, for example, based on any number of variables. In at least one instance, one or more PID controller parameters are adjusted based on the activation of a no-cartridge lockout. In at least one instance, the one or more PID controller parameters are adjusted based on an accuracy of the motor. For example, motor performance may vary over time. A rotary position sensor, such as a cross over gear encoder, for example, may be used to measure the accuracy of the motor. Depending on the measured accuracy, the gain, for example, of the PID controller can be modified according to the measured accuracy and, in at least one instance, modified to compensate for an increasing decline in accuracy, for example. In at least one instance, the one or more PID controller parameters are modified based on the position of a cutting edge. In at least one instance, the one or more PID controller parameters are modified based on the set values of the PID parameters themselves. For example, if a PID controller parameter is automatically adjusted beyond a threshold, for example, a new set of values may be selected for the PID controller parameters. In at least one instance, the one or more PID controller parameters are modified based on where the end of the staple firing stroke is. In at least one instance, the end of the staple firing stroke is predetermined. In at least one instance, the end of the staple firing stroke changes per use. For example, a user may not actuate a firing member through a full staple firing stroke. The actual end of the firing stroke can be utilized to adjust the gain of the PID controller.

In at least one instance, the one or more PID controller parameters are adjusted based on one or more staple cartridge characteristics such as, for example, the type of cartridge installed. In at least one instance, a sensor is used to determine the color of the cartridge color and one or more PID controller parameters are adjusted to values corresponding to the detected cartridge color. For example a cartridge of a first color may require more force to fire its staples than a cartridge of a second color. The one or more PID controller parameters can be adjusted to compensate for the increased force requirement, for example.

In at least one instance, the one or more PID controller parameters are adjusted based on motor impedance, the variation of Kt (motor torque constant)/Ke(back EMF constant) from a nominal Kt/Ke of the motor due to self-heating, and/or demagnetization of the motor due to prolonged use in heated conditions, for example.

In at least one instance, the one or more PID controller parameters are adjusted based on detected stress within the system. In at least one instance, traces are employed on a printed circuit board, or printed circuit board assembly, of a surgical instrument system to infer bending stresses within the system. For instance, the printed circuit board may be positioned within a surgical instrument handle. The PID controller parameters can be adjusted to compensate for the detected bending stresses, for example.

In at least one instance, heat buildup within the system can be detected and one or more PID controller parameters can be adjusted accordingly. For instance, output motor torque may be implicated by heat build up and, upon detecting a magnitude and/or threshold rate of heat build up that would, in turn, cause a certain threshold torque loss to be experienced, one or more PID controller parameters can be adjusted to reduce heat build up and/or compensate for loss in torque, for example.

In at least one instance, PID controller parameters are adjusted based on where a firing member is within its firing stroke. For example, a motor control circuit can adjust the PID controller parameters automatically when the firing member has been deployed through two thirds of the full staple firing stroke. In at least one instance, the force increases within the last third of the staple firing stroke and, thus, the PID controller parameters can be set to compensate for the expected increase in required firing force, for example. In at least one instance, one or more PID controller parameters are adjusted based on where, longitudinally, tissue is clamped between the jaws. Tissue clamped between the jaws near the distal end may require more force to cut and staple than tissue clamped between the jaws near the proximal end, for example. The one or more PID controller parameters can be adjusted accordingly. In various instances, system load, distal node system efficiency, and/or torsional drive shaft stiffness can be utilized to adjust the PID controller parameters. In at least one instance, one or more strain gauges are utilized to detect stress within the system.

In at least one instance, one or more PID controller parameters are adjusted based on the number of firings performed by a motor system, for example. For instance, an older motor may generate more heat during firings and, thus, the PID controller parameters can be adjusted so as to account for the increased heat risk.

In various instances, new values for PID controller parameters can be estimated by neural networks so as to anticipate the optimal value for the PID controller parameters for future firings, for example. In at least one instance, schedules are used by the motor control circuit to determine when to change the PID controller parameters. For example, after a predetermined amount of firings, the PID controller parameters can be adjusted automatically based on reaching the predetermined amount of firings. In at least one instance, previous uses of similar motors are logged and analyzed to determine PID controller parameters for a local motor system.

Figure 88:
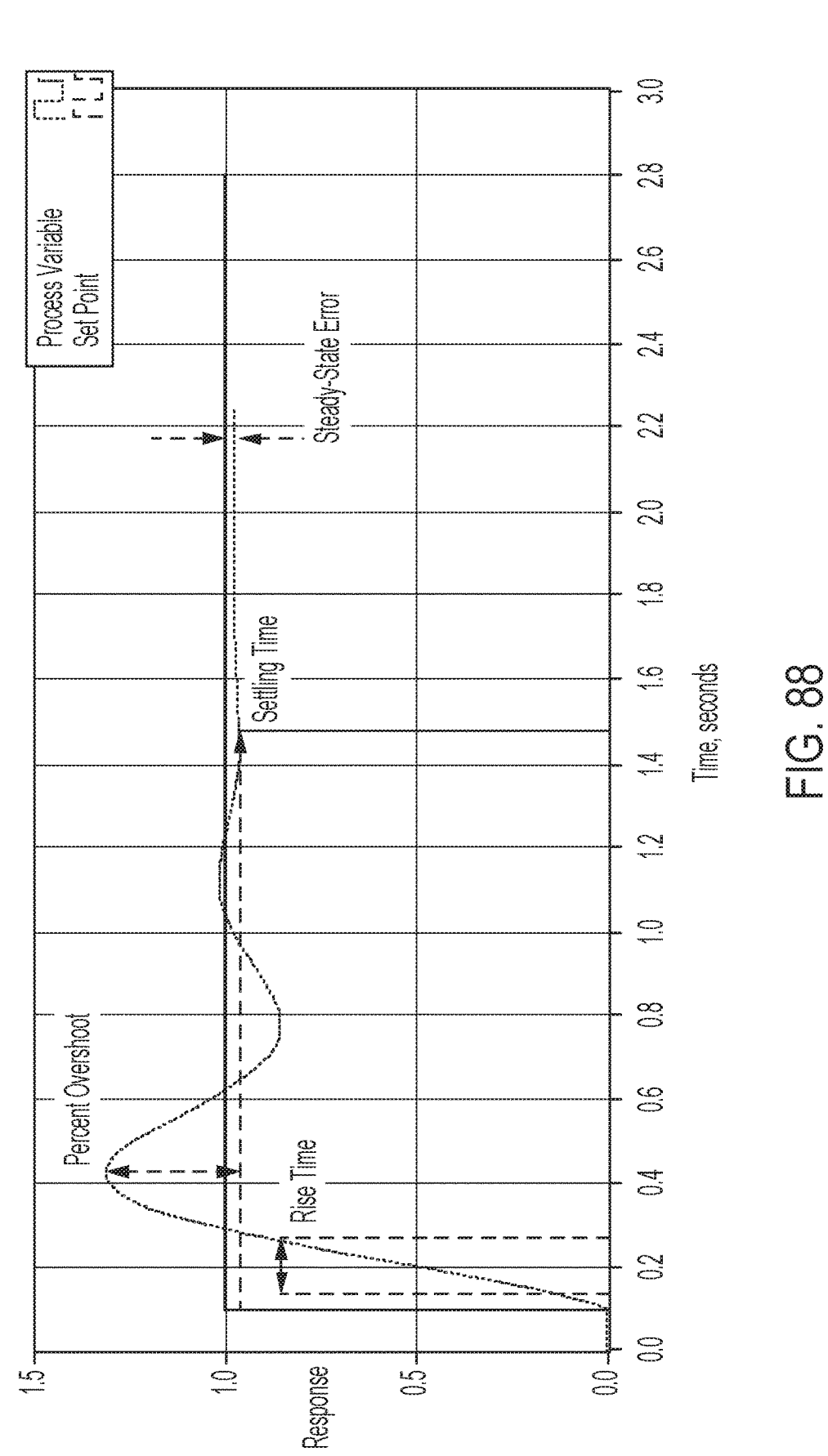
FIG. 88 is a graph depicting various types of signal variables affected by PID controller parameters adjustments.

In various instances, PID controller parameters are tuned to adapt during use of a motor system to increase motor efficiency and/or improve firing stroke outcomes, for example. Referring to FIG. 88, a graph 14030 is shown to describe various setpoint implications of a PID controller, for example. As can be seen in the graph rise time, percent overshoot, settling time, steady-state error can all be optimized, or improved, by adjusting the PID tuning parameters of a PID controller configured to control a motor of surgical instrument motor system. Adjustments can be made based on any combination of the methods and systems disclosed herein. For example, in the context of firing member displacement, automatically tuning the PID controller parameters to reduce percent overshoot (of displacement, for example) can reduce the likelihood of ramming a firing member into the end of a staple cartridge.

Figure 89:
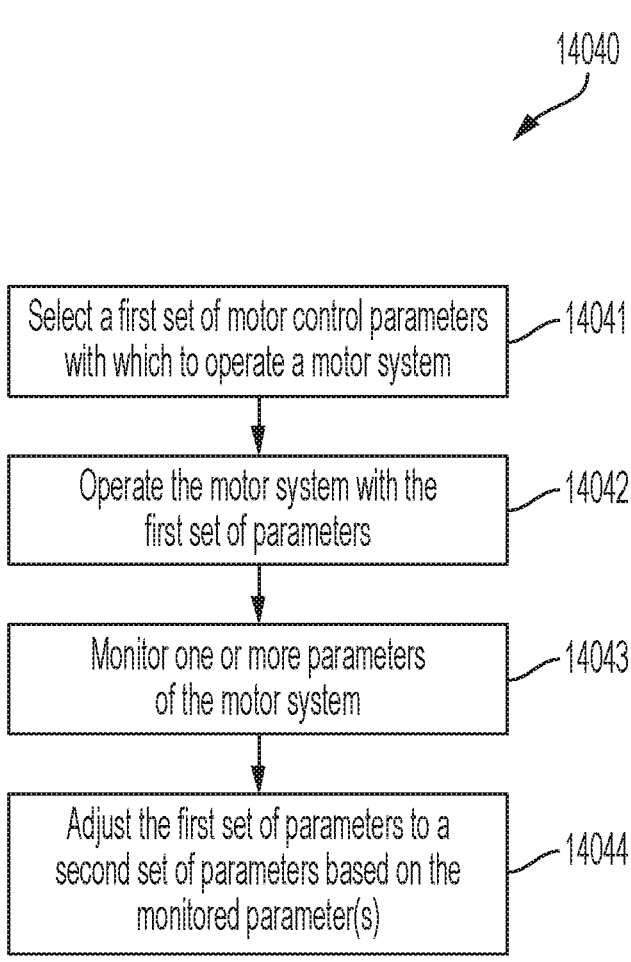
FIG. 89 is a logic flow chart depicting a process executable by a control circuit configured to adjust motor control parameters based on monitored parameters of a motor system.

FIG. 89 is a logic flow chart depicting a process 14040 executable by a control circuit, such as the control circuit 1932 illustrated in FIG. 13 and/or the control circuit illustrated in FIG. 14, for example, herein utilizing close loop control. In at least one instance, feedback is generated from one or more system sensors and an input signal is adjusted to optimize motor control. First, a first set of motor control parameters are selected 14041. In at least one instance, the motor control parameters include PID controller parameters. In at least one instance, the motor control parameters include PWM controller parameters. In at least one instance, the motor control parameters include a range of duty cycles. In at least one instance, the motor control parameters include any combination of proportional, integral, and derivative tuning parameters of the motor controller. The motor control parameters may include any suitable combination of control parameters disclosed herein. During operation 14042 of the motor system, one or more parameters of the motor system are monitored 14043. The one or more monitored parameters may include any suitable parameters such as, for example, position of the firing member, actual measured speed of the firing member, actual measured speed of the motor, and/or type of cartridge installed within the end effector. The monitored parameter may include any combination of parameters disclosed herein. The motor controller parameters are adjusted 14044 to a new set of motor controller parameters based on the monitored parameter(s).

For example, a tighter or greater range of duty cycles is selected and/or PID tuning parameter values are adjusted. Any suitable adjustment can be made such as those disclosed herein.

Referring still to FIG. 89, the motor control circuit is configured to deploy a firing member through a staple firing stroke. In at least one instance, the staple firing stroke includes an active stroke portion and an inactive stroke portion, where no adjustments are made to the motor controller parameters during the inactive stroke portion and adjustments are able to be made during the active stroke portion. In at least one instance, the magnitude of the adjustment made to the motor controller parameters is based on a magnitude of the monitored parameter(s). In at least one instance, the magnitude of the adjustment made to the motor controller parameters is based on a rate at which the monitored parameter(s) changes during a portion of the staple firing stroke. In at least one instance, the new set of motor controller parameters includes a first magnitude upon detecting that the firing member, or motor, is decelerating. In such an instance, the new set of motor controller parameters includes a second magnitude which is different than the first magnitude upon detecting that the firing member, or motor, is accelerating.

In various instances, a motor control circuit is configured to activate and/or deactivate one or more motor control circuits and/or algorithms such as those disclosed herein, for example. In at least one instance, the motor control circuit is configured to deactivate motor control adjustments during any suitable portion of a drive stroke of a motor system. For instance, motor system capacity interrogation and corresponding adjustments may be prohibited from occurring during one or more portions of the stroke of a firing member and only able to occur during one or more other portions of the stroke of the firing member. In at least one instance, motor control adjustments may only occur while the firing member is deploying staples within a staple deployment zone of the stroke. In at least one instance, only certain motor control adjustments corresponding to clamping tissue can occur during the clamping of tissue while other certain motor control adjustments corresponding to firing staples and cutting tissue can occur during the staple firing stroke. In at least one instance, the position of the firing member triggers active and/or inactive stages of motor control algorithms and circuits, such as those disclosed herein. For instance, once the firing member reaches a first position, which may be detectable in any suitable manner such as for example, with a position sensor, a first set of motor control algorithms can be activated. Similarly, when the firing member reaches a second position, a second set of motor control algorithms can be activated. Finally, when the firing member reaches a third position, real time motor control adjustments can be prohibited from being made. In at least one instance, portions of a stroke can permit PWM speed control adjustments while other portions of a stroke can prohibit PWM speed control adjustments.

In at least one instance, a motor control circuit is employs PWM speed control adjustments during the clamping of tissue and the articulation of an end effector while prohibiting PWM speed control adjustments during retraction of a firing member, unclamping of tissue, and/or de-articulating an end effector to a neutral position, for example. Various motor control circuits and/or algorithms disclosed herein which are configured to modify the speed of a motor of a motor system during a drive stroke may be referred to as active speed control. In various instances, active speed control is disabled for one or more reasons. In at least one instance, active speed control can be disabled due to an unforeseen event such as, for example, a detected spike in motor current. In at least one instance, the disabling of active speed control can be overridden and re-activated. In at least one instance, active speed control can be manually disabled and/or enabled by a user, for example. In at least one instance, disabling active speed control is configured to directly link a power source to the motor thereby removing any smart control of the motor. In at least one instance, PWM speed control can be deactivated and, in such an instance, the duty cycle of the motor is set to a fixed value such as, for example, 100% and no PWM motor controller adjustments are made. In at least one instance, motor control profiles are reset from stroke to stroke, patient to patient, and/or cartridge to cartridge. In at least one instance, motor control profiles are not reset.

In at least one instance, motor control circuits and algorithms disclosed herein are configured to maintain a constant speed of the firing member rather than constantly change the speed of the firing member as the firing member traverse through tissue, for example.

In various instances, a staple cartridge and/or a staple firing stroke is defined into multiple segments where certain motor control adjustments are confined to a predetermined adjustment range, for example. Such a control circuit can also be used during a closure stroke of a drive shaft, for example. Each segment corresponds to certain motor controller adjustments. For example, during a first third of a staple firing stroke, a control circuit may only be able to make a first range of adjustments to one or more motor controller parameters such as, for example, PID tuning parameters. During a second third of the staple firing stroke, the control circuit may only be able to make a second range of adjustments to the one or more motor controller parameters. Finally, during the third third of the staple firing stroke, the control circuit may only be able to make a third range of adjustments to the one or more motor controller parameters.

In at least one instance, the range of adjustments which may be made during the first third of the staple firing stroke may include a greater range as compared to the adjustment ranges of the second third and/or the third third. This can reduce the possibility of large motor control adjustments from being made during the final stages of the staple firing stroke where a user may not want a firing member to be increasing its speed toward the end of the staple firing stroke risking crashing the firing member into the end of the staple cartridge, for example, which can cause the firing member to get stuck or jam. In at least one instance, no limits are placed on motor controller adjustments during the first third of the staple firing stroke. In at least one instance, no motor controller adjustments can be made during the final third of the staple firing stroke.

The segmented sections of the staple firing stroke, for example, can be separated into any desired fraction. For example, the staple firing stroke may be segmented into fourths, fifths, hundredths, for example. In at least one instance, the staple firing stroke is split into two regions. In various instances, the segments vary in length. In at least one instance, the segments are broken into a beginning segment, a plurality of intermediate segments, and an ending segment.

In various instances, dividing the staple firing stroke into segments where motor control adjustments are limited, confined, or controlled specifically within each segment can control overshoot error during motor operation. Load, or force to fire, for example, can be monitored during each segment and can be used to set motor controller parameters such as, for example, PID tuning values specifically for each segment.

Figure 90:
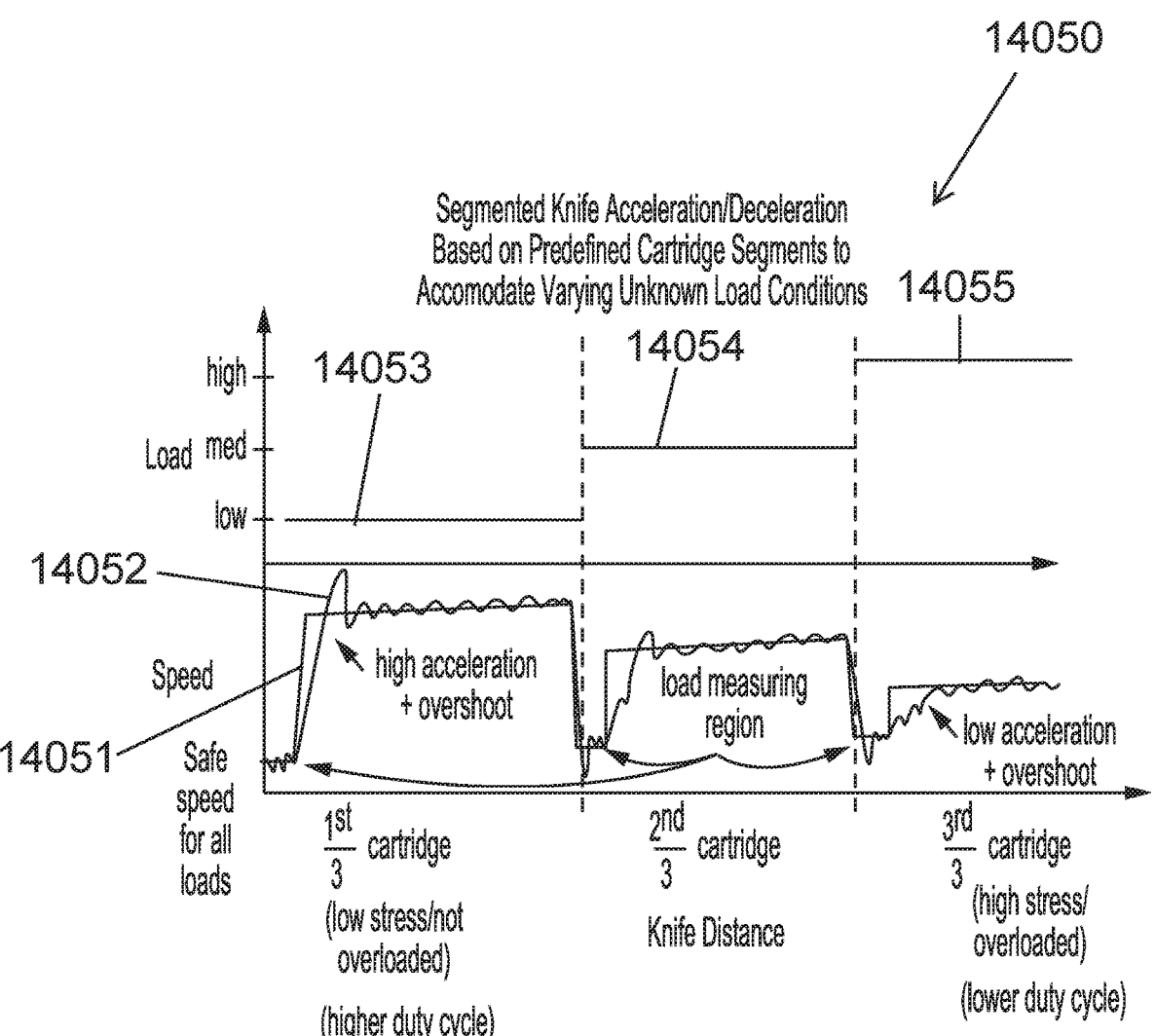
FIG. 90 Is a graph depicting a firing stroke of a motor system including a motor, a drive train, and a motor control circuit, wherein the motor control circuit segments the firing stroke into multiple portions and adjusts one or more motor control parameters of the motor according to each segment.

FIG. 90 is a graph 14050 illustrating a staple firing stroke of a motor system. A control circuit divides the staple firing stroke, or the cartridge, into segments: a first third, a second third, and a third third. The control circuit increases the target speed 14051 of the motor to a safe speed to initiate firing. The control circuit then increases the target speed 14051 of the motor by increasing the duty cycle to a relatively high duty cycle during the first third of the cartridge. As can be seen in the graph 14050, overshoot error of the actual speed 14052 is increased during rapid acceleration of the firing member. The actual speed 14052 of the firing member steadies toward the end of the first third of the cartridge. Then, the target speed 14051 is brought down to another safe target speed 14051. As can also be seen in the graph 14050, the load 14053 during the first third of the cartridge is relatively low as compared to the other segments of the cartridge. As the load increases 14054 during the second third of the staple cartridge, the control circuit sets the target speed 14051 and the actual speed 14052 of the firing member rises at a rate which lower than the rate of speed increase during the first third of the cartridge. This also results in less overshoot error. Finally, with yet another increase in load 14055 during the third third of the cartridge, the target speed 14051 is set and the firing member accelerates slowly to reduce overshoot within the third third of the cartridge. As the load increased throughout the firing stroke, the duty cycle of the motor decreased for each segment to reduce overshoot. High overshoot may cause damage to tissue or the firing system itself. Reducing overshoot during higher load conditions can reduce the possibility of damage to the tissue and/or the firing system. In at least one instance, the loads 14053, 14054, and 14055 are measured while the motor runs at safe speeds prior to increasing the target speed 14052 of the firing member for each segment of the cartridge. In such instances, the speed of the firing member is adjusted according to the magnitude of the measured load where higher loads result in lower set speeds and lower loads result in increased set speeds. In at least one instance, the speed can be increased substantially during low load conditions as there can be reduced risk to the tissue and/or firing system at high speeds with low detected loads. An increased overshoot error during higher load conditions can result in an additional unintended speed increase from a target speed where no tissue or system damage was expected at the target speed but would occur if the increased speed was achieved when overshooting the target speed.

In various instances, PID controller parameters are adjusted automatically to reduce overshoot in higher load conditions. In lower load conditions, the PID controller parameters can be automatically adjusted to optimize speed where overshoot is not an issue. In at least one instance, a threshold of the proportional limit value of a PID controller is lowered in higher load conditions to reduce overshoot. In at least one instance, a threshold of the integral value and a threshold of the derivative value of the PID controller are lowered to reduce overshoot. In various instances, the rate at which the speed of the firing member changes is monitored to determine motor control adjustments such as, for example, PID tuning value adjustments, for the rest of the segment.

In at least one instance, overshoot and/or irregular motor response may be acceptable and/or anticipated during certain portions of a firing stroke. During such portions of the firing stroke, utilizing the location of the firing member to determine when the firing member is in such portions of the firing stroke, the motor control circuit can specifically tune the PID controller values accordingly. In at least one instance, a predicted amount of overshoot is acceptable during a certain portion of the firing stroke. As a result, the PID controller values are adjusted accordingly. In at least one instance, the PID controller values are not adjusted at all during such portion of the firing stroke. In various instances, firing strokes include a predicted force to fire spike location where the force to fire increases at the spike location every time the firing member passes the spike location. Such a location may include where an i-beam contacts and traverses a metal irregularity in a cartridge channel which is the result of the manufacturing process of the cartridge channel. In such instances, a motor control circuit is configured to not adjust PID controller values as the firing member passes the spike location. The location of the firing member can be used to determine when the firing member is going to pass the spike location to prevent the motor control circuit from adjusting the motor controller parameters as the firing member passes this spike location/as a result of the spike in force to fire. In at least one instance, the motor control circuit adjusts the PID controller values at the spike location; however, the magnitude of the adjustment is lower than if the same spike in force was detected during other portions of the staple firing stroke.

Figure 91:
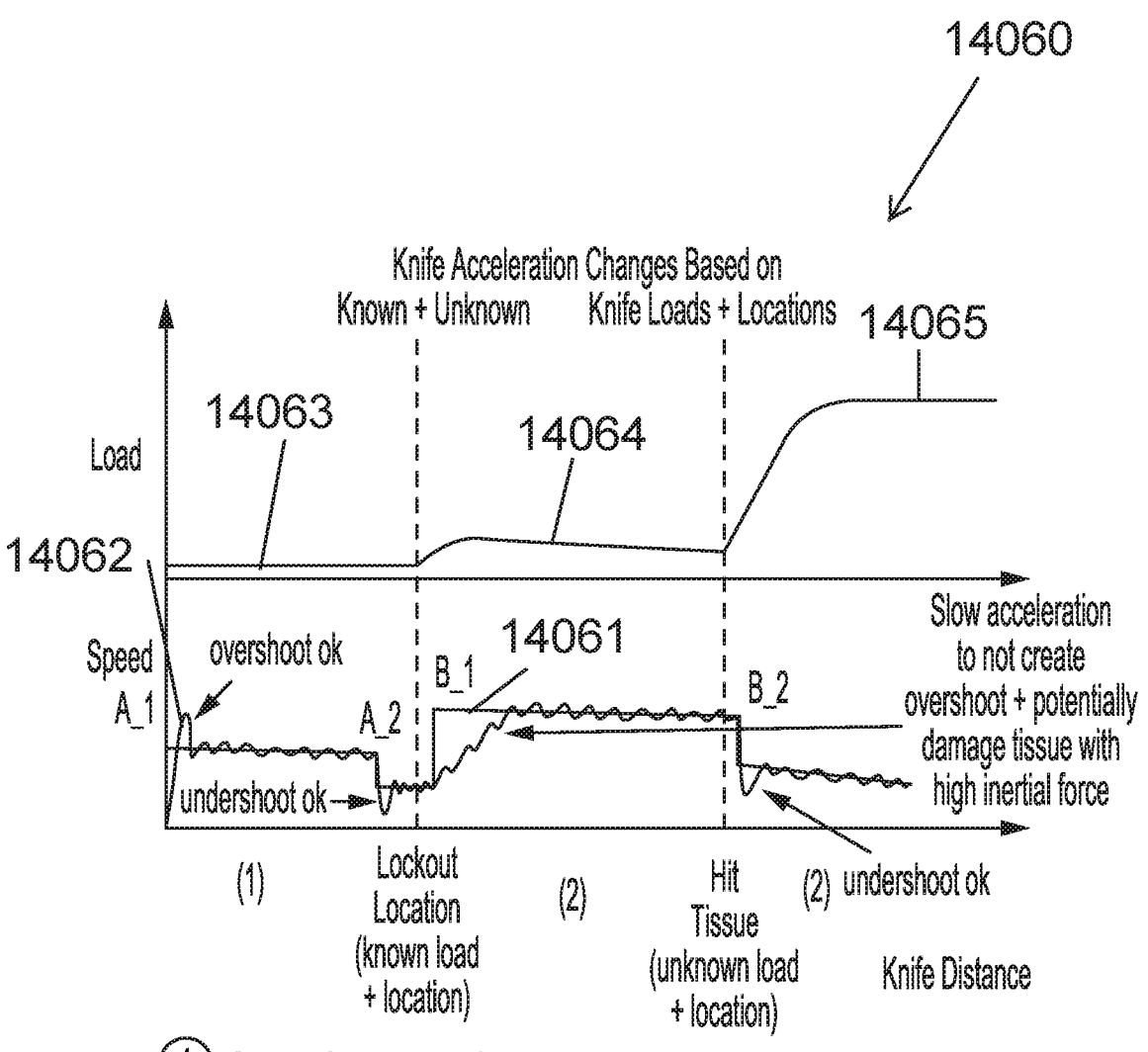
FIG. 91 is a graph depicting a firing stroke of a motor system including a motor, a drive train, and a motor control circuit, wherein the motor control circuit segments the firing stroke into multiple portions and adjusts one or more motor control parameters of the motor according to expected loads and/or monitored location of firing member within the firing stroke.

In various instances, the rate of speed increase or decrease (acceleration/deceleration) by a motor control circuit is adjusted based on a level of overshoot concern and/or undershoot concern as it relates to predictable loads at certain locations, for example. FIG. 91 is a graph 14060 illustrating a firing stroke of a motor system. Target, or set, speed 14061, actual measured speed 14062, and firing loads 14063, 14064, and 14065 are illustrated. During stage (1), the speed of the motor is increased at the beginning A_1 of the firing stroke. During stage (1), overshoot concern is low and, thus, the motor control circuit sets the motor control parameters accordingly (to permit overshoot, for example). The overshoot concern is low because, at this stage of the firing stroke, no tissue is being cut or stapled. Rather, the firing member moves from an unfired position A_1 to a lockout location where the firing member is either locked out from continuing or defeats the lockout. During this stage, the overshoot concern is low. Prior to reaching the lockout location, the speed 14061 is decreased. During this decrease, undershoot is not a concern and, thus, the motor control parameters are set/can be adjusted accordingly. The speed 14061 may be decreased just before the firing member reaches the lockout location to decrease the effective speed before the firing member either locks out or defeats the lockout. The increased speed prior to the decrease in speed at A_2 increases the operating efficiency of the motor prior to the firing member reaching the lockout location. The load 14063 during stage 1 may be known and/or predicted with acceptable accuracy such that there may be no unpredictable load increases/decreases during this stage. Because the load is predicted within this stage, the motor controller parameters can be set accordingly.

After the firing member defeats the lockout and moves past the lockout location, stage 2 begins. At B_1, the speed 14061 is increased because the load 14064 is unknown. The load 14064 is unknown because at any point during stage 2, the firing member (or cutting member) can hit tissue. Also, because the load 14064 is unknown, overshoot is of a higher concern than of stage 1. Overshoot when hitting tissue during this stage can cause tissue damage by applying a higher than predicted inertial force. This higher than predicted inertial force is because of the initial spike of input speed experienced (overshoot) beyond the set target speed. Because overshoot is of higher concern, the motor control parameters can be set accordingly to decrease the rate at which the speed of the firing member increases. As can be seen on the graph 14060, overshoot of the actual speed 14062 is low because the motor control parameters were set accordingly. At stage 3, load 14065 is unknown and speed 14062 is decreased at B_2 with the concern of undershoot being relatively low. Undershoot may be okay in several scenarios because slowing of a firing member below a target speed from a higher speed may not pose a risk for damaging tissue.

In various instances, dynamic breaking can be employed by a motor control circuit to reduce overshoot. In at least one instance, actual speed is monitored and compared to the target speed and, as the actual speed approaches the target speed, the motor can be slowed or braked dynamically to reduce and/or eliminate overshoot and/or undershoot. In at least one instance, dynamic breaking is used in combination with acceleration limiting to control overshoot. In at least one instance, inertia of a motor system is monitored during a firing stroke and is used to determine acceleration limit adjustments.

In various instances, an importance magnitude is utilized in a motor control circuit. The importance magnitude is a value assigned to predetermined sections of a firing stroke, for example. The value indicates the importance, or lack thereof, of reducing overshoot and/or undershoot, for example during the identified firing stroke section. With reference to FIG. 91, an importance magnitude at position B_1 can be assigned a "1" being the most important location to reduce overshoot, an importance magnitude at positions A_1, A_2, and B_2 can be assigned a "2" indicating a lower importance of reducing overshoot and/or undershoot, for example.

In various instances, the rate of change of speed can be monitored (by way of PWM duty cycle, PWM frequency, PWM amplitude (voltage)) relative to a target threshold to adjust motor control parameters to reduce and/or eliminate overshoot, for example. In at least one instance, a motor control circuit is configured to monitor the magnitude of PID deviation from an instantaneous target over time at a certain frequency and monitor the rate of change of PID deviation during the period of time to determine if the motor system is falling behind further with each subsequent target or if the motor system is accelerating closer to the target with each subsequent target. This determination can be used in conjunction with how far away from the target the actual value is at each target to dampen the acceleration/deceleration to prevent overshoot/undershoot. In at least one instance, the rate of change of speed is monitored at the initial part of each stage, cycle, or firing stroke section, and/or at the end part of each stage, cycle, or firing stroke section, for example.

Figure 92:
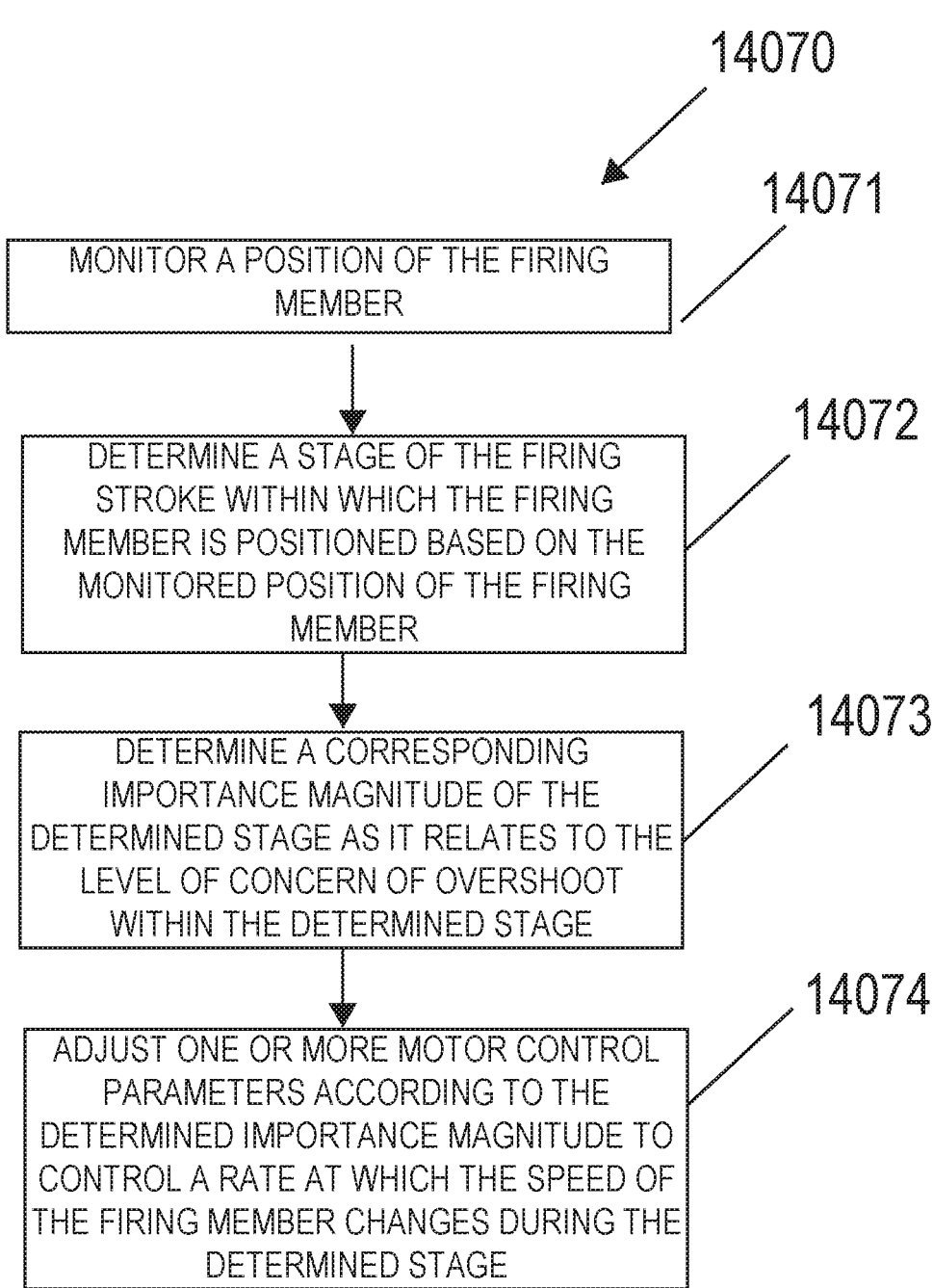
FIG. 92 is a logic flow chart depicting a process executable by a control circuit configured to control a motor of a motor system.

FIG. 92 is a logic flow chart depicting a process 14070 executable by a control circuit, such as the control circuit 1932 illustrated in FIG. 13 and/or the control circuit illustrated in FIG. 14, for example, configured to control a motor of a motor system. The motor control circuit is configured to monitor 14071 a position of the firing member. The position of the firing member may be monitored in any suitable manner such as, for example, by a position sensor, a displacement sensor, and/or an encoder configured to measure motor rotation. The motor control circuit is further configured to determine 14072 a stage of the firing stroke within which the firing member is position based on the monitored position of the firing member. For example, the motor control circuit, based on the monitored position of the firing member, can determine that the firing member is within a first third of the cartridge, or first segment of three segments of the firing stroke, for example. The motor control circuit is further configured to determine 14073 a corresponding importance magnitude of the determined stage as it relates to the level of concern of overshoot occurring within the determined stage. In at least one instance, the importance magnitude includes a scale including low importance, medium importance, and high importance. Low importance indicates that the occurrence of overshoot is of little concern. High importance indicates that the occurrence of overshoot is of high concern. High importance may be associated with a stage of the firing stroke where load on the firing member is high. In at least one instance, the importance magnitude is determined based on the position of the firing member. In at least one instance, load on the firing member is monitored and is used to determine the importance magnitude. Higher load on the firing member can be associated with a high level of concern of overshoot, for example. The motor control circuit is further configured to adjust 14074 one or more motor control parameters according to the determined importance magnitude to control a rate at which the speed of the firing member changes during the determined stage. The one or more parameters may include any suitable parameters such as motor controller parameters, PID controller tuning parameters, and/or PWM duty cycle ranges, for example.

In various instances, motor control parameters, circuits, and/or algorithms such as those disclosed herein, are adjusted in an effort to limit loads experienced within an end effector. Such loads can be caused by thick and/or tough tissue, for example. Loads can be experienced by the motor through various stages of the use of a surgical instrument. For example, loads can be experienced by the motor through a firing member as the firing member is advanced through a staple firing stroke, by the motor through a closure member during the clamping of tissue, for example. Load levels can be detected in any suitable manner such as, for example, by monitoring motor current of a motor configured to drive a firing member and/or through a force sensor, such as a strain gauge, for example, positioned on a firing member. In at least one instance, the speed of the motor of a motor system is decreased to decrease load experienced by the firing member.

In at least one instance, a motor control circuit is configured to modulate torque (force) and speed (voltage) of the motor simultaneously in an effort to reduce load experienced by a drive train. In at least one instance, the speed of the motor is reduced to decrease the load experienced within the end effector. In at least one instance, controlled pause, or wait, periods are utilized to decrease the load experienced within the end effector.

Figure 93:
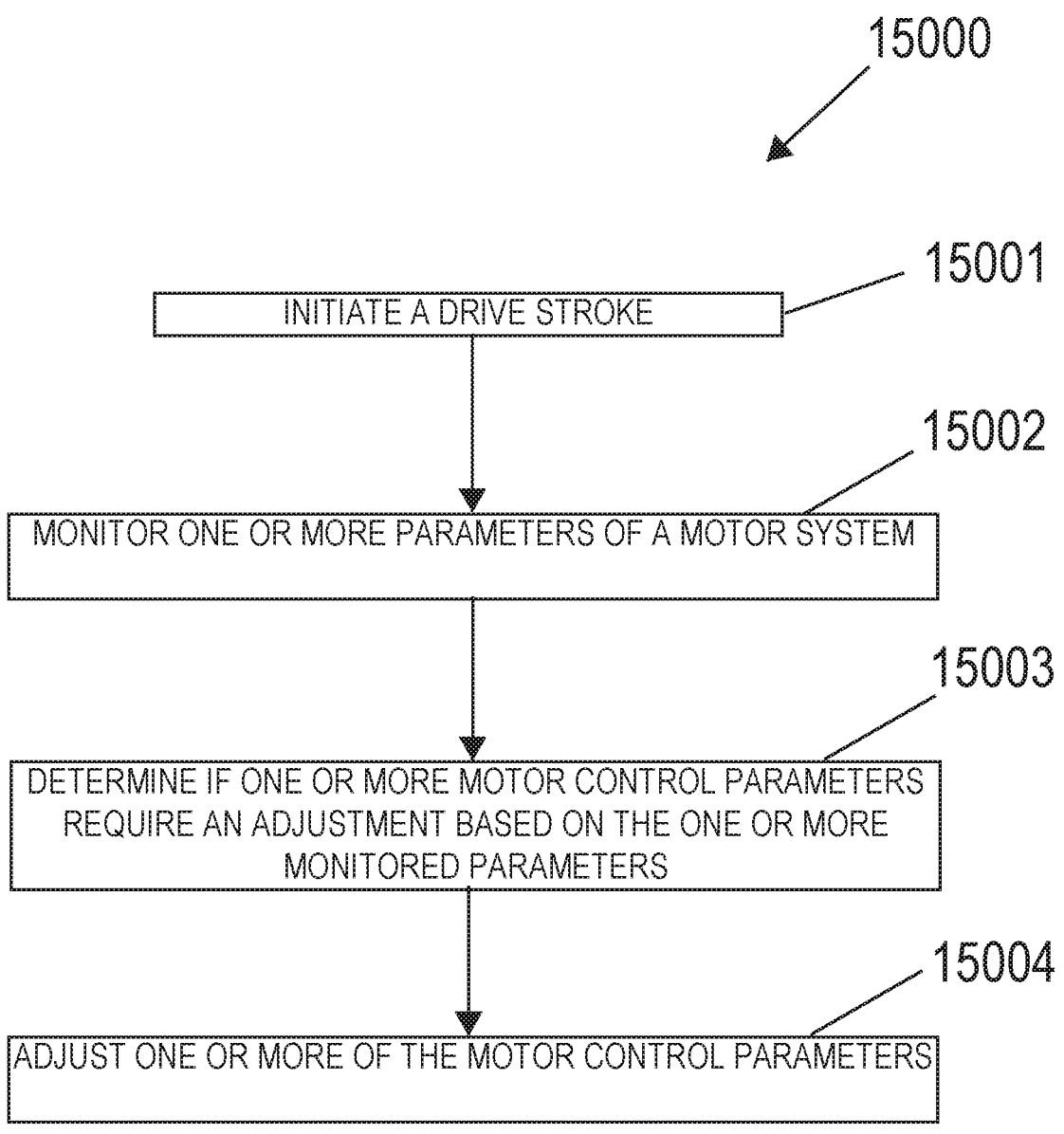
FIG. 93 is a logic flow chart depicting a process executable by a control circuit configured to control a motor system of a surgical instrument system.

FIG. 93 is a logic flow chart depicting a process 15000 executable by a control circuit, such as the control circuit 1932 illustrated in FIG. 13 and/or the control circuit illustrated in FIG. 14, for example, for use with a surgical instrument system such as those disclosed herein. The control circuit is configured to control the motor of a motor system within a surgical instrument system. The control circuit is configured to receive one or more inputs and produce an output signal to the motor corresponding to the one or more inputs. The control circuit is configured to monitor one or more electrical and/or mechanical parameters of the motor system such as, for example, rotational output speed of the motor, linear output speed of a firing member, current draw of the motor, and/or load experienced by the motor system. In at least one instance, the control circuit is configured to convert one or more analog outputs such as motor speed, current draw, firing member speed, etc., to a digital signal. In at least one instance, a digital control signal is configured to be converted to an analog input signal for the motor. In at least one instance, the one or more analog output signals are configured to be converted to digital signals which can be fed back into the control circuit and be utilized as inputs of the control circuit.

The control circuit is configured to initiate 15001 a drive stroke such as, for example, a staple firing stroke. In at least one instance, the drive stroke includes a closure stroke, a retraction stroke, and/or any portion of any stroke within a surgical instrument system. In at least one instance, the control circuit is configured to adjust one or more motor control parameters while the motor is not running, prior to a drive stroke, and/or after a drive stroke, for example. The motor control circuit is further configured to monitor 15002 one or more parameters of the motor system such as those disclosed herein. As discussed above, in at least one instance, the motor control circuit is configured to convert an analog signal of the one or more monitored parameters to a digital signal and feed the digital signal back into the control circuit. The motor control circuit is further configured to determine 15003 if one or more motor control parameters require an adjustment based on the one or more monitored parameters. Any suitable trigger and/or threshold can be employed such as those disclosed herein. In at least one instance, a load threshold is employed and, when the load threshold is exceeded, the control circuit adjusts 15004 one or more motor control parameters.

In an instance where a load threshold is triggered, for example, it can be determined that a section of stiff, or thick, tissue is being encountered by the firing member. In at least one instance, the control circuit adjusts one or more motor control parameters to power through the stiff tissue. In at least one instance, an oscillating signal is delivered to the motor causing the motor to repeatedly impact the tissue for a period of time in an effort to burst through the thick tissue. In at least one instance, a PWM signal is used to provide motor oscillation. In at least one instance, the motor oscillation involves a sequence of quick bursts of energy. In at least one instance, the control circuit is configured to move the firing member in a proximal direction prior to each burst of energy in an effort to increase the moment of inertia while impacting thick tissue. In at least one instance, a combination of pulse width modulation in addition to pulse amplitude modulation is utilized.

The width (time) of each pulse can be adjusted based on the one or more monitored parameters such as, for example, the magnitude of the load experienced by the firing member. Similarly, the amplitude (voltage) of each pulse can be adjusted based on the one or more monitored parameters such as, for example, the magnitude of the load experienced by the firing member. In various instances, the width of each pulse and/or the amplitude of each pulse are varied as the firing member is traversing thick tissue. In at least one instance, the firing member is oscillated in the manner described above for a period of time, paused, and oscillated again. In at least one instance, the duration of the oscillating motor operation can be dependent on the one or more monitored parameters. For example, when the load experienced by the firing member decreases below a predetermined load threshold, for example, normal firing member operation can resume. In at least one instance, a delay is employed by the control circuit so as to ensure the firing member is beyond the section of thick tissue, allowing the oscillating signal to power the firing member a predetermined distance beyond the moment that the load on the firing member falls below the predetermined threshold.

Figure 94:
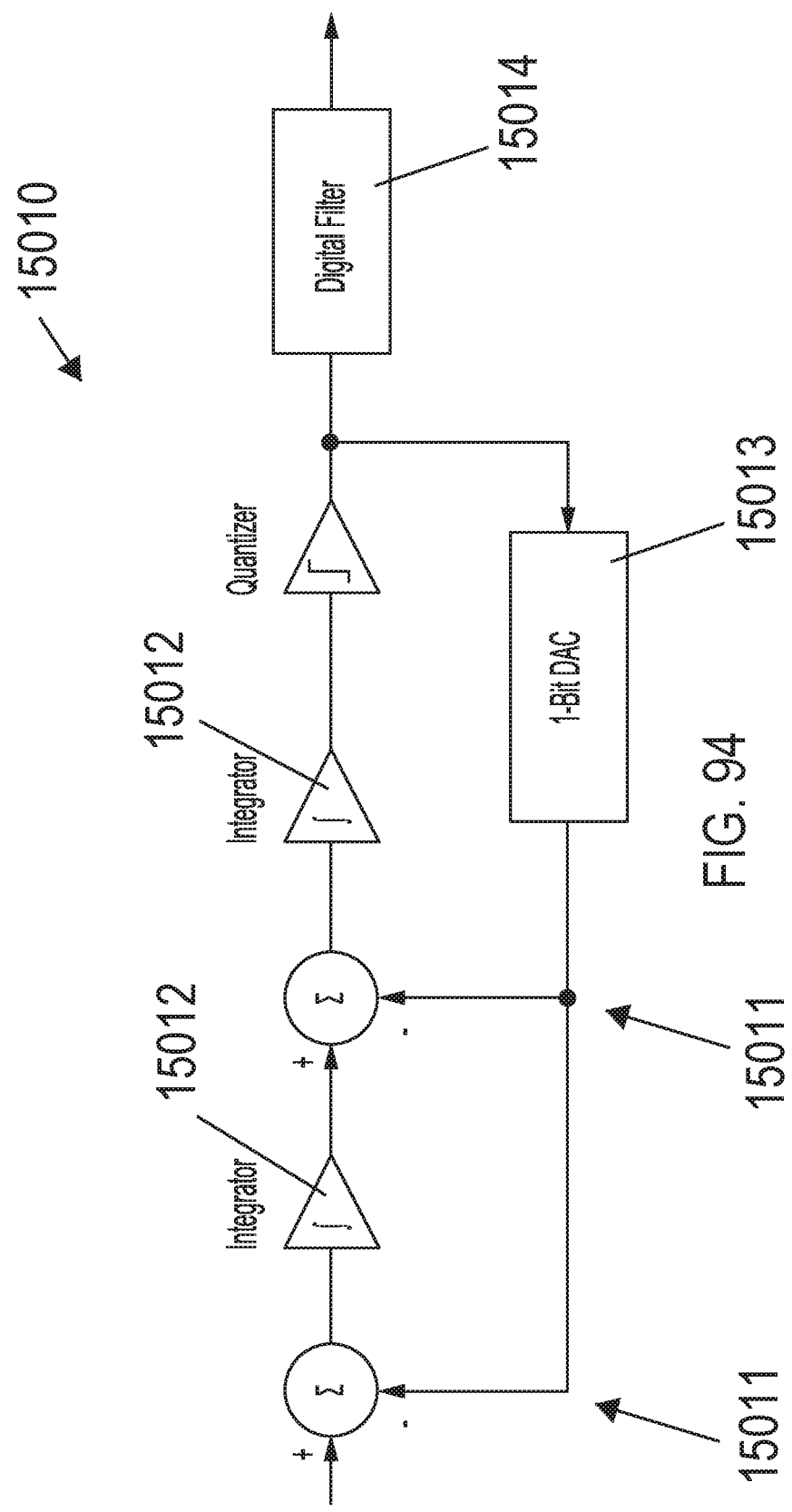
FIG. 94 is a control diagram of a delta-sigma modulator.

In at least one instance, a delta-sigma modulation based bit-stream controller is utilized in the control circuit to drive the motor. Such a controller can utilize an analog output and generate a digital control signal. One example of a delta-sigma modulator 15010 can be seen in FIG. 94. The delta-sigma modulator 15010 is a second-order delta-sigma modulator. As can be seen in FIG. 94, two feedback loops 15011 are utilized in addition to two integrators 15012. A 1-bit DAC 15013 is also used. Finally, a digital filter 15014 is employed to form a higher-resolution digital output.

Figure 95:
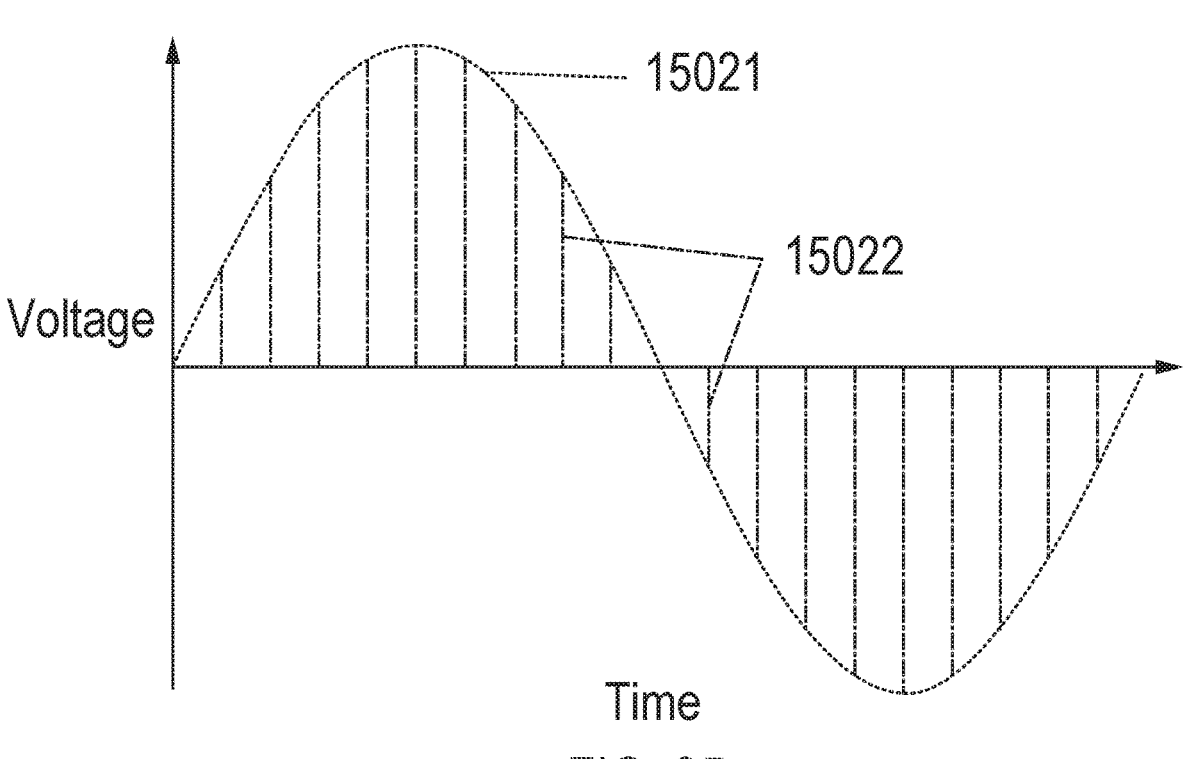
FIG. 95 is a graph of an analog signal and a resulting pulse amplitude modulation signal.

As discussed herein, pulse amplitude modulation can also be used by a control circuit to control the motor. FIG. 95 depicts a graph 15020 depicting a first signal 15021 and a pulse amplitude modulation signal 15022 representing the first signal 15021. Pulse amplitude modulation can supply varying voltage amplitudes for motor control. In at least one instance, a combination of variable output forces can be achieved by moving up and/or down on the torque-power curve of the motor. In at least one instance, duty cycle is also used in conjunction with pulse amplitude modulation to regulate voltage and/or power into the motor to control motor speed.

Figure 96:
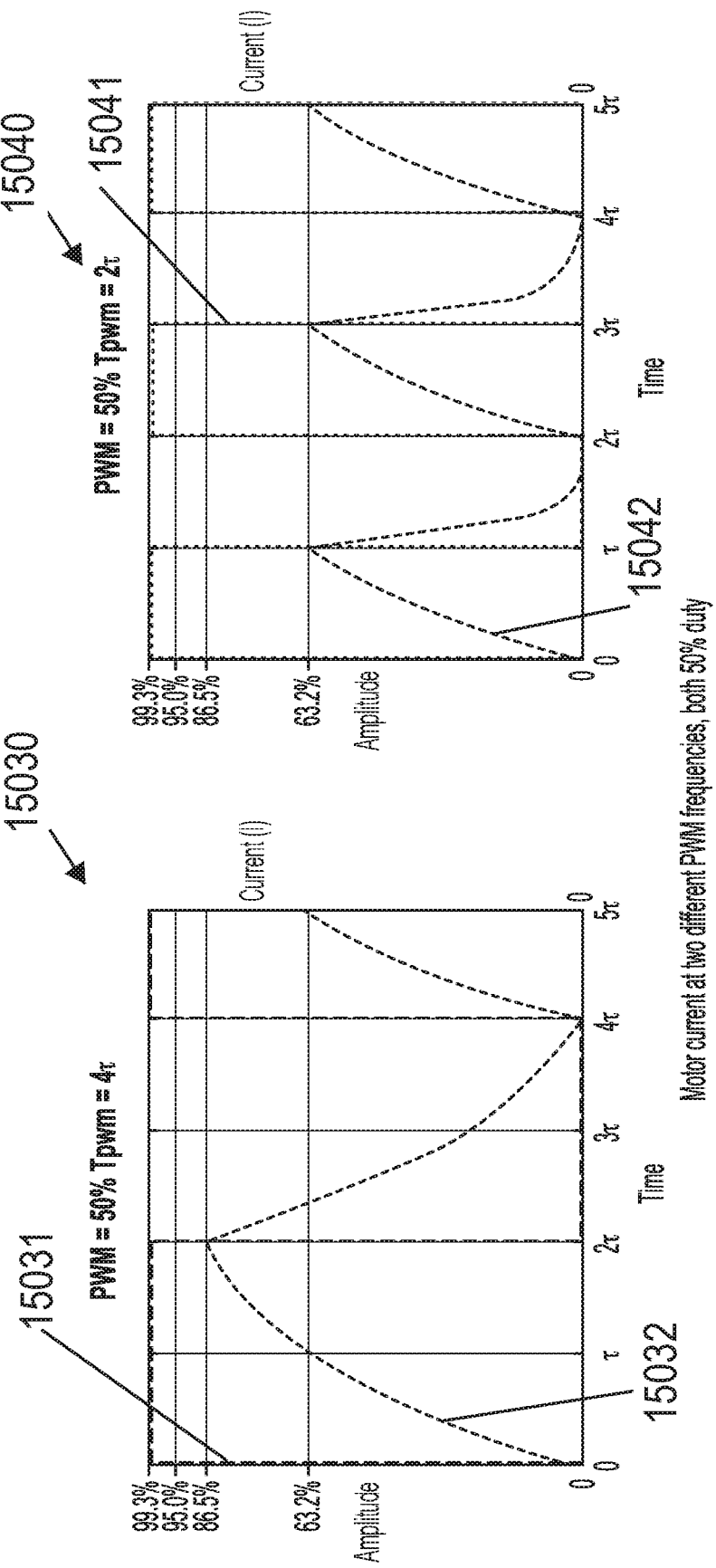
FIG. 96 is a comparison of motor current at two different pulse width modulation frequencies, wherein each signal includes the same duty cycle.

In various instances, pulse width frequency modulation is used to control the speed of a motor in a surgical instrument system. In at least one instance, a control circuit is configured to monitor the current through a motor. In addition to, or in lieu of, varying a duty cycle of a PWM signal, the control circuit can be configured to modulate the frequency of the pulse. The modulation of the frequency of the pulse can be adjusted according to one or more monitored parameters of a drive stroke, for example. In at least one instance, the control circuit is configured to adjust the frequency of the pulse to a first frequency upon detecting a first parameter threshold and a second frequency upon detecting a second parameter threshold. The first frequency is different than the second frequency and the first parameter threshold is different than the second parameter threshold. In at least one instance, a faster frequency may reduce current draw through the motor. FIG. 96 depicts two graphs 15030, 15040 of PWM signals 15031, 15041 at two different frequencies relative to current draw (I) through the motor. As can be seen in FIG. 96, the current draw 15032 is greater than the current draw 15042 for the same 50% duty cycle. In at least one instance, pulse frequency modulation can be beneficial in a brushless DC motor where multiple electromagnets are used in a frequency cascade. Speed of the brushless DC motor can be controlled with little to no impact to motor torque output.

Figure 97:
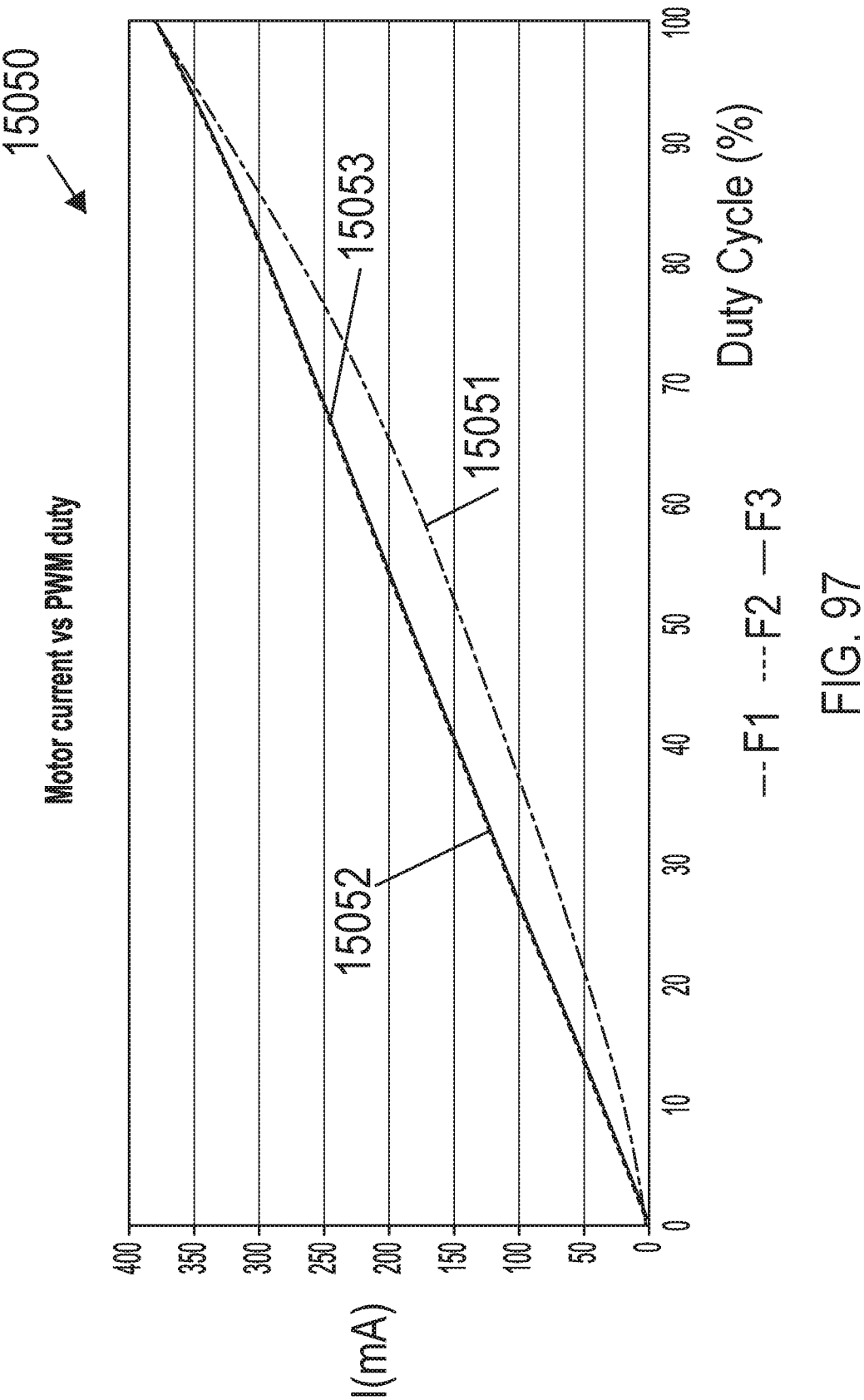
FIG. 97 is a graph illustrating motor current at different duty cycles and pulse width modulation frequencies.

FIG. 97 is a graph 15050 of various signals 15051, 15052, and 15053 depicting duty cycle of the signal relative to current draw through the motor at different frequencies F1 (the frequency of signal 15051), F2 (the frequency of signal 15052), and F3 (the frequency of signal 15053). In at least one instance, $F_1$ is greater than F2, and F2 is greater than F3. In at least one instance, a higher frequency can reduce current draw through a motor.

In various instances, a control circuit configured to control the motor of a motor system is configured to use pulse amplitude modulation and/or pulse width frequency modulation in conjunction with wait, or pause, periods. In at least one instance, the control circuit is configured to monitor current through the motor and adjust, based on the monitored current, a pulse width frequency and/or a pulse amplitude based on the monitored current. In at least one instance, the adjustment occurs after a wait, or pause, period. In at least one instance, the wait, or pause, period is predetermined. In at least one instance, the wait period varies. In at least one instance, the wait period depends on the magnitude of the monitored current. For example, a control circuit can set a wait period to a first time period after a first current is monitored and set a wait period to a second time period which is greater than the first time period after a second current is monitored which is greater than the first current. In at least one instance, such controlled wait, or pause, times can reduce the load experienced by a firing member during a firing stroke upon surpassing a predetermined level of current through the motor. Setting the magnitude of the time period corresponding to the level of current detected through the motor can allow for situational specific wait times where a longer wait period, for example, may not be necessary at a lower current threshold.

Figure 98:
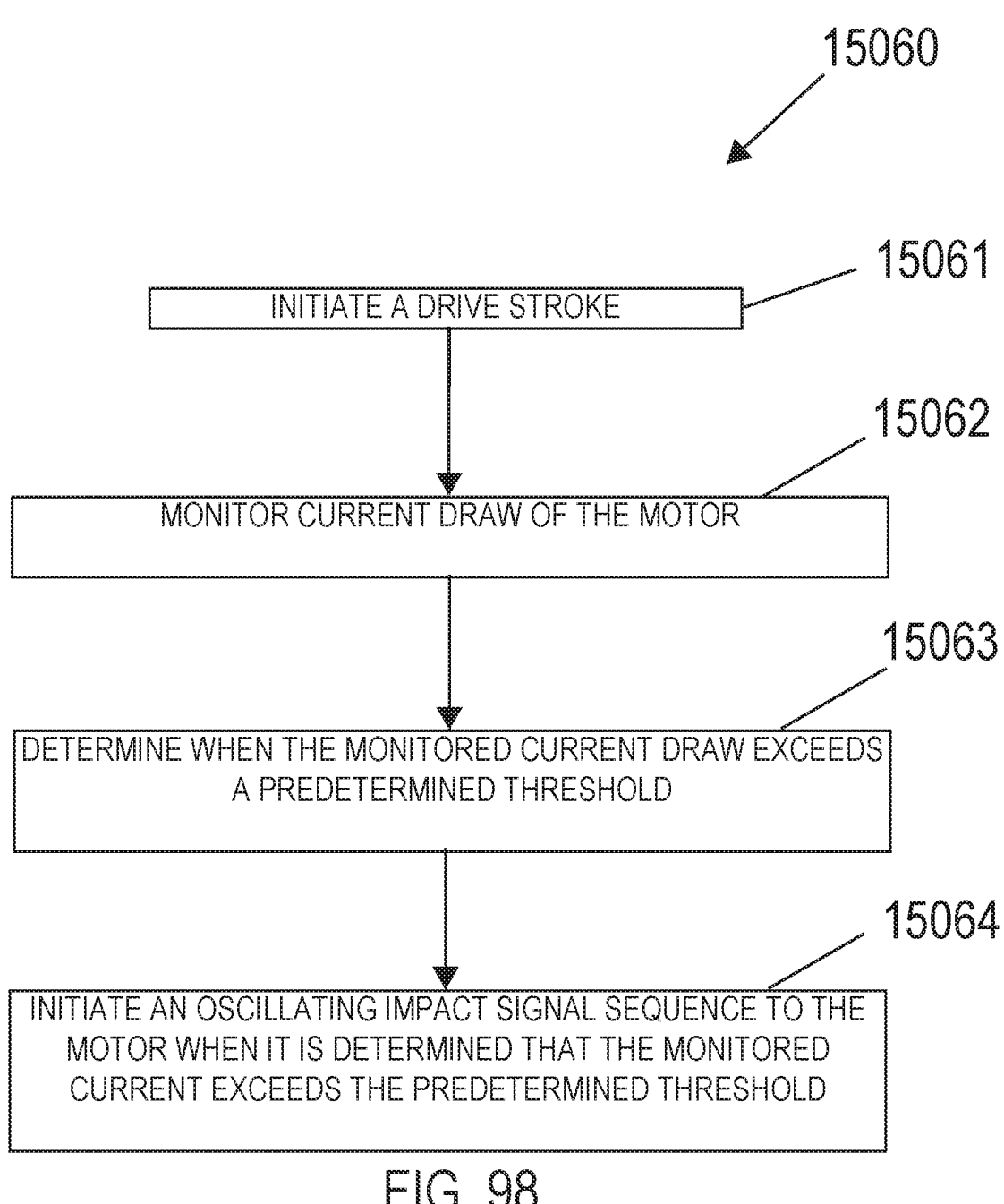
FIG. 98 is a logic flow chart depicting a process executable by a control circuit configured to control a motor system of a surgical instrument system, wherein the control circuit is configured to initiate an oscillating drive signal to a motor of the motor system upon detecting that current through the motor exceeds a predetermined threshold.

FIG. 98 is a logic flow chart depicting a process 15060 executable by a control circuit, such as the control circuit 1932 illustrated in FIG. 13 and/or the control circuit illustrated in FIG. 14, for example, configured to control a motor of a motor system of a surgical instrument system. The control circuit is configured to initiate 15061 a drive stroke of the motor system. Such a drive stroke can include a staple firing stroke of a firing member, for example. During the drive stroke, the control circuit is configured to monitor 15062 current draw of the motor. Any suitable monitoring method can be used such as, for example, utilizing a current transducer. The control circuit is configured to determine 15063 when the monitored current exceeds a predetermined threshold. The predetermined threshold can indicate an over-current situation where thick tissue, for example, has been encountered by the firing member thereby increasing the load on the firing member and, thus, the current draw by the motor. Upon determining that the predetermined threshold has been exceeded, the control circuit is configured to initiate 15064 an oscillating impact signal sequence to the motor.

In at least one instance, the oscillating impact signal sequence includes a digital motor control signal. In at least one instance, a pulse width, a pulse amplitude, and/or a pulse frequency is preselected. In at least one instance, a pulse width, a pulse amplitude, and/or a pulse frequency is selected upon determining that the predetermined current threshold has been exceeded. In at least one instance, the pulse width, the pulse amplitude, and/or the pulse frequency is selected based on one or more monitored parameters of the motor system such as, for example, the magnitude at which the current exceeded the predetermined current threshold, for example. In at least one instance, each pulse delivered to the motor can correspond to a distal impact motion of the firing member. In various instances, a reversing movement, or pulse, can be utilized for each distal pulse movement so as to allow the firing member a certain amount of distance to gain momentum in an effort to pass the thick section of tissue, for example. In at least one instance, the oscillating impact signal sequence further includes a pause period configured to allow for tissue to relax. In at least one instance, a predetermined number of distal pulse movements of the firing member occur prior to the pause period. In at least one instance, several pause periods can be used until the thick tissue is traversed by the firing member.

As disclosed above, a powered surgical stapling system is composed of multiple mechanical and electrical subsystems. The components may include, without limitation, an end effector composed of a first jaw and a second jaw, in which the first jaw is configured to include a staple cartridge and the second jaw includes an anvil configured to clamp one or more staples to a tissue grasped by the jaws when they close.

The end effector may also include a blade or tissue cutting edge capable of a reciprocating motion to sever the tissue once the one or more staples have been affixed to the tissue. The end effector may be mounted on a shaft assembly which may further include an articulation joint. The articulation joint may be configured to rotate about an articulation axis, thereby rotating the end effector about the articulation axis with respect to a longitudinal axis of the shaft assembly.

In some aspects, a user may cause the anvil to close on a tissue supported by the first jaw using a manual trigger mechanism. In an alternative aspect, the anvil may be closed on the first jaw by a drive train actuated by a motor energized by a motor power supply when the trigger mechanism is depressed. In some aspects, the reciprocating motion of the blade or tissue cutting edge may be driven by an electrically activated motor. In some other aspects, the articulation joint may be rotated either by the same electrically activated motor that drives the blade, or a separate motor. The motor may be controlled by a combination of activation switches and one or more motor controllers through a series of motor control signals.

Thus, as disclosed above, the powered surgical stapling device is composed of a number of high-precision mechanical components working together to effect the stapling and cutting of the tissue. In some sub-systems, mechanical components may work together to cause the blade to slide in a distal direction to cut tissue, and slide back to a home position once the cutting operation is completed. In another sub-system, mechanical components may work together to cause the articulation joint to rotate in a first direction and then back to a second position. In yet another sub-system, mechanical components may work together to cause the anvil to close on the first jaw, thereby compressing and stapling a tissue and then cause the anvil to move away from the first jaw after the tissue has been compressed and stapled. These sub-systems may require the interaction of multiple mechanical linkages (drive-trains) with a motor with or without a gear reducer assembly. One or more sensors may be used to detect the types and speeds of the motions of the components of the drive-trains for use as feed-back to a motor controller.

The motor controller may include one or more algorithms—implemented either in hardware, software, or firmware—designed to actuate the drive-trains in a manner responsive to the surgical environment. In one aspect, the surgical environment may reflect the type or thickness of a tissue grasped, stapled, and cut in the jaws. In another aspect, the surgical environment may reflect obstructions around the articulation joint. In yet another aspect, the surgical environment may reflect the thickness of a tissue being compressed and stapled by the anvil and the first jaw. The motor controller should be configured to adjust the motor control signals so that the activation of the motor or motors may be optimized for the task at hand.

Additionally, the powered stapling system may be designed to proactively make small performance corrections to negate any performance deficiencies of a sub-system, such as the tissue cutting sub-system, the jaw-clamping sub-system, or the articulation sub-system. These adjustments may be gauged against past historical data from pervious cycles or anticipated for subsequent cycles based on the trending performance. These type of enhancements may normalize the performance of the device over repeated uses or normalize manufacturing deviations in performance between devices.

In the operation of various DC motors, the motor operation may be controlled by a pulse-width modulation (PWM)

system A PWM system generates a signal based on a base frequency defined by a time period in which current pulses are supplied to the motor. Each current pulse occurs over some portion of the time period of the base frequency and may represent any percentage of the time period from 0% (no current supplied over the time period) to 100% (current supplied over the entire time period). The speed of the motor may depend on the portion of the time period during which the current is supplied. Hence, the motor speed may be modulated by the pulse width of the current over the time period.

Typically, the PWM pulse train is composed of square-wave signals, in which the current pulses are either off or on at a fixed current for the duration of the pulse. The motor may actuate during the on-current phase, and may be unactuated when the current is off. This rotational motion may be transferred to a gear reducer assembly mechanically coupled to the motor. The gear reducer assembly is then mechanically coupled to the components of one or more drive trains, associated, for example, with a rotational motion of the anvil, a transverse motion of the tissue cutting blade, or rotational motion of an articulation joint. Under ideal conditions, the motions associated with the gear reducer assembly and the associated components of the drive trains would move synchronously with the motion of the motor and with the square pulse train of the PWM motor control signal Thus, all of the drive train components may move during the on-current phase, and may be unactuated when the current is off.

However, non-idealities may exist in the notions of the gear reducer assembly and the drive train components. Such non-idealities may include, without limitations, gear back-lash, stiction at gear interfaces, friction at the interfaces of smooth components, and bowing of elongated components such as a firing member, an articulation system, or a firing shaft portion. It may be further recognized that such mechanical non-idealities may change over time reflecting wear and use of the mechanical components. As a result, the motions of the gear reducer assembly and the drive train components may not follow the sharp rise and fall of the current pulse train. It would therefore be useful to modify the shape of the PWM current pulses so that the mechanical components would be more aligned with the PWM current output. In this manner, the mechanical coupling of the motor to the overall system response may be accomplished by adapting the motor control signal to system configurations or physical properties of the parts of the drive train. Such control system adaptation may compensate for the previously identified variances in the surgical stapling system from the nominal, ideal, or average system.

Adjustments may be made to the motor control algorithm based on detection of individual device drive train properties. The powered surgical stapler system may monitor system drive train reaction relative to input motor control signals and adjust the input control signals based on the individual system response relative to pre-established baseline performance. In some non-limiting aspects, the monitored responses could be frictional loss, acceleration or deceleration responses to a stepped input signal, PID control variation, harmonics of the system, noise, or force/speed of the motor. In some aspects, the adaptation to the motor control algorithm may include modifications of the PID control parameters, triggering delay of dynamic braking, level or function window around the triggering thresholds, power, current, voltage, or PWM signals.

Figure 99:
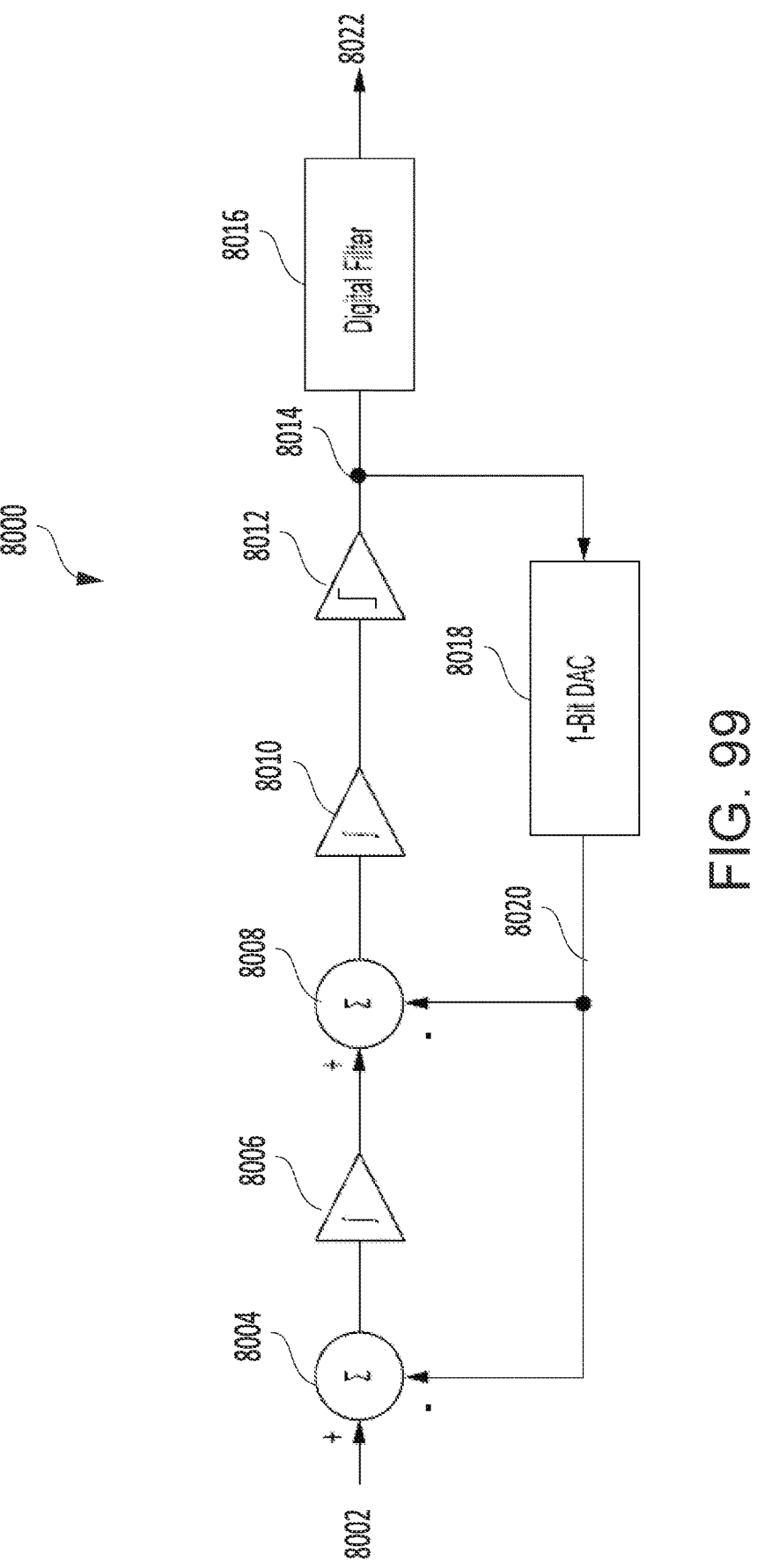
FIG. 99 illustrates a block diagram of one example of a delta-sigma modulation (DSM) based bit-stream controller according to one aspect of this disclosure.

In some aspects, variation to the waveform of the PWM signal (either as current or voltage to the motor) may include the use of a delta-sigma modulation (DSM) based bit-stream controller to a drive a motor. The DSM may essentially be configured as an analog output to generate a quasi-PWM signal in hardware. FIG. 99 illustrates a block diagram of one example of a DSM controller 8000. In the example of the DSM controller 8000, a signal input 8002 enters the positive branch of a first summer 8004. The output of the first summer 8004 is sourced to a first signal integrator 8006. The output of the first signal integrator 8006 is used in the positive branch of a second summer 8008. The output of the second summer 8008 is integrated by second signal integrator 8010. The output of the second signal integrator 8010 becomes the input of a comparator 8012. It may be understood that the signal input 8002, and the outputs of the first summer 8004, first signal integrator 8006, the second summer 8008, and the second signal integrator 8010 are all analog signals. The output of the comparator 8012 is a digitized signal ranging from a first (low) voltage to a second (high) voltage. The output of the comparator 8012 becomes an input to both a digital filter 8016 and a 1-bit digital-to-analog converter (DAC) 8018. The DAC output 8020 is used in a negative feedback manner at the negative branches of both the first summer 8004 and the second summer 8008. The output 8022 of the digital filter 8016 may be used as a motor control signal.

Figure 100:
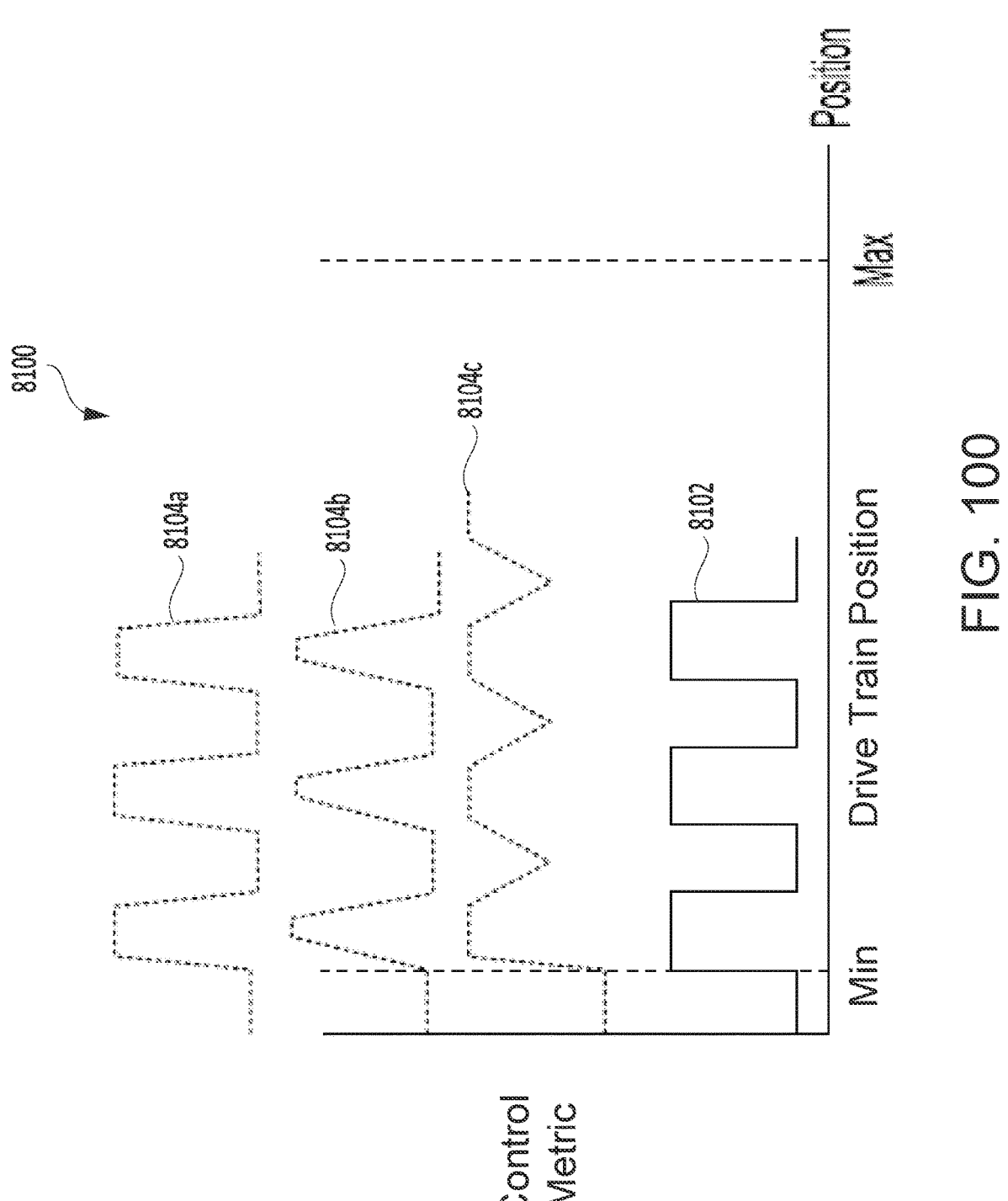
FIG. 100 illustrates a graph of irregular pulse-width modulation (PWM) motor control signals according to one aspect of this disclosure.

The DSM signal may be used to control the waveform shape of a motor control signal to compensate for changes in motor, gear, or drive train performance due to friction, changes in component tolerance, component fit, or wear. The adjusted motor control signal may be characterized as an irregular PWM which may be used to simulate a ramped response (instead of traditional sinusoidal) to drive a motor. FIG. 100 illustrates a graph 8100 of some irregular PWM motor control signals compared to a desired drive train component response. The y-axis of the graph 8100 represents any control metric such as component speed, motor signal amplitude or current, or similar. The x-axis of graph 8100 represents the motion of the drive train component from its minimal position (Min) to its maximum position (Max). The idealized waveform 8102 is a square wave of drive train component motion corresponding to a square wave current input to the motor. Irregular PWM wave signals 8104a, 8104b, and 8104c may overcome the non-idealities of the drive train component motion (due to friction, stiction, and other effects disclosed above). As a result, the irregular PWM wave signals 8104a, 8104b, and 8104c may result in better control of the drive train component motion.

In some aspects, the irregular PWM wave signals may be used intermittently in addition to the regular PWM wave signals. For example, the irregular PWM wave signals may be used only when the drive train components are moving within a portion of their complete range of motion. Thus, the irregular PWM wave signal may be used when a drive train component corresponds to a sub-system operating within a lockout zone and not when the sub-system is operating within the rest of the range of motion. In one non-limiting example in the last 0.02" of closure tube stroke of a tissue cutting blade with respect to the first 0.23".

Alternatively, the irregular PWM wave signals may be used throughout the entire range of motion of the drive train components. Additionally, the pulse shape of the irregular PWM wave signals may be adjusted over time. Non-limiting examples of pulse shape changes may include adjusting a leading edge of an irregular PWM wave signal differently than a trailing edge of the signal (for example, a triangular rising edge versus a square trailing edge.) Such different edge shapes may work to compensate against frictional loss at the beginning of the motion versus working with frictional losses at the end of the motion. Thus, the leading edge of the signal describes the rising profile of the "on" time of the motor, while the trailing edge of the signal describes the falling profile from the "on" time of the motor. These asymmetric adjustments to the motor signal profile may be used for tissues that may respond to varies types of leading and trailing edge motions of the tissue cutting blade. The powered surgical stapling system may detect the slope of the leading or trailing signals which indicate the system response based on the set profile. The powered surgical stapling system may then adjust the next profile to react to the system and provide increased control performance to benefit patient outcomes.

FIG. 101 depicts a flow chart 8200 of a method of controlling a motor in a powered surgical stapling system based on changing a shape of a motor control signal. A motor controller may apply 8202 a first motor control signal, for example a square wave PWM control signal. The motor controller may then receive 8204 data associated with an operation of one or more components of the drive train. Such data may include, without limitation, a position, a speed, an acceleration, or a deceleration of one or more components of the drive train throughout their respective motions. Such data may be obtained from sensors configured to detect these data, such as positional sensors. The motor controller may compare 8206 the data associated with the operation of the drive train to baseline data associated with the operation of the drive train. Such baseline data may be acquired either from manufacturer testing or acceptance trials, or may be obtained from the powered surgical stapling system during its initial use. The motor controller may apply 8208 a second motor control signal based on the comparison. The second motor control signal may differ from the first motor control signal in a pulse train shape from the first motor control signal. The change in pulse train shape may reflect a change in pulse amplitude, a change in a pulse leading edge, a change in a trailing edge, or other change in the pulse train shape. As discussed above, in some aspects, such a change may result in an irregular PWM control signal.

In some aspects, the data associated with an operation of the drive train may include data associated with a frictional loss of the drive train, an acceleration response of the drive train, a deceleration response of the drive train, or mechanical harmonics of the drive train.

In some additional aspects, applying the first motor control signal may include using a delta-sigma modulation based bit-stream controller to generate the motor control signal. In alternative aspects, applying the second motor control signal may include using a delta-sigma modulation based bit-stream controller to generate the motor control signal.

In yet another aspect, applying the second motor control signal may include adjusting a PID control parameter, triggering a delay of a dynamic braking function, changing a level or a function window around a triggering threshold, adjusting a power applied to the motor from the motor power supply, or adjusting a pulse-width modulation signal applied to the motor. In a non-limiting example, adjusting a pulse-width modulation signal applied to the motor may include adjusting a shape of the pulse-width modulation signal rising portion, maximum amplitude portion, or falling portion.

In some further aspects, it may be useful to characterize one or more functions of the sub-systems of the powered surgical stapling system during operation. Such characterizations may be useful if a fault condition or an anomalous behavior is detected during the course of a surgical procedure. An example of a fault condition may include, without limitation, a stall condition in the operation for example of a tissue cutting knife, or in a rotation motion about an articulation joint. The motor control signal may be reduced under load, and a perturbation signal at a known frequency may be applied to the motor in order to extract drive train loading information when a motor is in a stalled or full torque condition. This perturbation signal may be introduced to the regular motor control signal during the operation of the drive trains in order to interrogate combined sub-system component loss.

One type of perturbation signal may be characterized as a "load dithering" signal of the system. A "dithering" signal may be one which may cause a sub-system component to alternately operate in a forward and reverse direction at a frequency higher than a standard frequency of motion. The motor controller may use this signal to derive loading information of the system based on the motor operations. "Load dithering" or load fluctuation could be used to determine the amount of current used by the motor, and therefore characterize the load on the drive train. Such motor loading fluctuation may be used while the drive train is moving to also interrogate combined drive train component loss (for example, how fast the entire drive train slows when the motor load is reduced by a predetermined amount). Additionally, inertial aspects of the drive train may be determined. An example of the inertial aspects may include how fast the system re-accelerates given a known motor signal input power from an initial slower speed to a pre-set higher speed. The dithering signal may be applied when the drive train is driven into a portion of the stroke in which the system is unable to move. Exemplary conditions resulting in stall conditions may include driving the tissue cutting blade into a lockout tab or into the fully retracted-proximal—position. Similarly, the inertia of the tissue cutting blade sub-system drive train may be characterized in the portion of the tissue cutting blade sub-system drive train motion where there is not additive loss, for example at the first 0.150" of the drive train travel prior to engagement with the anvil cam while the tissue cutting blade remains in the anvil pocket. Analysis of the response to the dithering signal under such conditions may help characterize motor stall conditions, and may be used to update motor and/or drive operational calibration.

As disclosed above, a perturbation signal may be imposed on a typical motor control signal in order to characterize the operation of one or more sub-systems of the powered surgical stapling system. A "dithering" signal has been disclosed above. Another type of signal may be a "chirp" signal. A chirp signal may be considered as a short duration electrical signal in which the signal frequency increases and/or decreases over time. A chirp signal may be used to characterize a system response over the range of frequencies comprising the chirp. As with the dithering signal, the chirp signal may be overlaid on the motor control signal during operations of the motor. Alternatively, the term chirp is used interchangeably with a frequency swept signal. The change in frequency arising from the chirp signal may be coupled with the PWM motor control signal generated by the motor controller in order to interrogate differences of the motor output at different speed and torque performance levels. The response of the motor may allow a diagnosis of the system stability and mechanical elements of the drive system over a range of frequencies. A spectrum analysis of the motor response, such as speed, acceleration, deceleration, or torque may be monitored for to determine, for example, inertia, damping, losses, backlash, and tolerance slope with a threshold of the return signal being used to determine if any adjustments to the motor control signal are necessary. In some aspects, the dithering signal may be considered a type of chirp signal.

Figure 102:
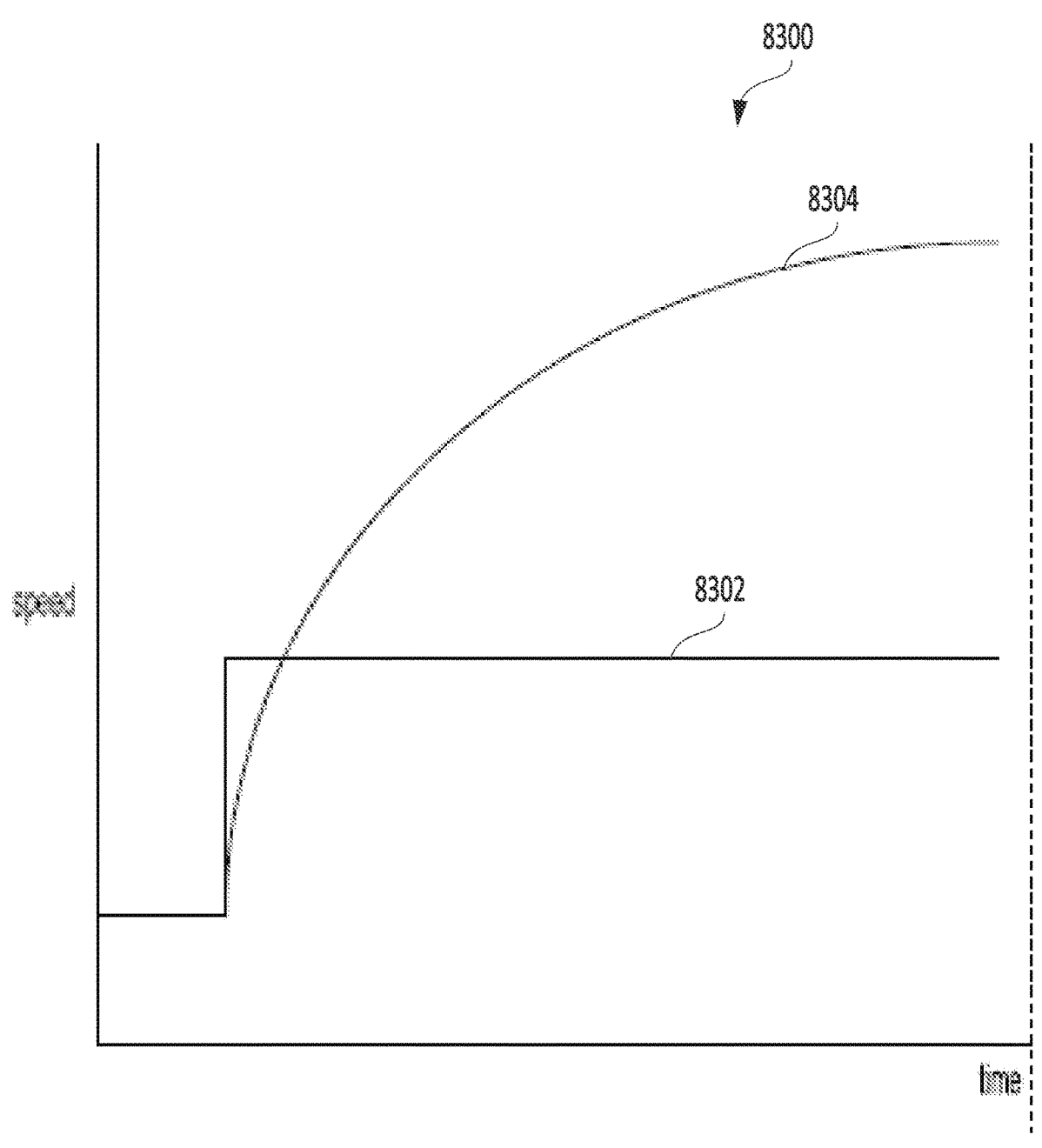
FIG. 102 illustrates a graph of a response of motor speed to the application of a step-function signal over time according to one aspect of this disclosure.

In another aspect, the response of a motor or drive train of a powered surgical stapling system may be determined by the application of a step-function signal to the motor. A step-function signal may be used to characterize motor response latency to improve the estimation of a future input speed target. The motor response to the step-function may be measured as well as the response of any components of a drive train in mechanical communication with the motor. In one non-limiting example, changes in the motor or drive train component speed over a time period after the step-function signal is applied may be measured. FIG. 102 illustrates a graph 8300 of a response of motor speed 8304 to the application of a step-function signal 8302 over time. In another example, a measurement of a time delay in response to the step-function signal of the motor and/or drive train components may also be analyzed. The time delay of the response of the motor to the applied step-function signal may characterize the electrical dynamics of the motor such as the resistance and/or inductance of the motor windings. The motor winding inductance may slow down the overall response of the system. Additionally, the motor mechanical dynamics may be assessed, such as rotor inertia and/or friction. An analysis of the motor response to the step-function signal may also indicate that the motor shaft is not perfectly straight, which may lead to additional friction to the system. A non-linearity of the motor shaft may also impact the inertia of the system.

In some aspects, the motors used in the powered surgical stapling system may include DC brushed motors. The brushes are used to transfer energy from the motor control signal to through a motor commutator. A commutator may be a rotary electrical switch that periodically reverses the current direction between the rotor and the external circuit. The electrical brushes may press against the commutator, making sliding contact with successive segments of the commutator as it rotates. The windings (coils of wire) on the armature are connected to the commutator segments. Variations in the brush pressure can cause variations to the friction of the system. Further, changes in the shape of the motor brushes may change the amount of current supplied to the commutator. Additionally, changes in brush shape may increase the friction between the brushes and the commutator, thereby effecting motor performance. In one aspect, the contact between the brush and the commutator may be intermittent ("brush bounce"). As a result of brush bounce, the brush may partially or entirely fail to make electrical contact with the commutator. As a result, current flow to the commutator may be reduced, modulated, or even interrupted. Thereby resulting in inconsistent motor torque generating capability.

Figure 104:
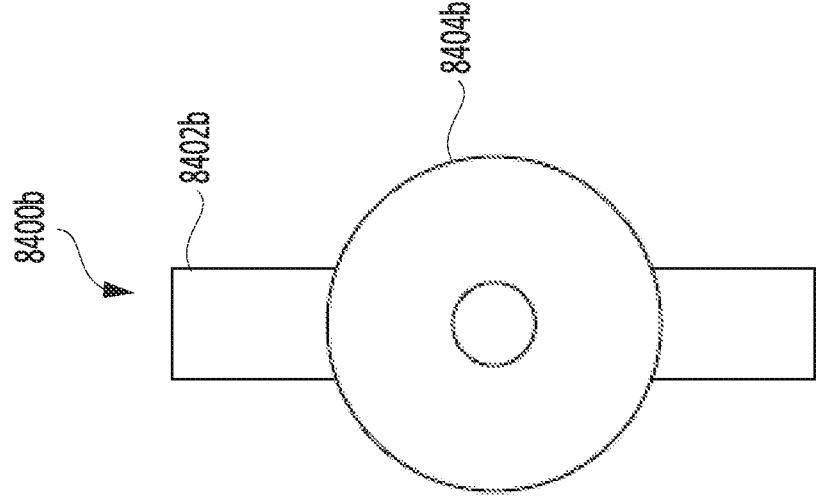
FIG. 104 illustrates a DC brushed motor having worn brushes according to one aspect of this disclosure.
Figure 103:
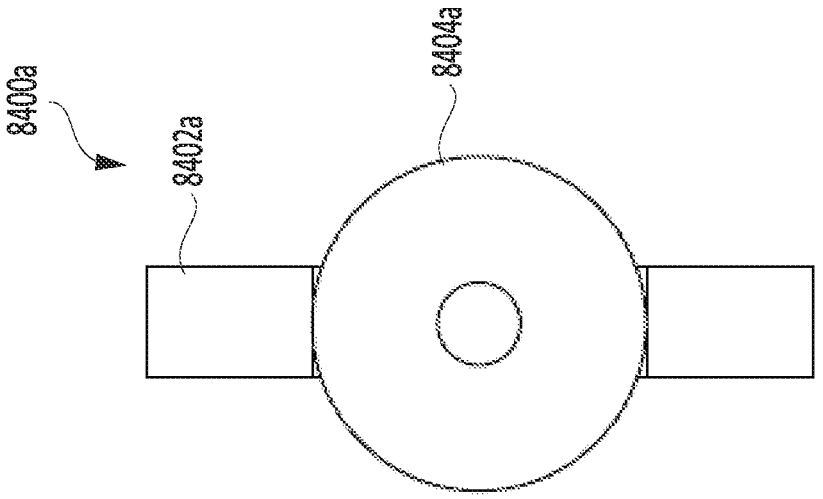
FIG. 103 illustrates a DC brushed motor having un-worn brushes according to one aspect of this disclosure.

FIGS. 103 and 104 illustrate DC brushed motors including their brushes and commutators. DC brushed motor 8400a includes an un-worn brush 8402a in contact with a commutator 8404a. DC brushed motor 8400b includes a worn brush 8402b in contact with a commutator 8404b. It can be observed that the un-worn brush 8402a is flat and makes a single point of electrical and mechanical contact with the commutator 8404a. The single point of contact is the only point of contact permitting the current to flow through each of a successive segment of the commutator 8404a as it rotates. The worn brush 8402b is rounded and can make multiple electrical and mechanical contacts with the multiple segments of the commutator 8404b as it rotates. It may be recognized that the multiple contacts may result in the worn brush having electrical contact with multiple successive segments of the commutator 8404b simultaneously. This may impact the smoothness of rotor turning.

In one aspect, powered surgical stapling system may include a motor gear reducer assembly in mechanical communication with a motor shaft. Before being assembled into the surgical stapling system, the motor gear reducer assembly and its associated motor may be tested using, for example, a step-function input, and characteristics related to the motor with motor gear reducer assembly operation may be collected. Such initial motor with motor gear reducer assembly data may include the output speed, current to run at no load, and numerous other electrical parameters of the motor. Mechanical aspects like gear backlash and varying frictions during operation can also be collected. Once assembled into the device, the motor with motor gear reducer assembly may be integrated into the larger mechanical system. By applying power to the motor with motor gear reducer assembly and re-running the same characterizing tests—in both the forward and reverse directions—information about the system including the motor can be characterized. A comparison of the initial motor with motor gear reducer assembly data against the data obtained from the motor with motor gear reducer assembly in the complete surgical stapling system after use can shed light on the overall system frictional requirements. In some aspects, the characterized frictional response of the motor with motor gear reducer assembly may differ between the forward and reverse directions. It is understood that a cutting blade moving in the forward direction may encounter additional friction due to the interaction of the tissue cutting blade and the tissue. However, when the tissue cutting blade operates in the reverse direction, away from the tissue, it is expected that the blade motion friction should be reduced since there is no tissue operating against the tissue cutting blade. The initial forward and reverse frictional response of the tissue cutting blade in an unused device may be used to set the threshold values for the operation of the tissue cutting blade. In this manner, a user of the powered surgical stapling system may be alerted to additional friction due to the tissue being cut, and not to friction inherent in the tissue cutting blade sub-system.

It may be generally understood that initial operations of the various sub-systems of a powered surgical stapling system may be used to gather initial data about the motor, motor gear reducer assembly, and drive train components. The motor may be coupled to each of the separate sub-systems—such as the articulation sub-system and the tissue blade sub-system—to characterize motor and/or motor gear reducer assemblies. The motor may be operated at various speeds and directions to characterize their operations when coupled to the sub-systems. Parameters that can characterize the motor and/or motor gear reducer assembly may include, without limitation, backlash and latency from the receipt of the motor control signal to the operations of the mechanical components. By characterizing these timings, the motor controller algorithms may be adjusted to minimize these latencies.

Figure 105:
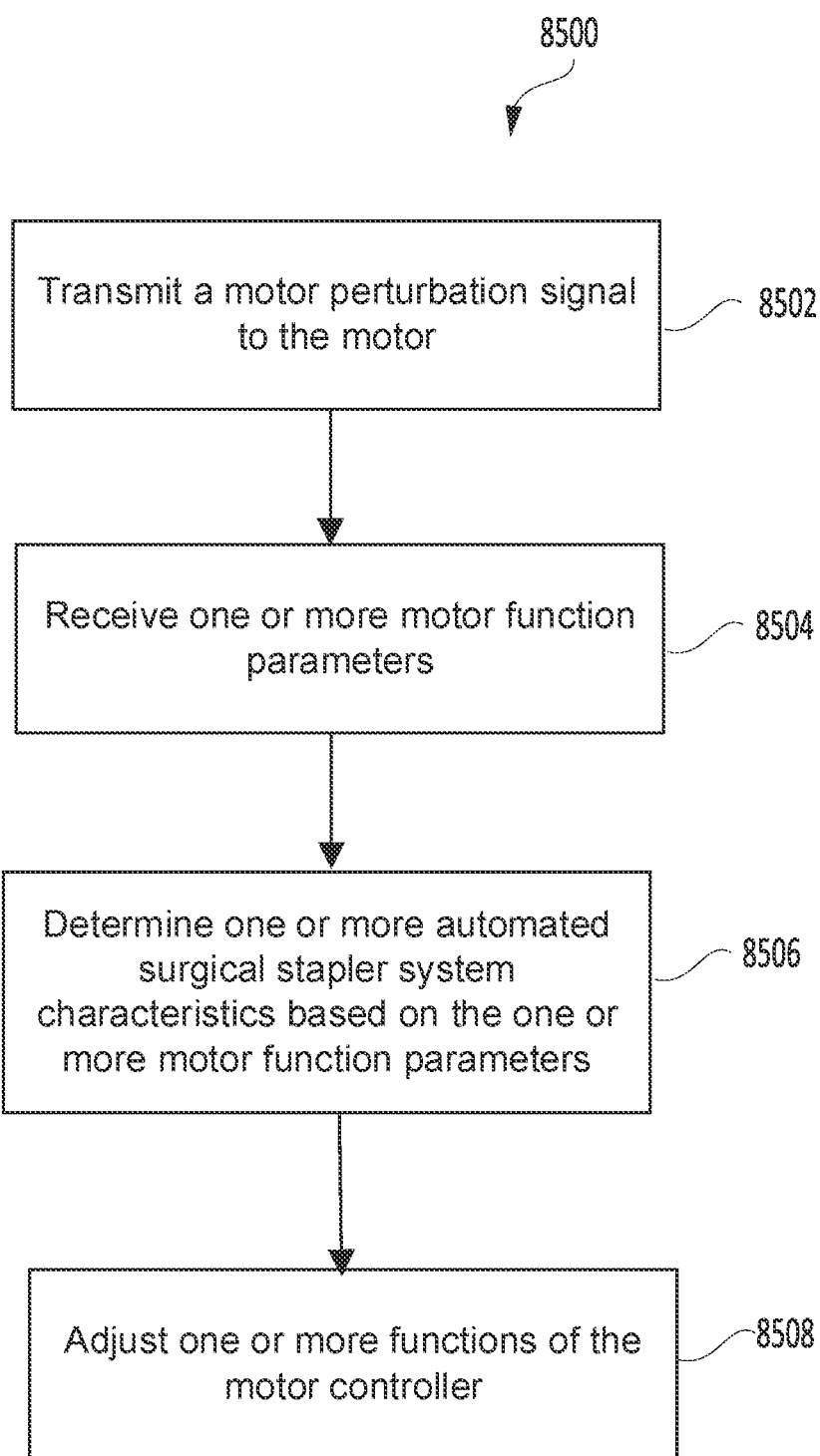
FIG. 105 is a flow chart of a method of characterizing a motor in a powered surgical stapling system, according to one aspect of this disclosure.

FIG. 105 depicts a flow chart 8500 of a method of characterizing a motor in a powered surgical stapling system. The motor controller may transmit 8502 to the motor a motor a perturbation signal. In one example, the perturbation signal may include a step signal. In another example, the perturbation signal may be transmitted to the motor along with the operational motor control signal. In some examples, the perturbation signal transmitted with the operational motor control signal may include a chirp signal or a dithering signal. The motor controller may receive 8504 one or more motor function parameters. Non-limiting examples of the motor function parameters may include a motor latency parameter, a motor frequency dependent torque parameter, or a motor current draw parameter. The motor controller may determine 8506 one or more automated surgical stapler system characteristics based on the one or more motor function parameters. Non-limiting examples of the automated surgical stapler system characteristic may include a system friction, a system inertia, a system backlash, or a system latency. The motor controller may then adjust 8508 one or more functions of the motor controller. Examples of motor controller functions that may be adjusted in response to the system characteristics may include, without limitation, a motor drive pulse-width modulation phase, a motor drive frequency, or a motor drive current.

In some aspects, the motor or motors of a powered surgical stapling system may include stepper motors. Stepper motors are digitally controlled brushless DC motors that divide a full rotation of the rotor into a number of equal steps. The stepper motor includes a number of electromagnets arranged around a central rotor. As each electromagnet is energized, the rotor rotates a fixed amount. When the electromagnets are energized in turn, for example by a series of pulse trains, the rotor turns synchronously with the energized electromagnet. A stepper motor can be characterized according to several different torque values. In one aspect, a pull-in torque may represent the amount of torque in which the motor may move the load without acceleration. Generally a pull-in torque-speed curve illustrates the speeds at which the motor may start, stop and reverse without losing synchronicity with the incoming pulses. A pull-out torque may relate to the amount of torque the motor may dynamically produce at various speeds. Generally this torque may be represented in conventional torque-speed curves. If the motor exceeds this torque, it loses synchronicity with the incoming pulses and stalls. A holding torque may represent the amount of external torque which must be exerted on the motor shaft when the motor is at full rated current and is at rest (zero speed). This condition may be met when only a single electromagnet is energized, and the motor does not move. This is a static torque and is generally not depicted on a torque-speed curve. The holding torque is generally about 20% higher than the low speed torque of a dynamic torque-speed curve. Finally, a detent torque represents the amount of torque required to move the motor rotor when the motor is not energized. This condition is met when no current passes through the winding and the motor is at rest.

Figure 106:
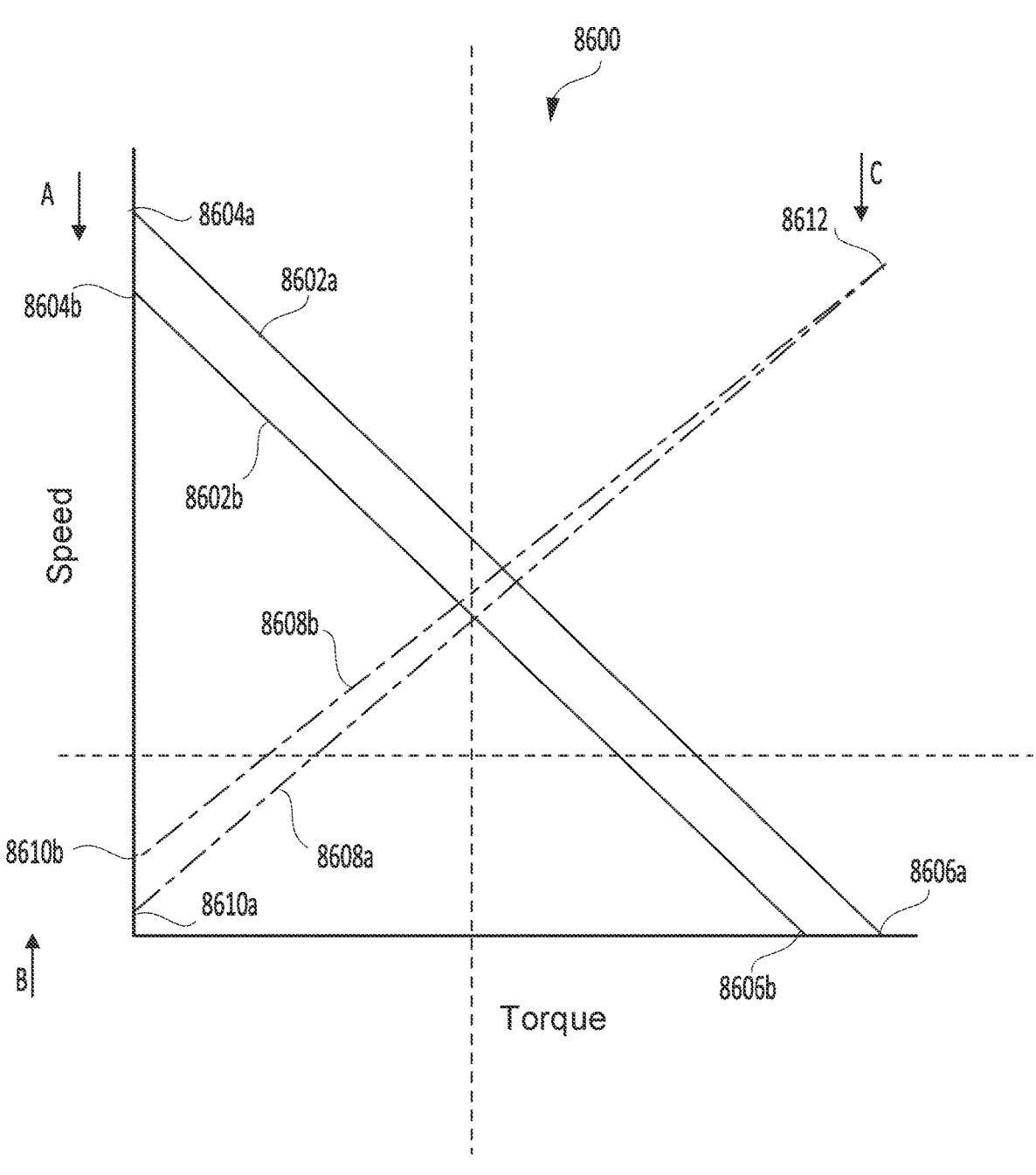
FIG. 106 illustrates a graph of stepper motor speed versus torque curves according to one aspect of this disclosure.

FIG. 106 is a graph 8600 that illustrates various speed versus torque curves for a stepper motor that may be used in a powered surgical stapling system. Curves 8602*a* and 8602*b* depict maximum speed versus torque curves for a stepper motor under various conditions. As discussed above, curves 8602*a* and 8602*b* may represent the stepper motor pull-out torque. An initial maximum speed versus torque curve 8602*a* illustrates a maximum speed attainable by the motor under various load conditions. Under a no-load condition 8604*a*, the motor can attain its maximum speed. As the load increases—requiring the motor to generate more torque—the maximum speed may decrease until the motor attains a stall torque 8606*a*. The stall torque 8606*a* occurs when the motor is unable to move due to the load. The initial speed versus torque curve 8602 may be obtained from a motor operating alone. As an example, the initial speed versus torque curve 8602 may be a speed versus torque curve supplied by the motor manufacturer. Parameters or data related to the initial speed versus torque curve 8602 may be obtained from the manufacturer and stored in a memory unit of the motor controller. Alternatively, the parameters or data related to the initial speed versus torque curve 8602 may be obtained through independent measurements of the motor alone or with the motor gear reducing assembly. The data may be stored directly in the memory unit of the motor controller or may be read from an external memory device, such as from a chip or thumb drive, or may be down-loaded from a server from a remote communication system.

Once the motor is installed in a powered surgical stapling system, the motor is required to move the various components of the drive trains. As the components of the drive trains have various frictional characteristics, the speed versus torque curve 8602*b* of the complete mechanical sub-system may be shifted down (arrow A) to lower values. Further, as the powered surgical stapling system is used, additional friction and wear may develop in the drive train components further reducing the speed versus torque curve 8602*b*. It may be understood that the motor and/or motor gear reducer assembly may suffer from wear, including, as one non-limiting example, loss of motor shaft, rotor, or gear reducer assembly concentricity. All of these effects may further reduce the speed versus torque curve 8602*b*. Reduction of the speed versus torque curve 8602*b* may result in both a lowering of the maximum speed under no-load condition 8604*b* and the maximum torque achievable (as measured at the stall torque 8606*b*).

Curves 8608*a,b* represent minimum speed (or current) versus torque curves. These curves illustrate the minimum speed or current the motor requires to generate a specific amount of torque. Curve 8608*a* may represent the minimum speed or current required to generate torque for a motor alone or only with the motor gear reducer assembly. Under no-load conditions, 8610*a*, the motor may require a minimum speed or current to overcome its internal resistance. In some aspects, the no-load minimum speed or current 8610*a* may represent the speed or current required to overcome the detent torque. The minimum speed or current able to generate the maximum torque 8612 may be related to the stall torque.

Once the motor is installed in a powered surgical stapling system, the motor is required to move the various components of the drive trains. As the components of the drive trains have various frictional characteristics, the minimum speed or current versus torque curve 8608*b* of the complete mechanical sub-system may be shifted upwards (arrow B) to higher values. Thus, even under no-load conditions 8610*b*, the minimum speed or current required to overcome the complete drive train resistance will be increased over the no-load condition 8610*a* of the minimum speed or current versus torque curve 8608*a* of the motor alone. Further, as the powered surgical stapling system is used, additional friction and wear may develop in the drive train components further increasing the minimum speed or current versus torque curve 8608*b*. It may be understood that the motor and/or motor gear reducer assembly may suffer from wear, including, as one non-limiting example, loss of motor shaft, rotor, or gear reducer assembly concentricity. All of these effects may further increase the minimum speed or current versus torque curve 8608*b*. An increase of the minimum speed or current versus torque curve 8608*b* may result in an increase of the minimum speed or current under no-load condition 8610*b* although the minimum speed or current at maximum torque 8612 may not be affected. However, the minimum current during motor use may result in motor coil heating. As the coils heat, their electrical resistance may increase, thereby reducing the amount of current through the motor windings. The reduction of motor current due to temperature-dependent changes in winding resistance may result in a decrease in the minimum speed or current at maximum torque 8612, as indicated by arrow C.

Figure 107:
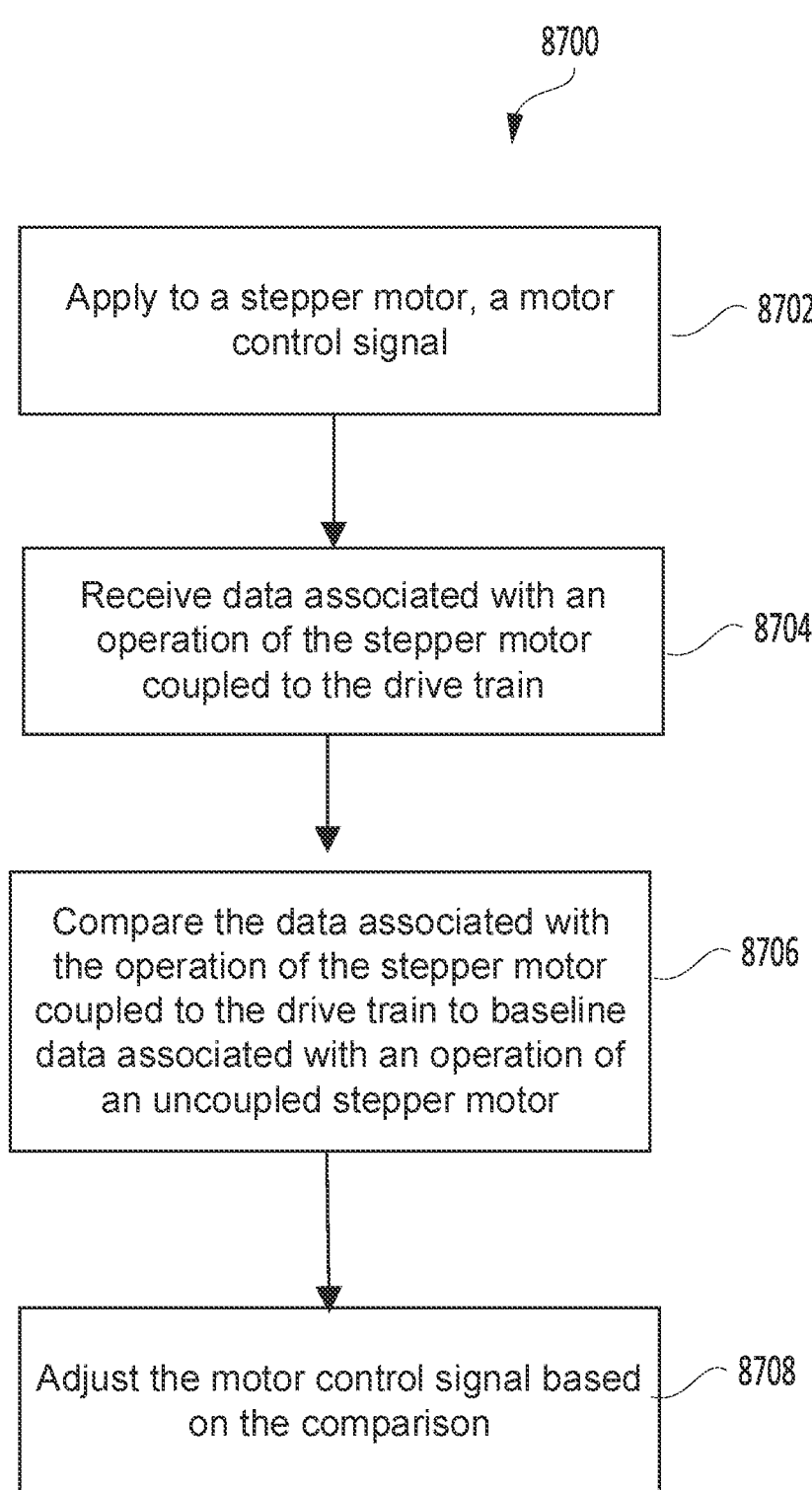
FIG. 107 is a flow chart of a method of controlling a stepper motor in a powered surgical stapling system according to one aspect of this disclosure.

FIG. 107 depicts a flow chart 8700 of a method of controlling a stepper motor in a powered surgical stapling system. The motor controller may apply 8702 to the stepper motor a motor control signal. The motor controller may receive 8704 data associated with an operation of the stepper motor coupled to the drive train. The motor controller may compare 8706 the data associated with the operation of the stepper motor coupled to the drive train to baseline data associated with an operation of an uncoupled stepper motor. In some non-limiting examples, the baseline data may include one or more of a motor pull-in torque, a motor pull-out torque, or a motor holding torque of the uncoupled stepper motor. The motor controller may then adjust 8708 the motor control signal based on the comparison. Examples of motor controller signals that may be adjusted in response to the comparison may include, without limitation, a motor drive frequency, a motor drive pulse width, or a motor drive current.

As disclosed above, a motor in a powered surgical stapling system may be coupled to one or more drive train components. In some non-limiting examples, the drive train may include a drive train to actuate a tissue cutting blade or a drive train to actuate an articulation joint. The drive trains may be composed of multiple components mechanically coupled to each other. In some aspects, the motor may drive the drive trains directly, or the motor may drive the drive trains through a motor gear reducer assembly. It may be recognized that each mechanical component of the drive train may exhibit its own mechanical operation which may suffer from friction, stiction, and backlash associated with the shape and linkage of the component. While knowledge of the overall operation of the drive train is useful, it may be important to characterize anomalous operations of each of the drive train components in order to better characterize the entire motor plus drive train assembly. Thus, differential measure and analysis of at least two separate portions of a linked or coupled drive train may insure better mechanical operation (verification of response) or quantify losses/inefficiencies that may differ between an ideal or intended response and an actual response of the system.

In some aspects, the motor controller algorithm may include detection of individual device drive train component properties. The powered surgical stapling system may monitor sub-system drive train component operations relative to input motor control signals from data obtained from sensors of the drive train component motions. The motor controller algorithm may then adjust the motor control signals based on the individual system response relative to pre-established baseline performance. In some non-limiting aspects, the monitored responses may be frictional loss, acceleration or deceleration responses to a stepped input signal, PID control variation, harmonics of the system, noise, or force versus speed. The adjustments to the motor controller algorithms may include adjustments to the PID control parameters, triggering delay of dynamic braking, level or function window around the triggering thresholds, motor power, motor current, motor voltage, or PWM signal characteristics.

In some aspects, multiple sensors may be configured to monitor separate components of the same drive system to enable the system to detect slop, backlash, or losses for each component. In one non-limiting example, rotational data from a rotary encoder coupled to the shaft of the motor may be compared to rotational data of an encoder coupled to the motor gear reducing assembly. A firing rack may be coupled to the motor gear reducing assembly. The comparison between the data from the motor shaft encoder and the motor gear reducing assembly may be used to determine the backlash, slop, clearances, and other losses of the motor gear reducing assembly. The comparison may result in better compensation by the motor controller, which may adjust one or more of the functions of the motor controller including, without limitation, a target motor speed, a PID duty cycle of the PWM, a voltage limit, or a current limit. By adjusting the one or more motor controller functions, the motor controller may cause the motor to operate drive train at desired operational speeds, braking, and holdings.

In some aspects, a sensor may be coupled to a drive bar actuated by the motor. The encoder associated with the motor shaft may provide rotational data for the operation of the motor, while the drive bar sensor may sense the linear actuation of the drive bar. The data from the encoder and the drive bar sensor may be used to calculate a mechanical transfer function between the motor rotational speeds to the drive bar linear movement. The transfer function can help determine the latency of the motor movement to the drive bar response. The resulting analysis may provide a measure of gear "slop" or backlash, and permit a determination of the requirements to take up the backlash in the gear train. In this manner, the motor response latency can be characterized to improve the estimation of future input speed target by the motor controller algorithms.

In another aspect, sensors may be associated with the clamping trigger and the anvil/channel area. The motor controller may determine the movement and timing of the closure trigger. The motor controller may then sense the movements of the anvil. With these data, the motor controller can determine a time delay between the input of the closure trigger and the movement of the anvil. Such data may be obtained for both the opening and closing functions of the anvil. As disclosed above, a transfer function based on the sensor data and the motor rotation data may be used to estimate the motor rotational speed in order to reduce position/velocity errors of the device.

FIG. 108 depicts a flow chart 8800 of a method of controlling a motor in a powered surgical stapling system based on data received from multiple sensors of the operation of sub-system components. A motor controller may receive 8802 rotational data from a first rotational sensor affixed to a shaft of the motor. The first rotational sensor may be, for example, a rotary encoder positional sensor. The motor controller may then receive 8804 gear rotation data from a second rotational sensor affixed to an output shaft of the gear reducer assembly. Again, in some non-limiting examples, the second rotational sensor may be a rotary encoder positional sensor. Additional sensor data may also be received by the motor controller, such as trigger motion data from a motion sensor in mechanical communication with an anvil clamping trigger or anvil position data from an anvil position sensor. The motor controller may calculate 8806 a mechanical transfer function based at least in part on the rotational data and the gear rotation data. In some alternative aspects, the motor controller may also receive linear motion data from a sensor of a linear position of the drive bar. The motor controller may then calculate a second mechanical transfer function based at least in part on the rotational data, the gear rotation data, and the linear motion data. The motor controller may also include a motor response latency. The motor controller may determine 8808 mechanical system non-idealities of the powered surgical stapling system. Mechanical non-idealities may include, without limitation, system component delays, backlash, gear slop, gear clearance, and a mechanical loss of the gear reducer assembly. The motor controller may modify 8810 a motor control signal based on the determined mechanical system non-idealities. In some aspects, the motor controller may modify one or more of a motor control signal voltage, a motor control signal current, and a motor control pulse duty cycle. In some additional aspects, the motor controller may receive trigger motion data from a motion sensor in mechanical communication with the anvil clamping trigger as well as anvil position data from an anvil position sensor. The motor controller may then determine a time delay between a motion of the anvil clamping trigger and a motion of the anvil.

As disclosed above, a powered surgical stapling system is composed of multiple mechanical and electrical subsystems. The components may include, without limitation, an end effector composed of a first jaw and a second jaw, in which the first jaw is configured to include a staple cartridge and the second jaw includes an anvil. The first and second jaws cooperatively deploy staples to a tissue grasped by the jaws when they close. The end effector may also include a blade or tissue cutting edge movable to sever the stapled tissue. The end effector may be mounted on a shaft assembly which may further include an articulation joint. The articulation joint may be configured to rotate about an articulation axis, thereby rotating the end effector about the articulation axis with respect to a longitudinal axis of the shaft assembly.

In some aspects, a user may cause the anvil to close on a tissue supported by the first jaw using a manual trigger mechanism. In some aspects, the tissue cutting edge may be driven by an electrically activated motor. In some other aspects, the articulation joint may be rotated either by the same electrically activated motor that drives the cutting edge, or a separate motor. The motor may be controlled by a combination of activation switches and one or more motor controllers through a series of motor control signals.

Thus, as disclosed above, the powered surgical stapling system is composed of a number of high-precision mechanical components working together to effect the stapling and cutting of the tissue. In some sub-systems, mechanical components may work together to cause the cutting edge to slide in a distal direction to cut tissue, and slide back to a home position once the cutting operation is completed. In some other sub-systems, mechanical components may work together to cause the articulation joint to rotate in a first direction and then back to a second position. These sub-systems may require the interaction of multiple mechanical linkages (drive-trains) with a motor with or without a gear reducer assembly. One or more sensors may be used to detect the types and speeds of the motions of the drive-trains for use as feed-back to a motor controller.

The motor controller may include one or more algorithms—implemented either in hardware, software, or firmware—designed to actuate the drive-trains in a manner responsive to the surgical environment. In one aspect, the surgical environment may reflect the type or thickness of a tissue grasped, stapled, and cut in the jaws. In another aspect, the surgical environment may reflect obstructions around the articulation joint. The motor controller should be configured to adjust the motor control signals so that the activation of the motor or motors may be optimized for the task at hand.

Additionally, the powered stapling system may be designed to proactively make small performance corrections to negate any performance deficiencies of a sub-system, such as the tissue cutting sub-system, the jaw-clamping sub-system, or the articulation sub-system. These adjustments may be gauged against past historical data from pervious cycles or anticipated for subsequent cycles based on the trending performance. These types of enhancements may normalize the performance of the device over repeated uses or normalize manufacturing deviations in performance between devices.

Time (age) and use may result in structural changes in the components of the drive-trains as well as in the motor or motors. Narrow elongated structures—such as the drive member, the intermediate firing shaft portion, the firing member, the articulation lock bar, the articulation rods, and the articulation system—may warp or bend with continued use. The teeth of the gears in the gear reducer assembly may chip, bend, or wear with use. In some aspects, plastic gears comprising the gear reducer assembly may become brittle and fracture with age. It may be understood that the sub-systems may become less responsive to the motor control signals unless the motor controller is able to adapt the motor control signals to the mechanical changes in the motors and drive-trains.

It is therefore understood that the motor controller should be able to adapt not only to changes in the surgical environmental, but also to the changes in the motor or motors and drive-train components as the powered surgical stapling system is used. Adaptation of the motor controller and motor control signals may result from comparative data of the motors and/or drive-train under different conditions or over time. In some non-limiting examples, such data may include operational data from the motors or sensors associated with the drive-trains. Thus, the motor controller may receive first data indicative of an operation of the motor operating under a first condition, receive second data indicative of an operation of the motor operating under a second condition, and adjust a motor control signal based on a difference between the first data and the second data.

Figure 109:
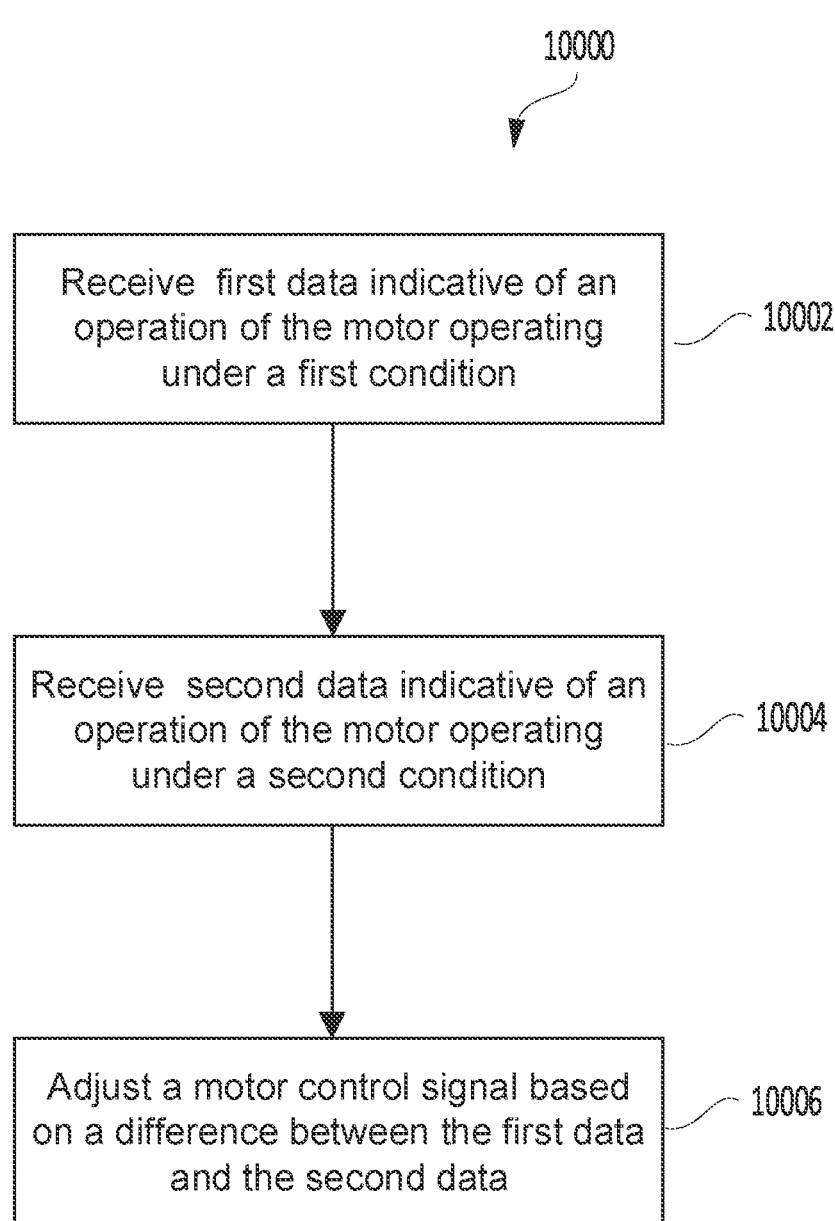
FIG. 109 is a flow chart of a method of adjusting a motor control signal based on motor operational data according to one aspect of this disclosure.

FIG. 109 depicts a flow chart 10000 of a method of controlling a motor in a powered surgical stapling system based on differential measurements of motor and/or drive-train operations. Thus, the motor controller may receive 10002 first data indicative of an operation of the motor operating under a first condition. Further, the motor controller may receive 10004 second data indicative of an operation of the motor operating under a second condition. The motor controller may then adjust 10006 a motor control signal, such as a pulse width modulation (PWM) signal, based on a difference between the first data and the second data.

In some aspects, a determination of motor and motor gear reducer assembly operations may be obtained from a first rotary encoder affixed to the motor drive shaft and a second rotary encoder affixed to the motor gear reducer assembly. In some aspects, the motor controller may receive first data including first rotational position data from the first rotary motion encoder mechanically associated with a shaft of the motor and first rotational position data from the second rotary motion encoder mechanically associated with an output of the motor gear reducer assembly. In some aspects, the motor controller may receive second data including second rotational position data from the first rotary motion encoder and second rotational position data from the second rotary motion encoder. The speed of the motor drive shaft and the motor gear reducer assembly may be measured from the respective encoders based on the change in positional output of the encoders over time. Thus, the motor controller may receive first data including one or more of first motor torque data or first motor speed data, and the second data indicative of the operation of the motor may include one or more of second motor torque data or second motor speed data.

Alternatively, the motor controller may receive first data including one or more of first motor gear reducer assembly torque data or first motor gear reducer assembly speed data, and the second data indicative of the operation of the motor gear reducer assembly data may include one or more of second motor gear reducer assembly torque data or second motor gear reducer assembly speed data. As a result, adjusting the motor control signal based on the difference between the first data and the second data may include adjusting the motor control signal based on a difference between the first rotational position data from the first rotary motion encoder and the first rotational position data from the second rotary motion encoder, or between the second rotational position data from the first rotary motion encoder and the second rotational position data from the second rotary motion encoder.

The speed of the motor drive shaft and the motor gear reducer assembly should be related by the gear-reduction ratio of the gear reducer assembly under no-load conditions. This may provide a no-load, maximum speed, minimum torque condition. Without load, the motor drive shaft output, as well as the output of the motor gear reducer assembly, should be in phase with the motor control signal. However, as the load increases, the motor drive shaft output or the output of the motor gear reducer assembly may shift in phase with respect to the motor control signal. As a result, the measured speed signals from either rotary encoder may deviate from the no-load conditions. Thus, in some aspects, the first data indicative of the operation of the motor operating under the first condition may include first data indicative of an operation of the motor in a mechanically unloaded condition, and the second data indicative of an operation of the motor operating under a second condition may include second data indicative of an operation of the motor in a mechanically loaded condition.

Similarly, the first data indicative of the operation of the motor gear reducer assembly operating under the first condition may include first data indicative of an operation of the motor gear reducer assembly in a mechanically unloaded condition, and the second data indicative of an operation of the motor gear reducer assembly operating under a second condition may include second data indicative of an operation of the motor gear reducer assembly in a mechanically loaded condition. A comparison thus may be made of the operations of the motor and/or motor gear reducer assembly between a mechanically un-loaded condition and a mechanically loaded condition.

The output speed of the motor gear reducer assembly may slow at a higher proportion than the motor speed signal phase. With increased mechanical wear, motor backlash due to gear take-up may increase. The increased backlash may also result in reduced speed of the motor gear reducer assembly. Thus, a comparison of the motor encoder data with the encoder data from the motor gear reducer assembly may be used to estimate output gear response, such as speed or torque, over time. The backlash may be measured under various loading conditions, including under no-load, as well as during a motor stall condition.

In other aspects, a comparison of motor characteristics under different conditions may include a measurement of current/power draw from each motor, motor temperature, motor acceleration/deceleration rates, and/or back electromagnetic force (EMF). These metrics may also be used to characterize changes in the motor operations, including, without limitation, output speed or torque.

In another aspect, physical measurements related to drive-train components may also be used to determine changes in motor and/or motor gear reducer assembly operations. Comparisons may be made of physical displacements, speed or positional losses, and component backlash associated with the components of the drive-train or drive-trains. For example, a drive-train operation may include positioning the components of drive-train at a known reset or re-configuration condition. In one aspect, a drive-train configured to actuate a tissue cutting blade may have a reset position in which the tissue cutting blade is located at a fully retracted position (proximal most position). In another aspect, a drive-train configured to rotate an end effector about an articulation joint may have a reset position in which a longitudinal axis of an end effector is aligned with a longitudinal axis of a shaft assembly (about a 180 degree angle between the longitudinal axis of the end effector and the longitudinal axis of the shaft assembly). In a further example, measurements of an angular motion of an articulation joint, a rate of change of the angular motion of the articulation joint, a location of a tissue cutting blade, or a rate of change of the location of the tissue cutting blade may be made using data obtained from relevant positional sensors over time. Thus, the first data indicative of the operation of the motor operating under the first condition may include first data indicative of one or more of an angular motion of the articulation joint, a rate of change of the angular motion of the articulation joint, a location of the tissue cutting blade, or a rate of change of the location of the tissue cutting blade, and the second data indicative of an operation of the motor operating under a second condition may include one or more of the angular motion of the articulation joint, the rate of change of the angular motion of the articulation joint, the location of the tissue cutting blade, or the rate of change of the location of the tissue cutting blade. These data may permit the motor controller to track changes in those parameters as the powered surgical stapling system is used. In a system that uses the same motor to drive two different drive-trains (for example the tissue cutting drive-train and the articulation motion drive-train), an exchange location which positions a first drive-train to a reset position before allowing the mechanical switch to engage a second drive-train could be used to monitor a "home position" over time. With these data, the motor controller may generate motor control signals of the motor speed and motor rotational position that are compensated for system variations over time.

As disclosed above, changes in data associated with the use of a powered stapling system may be used by the motor controller to update or change the algorithms used to control the operation of a motor in concert with a gear reducer assembly. Additional data, not associated with the active use of the device, may also be incorporated into the motor controller algorithms regarding the history of the device before deployment. Knowing the age of the device, shipping and storage conditions, and total run time of the components can all add valuable information to the system. Adjustments to the motor control signal based on such initial conditions may normalize the use of the powered stapling system by the surgeon over time and between devices. As a result, normalization of the device operation will keep surgical outcomes more consistent and predictable.

In one aspect, the first data received by the motor controller that is indicative of the operation of the motor under the first condition may include data indicative of an operation of the motor at initial manufacture. The second data received by the motor controller that is indicative of the operation of the motor under the second condition may include data indicative of an operation of the motor at some time after initial manufacture. Non-limiting examples of data indicative of an operation of the motor at some time after initial manufacture may include data obtained regarding a time that the powered surgical stapling system lies in storage, a total time of use of the powered surgical stapling system, a time between actuations of the tissue cutting blade, a time between rotations about the articulation joint, a total run-time between firings of the tissue cutting blade, a number of firings of the tissue cutting blade, a total time since build, and/or a total number of uses of the powered surgical stapling system.

The data indicative of an operation of the motor at initial manufacture may include any relevant electrical or mechanical data associated with the operation. Such data may include, without limitation, a starting current of the motor, a starting acceleration of the motor, a speed of the motor under no-load conditions, a time of motor operation for a complete actuation of the tissue cutting blade in a distal direction, a time of motor operation for a complete actuation of the tissue cutting blade in a proximal direction, a time of motor operation for a complete actuation of the tissue cutting blade in a proximal direction, a time of motor operation for a complete actuation of the articulation joint in a first motion (clockwise), a time of motor operation for a complete actuation of the articulation joint in a second motion (counter-clockwise), and a motor temperature under operation. Thus, a motor control signal may be adjusted based on the difference the operation of the motor at initial manufacture and the operation of the motor at the time after initial manufacture.

The data indicative of an operation of the motor at initial manufacture may be generated by executing a calibration sequence after full assembly of the powered stapling system. For statistical purposes, multiple calibration sequences may be run after initial manufacture, and appropriate statistics—such as mean values and standard deviation values—may be retained. The data indicative of an operation of the motor at initial manufacture may be stored in a memory device of the powered surgical stapling device, or may be accessible to the motor controller of the powered surgical stapling device over a network connection to any one or more of a surgical hub or a cloud-based networked system.

The data associated with the powered surgical stapling system immediately after manufacture may serve as a baseline against which the operation of the powered surgical stapling system may be compared. In this manner, operational degradation may be measured, and the control algorithms of the motor controller may be adjusted to compensate for the degradation. The adjustments to the control algorithms may include adjustment to control threshold values for the operation of the motor and/or the motor gear reducer assembly (such as motor current, motor voltage, or motor and/or the motor gear reducer assembly speed thresholds). Algorithms designed to adjust a pulse-width modulation (PWM) motor control signal may also be adjusted to compensate for non-use conditions.

As disclosed above, a comparison may be made between the operation of the powered surgical stapling system immediately after manufacture and at some time after manufacture. The time after manufacture may include a time after the powered surgical stapling system has been used for a predetermined number of cases. The time after manufacture may include a time of receipt of the powered surgical stapling system by a user. Additionally, initial operation data from the motor and/or motor gear reducer assembly manufacture may be obtained separately. In some aspects, the time after motor and/or motor gear reducer assembly manufacture may include the time of initial use of the powered surgical stapling system. Thus, the motor controller may receive initial manufacture motor and gear reducer assembly characteristic data from a manufacturer. The motor controller may then receive operational motor and gear reducer assembly data during an initial use of the powered surgical stapling system. The algorithms in the motor controller used to control the operation of the motor may then adjust one or more parameters of a motor control signal based on a comparison of between the initial manufacture motor and gear reducer assembly characteristic data and the operational motor and gear reducer assembly data during the initial use of the powered surgical stapling system. In certain aspects, the adjustment is based on a difference between the initial manufacture motor and gear reducer assembly characteristic data and the operational motor and gear reducer assembly data during the initial use of the powered surgical stapling system.

Figure 110:
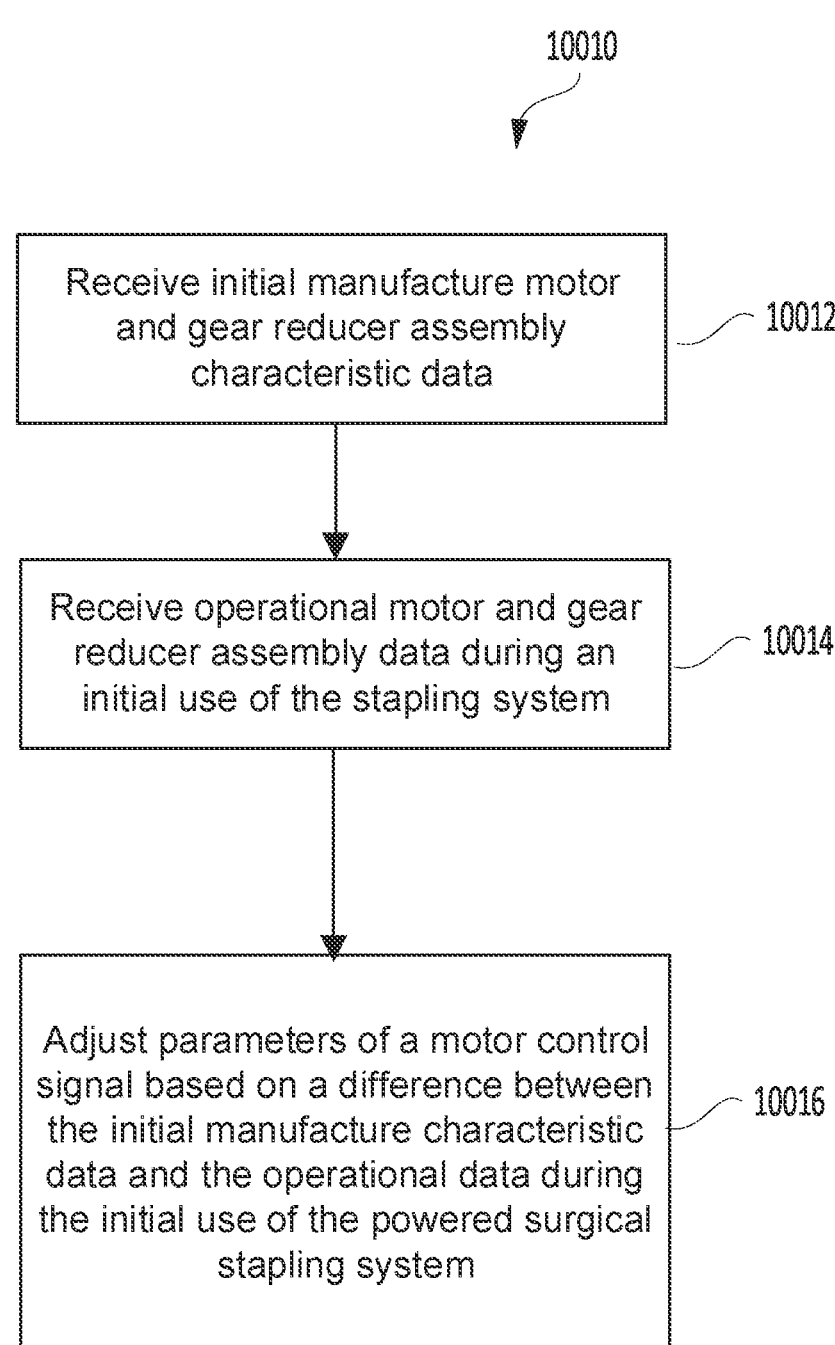
FIG. 110 is a flow chart of a method of adjusting parameters of a motor control signal based on differences between initial manufacture data and initial use data according to one aspect of this disclosure.

A method of adjusting an operation of a motor and/or a motor gear reducer assembly is depicted in flow chart 10010 in FIG. 110. Thus the motor controller may receive 10012 initial manufacturer motor and gear reducer assembly characteristic data from a manufacturer. The motor controller may receive 10014 operational motor and gear reducer assembly data during an initial use of the powered surgical stapling system. The motor controller may then adjust 10016 parameters of a motor control signal based on a difference between the initial manufacture motor and gear reducer assembly characteristic data and the operational motor and gear reducer assembly data during the initial use of the powered surgical stapling system.

In some aspects of the method, receiving the initial manufacture motor and gear reducer assembly characteristic data may include receiving one or more of initial motor speed data, initial motor torque data, initial gear reducer assembly torque transmission data, initial motor temperature data, or initial gear reducer assembly temperature data.

In some aspects of the method, receiving the operational motor and gear reducer assembly data during an initial use of the powered surgical stapling system may include receiving first use motor back electromagnetic force (EMF) data, first use motor temperature data, or first use gear reducer assembly temperature data.

In some aspects, the method may also include receiving, by the motor controller, initial manufacture motor and gear reducer assembly acceptance data.

In some aspects, the method may also include adjusting, by the motor controller, one or more parameters of the motor control signal based on a difference between the initial manufacture motor and gear reducer assembly acceptance data and the operational motor and gear reducer assembly data during the initial use of the powered surgical stapling system.

In some aspects of the method, adjusting one or more parameters of the motor control signal comprises adjusting one or more of a motor current maximum, a motor voltage, a PID controller parameter, a timing parameter, a motor speed or threshold step, or a motor control signal waveform.

The data received from the motor and/or motor gear reducer assembly manufacturer may be stored in non-volatile memory of the powered surgical stapling system after the data have been determined. Alternatively, the data received from the manufacturer may be shipped as a memory device—such as a flash drive—for a user to install in the powered surgical stapling system. In another alternative, the data received from the manufacturer may be accessible to the powered surgical stapling system over a computer network such as over a cloud-based computing system or through a direct connection to a server under control by the motor and/or motor gear reducer assembly manufacturer. As disclosed above, the initial data from the manufacturer may serve as a base-line for similar data obtained during or after use of the powered surgical stapling system.

The initial motor and/or motor gear reducer assembly manufacturing data may include, besides data associated with operation of a motor, data associated with a gear reducer assembly. Speed, torque, and operational temperature data may also be obtained separately for the gear reducer assembly. The operational temperature profile data for the gear reducer assembly may be overlaid with that of the equivalent motor heating, speed, and torque data to determine specific critical points. Non-concentric motor shaft issues could be discovered, which could help determine uneven rotor alignment in the motor. Additionally, motor torque variations over time may be identified, and parameters of the motor control signal algorithms may be adjusted to compensate for the variations. Additional data that may be obtained from the initial motor manufacturer may relate to motor winding variations, magnet strength of permanent magnets used in the motors, and brush/rotor contact area for DC brushed motors.

The initial temperature of motor assembly (either the motor alone or combined with the gear reducer assembly) may be used to determine initial performance characteristics of the powered surgical stapling system. An initial motor/ heating transfer function may be used to better predict future motor performance. In addition to motor back EMF measurements, other current and/or voltage measurements may be obtained for either brushed or brushless DC motors. As disclosed above, the powered surgical stapling system may be usable with multiple interchangeable surgical shaft assemblies. By including the manufacturer data for both the motor and the motor gear reducer assembly, the motor control algorithm may adjust to the different shaft assemblies, thereby "normalizing" or matching the motor operations across all interchangeable shaft assemblies.

In some aspects, the initial motor and motor gear reducer assembly data may permit matching a higher performing motor with a slightly lower performing motor gear reducer assembly. In this manner, it is possible to keep the motor gear reducer assembly performance error bands narrower and minimize component scrap potential. This may permit the use of a wider range of components that under normal conditions would be scrapped.

As disclosed above, it may be useful to control component performance characteristics to normalize overall system performance outputs over a number of interchangeable shaft assemblies. In one non-limiting example, the motor and motor gear reducer assembly may undergo acceptance testing after final assembly to verify the assemblies are within performance targets. Both the motors and motor gear reducer assemblies may have target acceptance values for a normal system, including tolerance bands for minimum and maximum outputs. The target nominal performance of the motors and motor gear reducer assemblies could be affected by component tolerances and/or assembly, which may impact the drive variation in efficiencies and performance.

Presently, all motors and motor gear reducer assemblies that are within the target performance tolerances can be assembled together for a final system. As an alternative matching performance of the motor to performance of the motor gear reducer assembly could drive the target output of the system to a defined target and minimize the variation of the overall system. Thus, a motor having 80% efficiency coupled to a 70% efficient motor gear reducer assembly with have an overall system efficiency of 75%. Alternatively, a motor having 70% efficient motor coupled to a 85% efficient motor gear reducer assembly would have an efficiency of 75%. Although independently the components differ in their respective efficiencies, the combination of components with the powered surgical stapling system would equalize the final output and drive for devices that have the same final output. In this manner, properly combining the motor and motor gear reducer assembly may lead to a reduction of variation between devices and performance outputs.

In some aspects, the initial manufacture data of the motors and motor gear reducer assemblies may be used as inputs to set and adjust motor control signal algorithm limits. In one non-limiting example, a manufacture may supply motor and motor gear reducer assembly acceptance data after final assembly to verify the motor assembles are within performance targets. These data could be stored onto the components by means of RFID or embedded into the cloud based on serial number. During manufacturing/assembly of the powered surgical stapling system, these data could be stored in and read by the motor controller to set various operational limits of that device. For example, the motor may have different outputs in voltage/temperature determined at a component level. The motor control algorithm could adapt to those limits for a specific powered surgical stapling system configuration to only run the algorithm within the predetermined motor operational range. Additionally the motor gear reducer assembly may have different efficiencies at different speeds. The motor gear reducer assembly acceptance data could be an input to drive the algorithm to operate at its most speed for that specific powered surgical stapling system configuration.

In the operation of various DC motors, the motor operation may be controlled by a pulse-width modulation (PWM) system. A PWM system generates a signal based on a base frequency defined by a time period in which current pulses are supplied to the motor. Each current pulse occurs over some portion of the time period and may represent any percentage of the time period from 0% (no current supplied over the time period) to 100% (current supplied over the entire time period). The speed of the motor may depend on the portion of the time period during which the current is supplied, hence the motor speed is modulated by the pulse width of the current over the time period.

Typically, the PWM base frequency is kept constant throughout the motor control sequence. However, additional tuning of motor action may be obtained by changing not only the pulse widths, but also the base frequency of the PWM system. Adaptation of the frequency of the PWM to change the motor output may improve active control of the dynamic inertia of the drive-train by shifting between two or more different operational states. The ability to make adjustments to the motor control algorithm after initial programming may be useful in intelligent surgical devices. In some operational states, the motor controller processor may run at a fixed frequency and outputting command information based on that fixed frequency. An independent system having greater processing capability, and running at a faster speed, can bring additional, more up to date information to the command signal from the processor. By merging or adapting the two signals, a more desirable signal may be generated to command the motor controller.

In one aspect, a PWM system could operate in at least two modes. In a first mode, the PWM motor control signal may drive the system in a single direction only, at a single PWM base frequency. In a second mode, the PWM motor control signal may operate at a frequency lower than the base frequency, which may cause the system to alternate between driving the motor and associated drive-train in the directed system and braking in the frictionally opposite direction. This second mode could enable a slower controlled motion of systems that use brushless motors or in systems where the gears in the gear reducer assembly may differ significantly in response as they age, as their working temperature increases, or with use. A reduction in base frequency of the PWM system may allow the motor controller to better control slower speeds and stops.

In one example, a powered surgical stapling system may clamp on a large bundle of tissue. Initially, the motor controller may supply constant power to the tissue blade drive system in order to increase its overall inertia. This may be done to ensure the necessary performance to begin cutting/stapling the tissue. During the initial part of the drive, the PWM base frequency may be increased to have more resolution in the small changes occurring to the tissue blade drive-train. These changes may be a function of both the tissue grasped in the jaw and the tissue blade drive-train. Once the tissue blade drive-train has established an initial nominal speed, the PWM frequency may be decreased for most of the remaining drive distance. Only if an operational anomaly is detected—such as a sudden increase in the tissue thickness that may affect the cutting speed—would the PWM frequency quickly increase again for finer motion control. At the end of the tissue cutting cycle, the PWM algorithm may again be adjusted when the knife stops travel. This adjustment of the PWM frequency during the complete cutting stroke operation may ensure a complete knife extension while also ensuring that the knife does not over travel at the end of the cut.

The adaptation of the PWM base frequency to operational conditions is a time based approach to modifying the interaction between the tissue blade drive-train and the tissue. By increasing the PWM signal base frequency for motors coupled to the tissue blade drive-train, the tissue would not have time to relax or react to the tissue cutting process. By slowing down the PWM signal base frequency, the motor controller may provide the tissue additional time to react or relax during the "off" cycle of the PWM.

Figure 111:
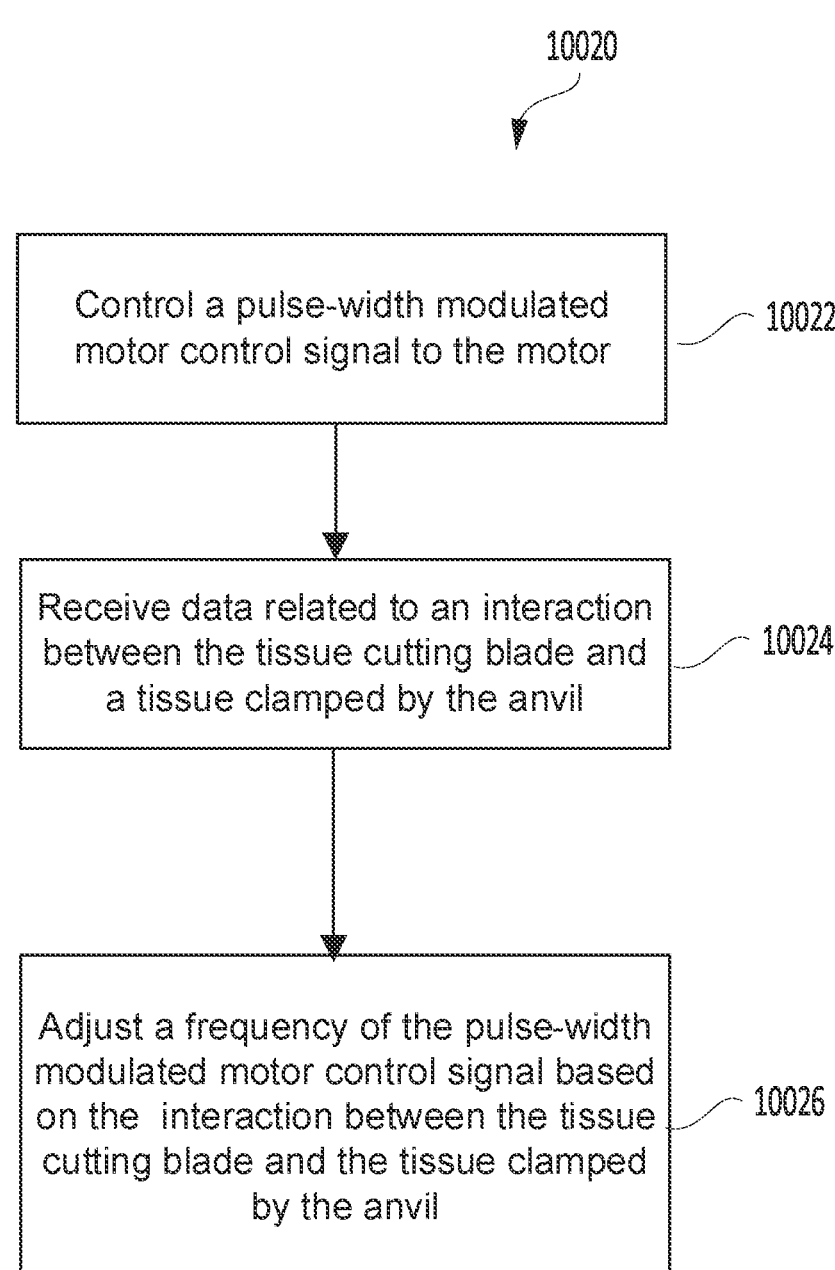
FIG. 111 is a flow chart of a method of adjusting a frequency of a pulse-width modulation motor control signal according to one aspect of this disclosure.

FIG. 111 presents a flow chart 10020 of a method for adjusting a motor and/or drive-train operation based on a change in the PWM base frequency. Thus, the motor controller may control (10022) a pulse-width modulated motor control signal to the motor. The motor controller may receive (10024) data related to an interaction between the tissue cutting blade and a tissue clamped by the anvil of the powered surgical stapling device. In one example, the data may relate to a current required to maintain a speed of the tissue cutting blade as it cuts the tissue. In another example, the data may relate to a time for the tissue cutting blade to traverse a given distance while cutting the tissue. In an alternative example, the data may relate to a change in tissue cutting blade speed when the tissue cutting blade first begins to cut the tissue. In yet another example, the data may relate to a change in tissue cutting speed when the tissue cutting blade finishes cutting the tissue and continues moving after encountering a tissue load. The motor controller may then adjust (10026) a frequency of the pulse-width modulated motor control signal based on the data related to the interaction between the tissue cutting blade and the tissue clamped by the anvil.

In one aspect, adjusting the frequency of the pulse-width modulated motor control signal includes maintaining a first frequency of the pulse-width modulated motor control signal when the tissue cutting blade makes no contact with the tissue.

In another aspect, adjusting the frequency of the pulse-width modulated motor control signal may include changing the frequency of the pulse-width modulated motor control signal between a first frequency and a second frequency. As one example, the motor controller may alternatingly drive the tissue cutting blade into the tissue at the first frequency and drive the tissue cutting blade away from the tissue at the second frequency. In another example, the tissue cutting blade may be driven at the first frequency when the tissue cutting blade first contacts the tissue and may be driven at the second frequency after the tissue cutting blade first contacts the tissue. In some examples, the second frequency may be less than the first frequency.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610.

In certain instances, the memory 624 may include program instructions for controlling each of the motors of the surgical instrument that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

Figure 112:
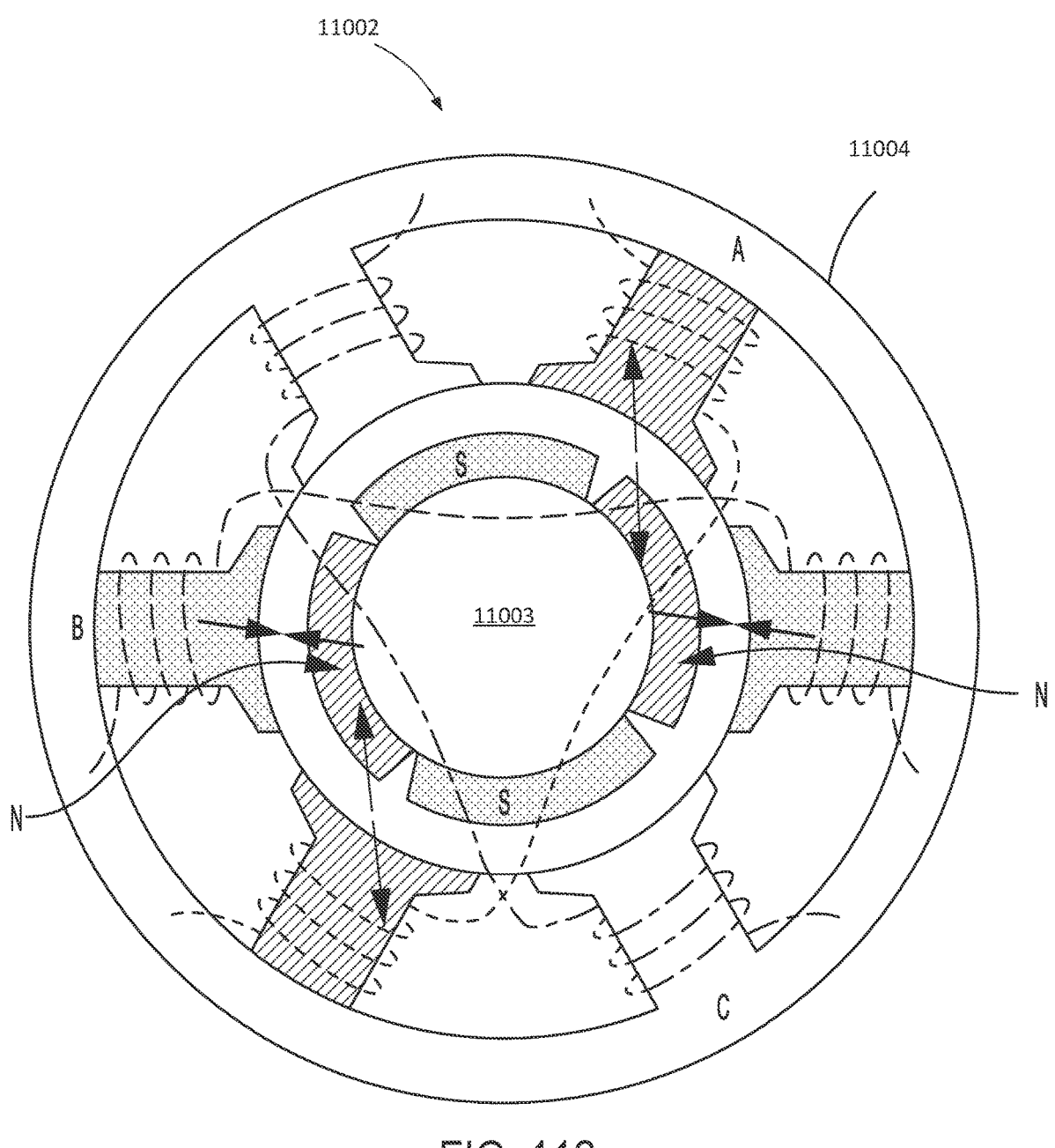
FIG. 112 illustrates a motor, in accordance with at least one aspect of the present disclosure.

In various instances, referring primarily to FIG. 13 and FIG. 112, a surgical system 1930 adaptively controls a motor 11002, for example, independent of, or in absence of, a motor drive signal that motivates the motor 11002 to effect a tissue treatment motion of the end effector 1940, for example. As described in greater detail elsewhere herein, a control circuit (e.g. microcontroller 1933, 620) may cause a motor drive signal to be transmitted from a power source (e.g. 1942, 628) to the motor 11002, or any suitable motor of the motor assembly 1939, for example, to effect the tissue treatment motion. In one aspect, the motor can be a firing motor that motivates a firing drive assembly to deploy staples from the end effector 1940 into tissue grasped by the end effector 1940, and optionally cut the tissue. In one aspect, the motor can be a closure motor that motivates one or more jaws of the end effector 1940 to transition toward a closed configuration to grasp tissue. In one aspect, the motor can be an articulation motion that motivates an articulation of the end effector about an articulation joint, for example. In one aspect, the motor can be a rotation motor that motivates a rotation of the end effector 1940 about a longitudinal axis.

Further to the above, the adaptive control of the motor 11002, for example, independent of, or in absence of, the motor drive signal facilitates an additional layer of motor control beyond, or in addition to, the control afforded by the motor drive signal. In various instances, the adaptive control of the motor 11002 is achieved by an adaptation, or adjustment, of elements of a motor drive circuit of the motor assembly 1939, or motor driver 626, for example, by a control circuit (e.g. microcontroller 1933, 620), for example, to control motor performance in absence of the motor drive signal.

In one aspect, the motor drive circuit is adjusted by the control circuit, in the absence of the motor drive signal, while the motor is in a dynamic state, to control deceleration of the motor, for example. In one aspect, the control circuit adaptively effects modifications to parameters of the motor drive signal, and adjustments to electronics of the motor drive circuit in the absence of the motor drive signal, to control performance of the motor during a tissue treatment motion, for example. In certain instances, the adaptive adjustment, or control, of the motor drive circuit by the control circuit yields a dynamic braking mode, an active braking mode, a coasting mode, or a combination thereof, as described in greater detail below. In certain instances, the control circuit achieves a desired deceleration, in absence of the motor drive signal, by adjusting the electronics of the motor drive circuit to generate a resistance to the dynamic inertia of the motor, by activating, for example, the dynamic braking mode, the active braking mode, the coasting braking mode, or a combination thereof, of the electronics of the motor drive circuit.

Figure 113:
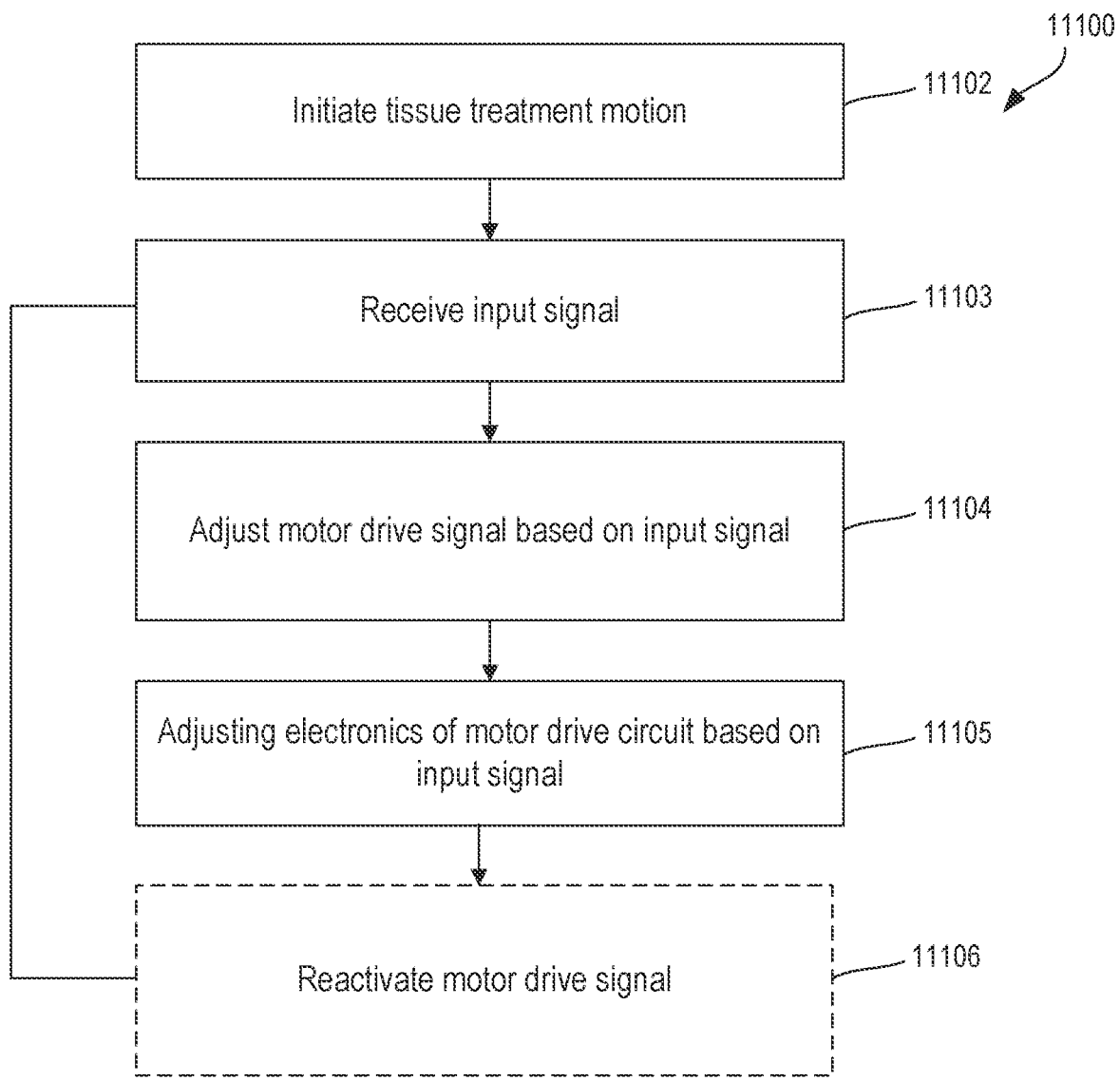
FIG. 113 is a flow diagram illustrating a method for controlling electronics of a motor drive circuit of a motor in absence of the motor drive signal, in accordance with at least one aspect of the present disclosure.

In one aspect, the control circuit adaptively effects modifications to parameters of the motor drive signal, and adjustments to electronics of the motor drive circuit in absence of the motor drive signal, the modifications and/or adjustments based on one or parameters known, measured, and/or monitored by the sensors 1938, for example. FIG. 113 is a flow diagram illustrating a method 11100 for controlling electronics of motor drive circuit of a motor (e.g. motor 11002) of the motor assembly 1939, in absence of the motor drive signal. The method 11100 can be implemented by any suitable control circuit (e.g. microcontroller 1933, 620). In the illustrated example, the method 11100 includes initiating 11102, for example by the control circuit, a tissue-treatment motion of a surgical system 1930, for example. In one exemplification, the control circuit causes the power source 1942 to transmit a motor drive signal to the motor by way of the motor drive circuit to cause the motor to advance the drive assembly 1941 to effect the tissue treatment motion (e.g. closure, firing, rotation, articulation) at the end effector 1940, for example.

The method 11100 further includes receiving 11103 an input signal from one or more of the sensors 1938 and/or the surgical hub 1953 indicative of one or more parameters of the tissue, the motor assembly 1939, drive assembly 1941, and/or the end effector 1940. In certain aspects, the input signal is indicative of a tissue property such as, for example, tissue thickness, tissue type, and/or tissue impedance. In certain aspects, the input signal is indicative of a parameter of an inertia, a frictional loss, a tolerance stack, a tissue creep, for example.

The method further includes adjusting 11104 the motor drive signal based on the input signal. In one exemplification, the control circuit deactivates, or cuts off, the motor drive signal based on the input signal, which can be a temporary deactivation. In another exemplification, the control circuit increases a parameter of the motor drive signal, then decreases the same parameter, or another parameter, of the motor drive signal. In another exemplification, the control circuit maintains the motor drive signal at a current level, for example by interrupting an increase in the motor drive signal set by a default control program, and then executes a following decrease in the motor drive signal. Other suitable adjustments 11104 in response to the input signal are contemplated by the present disclosure.

The method 11100 further includes adjusting 11105, modifying, or adapting electronics of the motor drive circuit, in absence of the motor drive signal, to adjust motor performance based on the input signal. In certain instances, adjusting the electronics of the motor drive circuit comprises generating a resistance to the dynamic inertia of the motor, by activating, for example, the dynamic braking mode, the active braking mode, the coasting braking mode, or a combination thereof, of the electronics of the motor drive circuit.

Further to the above, in certain instances, the method 11100 may include reactivating 11106, for example by the control circuit, the motor drive signal based on the input signal. In one exemplification, the input signal indicates a change in the monitored parameter that gave rise to the adjustments, which causes the control circuit to reactivate the motor drive signal in accordance with the default control program of the tissue treatment motion.

In certain instances, the adaptive control is based on a tissue property such as, for example, tissue thickness, tissue type, and/or tissue impedance. In such instances, the control circuit initiates a firing stroke to seal, by staples or energy application, and cut tissue grasped by the end effector 1940. During the firing stroke the control circuit receives input from the sensors 1938 indicative of a tissue thickness, and determines that the received tissue thickness is of a magnitude beyond an acceptable threshold associated with the current speed of the motor. Such determination can be achieved by way of a predetermined threshold, an equation, and/or a look-table, for example, stored in a memory communicably coupled with the control circuit. Based on the determination, the control circuit temporarily cuts off the motor drive signal, and adjusts the electronics of the motor drive circuit to execute the dynamic braking mode, the active braking mode, the coasting braking mode, or a combination thereof, to reduce the speed of the motor to an acceptable speed based on the detected tissue thickness. In certain instances, the control circuit adjusts the electronics of the motor drive signal to generate sufficient resistance to the dynamic inertia of the motor to ensure reaching the acceptable speed before the firing stroke reaches the tissue portion possessing the detected tissue thickness.

In certain instances, the control circuit incrementally, and slightly, increases the speed of the motor to test whether the capacity of the motor is capable of accommodating a speed adjustment. In such instances, the control circuit incrementally modifies the motor drive signal, while receiving sensor input regarding the resulting speed of the motor. If the control circuit determines that an incremental increase is beyond the capacity of the motor, the control circuit may respond by temporarily cutting off the motor drive signal. In such instances, the control circuit may switch to performing adjustments of the electronics of the motor drive circuit to implement further manipulations of the motor speed, in the absence of the motor drive signal, to yield a deceleration, for example, to a speed within the capacity of the motor. At such point, the motor drive signal can be reactivated, and the adjustments to the electronics of the motor drive circuit stopped.

Figure 114:
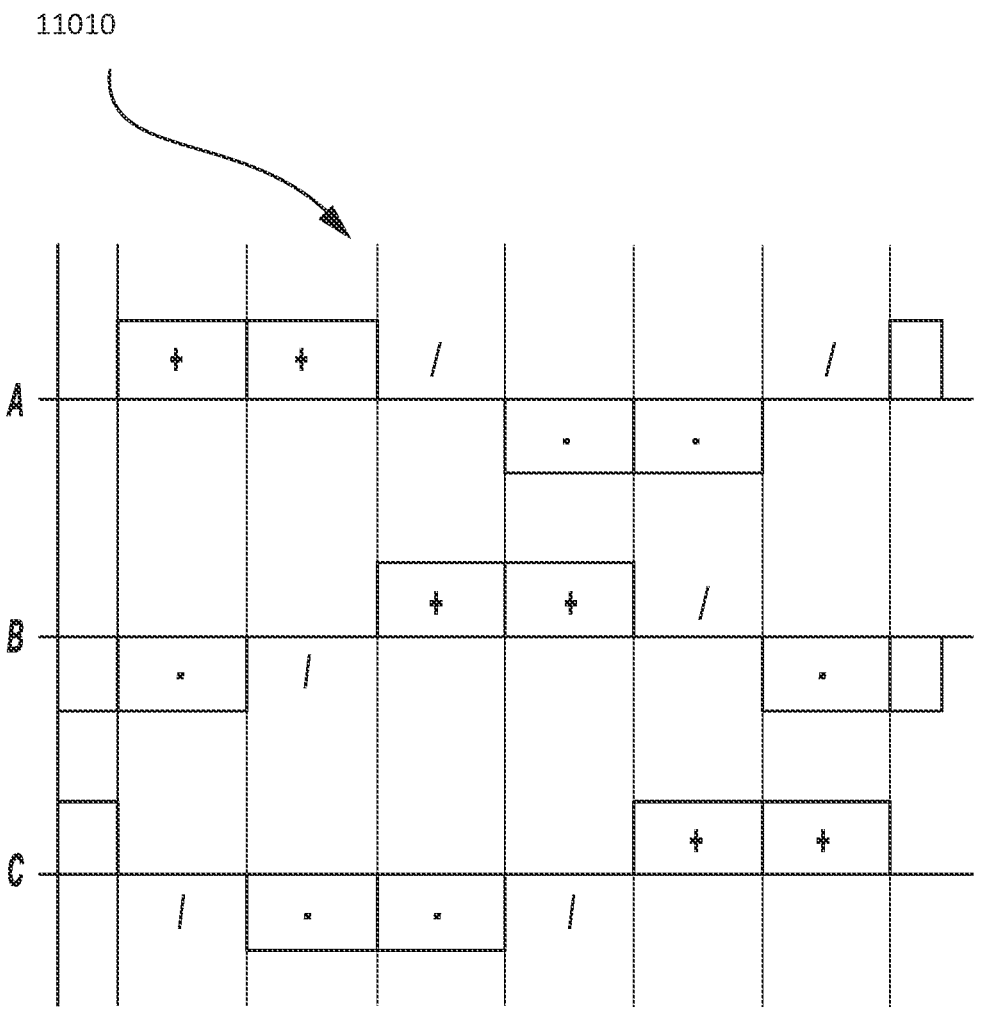
FIG. 114 illustrates a motor drive signal, in accordance with at least one aspect of the present disclosure.

Referring to FIG. 112 and FIG. 114, one or more of the methods described herein can be implemented to control performance of a brushless motor such as, for example, the motor 11002 to effect a tissue treatment motion. As previously discussed, the performance of the motor 11002 can be controlled by adjusting the motor drive signal, and in the absence of the motor drive signal, by adjusting electronics of the motor drive circuit. FIG. 114 illustrates an exemplification of a motor drive signal for the motor 11002. In the illustrated example, the motor drive signal is defined by a motor current waveform 11010 configured to generate a rotational drive motion of the motor 11002.

In the illustrated example, the motor 11002 is a brushless DC (BLDC) motor that includes a rotor 11003 and a stator 11004. The stator 11004 includes three electromagnet pairs A, B, C disposed around the rotor 11003 which includes permanent magnets disposed around a rotatable shaft. While an inrunner motor is depicted, it is understood that the BLDC motor 11002 can be an outrunner motor, for example. Moreover, other types of suitable motors are contemplated by the present disclosure. In order to increase the efficiency of the motor 11002, two opposite coils are wound as a single coil that generates each of the electromagnet pairs A, B, C.

As shown in FIG. 112, the rotor 11003 includes a plurality of poles alternating between North and South. In operation, the electromagnet pairs A, B, C around the rotor 11003 are alternated between high, low, and inactive in a sequenced manner, as illustrated in FIG. 114, for example, which causes the rotor 11003 to move from one position to the next in a rotational drive motion due to sequenced attraction and repulsion forces. The current flowing through the electromagnet pairs A, B, C dictates the polarity of the electromagnet pairs A, B, C, thereby generating an alternating attraction and repulsion forces that cooperatively yield the rotational drive motion of the rotor 11003, and producing a controlled torque and discrete stopping and/or holding positions.

While the motor 11002 is illustrated with three electromagnet pairs A, B, C, this is not limiting. Other embodiment of the present disclosure can include motors with more or less electromagnet pairs and more or less permanent magnets in any arrangement suitable for balancing attraction and repulsion over small increments of the rotor motion.

Figure 115:
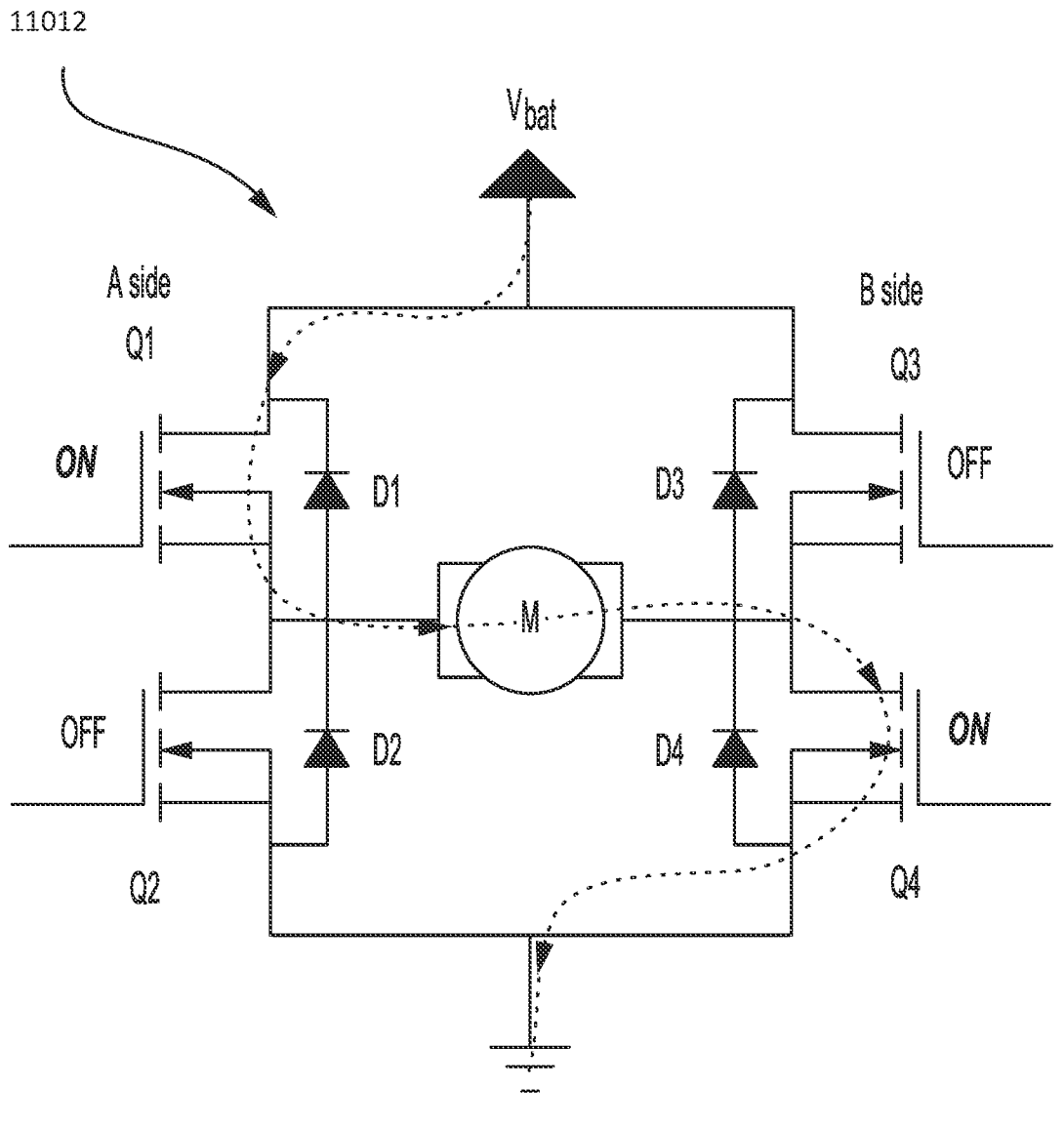
FIG. 115 is an H-Bridge FETs circuit in a drive mode, in accordance with at least one aspect of the present disclosure.
Figure 116:
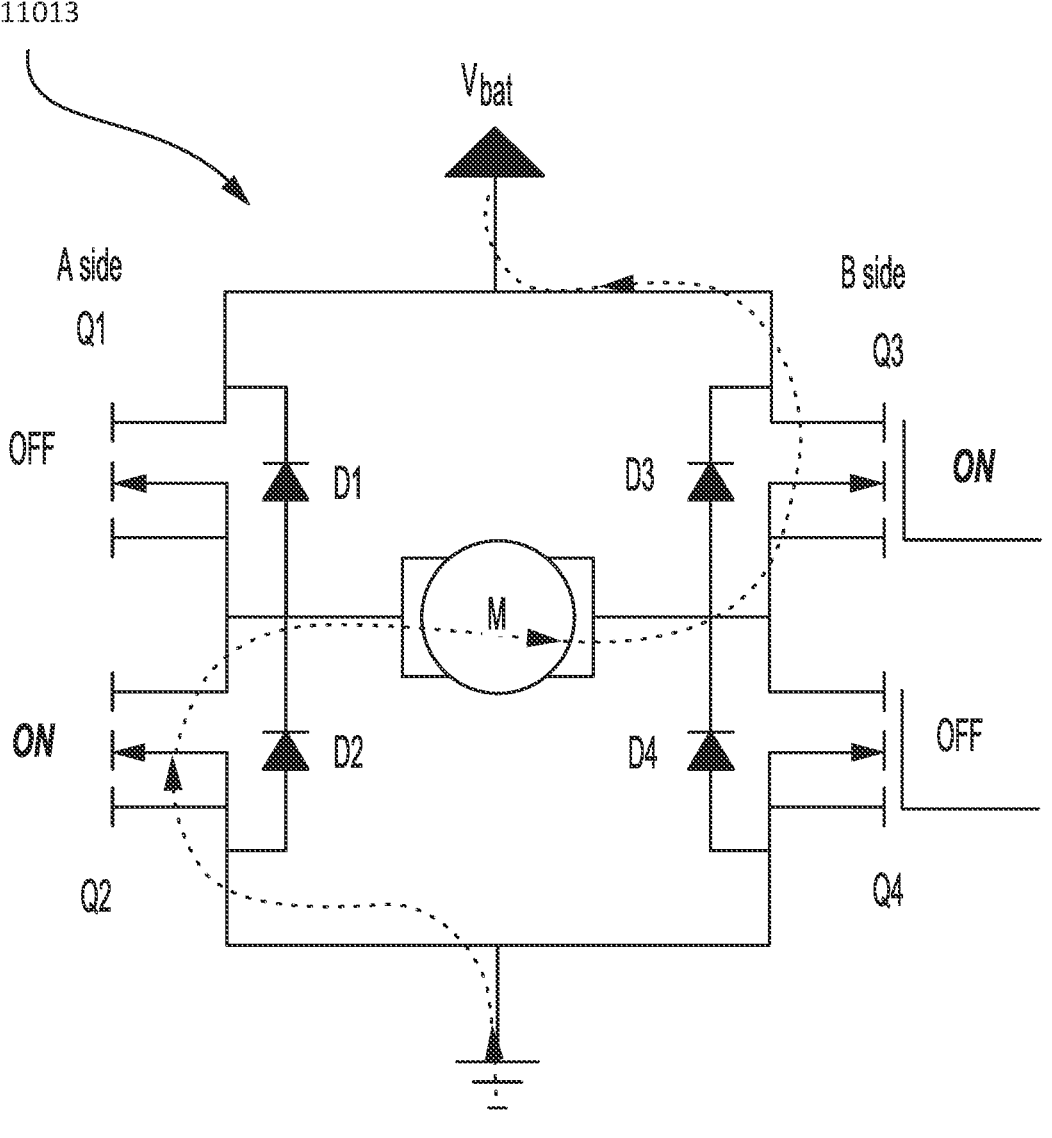
FIG. 116 is an H-Bridge FETs circuit in a reverse mode, in accordance with at least one aspect of the present disclosure.
Figure 117:
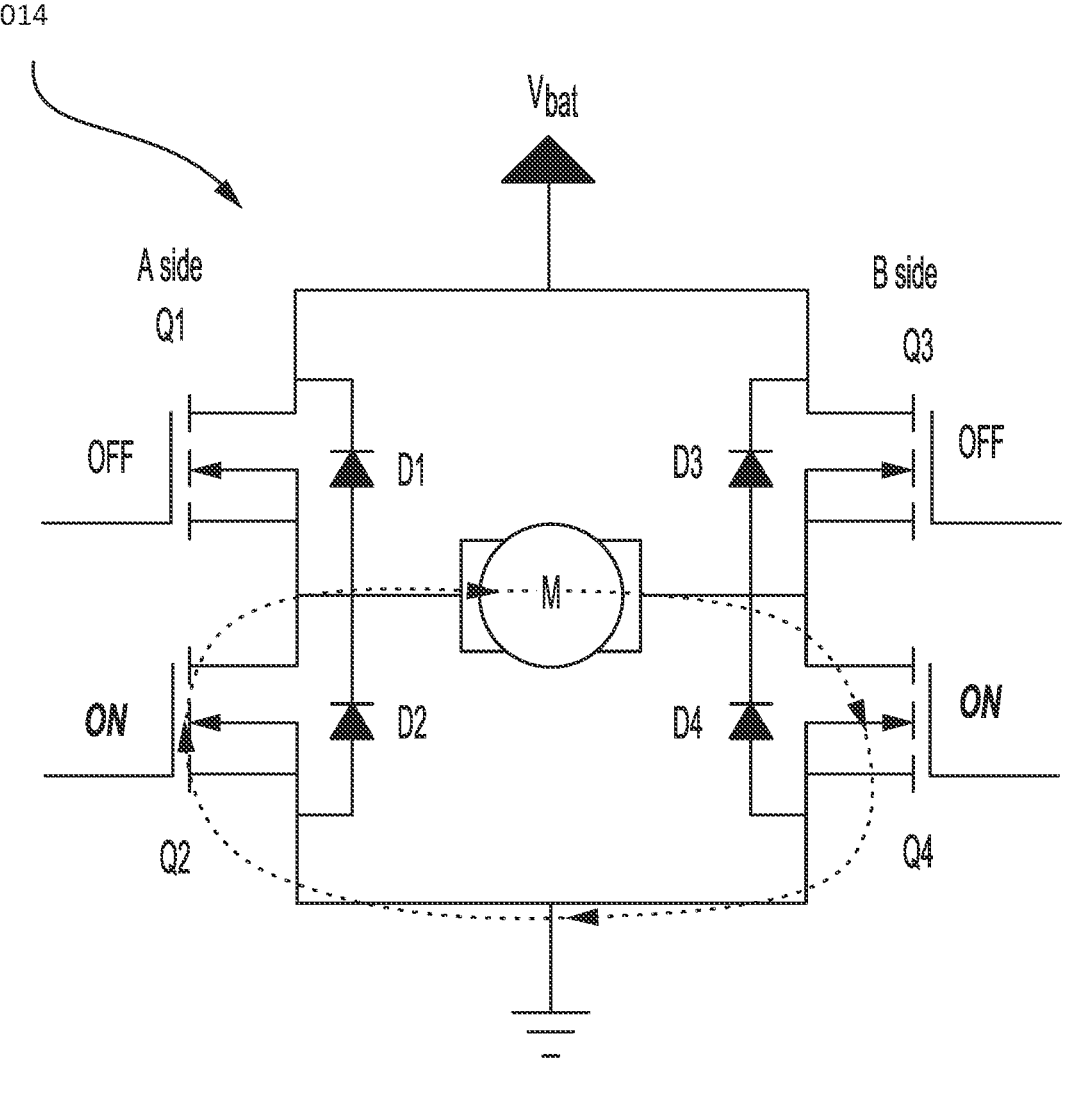
FIG. 117 is an H-Bridge FETs circuit in a dynamic braking mode, in accordance with at least one aspect of the present disclosure.
Figure 118:
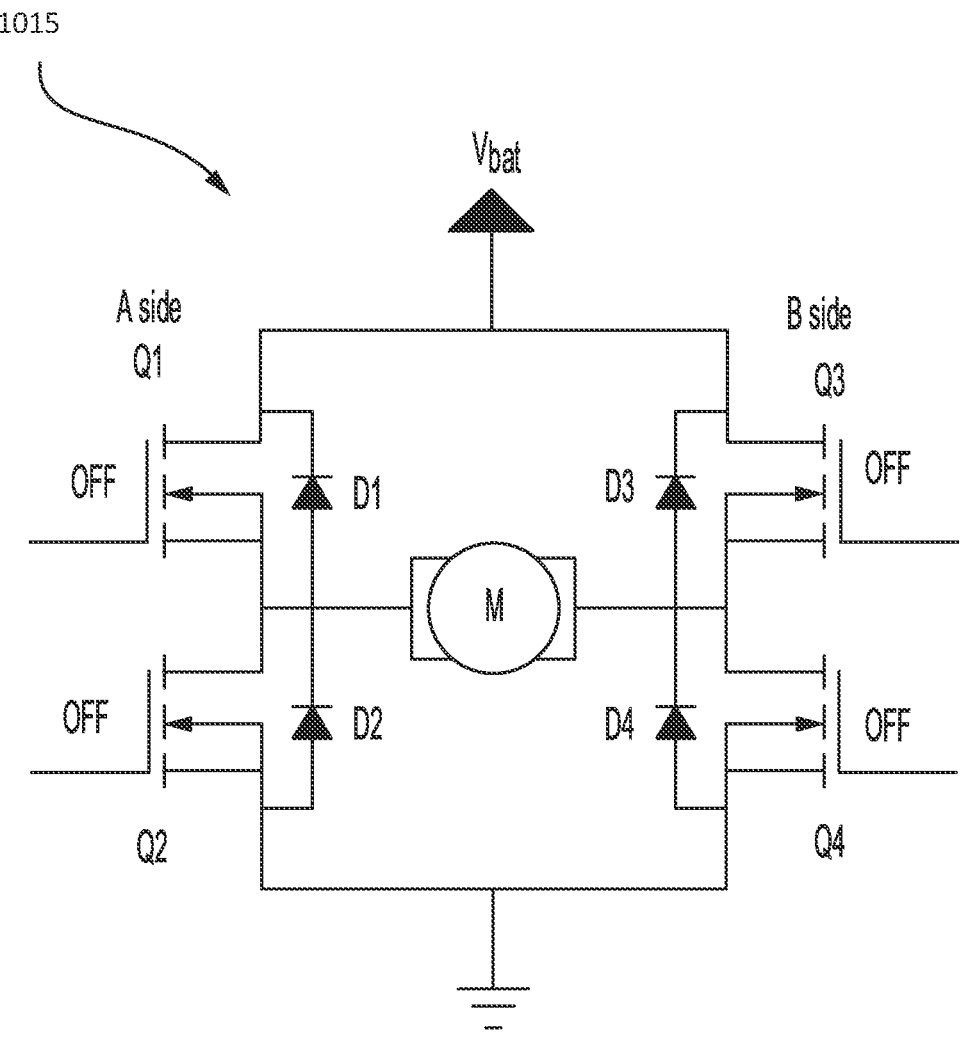
FIG. 118 is an H-Bridge FETs circuit in a coasting mode, in accordance with at least one aspect of the present disclosure.

In various instances, the motor assembly 1939 includes one or more H-Bridge FETs that are controlled by the control circuit to implement a motor drive sequence, in accordance with FIG. 114, for example. FIGS. 115-117 illustrate an example H-Bridge FETs in three phases: a positive phase, a negative phase, and an inactive phase. The control circuit selects the H-Bridge FETs phases per a predetermined sequence that yields the rotational drive motion of the rotor 11003. The power supply to the motor 11002 can continually increase the inertia of the drive assembly 1941. In certain instances, the inertia can be increased by one of the upper H-bridge FETs being open and one of the lower H-bridge FETs being open. The open FETs will correspond to the direction of the motion of the motor, as illustrated in FIGS. 115, 116, which yields a drive mode 11012 and an active reverse mode 11013, respectively.

As previously described, electronics of the motor drive circuit such as, for example, one or more of the H-Bridge FETs are adjusted by the control circuit independent, or in absence, of the motor drive signal, to adjust performance of the motor while in a dynamic state, for example. FIG. 117 presents an H-bridge FETs configuration implemented by the control circuit in the absence of the motor drive signal to yield an active or dynamic braking mode 11014. In the illustrated example, the upper H-bridge FETs are both open and the lower H-bridge FETs are both closed. In an alternative embodiment, an active or dynamic braking mode can also be achieved by the control circuit, in absence of the motor drive signal, by causing the upper H-bridge FETs to be open and the lower H-bridge FETs to be closed, for example.

The H-bridge FETs configuration illustrated in FIG. 117 yields the active or dynamic braking mode 11014, in the absence of the motor drive signal, which resists the inertia of the motor resulting in a discrete, quick, cessation of the rotational motion of the motor 11002. In the illustrated example, no applied voltage is present to force a rapid discharge of the current in the system. Accordingly, current dissipates slowly as heat, for example, as the current flows through the resistance of the inductor and the on-state resistance of the lower H-Bridge FETs. Despite the slower current decay, active braking mode provides a faster reduction in motor speed, due to the EMF generated by the decaying current.

FIG. 21 presents an H-bridge FETs configuration implemented by the control circuit in the absence of the motor drive signal to yield a passive braking, or coasting, mode 11015. In the illustrated example, the upper and lower H-bridge FETs are open in the passive braking, or coasting, mode, preventing current from the power source or any interactive motor current creation and braking. The system still brakes but based on the friction losses and inertia of the system. The removal of the motor drive signal, and the application of the passive braking, or coasting, mode can be beneficial in a closure tissue-treatment motion, for example.

The control circuit can initiate a closure tissue-treatment motion by causing a motor drive signal to be transmitted to a motor (e.g. motor 11002), in a drive mode 11012, to generate a rotational drive motion. A drive assembly (e.g. drive assembly 1941) causes at least one of the jaws of the end effector 1940 to move relative to the other jaw to grasp tissue. As the end effector 1940 transitions from an open configuration, see FIG. 13, toward a closed configuration, tissue between the jaws of the end effector 1940 is compressed. In certain instances, the control circuit deactivates, or cuts off, the motor drive signal, and then activates the passive braking, or coasting, mode 11015 to allow the compressed tissue to relax and/or push back against the drive assembly 1941.

In certain instances, the motor drive signal is based on a default control program. The default control program can be saved in a memory 1935, for example, and can be accessed by the control circuit for execution. The electronics of the motor drive circuit can be separately controlled by an adaptive motor control program. The adaptive motor control program can be adjusted based on measured parameters, such as data gathered by sensors 1938, for example. As previously described in greater detail, the adaptive motor control program may include one or more modes. The modes can be a driving mode 11012, a dynamic braking mode 11014, an active reverse mode 11013, a coasting braking mode 11015, or a combination thereof.

As discussed above, a surgical system can include a motor that motivates a firing member to effect a deployment of staples from a staple cartridge into tissue grasped by jaws of an end effector in a tissue treatment motion of the end effector. The tissue treatment motion may also encompass a concurrent advancement of a cutting member to sever the stapled tissue. In certain aspects, the tissue treatment motion of the end effector encompasses a closure motion of the jaws of the end effector to grasp the tissue.

Force to fire is a critical parameter in the tissue treatment motion of the firing member. The force to fire being too high or too low can interfere with proper staple formation and surgical outcomes. There are a variety of parameters that can affect the force to fire. Tissue thickness, tissue compression, articulation angle, staple type, and firing speed are just a few. Some of the parameters can be related to the tissue treatment motion of the end effector, such as closing speed, firing speed, and etc., while others can be independent of the tissue treatment motion of the firing member, such as staple cartridge configuration, tissue thickness, articulation angle, and etc. Adapting parameters of the tissue treatment motion such as, for example, firing speed, closure speed, or wait times based on monitored factors independent of the tissue treatment motion can improve surgical outcomes.

FIG. 119 depicts a flow diagram 17000 that shows a process that can be executed by a control circuit, such as control circuit 1932 (FIG. 13), surgical hub 1953 (FIG. 13), or control circuit 620 (FIG. 14), to control the tissue treatment motion of the end effector during a surgical procedure. At 17002, the control circuit determines a default control algorithm to affect the tissue treatment motion of the end effector. For example, a default control algorithm could be chosen based on the surgical procedure that is being performed. In another instance, the default control algorithm could be chosen based on a tissue type to be treated by the end effector. The default control algorithm can have default values, or profiles, set for a default speed of the motor, a default current of the motor, a default maximum load of the drive train, and a default travel distance of the drive train, among other possible parameters of the tissue treatment motion.

At 17004, the control circuit receives an input indicative of a situational parameter associated with the surgical procedure or an aspect of the surgical site that is independent of the tissue treatment motion of the end effector. For example, the parameter can be independent of parameters associated with the firing member or other portions of the firing train. In certain aspects, the situational parameter is an articulation angle of the end effector, a presence of a buttress on a staple cartridge, a configuration of a staple cartridge, a shelf life of a staple cartridge, a tissue thickness, or any suitable parameter independent of the tissue treatment motion of the end effector. In various instances, the control circuit could receive the situational parameter from sensors coupled to the control circuit. For example, sensors 1938 (FIG. 13) or sensors 630 (FIG. 14) could provide an input to the control circuit indicative of the situational parameter. In an alternative instance, the control circuit could receive image data and the parameter could be calculated by the control circuit based on the image data. In yet another instance, the parameter could be entered directly by a user through a user interface, for example.

Once the control circuit receives the situational parameter, the control circuit can adjust 17006 various parameters of the default control algorithm effecting the tissue treatment motion of the end effector based on the situational parameter. In various instances, the control circuit can adjust velocity, rate-of-change of velocity, strokes, load limits, or delay times of the default control algorithm, for example, based on the situational parameter. For example, the velocity of firing member, or other portions of the firing trains, could be lowered or increased based on the situational parameter to improve a surgical outcome.

After the default control algorithm is adjusted, the control circuit can control 17008 a motor of the surgical system based on the adjusted control algorithm to effect the tissue treatment motion of the end effector. In various instances, the adjustment to the default control algorithm could occur pre-operatively. In other instances, the adjustment to the default control algorithm could occur intra-operatively. Using the adjusted control algorithm benefits the surgical procedure since it accounts for the effects to the tissue treatment motion caused by the situational parameter.

In various instances, the situational parameter is an articulation angle of the end effector of the surgical system. While the articulation angle of the end effector is independent of the tissue treatment motion, the articulation angle influence can, in certain instances, influence one or more parameters of the tissue treatment motion such as, for example, the force to fire (FTF). A larger articulation angle causes a non-linearly increasing loss in the firing drive train as it is pushed around an articulation joint defining the larger articulation angle. Moving the firing drive train around the articulation joint can cause a large force on the motor based on the articulation angle. For example, when the articulation angle is zero (a straight configuration) then there is minimal to no additional force on the motor due to the articulation angle. On the other hand, when the end effector is articulated by the articulation joint, the FTF, for example, increases based on the articulation angle of the end effector. Accordingly, adjustments to the default control algorithm effecting the tissue treatment motion in response to an articulation angle can mitigate the effects of articulation on firing system loads.

A default control algorithm could be configured for the articulation joint to be in a straight configuration. For example, the default control algorithm has the threshold forces set for the articulation joint to be in a straight configuration. However, the articulation joint could need articulated to reach the area of the tissue that needs treated. The articulation joint being articulated increases the force on the motor that is required to close and fire the end effector. The control circuit can recognize that the end effector is articulated prior to closing and firing the end effector. The control circuit can use the current articulation angle and calculate an increase in the force that "should" be required to maintain the same force on the tissue if the articulation joint was in the straight configuration. The force to close and fire is directly linked to the articulation angle, and thus the force boundary values on the motor have to be adjusted higher due to the articulation angle.

In various aspects, the default control algorithm defines a threshold force associated with the tissue treatment motion of the end effector. The threshold force ensures that the FTF remains within a safe operational range, by triggering a change in the tissue treatment motion such as a pause, or at least a speed reduction, in the tissue treatment motion to permit the tissue being treated to reach a better compression state, for example. As previously explained, while the articulation angle of the end effector is independent of the tissue treatment motion, it can interfere with force transmission to the end effector and, consequently, rendering inaccurate the threshold force set by the default control algorithm.

To compensate for the articulation angle, the default control algorithm can be adjusted to change the threshold force, or select a different threshold force based on the articulation angle of the end effector. Other parameters associated with the tissue treatment motion also can be adjusted based on the articulation angle of the end effector such as speed of closure, a pause time (e.g. a pause between clamping and firing), and an initial speed of firing member. For example, the initial speed of the firing member may need to be lowered as the articulation angle increases to ensure the proper force is being applied to the cutting member.

In various aspects, the default control algorithm can be adjusted to change the velocity of the motor to control the impact force on the motor to within a desirable range. The impact force on the motor is also affected by the articulation angle. The force loss due to the articulation angle can cause the motor to work harder to achieve a desired FTF. In certain instances, the control circuit can pause the tissue treatment motion to provide additional time for tissue relaxation by fluid egress, for example, to reduce the FTF required for completion of the tissue treatment motion.

Figure 120:
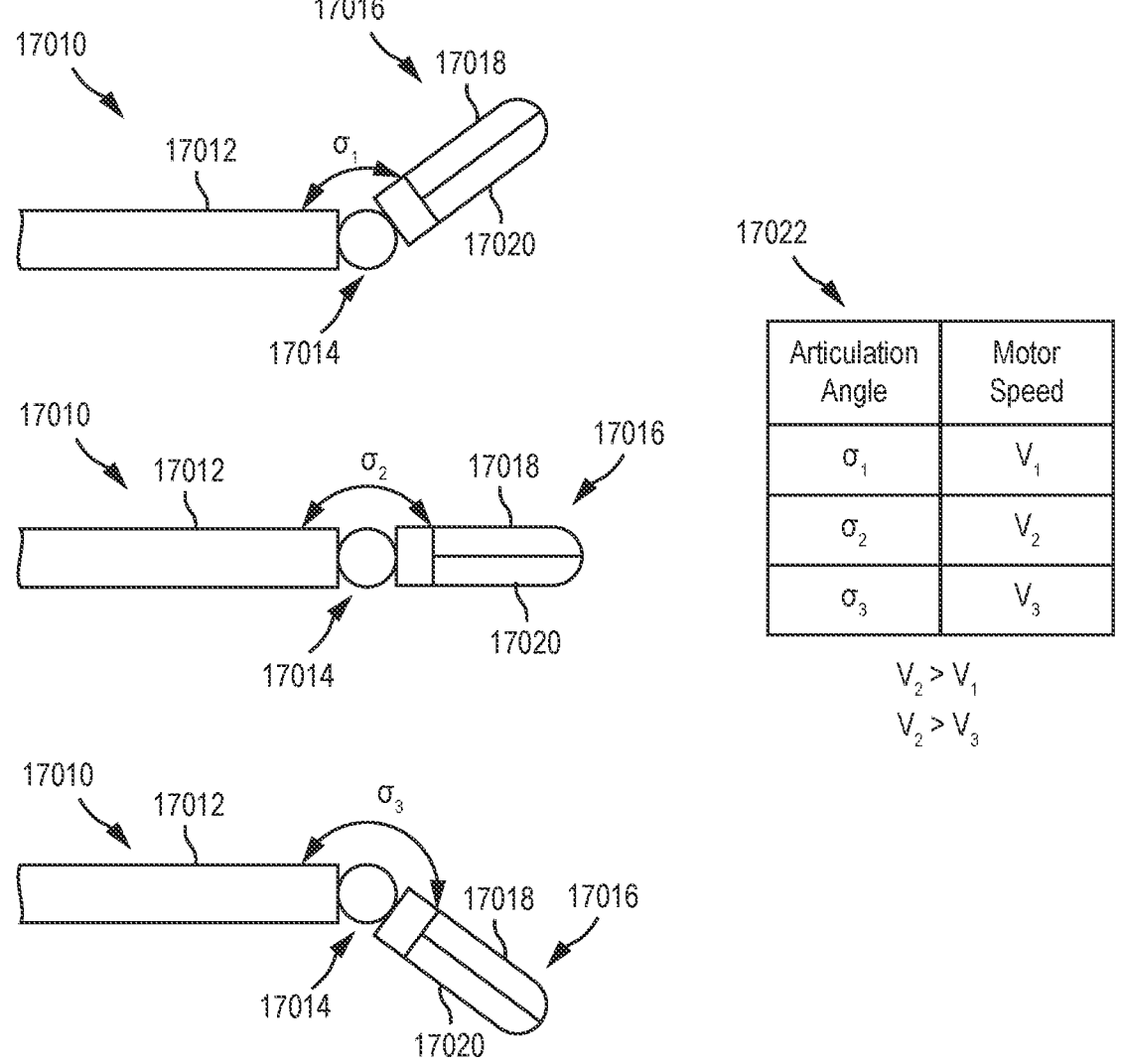

FIG. 120 depicts a diagram showing a surgical instrument 17010 at three different articulation angles. The articulation angles are measured across the articulation joint 17014 between a shaft 17012 and an end effector 17016. The diagram shows the end effector 17016 having two jaws 17018, 17020. The articulation angle $\sigma_2$ shows the surgical instrument 17010 in a straight, or substantially straight, configuration. The articulation angles $\sigma_1$ and $\sigma_3$ show the surgical instrument articulated in two different directions. The more the surgical instrument is articulated away from the straight configuration the higher force required by the motor to drive a drive train through the articulation joint 17014 to effect the tissue treatment motion. The additional force increases the impact force on the motor. One way to lower the impact force on the motor is to drive the motor at a different speeds based on the articulation angle. For example, as shown in table 17022, the velocity of the motor could be lowered when the articulation joint 17014 is articulated away from the straight configuration. Thus, the articulation angle could be used as an input into the control circuit to adjust a firing speed of the default control algorithm.

Figure 121:
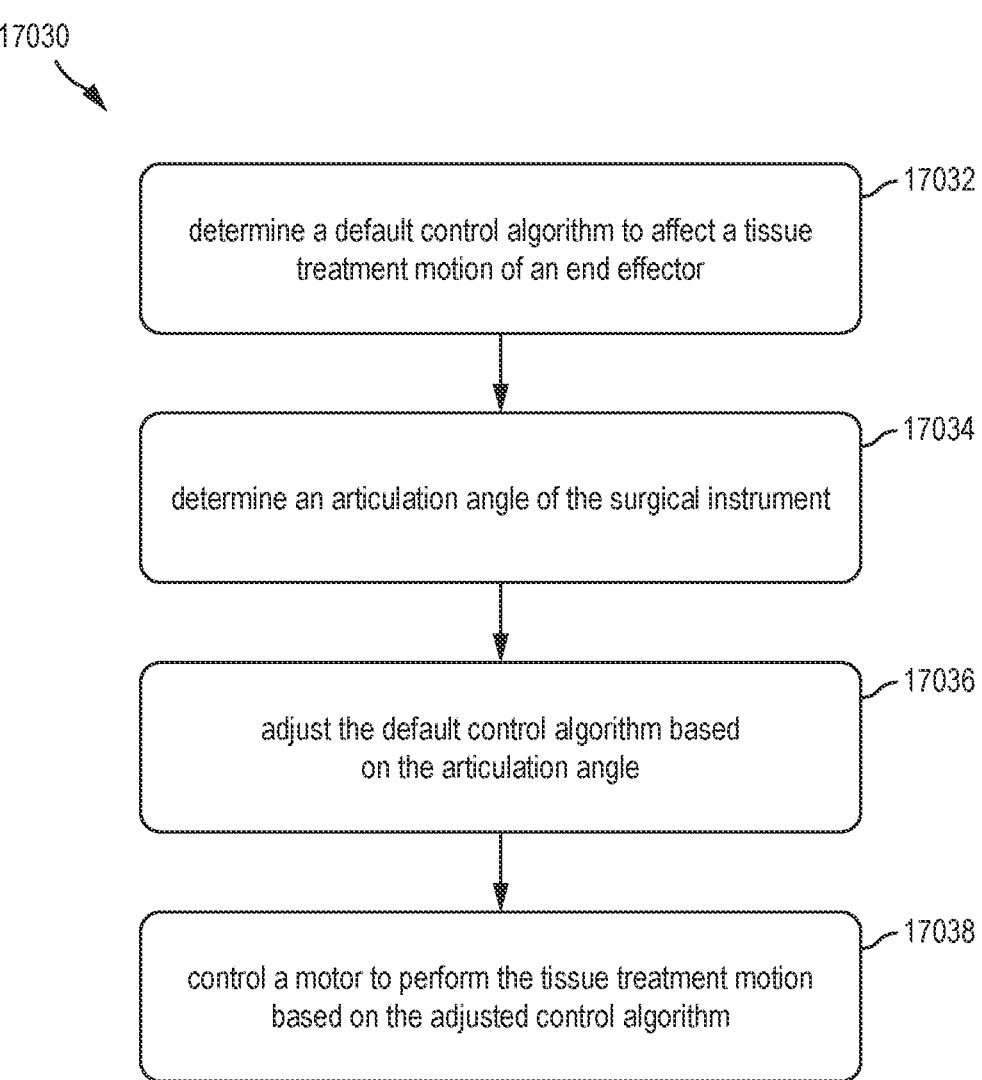

FIG. 121 depicts a flow diagram 17030 that shows a process that can be executed by a control circuit, e.g. control circuit 1932 (FIG. 13), surgical hub 1953 (FIG. 13), or control circuit 620 (FIG. 14), to adjust the tissue treatment motion of a surgical procedure, in accordance with at least one aspect of the present disclosure. In the illustrated example, the control circuit determines 17032 a default control algorithm to affect the tissue treatment motion of the end effector, as described in connection with the process of FIG. 119.

At 17034, the control circuit determines an articulation angle of the surgical instrument, as illustrated in FIG. 120. In at least one aspect, the control circuit receives data indicative of the articulation angle that the control circuit uses to determine the articulation angle. In one aspect, the control circuit determines the articulation angle from image data. In another aspect, the control circuit determines the articulation angle from sensor data. In yet another aspect, the control circuit determines the articulation angle based on a linear motion of an articulation drive effecting the articulation motion of the end effector. The motion of the articulation drive can be measured by any suitable sensor. Additionally, or alternatively, the linear motion of the articulation drive can be calculate based on the speed of a motor driving the linear motion of the articulation drive and the time the motor was operated to effect the linear motion of the articulation drive. Other suitable mechanism for determining the articulation angle of the surgical instrument are contemplated by the present disclosure, but are not described for the sake of brevity.

At 17036, the control circuit adjusts the default control algorithm based on the articulation angle. The default control algorithm could be configured for the articulation joint being in a straight configuration. The control circuit can adjust one or more parameters of the default control algorithm such as, for example, the force thresholds based on the articulation angle. In at least one aspect, a target magnitude of compression exerted by the jaws of the end effector onto tissue can be adjusted based on the articulation angle. The control circuit can also adjust a speed of the tissue treatment motion based on the articulation angle. In at least one example, the control circuit decreases the clamping speed and/or the firing speed in the default control algorithm to lower the impact forces on the motor. The control circuit can also adjust delay times in the default control algorithm based on the determined articulation angle. In at least one instances, the delay time is firing delay time, which represents the time between the completion of an end effector closure and the initiation of a firing stroke. The firing delay time allows for fluid egress from the grasped tissue prior to initiating the firing stroke. In at least one example, the firing delay time is based on the articulation angle of the end effector. In at least one example, for a first angle $\alpha1$, a first delay time t1 is selected, and for a second angle $\alpha2$, greater than the first angle $\alpha1$, a second delay time t2 is selected, wherein the second delay time is greater than the first delay time. In certain instances, the control circuit selects the firing delay time based on a proportional relationship between the firing delay time and the articulation angle. In other instances, the control circuit selects the firing delay time based on an inverse proportional relationship between the firing delay time and the articulation angle. The relationship between the firing delay time and the articulation angle can be defined by an equation, a look-up table, or any suitable format accessible by the control circuit.

Once the default control algorithm is adjusted based on the articulation angle, then the control circuit can proceed to control the motor at the appropriate time in the procedure. In various aspects, the adjustment to the default control algorithm can occur pre-operatively or intra-operatively. At 17038, the control circuit controls the motor, e.g. motor assembly 1939 (FIG. 13), closure motor 603, or firing motor 602, to perform the tissue treatment motion based on the adjusted control algorithm. Using the adjusted control algorithm benefits the surgical procedure since it accounts for the effects to the tissue treatment motion caused by the articulation angle.

The control circuit can determine the articulation angle in a variety of ways. In one aspect, the articulation angle is calculated from the distance that a motor, such as motor 606a, 606b or motor assembly 1939, drives a drivetrain member, such as drive assembly 1941. In one aspect, the articulation angle is determined based on movement of an articulation drive member. The movement of the longitudinally movable drive member can be tracked by a positioning system, where the articulation drive is driven by the motor. As a result of tracking the movement of the articulation system, the control circuit can track the articulation angle of the end effector, for example. In various circumstances, as a result, the articulation angle can be determined as a function of longitudinal displacement of the articulation drive member. Thus, a position signal provided by the positioning system to the control circuit can be used as an input to calculate the articulation angle.

In another aspect, the articulation angle can be determined by locating sensors on the articulation joint. The sensors can be configured to sense rotation of the articulation joint using a positioning system adapted to measure absolute rotation of the articulation joint. For example, the sensor arrangement can comprise a position sensor, a magnet 1202, and a magnet holder adapted to sense rotation of the articulation joint. The position sensor comprises one or more than one magnetic sensing elements such as Hall elements and is placed in proximity to the magnet. The position sensor can be adapted to measure the rotation angle of the articulation joint. Accordingly, as the magnet rotates, the magnetic sensing elements of the position sensor determine the angular position of the magnet located on the articulation joint. This information is provided to the control circuit to calculate the articulation angle of the articulation joint. Accordingly, the articulation angle of the end effector can be determined by the positioning system adapted to measure absolute rotation of the articulation joint.

Figure 122:
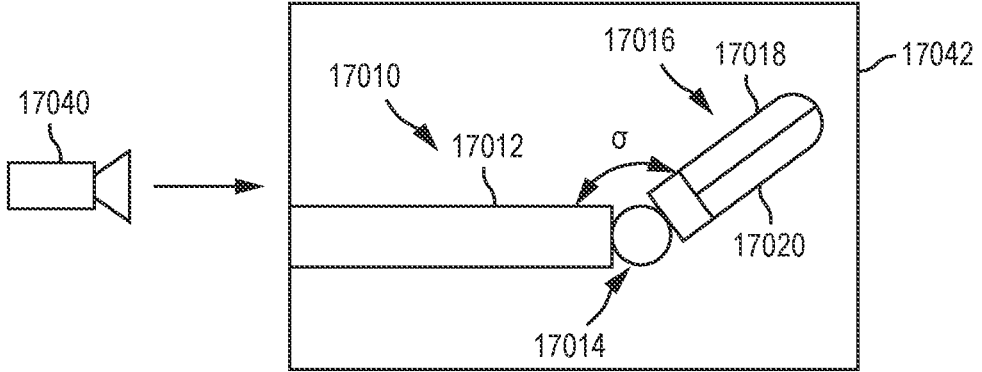

In another aspect, the articulation angle could be determined from visual data of a surgical site. Referring to FIG. 122, the surgical instrument 17010 is shown in the view 17042 of the surgical site. A camera 17040 located on a different surgical device could be used to view the surgical instrument 17010 at the surgical site. For example, the camera 17040 could provide image data of the shaft 17012 relative to the end effector 17016. In some aspects the image data is video data. In some other aspects, the image data is a still image of the surgical site. The control circuit can receive the image data from the camera 17040 and then use that image data to determine the articulation angle. In at least one example, the control circuit performs image analysis to locate the shaft 17012 and the end effector 17016 in the image. Then the control circuit determines the orientation of the shaft 17012 and the orientation of the end effector 17016. The control circuit then determines the articulation angle based on the orientation of the shaft 17012 and the orientation of the end effector 17016. The control circuit then adjusts the default control algorithm based on the articulation angle.

FIG. 123 depicts a flow diagram 17070 that shows a process that can be executed by a control circuit, e.g. control circuit 1932 (FIG. 13), surgical hub 1953 (FIG. 13), or control circuit 620 (FIG. 14), to control the tissue treatment motion, in accordance with at least one aspect of the present disclosure. In the illustrated example, the control circuit determines 17072 a default control algorithm to affect the tissue treatment motion of the end effector, as described in connection with the process of FIG. 119.

The control circuit receives 17074 image data from a camera 17040 at a surgical site. In at least one instance, the image data is received from one camera 17040. In other instances, multiple cameras are utilized to obtain a three dimensional image of the articulation joint. Then the control circuit performs 17076 image analysis on the image data to determine the orientation of the shaft and the orientation of the end effector. Once the orientations of the shaft and end effector are known, the control circuit determines 17078 the articulation angle based on the image analysis. This process of calculating the articulation angle from image data is described in more detail in connection with FIG. 122. In at least one aspect, the image analysis occurs on a remote server or a surgical hub, e.g. surgical hub 1953 (FIG. 13). In at least one example, the remote server receives the image data directly from the camera 17040 or from the control circuit. Then the remote server performs the image analysis to determine the articulation angle, as described above in connection with FIG. 122. After the articulation angle is determined, the remote server transmits the articulation angle to the control circuit.

Once the articulation angle is determined, the control circuit adjusts 17080 the default control algorithm based on the articulation angle, as described in connection with the process of FIG. 121. For example, the control circuit can adjust the speed of the tissue treatment motion, force produced at the motor driving the tissue treatment motion, delay times during the tissue treatment motion, and etc. In various aspects, the adjustment to the default control algorithm can occur pre-operatively or intra-operatively. At 17082, the control circuit controls the motor, e.g. motor assembly 1939 (FIG. 13), closure motor 603, or firing motor 602, to perform the tissue treatment motion based on the adjusted control algorithm. Using the adjusted control algorithm benefits the surgical procedure since it accounts for the effects to the tissue treatment motion caused by the articulation angle.

There are many parameters that are situational and independent from the tissue treatment motion that can be used to adjust a default control algorithm to benefit a surgical procedure. As discussed above articulation angle is one of these parameters. Tissue parameters, staple cartridge configuration, and/or buttress parameters are also examples of situational parameters that independent of the tissue treatment motion, which can be utilized to adjust the default control algorithm of a surgical system, for example.

The cartridge configuration includes one or more of a cartridge type, cartridge age (e.g. time since manufacturing or production), a sled type, staples type, staples height, and/or staples material composition (e.g. stainless steel, magnesium, etc.). Tissue parameters include tissue type (e.g. stomach, liver, lung), tissue thickness, tissue disease state, and/or tissue compressibility. Buttress parameters include buttress type, buttress material composition, buttress thickness, buttress compressibility, buttress position (e.g. on the anvil, on the staple cartridge, on both of the anvil and the staple cartridge), and/or attachment type of the buttress. In some aspects, the control circuit, e.g. control circuit 1932 (FIG. 13), surgical hub 1953 (FIG. 13), or control circuit 620 (FIG. 14), adjusts the default control algorithm based on one or more of the tissue parameters, the buttress parameters, the articulation angle, and/or the staple cartridge configuration, for example.

In some aspects, the control circuit adjusts the default control algorithm to change the maximum speed and/or the maximum load of the staple firing to correspond to the requirements of the material of the staples in the staple cartridge. In another aspect, the control circuit takes into account the age of the staples in the staple cartridge and slows the actuation speed of the staple firing stroke to fire the staples slower due to their age. In yet another aspect, the control circuit detects the presence of a buttress and adjusts the speed of the firing stroke based on the buttress and the material of the staples. It is also possible for the control circuit to adjust the default control algorithm based on all the information determined based on the cartridge configuration.

The control circuit can determine the cartridge configuration in a plurality of ways. In one aspect, the cartridge configuration could be entered directly by a user through a user interface after or before inserting the staple cartridge into the elongate channel of the end effector, for example. In another aspect, the cartridge configuration can be determined by the control circuit. In at least one aspect, the control circuit receives image data of the staple cartridge after or before insertion of the staple cartridge into the elongate channel of an end effector jaw. In some instances, the image data are received from a camera at the surgical site. In such instances, the control circuit determines the cartridge configuration based on the image data. In at least one aspect, the control circuit determines a cartridge configuration based on a visual identification characteristic of the staple cartridge, which is recognized from the image data. The visual identification characteristic can be an identification color, an identification number, and/or an identification shape, for example. In certain instances, the control circuit retrieves the cartridge configuration from a memory storing a look-up table, for example, listing visual identification characteristics, e.g. colors, and corresponding cartridge configurations.

Another way for the control circuit to determine the staple cartridge configuration is through an RFID chip located inside of the staple cartridge, for example.

Figure 124:
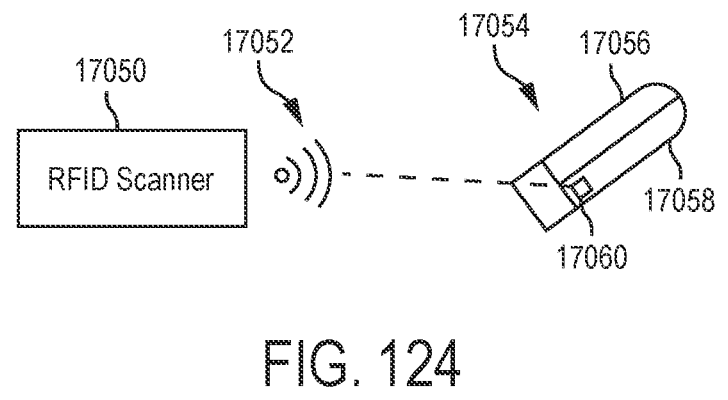

FIG. 124 illustrates an end effector 17054 having two jaws 17056, 17058. The jaw 17058 includes an elongate channel configured to receive a staple cartridge that has an RFID chip 17060. In one aspect, a control circuit, e.g. control circuit 1932 (FIG. 13), surgical hub 1953 (FIG. 13), or control circuit 620 (FIG. 14), can be coupled to an RFID scanner 17050. The RFID scanner 17050 can wirelessly 17052 read the RFID chip 17060 upon inserting the staple cartridge to determine the cartridge configuration of the inserted staple cartridge. For example, the insertion of the staple cartridge could activate a switch. The control circuit upon receiving a signal from the switch, activates the RFID Scanner 17050 to scan the RFID chip 17060 inside of the inserted staple cartridge. In one aspect, the RFID chip 17060 provides the RFID scanner 17050 and the control circuit with an identification number for the staple cartridge. In such an aspect, the control circuit uses the identification number to determine the staple cartridge configuration. For example, the identification number could be compared to a look-up table to determine information about the staple cartridge configuration.

FIG. 125 depicts a flow diagram 17090 that shows a process that can be executed by a control circuit, e.g. control circuit 1932 (FIG. 13), surgical hub 1953 (FIG. 13), or control circuit 620 (FIG. 14), to control the tissue treatment motion, in accordance with at least one aspect of the present disclosure. In the illustrated example, the control circuit determines 17092 a default control algorithm to affect the tissue treatment motion of the end effector, as described in connection with the process of FIG. 119.

At 17094, the control circuit detects the presence of a staple cartridge. In at least one aspect, the control circuit receives data indicative of the presence of a staple cartridge. For example, the insertion of the staple cartridge activates a switch, or proximity sensor, that sends a signal to the control circuit, which allows the control circuit to determine that a staple cartridge has been inserted. In an alternative aspect, the control circuit could receive image data and the presence of a staple cartridge could be determined by the control circuit based on the image data. For example, the control circuit, a remote server, or a surgical hub, e.g. surgical hub 1953 (FIG. 13), could perform image analysis on the image data to determine the presence of a staple cartridge, similar to the process described in connection to FIG. 123. In yet another aspect, the presence of a staple cartridge is entered directly by a user through a user interface.

Once the presence of a staple cartridge is detected, the control circuit determines 17096 the configuration of the staple cartridge. In at least one aspect, the control circuit receives data indicative of the configuration of the staple cartridge. As discussed above, the control circuit can determine the configuration of the staple cartridge in a plurality of ways, including through an RFID signal, as described in connection to FIG. 124, for example.

After the control circuit determines the staple cartridge configuration, the control circuit adjusts 17098 the default control algorithm based on the staple cartridge configuration. In at least one aspect, the control circuit adjusts one or more parameters of the tissue treatment motion based on the staple cartridge configuration. In one aspect, the control circuit adjusts the default control algorithm to change the maximum speed and/or the maximum load during the tissue treatment motion to correspond to the requirements of the material composition of the staples in the staple cartridge. Different material compositions require different tissue treatment motions for optimal staple formation or deformation. Parameters of the tissue treatment motion can be selected to optimize the tissue treatment motion based on the material composition of the staples to be deployed into the tissue by the tissue treatment motion. Such aspects include firing speed, FTF, delays or pauses during firing, and/or firing acceleration, for example.

In one aspect, a memory stores tissue treatment motion parameters and corresponding staple material compositions. In such aspect, the control circuit selects tissue treatment motion parameters based on a detected staple material composition. In one aspect, the material of the staples requires an amount of force to form the staple properly and having too much force could cause a staple to break. By lowering the speed and/or maximum load, the control circuit can mitigate this issue.

In another aspect, the control circuit lowers the initial acceleration of the motor during the tissue treatment motion based on the cartridge configuration. In yet another aspect, the control circuit can take into account the age of the staples in the staple cartridge and adjust the default control algorithm to slow the actuation speed of the staple firing stroke to fire the staples slower due to their age. For example, as the staples age in the staple cartridge, they could slightly degrade, which may reduce their ability to withstand the forces associated with staple formation without breaking. The control circuit could lower the actuation speed, which in turn could apply less force to the staples during firing to prevent any damage to them.

In yet another aspect, the control circuit determines the presence of a buttress from the staple cartridge configuration and adjusts the tissue treatment motion based on the presence of the buttress, as described in more detail in connection with FIG. 126. In yet another aspect, the control circuit adjusts delay times in the default control algorithm based on the staple cartridge configuration, similar to the delay time adjustment described in connection with the process of FIG. 121. For example, the firing delay time could be based on the staple cartridge configuration instead of or along with the articulation angle. In at least one instance, the delay time occurs during application of staples to tissue. For example, the control circuit applies a delay after applying a percentage of the staples in the staple cartridge to allow anticipated forces during the stapling and cutting to decrease. In some aspects, this delay is determined based on the staple cartridge configuration.

In some aspects, the control circuit uses a plurality of parameters determined based on the staple cartridge configuration to adjust the default control algorithm. For example, the control circuit can adjust the default control algorithm based on the age of the staples in the staple cartridge and the material of the staples in the staple cartridge. However, any number of parameters from the staple cartridge configuration may be used to determine the adjustment to the tissue treatment motion of the end effector.

At 17100, the control circuit controls the motor, e.g. motor assembly 1939 (FIG. 13), closure motor 603, or firing motor 602, to perform the tissue treatment motion based on the adjusted control algorithm. Using the adjusted control algorithm benefits the surgical procedure since it accounts for the effects to the tissue treatment motion caused by the staple cartridge configuration.

Figure 126:
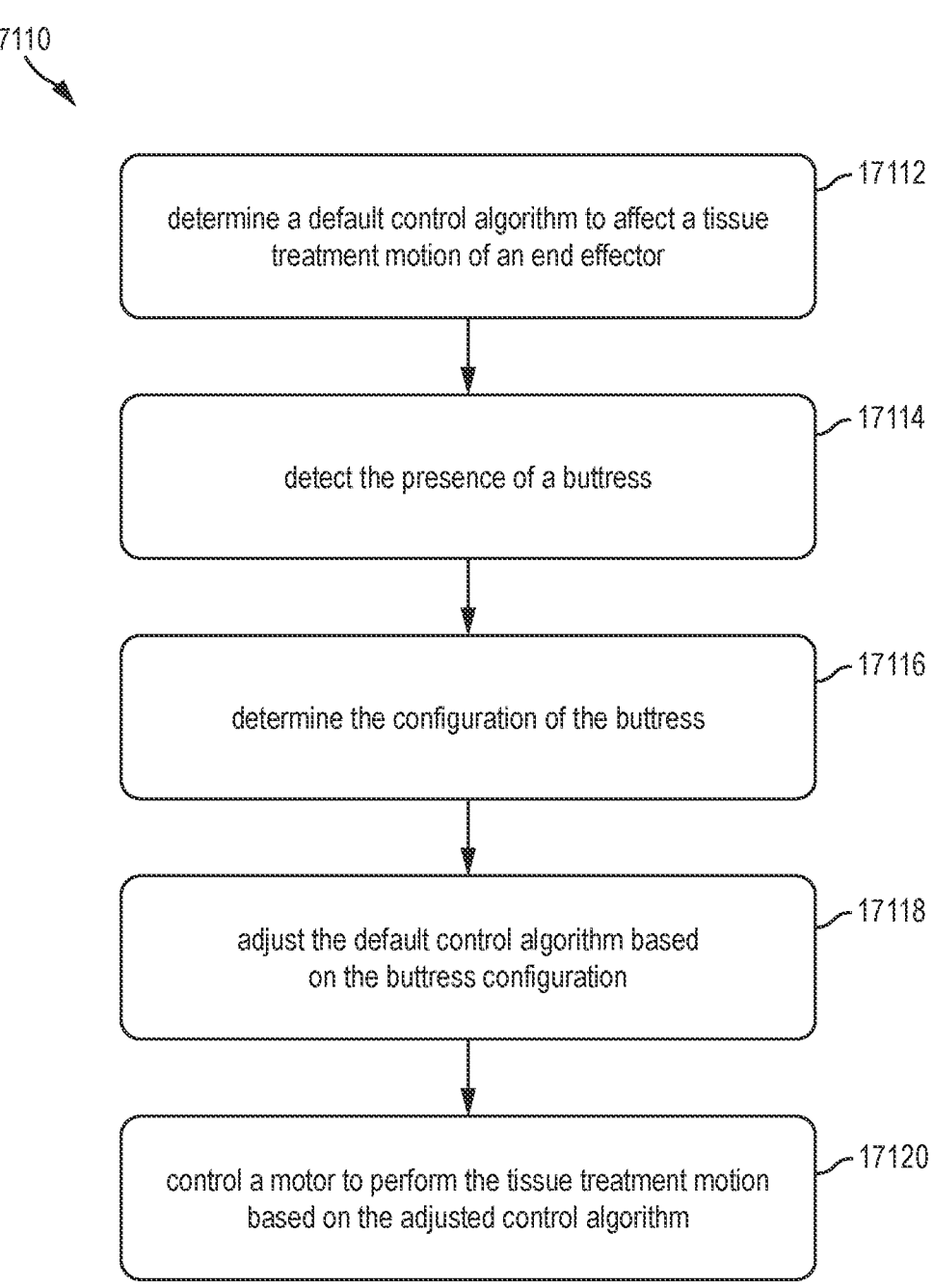

FIG. 126 illustrates a flow diagram 17110 that depicts a process that can be executed by a control circuit, e.g. control circuit 1932 (FIG. 13), surgical hub 1953 (FIG. 13), or control circuit 620 (FIG. 14), to adjust the tissue treatment motion of a surgical procedure, in accordance with at least one aspect of the present disclosure. In the illustrated example, the control circuit determines 17112 a default control algorithm to affect the tissue treatment motion of the end effector, as described in connection with the process of FIG. 119.

At 17114, the control circuit detects the presence of a buttress. In at least one aspect, the control circuit receives data indicative of the presence of a buttress. In one aspect, the control circuit can detect a buttress from a sensor that detects light located on the staple cartridge. For example, when it is dark over the sensor, then there is a buttress covering the sensor. The sensor can transmit a signal to the control circuit, and the control circuit determines that there is a buttress seated on the staple cartridge based on the signal. In another aspect, the control circuit receives image data and the presence of a buttress could be determined by the control circuit from the image data, as described in connection with the process of FIG. 127. In yet another aspect, the presence of a buttress could be entered directly by a user through a user interface. In yet another aspect, the control circuit could receive data indicative of the presence of a buttress during identification of the configuration of the staple cartridge that was inserted into the end effector, as described in connection with the process of FIG. 125. In this aspect, the staple cartridge configuration indicates that a buttress is attached to the staple cartridge.

Once the presence of a buttress is detected, the control circuit determines 17116 the configuration of the buttress. The configuration of the buttress includes all the buttress parameters as described above. In at least one aspect, the control circuit receives data indicative of the configuration of the buttress. The control circuit can determine the configuration of the buttress in a plurality of ways. In one aspect, the configuration of the buttress is entered directly by a user through a user interface. For example, the user can input an identification number for the buttress and/or staple cartridge by directly inputting the number or scanning a code on the buttress, buttress packaging, staple cartridge, or staple cartridge packaging. Then the control circuit compares the identification data to a look-up table to determine the configuration of the buttress, for example. In another aspect, the control circuit receives image data from a camera at the surgical site and the configuration of the buttress could be determined from the image data. For example, the control circuit, a remote server, or a surgical hub, e.g. surgical hub 1953 (FIG. 13), could perform image analysis on the image data to determine the configuration of the buttress, similar to the process described in connection to FIG. 123. For example, the buttress can have an identification number, a color, or other indicator that could be detected by the control circuit from an analysis of the image data. In one aspect, the control circuit compares the identification data to a look-up table to determine the buttress parameters. Additionally, the attachment type of the buttress could be determined from an identification number on a sleeve of the buttress or an identification number on the threads of the buttress depending on the type of buttress. In yet another aspect, the control circuit is provided the buttress configuration from an RFID scanner, similar to the process described in connection to FIG. 124.

After the control circuit determines the buttress configuration, the control circuit adjusts 17118 the default control algorithm based on the buttress configuration. In at least one aspect, the control circuit adjusts one or more parameters of the tissue treatment motion based on the buttress configuration. In one aspect, the control circuit adjusts the default control algorithm to change the motor velocity profile to have a slower initial speed to minimized issues related to starting the tissue treatment motion, when there is a buttress. In another aspect, the control circuit adjusts the velocity of the motor, e.g. motor assembly 1939 (FIG. 13) or closure motor 603 (FIG. 14), during a clamping portion of the tissue treatment motion to clamp the tissue slower. In another aspect, the control circuit can adjust the velocity of the motor, e.g. motor assembly 1939 (FIG. 13) or firing motor 602 (FIG. 14), during the firing stroke based on the buttress configuration to increase cut ability when a buttress is present. For example, the control circuit can adjust the firing speed to slow down or speed up based on the elasticity of the buttress and how much the buttress is compressed. In yet another aspect, the control circuit adjusts delay times in the default control algorithm based on the buttress configuration, similar to the delay time adjustment described in connection with the process of FIG. 121. In one aspect, the firing delay time could be based on the buttress configuration instead of or along with the articulation angle.

As discussed above, the control circuit can use the presence of a buttress, the configuration of the buttress, and/or the thickness of the buttress as an input to adjust the default control algorithm. This process can allow the control circuit to adjust the default control algorithm to adapt the device speeds and delay periods based on the buttress. In addition to the buttress, the control circuit detects if there are higher rigidity adjuncts as part of the buttress. For example, the control circuit obtains this information from the buttress configuration. The higher rigidity adjuncts can be melt-blown non-woven, mesh based reinforcements, or some other kind of reinforcement. The control circuit adjusts the default control algorithm to change the device speeds and delay periods based on the higher rigidity adjuncts. In at least one aspect, the control circuit adjusts the default control algorithm to decrease the firing speed when moving through the higher rigidity adjuncts.

At 17120, the control circuit controls the motor, e.g. motor assembly 1939 (FIG. 13), closure motor 603, or firing motor 602, to perform the tissue treatment motion based on the adjusted control algorithm. Using the adjusted control algorithm benefits the surgical procedure since it accounts for the effects to the tissue treatment motion caused by the buttress configuration.

FIG. 127 illustrates a flow diagram 17130 that depicts a process that can be executed by a control circuit, e.g. control circuit 1932 (FIG. 13), surgical hub 1953 (FIG. 13), or control circuit 620 (FIG. 14), to adjust the tissue treatment motion of a surgical procedure, in accordance with at least one aspect of the present disclosure. In the illustrated example, the control circuit determines 17132 a default control algorithm to affect the tissue treatment motion of the end effector, as described in connection with the process of FIG. 119.

At 17134, the control circuit receives image data from a camera at the surgical site where the tissue treatment motion is to be performed, as described in connection with the process of FIG. 123. Then the control circuit detects 17136 the presence of a buttress seated on the staple cartridge, as described in connection with the process of FIG. 126. In one aspect, the control circuit performs image analysis on the image data to determine the presence of the buttress. Once the presence of the buttress is detected, the control circuit performs 17138 image analysis on the image data to determine the compression of the buttress after the clamping motion of the end effector was complete. In one aspect, the imaging analysis determines the compression of the buttress by comparing the thickness of the buttress after the clamping motion to the thickness of the buttress prior to the clamping of the tissue. In at least one example, the imaging data collected during the surgical procedure provides image data of a side view of the buttress prior to clamping and image data after clamping of the tissue. In one aspect, the imaging analysis can extract the thickness of the buttress from the image data by using a known length or distance on the image to give the objects a size. For example, the imaging analysis can use the length of the end effector or some markings on the surgical instrument of known size to extract the thickness of the buttress. In one aspect, the control circuit then determines the compression of the buttress based on the thickness of the buttress before and after the clamping. As described above in connection to FIG. 123, the image analysis could be performed on a remote server or surgical hub, e.g. surgical hub 1953 (FIG. 13).

At 17140, the control circuit adjusts the default control algorithm based on the buttress compression. In at least one aspect, the control circuit adjusts the motor velocity during the tissue treatment motion to improve cut ability through the compressed buttress. For example, the control circuit adjusts the motor speed to slow down or speed up based on the compression. At 17142, the control circuit controls the motor, e.g. motor assembly 1939 (FIG. 13), closure motor 603, or firing motor 602, to perform the tissue treatment motion based on the adjusted control algorithm. Using the adjusted control algorithm benefits the surgical procedure since it accounts for the effects to the tissue treatment motion caused by compression of the buttress seated in the staple cartridge.

FIG. 128 illustrates a flow diagram 17150 that depicts a process that can be executed by a control circuit, e.g. control circuit 1932 (FIG. 13), surgical hub 1953 (FIG. 13), or control circuit 620 (FIG. 14), to adjust the tissue treatment motion of a surgical procedure, in accordance with at least one aspect of the present disclosure. In the illustrated example, the control circuit determines 17152 a default control algorithm to affect the tissue treatment motion of the end effector, as described in connection with the process of FIG. 119. At 17154, the control circuit receives a first input indicative of a first situational parameter associated with the surgical procedure or an aspect of the surgical site that is independent of the tissue treatment motion of the end effector. At 17156, the control circuit receives a second input indicative of a second situational parameter associated with the surgical procedure or an aspect of the surgical site that is independent of the tissue treatment motion of the end effector. For example, the first and second situational parameters can be similar to the situational parameter described in connection with the process of FIG. 119.

After the control circuit receives the first situational parameter, the control circuit performs 17158 a first adjustment to the default control algorithm based on the first situational parameter. In some aspects, the first adjustment is made prior to the control circuit receiving the second input indicative of the second situational parameter. After the control circuit receives the second situational parameter, the control circuit performs 17158 a second adjustment to the default control algorithm based on the second situational parameter. In various instances, the control circuit can adjust velocity, rate-of-change of velocity, strokes, load limits, or delay times of the default control algorithm based on the first situational parameter or the second situational parameter. For example, the velocity of the firing member, or other portions of the firing trains, could be lowered or increased based on the first situational parameter or the second situational parameter to improve a surgical outcome. In some aspects, the control circuit makes the first adjustment to the default control algorithm before the second adjustment is made. In some aspects, the first and second adjustments are made at the same time.

After all the adjustments are made to the default control algorithm, then the control circuit can proceed to control the motor at the appropriate time in the procedure. In at least one aspect, both of the adjustments to the default control algorithm occur pre-operatively. In at least one alternative aspect, both of the adjustments to the default control algorithm occur intra-operatively. In at least one other aspect, one of the adjustments to the default control algorithm occurs pre-operatively and the other adjustment occurs intra-operatively. Once the time to perform the tissue treatment is reached, the control circuit controls 17162 the motor, e.g. motor assembly 1939 (FIG. 13), closure motor 603, or firing motor 602, to perform the tissue treatment motion based on the adjusted control algorithm. Using the adjusted control algorithm benefits the surgical procedure since it accounts for the effects to the tissue treatment motion caused by the first situational parameter and the second situational parameter.

Following along the same process described in the flow diagram 17150, there can be any number of adjustments made to the default control algorithm. For example, 3, 4, 5, or any number of adjustments can be made to the default control algorithm based on different situational parameters.

FIG. 129 illustrates a flow diagram 17170 that depicts a process that can be executed by a control circuit to adjust the tissue treatment motion of a surgical procedure, in accordance with at least one aspect of the present disclosure. In the illustrated example, the control circuit determines 17172 a default control algorithm to affect the tissue treatment motion of the end effector, as described in connection with the process of FIG. 119.

The control circuit detects 17174 the presence of a staple cartridge and determines 17176 the configuration of the staple cartridge, as described in connection with the process of FIG. 125. At 17178, the control circuit determines an articulation angle of the surgical instrument, as described in connection with the process of FIG. 121.

After the control circuit determines the staple cartridge configuration, the control circuit performs 17182 a first adjustment to the default control algorithm based on the staple cartridge configuration, as described in connection with the process of FIG. 125. After the control circuit determines the articulation angle, the control circuit performs 17180 a first adjustment to the default control algorithm based on the articulation angle, as described in connection with the process of FIG. 121. In some aspects, the first adjustment to the default control algorithm could occur before the control circuit determines the articulation angle. In one aspect, the user inserts a staple cartridge into the end effector causing the control circuit to detect the presence of a staple cartridge and then the control circuit determines the configuration of the staple cartridge. Then the control circuit makes an adjustment to the default control algorithm based on the configuration of the staple cartridge. After that process, the user moves the end effector to the surgical site and articulates the articulation joint to reach the desired location. Then the control circuit could determine the articulation of the articulation joint and make a second adjustment to the default control algorithm based on the articulation angle. In some aspects, the control circuit can make the first adjustment to the default control algorithm before the second adjustment. In some aspects, the first and second adjustments can be made at the same time prior to execution of the tissue treatment motion. As described in connection to FIG. 128, in some aspects the adjustments the default control algorithm can occur pre-operatively, intra-operatively, or both pre-operatively and intra-operatively.

After all the adjustments are made to the default control algorithm, the control circuit controls 17184 the motor, e.g. motor assembly 1939 (FIG. 13), closure motor 603, or firing motor 602, to perform the tissue treatment motion based on the adjusted control algorithm. Using the adjusted control algorithm benefits the surgical procedure since it accounts for the effects to the tissue treatment motion caused by the articulation angle and the staple cartridge configuration.

As discussed above, surgical devices can record a plurality of surgical data during a surgical procedure. As surgical devices have become "smarter" there has been an increase in the size of data recorded and analyzed, in some instances, beyond the capabilities of the surgical devices within a suitable time frame. In such instances, distributed processing is sought as one solution for processing data beyond the capabilities of a surgical device that generated, or received, the surgical data. Thus the processing can be shared allowing larger datasets to be processed in real-time. In addition to processing larger datasets, the decentralized processing can decrease part cost and increase modular functionality between devices.

FIG. 130 illustrates a diagram of a distributed processing system 12000 that includes at least two control circuits 12002, 12010. These control circuits 12002, 12010 can be associated with a surgical device, surgical hub, or remote processing device. For example, one of the control circuits 12002, 12010 could be control circuit 1932 (FIG. 13), surgical hub 1953 (FIG. 13), or control circuit 620 (FIG. 14). The control circuit 12002 has a processor 12004 coupled to a memory 12006 and the control circuit 12010 has a processor 12012 coupled to a memory 12014. In one aspect, the processor 12004 can act as a master processor and processor 12012 can act as a follower, or slave, processor.

As illustrated, the control circuit 12002 receives surgical procedure data 12008. The surgical procedure data 12008 could be any data received from surgical devices and/or users related to the surgical procedure. In one aspect, the surgical procedure data 12008 includes data representing sensor readings from one or more sensors associated with one or more surgical devices. In one aspect, the surgical procedure data 12008 includes imaging data from one or more imaging devices. In certain instances, the imaging data can represent single or multiple frames of a surgical site. The imaging data can represent single or multiple frames taken before and/or during the surgical procedure.

In the illustrated example, the processor 12004 elects a distributed processing of the surgical procedure data 12008 due to the large size of the surgical procedure data 12008 and/or due to the limited available processing time. As such, the control circuit 12002 sends a subset of the surgical procedure data to the control circuit 12010. The processor 12012 performs an analysis on that subset of data and sends the result to the control circuit 12002. In one aspect, a specific task is requested of the follower processor 12012 by the master processor 12004. While the processor 12012 performs an analysis, the processor 12004 performs a different analysis on a different subset of the surgical procedure data. Thus, the processing is distributed between the two control circuits 12002, 12010.

The distributed processing can be extended to any number of control circuits. FIG. 131 illustrates the same distributed processing approach shown in FIG. 130 but applied to multiple follower, or slave, processors. Similar to FIG. 130, the processor 12004 can act as a master processor and the processor 12012 can act as a follower processor; however, now there is an additional follower processor 12013. Each of these control circuits 12002, 12010, 12011 could be from a surgical device, surgical hub, and/or remote processing device. For example, one of the control circuits 12002, 12010, 12011 could be control circuit 1932 (FIG. 13), surgical hub 1953 (FIG. 13), or control circuit 620 (FIG. 14). The control circuit 12011 functions similar to control circuit 12010. The control circuit 12011 has the processor 12013 coupled to a memory 12015.

As illustrated, the control circuit 12002 sends a first subset of the surgical procedure data to the control circuit 12010 and a second subset of the surgical procedure data to the control circuit 12011. In one aspect, one task is requested of the follower processor 12012 by the master processor 12004 and a different task is requested from processor 12013 by the master processor 12004. The processor 12012 performs an analysis on the first subset of data and sends the result to the control circuit 12002. The processor 12013 performs a different analysis on the second subset of data and sends the result to the control circuit 12002. While the processors 12012, 12013 perform analyses, the processor 12004 can perform a third analysis on a third subset of the surgical procedure data. Thus, the processing is distributed between the three control circuits. However, this approach can be expanded to include any number of follower processors.

FIG. 132 illustrates a diagram 12300 depicting some of the potential control circuits that a master processor has access to for distributed processing in a surgical suite 12304 of a medical facility 12302. The surgical procedure data 12008 can come from any number of sensors 12307 and/or user inputs 12306. In at least one aspect, the sensors 12307 are located on different devices in the surgical suite 12304. In at least one aspect, the user inputs 12306 come from a variety of devices in the surgical suite that a person can access. The data from the sensors 12307 and the data from the user inputs 12306 are received by the control circuit 12002 and master processor 12004 and used as inputs to determine control adjustments to a surgical device.

The master processor 12004 (FIG. 130) can perform distributed processing with any number of devices 12310 in the surgical suite 12304, where each of these devices has a processor coupled to a memory. In one aspect, these devices 12310 are surgical instruments in the surgical suite 12304 that are not overly burdened and have processor capacity remaining. In some aspects, a medical facility 12302 has dedicated processor farms 12312 at different locations. For example, the dedicated processor farm location 1 can be dedicated to data processing for operating rooms of the hospital, while location 2 can be dedicated to data processing for intensive care units of the hospital, and etc. The master processor 12004 can perform distributed processing with one of these processor farms 12312 located within the medical facility 12302. The control circuit 12002 and the master processor 12004 can also perform distributed processing with an offsite processor farm 12314 that is located outside of the medical facility 12302.

Various methods and systems associated with performing distributed processing are described in U.S. Pat. No. 11,419, 630, titled SURGICAL SYSTEM DISTRIBUTED PROCESSING, issued Aug. 23, 2022, which is incorporated by reference herein in its entirety.

One of the benefits of performing distributed processing is processing decentralization to decrease part cost and increase modular functionality. For example, allowing the processing to be spread across multiple processors allows the individual processors to be smaller and thus cheaper. One approach to decentralizing processing is to offload software, or processes, to appropriate processors based on utilization needs. For example, a processor that is not being used at a specific time in a surgical procedure could be processing data for a device that is being used. A "dummy" device can also be created that can be used for distributed processing in a surgical suite. This device is added into the surgical suite and can have the sole purpose of being used for distributed processing. A master processor relationship is created, where a processor that is not fully utilized connects to a master processor and performs distributed processing as described in FIGS. 130 and 131.

For some processes it can be beneficial to have a closed loop system. For example, a process that requires a quick response time could benefit from a dedicated high frequency micro-controller that could run in a closed loop system control. This could allow any response from the micro-controller to be as fast as possible. In some aspects, the micro-controller could be separate from any distributed processing.

An example process that requires a quick response time is safety monitoring, which needs to occur constantly. Having a dedicated safety monitoring system can be beneficial to the safety of the patient and the device. The tasks that are associated with safety activities could be isolated from the potential data distribution and kept locally on the device. In one aspect, the processing of safety tasks is executed via a dedicated thread on a device with no parallel processing. FIG. 133 illustrates a device, e.g. surgical instrument 1010 (FIG. 1), surgical instrument assembly 200 (FIG. 8), control circuit 1992 (FIG. 13), surgical hub 1953 (FIG. 13), or control circuit 620 (FIG. 14), that participates in distributed processing for some tasks but also has a dedicated thread outside of the distributed processing. The distributed processing includes control circuits 12400, 12412, 12418. Each of these control circuits 12400, 12412, 12418 could be from a surgical device, surgical hub, or remote processing device. For example, one of the control circuits 12400, 12412, 12418 could be control circuit 1932 (FIG. 13), surgical hub 1953 (FIG. 13), or control circuit 620 (FIG. 14).

The control circuit 12400 has at least two processors 12402, 12406 coupled to two memories 12404, 12408, respectively. The control circuits 12412, 12418 have processors 12414, 12420 coupled to memory units 12416, 12422, respectively. As described in connection to FIG. 131, the processor 12402 acts as a master processor and processors 12414, 12420 act as follower processors. The control circuit 12400 receives surgical procedure data 12410, and performs distributed processing with control circuits 12412, 12418. The master processor 12402 isolates tasks associated with safety activities, and provides these tasks to processor

12406 to be completed locally on the device. The master processor 12402 distributes the non-safety related tasks to the distributed processing.

In various aspects, a process, which can be executed by the processor 12402, includes receiving surgical data, determining whether the received surgical data is associated with a safety task. In one aspect, the process includes categorizing the surgical data as safety data or non-safety, or functional, data. The process further includes transmitting the safety data to a dedicated processor (e.g. 12406), and transmitting the non-safety data to another non-dedicated, or general, processor (e.g. 12414, 12420) for distributed processing. This process allows distributed processing between multiple control circuits, while keeping the safety monitoring locally with processor 12406. This approach can be expanded to include any number of follower processors.

In various aspects, the surgical data may include a safety tag or label that permits identification of the surgical data as safety data. Additionally, or alternatively, determining that a received surgical data is safety data can be achieved based on the source of the surgical data. For example, surgical data from particular sensors can be automatically considered safety data.

Referring still to FIG. 133, if the control circuit 12400 did not have processor 12406 and memory 12408, the safety monitoring could still be kept local to the device and not part of the distributed processing. For example, while the processors 12414, 12420 perform analyses, the processor 12402 performs the safety monitoring tasks. This process would allow the processing to be distributed between the three control circuits, while keeping the safety monitoring local to the device, for example.

Another benefit of distributed processing is that there could be a dedicated device, or control circuit, tasked with data storage. The distributed processing can function similar to the distributed processing described in connection to FIG. 131. However, in this instance, the control circuit 12010 is utilized as a dedicated storage device tasked with storing the surgical procedure data 12008 and any other data sent to the control circuit 12010. In some aspects, the control circuit 12010 could receive sensor data from sensors (e.g. sensors 12307, FIG. 132), user inputs (e.g. user inputs 12306, FIG. 132 and devices (e.g. devices 12310, FIG. 132) in the surgical suite during a surgery. In some instances, the master control circuit 12002 and follower control circuit 12011 route surgical data to the control circuit 20210 for storage in the memory 12014, for example.

In some aspects, the control circuit 12010 stores all the data that is being generated during a surgical procedure. Having a dedicated storage device in the surgical suite allows other devices in the surgical suite to not spend processor capacity on data storage and/or categorization, and instead focus on data processing. In some aspects, the control circuit 12010 categorizes the received data and/or assigns labels to the received data. In at least one aspect, the control circuit 12010 stores the data in a database. The database allows the user, the control circuit 12002, and/or the control circuit 12011 to query desired information and analyze it along with other data in the database anytime during or after the surgery. In some aspects, the control circuit 12010 anonymizes the database and transmits a summary to a remote server or surgical hub, e.g. surgical hub 1953 (FIG. 13).

Another benefit of performing distributed processing is increasing modular functionality. Different processors can be assigned different processing tasks in a decentralized processing environment. As illustrated in FIG. 132, a surgical suite 12304 includes devices 12310 and sensors 12307 that are used during a surgical procedure. Decentralized processing allows data from these devices and sensors to be processed faster and to be communicated where needed automatically, which can improve overall surgical outcomes. For example, a surgical stapling and cutting device, e.g. surgical instrument 1010 or surgical instrument assembly 200, which is used to perform a tissue treatment motion that seals and cuts tissue at a surgical site in a patient, can benefit from surgical data indicative of the patient blood pressure. If blood pressure of the patient can be abnormally high, it is desirable to delay sealing and cutting a tissue including a blood vessel, for example, until the blood pressure stabilizes. In one aspect, a control circuit, e.g. control circuit 1932 (FIG. 13), of the surgical device overrides a user input to begin a firing stroke for sealing and cutting the tissue based on the detection of the blood vessel in the tissue and the detection of a blood pressure higher than a predetermined value.

Further to the above, overriding the user input requires simultaneous data processing of surgical data from multiple sources such as, for example, data from a blood pressure sensor, that can be in a separate device or on the surgical device, data from one or more imaging devices, data from a user input, and/or data from the surgical device indicative of a clamped state of an end effector grasping the tissue to be treated. In one aspect, all the data are received by the control circuit of the surgical device, and all the data processing is performed by a single processor of the surgical device. In other aspects, however, a decentralized approach is taken as discussed in connection with FIGS. 130 and 131, wherein the blood pressure sensor data and/or the imaging data are analyzed at separate processors, independent from the processor of the surgical device. In such aspects, the control circuit of the surgical device receives from a first independent processor a communication indicating that the blood pressure is equal to or higher than a predetermined threshold, for example, and received from a second independent processor a communication indicating the detection of a blood vessel in the tissue being grasped by an end effector of the surgical device. The separate processing of the blood pressure sensor data and the imaging data, external to the control circuit of the surgical device, facilitates a timely override of the user input to begin the firing stroke, or at least a timely pause to permit the user to make an informed decision to continue the firing stroke, or wait until the blood pressure stabilizes.

Additionally, or alternatively, the surgical device control circuit adjusts the tissue treatment motion based on the blood pressure. For example, the control circuit can decrease the speed of the tissue treatment motion or decrease the force applied to the tissue during the tissue treatment motion based on the blood pressure.

Further to the above, a similar override of the firing stroke can be performed by the control circuit of the surgical device based on the detection of a solid object such as, for example, previously fired staples or clips in a tissue grasped by an end effector of the surgical device. Imaging data can be analyzed by a separate processor that identifies the presence of a solid object in the tissue being grasped by the end effector. Additionally, or alternatively, sensor data indicative of the presence of the solid object can also be processed by the same, or a different, separate processor.

Further to the above, the control circuit of the surgical device overrides a user input to begin the firing stroke based on a communication from the separate processor(s) indicating the presence of the solid object. Additionally, the control circuit may alert the user to the presence of the solid object and may request an input as to whether the user wishes to continue the firing stroke. In certain instances, the communication from the separate processor(s) can include an image showing the solid object, or information regarding the position of the solid object with respect to the tissue being grasped by the end effector. The control circuit may present, through a user interface, the image and/or the information to the user along with a request for a decision as to whether or not to perform the firing stroke.

In various aspects, similar surgical situations can be benefit from a decentralized approach of sensor and/or imaging data processing by one or more control circuits communicably coupled to the control circuit of a surgical device. For example, a surgical hub, e.g. surgical hub 1953 (FIG. 13), control circuit could monitor sensor information and adjust a surgical device, e.g. surgical instrument 1010 (FIG. 1), surgical instrument assembly 200 (FIG. 8), control circuit 1992 (FIG. 13), or control circuit 620 (FIG. 14), based on the sensor information. In at least one aspect, the surgical hub receives data from multiple sources including surgical devices (e.g. devices 12310), sensors (e.g. sensors 12307), and surgeons (e.g. user inputs 12306). The surgical hub makes adjustments to the surgical device based on the received data. In one aspect, the surgical hub stops and/or delays the tissue treatment motion of the surgical device until a predefined threshold is reached. Additionally, or alternatively, the surgical hub adjusts the tissue treatment motion of the surgical device based on the data received.

The decentralized processing approach allows additional sensors to become part of a surgical device, e.g. surgical instrument 1010 (FIG. 1), surgical instrument assembly 200 (FIG. 8), or surgical hub 1953 (FIG. 13), without having to update the hardware of the device. This is due to the surgical device being communicably coupled to different devices and having the capability to have more data analyzed through distributed processing. In at least one aspect, the surgical device control circuit is communicably coupled to a new sensor that is added to the surgical device or surgical procedure. The new sensor provides data to the control circuit, e.g. control circuit 1992 (FIG. 13), surgical hub 1953 (FIG. 13), or control circuit 620 (FIG. 14), of the surgical device that can improve surgical outcomes. In one aspect, the new sensor provides more accurate data than a sensor already connected to the surgical device. In such aspect, distributed processing, as described in connection to FIGS. 130 and 131, can be employed to analyze the new data and prioritize the improved data results over the old data result from the less reliable sensor. This process improves the performance of a surgical device without upgrading or replacing the surgical device itself. If multiple sensors, or devices, are added to the device system, then some of these additions can be used to ensure that there is a backup component if a primary component fails. In some aspects, a component from a first device system is removed from the first device system and added to a second device system due to a failure of a component in the second device system.

Further to the above, the decentralized processing approach permits a control circuit of a surgical device to benefit from contextual perioperative data about a surgical procedure that impacts the algorithms within a surgical device, e.g. surgical instrument 1010 (FIG. 1) or surgical instrument assembly 200 (FIG. 8), without overloading a processor of the control circuit of the surgical device with additional processing tasks. For example, a surgeon supplies information to a control circuit, e.g. control circuit 1992 (FIG. 13), surgical hub 1953 (FIG. 13), or control circuit 620

(FIG. 14), through a user interface. In some aspects, the user interface could be a surgical hub, e.g. surgical hub 1953 (FIG. 13). The data from the surgeon is received by the control circuit and used in distributed processing, as described in connection to FIGS. 130 and 131, with data from other sources, for example from sensors and devices in the surgical suite. The control circuit receives results on different analyses performed on the data received by the control circuit. The data from the surgeon and the results allow the control circuit to make control adjustments to the surgical device during the surgical procedure. For example, the surgeon inputs information about the staple cartridge that is being used during the surgical procedure. The information is processed in a separate processor, and an outcome of the data processing is communicated to the control circuit of the surgical device. The control circuit adjusts various operational parameters of the surgical device based on processed data associated with the staple cartridge. The control circuit then uses the determined parameters to perform the tissue treatment motion that accounts for all the information received by the control circuit including the staple cartridge information supplied by the surgeon.

The decentralized processing approach allows for some processing to be performed by compiler/processor farms. Referring back to FIG. 132, the dedicated processor farms 12312 are located in the medical facility 12302 and can be decentralized to high activity zones in the medical facility 12302 such as operating rooms, intensive care units, emergency rooms, and etc. By having a dedicated processor farm for each of these departments in the hospital, the processor farms become strategically positioned to better handle the data within the hospital. It is beneficial to allow surgical devices, e.g. surgical instrument 1010 (FIG. 1), surgical instrument assembly 200 (FIG. 8), control circuit 1992 (FIG. 13), surgical hub 1953 (FIG. 13), or control circuit 620 (FIG. 14), in high activity zones in a hospital to have access to multiple dedicated processor farms, to avoid bandwidth issues. For example, there is a limit to the amount of data that can be sent at once to a processor farm. Thus, having more than one processor farm allows different devices in the medical facility to have access to a processor farm even if there is not bandwidth to communicate with one of them.

Additionally, having a dedicated processor farm for a specific zone, such as operating rooms, allows the processor farm to prioritize processing data for that specific zone. For example, the processor farm could prioritize processing for a control circuit located in the specific zone over another control circuit located outside of the zone. In at least one example, a processor farm associated with a first zone, e.g. operating rooms, in a medical facility receives a first processing request of a first data from a first control circuit located in the first zone, and a second processing request of a second data from a second control circuit located outside the first zone or in a second zone such as emergency rooms. In one instance, the processor farm priories the first request over the second request based on location information. The processing requests can be tagged or accompanied by location information of their origin control circuits.

In one instance, the processor farm further considers the priority level of the first and second requests. The priority level can be a risk priority level. For example, a device that is in an operation where someone is undergoing emergency life-saving surgery has a higher priority access to the processor farm than a device being used in a routine low risk surgery. This approach allows the processor farm to benefit the people that are the most at risk. However, other priority schematics can be envisioned to allow devices access to the processor farms, when needed.

In some aspects, referring again to FIG. 130, the follower device can be remote from the master device. In one aspect, the master device is a surgical hub, e.g. surgical hub 1953 (FIG. 13), and the follower device is a remote processing device such as, for example, a processor farm. The follower device can also be a surgical device, e.g. surgical instrument 1010 (FIG. 1) or surgical instrument assembly 200 (FIG. 8), with a control circuit, e.g. control circuit 1992 (FIG. 13) or control circuit 620 (FIG. 14). In another aspect, the master device is a surgical device, e.g. surgical instrument 1010 (FIG. 1) or surgical instrument assembly 200 (FIG. 8), with a control circuit, e.g. control circuit 1992 (FIG. 13) or control circuit 620 (FIG. 14), and the follower device is a surgical hub, e.g. surgical hub 1953 (FIG. 13) and/or a processor farm. During distributed processing, as described in connection to FIGS. 130 and 131, follower devices send results, or post processed data, to the master device for use in control of a surgical instrument subsystem, for example, where the master device combines the result, or post-processed data, from a follower device with other results and post processed data from another follower device, and/or results and post processed data from the master device, to execute a control algorithm for controlling a surgical device, for example. For this process to function properly, a master processor and a follower processor need to synchronize so that any results sent between them are accurately used. The synchronization insures the prevention of out of sequence combinations of results or processes feeding information to a control circuit of a surgical device.

A control system can couple to a remote processing device to execute distributed processing. In one aspect, the control system is a surgical hub, e.g. surgical hub 1953 (FIG. 13). In another aspect, the control system is a control circuit of a surgical device, e.g. control circuit 1932 (FIG. 13) or control circuit 620 (FIG. 14), and the remote processing device is a surgical hub, e.g. surgical hub 1953 (FIG. 13). In one aspect, the control system is the master and the remote processing device is the follower during distributed processing as described in connection to FIGS. 130 and 131. For example, the control system receives surgical data and transmits some of the data to the remote processing device along with a synchronization feature. The synchronization feature is used to prevent out of sequence combinations of results or processes feeding information back to the device control. Thus, the synchronization between the processors can prevent mismatch or loss of data, data overlap, and other errors due to the distributed processing. In one aspect, the synchronization feature enables the system to remove a dataset that is not paired to the current processing, which can prevent mismatching two sets of incompatible or out of temporal sequence data.

FIG. 134 is a flow diagram depicting a distributed processing method 12020 that can be executed by a plurality of control circuits to concurrently perform data processing tasks, for example. In one aspect, the control circuits include separate processors. In one aspect, the control circuits include a master device, e.g. control circuit 12002 (FIG. 130), and a follower device, e.g. control circuit 12010 (FIG. 130), that simultaneously perform separate data processing tasks to determine parameters required to control a surgical device, e.g. surgical instrument 1010 (FIG. 1) or surgical instrument assembly 200 (FIG. 8). The method 12020 includes receiving 12022, for example by a master control circuit, surgical data associated with a surgical procedure. In one aspect, the surgical data is transmitted from the surgical device.

The method 12020 further includes determining 12024, for example by the master control circuit, that distributed processing of the surgical data is needed. In one aspect, the master control circuit receiving the data determines that distributed processing is needed based on a processing rate of a processor of the control circuit, type, amount, and/or other parameters of the surgical data, and/or a time threshold for the results, for example.

After determining 12024 that distributed processing is needed, the method 12020 can further include connecting the master control circuit with at least one other device to perform the distributed processing. Additionally, the master control circuit can break the data associated with the surgical procedure into subsets for use in the distributed processing. For example, the master control circuit can section out specific tasks, or analyses, and corresponding data, for sending to the at least one other device to perform distributed processing.

The method 12020 further includes transmitting 12026, for example by the master control circuit, a synchronization feature and a first subset of data to a remote processing device to perform a first analysis on the first subset of data. In one aspect, the synchronization feature is a synchronization signal. In one aspect, the first analysis comprises data processing of the first subset of the data. In another aspect, the first analysis includes performing calculations based on the first subset of data to determine a parameter, or multiple parameters, needed by the control circuit to control the surgical device. In yet another aspect, the first analysis includes completing a desired task with the data.

In at least one example, the first subset of data includes image data, and the first analysis includes performing an image processing task on the first subset of data, for example to identify a relevant structure such as an anatomical structure or a component of a surgical device, and to determine, based on the image processing, a parameter, or multiple parameters, required to control the surgical device. Such parameters include, for example, an articulation angle between an end effector and a shaft of the surgical device, staple cartridge configuration of a staple cartridge used in the surgical device, distance from the surgical device to a target object, and/or other relevant parameters.

In at least one example, the first analysis yields a firing force profile of the surgical device (e.g. the firing force applied to jaws 1921, 1931), a closure force profile of the surgical instrument (e.g. the closure force applied to jaws 1921, 1931), a motor (e.g. motor assembly 1939 (FIG. 13), closure motor 603, firing motor 602, or articulation motors 606a, 606b) current profile, and/or a motor velocity profile.

Further to the above, the method 12020 includes performing 12028, by the master control circuit, a second analysis on a second subset of data. In one aspect, the second subset of data is different than the first subset of data. In another aspect, the second subset of data is the same as, or similar to, the first subset of data. The second analysis can be the same or different than the first analysis. In certain instances, the data is not divided, but rather the same analysis is performed 12028 on the same data twice to ensure accuracy.

Furthermore, the first and/or second analyses are based on instructions received by the control circuit along with the data. In another aspect, the first and/or second analyses are automatically selected based on the data received. For example, the first and/or second analyses can be based the type of data received.

Further to the above, the method 12020 includes determining 12030 a second result based on the second analysis. In one aspect, the second result is a parameter, or multiple parameters, required by the control circuit to complete a task. In certain instances, the first subset of data is associated with a first sensor and the second subset of data is associated with a second sensor, and the first and second results cooperatively modify a default parameter of a control algorithm of the surgical device such as, for example, a motor control algorithm.

Further to the above, the method 12020 includes receiving 12032, for example by the master control circuit, a first result from the first analysis from the remote processing device and synchronization data of the remote processing device. The first result could be any of the results described in connection to the first analysis. In one aspect, the first result is a parameter, or multiple parameters, required by the control circuit to complete a task.

Further to the above, the method 12020 includes assessing 12034, for example by the master control circuit, a synchronicity of the first result and the second result based on the synchronization data. In some aspects, the control circuit evaluates the synchronization data based on a predetermined synchronization tolerance threshold. For example, if the synchronization data is within the predetermined synchronization tolerance threshold, then the control circuit determines that the first result and the second result are in sync, or in proper sequence. Alternatively, if the synchronization data is beyond the predetermined synchronization tolerance threshold, then the control circuit determines that the first result and the second result are out of sync, or out of proper sequence. In this instance, the master control circuit addresses the detected unsynchronicity, for example as described in connection to FIGS. 137-140.

In at least one aspect, when the master control circuit and the remote processing device are synchronized, then their clocks are synchronized. In at least one aspect, the synchronization data is the internal clock time of the remote processing device at transmission of the first result. In this aspect, the control circuit compares the remote processing device's internal clock time to the clock time that the master control circuit received the first result. If the difference between the clock times is larger than a transmission time between the control circuit and the remote processing device, then the results are not synchronized. In one aspect, the transmission time between the master control circuit and the remote processing device can be determined prior to synchronization.

If the results are synchronized, or in proper sequence, then the control circuit can use both results in making decisions and calculations. If the master control circuit determines that the first result and the second result are not synchronized, or out of proper sequence, then the master control circuit does not use both results in making decisions or calculations. Instead, as described in greater detail in connection with FIGS. 137-140, the master control circuit may first address the lack of synchronicity in the data.

Further to the above, the method 12020 includes determining 12036, for example by the master control circuit, control adjustments for a surgical device, e.g. surgical instrument 1010 (FIG. 1) or surgical instrument assembly 200 (FIG. 8), being used in the surgical procedure based on the first result and/or the second result. In one aspect, the control adjustments could be to a motor, e.g. motor assembly 1939 (FIG. 13), firing motor 602, closure motor 603, or articulation motor 606a, 606b, in the surgical device. In another aspect, the control adjustments could be to a power supplied to the surgical device. Further to the above, the method 12020 includes controlling 12038, for example by the master control circuit, the surgical device based on the control adjustments.

FIG. 135 is a flow diagram of a distributed processing method 12050 that can be executed by a plurality of control circuits to concurrently perform data processing tasks, for example. In one aspect, the control circuits include separate processors. In one aspect, the control circuits include a master device, e.g. control circuit 12002 (FIG. 130), and a follower device, e.g. control circuit 12010 (FIG. 130), that simultaneously performs separate data processing tasks to determine parameters required to control a surgical device, e.g. surgical instrument 1010 (FIG. 1) or surgical instrument assembly 200 (FIG. 8). The method 12050 includes receiving 12052, for example by a follower control circuit, a synchronization feature from another control circuit. In one aspect, the synchronization feature is transmitted from a master control circuit, e.g. control circuit 12002 (FIG. 130). In one aspect, the synchronization feature is a synchronization pulse or signal. The method 12050 further includes synchronizing 12054, for example by the follower control circuit, with the other control circuit, for example the master control circuit, based on the synchronization feature. For example, the follower control circuit can use the synchronization feature to synchronize the follower control circuit with the master control circuit. This can be done by a variety of methods that will be described in more detail in connection to FIGS. 141-143.

Further to the above, the method 12050 includes receiving 12056, for example by the follower control circuit, a subset of data related to a surgical procedure, performing 12058, for example by the follower control circuit, an analysis on the subset of the data, and determining 12060, for example by the follower control circuit, a result based on the analysis, as described in connection to FIG. 134.

Further to the above, the method 12050 includes transmitting 12062, for example by the follower control circuit, the result from the analysis to the other control circuit, for example the master control circuit. The method 12050 further includes transmitting 12064, for example by the follower control circuit, synchronization data based on the synchronization. In one aspect, the synchronization data is generated through the synchronization of the follower control circuit with the master control circuit. In at least one aspect, the synchronization data is the internal clock time of the follower control circuit at transmission of the result.

FIG. 134, in one aspect, describes a distributed control process between one master device and one follower device. However, there can be any number of follower devices. FIG. 136 is a flow diagram of a distributed control processing method 12021 that can be executed by a plurality of control circuits to concurrently perform data processing tasks, for example. In one aspect, the control circuits include separate processors. In one aspect, the control circuits include a master device, e.g. control circuit 12002 (FIG. 131), and follower devices, e.g. control circuits 12010, 12011 (FIG. 131), that simultaneously perform separate data processing tasks to determine parameters required to control a surgical device, e.g. surgical instrument 1010 (FIG. 1) or surgical instrument assembly 200 (FIG. 8). The method 12021 further includes receiving 12023, for example by a master control circuit, surgical data associated with a surgical procedure. The method 12021 further includes determining 12025, for example by the master control circuit, that distributed processing of the surgical data is needed, as described in connection with the process of FIG. 134 The method 12021 further includes transmitting 12027, for example by the master control circuit, a synchronization feature and a first subset of data to a first remote processing device to perform a first analysis on the first subset of data, as described in connection with the methods 12020, 12050 of FIGS. 134 and 135.

Further to the above, the method 12021 includes transmitting 12029, by the master control circuit, the synchronization feature and a second subset of data to a second remote processing device to perform a second analysis on the second subset of data. In some aspects, the synchronization feature is the same or similar to the synchronization feature transmitted to the first remote processing device. In one aspect, the second subset of the data is different than the first subset of the data. In another aspect, the second subset of the data is the same as the first subset of the data. The second subset of data and the second analysis could be any data or analysis as described in connection with the methods 12020, 12050 of FIGS. 134 and 135.

Further to the above, the method 12021 includes performing 12031, by the master control circuit, a third analysis on a third subset of the data. In one aspect, the third subset of the data is different than the first subset of the data and/or the second subset of the data. In another aspect, the third subset of the data is the same as the first subset of the data and/or the second subset of the data. The third subset of the data and the third analysis could be any data or analysis as described in connection with the methods 12020, 12050 of FIGS. 134 and 135.

Further to the above, the method 12021 includes determining 12033, by the master control circuit, a third result based on the third analysis. The third result could be any result as described in connection with the methods 12020, 12050 of FIGS. 134 and 135. For example, the third result could be a parameter, or multiple parameters, required by the control circuit to complete a task.

Further to the above, the method 12021 includes receiving 12035, by the master control circuit, a first result from the first analysis from the first remote processing device and first synchronization data of the first remote processing device. Further to the above, the method 12021 includes receiving 12037, by the master control circuit, a second result from the second analysis from the second remote processing device and second synchronization data of the second remote processing device. The first result, first synchronization data, second result, and second synchronization data could be any result or synchronization data as described in connection with the methods 12020, 12050 of FIGS. 134 and 135. For example, the first result and the second result could be parameters that are required by the control circuit to complete a task.

Further to the above, the method 12021 includes assessing 12039, by the master control circuit, a synchronicity of the first result, the second result, and the third result based on the first synchronization data and the second synchronization data. The process of assessing the synchronization can be similar to that described in connection with the process of FIG. 135. In one aspect, the synchronicity between the two remote processing devices and the master device is assessed based on a predetermined synchronization tolerance threshold. For example, the master control circuit could evaluate the first synchronization data and the second synchronization data based on the predetermined threshold, as described in greater detail in connection with FIG. 135. If the first synchronization data and second synchronization data are within the predetermined synchronization tolerance threshold, then the control circuit can determine that the first result, the second result, and the third result are synchronized. This allows the master control circuit to use these results in making decisions and calculations. If the master control circuit determines that the results are not synchronized, then the master control circuit cannot combine and use the results. In this instance, the master control circuit addresses the detected unsynchronicity, for example as described in connection to FIGS. 137-140. While the methods described in connection to FIG. 137-140 describe methods to handle unsynchronized results for one remote processing device and a master device, they can be expanded to include any number of remote processing devices.

Further to the above, the method 12021 includes determining 12041, by the master control circuit, control adjustments for a surgical device, e.g. surgical instrument 1010 (FIG. 1) or surgical instrument assembly 200 (FIG. 8), being used in the surgical procedure based on the first result, the second result, and the third result. In one aspect, the control adjustments could be to a motor, e.g. motor assembly 1939 (FIG. 13), firing motor 602, closure motor 603, articulation motor 606a, 606b, in the surgical device. In another aspect, the control adjustments could be to a power source supplying power to the surgical device. After the control adjustments are made, the master control circuit can control the surgical device based on the control adjustments.

There are a variety of approaches to handle unsynchronized data. For example, if a control circuit detects a loss of synchronization, the control circuit could drop both parts of the un-synchronized result and look for the next received set to be synchronized. Alternatively, the control circuit could drop an unsynchronized result and either does not use it or substitutes it with a nominal, pre-determined value, or with the last valid result. However, in most instances, the substituted value could only be used for a limited time before the system would shut down for safety concerns due to not having updated results. FIGS. 137-140 describe some of these approaches.

FIG. 137 is a flow diagram depicting a method 12070 for a control circuit to execute when results of a distributed processing method are out of synchronization. In one aspect, the control circuit includes a separate processor. In one aspect, the control circuit is a master device, e.g. control circuit 12002 (FIG. 130). Specifically, the method 12070 includes deleting the out of sync result and determining control adjustments with the remaining result. In the illustrated example, the method 12070 includes assessing 12072, for example by a master control circuit, a synchronicity of the results based on the synchronization data, as described in connection with FIG. 134. The method 12070 further includes detecting 12074, for example by the master control circuit, that the first result is out of synchronization with the second result. The method 12070 further includes deleting 12076 is the first result. The method 12070 further includes determining 12078 control adjustments for a surgical device, e.g. surgical instrument 1010 (FIG. 1) or surgical instrument assembly 200 (FIG. 8), being used in a surgical procedure based on the second result, but not the deleted first results. The control adjustments can be any of the control adjustments described in connection to FIG. 134. The method 12070 may further include controlling 12080 the surgical device based on the control adjustments. In some aspects, if the master control circuit and the follower control circuit are not able to resynchronize after a predetermined time period from the detection 12074 of the out of sync status, then the master control circuit can appropriate safety measure such as, for example, shutting down the surgical device and/or alerting a user through any suitable user interface.

FIG. 138 is a flow diagram depicting a method 12090 for a control circuit to execute when results of a distributed processing method are out of synchronization. In one aspect, the control circuit includes a separate processor. In one aspect, the control circuit is a master device, e.g. control circuit 12002 (FIG. 15130 The method 12090 includes assessing 12092 a synchronicity of the results based on the synchronization data, as described in connection with FIG. 134. The method 12090 further includes detecting 12094 that the first result is out of synchronization with the second result. The method 12090 further includes replacing 12096 the out of synchronization result, which in this instance is the first result, with a predetermined default value. In at least one aspect, a predetermined value in accordance with predetermined safety practices is used in place of the first result. The method 12090 further includes determining 12098 control adjustments for a surgical device, e.g. surgical instrument 1010 (FIG. 1) or surgical instrument assembly 200 (FIG. 8), being used in a surgical procedure based on the pre-determined default value and the second result. The control adjustments can be any of the control adjustments described in connection to FIG. 134. The method 12090 may further include controlling 12100, for example by the master control circuit, the surgical device based on the control adjustments. In some aspects, if the master control circuit and the follower control circuit are not able to resynchronize after a predetermined time period from the detection 12094 of the out of sync status, then the master control circuit can appropriate safety measure such as, for example, shutting down the surgical device and/or alerting a user through any suitable user interface.

In another aspect, the method 12090 described in connection to FIG. 138 could be performed by replacing both the first result and the second result by default values, when either the first result or the second result is out of synchronization. Then the control circuit could determine control adjustments for the surgical device being used in the surgical procedure based on a first default value and a second default value. For example, the first default value could replace the first result and the second default value could replace the second result.

FIG. 139 is a flow diagram depicting a method 12110 for a control circuit to execute when results of a distributed processing method are out of synchronization. In one aspect, the control circuit includes a separate processor. In one aspect, the control circuit is a master device, e.g. control circuit 12002 (FIG. 130). Specifically, the flow diagram illustrates resyncing the out of sync result. The method 12110 includes assessing 12112, for example by a master control circuit, a synchronicity of the results based on the synchronization data, as described in connection with FIG. 134. The method 12110 includes detecting 12114 that the first result is out of synchronization with the second result. The method 12110 further includes resynchronizing 12116 the first result with the second result. In at least one aspect, the master control circuit resynchronizes the first result and the second result based on the synchronization feature and/or synchronization data. For example, in one aspect, the master control circuit could determine an amount of time that the remote processing device drifted out of synchronization based on the synchronization data and resynchronize the first result based on the determined amount of time. The method 12110 further includes determining 12118 control adjustments for a surgical device, and optionally controlling 12120 the surgical device based on the control adjustments, as described in connection with FIG. 134.

FIG. 140 is a flow diagram depicting a method 12130 for a control circuit to execute when results of a distributed processing method are out of synchronization. In one aspect, the control circuit includes a separate processor. In one aspect, the control circuit is a master device, e.g. control circuit 12002 (FIG. 130). Specifically, the method 12130 uses a previously synchronized result in substitute of the current unsynchronized results. The method 12130 includes assessing 12132 a synchronicity of the results based on the synchronization data, as described in connection with FIG. 134. The method 12130 further includes detecting 12134 that the first result and the second result are synchronized, determining 12136 control adjustments for a surgical device based on the first and second results, and controlling 12138 the surgical device based on the first control adjustments.

Later in the surgical procedure the control circuit, for example by the master control circuit, receives new data associated with the surgical procedure. The control circuit, for example by the master control circuit, performs distributed processing with the new data, as described in connection to FIG. 134, and the control circuit receives, for example by the master control circuit, a third result and calculates a fourth result.

The method 12130 further includes assessing 12140 a synchronicity of third and fourth results of analyses performed on new data subjected to distribute processing, wherein the synchronicity of the third and fourth results is based on new synchronization data. The method 12130 further includes detecting 12142 that the third result is out of synchronization with the fourth result. The method 12130 further includes deleting 12144 the third result and the fourth result, and determining 12146 second control adjustments for the surgical device based on the first result and the second result. Stated another way, the master control circuit deletes the current results if they are not synchronized and determines control adjustments for the surgical device based on the previous results that were synchronized. In some aspects, the second control adjustments can be the same or similar to the first control adjustments. In other aspects, the second control adjustments can be different from the first control adjustments. The method 12130 further includes controlling 12148 the surgical device based on the second control adjustments.

Various methods and systems of the present disclosure utilize the transmission of synchronization features and/or retrieval of synchronization data to ensure synchronicity of surgical data subjected to distributed processing by multiple processors, e.g. processors 12004, 12012, 12013, to prevent the mismatch or loss of results. There are many approaches to synchronizing processors. In various examples, communication protocols are utilized to insure synchronization and minimizing of data loss. The processors can use these communication protocols when sending data between processors to help keep the processors synchronized. Non-limiting examples communication protocols include Integrating Simple Network Time Protocol (SNTP), Network Time Protocol (NTP), and Precision Time Protocol (PTP). These protocols allow for multiple embedded systems to be synchronized.

In some aspects, multiple processors need to be synchronized to complete certain tasks. For example, a surgical device, e.g. surgical instrument 1010 (FIG. 1) or surgical instrument assembly 200 (FIG. 8), can include multiple motors, where each motor has a motor control circuit that controls that motor. In one aspect, the surgical device includes a main control circuit that is communicably coupled to the motor control circuits to transmit motor control signals to the motor control circuits for multi-motor control. In various aspects, the main control circuit and the motor control circuits are synchronized for smooth multi-motor control by the main control circuit.

FIG. 141 is a flow diagram depicting a method 12150 for a control circuit to execute to synchronize with another control circuit, or a plurality of control circuits. In one aspect, the control circuits include separate processors. In one aspect, the control circuits include a master device, e.g. control circuit 12002 (FIG. 130) and a follower device, e.g. control circuit 12010 (FIG. 130). In various aspects, a master clock can be accessible by all the processors, e.g. processors 12004, 12012, 12013, to adjust and sync The method 12150 includes transmitting 12152 a synchronization signal to a remote processing device, and accessing 12154 a master clock to adjust its internal clock to match the master clock. In at least one aspect, the master device and the remote processing device both have access to the master clock, which allows the master device and the remote processing device to synchronize their clocks to the master clock. In an alternative aspect, the master device could contain the master clock. In this aspect, the follower device would synchronize directly to the master device clock.

Further to the above, the method 12150 includes receiving 12156, by the master control circuit, synchronization data containing a first time that corresponds to the remote processing device's internal clock time at transmission of the synchronization data. The method 12170 further includes determining 12158 a second time that corresponds to the internal clock time at which the synchronization data was received. To assess the synchronization between the devices, the method 12150 further includes comparing 12160 the difference between the first time and the second time to a predetermined transmission time. In at least one aspect, the predetermined transmission time is determined prior to performing any distributed processing or synchronizing. In some aspects, the predetermined transmission time is the time that it takes for the remote processing device to transmit a message to the master device. The method 12150 further includes determining 12162 if the remote processing device is synchronized. In one aspect, if the difference between the first time and the second time is below the predetermined transmission time, then the master device and the remote processing device are determined to be synchronized. If not, then the master device will transmit another synchronization signal and repeat the synchronicity testing until synchronized.

One method to maintain synchronization between processors, or control circuits, is to send a synchronization byte pattern, or timing mark, from the master processor, e.g. processor 12004, to the follower processors, e.g. processors 12012, 12013. For example, the pattern could be a signal that is a sequence of ones and zeroes which includes a timing element. The follower processors all check the byte pattern to verify that no packets have been lost and use the timing element to help assure timing is maintained. For example, if the byte pattern received by the follower processor is not the expected byte pattern, then the follower processor determines that it is out of synchronization with the master processor. Additionally, if a packet has been determined to be lost, then the follower processor can also determine that it is out of synchronization with the master processor. In either case, the follower processor can attempt to resynchronize with the master processor as described above in connection to FIG. 141.

The latency between two or more synchronized processors can be characterized for fine tuning their synchronization. One method is to use an electric sync with a hardware clock. The hardware clock could have a crystal oscillator that is compensated for temperature and humidity. This approach can produce a very staple signal. This signal is used to synchronize the processors, e.g. processors 12004, 12012, 12013, and measure any drift by any of the processors. In one aspect, the electric sync is coupled to the processors 12004, 12012, 12013 such that it can transmit a signal to the processors. In one aspect, the signal is transmitted to each processor at the same time and the processors sync their internal clocks based on the received signal. At a predetermined set time interval, a signal could be sent from the electric sync and received by the processors. In one aspect, the processors use the received signal to resync and record any drift in time. For example, if the processor knows that the predetermined resync time interval is 10 minutes and it receives the sync signal from the electric sync at 9 minutes and 59 seconds, the processor knows that it drifted by 1 second, for example. In certain instances, drift data can be transmitted back to the master control circuit along with the result of a data analysis. The master control circuit can resynchronize the result with other results from data subjected to distributed processing on multiple devices based on the drift data.

Another method to characterize the latency between processors is to use a software clock approach. This is a process where the master device, e.g. control circuit 12002, can transmit a sync pulse to each of the follower devices, e.g. control circuits 12010, 12011, that have already synced with the master device. In at least one aspect, the master device is a surgical hub, e.g. surgical hub 1953 (FIG. 13), and the follower device is a remote processing device. The pulse can be used to check the latency of the follower device and adjust the follower device to be in better synchronization with the master device. The master device, e.g. control circuit 12002, can transmit a message to the follower devices, e.g. control circuits 12010, 12011, that includes a fixed frequency. Later the master device transmits a signal at the fixed frequency to each follower device. The follower devices can measure the actual frequency coming from the master device and adjust their clock signals accordingly to align with the master device.

FIG. 142 is a flow diagram depicting a method 12170 that can be executed by a control circuit to characterize the latency of another synchronized control circuit. In one aspect, the control circuits include separate processors. In one aspect, the control circuits include a master device, e.g. control circuit 12002 (FIG. 131), and a follower device, e.g. control circuits 12010, 12011 (FIG. 131). The method 12170 includes receiving 12172, for example by the follower device, a message containing a fixed frequency for a sync pulse. The method 12170 further includes receiving 12174, for example by the follower control circuit, a sync pulse signal from a control circuit, for example from the master control circuit. In at least one aspect, the follower control circuit stores the received sync pulse signal in a memory, e.g. memory 12014 or memory 12015. The method 12170 further includes calculating 12176, for example by the follower control circuit, the actual frequency of the sync pulse signal. The method 12170 further includes comparing 12178, for example by the follower control circuit, the received fixed frequency to the calculated actual frequency. The method 12170 further includes adjusting 12180, for example by the follower control circuit, the internal clock based on the comparison. For example, in one aspect, the follower control circuit could adjust its internal clock if there was a difference between the actual frequency measured and the fixed frequency that it received. In an alternative aspect, if there was no difference between the actual frequency and the fixed frequency, then the follower device is already synchronized with the master device.

FIG. 143 is a flow diagram depicting a method 12190 that can be executed by a control circuit to characterize the latency of another synchronized control circuit. In one aspect, the control circuits include separate processors. In one aspect, the control circuits include a master device, e.g. control circuit 12002 (FIG. 131), and a follower device, e.g. control circuit 12010 (FIG. 131) or control circuit 12011 (FIG. 131). The master device could periodically send out a specific number of pulses to a follower device and then request the number of pulses that have occurred within a set time period from the follower device. If the follower's counted number of pulses does not agree with the number sent by the master device, the master device could try to re-sync the follower device to better align the master and follower devices. This can help prevent data loss (loss of packets) or timings being slightly off of each other.

The method 12190 includes transmitting 12192, for example by the master control circuit, a plurality of pulses within a set period of time to another control circuit, for example the follower control circuit. The method 12190 further includes transmitting 12194, for example by the master control circuit, a message to the other control circuit, for example the follower control circuit, requesting the number of pulses that were sent in a set period of time. The method 12190 further includes receiving 12196, for example by the master control circuit, a message from the other control circuit, for example the follower control circuit, containing the number of pulses received by the other control circuit, for example the follower control circuit, during the requested time. The method 12190 further includes comparing 12198, for example by the master control circuit, the number of pulses sent to the other control circuit, for example the follower control circuit, to the number received by the other control circuit, for example the follower control circuit. The method 12190 further includes determining 12200, for example by the master control circuit, if the two numbers are the same or not. If the two numbers are the same, then the method proceeds down the "Yes" branch, where the method further includes determining 12202, for example by the master control circuit, that the other control circuit, for example the follower control circuit, is synchronized. If the two numbers are not the same, then the method proceeds down the "No" branch, where the method further includes resynchronizing 12204, for example by the master control circuit, the other control circuit, for example through the method described in connection to FIG. 141. After the other control circuit, for example the follower control circuit, is resynchronized, the method proceeds to repeat 12192-12200 to ensure that the other control circuit synchronized properly.

The transmissions between a master control circuit, e.g. control circuit 12002, and the follower control circuit, e.g. one of control circuits 12010, 12011, during distributed processing, as described in connection to FIGS. 134 and 135, can have a specific packet that includes time stamps associated with sending time (message assembly time and assembly time of the data) and transmission time. In one aspect, the master control circuit receives this information from the follower control circuit each transmission of the follower control circuit. The master control circuit uses this information to track the time the follower control circuit spends on the data processing. From this amount of time, the master control circuit determines more control circuits need added to the distributed processing to complete tasks on time. In at least one aspect, the master control circuit can compare the amount of time the follower control circuit took to process the data to a predetermined process time. For example, if the time the follower control circuit took to process the data exceeds the predetermined process time, then the master control circuit can determine that more follower control circuits need added to the distributed processing.

In one aspect, the transmission of the data from the follower control circuit to the master control circuit could be delayed due to it being a lower priority than another function the follower control circuit is performing. This delay time can be captured and transmitted when allowed to the other control circuits, e.g. the master control circuit. This information can allow the master control circuit to determine where and why a delay occurred. In some aspects, the master control circuit could communicably couple to another follower control circuit if the delays are too large.

Multiple timestamps can be used by the master control circuit to make decisions about the distributed processing. The propagation time can be tracked. This is a time period represented by the time required for the master control circuit to send a data packet to the time the follower initially receives the data packet. The reception time, or receive time, is a time period from the timestamp the message was first received by the follower control circuit to the timestamp the message was processed. The decoding time is a timestamp to indicate a time period required to unpack the data. These different time periods allow the master control circuit to track what each follower control circuit is doing and detect any delays that are occurring. This information is used to keep the control circuits in sync and completing tasks in a timely manner.

In some situations it can be beneficial to have a subsystem post processor adaptation of motor control. This brings an additional level of control to the motor control system. This concept is implemented after the main control circuit, e.g. control circuit 1932 (FIG. 13), surgical hub 1953 (FIG. 13), or control circuit 620 (FIG. 14), to give an additional layer of control and/or safety to the system. The subsystem could be electrical and/or mechanical in nature. For example, the subsystem could provide physical and/or electrical adaptations after a motor command signal. In some aspects, the subsystem is sampling at a much higher rate to see situations that the main control circuit missed while making decisions with current data.

Some surgical devices, e.g. surgical instrument 1010 (FIG. 1) or surgical instrument assembly 200 (FIG. 8), can have onboard local processing. The on-device processor monitors the voltage and/or current applied to a motor, e.g. motor assembly 1939 (FIG. 13), closure motor 603, firing motor 602, or and articulation motors 606a, 606b, as well as at least one other electrical sensor coupled to the drive train. These monitored parameters can be processed locally and used to adjust electrical controls to a controller, e.g. control circuit 1932 (FIG. 13), surgical hub 1953 (FIG. 13), or control circuit 620 (FIG. 14), of the motor. In some aspects, each motor control command can be accompanied by a max current threshold. In at least one aspect, hall effect switches are placed on control locations, e.g. an articulation joint between a shaft of the surgical device and an end effector of the surgical device, and used to initiate different commands from the motor through the controller. In at least one aspect, the controller controls the motor through a proportionalintegral-derivative control of a pulse-width modulation duty cycle based on velocity and position monitoring. The data is all processed on the device on the main processors or within the motor controller sub-processor to adjust operations of the device.

FIG. 144 illustrates a diagram 12440 of a surgical system 12442, e.g. surgical instrument 1010 (FIG. 1) or surgical instrument assembly 200 (FIG. 8), that has a control circuit 12444, e.g. control circuit 1932 (FIG. 13), surgical hub 1953 (FIG. 13), or control circuit 620 (FIG. 14). The surgical system 12442 includes a processor 12446 coupled to a memory 12448. The surgical system 12442 can include a plurality of subsystems 12450 that can be communicably coupled to the control circuit 12444 or, alternatively, operate independently of the control circuit 12444. The subsystems 12450 are configured to perform specialized adjustments outside, or beyond, the control of the control circuit 12444. In one aspect, the subsystems 12450 include an electrical subsystem 12452 that can make adaptations to a motor control command after the processor 12446 transmits a command signal to a motor, e.g. motor assembly 1939 (FIG. 13), closure motor 603, firing motor 602, or and articulation motors 606a, 606b. In one aspect, subsystem control circuit 12452 modifies a motor drive signal set by the control circuit 12444, wherein the modification is beyond the control of the control circuit 12444.

The electrical subsystem 12450 brings an additional level of control of the motor, and may interact with the motor separate from the control circuit 12444. In one aspects, the electrical subsystem 12450 receives an input signal from dedicated sensors, separate from the sensors 1938 that are communicably coupled to the control circuit 12444. The electrical subsystem 12450 may perform an adjustment of the motor drive signal set by the control circuit 12444 based on the input signal from the dedicate sensors. The adjustments can be performed independent of, or beyond the control of, the control circuit 12444.

In at least one aspect, the subsystem 12452 receives a signal indicative of a parameter of the surgical device from a sensor, and limits the power (voltage or current) available to the motor based on the sensor value. In one aspect, the subsystem 12452 includes an electrical element diverts a portion of the power through a non-functional circuit branch effectively limiting the overall power available to the motor. In one aspect, the sensor signal could be indicative of an articulation angle between the shaft of the surgical device and the end effector of the surgical device.

There are a variety of methods that could be employed by the electrical subsystem to control or limit the available power to the motor, e.g. motor assembly 1939 (FIG. 13), firing motor 602, closure motor 603, articulation motor 606a, 606b. In one aspect, a subsystem 12452 receives an operational system positional location and changes the power available to the motor based on the location. In another aspect, a subsystem control circuit 12452 receives a detected an input signal indicative of a load on the system, e.g. a force on the motor or a force on the end effector of the surgical device, and limits the current available to the motor based on the detected load. In at least one aspect, the subsystem control circuit 12452 uses the load as an input to control the available current to the motor. This process can help prevent damage to the motor assembly 1939 and/or the drive assembly 1941. In one aspect, a subsystem 12452 directs the current to the motor through an in-line power resistor to limit the power to the motor. In another aspect, a subsystem 12452 regulates a high powered voltage regulator that solely supplies power to the motor. In this aspect, a subsystem 12452 pulse-width modulates the regulator to supply a standard signal to the motor control circuitry based on the sensor signal.

While the illustrated example shows multiple subsystems 12452 with identical components, it is understood that various subsystems 12452 that perform dedicated functions downstream from the control circuit 12452 can include any suitable circuit components, as previously described, to perform their specific functions.

In certain aspects, a subsystem 12452 directly alters the commands from the control circuit 12444. For example, the control circuit 12444 could place a 50% duty cycle to an H-Bridge circuit of the motor assembly 1939. In such aspects, the subsystem 12452 intercepts the signal the control circuit 12444 generates for the H-Bridge circuit, beyond control of, or even awareness of, the control circuit 12444. In some aspects, the subsystem 12452 can perform sampling tasks, for example based on input signals from one or more sensors, at a much higher rate than that available to the control circuit 1244 to address situations that the control circuit 12444 missed while making calculations with current data. In one exemplification, the control circuit 12444 transmits a command of a duty cycle of 80% with an over current protection flag; however, the subsystem 12452 overrides that command due to a higher risk level event which prohibits the increase.

In at least one aspect, the subsystem 12452 interacts directly with the motor. In other aspects, a subsystem 12452 includes mechanical and/or electrical components, in addition to, or instead of, the processor and memory components, which bring an additional level of control to the motor control system. Such components include, for example, a system dampener. In some aspects, the subsystem 12452 comprises a sensing array. In one aspect, a subsystem 12452 includes mechanical and/or electrical components that adjust motor parameters based on input signals from the sensor array. In at least one aspect, the sensor signal is indicative of a parameter of the surgical device. In at least one aspect, a portion of the force or stroke of the motor is compensated for by an adjustment of the mechanical and/or electrical components. For example, the subsystem 12452 may include a system dampener controllable to provide a rigid response or an adjustable response based on the detected sensed parameter.

In some aspects, the motor is coupled to a gearbox and the subsystem 12452 adjusts the motor gearbox based on the sensed parameter. For example, the subsystem 12452 can shift the gears within the gearbox to change speeds and torques of the motor assembly 1939. In another aspect, the subsystem could make motor magnetic adjustments. In at least one aspect, the motor includes internal permanent magnets and the subsystem 12452 adjusts the magnetics of the motor internal permanent magnets based on the sensed parameter, which adjusts the motor output as desired. In another aspect, the motor includes a shaft that is coupled to a linear brake and the subsystem control circuit 12452 adjusts the pressure brake applied to the motor based on the sensed parameter. In another aspect, the motor includes a drive member that is coupled to a closed loop hydraulic or pneumatic dampener.

The closed loop hydraulic or pneumatic dampener is coupled to an electrical release valve that is configured to be controlled based on the load applied to the drive member, e.g. a force on the motor or a force on the end effector of the surgical device. In one aspect, the subsystem 2452 is coupled to the electrical release valve and transmits a signal to control the electrical release valve based on the sensed parameter. This enables a primary resisting spine of the pneumatic dampener to expand or contract under the load applied by the drive member of the motor. If the valve is kept closed the dampener would have a first length of the restraining system. If the valve is opened it would allow the dampener to elongate or contract thereby adjusting the effective forces applied to an end-effector, e.g. end effector 130 (FIG. 6), end effector 230 (FIG. 8), or end effector 1940 (FIG. 13). The subsystem 12452 controls the amount of opening, which controls the rate of change of the dampener. In one aspect, the subsystem 12452 transmits a signal to the electrical release valve that opens the electrical release valve. Alternatively, the subsystem 12452 could open and close the value in a pulsing manner to control the rate of change of the restraint.

Distributed processing, as described in connection with FIGS. 130 and 131, can be useful in effectively analyzing large amounts of data under tight time constraints. As described elsewhere herein in greater detail, a control circuit, e.g. control circuit 12002 or control circuit 12400, can access additional processing resources through distributed processing to efficiently perform multiple tasks during a surgical procedure. In some aspects, the control circuit employs a prioritization algorithm and/or a delegation algorithm to control aspects of the distributed processing. In one aspect, the prioritization algorithm, when executed by the control circuit, selects certain tasks for local processing and other tasks for external processing. In one aspect, the prioritization algorithm, when executed by the control circuit, assigns priority levels to upcoming tasks to prioritize mission critical tasks and/or time critical feedbacks based on risk levels associated with such tasks, for example.

Further to the above, in certain aspects, the prioritization algorithm, when executed by the control circuit, prioritizes decision making, or signal processing, required for local primary control of actuators, e.g. motor assembly 1939 (FIG. 13), firing motor 602, closure motor 603, articulation motor 606a, 606b, of a surgical device, e.g. surgical instrument 1010 (FIG. 1) or surgical instrument assembly 200 (FIG. 8), over other secondary, commentary, or non-real-time, decision making, or signal processing. In one aspect, the decision making, or signal processing, that is required for local primary control of actuators is performed locally on processor 12406 (FIG. 133) and the other secondary, commentary, or non-real-time the decision making, or signal processing, are delegated, through distributed processing, one or more of the processors 12402, 12414, 12420 (FIG. 133). The secondary, commentary, or non-real-time tasks take advantage of distributed processing without compromising the primary tasks.

Further to the above, in some aspects, the prioritization algorithm, when executed by the control circuit, adjusts a default control algorithm for controlling a motor during a tissue-treatment motion, for example, by causing the default control algorithm to bypass a control function that involves a secondary or complimentary signal that is missing, out of sequence, or unsynchronized. In another aspects, the prioritization algorithm causes the default control algorithm to rely instead on locally processed data or a default, or nominal, value or, alternatively, a last received, in sync, value of the secondary signal as actuator controller signals.

In one exemplification, a surgical device, e.g. surgical instrument 1010 (FIG. 1) or surgical instrument assembly 200 (FIG. 8), includes a motor, e.g. motor assembly 1939 (FIG. 13), firing motor 602, closure motor 603, articulation motor 606a, 606b, a speed sensor that monitors the speed of the motor, and a control circuit, e.g. control circuit 1932

(FIG. 13), surgical hub 1953 (FIG. 13), or control circuit 620 (FIG. 14). The control circuit is coupled to the motor and the speed sensor. The control circuit is continually receiving a signal from the speed sensor. If the signal from the speed sensor stops, then the control circuit replaces the sensor signal with a default or an estimation to continue controlling the motor. The control circuit monitors the signal from the sensor to determine if the sensor is operational. If a predetermined amount of time is exceeded without receiving a signal from the sensor, then control circuit shuts down the motor for safety, and/or issues an alert through a user interface. In such exemplification, the default parameter can only be used or substituted for a set amount of time.

In at least one aspect, there could be some additional speed sensors, for example, one on the motor itself, a second speed sensor on an output of a gearbox coupled to the motor, and a third speed sensor on a drive bar coupled to the gearbox. In one aspect, the processing of these three signals is done with distributed processing. In this instance, the control circuit continues to make decisions if one or two of these sensors stops sending a signal. As long as not all 3 sensors are "off-line", the control system continues to function. If all three sensors go "off-line", then the control circuit responds by shutting down the motor for safety purposes, as described above. In other words, the control circuit executing the prioritization algorithm bypasses a calculation that takes into consideration a missing sensor signal in favor of available sensor signals.

In various aspects, the prioritization algorithm involves a tiered matrix based on task criticality, task urgency, and/or processor capabilities and/or constraints. In at least one aspect, a threshold that determines what is processed locally, remotely, or non-real-time is based on the capacity of the master processor, e.g. processor 12004. This threshold could be some percentage of the max capacity such as, for example, 85%-95% of the max capacity to avoid overloading the processor. In addition to processor capacity, the processor power requirements, temperature/heat generation, or communication can all be requirements used as a part of the differentiating threshold.

FIG. 145 is a flow diagram depicting a prioritization method 12500 that can be executed by a control circuit for processing tasks based on a tiered matrix. In one aspect, the control circuit includes a master device, e.g. control circuit 12002 (FIG. 130). The method 12500 includes initiating 12502 a tissue-treatment motion by a surgical device. In at least one aspect, the surgical device includes a control, e.g. control circuit 1932 (FIG. 13) or control circuit 620 (FIG. 14). The method 12500 further includes receiving 12504 an input signal indicative of a surgical task to be performed. In at least one aspect, the input signal is received from a surgical hub, e.g. surgical hub 1953 (FIG. 13). For example, the surgical device during a cycle, receives a time critical surgical task from the surgical hub or any sensor element. The method 12500 further includes determining 12506, based on a tiered matrix, for example by the surgical device control circuit, how to address such surgical task. In various instances, the surgical task can be a computational task, a data processing task, or any other task suitable for performance by a processor.

In the illustrated example, the tiered matrix includes three possible paths. It is, however, understood that more or less than three paths can be adopted. Under "Path 1", the method 12500 includes transmitting 12508, by the surgical device control circuit, the surgical task to another processor. Accordingly, the surgical task is delegated to the other processor. In certain instances, the transmission 12508 can include a feedback request regarding whether the other processor is able to timely perform the surgical task. In one aspects, Path 1 is selected for secondary, commentary, or non-real-time tasks. On the contrary, for primary tasks, Path 2 is selected, where the control circuit locally performs 12510 the surgical task. For Path 3, the method 12500 includes delaying 12512 a performance of the surgical task based on the priority level. In certain instances, a reply notification is issued indicating a decision to locally perform 12514 the task when processing allocation becomes available.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, and is incorporated herein by reference in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRU-MENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRU-MENT WITH ELECTRIC ACTUATOR DIREC-TIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGE-MENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SEN-SOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SEN-SOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCK-ING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

While several forms have been illustrated and described, it is not the intention of Applicant to restrict or limit the scope of the appended claims to such detail. Numerous modifications, variations, changes, substitutions, combina-tions, and equivalents to those forms may be implemented and will occur to those skilled in the art without departing from the scope of the present disclosure. Moreover, the structure of each element associated with the described forms can be alternatively described as a means for provid-ing the function performed by the element. Also, where materials are disclosed for certain components, other mate-rials may be used. It is therefore to be understood that the foregoing description and the appended claims are intended to cover all such modifications, combinations, and variations as falling within the scope of the disclosed forms. The appended claims are intended to cover all such modifica-tions, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distri-bution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or trans-mitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, program-mable circuitry (e.g., a computer processor including one or more individual instruction processing cores, processing unit, processor, microcontroller, microcontroller unit, con-troller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in one or more aspects of the present disclosure, a microcontroller may generally comprise a memory and a microprocessor ("processor") operationally coupled to the memory. The processor may control a motor driver circuit generally utilized to control the position and velocity of a motor, for example. In certain instances, the processor can signal the motor driver to stop and/or disable the motor, for example. In certain instances, the microcontroller may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet.

It should be understood that the term processor as used herein includes any suitable microprocessor, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In at least one instance, the processor may be any single core or multicore processor such as those known under the trade name ARM Cortex by Texas Instruments. Nevertheless, other suitable substitutes for microcontrollers and safety processor may be employed, without limitation.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Various instruments, tools, hubs, devices and/or systems, in accordance with the present disclosure, may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

One or more motor assemblies, as described herein, employ one or more electric motors. In various forms, the electric motors may be a DC brushed driving motor, for example. In other arrangements, the motor may include a brushless motor, a cordless motor, a synchronous motor, a stepper motor, or any other suitable electric motor. The electric motors may be powered by a power source that in one form may comprise a removable power pack. Batteries may each comprise, for example, a Lithium Ion ("LI") or other suitable battery. The electric motors can include rotatable shafts that operably interface with gear reducer assemblies, for example. In certain instances, a voltage polarity provided by the power source can operate an electric motor in a clockwise direction wherein the voltage polarity applied to the electric motor by the battery can be reversed in order to operate the electric motor in a counter-clockwise direction. In various aspects, a microcontroller controls the electric motor through a motor driver via a pulse width modulated control signal. The motor driver can be configured to adjust the speed of the electric motor either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminal of the drive motor are shorted and the generated back EMF counteracts the rotation of the electric motor allowing for faster stopping and greater positional precision.

As used in any aspect herein, a wireless transmission such as, for example, a wireless communication or a wireless transfer of a data signal can be achieved, by a device including one or more transceivers. The transceivers may include, but are not limited to cellular modems, wireless mesh network transceivers, Wi-Fi® transceivers, low power wide area (LPWA) transceivers, and/or near field communications transceivers (NFC). The device may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers may be configured to receive serial transmit data via respective universal asynchronous receiver-transmitters (UARTs) from a processor to modulate the serial transmit data onto an RF carrier to produce a transmit RF signal and to transmit the transmit RF signal via respective antennas. The transceiver(s) can be further configured to receive a receive RF signal via respective antennas that includes an RF carrier modulated with serial receive data, to demodulate the receive RF signal to extract the serial receive data and to provide the serial receive data to respective UARTs for provision to the processor. Each RF signal has an associated carrier frequency and an associated channel bandwidth. The channel bandwidth is associated with the carrier frequency, the transmit data and/or the receive data. Each RF carrier frequency and channel bandwidth is related to the operating frequency range(s) of the transceiver(s). Each channel bandwidth is further related to the wireless communication standard and/or protocol with which the transceiver(s) may comply. In other words, each transceiver may correspond to an implementation of a selected wireless communication standard and/or protocol, e.g., IEEE 802.11 a/b/g/n for Wi-Fi® and/or IEEE 802.15.4 for wireless mesh networks using Zigbee routing.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method of controlling a surgical system including a manually-drivable closure system configured to effect a closure motion at an end effector to clamp tissue and a motor-powered firing system configured to motivate a firing member to effect a firing motion at the end effector to seal and cut the tissue, the method comprising:
   detecting, by a control circuit, the end effector reaching an initial clamped state around the tissue with the manually-drivable closure system;
   initiating, by the control circuit, a timer based on the end effector reaching the initial clamped state;
   detecting, by the control circuit, the end effector transitioning away from the initial clamped state after initiating the timer;
   maintaining, by the control circuit, the timer, based on the end effector failing to transition a threshold amount away from the initial clamped state;
   detecting, by the control circuit, the end effector reaching a second clamped state after failing to transition the threshold amount away from the clamped state;
   detecting, by the control circuit, an actuation of the motor-powered firing system after detecting the end effector reaching the second clamped state;
   set, by the control circuit, a firing motion parameter of the motor-powered firing system based on an elapsed time from the initiation of the timer to the actuation of the motor-powered firing system; and
   causing, by the control circuit, the motor-powered firing system to drive the firing member to effect the firing motion using the firing motion parameter.

2. The method of claim 1, further comprising resetting, by the control circuit, the timer, based on the end effector transitioning the threshold amount away from the initial clamped state.

3. The method of claim 2, further comprising detecting, by the control circuit, the end effector reaching the second clamped state after resetting the timer.

4. The method of claim 3, further comprising reinitiating, by the control circuit, the timer, based on the end effector reaching the second clamped state after resetting the timer.

5. The method of claim 4, detecting, by the control circuit, the actuation of the motor-powered firing system after reaching the second clamped state.

6. The method of claim 5, further comprising setting, by the control circuit, a second firing motion parameter of the motor-powered firing system based on an elapsed time from the reinitiation of the timer to the actuation of the motor-powered firing system.

7. The method of claim 6, further comprising causing, by the control circuit, the motor-powered firing system to drive the firing member through a firing stroke using the second firing motion parameter.

8. The method of claim 7, wherein the firing motion parameter comprises a duty cycle of the motor.

9. The method of claim 7, wherein the firing motion parameter comprises a velocity of the motor.

10. The method of claim 7, further comprising detecting, by the control circuit, a first elapsed clamp time taken to transition the end effector toward the initial clamped state, and wherein setting the firing motion parameter of the motor-powered firing system is further based on the first elapsed clamp time.

11. The method of claim 10, further comprising detecting, by the control circuit, a second elapsed clamp time taken to transition the end effector toward the second clamped state, and wherein setting the firing motion parameter of the motor-powered firing system is further based on the second elapsed clamp time.

12. The method of claim 7, further comprising dynamically adjusting, by the control circuit, the firing motion parameter during the firing stroke based an elapsed time from the end effector reaching the initial clamped state to a current time point.

* * * * *